US012042508B2

(12) United States Patent
Hastings

(10) Patent No.: US 12,042,508 B2
(45) Date of Patent: Jul. 23, 2024

(54) ANTISENSE COMPOUNDS TARGETING GENES ASSOCIATED WITH CYSTIC FIBROSIS

(71) Applicant: Rosalind Franklin University of Medicine and Science, North Chicago, IL (US)

(72) Inventor: Michelle L. Hastings, North Chicago, IL (US)

(73) Assignee: ROSALIND FRANKLIN UNIVERSITY OF MEDICINE AND SCIENCE, North Chicago, IL (US)

( * ) Notice: Subject to any disclaimer, the term of this patent is extended or adjusted under 35 U.S.C. 154(b) by 187 days.

(21) Appl. No.: 17/472,046

(22) Filed: Sep. 10, 2021

(65) Prior Publication Data

US 2022/0054526 A1 Feb. 24, 2022

Related U.S. Application Data

(63) Continuation of application No. 16/730,517, filed on Dec. 30, 2019, now Pat. No. 11,116,785, which is a continuation of application No. 15/835,698, filed on Dec. 8, 2017, now Pat. No. 10,525,076, which is a continuation-in-part of application No. 15/045,999, filed on Feb. 17, 2016, now Pat. No. 9,840,709.

(60) Provisional application No. 62/118,794, filed on Feb. 20, 2015.

(51) Int. Cl.
*A61K 31/712* (2006.01)
*C12N 15/113* (2010.01)

(52) U.S. Cl.
CPC ........ *A61K 31/712* (2013.01); *C12N 15/1138* (2013.01); *A01K 2267/0306* (2013.01); *C12N 2310/11* (2013.01); *C12N 2310/321* (2013.01); *C12N 2310/3233* (2013.01); *C12N 2320/33* (2013.01)

(58) Field of Classification Search
CPC ............ C12N 15/1138; C12N 2310/11; C12N 2310/321; C12N 2310/3233; A61K 31/712
See application file for complete search history.

(56) References Cited

U.S. PATENT DOCUMENTS 6,573,073 B2 6/2003 Harris
9,840,709 B2 12/2017 Hastings
9,976,143 B2 5/2018 Krainer et al.
10,525,076 B2 1/2020 Hastings
10,544,417 B2 1/2020 Hastings
10,822,369 B2 11/2020 Crooke et al.
2002/0086836 A1 7/2002 Harris
2003/0008281 A1 1/2003 Weston et al.
2004/0096844 A1 5/2004 Accola et al.
2004/0096871 A1 5/2004 Accola et al.
2004/0229269 A1 11/2004 Hashmi
2005/0048544 A1 3/2005 Gardner et al.
2005/0186588 A1 8/2005 Lyamichev et al.
2006/0147938 A1 7/2006 Accola et al.
2006/0252722 A1 11/2006 Lollo et al.
2008/0221317 A1 9/2008 Khvorova et al.
2009/0149403 A1* 6/2009 MacLachlan ...... A61K 31/7088 435/375
2009/0170799 A1* 7/2009 Crooke ..................... A61P 9/12 536/24.5
2011/0230544 A1* 9/2011 Crooke ................ C12N 15/113 435/375
2012/0094846 A1 4/2012 Hantash
2013/0203055 A1 8/2013 Aurich-Costa
2015/0232878 A1 8/2015 Hyde et al.
2017/0022507 A1* 1/2017 Reyon ................ C12N 15/1138
2018/0009837 A1 1/2018 Crooke et al.
2018/0117073 A1 5/2018 Hastings

FOREIGN PATENT DOCUMENTS

WO 96/06190 A2 2/1996
WO WO 97/35005 9/1997
WO 01/73002 A2 10/2001
WO WO 2007/110628 10/2001
WO 2005006951 A2 1/2005
WO 200600057 A1 1/2006
WO 2007135105 A1 11/2007
WO 2008/102057 A1 8/2008
WO 2014/045283 A1 3/2014
WO WO 2016/077837 5/2016
(Continued)

OTHER PUBLICATIONS

Friedman, K.J., et al., "Correction of Aberrant Splicing of the Cystic Fibrosis Transmembrane Conductance Regulator (CFTR) Gene by Antisense Oligonucleotides", Journal of Biological Chemistry, Dec. 17, 1999, vol. 274 (51), pp. 36193-36199.
(Continued)

*Primary Examiner* — Brian Whiteman
(74) *Attorney, Agent, or Firm* — McDonnell Boehnen Hulbert & Berghoff LLP

(57) ABSTRACT

The present disclosure relates generally to compounds comprising oligonucleotides complementary to a cystic fibrosis transmembrane conductance regulator (CFTR) RNA transcript. Certain such compounds are useful for hybridizing to a CFTR RNA transcript, including but not limited to a CFTR RNA transcript in a cell. In certain embodiments, such hybridization results in modulation of splicing of the CFTR transcript. In certain embodiments, such compounds are used to treat one or more symptoms associated with Cystic Fibrosis.

27 Claims, 41 Drawing Sheets

Specification includes a Sequence Listing.

(56) References Cited

FOREIGN PATENT DOCUMENTS

| | | | |
|---|---|---|---|
| WO | 2016134021 | A1 | 8/2016 |
| WO | 2020194320 | A1 | 10/2020 |
| WO | 2020194321 | A1 | 10/2020 |

OTHER PUBLICATIONS

Igreja, Susana, et al., "Correction of a Cystic Fibrosis Splicing Mutation by Antisense Oligonucleotides" Human Mutation, Nov. 10, 2015, pp. 1-7.
Qiao, W., et al, "Charge-Neutral Morpholino Microarrays for Nucleic Acid Analysis", Anal. Biochem., Mar. 15, 2013, vol. 434(2), pp. 207-214, doi:10.1016/j.ab.2012.12.001, Epub Dec. 12, 2012.
Sazani, P., et al., "Therapeutic Potential of Antisense Oligonucleotides as Modulators of Alternative Splicing", Journal of Clinical Investigation, Aug. 1, 2003, vol. 112(4), pp. 481-486.
Tsui, L-C., "The Spectrum of Cystic Fibrosis Mutations", Trends in Genetics, Nov. 1, 1992, vol. 8(11), pp. 392-398.
PCT International Search Report and Written Opinion, European Patent Office—International Searching Authority, Jun. 20, 2016, pp. 1-14.
Crooke et al., "Pharmacokinetic properties of several novel oligonucleotide analogs in mice." J. Pharmacol. Exp. Ther., 277(2):923-37 (May 1996).
Kabanov et al., "A new class of antivirals: antisense oligonucleotides combined with a hydrophobic substituent effectively inhibit influenza virus reproduction and synthesis of virus-specific proteins in MDCK cells" FEBS Lett, 259:327-330 (Jan. 1990).
Letsinger et al., "Cholesteryl-conjugated oligonucleotides: synthesis, properties, and activity as inhibitors of replication of human immunodeficiency virus in cell culture." Proc. Natl. Acad. Sci. USA, 86(17):6553-6556 (Sep. 1989).
Manoharan et al., "Cholic acid-oligonucleotide conjugates for antisense applications" Bioorganic & Medicinal Chemistry Letters, 4(8):1053-1060 (Apr. 1994).
Manoharan et al., "Chemical modifications to improve uptake and bioavailability of antisense oligonucleotides." Ann. N.Y. Acad. Sci., 660:306-309 (Oct. 1992).
Manoharan et al., "Introduction of a lipophilic thioether tether in the minor groove of nucleic acids for antisense applications" Bioorganic & Medicinal Chemistry Letters, 3(12):2765-2770 (Dec. 1993).
Manoharan et al., "Lipidic nucleic acids" Tetrahedron Letters, 36(21):3651-54 (May 1995).
Manoharan et al., "Oligonucleotide Conjugates: Alteration of the Pharmacokinetic Properties of Antisense Agents" Nucleosides & Nucleotides, 14(Issue 3-5): 969-973 (1995).
Mishra et al., "Improved leishmanicidal effect of phosphorotioate antisense oligonucleotides by LDL-mediated delivery." Biochim. Biophys. Acta, 1264(2):229-237 (Nov. 1995).
Oberhauser et al., "Effective incorporation of 2'-O-methyl-oligoribonucleotides into liposomes and enhanced cell association through modification with thiocholesterol." Nucl. Acids Res., 20(3):533-538 (Feb. 1992).
Saison-Behmoaras et al., "Short modified antisense oligonucleotides directed against Ha-ras point mutation induce selective cleavage of the mRNA and inhibit T24 cells proliferation." EMBO J., 10(5):1111-18 (May 1991).
Shea et al., "Synthesis, hybridization properties and antiviral activity of lipid-oligodeoxynucleotide conjugates." Nucl. Acids Res., 18(13):3777-83 (Jul. 1990).
Svinarchuk et al., "Inhibition of HIV proliferation in MT-4 cells by antisense oligonucleotide conjugated to lipophilic groups" Biochimie, 75(1-2):49-54 (1993).
The International Search Report and Written Opinion for International Application No. PCT/US2016/018275 from the European Patent Office—International Searching Authority; dated Jun. 20, 2016, pp. 1-14.
Kim & Krainer, "Allele-Specific Inhibition of Nonsense-Mediated mRNA Decay in Cystic Fibrosis" Poster No. 804, Abstract Submitted. The 32nd Annual North American Cystic Fibrosis Conference, Denver, Colorado, Oct. 18-20, 2018, Pediatric Pulmonology vol. 53, Issue S2, Sep. 2018, one page.
Martinovich et al., "Rescue of CFTR Function Impaired by Mutations in Exon 15 in Children with Cystic Fibrosis" Poster No. 205, Abstract Submitted. The 32nd Annual North American Cystic Fibrosis Conference, Denver, Colorado, Oct. 18-20, 2018, Pediatric Pulmonology vol. 53, Issue S2, Sep. 2018, p. 224.
Friedman, Kenneth J., et al., "Correction of Aberrant Splicing of the Cystic Fibrosis Transmembrane Conductance Regulator (CFTR) Gene by Antisense Oligonucleotides," The Journal of Biological Chemistry (1999), vol. 274, No. 51, pp. 36193-36199.
Kim, Young Jin, et al., "Exon-Skipping Antisense Oligoneculeotides for Cystic Fibrosis Therapy," BioRxiv reprint doi: https://doi.org/10.1101/2021.08.11.455936 (2021), pp. 1-37.
Form PCT/ISA/220, Notification of Transmittal of the International Search Report and the Written Opinion of the International Searching Authority, or the Declaration, Issued in the International Application No. PCT/US2022/015794 dated May 4, 2022.
Form PCT/ISA/237, Written Opinion of the International Searching Authority, Issued in the International Application No. PCT/US2022/015794 dated May 4, 2022.

* cited by examiner

FIG. 4

>human CFTR intron 1, exon 2, intron 2 region (SEQ ID NO: 131)
ATATGCCAGAAAAGTTGAATAGTATCAGATTCCAAATCTGTATGGAGACCAAATCAAGTGAATATCTGTT
CCTCCTCTCTTTATTTTAGCTGGACCAGACCAATTTTGAGGAAAGGATACAGACAGCGCCTGGAATTGTC
AGACATATACCAAATCCCTTCTGTTGATTCTGCTGACAATCTATCTGAAAAATTGGAAAGGTATGTTCAT
GTACATTGTTTAGTTGAAGAGAGAAATTCATATTATTAATTATTTAGAGAAGAGAAAGCAAACATATTAT
AAGTTTAATTCTTATATTTA

FIG. 5

>human CFTR intron 3, exon 4, intron 4 region (SEQ ID NO: 132)
TCTCCTCTAAAGATGAAAAGTCTTGTGTTGAAATTCTCAGGGTATTTTATGAGAAATAAATGAAATTTAA
TTTCTCTGTTTTTCCCCTTTTGTAGGAAGTCACCAAAGCAGTACAGCCTCTCTTACTGGGAAGAATCATA
GCTTCCTATGACCCGGATAACAAGGAGGAACGCTCTATCGCGATTTATCTAGGCATAGGCTTATGCCTTC
TCTTTATTGTGAGGACACTGCTCCTACACCCAGCCATTTTTGGCCTTCATCACATTGGAATGCAGATGAG
AATAGCTATGTTTAGTTTGATTTATAAGAAGGTAATACTTCCTTGCACAGGCCCCATGGCACATATATTC
TGTATCGTACATGTTTTAATGTCATAAATTAGGTAGTGAGCTGGTACAAGTAAGGGATAAATGCTGAAAT

FIG. 6

>human CFTR intron 4, exon 5, intron 5 region (SEQ ID NO: 133)
CCTTTACTTAATAATGAATGCATAATAACTGAATTAGTCATATTATAATTTTACTTATAATATATTTGTA
TTTTGTTTGTTGAAATTATCTAACTTTCCATTTTTCTTTTAGACTTTAAAGCTGTCAAGCCGTGTTCTAG
ATAAAATAAGTATTGGACAACTTGTTAGTCTCCTTTCCAACAACCTGAACAAATTTGATGAAGTATGTAC
CTATTGATTTAATCTTTTAGGCACTATTGTTATAAATTATACAACTGGAAAGGCGGAGTTTTCCTGGGTC
AGATAATAGTAATTAGTGGT

FIG. 7

>human CFTR intron 6, exon 7, intron 7 region (SEQ ID NO: 134)
TTGAATAAAAGAAATATGACTTAAAACCTTGAGCAGTTCTTAATAGATAATTTGACTTGTTTTTACTATT
AGATTGATTGATTGATTGATTGATTGATTTACAGAGATCAGAGAGCTGGGAAGATCAGTGAAAGACTTGT
GATTACCTCAGAAATGATTGAAAATATCCAATCTGTTAAGGCATACTGCTGGGAAGAAGCAATGGAAAAA
ATGATTGAAAACTTAAGACAGTAAGTTGTTCCAATAATTTCAATATTGTTAGTAATTCTGTCCTTAATTT
TTTAAAAATATGTTTATCAT

FIG. 8

>human CFTR intron 8, exon 9, intron 9 region (SEQ ID NO: 135)
ATTATTAAAATTCATATATAAGATGTAGCACAATGAGAGTATAAAGTAGATGTAATAATGCATTAATGCT
ATTCTGATTCTATAATATGTTTTTGCTCTCTTTTATAAATAGGATTTCTTACAAAAGCAAGAATATAAGA
CATTGGAATATAACTTAACGACTACAGAAGTAGTGATGGAGAATGTAACAGCCTTCTGGGAGGAGGTCAG
AATTTTTAAAAAATTGTTTGCTCTAAACACCTAACTGTTTTCTTCTTTGTGAATATGGATTTCATCCTAA
TGGCGAATAAAATTAGAATG

FIG. 9

>human CFTR intron 9, exon 10, intron 10 region (SEQ ID NO: 136)
GCATCTATTGAAAATATCTGACAAACTCATCTTTTATTTTTGATGTGTGTGTGTGTGTGTGTGTTTTT
TTAACAGGGATTTGGGGAATTATTTGAGAAAGCAAAACAAAACAATAACAATAGAAAAACTTCTAATGGT
GATGACAGCCTCTTCTTCAGTAATTTCTCACTTCTTGGTACTCCTGTCCTGAAAGATATTAATTTCAAGA
TAGAAAGAGGACAGTTGTTGGCGGTTGCTGGATCCACTGGAGCAGGCAAGGTAGTTCTTTTGTTCTTCAC
TATTAAGAACTTAATTTGGTGTCCATGTCTCTTTTTTTTTCTAGTTTGTAGTGCTGGAAGGTATTTTTGG
AGAAATTCTT

FIG. 10

>human CFTR intron 10, exon 11, intron 11 region (SEQ ID NO: 137)
CAAATAAGAATATACACTTCTGCTTAGGATGATAATTGGAGGCAAGTGAATCCTGAGCGTGATTTGATAA
TGACCTAATAATGATGGGTTTTATTTCCAGACTTCACTTCTAATGGTGATTATGGGAGAACTGGAGCCTT
CAGAGGGTAAAATTAAGCACAGTGGAAGAATTTCATTCTGTTCTCAGTTTTCCTGGATTATGCCTGGCAC
CATTAAAGAAAATATCATCTTTGGTGTTTCCTATGATGAATATAGATACAGAAGCGTCATCAAAGCATGC
CAACTAGAAGAGGTAAGAAACTATGTGAAAACTTTTTGATTATGCATATGAACCCTTCACACTACCCAAA
TTATATATTTGGCTCCATATTCAATCGGTTAGTCTACATATATTTATGTTTCCTCTATGGGTAAGCTACT

FIG. 11

>human CFTR intron 12, exon 13, intron 13 region (SEQ ID NO: 138)
CATGTAGTGAACTGTTTAAGGCAAATCATCTACACTAGATGACCAGGAAATAGAGAGGAAATGTAATTTA
ATTTCCATTTTCTTTTTAGAGCAGTATACAAAGATGCTGATTTGTATTTATTAGACTCTCCTTTTGGATA
CCTAGATGTTTTAACAGAAAAAGAAATATTTGAAAGGTATGTTCTTTGAATACCTTACTTATAATGCTCA
TGCTAAAATAAAAGAAAGACAGACTGTCCC

FIG. 12

>human CFTR intron 14, exon 15, intron 15 region (SEQ ID NO: 139)
GATTCAAGTAATACTATTCTTTTATTTTCATATATTAAAAATAAAACCACAATGGTGGCATGAAACTGTA
CTGTCTTATTGTAATAGCCATAATTCTTTTATTCAGGAGTGCTTTTTTGATGATATGGAGAGCATACCAG
CAGTGACTACATGGAACACATACCTTCGATATATTACTGTCCACAAGAGCTTAATTTTTGTGCTAATTTG
GTGCTTAGTAATTTTTCTGGCAGAGGTAAGAATGTTCTATTGTAAAGTATTACTGGATTTAAAGTTAAAT
TAAGATAGTTTGGGGATGTA

FIG. 13

>human CFTR intron 15, exon 16, intron 16 region (SEQ ID NO: 140)
GTGATGTGAATTTAGATGTGGGCATGGGAGGAATAGGTGAAGATGTTAGAAAAAAAATCAACTGTGTCTT
GTTCCATTCCAGGTGGCTGCTTCTTTGGTTGTGCTGTGGCTCCTTGGAAAGTGAGTATTCCATGTCCTAT
TGTGTAGATTGTGTTTTATTTCTGTTGATTAAATATTGTA

FIG. 14

>human CFTR intron 19, exon 20, intron 20 region (SEQ ID NO: 141)
TTTCAGGTACAAGATATTATGAAATTACATTTTGTGTTTATGTTATTTGCAATGTTTTCTATGGAAATAT
TTCACAGGCAGGAGTCCAATTTTCACTCATCTTGTTACAAGCTTAAAAGGACTATGGACACTTCGTGCCT
TCGGACGGCAGCCTTACTTTGAAACTCTGTTCCACAAAGCTCTGAATTTACATACTGCCAACTGGTTCTT
GTACCTGTCAACACTGCGCTGGTTCCAAATGAGAATAGAAATGATTTTTGTCATCTTCTTCATTGCTGTT
ACCTTCATTTCCATTTTAACAACAGGTACTATGAACTCATTAACTTTAGCTAAGCATTTAAGTAAAAAAT
TTTCAATGAATAAAATGCTGCATTCTATAGGTTATCAATTTTTGATATCTTTAGAGTTTAGTAATTAACA

FIG. 15

>human CFTR intron 21, exon 22, intron 22 region (SEQ ID NO: 142)
TAACCAAGTGACAAATAGCAAGTGTTGCATTTTACAAGTTATTTTTTAGGAAGCATCAAACTAATTGTGA
AATTGTCTGCCATTCTTAAAAACAAAAATGTTGTTATTTTTATTTCAGATGCGATCTGTGAGCCGAGTCT
TTAAGTTCATTGACATGCCAACAGAAGGTAAACCTACCAAGTCAACCAAACCATACAAGAATGGCCAACT
CTCGAAAGTTATGATTATTGAGAATTCACACGTGAAGAAAGATGACATCTGGCCCTCAGGGGGCCAAATG
ACTGTCAAAGATCTCACAGCAAAATACACAGAAGGTGGAAATGCCATATTAGAGAACATTTCCTTCTCAA
TAAGTCCTGGCCAGAGGGTGAGATTTGAACACTGCTTGCTTTGTTAGACTGTGTTCAGTAAGTGAATCCC
AGTAGCCTGAAGCAATGTGTTAGCAGAATCTATTTGTAACATTATTATTGTACAGTAGAATCAATATTAA
ACACACATGTTTTATTATATGGAGTCATTATTTTTAATATGAAATTTAATTTGCAGAGTCCTGAACCTAT
ATAATGGGTTTATTTTAAATGTGATTGTACTTGCAGAATA

FIG. 16

>human CFTR intron 22, exon 23, intron 23 region (SEQ ID NO: 143)
TTCCAATGGTTTTTATTGAAGTACAATACTGAATTATGTTTATGGCATGGTACCTATATGTCACAGAAGT
GATCCCATCACTTTTACCTTATAGGTGGGCCTCTTGGGAAGAACTGGATCAGGGAAGAGTACTTTGTTAT
CAGCTTTTTTGAGACTACTGAACACTGAAGGAGAAATCCAGATCGATGGTGTGTCTTGGGATTCAATAAC
TTTGCAACAGTGGAGGAAAGCCTTTGGAGTGATACCACAGGTGAGCAAAAGGACTTAGCCAGAAAAAAGG
CAACTAAATTATATTTTTTACTGCTATTTGATACTTGTACTCAAGAAATTCATATTACTCTGCAAAATAT
ATTTGTTATG

FIG. 17

>human CFTR intron 23, exon 24, intron 24 region (SEQ ID NO: 144)
GGGTGTTTCTTATTTTAAAATAATTTTTCTACTTGAAATATTTTACAATACAATAAGGGAAAAATAAAAA
GTTATTTAAGTTATTCATACTTTCTTCTTCTTTTCTTTTTTGCTATAGAAAGTATTTATTTTTTCTGGAA
CATTTAGAAAAAACTTGGATCCCTATGAACAGTGGAGTGATCAAGAAATATGGAAAGTTGCAGATGAGGT
AAGGCTGCTAACTGAAATGATTTTGAAAGGGGTAACTCATACCAACACAAATGGCTGATATAGCTGACAT
CATTCTACACACTTTGTGTGCATGTATGTGTGTGCACAACTTTAAAATGGAGTACCCTAACATACCTGGA
GCAACAGGTA CFTR Exon 4 Deletion in FRT cells
CFTR Exon 7 Deletion in FRT cells
CFTR Exon 23 Deletion in FRT cells
CFTR Exon 24 Deletion in FRT cells
Forskolin
Inh-172
HCAI Δex4
HCAI Δex7
HCAI Δex23
HCAI Δex24
HCAI empty vector
Gt (mS/cm2)
Time (min)

```
                         SEQUENCE LISTING

    <160> NUMBER OF SEQ ID NOS: 151

    <210> SEQ ID NO 1
    <211> LENGTH: 25
    <212> TYPE: DNA
    <213> ORGANISM: Artificial Sequence
    <220> FEATURE:
    <223> OTHER INFORMATION: Synthetic oligonucleotide

    <400> SEQUENCE: 1

    ggtccagcta aaagagaaga gggca                                            25

    <210> SEQ ID NO 2
    <211> LENGTH: 25
    <212> TYPE: DNA
    <213> ORGANISM: Artificial Sequence
    <220> FEATURE:
    <223> OTHER INFORMATION: Synthetic oligonucleotide

    <400> SEQUENCE: 2

    ctttcctcaa aattggtgtg gtcca                                            25

    <210> SEQ ID NO 3
    <211> LENGTH: 25
    <212> TYPE: DNA
    <213> ORGANISM: Artificial Sequence
    <220> FEATURE:
    <223> OTHER INFORMATION: Synthetic oligonucleotide

    <400> SEQUENCE: 3

    tatgtctgac aactccaagt ggtgt                                            25

    <210> SEQ ID NO 4
    <211> LENGTH: 25
    <212> TYPE: DNA
    <213> ORGANISM: Artificial Sequence
    <220> FEATURE:
    <223> OTHER INFORMATION: Synthetic oligonucleotide

    <400> SEQUENCE: 4

    ctagtttttc agacaagtgg tcagc                                            25

    <210> SEQ ID NO 5
    <211> LENGTH: 25
    <212> TYPE: DNA
    <213> ORGANISM: Artificial Sequence
    <220> FEATURE:
    <223> OTHER INFORMATION: Synthetic oligonucleotide

    <400> SEQUENCE: 5

    ttcctagcaa gacaggctgg acagc                                            25

    <210> SEQ ID NO 6
    <211> LENGTH: 25
    <212> TYPE: DNA
```

```
<213> ORGANISM: Artificial Sequence
<220> FEATURE:
<223> OTHER INFORMATION: Synthetic oligonucleotide

<400> SEQUENCE: 6

ataggatgct atgattcttc ctagc                                    25


<210> SEQ ID NO 7
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 7

ataagcctat gccaaggtaa atggc                                    25


<210> SEQ ID NO 8
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 8

tgtcctgaca atgaagagaa ggcat                                    25


<210> SEQ ID NO 9
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 9

aatgcgatga aggccaaaaa tagct                                    25


<210> SEQ ID NO 10
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 10

tagctgttct catctgcatt ccaat                                    25


<210> SEQ ID NO 11
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 11

catcttccaa aaagtattac cttct                                    25


<210> SEQ ID NO 12
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 12

ttgttcaggt tgttggaaag aagac                                    25
```

<210> SEQ ID NO 13
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 13
atcaagaacg cggcttgaca acttt 25

<210> SEQ ID NO 14
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 14
cacgagtctt tcattgatct ttgca 25

<210> SEQ ID NO 15
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 15
ctgattccca acaatatgcc ttaac 25

<210> SEQ ID NO 16
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 16
caatcatttt ctccatcgct gattc 25

<210> SEQ ID NO 17
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 17
attatgtcaa cttactctct caagt 25

<210> SEQ ID NO 18
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 18
gcctgtggtc attaagttat actcc 25

<210> SEQ ID NO 19
<211> LENGTH: 25
<212> TYPE: DNA
<213> ORGANISM: Artificial Sequence
<220> FEATURE:

<223> OTHER INFORMATION: Synthetic oligonucleotide

<400> SEQUENCE: 19
ctcctcccaa aatgctgtta cattt 25

<210> SEQ ID NO 20
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 20
tatttagaaa tctcacctcc tccca 25

<210> SEQ ID NO 21
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 21
ctttctccag taattcccca aatcc 25

<210> SEQ ID NO 22
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 22
gtcaccattg ctttgttgta ctttc 25

<210> SEQ ID NO 23
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 23
ctgaaactga cattgttctc atcac 25

<210> SEQ ID NO 24
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 24
aggatttccc acaaggcaga gatga 25

<210> SEQ ID NO 25
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 25
atagccaaca tctctccttt ctcta 25

<210> SEQ ID NO 26
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 26
ctttcctgat ccagtagatc cagta 25

<210> SEQ ID NO 27
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 27
ctttcctgat ccagtagatc cagta 25

<210> SEQ ID NO 28
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 28
tccagttctc ccaaaatcaa catca 25

<210> SEQ ID NO 29
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 29
tgtgcttaat aattccctct gaagc 25

<210> SEQ ID NO 30
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 30
attgagagca gaatgaaact cttcc 25

<210> SEQ ID NO 31
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 31
gatattttct ttgatagtac ccggc 25

<210> SEQ ID NO 32
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 32
acactcttat atctgtactc atcat 25

<210> SEQ ID NO 33
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 33
ctgctgtagt tggcaagctt tgaca 25

<210> SEQ ID NO 34
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 34
cataaatatg cttacctgct gtagt 25

<210> SEQ ID NO 35
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 35
gggaatctaa taggtacaaa tcagc 25

<210> SEQ ID NO 36
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 36
caaatcagca tctttatata ctgct 25

<210> SEQ ID NO 37
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 37
actcagtcat agaacatacc tttca 25

<210> SEQ ID NO 38
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 38
aacaaacata cttacctcaa ccaga 25

<210> SEQ ID NO 39
<211> LENGTH: 25

-continued

<212> TYPE: DNA
<213> ORGANISM: Artificial Sequence
<220> FEATURE:
<223> OTHER INFORMATION: Synthetic oligonucleotide

<400> SEQUENCE: 39
cctgcctgta aatcatccca tagga 25

<210> SEQ ID NO 40
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 40
caaggtgggt gaaaattgga ctcct 25

<210> SEQ ID NO 41
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 41
cgaagtgtcc agagtccttt taagc 25

<210> SEQ ID NO 42
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 42
cagagtttca aagtaagtct ggcgt 25

<210> SEQ ID NO 43
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 43
ttggcagtgt gcaaattcag agctt 25

<210> SEQ ID NO 44
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 44
ctattctcat ttggaaccag cgcaa 25

<210> SEQ ID NO 45
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 45

-continued agaggacaaa tatcatgtct attct 25

<210> SEQ ID NO 46
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 46
atggagatga aggtaacaac aatga 25

<210> SEQ ID NO 47
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 47
aacttaaaca ctctgctcac agatc 25

<210> SEQ ID NO 48
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 48
ctaaaacgtc agatgatcct tctct 25

<210> SEQ ID NO 49
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 49
tatcactttt cttcacatgc tcatt 25

<210> SEQ ID NO 50
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 50
accatttcgc ctccagaggg ccaga 25

<210> SEQ ID NO 51
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 51
catccatgta tttcacagta aggtc 25

<210> SEQ ID NO 52
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 52
atgttctcta atacggcatt tccat 25

<210> SEQ ID NO 53
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 53
cctctgtcca ggacttattg aaaaa 25

<210> SEQ ID NO 54
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 54
gtaatgctga aatctcaccc tctgt 25

<210> SEQ ID NO 55
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 55
aattccatga gacaccatca atctc 25

<210> SEQ ID NO 56
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 56
gtactttttc ctgatccagt tcttc 25

<210> SEQ ID NO 57
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 57
catttttgtg ctcacctgtg ttatc 25

<210> SEQ ID NO 58
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 58
catctttcca ttttccattg ggatc 25

<210> SEQ ID NO 59
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 59
ctcatctgca actttccata tttct 25

<210> SEQ ID NO 60
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 60
tatttgtcat ccttacctca tctgc 25

<210> SEQ ID NO 61
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 61
atcctttcct caaaattggt ctggt 25

<210> SEQ ID NO 62
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 62
gtatatgtct gacaattcca ggcgc 25

<210> SEQ ID NO 63
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 63
cagatagatt gtcagcagaa tcaac 25

<210> SEQ ID NO 64
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 64
gtacatgaac ataccttcc aattt 25

<210> SEQ ID NO 65
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 65
gaggctgtac tgctttggtg acttc 25

<210> SEQ ID NO 66
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 66
gaagctatga ttcttcccag taaga 25

<210> SEQ ID NO 67
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 67
gtgtaggagc agtgtcctca caata 25

<210> SEQ ID NO 68
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 68
aatgtgatga aggccaaaaa tggct 25

<210> SEQ ID NO 69
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 69
gctattctca tctgcattcc aatgt 25

<210> SEQ ID NO 70
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 70
cctgtgcaag gaagtattac cttct 25

<210> SEQ ID NO 71
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 71
ctagaacacg gcttgacagc tttaa 25

<210> SEQ ID NO 72

<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 72
tggaaaggag actaacaagt tgtcc 25

<210> SEQ ID NO 73
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 73
actgatcttc ccagctctct gatct 25

<210> SEQ ID NO 74
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 74
atttctgagg taatcacaag tcttt 25

<210> SEQ ID NO 75
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 75
agtatgcctt aacagattgg atatt 25

<210> SEQ ID NO 76
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 76
attttttcca ttgcttcttc ccagc 25

<210> SEQ ID NO 77
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 77
attggaacaa cttactgtct taagt 25

<210> SEQ ID NO 78
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 78
tccatcacta cttctgtagt cgtta 25

<210> SEQ ID NO 79
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 79
ctcctcccag aaggctgtta cattc 25

<210> SEQ ID NO 80
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 80
ttaaaaattc tgacctcctc ccaga 25

<210> SEQ ID NO 81
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 81
ggctgtcatc accattagaa gtttt 25

<210> SEQ ID NO 82
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 82
aattactgaa gaagaggctg tcatc 25

<210> SEQ ID NO 83
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 83
taatatcttt caggacagga gtacc 25

<210> SEQ ID NO 84
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 84
gatccagcaa ccgccaacaa ctgtc 25

<210> SEQ ID NO 85
<211> LENGTH: 25
<212> TYPE: DNA

-continued

<213> ORGANISM: Artificial Sequence
<220> FEATURE:
<223> OTHER INFORMATION: Synthetic oligonucleotide

<400> SEQUENCE: 85
agaacaaaag aactaccttg cctgc 25

<210> SEQ ID NO 86
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 86
ctcccataat caccattaga agtga 25

<210> SEQ ID NO 87
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 87
attttaccct ctgaaggctc cagtt 25

<210> SEQ ID NO 88
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 88
acagaatgaa attcttccac tgtgc 25

<210> SEQ ID NO 89
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 89
gtgccaggca taatccagga aaact 25

<210> SEQ ID NO 90
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 90
atgctttgat gacgcttctg tatct 25

<210> SEQ ID NO 91
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 91
ttttcacata gtttcttacc tcttc 25

<210> SEQ ID NO 92
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 92
tctaggtatc caaaaggaga gtcta 25

<210> SEQ ID NO 93
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 93
ggtattcaaa gaacatacct ttcaa 25

<210> SEQ ID NO 94
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 94
acaatagaac attcttacct ctgcc 25

<210> SEQ ID NO 95
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 95
tcgttatttg gcagccaaag ttact 25

<210> SEQ ID NO 96
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 96
gagccacagc acaaccaaag aagca 25

<210> SEQ ID NO 97
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 97
tccaaggagc cacagcac 18

<210> SEQ ID NO 98
<211> LENGTH: 18
<212> TYPE: DNA
<213> ORGANISM: Artificial Sequence
<220> FEATURE:

<223> OTHER INFORMATION: Synthetic oligonucleotide

<400> SEQUENCE: 98
ttccaaggag ccacagca 18

<210> SEQ ID NO 99
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 99
ttccaaggag ccacagcaca accaa 25

<210> SEQ ID NO 100
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 100
aacagaaata aaacacaatc tacac 25

<210> SEQ ID NO 101
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 101
tttccaagga gccacagcac aacca 25

<210> SEQ ID NO 102
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 102
acaatctaca caataggaca tggaa 25

<210> SEQ ID NO 103
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 103
cacaatctac acaataggac atgga 25

<210> SEQ ID NO 104
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 104
acacaatcta cacaatagga catgg 25

<210> SEQ ID NO 105
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 105 gactttttt ctaacatctt cacct 25

<210> SEQ ID NO 106
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 106
atggaacaac acacagttga ttttt 25

<210> SEQ ID NO 107
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 107
atcgaacaag acacagttga ttttt 25

<210> SEQ ID NO 108
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 108
gagtggaaca agacacagtt gattt 25

<210> SEQ ID NO 109
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 109
cacaatctac acaataagac atgga 25

<210> SEQ ID NO 110
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 110
caagatgagt gaaaattgga ctcct 25

<210> SEQ ID NO 111
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 111
cgaaggcacg aagtgtccat agtcc 25

<210> SEQ ID NO 112
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 112
aacagagttt caaagtaagg ctgcc 25

<210> SEQ ID NO 113
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 113
agttggcagt atgtaaattc agagc 25

<210> SEQ ID NO 114
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 114
ttctattctc atttggaacc agcgc 25

<210> SEQ ID NO 115
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 115
ggtaacagca atgaagaaga tgaca 25

<210> SEQ ID NO 116
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 116
atgtcaatga acttaaagac tcggc 25

<210> SEQ ID NO 117
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 117
ggccagatgt catctttctt cacgt 25

<210> SEQ ID NO 118
<211> LENGTH: 25

<212> TYPE: DNA
<213> ORGANISM: Artificial Sequence
<220> FEATURE:
<223> OTHER INFORMATION: Synthetic oligonucleotide

<400> SEQUENCE: 118
atctttgaca gtcatttggc cccct 25

<210> SEQ ID NO 119
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 119
ccaccttctg tgtattttgc tgtga 25

<210> SEQ ID NO 120
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 120
tctctaatat ggcatttcca ccttc 25

<210> SEQ ID NO 121
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 121
ccaggactta ttgagaagga aatgt 25

<210> SEQ ID NO 122
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 122
aagcagtgtt caaatctcac cctct 25

<210> SEQ ID NO 123
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 123
atccagttct tcccaagagg cccac 25

<210> SEQ ID NO 124
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 124

-continued agctgataac aaagtactct tccct 25

<210> SEQ ID NO 125
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 125
aagttattga atcccaagac acacc 25

<210> SEQ ID NO 126
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 126
ctaagtcctt ttgctcacct gtggt 25

<210> SEQ ID NO 127
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 127
gatcactcca ctgttcatag ggatc 25

<210> SEQ ID NO 128
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 128
ctcatctgca actttccata tttct 25

<210> SEQ ID NO 129
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 129
atttcagtta gcagccttac ctcat 25

<210> SEQ ID NO 130
<211> LENGTH: 250188
<212> TYPE: DNA
<213> ORGANISM: Homo sapiens

<400> SEQUENCE: 130
tgaatgagag gtgccccatc aactggactt ctcctgagtg ttgaaaaggt aagagggttt 60
tgcttcttta ttcactcctt tcttactatt tgcattgtaa tataactctc ttgggactca 120
agggaacaaa ccatacagtg tcttttgcta aatgccaaaa atcaagaagc cagttgaagt 180
tttcagttca aattatttca caagtgttac acagtagaaa acctttatgg tggctcacgc 240
ctgtaatccc aacactttgg gaggccgagg tgggtggatc atgaggtcag gagtttaaga 300

-continued

```
ccagcctggc caagatggtg aaaccccgtc tctacaaaaa atacaaaaat tagccaggcg    360
tggtggcggg cacctgtaat ctcaactact ggggaggctg aagtagggaa ttgcttgaac    420
ctaggaggca gagattgcag cgacctgaga tcgcgccact gcactctagc ctgggcgaca    480
gaccgagact ccatctccaa aaaaaaaaaa aaagaaaaga aaagaaaaga aaaagaaaaa    540
aaaaagaaaa acaacaacaa aaaaaaacca aaacaaaaaa cctttttttt tttttgtctc    600
agtttgaggt ctcttgttac aaatttaaag aaaattaatt ttacaatttc ctattctcaa    660
tgattttgat ttactgatat tttaccctac aacaatatag tgaaaaagtg tggtcatggg    720
attggttaga cctaattcag gactaccaat actagatgtg aggctatagg caggtgtgtt    780
aaagattctt tggaatctta ttttactcaa gagtaaaaag tatgtgtagt aataattatt    840
tcataagtat attgagagca ttaaatgggg aataacaacc atataaaagg cttagcatat    900
tagagactta atacaaatca atttcttgca ttttgcttat cctggatata tcgtgggttt    960
gcttcatatt ggaaaacaag acagcaacaa agatccatgt ttcattcttc agtgacttaa   1020
aatattagtt gttctggcca ggtgtagtgg ctcacacctg taatcccagc acttcaggat   1080
gctgaggtag gatgattgct ggagcccagg agtttgggac cagactgggc aacaaagtga   1140
ggccctgtat ctacaaaaaa taaaaatcgt agccaggcat ggtggtgtgc acctgtgatc   1200
ccagatacac gagaggctga agcaggaaga ttgcttgacc ttagaaggtt gaagctatag   1260
tgagccttgt ttatgccact gcattccatg tattagttgt tctacaaata aaaatatttt   1320
actttcaaaa catgttttac taaaagtttt tcagtaagga tgtaaaaact attaatggtc   1380
aactttgact acttccaaaa tgcttttttt gagtgaaatg ttacacctct ttgttagttc   1440
attgcaataa tacttaaata tttaaaattg aaagtcagta atggtaaata tagaagaatt   1500
agaggataaa atgagtggag atatggaaag gtacagattg aatataatta tttaagtaaa   1560
atcctttcct agagaaaata gaaaatagaa ctttgaggtt gaatctcttt taatgtaatg   1620
tttttctcga atccaagtgt ttttacacta tacaatagga gtagaaattt gtcaccactc   1680
tgtggccaaa ctcacttttt ctttcttttt ttatttttac attaaaaaaa aattttactt   1740
taagttccag gatacatgtg caggatgtgc aggtttgtta cataggtaaa tgttttattt   1800
taaatttaat ttaacacttt ttatttttaa gtcatacaac tctcatagcc agtagttaat   1860
attaccttgc aagtttggta tggttgatga attgcatcct gttaataatt gctacagatt   1920
tttgaataat tgcagaccag tttgatggtc ctgggttggc ataagtacat gaagatttac   1980
tttttcctgt gagctttctt gggatgaaga aatttagtgt ttttttttaa tttttaagaa   2040
atatttatta ttttttacat gatttatttc ccactgaaaa ataaatccca ccgggcataa   2100
agtgtatttt tttaagtcac agagtaaccc aacttgaagc tagtttttca gacttaggca   2160
gttcatgctg taagcccgag atctcatggt cacccttgca agagaaatat ctaattgaaa   2220
aaaaatatga agagtattaa ttttgatagt gctaaaatga cataaaggga tctcactggg   2280
cttgagatat taagtattaa aattgttaaa ggtttaaatt gttagtaact tgttattgca   2340
tagaaaatgt gccaaatgtc agtaaataaa aaaacttttt ttaaaataaa aatttacaga   2400
aaaattatga cgatactaca aagaggttct gtacaacccc ctcccagttt ctcttactat   2460
taacatctta aattagtatg ttacatttgt cacaattagt gaaccaatat tgatacatta   2520
gtactaacta aagtcagtgt tccttttact ggagaatggt gttagaaact aaggtctggg   2580
cactgtggta tggtggttgc tattgagatg ttgttatttt taggttcttt ctcagctgac   2640
```

-continued

```
agagcaaaga aatatatgtg tgtatattaa cctatgtgta cacatacatc tatgattatt   2700
tcgatatgta acatctgtat ctttattaag ctaaatatga gttcatatgg tgtcttcaat   2760
tctaatcaat tactgtatag attattctag cctcttcctc ttgcttatct gtaacttcct   2820
atttcaaacc gtgaaaaatc tgtcttccac cacctactat ctgcttacct aatttctcat   2880
ttccagttta tgtatacagt ggcttcagaa ttattacata tagccctgtg ggatacaact   2940
ttgtcaacta gagtggtgct tatgtaagtt cttctatctt tagttttact gactctactc   3000
attttcaaag ttgcttagtc cagaacattt cactcatact cctcctagtg aagttgtttc   3060
atatgttagt aacacagatt ctttttttgc agtctgcatt ccattttagg gttccctcct   3120
ctccaatctc ctaaattatt attttttaaa ttcatataca tcaaggttta ttctttgtgc   3180
tgtaaagttc tataggtttt gacaaataca aagtgtcatg tacccatcat tacaatgtca   3240
tacagaatcg tttcactgcc ctaaaaatat cccttgtcct ttgcctattc aacccttccc   3300
ctcctttccc aaactcctgg caaccactga tctgtttatc gtggagctgt gtctcttcca   3360
gaatgcatat aattgaaatc atacaatatg tagacttttc accctggctt attttgttag   3420
caatatgcat ttaacattca tccatgtcct tatgtggctt gtagttcatt actttttact   3480
gctgggtagt attctatcat agaaatgtac cacagtttgt ttatccattc gctgattgaa   3540
gtatatcaat ataccttgga acatgactgc tagatagtat agtaagacta tatttagctt   3600
tgcaagaaac tgccaaactg tattttaaag tggctgtacc attgtgccac cagcaactcc   3660
tgccagtgat ccagtattgt cagtttttttg gattttagcc attctaaaag gtgagtgatg   3720
gtatctcatt gtcgttttaa tttgtaatac tctaatgaca aatgatggtg gatttctttt   3780
catatgtttg tttcccattt gtatatcttc tttagtatgt gtctgttcgg atgttttgct   3840
tactttttt aaactgggtt gattgttttc tttttctttt tcttttttc ttttgagacg   3900
gagtctcgct ctttagccag gctggagtgc agtggcgcca tctcggctca ctgcaagctc   3960
tgccttccgg gttcaagtga ttttcgtacc tcagcctccc gagtagctgg gactacaggc   4020
gcccgccacc acacctggct aatttttttg tatttttggt ggagacgagg tttcaccatg   4080
tcggtcaggc tggtcttaaa ctcctgacca tagatgatct gcctgtcttg gcctcccaaa   4140
gctaggatta caggctagga ttgcaagtag gataggcgtg agccactatg cccggctgat   4200
tgttttctta ttgttgagtt ttatattcct ttattttgga atggagtaaa taagcacaat   4260
aaaactggtt gagaagataa tcattttaaa aaatcataat gaattatatg atacacattc   4320
tattatttca tgagaaaaat catggaagag tcagttcaat attcagtgaa tcattaatgt   4380
gaggatgtaa aatttgatac acacacaatt tattgagcac ttatcctatg tcaatcagtg   4440
cgctaaattt ttttctttta tattaactca tttaattccc actacagccc tgtgtaatgg   4500
aagctgttct tcccaccatt ttataaatga tgaaacctta gatcacactc agtggaagag   4560
ttctaaagcc ctatgtggtg ctgtctgata gaaaatatat tttaaaatga gatgatctaa   4620
ggtatgttta cctacagagc taaaggaaag tatgtcttaa atttaataat gagtgattat   4680
agaaacagat tacaggaaat agtccatctt tcttgaatta tccaaagtgt tacaagcctc   4740
aaattcattg ttgtttgtat gagaacacat ttaggtgatc ggatacaagt atatagtttt   4800
tcccagatgt ttatttcaca tcaacttttt tttcatcttt actttcttca aggcaagtag   4860
gatagaatgt aataatcaaa taggtttttc ccccacccca ttttagagca gtaaataatt   4920
ccaagaggca tttgctttgt tattggataa gtaattaaca aaaagaattc ctaaagacaa   4980
ttagaatcat gaccatactg ggtcttgaaa acatagcagt gcaatcacag ccaatggctg   5040
```

-continued

```
gcttggtggc tggcgatgag cctgcagcat gggactgggt gttccaccac ggcttggctg   5100
ttgtccaggg agctttcagt cgctggggtt cccacagtgc caagcacgag gcaggtgcag   5160
aaaggataaa ggtttctgtt ccccattagt gttgagggca tgcaggtcgt ctgacatgag   5220
gggcatgaga agtgaagttc ctgctttgct ttgggtaagg aatctgcatt gacaggggct   5280
taagaacctg ctcttatacc tcacatgtct tagcctggcc tttgagatga gtagggagtt   5340
tgagtgggag tttgagtttc ctcttagaga aacagaactg agtgaggcac tttcattttt   5400
tagtttccta gtaccttttg ttaaggaaaa aaaagccaaa atgagtgtta aaaatttaaa   5460
atttttagat tttaaatttg catttaaaaa attaatgctt tttttttag atggagtttt   5520
gctcctgttg cccaggctgg agtgcaatgg cgtgatcttg gctcactgca acctctgcct   5580
cccaggttca agcgattctc ctgcctcagc ctcctgagta gctgggatta caggcgcccg   5640
ccaccacacc cagctaattt ttgtattttt agtagagacg aggtttcacc atgttggcca   5700
ggctggtttc gaactcctga cctcaggtga tccacctgcc tcggcctccc aaagtgctgg   5760
gattacaggc gtgagccact gcgcccagcc aaaattaatg ctcttaacat gtaaaaagta   5820
aagtgcagtg gaactttggc acttatgcaa gataatacaa cttaaaagat ttataagaat   5880
attaactgct aatgaacagt agagggatct aattaacatt gaaagttaca tgaagaaagt   5940
gtttgtcttc tattcccaac agggcatctt tgtaactata atgactcttg agaagatttt   6000
gttttcagtc ttaaaacagg aatgggggaa aaatgtaggc ctgggtaagt acaaaaaagg   6060
gaaatcgaag gagactaggg agttactgta gattttgcag gactgaggaa agtcagaata   6120
aatacaagag acaatgatgc tggtaatttt ctttgggctc agagaagtaa tgctttgctt   6180
tgtcagagtt gtagtaaaat ttagatctaa gaagctcgtt ggaagttgta gcagaatcct   6240
gtcttgttta ctatgtccac tgcctggcac agagatggaa cactataagc tttccaaaaa   6300
catttgtgga atggaatcag aaagtcactt tactttccaa gatgcaattc tttattttga   6360
aacataaata tttaaaaagt ttataaattt ttgacataat tatgacatac atccttccag   6420
gctttttca atgcttatgc aaacatgtat atgtgacctg taggtctcct tttacccagt   6480
ttttggagta caaataaggt cacatctctt cttaacttta aatgtttaaa acattgaagt   6540
tagcaagaag cccagaaact ttttctaaag aactttttct acccctaatt gtccaagaac   6600
tccaagtttt cttggttcaa agaggtaatt tctgtttcta aacactagaa aaaggagaat   6660
atgaaggatc tgactagtcc attgtcacat gccccacccc attttctgct gcaagagcct   6720
ctgtcaccac agcattgtgt cactgatgaa aataggtcct cccacagagt cagatgcatc   6780
ccagtctatt gctactatta tcaccctgtt ggaacagatc cctgcacagg tcacagcagt   6840
tcctggaaga tgaaactcat tctcccagcc ttaatatcag ccaggaatac tttattcttg   6900
gacttccaaa gttgctatag tagtttccaa agcccaccta gcacctaagg atgggtgagt   6960
aaagacaagc ttccagtttc agctgcagaa acaagaaccc atctcccacc acatagtagg   7020
tgttggcatt aaacttctct cttatgatgt aatgtgttct ccttgggatc tttggtattt   7080
ctgtttgcat acttcatttg gggtcatctc aacacaccaa acagattcta actacactga   7140
atctcaaaag aaatagaagt agtctttgtc aagccacaga aaagagcttg ttcttctttc   7200
ttctcctcct agacacctgc atacttttca ttcctctaat gaagagggtc cattcaataa   7260
attcagaaga aatgaagaaa aaaatacaag tctagtttgt gataagtcct tgttttcacc   7320
taaacagaga agcaagaaca taaattatat aaggcacctt ctcttaatta aataaacaaa   7380
```

-continued

```
agagttctat gtggtctagt tacacagaga tcacagtgat taactactca gctctggagc   7440
cagacaactg ggtttgttca gattctggca ctctttcttg aatttgggca tggcatttga   7500
ccttctgtac ctcagtttct tcatttgtaa attgggatgt taataataaa atgtactaac   7560
tttatagggt ctttcctgag gcacataatg taatttaaac aacaaacaag tatacataac   7620
agacattttt ttcttacaaa gacggtacca tactaaactt aatttgcttt ttttgaaaaa   7680
ttatattttt aggtaaaact ttgtaagtta atttttttgg gtgaaaaaca tgatacaaat   7740
ttatcaattt gattttgctt cattagcatg atatactttg ttctagaaag tacttaggca   7800
attttcatac atgtctttaa atataatttt tgcacatgta aataagagtt ccaaagtatt   7860
ttgccatcac ttcatcagtg ttgcctctca acagcctttg aagcgaggag atgccagtca   7920
ctgtctcaga cacaaggatg caggctgtgg aggccagtga gccatagtca ctgaactggg   7980
aattggctgt ccttttgacc atacagatta atcactgtag tttcaccaat cacattgaac   8040
ttgaagatca ataaatgacc ctaaaacaat gagatttcat agactctttc tatatagtgg   8100
aagttaaagc aaatcagaaa ggagtcccta aacctgtgaa ttcttgaatt ttagttttcc   8160
aggtcaacaa gccttcttta agtgacttca tgtcccgtcc ttggtttttg atcatagact   8220
ggtataagaa atgaccataa aataaatgtt tttgagaaaa ttatagctga aaatactgtc   8280
catgatacca ctcagtgata taagtctcta aacagcaaac tcttccatga atggggtgga   8340
gggaagatgg tttttctttc caggtgaact tacatattgc cttttctcag atatcagatt   8400
atgagaataa tacaatggac tgggctttga cagccaagac tttcagaatt gctgttagtg   8460
cccatgtgca ataaaatttt tctatcatgt ctctcttatt atttcaaatg ccctgtttta   8520
ctgttttgat tactaattat ctatttagag ggaaacagtt ataaataaat aattcactgt   8580
tctacttact gtgcacccct gcctttctaa atataactct tctatgtagc atgtaaatta   8640
ccacagaact catctcagaa aaaagatcac tacttttctt tttagaattc aaatttataa   8700
tatctaattc tataggtggc atctggcctt tagcatgata tcaccaatga aaatttaatc   8760
tgtgttatga attcccttgt ttctagaaaa gcttcagcag gaaaatgaga agagaaccca   8820
taaaaaccat aaaacatttc atgaatggta gctttagaaa atcttacagg atttggtagc   8880
ttttacattt atgacaaagt gatatttttg atgttgttca taattatttc agttcattag   8940
cagcattaat aagctcccgt tttgtacagc ttgaagatct ttaagacttc cttaatgaga   9000
aactaccttt aagctacgga agacccatca gggtgccaaa ttccatctgg acacagttac   9060
aaatacacca ctgttgatga gctgaaaatt agagcaacca aacaacagag ctttaaaatg   9120
ttatttcaat gcaaagggac attttcacca tagaaaaata gaagtttgcc tctaaataaa   9180
aatgatttta caattgcaag agtacttgat ttaccccttt acatttagtt caaataccaa   9240
aaatttctta aggaatgaga aattccaatg ttcctgagaa ttctgatagc ttttagagag   9300
ttcagttttc tgtagcattc cattttgcaa tcctatacaa atttctaatt tataaccagt   9360
ggtatgtaat gataatttct aatatttatt aagtgtttat tgggttctaa gtgctttacg   9420
tctgatatat gtatcacatt taatttattt catccagtgg ttcttaactg gggacaactt   9480
tgtacctctc tccccaacat atttggcaat ctctggagat agtcctggat ctccagatct   9540
atctgtcaca acctaggatg tatgtggtcc tacgagcatc cagtgaatag aagctagaga   9600
tactgctgaa cattccacag tacaagggca acccccacat caaagaatta tccacaccca   9660
aatgtcagta gtactgaggt agagagaccc taacttaatc tgttcaacaa tcctatgagg   9720
tgattttttt tttttttttg agataaggtc ttactctgtc acctaaactg gagtgcagtg   9780
```

gcatgatcac agctcactgc agcctcgatc tcccaggctc aagccatcca cctgcctcag 9840
cctcccaagt agctgagatc agaagcatgc accaccacac ctggctattt tttttatttt 9900
tttgtagaga caaggtctta ctgtgttgcc caggctgatc tcaaactcct gagctcaagc 9960
aatcctcctg cctcagcttc tcaaagttct gggattacag gcatgagcca tggcacctga 10020
ccaaggtgag tgtatttaac ctcattttca ggcaaggaaa caaaagacag aaaagttaag 10080
tagcttactt aaggtcacag agctaagtgt ggtgccagga ttgaaaacct agttctttat 10140
tgctttagca caagctattt ccactatact ctgtcatgtt cagagaatgt tgatgtccat 10200
cagtggattc taaattttga aggatggaga tactgcctta ttctgtacat ctgctttagc 10260
acccaagctc ttgcttggtg aaaaattaat agtaaacatt catcttttga gcatcttcaa 10320
atatcccctt tagaatgaca ttcaattatt aggtcagtaa ccccaagaga aaacggttgt 10380
ttgagtgtat atactgtatt acaaaataag gggtgaattc aaaggaaaac ataagatgca 10440
attcgtgcct ccaaggaggt tgtagggaag aggggttatg aatgtatgta aatagaagtt 10500
ggtgtgcgtg tgtgtttata aacagaattg tcagaccaaa cattattttg gaagcagtaa 10560
aagtaaacta gaatctggcc tagtcatgtc ccaggacacc tctttcaagt cctgaaacat 10620
ctttgtaaga ctgtaatgtg tgtttacatc ctaggtaatc actgtggccc actgttgaag 10680
agctgtggct gttcttaccc ttctagctta gataaactta taagcacaac cagactacat 10740
atatgaagct gaagagacct tgtctttttt taacgagctt ttcttcccga taggagtgac 10800
tatttctttt cttcttccac attttcaggt tttagtgtac ttgtgattgc tacccactta 10860
tcactattaa agtctactca ggagagaatc tgagaaacac tctcaaatta agttgaacat 10920
gatggataag taaagtattg tgaaagttca ctctcatgat ttctaatggt gaaacctggc 10980
agggtgacta atctttgacg agaaggttat cacttataat ctttcatata ttgagatcat 11040
ttgtaagaag cacccagcac attgctgaac acaaagtagg tattaaataa atgttggctt 11100
ccttttctcc tactcatcct cgctcttctt tttaatatac ctttaaaatg atgccacaga 11160
aatggccacc caatcttcta tatttaaggt cagttcttgc attaggaaat tctatagggg 11220
aagtatgtga agtatgtgta gtcagtcatt aaatgcttgg gctctggcca cagattgttt 11280
aggtttaaat cccagtttcc tcttttatta ttaattgtgc aacttgcttg ggaaaacatg 11340
aaacttgttt ttcctcaggt tcattatctg taatatatag tgaatgaaga agtttcctgt 11400
cccatgaagg tgttgtaaag attaaaaaag gcaaattagg ctgtgtattt gtcataataa 11460
ttggcatata tggtaagtga ccaacaacca taaggtatta taaaattgtt ataaaatgat 11520
atgagctatc attgagcagc atgaaagaag agcttcactg tttcacctac tatcaccctg 11580
gcccattaat ctctttcctg ttcctgacat ttcagagata cgtttaggat ttcaatcatg 11640
accttaagcc acatttgaac aattttctgg tggataagtc ctcattccca cattatgtat 11700
gtacctagat gcaaatcctg aatatcatgt cgcaattagt gcatctggac atgcttgcta 11760
actgtgttaa agctctgaat aatggtaaag ttttatttct accaaaacaa atttgggctg 11820
taatgtttta tgataaaaat ctgtggtctt cctatgtaca tgtgtgtgta catgcttaaa 11880
atgcaatgtt atagttaaat gtaattcatt aaaagtatgt aactccagtg gctacttagt 11940
ttggctactt ggtttgtaga tttctgcttt cctgtttcat tgttaaacag gtctagaagt 12000
tattatttca tgaaactaat gtgaggaaaa agactatgtt gatatataag tgacattata 12060
taaatacatg agggatgatt tgattagaag cagtattaca cagtgatagg agtaatggtt 12120

-continued

```
tagaactaga ctcaggtttg aatcttagct ctatcattat aggcatttac ttaacttttc  12180
ttgtttgctt aactgaaaac tgaagataat aacacctatt tacatggttg ttataagggt  12240
tatatgaata atgtctggca aatagtaaga actcaagtaa ctgtttcact ctttccagaa  12300
ggagattggc tgaaaaatat ttggagtctc ctccagccat attccttggt cagcttctat  12360
gatcctcttt ggagcttaat tcttaatccc tttattttca cttgcttgtt gataacaaag  12420
aagaactaat tattaattta tttcaaaatg catgtattat atttgatggg ccacactaac  12480
agttataaac caaacaacag attgggaatg gggaagtgga tgtggtgagt tcaatcacat  12540
gtctgggaaa agtcaatagt gaagacagag tctcacaatt ttttgtcata atggagagat  12600
gaaaacacag gtagaggatt tcaaacaaca gagtggatgg tgagttaaaa atgctgaaat  12660
tctttcctgg tgtctaactt aatgcaatgt ggtttatctc tttgctcttt tctctactat  12720
tcaaatttag gataataaag attaaatgtt tctaaatctt actttacaat atcaagaaaa  12780
aaaggtatgc ttttgcccac ggaagggcaa agcagagcta tgaaaacctg ctgaacacat  12840
tctttatttt caacacaggt tcttgtcttt ccatcatgaa atgcacattt tatttgtact  12900
gtatttgggt gaccacaagt caacaacaag ataattcaca agacccttgc cttagatgtg  12960
tcggcaataa agtaatcagg ccaaaatttt tactttcctt tgaatttttc aattcaaaca  13020
caatgtatgc ttgcttttac acagtagggt tcagggatta gagggttggc tctttaaaaa  13080
ccgtcagaga cacaggcaat cctacacaaa attctcagaa ggaaggcgcc tacgcctggg  13140
aatgcccaga tgcccctcag agagttgaag atggcgtttc tctgagtcag gtcaaagtta  13200
acacattacc ttcgcttcaa agactgcttg gcttcctttc ggtggattag tcaagatgtt  13260
ttgctgactg agactaggaa atctatagga gggcgggtta gtttacattg ttccttgtca  13320
ttatcgctaa aacactccaa agccttcctt aaaaatgcgc actgggctaa aaaggataga  13380
caaggaacac atcctgggcc ggtaattacg caaagcatta tctcctctta cctccttgca  13440
gatttttttt tctctttcag tacgtgtcct aagatttctg tgccaccctt ggagttcact  13500
cacctaaacc tgaaactaat aaagcttggt tcttttctcc gacacgcaaa ggaagcgcta  13560
aggtaaatgc atcagaccca cactgccgcg gaacttttcg gctctctaag gctgtatttt  13620
gatatacgaa aggcacattt tccttccctt ttcaaaatgc accttgcaaa cgtaacagga  13680
acccgactag gatcatcggg aaaaggagga ggaggaggaa ggcaggctcc ggggaagctg  13740
gtggcagcgg gtcctgggtc tggcggaccc tgacgcgaag gagggtctag gaagctctcc  13800
ggggagccgg ttctcccgcc ggtggcttct tctgtcctcc agcgttgcca actggaccta  13860
aagagaggcc gcgactgtcg cccacctgcg ggatgggcct ggtgctgggc ggtaaggaca  13920
cggacctgga aggagcgcgc gcgagggagg gaggctggga gtcagaatcg ggaaagggag  13980
gtgcggggcg gcgagggagc gaaggaggag aggaggaagg agcgggaggg gtgctggcgg  14040
gggtgcgtag tgggtggaga aagccgctag agcaaatttg gggccggacc aggcagcact  14100
cggcttttaa cctgggcagt gaaggcgggg gaaagagcaa aaggaagggg tggtgtgcgg  14160
agtaggggtg ggtgggggga attggaagca aatgacatca cagcaggtca gagaaaaagg  14220
gttgagcggc aggcacccag agtagtaggt ctttggcatt aggagcttga gcccagacgg  14280
ccctagcagg gaccccagcg cccgagagac catgcagagg tcgcctctgg aaaaggccag  14340
cgttgtctcc aaactttttt tcaggtgaga aggtggccaa ccgagcttcg gaaagacacg  14400
tgcccacgaa agaggagggc gtgtgtatgg gttgggtttg gggtaaagga ataagcagtt  14460
tttaaaaaga tgcgctatca ttcattgttt tgaaagaaaa tgtgggtatt gtagaataaa  14520
```

```
acagaaagca ttaagaagag atggaagaat gaactgaagc tgattgaata gagagccaca  14580
tctacttgca actgaaaagt tagaatctca agactcaagt acgctactat gcacttgttt  14640
tatttcattt ttctaagaaa ctaaaaatac ttgttaataa gtacctaagt atggtttatt  14700
ggttttcccc cttcatgcct tggacacttg attgtcttct tggcacatac aggtgccatg  14760
cctgcatata gtaagtgctc agaaaacatt tcttgactga attcagccaa caaaaatttt  14820
ggggtaggta gaaaatatat gcttaaagta tttattgtta tgagactgga tatatctagt  14880
atttgtcaca ggtaaatgat tcttcaaaaa ttgaaagcaa atttgttgaa atatttattt  14940
tgaaaaaagt tacttcacaa gctataaatt ttaaaagcca taggaataga taccgaagtt  15000
atatccaact gacatttaat aaattgtatt catagcctaa tgtgatgagc cacagaagct  15060
tgcaaacttt aatgagattt tttaaaatag catctaagtt cggaatctta ggcaaagtgt  15120
tgttagatgt agcacttcat atttgaagtg ttctttggat attgcatcta ctttgttcct  15180
gttattatac tggtgtgaat gaatgaatag gtactgctct ctcttgggac attacttgac  15240
acataattac ccaatgaata agcatactga ggtatcaaaa aagtcaaata tgttataaat  15300
agctcatata tgtgtgtagg ggggaaggaa tttagctttc acatctctct tatgtttagt  15360
tctctgcatg tgcagttaat cctggaactc cggtgctaag gagagactgt tggcccttga  15420
aggagagctc ctccctgtgg atgagagaga aggactttac tctttggaat tatctttttg  15480
tgttgatgtt atccaccttt tgttactcca cctataaaat cggcttatct attgatctgt  15540
tttcctagtc cttataaagt caaaatgtta attggcataa attatagact tttttagcca  15600
gagaactttg aggaacctaa atgccaacca gtctaaaaat gcagttttca gaagaatgaa  15660
tatttcatgg atagttctaa atactaatga actttaaaat agcttactat tgatctgtca  15720
aagtgggttt ttatataatt ttctttttac aaatcacctg acacatttaa tataggttaa  15780
aaaatgctat caggctggtt tgcaaagaaa atgtattaca aaggctgcta agtgtgttaa  15840
gagcatactc atttctgttc tccaaaatat ttcataaggt gctttaagaa taggtatgtt  15900
tttaaaagtt aagttcctac tatttatagg aactgacaat cacctaaaat accaatgatt  15960
acaaacttcc ttctggcctt ctggactgca attctaaaag tgtaaaaaac atattttctg  16020
cattaagtta ggcagtattg cttagttttc aaagtggtag gctttggagt cagattattt  16080
tgattcagat cctacatcta ctgtttagta gctctgttgc ctgaggcagg tcccttaaca  16140
tctctgtgtg tgacttgacc tttaaaattt ggagactgtc ataggggtta atcccttgag  16200
aaaatgaatg tgaaaagtta gcctaatgtt aactgctatt attatggatt accatatttt  16260
cacattcatc acagtacatg caccttgtta atataagatg ctcaattcat ctttgagtat  16320
aattttgtga ctctcaatct ggatatgcaa tgagtgggcc tgtatgagaa tttaatttat  16380
gaaaaattgt gtttcacatg gccttaccag atatacagga aacacgtcac atgtttctat  16440
tgtatgttgt taaatgcctt agaatttaac tttctgaata ggatcccttc agtttgagag  16500
tcataaaaga gtaaaattat tatggtatga gttatagatt gtattgaata tctctttata  16560
tgtctaggtt ttgtcattgg aaaaccaaaa agtttggaaa aaaaatctaa gttatttctt  16620
actttcttaa ttttgtgtgg atttcacatc aagtataaaa tttgaagaac atctgaacta  16680
tcataatcca tatatatata taaaataaac ataatctaag agagaatttc accatgaaaa  16740
attcaggtag ttcatgacta tcagagcaaa caagtacatt aaattgaaac ttttatgaaa  16800
ataacattta tgaaatagga agctattttt aaactagaag tgatatatta gcatataatt  16860
```

-continued

```
tataattcat atacaagtgg gattgattta taaatggtca ccaacagaga ttgtgctatt  16920
taatttggga aaatttttta aatttacatt ttctcacaac ttttaaggta gttattcagt  16980
ttgttcctct ctgtctcttc tctcatgccc tgaatttttc atatttcgtt tagttgtaag  17040
agtgtatatc aaaccgtgtg tcacatgaca taacttgaat tttcgtcgtg atatctgtgc  17100
tatgtctagg tctatactga ggaactgtgg gaaccccaca gaatccaagt atacagtgcc  17160
actgatttct tacaagggat gtggggtctc ctgtaaactc tgcagttagt ctcaagtaag  17220
accaaagagt aaaatattgt taggatctaa ggtggaaatt cagcaaagaa tcacatagtc  17280
taagtctcga gtttaacagt aagataattt gagatacttt tgtaattatt aaacacaaag  17340
taatgagaga ttttaaaaca aacaaataca cctgaattta tatatcagaa taggtatggt  17400
ggttcaaaat agctatctaa taaaaaccac actcctattc taaacatttg cctttgatca  17460
aaataatttt gggtctctta ttatgaaatt gcctttctaa ataatacata aatttcttct  17520
cataagtata tattagccac attattttat tgttattgtt ttatattcat agcttgcttt  17580
agattaaaaa ttatattacc cagactggtc tcttggactt gcttccaagt gacttttgac  17640
tgtatcacaa aatcaaattc actctgaaaa tataaagatt tttcatcata atttcctttg  17700
ttaacagcca agtgctacct aattttaggt gttttcatta aaaaaaaatg cattgcaaac  17760
tttaaagaca attcttttgt ttgtttgttt ttaaaagaca gagtctcact ctgttgccca  17820
ggctagagtg cagtgacaca atcataactc actgcaacct ccacctcctg ggctcaagtg  17880
agccttccat cttgcctcac gagtagctgg gtcttcaggt gtacaggtgt gtaccaccat  17940
gcctggctaa cttttttttt ttttaagtta tatagagaca gtatctcact atgttgccca  18000
ggctgctctt ggagctcctg gcctcaagtt atcctcccac tcagtctccc aaagtgctgg  18060
gattacaggc gtaagccacc tcaccctgtc agcctaaaga cagtgcttaa tgaagagaaa  18120
tataagtgct ttgagcaatg gaagtataat taaaattata ctatgaaaga tttataaaga  18180
tgaccatttt gaatgggacc acacttattt ggttatataa attatgatac actattaaaa  18240
attcatcatg atgattttgt atttacattt tatttacatg tttgcaattt gtgaggaaag  18300
ctaaaattat ggctaagcca taaatatttt tgcagtttgt tgagggtgtt tgtaaaagtg  18360
ttgccaagga agaccagttg gctacccaaa caagggttta gtctaggtct gatcaataca  18420
tacacattat ctcaggtttg tctatcagaa aaaccttagg ttatccaaat caaaataaaa  18480
tagatgcata aaacaaaggc caatatgtgt tgaacaatta tattgtgata tacaactgcc  18540
aagcattccc gattaccatg actccattta gtcagtccat gggcaaatgc catcaatgag  18600
gacagcccag ggtttccata ttctctcttg gctttacatc ctataggaat tggaggggcc  18660
cacctctggg ataggagccc ttctgtcttg aacaatgttg tctgaacact aacaaatgtt  18720
gactttctac accagtccct caatagtctt ttctatttat ccttttgctg accatgtttt  18780
gttattacac agttgagatt tttcagctgg gaatctgtgt taattttgta ttaattttga  18840
ttagcttaac tctcagagtt ctaaaagtac ctcctgtacc tgatatatga caaaaaattat  18900
aattacattt atttatatat aaaatatctt tgtatatgta aaatatcttt gtatatataa  18960
ttatataatt gtttctttta attttgcaaa ttttaaaaag ttctcctttg ttttgaagtt  19020
tattcctata gtttttttata tgctagttaa attattaatc acttgattca agtaatattc  19080
ttatatactt ataaggaata gtgtagtttt aatatttaat tccttgctaa agagagaagt  19140
ggaatctatt tttcttagct acttcatcaa tattttatgt ttgatgtgac agtcaaaata  19200
tccctcagag ctaactgtta cactagggaa atcacggttt tccagttttc catttatgtg  19260
```

```
ttatgggagg gagtggaact tagtgtaata atattcaata cataaatgtt aacacttgtt  19320
taaaggtcct tgagtgagta ctgctataaa atgcattatt attgctagtg tcatttcaca  19380
agagcctata atttcagtgt gatagagcta caatataagt atagtattgc aaaaccatca  19440
ggaagggtgt taactattta gcatgcagtt atgtgttggt tgtcaaaacg ttaaaaacat  19500
ctctgactca gcagcaattt tggcaatttt gatcctgagg catctgtgta gggcatcttc  19560
ctggagaaaa acctctgaga tgcaatgagg tcaaaagggg aaaacagact atgataaaga  19620
tcaagttgtt tggagatctt gtagaaagat taatttacaa atatgtcaag tgcattatca  19680
tggaggaaaa cattgctatt tctgttggtt ctcttcagag ctctagaatc aatttaccac  19740
atagttgttt cagtgtgaaa ttagcattac agagtggctt tacggcttta ctgtagggca  19800
ttgtgtcagc aaagagctta ggcttctttt agcaagaagc ttgtaaaaat ttaatttact  19860
cttagattgc ttgatgtaga gaattacatt cctacagagc tctgaaaaat ctttttttcag  19920
agtttttcac agctgtattc aagttgcaag gcttgtcaac tttgctattt ttctgtgcag  19980
ctctgttaac ttattattat cttttgacat aaattatgat tccaaattgt aaagctctgg  20040
atgtcagggc cttttctaat ttgtttagta tgatattcag accatttcaa gactcttccg  20100
tggaacaatt taataaagat ttttttgtga tgttaatgag ttcatggtga tcaaccctag  20160
agacctgtgt ctattgtaga tcgatgacat tcaacagtcc tgcagtgctg gcatcatttt  20220
gataaaaagg ggtcaaagca agtgggactg tgggcagatt tttaatgctt agaacaatta  20280
ttccatcgaa gttttcttgt gtcccttctg ccttagcctt tgtaggatag catgcttgct  20340
aatttcttgc tcatggggta aggaaatgaa gatttttgct aggtccgtag gattattagg  20400
actactcagg cctgaagcta tgcctggata tagccagaaa actctcccat agcttgctcc  20460
aaggagctga gatacagcag tacttccttt gtaggtcatg attctgggta acctggaaga  20520
tgacctcatt catattctgt attctatgtg agacgttaag aaggtagagg tggccaagaa  20580
ggaaattgtt gctgccttta tggaacaaat tatctgaaac ccagctttct cgagggcttc  20640
attgaagtac tcaactgggg cacttaaccc agtctaaggc tggtcaagga aggcttgctg  20700
ggggaagtgt cttttgtatt cacacctaaa ggaggttatt caattagaat tatccaaaga  20760
gggtagggat gggctaggaa aaatttaaac aggtagtgtg gaggactgac aggataagta  20820
agcatggcac cttcaaaata tcctgagaag ttccctatga cgggaacata aaatatgtga  20880
cagagatttg tgggagatgg gtctggaaac tctagcaggg gccagatcgt aagggggctt  20940
tgtaggcttt gtaggctttg tttgggcttt atcatactgg aagtgaaaag ccatggcttt  21000
taaacaggag agggacataa tcagttcata tactgttgca gttttgtaaa agaaaagatg  21060
agctgaaaga gtggccatgg tggaggtggg tggggtgggg gggagggggc ggggagagag  21120
agagagagag agagatttga aagacattta ggaggtaaaa tcaactggtt tggtaatcaa  21180
ttagtagttg aaggtgaagg aaagagaaga gttaaggata acatctatat ttgttgattt  21240
ggataataga ggggacagtg gtgctgctta ttgaatgaga aaatttaatc ggagaagaag  21300
gcatggagca ggagtgcaga cctatgtgac tctacttctc tcaaaaccag aaacggaaat  21360
gatgtatatg gctcagggtt aggtaatatg gttatttgaa aatgtattaa agtgatttag  21420
agcttagtct taggtaagag atataagatg tctgaggtga cagttttata aatatgtaga  21480
gtgcccactt gtttggcctt attgtggcat agtgtgacct gagagtgtta ggaagaagca  21540
gctgagttct agggacagta ctggttaaat tctacttaga aattatactt agaactctcc  21600
```

```
tatataacct gctaactgat gtctgaacct cctgataact tcactccttt aggcagtgct  21660
tttcacatca cgggacacaa catatgagag atcatagaaa ttcaatgtgg tatgaaaatc  21720
tgcttgggac ttcagatatt gtctccagtg attgaataaa aataggagct cacctactat  21780
gatgaggttt ctgtgtgtgt taaaagaagg ttttcattac ttttgaaaag gttatgtatc  21840
cttgttttat gttaaaactt tgagctttgt taaatatgca gagttctctt tcttagcatg  21900
gactacagag gtgcaactac ctcctacctg acttcacatc tactcccaaa tgcctagtga  21960
aggcttaata atttcaaaaa gggactctag aatttcattt gataccagtc agacaaatgt  22020
gtgaaaatta agcataatag gcagaatccc aggggtactg acagctgtat taagaggtga  22080
ttcaagggct aaaccttaga gtccagcatt ggttatgggt gtgacaagaa aatgaagcct  22140
atgttggctg ggattagcaa ccacagttct agaggaagca aggtggagaa actatatagg  22200
gggctccctt tgtacgtttt atttatttta aacatctcta taaactctag aaattaaaac  22260
aacaatacca acacaaaagc atcacttttt cgaccaaaga ccattgctat actttttgt  22320
gtaaagggct agatagtaaa tattttcagc tttgtgggcc acataagtct ctgcaataga  22380
caatatgcaa acaaataagc atggctgtgt ttcaattaaa ctttattatg aacattaaaa  22440
tttgaatttc atataacttt tacatgttgc aaaatattct ttatttaaat tctattgcaa  22500
tatgctttaa aagatacagt ttttagtctt tcttagttta aaataaaatc tagaaaaaat  22560
tttaagtctt ctataacttt ttttcggtaa ctgaataatt ttaaaagtaa gtgaaacatt  22620
tagacatgca aaatggactt ttcagaagaa gaaaatggta gcttaacagt tattagatta  22680
ttgtccagaa taatttttga cttataagtc tctgttgacc atttcattgc ctcttttttt  22740
ggaatatgca tcttttaatg tgtccttcaa ggcaaaggct ctatcttatc tatcttgtgt  22800
cttgcatttt cccagggcaa tgtttttcac aatttttta aaaaacaata ctgtaatcaa  22860
ttttcaaata aaattttcca tgggaccgca gtgtatacaa atagcagtga caataaaaga  22920
taataactct cccataaata caaagaaaca gttaacctag tgctctaaag taaaggctac  22980
agtgattttg tataacattt atatgtaatt ttcttgatcc tacatggttg tgtttttcac  23040
agtgttatgt ttctgaaatc gagatgcctt ttataattga tgtcaaaaga aacttgtcag  23100
ccacaaggcc caggaataag ttgtaatatg ggaacttagc aatacataaa ggtatatata  23160
ctcctgtgac ctcagctgaa ttatttgcat tggttgcatc ccacaaggtt gactcttaaa  23220
taaatttagt ttgttgcttg aaatttcttg ggataaatta ctttgtgatg tagttttgaa  23280
aaaaaaacag gtaatattta gtctgaagtt tgtctgacat actaagcaat gtaattaaag  23340
tagaagtcgc ctaagctcag cactttatta tgccttgaaa ttatactgcc tgtcctacag  23400
gtgaaggtgt tatgaatgca gtttgtcact gtaactctat tcatagctct gaaaggctga  23460
gagtgactca gaagaatatt tttgctctga atatgaagaa cgcttagact aaaactttaa  23520
ttacgatgct gaagaagaaa gtggtaggtg attgcatgaa taagtatgta atattgttaa  23580
tttctaaaaa ctgtgtatag ttaatgtagt gcttcttttt ggaaaggcta ttgttaaatt  23640
gatggtaaat tctataacca atatcacctt aaagcaagta cgcatgataa agtattataa  23700
aaccatgata atatcatatg tggcttatta ttgttccctg agtgttgtac aactctgtta  23760
tgctgtgatg aaacctcatg caaacaggta tgtcaaagat atgatgggct gttaactgag  23820
cttggcccac atatggtgta gtgacatgct cactaatgca gtgcagagat aaccaataac  23880
agatcataac aggtttaaat atgtgcaagg agatgtcagc agaagctttc ctacatagtg  23940
aatactaaac aagcctgaca gcccaggatc atgttcggat caatctagtg tgctaaaatt  24000
```

-continued

```
aacatatagt cctacatttg agaatgtgtg attttcttgg ttcctgtcta taaaataata  24060
ttttaaaata catacatttc aaatcagaag ttggtgaatt cactgaaata tttctagaga  24120
acactaggta ttggggctca tagtgtgaaa accactgact taattcttcc cccatcttgg  24180
ttgttcctga tcttcccttg tgtccccatt ccagccattt gtatccttag aaaatgatct  24240
catattctac ttcatcttta tcttcattgt caactgtcag gtagcaatat atgatggaag  24300
aagcatgtac tttggaatca gacagacctg gctggaatcc taactctgtc acttattaac  24360
aatgtgatct taggcaattt acttaatctc tctgaacctc agctactctc gtcagtacaa  24420
tgagttatcc ttatctttac atggcacagt attattatga tatcaaaaat tcattgagta  24480
tttactctgc atattagtca aggttctcca gagaagtaga accaatgata cacacacaca  24540
cacacacaca cacacacaca cacacacaca caatttatta taaggaattg acttacatga  24600
ttatgatggc taacaagtcc aaaatctgca gtatgggtca gctggcagga aacccaggag  24660
agtcaatgtt ccagtttgag tctgaaggca gtctgttggg gaatttcgtc cttctctggg  24720
aggccagcct ttttgttcta tacaggcctt caaccgattg gatgaagttc acctttatta  24780
gtgagggcaa tctgctttaa ccaaagttta ctgatttaaa tgttaatctc atccaaaaac  24840
acccacccag ttgacacata aaattaacca tcactctctg taagcacttt ctatgcatta  24900
agtgatagca aataatgcca gacatagggc gtctttaata aatggtaagc actgttatca  24960
gcaacaacag gattattata attagcacct tttcatcttt ctgtctgggc tctgagaaag  25020
tacctctctt ctctaaattt atccctcctt tcctatgaat tagacccagt gctttctctg  25080
aattatgaag gtcacactcc tacaaatgcc ccttcccaat tgcacatctg tcggctttct  25140
ttgccattga cttttatctc tagcttttaa atttacaggc atatgtcagt taacaatggg  25200
aatgcgttct gggtaatatg tccttaggca attttatcgt tgtgagaata ctatagagta  25260
tacctacaca agcctagatg tcgtatagcc tactacacac ctaggcaata tgacatagtc  25320
ttttgcttct aggctacaaa cctgtacggc ttgttactat actgaatact gcaggcagtt  25380
gtgacacagt ggtatttgca tatcggaaca tgtctaaaca cagaaaaggt gcactaaaaa  25440
tactatgtag tgatctcatg ggaccaccat tgtatatgca gtctgctgta gactgaaatg  25500
tcatgcagtg cataactgta tcttaaatac tcaaagtatc acctttgttt gtttgtcccc  25560
ttgtgtgcat catcctaacg tggaatttct ctgttgatta gggccagcgt attagtttgc  25620
tagggctacc ataacaaaat accacaaatt tggtggctta aataacagga atttattatc  25680
ttatggtttt gaagactaga agtacaagat caaggtgttg gcaggttttt cttctaaggg  25740
ccatgaggaa gagtctattc catgcctttc ccctaccttc tggtggtttg ctagaaatcc  25800
ttggcattcc ttgacttaca gaggcatcac cctgatctct gttttcatct tcacatggca  25860
ttctccctgt gagcctgtct ctgtgtccaa acttctttac tattaatata aggacaccag  25920
tcatattgga ttagggtcta ctttagtgac ctcattggaa tgttattacc tctgtaaaga  25980
tcctatctct aaataaggtc acatccttag gtaccggggg ttaggactca aacatacctt  26040
tttttgggga aacacaattc aacctataac aattgataac actctttagg agcagaatgc  26100
gatatggaag taatttgaga ccataaagta tatacatgta gggagttaat ctatgaaacc  26160
tattgaaagc catatatacc tcatgtatag tggtccataa atagcatgga gacattgcag  26220
aggatgttaa gtgatatgat acaggaacaa tccaagaagg tcataagaaa aaggaccttt  26280
tgctcttgag aggactgaag aatgactttc catttatgaa attttggtac atgtccacta  26340
```

```
aaaataggat gaaggccaaa cttaggaaga atattttgat aatggagaag gttgcatata  26400
aaaacatttt attgaggaca attaaataat gttggctgga agttttagga tgatcatctt  26460
taggactcag aaaaagagaa gaaacattat taaagaattg tccctgaaca agtataggca  26520
ccctcacatt tgcattgcat ttactataga attgaaaaat gttttgacct tttttttttg  26580
gcttttaata tatttgacca agagtaacag ctaagcaata cctatttgca atcagtgtca  26640
tcatgtgggc tccaaacata tcatgtttgt gtaattaatt gattgaccca ttaatttgtt  26700
caatttctgc tctgttccag gcactgaaca acatgatgga gataaaagat aaatattaca  26760
cctgccttgt cctcaagaag ttagtcttct gagggaaaga aattagcaaa caaattgtaa  26820
tctcagttat gtgccatgtt ccatgctggg cacaggggat acagtagttt aaaaaaaaca  26880
caagatctat aaggtgtttc ttcttgtgga ccttacagtc tagggtgctt ggaaacatgg  26940
ggcgttggca gacaagtaaa tacacatttt gtggtaaagg ctcaggtaga agaagtacag  27000
gatagaatag agcacaccat ggggaattaa tctagacttc agagaggctc acacatacat  27060
aatttatgtg tgactatttc aatgcatttg aggtttcttg gaaatagagg ttaggtttta  27120
ttttaaggaa gttaccattt ttttttcag tgtgatgtgg ttgaaccaaa gaatgccatg  27180
cccagtgatg gtaataggat aatcttttta aaaattaaga gccacctaat aaatcaatag  27240
tttcattcag cgggagctcc tgcagagttc aaaaagaaga gaatctggca cagcgtttcc  27300
tttaaagttc attttcctag agtgtgaatg gaagcaagag attataacat tttgaggtca  27360
aaaaaattct gaaatgccta taaaaattat tttctccaaa ttatcatcat ttgtgctttt  27420
aatgacctga ttgcaaagat gaacattttg aattcttaaa ttgcttatta ggattggtta  27480
atgaatcaat tatctattac tgtatgtttt gctattggaa aaaatagcaa cttaagtgtt  27540
ttgcagacct ttacttaggt atatgttgct tttatgaaaa aaaagatgta aatattaagt  27600
aaaagggatt taaagcaagg cttttgaggt agagtcttat taattccttg gtaaaccttg  27660
agccaattgt tgtctatgtt ctctgcctct gtcttgctcc ttccttctgg gattcactgt  27720
gggaatgcgg gattgttaat ctggggatgc tgtccaatcc tgcctctctc aagctttgct  27780
attgatctcc ctcccagtga taataaagct tgaagaaaat gaaagtagcg ttagtattgg  27840
tcctcaaact caagaacagg atgaaactta aatcttgagt catacaattg tgtctacata  27900
ctgctcccca aaaagagaag taaagaagat gctaactttc ccttttaatt tgcagtactt  27960
agcaatttgt tttcttgagg gttaagtaat aacagtggaa gaaaaaaggg ttaaaatgcc  28020
accaagaacc caattccatg tttagtttga aagtgggaaa tcagctgcca ctgggaagtc  28080
tgaatccaat gccatgatgt tctttgaatc cttctgagaa ataatcatgt gtagccataa  28140
catacctgta taacagagca gagaacataa acaaatgaag gtgaagggaa gattaagaca  28200
gaagagaaaa attccagaat cgactgatca tttttatctg tttagatgat ttcaggcaga  28260
atcctagaga ccaactttat cacaactgaa ttttaaaaat caccagcttt gtcattgtga  28320
tgcagcatca gtttcagtat tatccttgga gtattaattc ttaatcatct tcatcttaga  28380
acatttttga ggtcacttct agtctctatt tcaccagtga agaaacaaaa atccccaaac  28440
tatatcaggt ggaattacac agtatttttt ttttaatttt ggggaaagtc gattcaaggc  28500
agtaacttgc aagctagtgt tagaaaggat ttaataaata gtggtttttc tgtacacata  28560
gtgagaggtc attacatcat ttggttgttg aaagtcataa ggatgtctag catgcgcttt  28620
gcctgtagtg gttcatgcca ggcagattcc tgactcctat aacccagagc ttatcagagc  28680
atttatgtcc ccaaagagaa atgtcacctc catctttcaa taaacacttt agcaaagaaa  28740
```

-continued

```
aatcaagtac tttaattcca aatcttgagt taattccaga ataacaatga tggctcggaa  28800
aaatatgggt atttctgtca aaggacagag aaacctagta gagagtattt actttgggtc  28860
ctagtgatgg tatctgaaca agctaggtga acaaagagcc tcaataaggg attttgaggt  28920
ctagaaaaag agaggaaata ccaaataaat ggaataatta taaaataaat accagcaaag  28980
ttaaatcaat atatcatgtg ggagatatcc ttatatcact catgtgattt ctattttgtt  29040
cctatattag gccaaggaga ggtggaactt gttttccttt ttccctctca gctacgaatg  29100
gacatactta aaactgtttc tctgcttctg ttctctaaaa tgtgattgtc taacagtaac  29160
cgtgatgacg ttttgacagt tgcacaagtt tctttcttta agctttaaaa atgccagcca  29220
gtaacccagt ggcatttcta ctataaaatc ttaaggccaa tccatttccc cttttcctta  29280
ttttcttggt ttcaaatata tttttattgc caatggaaat aaaaatccta aattagagag  29340
caatggcatc ccttgtcttg tgaataaaga gctcctaaat gtgaacttat acaggatgca  29400
gcaatttata gggtagttaa tcattcttct ttctagccag ttgttccagc tacagttttg  29460
tggctcttgt tagtggcttc attcccagat agaataaaaa tcaaaccaaa atcctggaaa  29520
ggcactctga ggatgcttct ctaaagtaga tgggcatcaa ctataaatca caatgctttg  29580
tttcctctgt tatgtttcaa gatgggtggg atttttttg tagcattact tattattgcc  29640
tctcaagtgc ttgagtcttt gaaatccaag tcatgtgagt gaattagata cagctgttag  29700
aagtggcctt tcaatgccaa tggtacacat tccttggttt ctttacgata ctattgctct  29760
tacaactttt atctgaagtc ataaattcat agttgtccca gaagttaagt tccttgcttc  29820
tagaggacag aaaacaaaca atttacacaa ctcatggtgc atgtcaccag tccttagatc  29880
tcatgaaata tgcatgaaat cttaaatcac ttgctgtagc cacccagcca ttgacatatt  29940
tgaaagactt tagtgtatca aagtcactat aatgaaaatt ttgatttcac cagttctagg  30000
agtgaaaaat caaatgttta gtaaaacttt ctaaaattaa cactgacagt tgatttctgt  30060
atactgttgt tcttaataat agctttattg agatataatt catattcaaa acaacttacc  30120
catttaaagc atacaatcca atgatttttt agtatcttca aagagttgcc tatcaccata  30180
accaatttta gaacactttc atcactgtaa aaagaaactc cattcctatt agcagtcatt  30240
ccttattcca aatccccctg ctcgccctag acaactacaa atgtactttc catctctata  30300
gatttgcctg ttctggaaat tttatgtaaa tagaacaaag tgttcttttg tgactggctt  30360
atttcactta gcattttttt tcaaagattc atccctgttg tagcgtgtat cagtgcatca  30420
ttctttttta tttttttaga gacagggcct tgctctgttg cccaggttgg aatgtgcagt  30480
ggcatgatca tgggtcacta tagctttgaa gtcataggcg aaagcggtcc tcccacctca  30540
gtctcccgag tagctgagac tacaggcttg caccacatga ctgtctaatt tataattttc  30600
tttagagaca gggtcttgtt atgttgtcta ggctgctctc aaactccagg gctcaagtgg  30660
tcctcctccc acagcatcct aaagtgctgg gattataggt gtgagccaca gcacctggct  30720
tgcatcattc tttttattgt tgaataatat cccacttgta agaatatgta ttttatttat  30780
cctttcccca gttaatagat atttcgattg ttcctaattc ttgtctatta taaataatgg  30840
tgctatgaac atttgtgtac aagtttttgt gcagacatcc attttccttt cttttgggca  30900
tatacctacg agtgtaatgg atgggccata tagtaacttt atgtttaata ttttgaggat  30960
ttttcaaact gttttccaaa gtggctgcat cattttaaat tccttccacc attgtgtgag  31020
tgtttcaatt tctccacata tttgcaacac ttactattat ctactcttaa aaattacagc  31080
```

-continued

```
catcctactg ggcatgaagt ggtatttcat tgtgagtttt tttttcttt ttcttttttt  31140
ctttttttgc taatgtttgt ggattttctt ttcattttct tgatggtgtc ctttgaagca  31200
caaaagtatt taattttgat aatttccaat ttatttttg ttattgctgt ttgtgcttct  31260
ggtgttgtat ctaagtgtat gctactttaa aaaattagtt gtaatatggc aaattggata  31320
catgtgtagg ctttggtgtc acaatcctaa ttttaaaatt ctgactctgc ccttgacaaa  31380
ttaactaatt aagcttcctt agcctcagtt tctcaactgt aagttggaga tattaccaag  31440
acctacctct tgaattgttg tggggatcag atgaaataat gtatgtgaaa tatttagaat  31500
tatgcaagtc tgtggtaatg aatactaatg ttagctatca ttattgttat aatcccaata  31560
ataaattctg gtgctttgaa aattaaacca aagccaagca gttgatatga agaagcatgt  31620
aataatgtac agacataatg ctttatagac aacattgaat ttggctctca tgaacatcag  31680
gaatagtggt catggtagtt attatctcca gcaggaactg tagctgagag atcttcagag  31740
ctttttccaa ggcgatatca ctgggaaata atagagacaa ggttacaagc tagggctgtg  31800
ttttcttctt aaaatcttta gttcagtttt tttcaataac agatttgtag taggcatcag  31860
gtgactgggg attcgtattc ttcaagttga aatattacct tgttgagaaa gaaaccatgt  31920
gtgagacaac catgttgaga aagaaaaagt gattttatag aaaattaata ttgatagtga  31980
gcattatatg aaaatcatga agttagaaca tatttggcca gaaaatttac attaatagtt  32040
acccatagca attaatgcat tataattaca catacctttt ctttaatgaa aaagaattct  32100
ttccttccaa agttatgcat gctattgtta aacattagag aatatagaga agcaaaaaag  32160
aaaatatctt ttttgatatt ttcttaacat acgtctgttc ctaataatgt ttatagttta  32220
gaagcattgc atgaaatggg tagatcaatt ttctatttaa tgtttggatt cattaggtac  32280
gaagttagca aattaatttc cattagggtg cctgtatggt tgtaaatcct ggacctgcag  32340
aagatttttc agtattggtt tgtagtcttt tgtttagcag caaataatta gttctccaga  32400
gcttctgaaa ttaattgacc actttaatgg tgtttaccta cctagagaaa gaaaaagaac  32460
ttctccaagt cccttggtaa aattaagcct catgaacaat taactcaaat atacacaagg  32520
cttgtcttta gcgagcatat actccctaaa gttgattaag ctgaccaagt gattactgct  32580
tataaattca ccattttatg gagaagaagc aaacactgct aaataccttg tggaatcaga  32640
ggaggggaaa ttagtaactt gaccccaata ctgcgatttt aaattgaatt cttgaagcct  32700
acaagtttta cacaggactt tagagagctg gatagtatca ctttgtcaag tcctactttt  32760
actatgattc tttgagaaaa atacatctga ctaaataact ctgaatctaa attggataaa  32820
ataaatgtga cattcaaaat gttatttatg attttagaaa aatatcctta tagacactag  32880
atgagtttta gtctcaaatc aatcctccct atcatagtca cttatcaaaa taactaaagc  32940
aaagtggtag agctgtgctc tagaagtttg ggatttatga tcacaatctt ttccaatgag  33000
tcccctcttt cctctgcctg tcttcaacat ttgttttttt tttttttgg ttaggactat  33060
ccagattgtg tggcctattt caaactcatg gcaaatacat tggatgatca gaaattttct  33120
aatgtatttg aatttgtcta cacaaactag agtaattgct attaattcct caagtgttaa  33180
ttatttcatg caaaaaggaa aaaggctatt agtctttaag tgtattagta tgtcaatatt  33240
tgggagaagt gtcatgcaat tagtggtttg aatttcctat tttattttat tgcattttat  33300
tttatttgcc tagtcaaata aaaagtaatg ttaaatacat ggaagcatga ttgttttcta  33360
cactaaaaat cattttgact tgaaaagatc tgatatccat gaccttcatc tgaagttttg  33420
gcagatgaaa atgtcagatg cgtcttttgg attaataaaa ggcaaaagtc agatcgaaaa  33480
```

-continued

```
atgagtataa gctttaatta tatgacttta ggaggatatg ttatgaaaat caaagcttta  33540
atagtgatta taattggcaa gttctttttt tataaggaat tacaagtcac tctatacaaa  33600
aattggaatt tttgtcctaa gaaatgaaat ttactatagt ttcatctgtg tgtgtgtgtg  33660
tgtgtgtgtg tgtgtgtgtt taaaaaatca agtgataggg cttttcctca ataaaatctg  33720
aaatctctta tagttaagtg aacagaacag tgtatctagg atgctagact tttttttcaa  33780
agttagttta aaacttatac atagtaaaat ctgtatgcct tagggatctc tgtttgctat  33840
cccatagtga atgattaatt agtttctgtt agaaatagtc agaactaggc tgggtgtggt  33900
ggtggctcat gcctgtaatt ccaggacttt gggaggccaa ggcaggagga tctcttaagc  33960
ccaggaattt gcaaccagct tgggcaggct ggtgagatcc tatctctaca aaaacaaaca  34020
aacaaacaaa ggacaataag aaagaaagaa atagccagag ctttgaacaa aatttctaag  34080
tagaccaatg taaaagtctg tcgtcaatat gtagtggcta tgaatggagg ttatgaatga  34140
aagagaagga taagatgaac tagaggtgag aggggaagac agcaggccca agtgaaaggc  34200
agagccgagt ttattgcttt ttggttattc caggtgtgtc tgctttgtct catgaaacac  34260
ctggatgatc actgatttct agtggaagaa atgctgaaaa gtccttactg tgcatttaaa  34320
cattctaggt ttaatatact cagggttttt caaaagaaag ggtggctgga gttttgcact  34380
aactaatatt tcataaagtg tctaagtata gatgtctggt tttttttgt atttctaaga  34440
ctggcttgag gtaggcatgg agaattcttt gatgggacat aattttcttc ctttcttttt  34500
ttttttttt ttttttttt gagacggagt tttgctcttg ttgcccaggc tggagtgcaa  34560
tggcacaatc tcggctcact gcaacctccg cctcccaggt tcaagcaatt ctcccacctc  34620
agcctcccgc gtagctggga ttacaggcat gtgcccccat gcctggctaa tttttttgt  34680
atttttagta gagatggggt ttctccatgt tggtcaggct ggtctcgaac tccttacctc  34740
aggtgatcca cccacctcgg cctcccaaag tgctgggatt acaggcgtga gccaccgcgc  34800
ctggcctgat gggacatatt tttcattcaa ttttattgat ttaacctcac aaaataaaat  34860
atttccttaa gatgactctg tggtcattgt tgggcagcat aagcttaatg gattttagtt  34920
atcataattt accttaaacc caatttgtat ttcaggatat aaatagaggt ttattgtagt  34980
gaatcttcca ggaaatacta agtgatacta ataattatag atggtgaact taagtcttta  35040
tattactgaa tttgtttggt ttgatgatgc taggctatgg cattcttgct aatcaaaacg  35100
atgtgtcatg gtgtaacata acttattaaa atgggcacag ataacacagg aagcttttta  35160
taaaagcagc tcacaaattg tgttactttg aactgaactg gccatttatg ggaaaggtca  35220
ctgggttgta aataaggacc aaaagagtta cgtttatatt ttttaaaaga gattgaggag  35280
atttattttt acatttcttg aaaatgcctt attttggtat ggtattgaca gatagtgaaa  35340
ttctgctcat ttgtaaatat agtgtcatat tttaataatt tcaaacatat tgaaaatgca  35400
gaatttatta atagtgggag cacattttcc tttttactaa atgttctaca ggttcttttc  35460
tttccatcca cacacagtgc cattaccctc attctaagcc tttcaaacat ctggcagtaa  35520
gtgatctgct gcacttagct ctttccagct gagctgattt ttaaattttc agaaaatttg  35580
tgagctaatt gttaaacatg gccattatta aaaattaaat tatttcaact tataattaaa  35640
taaattatat taaaacaaaa gtattaaaaa ctcaaaagtt ggctgggcgc actggctcac  35700
gtctgtaatc ccagcacttt gggagaccga ggcaggtgga ttgcctgaag tcaggggttc  35760
gagaccaacc tgaccaacat ggagaaaccc tgtctctact aaaaatataa aaaaatagcc  35820
```

gggcatggtg gtgcatgcct gtaatcccag ctactcagga ggctgaggca ggagaattgc 35880
ttgaacccag gaggtggagg ttgtggtgag ctgagattgc gccattgcgc tccagcctgg 35940
gcaacaagag tgaaactctg tctcaaaaaa aaaaaaaaaa aaaaaaaaga aacaaaaaaa 36000
aaaaaaaaac aaaaagcaaa caaacaaaaa aacaaaaatt atcacttcct aattattttg 36060
cattttacta ttatctatgc tattaacgtt atttgccttc attgtatttg aaaggtggac 36120
tatattctat tgcactttca ttgtactata ttctaatatg caactgtgta tcccttccca 36180
actctgtgtt caatgacttt atatttggtt gctttaaaat gatgacgatg agagtattta 36240
tatcatagaa attggcaaat gccgtaagtc agtttttgtt tttgtttttg ttttccggag 36300
aggggattgt taaatatttg cctgcatgca acaccactac atgcagtctg ctatcttttg 36360
ttcttcctgc tttcaggctc ctctcccagc tgtctgtcta gcacaaccca gcataccaaa 36420
ttttcttaaa tagggaaagt tgaacatggt aaaagaatga atgaagtcaa aagaatgtgg 36480
aaagacctag gctttgccat ttagtaaagt ttagcatctc taagcctcca tctctttatc 36540
aataaaattg agcaatgatc ccttttagtt ctacccattt aagaagattt tcaaatgaaa 36600
accacaacct gctcatgttt atgaaggcac tttggaaagc gctaaataca cgggttttta 36660
ttagtagtaa acacttactt caccttttc acttcttgac tttagtttac aagggctcat 36720
aatctaaatt atatcataaa ttgctgtccc agattttttt acagcctaat tgccacctgt 36780
atgttcgact ttccttctgt tctttatgtt agatactggg atagtatgca ccaggtgggt 36840
gtgccatcac tttctcagat gatgtccact gaagaccttg catgatcatg gcattcattt 36900
tcctgctgta ttcagactgg cctcaactat tttctttatt gctctccagg aaaaattaca 36960
aatgaatcag actgggcaat gaagggtaaa cctaattatc gctctttgtt aaagacagct 37020
cttgttaaaa tgcggatatt gcaaattaat ggaaaaaata tgacatagta aaccatactc 37080
acttattaat atcttagtaa ggaataattg atgaagttac ttaaccttag agccctaatt 37140
cagttaagtt ttaatgaagg acaagttgta gagatatcga gaacccaggg caggtgccta 37200
ctgaagaagt tccagaccaa ggaagtataa agaaggacct gggtgggagc agtgagattg 37260
gatatgaggg ccactggcaa agttttgccc cagaacagtg tcaaaatgtt tgcatttggc 37320
atagcccttt ctctttttgt tctgaatggc tttgctagaa tatcttttct ataatgaatt 37380
tatcctgctt ctcagatatt gctaaagcac tccctttga attttggtgc tttaacatgc 37440
attttgatac attaccaaat aaggtctgaa tgacacaaat tttagaactc tccagagaaa 37500
agaaagatgc tgagggaaaa agcataggtt tgggactcac taaatcccag ttcaattcct 37560
ttctttaata aatatattca attttacctg agaaagctct cgtgctctcg aattttattt 37620
agaaatttct ctttgtacat gattgatttc acaatccttc ttctgcctcc tcttctactt 37680
tcttctttct agattttcct atctttatga agattattct gccttatcct caacagttag 37740
aaacaatatt tttgaaaatc actacggtat cctgcatagt gatttcccat gccaacttta 37800
ctaatttcca ttataaatta ttatttattg atgcctagag ggcagatgag tgtagctgct 37860
atggagtgag gagacaaaac ataagaaagt tatgatccta ccctcaggta atgattcaga 37920
catgataatt aagtcaacaa attgatagaa actaatcact aactctctgg ctatagtcat 37980
tctttcaatg aatagctcat tactgagtat gcatgctaca gtaacaaaat tatataaggc 38040
tgttgattaa atgttgatta agtgcatgtc ttattcagag tttttttata tttgaaatgg 38100
aagaggctgg acttcagtaa tttgctataa actgctagta tatgattatt tgggggcagt 38160
tattttttaa agaataattt aaatatggaa tgtttagcag tttgtttttt ccctgggaaa 38220
aaccatacta ttattccctc ccaatccctt tgacaaagtg acagtcacat tagttcagag 38280
atattgatgt tttatacagg tgtagcctgt aagagatgaa gcctggtatt tatagaaatt 38340
gacttatttt attctcatat ttacatgtgc ataattttcc atatgccaga aaagttgaat 38400
agtatcagat tccaaatctg tatggagacc aaatcaagtg aatatctgtt cctcctctct 38460
ttattttagc tggaccagac caattttgag gaaaggatac agacagcgcc tggaattgtc 38520
agacatatac caaatccctt ctgttgattc tgctgacaat ctatctgaaa aattggaaag 38580
gtatgttcat gtacattgtt tagttgaaga gagaaattca tattattaat tatttagaga 38640
agagaaagca aacatattat aagtttaatt cttatattta aaaataggag ccaagtatgg 38700
tggctaatgc ctgtaatccc aactatttgg gaggccaaga tgagaggatt gcttgagacc 38760
aggagtttga taccagcctg ggcaacatag caagatgtta tctctacaca aaataaaaaa 38820
gttagctggg aatggtagtg catgcttgta ttcccagcta ctcaggaggc tgaagcagga 38880
gggttacttg agcccaggag tttgaggttg cagtgagcta tgattgtgcc actgcactcc 38940
agcttgggtg acacagcaaa accctctctc tctaaaaaaa aaaaaaaaaa ggaacatctc 39000
attttcacac tgaaatgttg actgaaatca ttaaacaata aaatcataaa agaaaaataa 39060
tcagtttcct aagaaatgat ttttttcct gaaaaataca catttggttt cagagaattt 39120
gtcttattag agaccatgag atggattttg tgaaaactaa agtaacacca ttatgaagta 39180
aatcgtgtat atttgctttc aaaaccttta tatttgaata caaatgtact ccctgggaag 39240
tcttaaggta atggctactg gttatcaaac aaatgtaaaa attgtatatt tttgagtacc 39300
tgttacatgc caggtagaat atctcctctc agccactctg agtggaaagc atcattatct 39360
ctattttaca gaaaagcaaa ctgaggctca gagagataat atactttgcc agttaatgaa 39420
tgatggagcc atgattccag ctgaggtctg tattgccttg ctctctagga atggtagtcc 39480
cccccataaa gaatctctca gtttcctttc caatcaaaag gttaggatcc ttttgattgc 39540
cagtgacaga aacccaattt actagcttaa gtaaataaaa ggaacgaatt tattggctca 39600
tgaagcctga actatgtgaa gacctaggtg gagaactggc cttaggaact caatgggacc 39660
aaggactcaa atgccacctg gtggcatttg ccttatgctg gttttatttt ctcagaccgg 39720
accagctttc tacataaagt gggtccctgg ttagaactct ttgctcctat ctttaaggac 39780
cacgaaagaa ggagcccttt gtccttggct aaatgtgaaa aatcccagag actcttgagt 39840
catagtgctt accccttggg ccactcatag tctagaatga actaggctga gtctcgtgcc 39900
aacagcacag gcctgatgcc agataaaagg gtgagtgaag ggggataaaa aataagacat 39960
agctactaaa ttattgcacc aaagtaaaaa cattgagttg acttgcaatt tgtttctttt 40020
aattaaattc atttcctttt tttggcattt tgaaggcaaa gtaagatatt aaactttatt 40080
tttattgatt ttattcaaag aattaagcta gtgggagtag cagattcaca cttctaagat 40140
caagggccag cttctattat tgaacacttg gtgtgtgcaa atgccatgag gtagggatac 40200
tttgttttgt tttttatttt ttattgggtt cgatctcttt tgtttatgat gtatccccaa 40260
gtgcctagaa tagggcctgg catatggtat atactcaata aatatttgtt gaatgaatcc 40320
atgatggaat gtgaaatggc tagcattaca tagaaacctg tagcattgct ggagagataa 40380
aatatataaa cataatccat tgcaggtata ttgacaagtt caaaataata taatgggtat 40440
tgaatatcta aatgtttgtt gttgttgttg ctgttgtttt tgagacagag tcttgctctg 40500
ttgcccaggc tggagtgtaa tggtgcaatt ttggctcact gcaaacttcg tctcctgggt 40560

-continued

```
tcaagtgatt ctcctgcctc agcctctcga gtagctgggt ttacaggcac tcgccacaat  40620
gcctggctaa tttttgtatt ttagtagatg tggagtttcg ccatgttggc caggctggtc  40680
ttgaactcct gacctcaagt gatctgccca ccttggcctc ccaaaatgct gggattatag  40740
gtgtgagcca ctatgcccag ctttgaatat ctaagtttta attggatgct gagggaatga  40800
ttaatcagag tagggctggg ttaattgaaa aatgtgatac atttgtattt atggccagat  40860
agagaacatg aatctgaatt tgcagaatta tctggcttaa cattttttc tttccagttt  40920
tcactgtatc ccccatgttg attcaattta aaaaatatac ctattttact tcaattcaac  40980
aatgctatgc cagtacaaac ccatacgttc tattatttt gttttgtttt gtttttgtat  41040
ctccaccctg ttacttcttt tcttataaaa ttggtatttg aaatttattg aaatattttg  41100
gaagagtgac ataccatttt tggtactttg tacctctgca cccttgggaa gtgaccctgg  41160
cttcacattt cataactgcc ttgtgaccat ggccctcaag tggttgccag atggttgaag  41220
aacattaacc tatctggctc aattttgtga ccatggattg aatcctctac ataactgcag  41280
tgtgcaaacc acacatccgt tccaagattg tagtcaggat atgaactttt taagaataaa  41340
acttcttccc ttctgatctg ggcctggtat gtggtcctac tagaaccaca tcacctactc  41400
ttggtgctaa caatttgtgg caccaagttg ttcaagtttc acccattaaa gaaattcccc  41460
gaccttgcct tctcctcagg taactacccc attctatttt ttctttcata gctaacattc  41520
tctgctctcc tggtctctct acttcacttt catttacatc tcagctcctg aagtatggtt  41580
tccaccatgt tcctaaaact acattgccca gggtcactag agacctctta tgaaatataa  41640
caacaccttt ctacattact tccgtgtgga ccactttttc acattgaacc cattttgttg  41700
gtttatgtac acaccccttc cttggctttc ccatctgatc catttctcct ttgatggaga  41760
aggtgagtct gctccatatt tagcttctta ctctgagtaa ccaaatgtta tggatgggag  41820
gttagctctg tgtgtgagag aaaggtggag aagcatgtgg ggagggaaat agatgggaaa  41880
aggtaattag gctttataga agggctctca ttagcaagct tctaggggat gccaagatcc  41940
atgcttagag attgccaggc ttgtcttcaa atctcagctg tgtattactc ctttatgttt  42000
tttgtttgtt tgtgttgttt gtttttgaga cagagtctcg ctgtgtcacc caggctggag  42060
tgtagtggtg tgatctcagc tcactgcaaa ctctgcctcc tgggttcaag cgaatctcag  42120
tctcctgagt agctgggact acaggcatgc accaccaggc ctggctaatt tttgtagaga  42180
cggggttttg ctatgctggc caggctggtc ttgaactcct gacctcaagt gatctgcccg  42240
ccttggcctc ccaaagtgtt gggattagtg gcgtgagcca ctgccccggc ctattactcc  42300
tttagagtga tttagagcca tgtttactta tggtaacttg acagtaatgg gaataaccac  42360
tgatgaaacg taaagccttt gtctaattgt ttacctagtt cttccttgtg gttcatgaaa  42420
tttttcatct ctgtacagtt tgaaaattaa gatgataata tttagagata ttttattcct  42480
ttgtgaagag aaaaaaggct ttcattaaca gaaatcagtg gcaataactt aataaataca  42540
atcagctggt gttcctatag tatttaaaag aaaacagaaa gtttactaga tttcagccag  42600
ttttcagact atttaatgtc tattcttact ataatagaaa atatataatt tgatcttgtt  42660
ctcatttttc aaagaccttt aatacatgat tttagtagtt gaaaatgaag tttaatgata  42720
gtttatgcct ctacttttaa aaacaaagtc taacagattt ttctcatgtt aaatcacaga  42780
aaaagccacc tgacatttta acttgttttt gatttgacag tgaaatctta taaatctgcc  42840
acagttctaa accaataaag atcaaggtat aagggaaaaa tgtagaatgt ttgtgtgttt  42900
attttttcca ccttgttcta agcacagcaa tgagcattcg taaaagcctt actttatttg  42960
```

-continued tccacccttt tcattgtttt ttagaagccc aacacttttc tttaacacat acaatgtggc 43020
cttttcatga aatcaattcc ctgcacagtg atatatggca gagcattgaa ttctgccaaa 43080
tatctggctg agtgtttggt gttgtatggt ctccatgaga ttttgtctct ataatacttg 43140
ggttaatctc cttggatata cttgtgtgaa tcaaactatg ttaagggaaa taggacaact 43200
aaaatatttg cacatgcaac ttattggtcc cactttttat tcttttgcag agaatgggat 43260
agagagctgg cttcaaagaa aaatcctaaa ctcattaatg cccttcggcg atgtttttc 43320
tggagattta tgttctatgg aatcttttta tatttagggg taaggatctc atttgtacat 43380
tcattatgta tcacataact atattcattt ttgtgattat gaaaagacta cgaaatctgg 43440
tgaataggtg taaaaatata aaggatgaat ccaactccaa acactaagaa accacctaaa 43500
actctagtaa ggataagtaa aaatcctttg gaactaaaat gtcctggaac acgggtggca 43560
atttacaatc tcaatgggct cagcaaaata aattgcttgc ttaaaaaatt attttctgtt 43620
atgattccaa atcacattat cttactagta catgagatta ctggtgcctt tattttgctg 43680
tattcaacag gagagtgtca ggagacaatg tcagcagaat taggtcaaat gcagctaatt 43740
acatatatga atgtttgtaa tattttgaaa tcatatctgc atggtgaatt gtttcaaaga 43800
aaaacactaa aaatttaaag tatagcagct ttaaatacta aataaataat actaaaaatt 43860
taaagttctc ttgcaatata ttttcttaat atcttacatc tcatcagtgt gaaaagttgc 43920
acacctgaaa atccaggctt tgtggtgttt aagtgccttg tatgttcccc agttgctgtc 43980
caatgtgact ctgatttatt attttctaca tcatgaaagc attatttgaa tccttggttg 44040
taacctataa aaggagacag attcaagact tgtttaatct tcttgttaaa gctgtgcaca 44100
atatttgctt tggggcgttt acttatcata tggattgact tgtgtttata ttggtcttta 44160
tgcctcaggg agttaaacag tgtctcccag agaaatgcca tttgtgttac attgcttgaa 44220
aaatttcagt tcatacaccc ccatgaaaaa tacatttaaa acttatctta acaaagatga 44280
gtacacttag gcccagaatg ttctctaatg ctcttgataa tttcctagaa gaaatttttc 44340
tgacttttga aataatagat ccataatata tattcttatg gaaatctgaa accatttggg 44400
catttggggg taaaaagtat tttattagta aatttaaatg aggtagctgg ataattaaat 44460
tacttttaag ttacctttga gatgattttt ctcaatcaga gcaccaccca gagctttgag 44520
aaacaatttt attcacagct tctgattcta tttgatgtaa tttttagaaa ataagttttg 44580
ctggttgctt tgaatcaggg tatggagtac agttcactct gatcctatca tataaatcat 44640
gtaagtatat aacatttttca ataagtgatt gttggattga agtgaatgat atttcaagta 44700
attgttatgt catggccaag atttcagtga aactcaaaat ttctcctggt tgtgttctcc 44760
attgcatgct gcttctattg attaacctaa gcactactga gtagaagctg gaagaggggt 44820
ctaattagaa ggcccctttc tatgctctgc ttggcttgta aaataattta tttctctaga 44880
tcccaccaac atagtagttt catgtatgca aaaacaccca cctaaatgtc aaagtttgta 44940
tgatacatgg acatatctat agaatttttt ttggtctggt gcatgccaaa aaataaacat 45000
gatatagaag aatttaatat ttattgagta cctaatctgt tccagttcaa tatgaaggtc 45060
tttatgcaga ttattttact taattttcct agtaactcca tggagcaaaa attatctcta 45120
atttatataa caggaagttg agcgtgaggc aaattaagta actttcccaa agttacacat 45180
atggtaagtt tgagagatat cccagtctct ttagctccaa agcctttgac cctttcacca 45240
taccagatta tgattgctat taatatataa ttataattat aatgattgta tttaggtact 45300

```
caacagaatg gtgactctag taaccagcct tggttctgct gagcttctct gcgtcttctc  45360
aggagacaca ggctacagag cttgaaggct gaggattctt ccagggtcac ttcaggggca  45420
aatctgaaac tttcttcagg acaggaatca acgagatctt ctcacttact tatacctggg  45480
ggaggaactg tatgaaatcc acccaagaac cagtcatgct aagggccaaa cctatagaca  45540
aaaaaaggga taggagaatg gagtatgtat ggagaaagac taaattgttc ttaaacttct  45600
caagcttaaa aatatcccag caaaagagat cgtaaaagcc cttcatggcg tattaattat  45660
ccatgcatgg gggtgagtgg aaaggtactc ctgagcccga ggctacagct ttggaactag  45720
cagcaccttt gaaggggaaa gcgtgtttcc atcatctcaa ctcctactga taaccaatgg  45780
aatattggtg agtaaaggat cctgggggaa gaagcagctg aaatgtgtag gtgagaaggc  45840
agagagaaga atatttatat tgggaatggc acaagtgtga tgaggctgca ggtttttcac  45900
ccttgtcata gagaaaaaac cacgctgaca ccatgcagtt ttaaatagtg agaaatttgc  45960
aaattgttag atcttaaata atttagataa acatagtggc catttagatt attgcagttt  46020
tttcaggata tctgatctct tgatttcatt ctttttgtct cttataagaa taaaaggggg  46080
ggagaaaatt tagccattat agtatttctc tacattttct ctgtcctttt acataactta  46140
caccagtgcc ttcctattta tggtattatt tatgggtatt tcttcttttc tttcactgag  46200
caaggataaa tgagccaggg attcttgaaa ctactgtaac acttctctta gaaatagatg  46260
gtcatacttt cagaatctct acacattctt agtccctcta aacaatgata gttgtggcat  46320
aaaaatattt gcttggtttc aggactgata gagaaaagta ctataaaatt tgctgttaac  46380
tgtgaaaggt taaaaaaaag gaggtgccat catgaaggag ctaatctttc tgaagtactg  46440
ctgtagtttt aaatattatt agctatgact tctcaccatt aactatgcac ttgctttttc  46500
ttcatctgac tcagcagcca gatagatgca acattgtctt taacatttaa gactcctagc  46560
aagtccgggc acgggggctc acacctgtaa tcccagcact ttgggaggcc gaggtgggca  46620
aatcacaagg tcaggagttt gagaccagcc tggccaatat ggtgaaaccc tgtctctact  46680
aaaagtacaa aaatcagcca ggtgtggtgg cgtggtggcg ggcacctgtg gtcccagcta  46740
cttgggaggc tgaggcagga gaatagcttg aacctgggag gcagaggttg cagtgagctg  46800
agatcgcacc actgcactcc agcctgggtg acagagcgag actccatctc aaaaaaaaaa  46860
aaaaaaaaaa agactcctag catggaagag aaactggctg ttgaaaacct gaatgtgaga  46920
gtcagtcaag gatagtttga gggaagccaa gtagaggaag ctctcacaag cagattggtg  46980
agagaatatg attatacaat gcatttatta tgataagaaa ttcacaagca ttcattcaaa  47040
atactcttga ttcctaggca gctctgggca tatttccacc aacaaattga ggcatatgtc  47100
agtgcagcct aggtcagact accttttttc attaaacctc acaaaattaa aggacataca  47160
ggagaagtcc tggtactcat gttgcagact acagtctata tggcaaagga ggatctctgt  47220
cccttatgtt tggatgaaaa cattgggtag gcatttgaat acaagcctac tgctaatatg  47280
gggctaaggt ctttggcccc ctaaaggttt gctgaaatat tactgacagg aggcagattg  47340
ataagaggaa aagcacataa atgtatttga catgtataca tgggagcctt caggatgaag  47400
acctaccctc tcagtgcagt atggaagctt gtataccatc ttgaggttac agaaagaatg  47460
ggggtttgga tctttgtaaa acaggtttca gtggcaagac aggttatgag aaggagaaag  47520
gaagagactt gggtagcaaa gggggtcttg ttttgtaggt aaatcgttgg cagcccacag  47580
agaaaataga tggagaatgt ttcttttcag accttggcag gtgtcagatt ctcagttaat  47640
ctctcctaga tttgaaaaaa aaaaaaaagg tctagaaagg gagagcctgg ctgcactaac  47700
```

-continued

```
acattttcta cagatgcaaa tttctcccac aaaatacagc tttgcaggtc cacttctatc  47760
tgctgggcct gtggcaacca tttcaaaata tgtgaatgaa atatatgtgg gggtaaacta  47820
tttttattta cttccctaaa gaagggatgg tgttctctcg ggaattctgt gcatagagag  47880
cctgtggctt aggcactttg atttatgtat atctcttcct gtgattggct atctagggac  47940
tgctatctcc agcaaatctt ctaaatgtct gccatgtaga attcctttct catctttctg  48000
tctcaccccc ttatctagct gcttctctaa ccctagagtg acactgcact ccccacaatc  48060
tcctatgtcc tgaatatttt accccatcct aaactccatc tctaacacag atgcactttc  48120
ttgtgctgcc tactgcattg tacatcttcc ccttagttcc catgatgcaa ctctgcccta  48180
ccccagaaaa tgtaatttaa ttggtctggg ataaaacctg ggacactatc attcttgaaa  48240
tattccccaa gcgattctaa ttatatagcc aaagttgaga actatttgta gacaggcatc  48300
agcatgatca cttaatgatt tgacttttgc tagatctaag gtgaggaaat tggagagtgg  48360
tatccatagg aagaactgtt tagtttaatt ttttttttat tttttcttct aaaaaaaaat  48420
ccaacaacga gatacatgtg cggaacatgc aggtttgtta cataggtata atgtgccatg  48480
gtagtttgtt gcacctattg acccatcctc taagttccct cccctactcc ttacttccca  48540
acaggccctg gtgtatgttg ttcccctctc tgggtccacc tgttctcaat gttcaactcc  48600
cttttacgag tgagaacaca tggtgtttga ttttctgttc ctgtgttaat ttgctgagga  48660
tgatagtttc cagcttcatc cacgtccctg caaaggacat gatctcattc ctttttatgg  48720
ctgcatagta ttccatgatg tatatgtacc acattttctt tatccagtct gtcattgatg  48780
ggcatttggg ttggttccat gtctttgcta ttgtaaatag ttctgcagta aacatatatg  48840
tccatgtgtc tttatagtag aatgatttat attactttgg gtatataccc agtaatgaga  48900
ttgctgggtc aaatggcatt tctggttcta gatacttgag gaatcgccac actgtcttcc  48960
acaatggttg aactaattta cactcccact aacagtgtaa aagcgttcct atttctccac  49020
agcctcacca gcatctattg tttcctaaca ttttaataac tgctattctg actggcatga  49080
gatggtatct cattgtggtt ttgatttgca tttatctgat gatcagtgat gctgagattt  49140
ttaaaatatg tttgttggcc atgtaaatgt cttttgtgaa gtgtctgttc atatcctttg  49200
cccaccttaa tagggttttt tttttcttgt gaatttgttt aagtgccttg taaattctgg  49260
aaattagatc tttgtcagat ggatagattg caaaaatttt ctcccatttt gtaggttgcc  49320
tgttcactct gatgataggt tcttttgctg tgcagaagct ctttagttta attagatcca  49380
atttgtcaat tttggctttt tttgcaattg cttttggcat tttcctcgtg aagtctttgc  49440
ccgtgcctat gtcctgaatg gtattgcgta ggttttcttc tagggttttt atagttttgg  49500
gttttacatt taagtcttta atacatcttg agttaatttt tgtataaggt ataaggaagg  49560
ggtccagttt cagttttatg cataatggct aggcagtttt cccaccacca tttactgaat  49620
aggagatctt ttcctcattg cttgtttttg tcagatttgt cgaagatcag atggttgtag  49680
atgtgtggtg ttatttctga ggtctctgtt ctgcaccatt ggtctatatg tctgttatcg  49740
taccagtccc atgctgtttt ggttaccgta gccttgtagt atattttgaa gtctggtagc  49800
gtgatgcctc cagctttgtt ctttttgctt aggattgtct tggctatatg gagtcttctt  49860
tgattccata tgaaatttaa aataattttt ttttattctg tgaagaatgt caatggtagt  49920
ttgatgggaa tagcattgaa attataaatt actttgggca gtatagccat gttcacaata  49980
ttgattcttt ctatccgtaa ggacgacact ttttccattt gtttgtgttc tctcttattt  50040
```

```
ccttgagcag tggtttgtag ttctccttaa agaggtcttt cacatccttt gttagctgtg  50100
ttcctaggta ttttgttctc tttgtagtga ttgtgaatgg gaattcattc ttgatttgcc  50160
tctctgctgc ctgttgttgg tgtaaacaaa attcatttct tgttcttatt tgtgaaattt  50220
tggaaccaaa tctattttca aattagaaat tgcttgtgat aatggttttg caacttagac  50280
tggatatgag acgatgagat attagttctt tcattccttt gtaggaatat ggtgcatctt  50340
gcattatttt agctaactag tgtcctttaa tgactaatga atatgacatg gtgaaacaaa  50400
gtaaaatata tatgatgcac taagtatgca ttgtttccaa aggttcagca tttttttttt  50460
gttaactctg ctgggatctg ctttatgcac tgataacata acttatttta tgatcttaag  50520
caaataaaaa cacttatctg gacctcagtt tccttaactg tacaactgag ggaaactgta  50580
tagtatagct atagtacagt ataccatctt taccgtcact tccatctttt aaattatgtg  50640
tatataagat agggcctaga taaatggtat ttatcttaaa ttacagtgat actagcttat  50700
aacttaattt gctaggtcat gttgaactga taacaatgtg tgaactgatg agcaactgag  50760
aagtaaccag gttgtgttat aacagtttgt ttttgattta gggttatcag tgagggtggc  50820
ggtggggagg ggactttgga gtctaactgt ctagttcaaa tattagtttt tgtttatttt  50880
tatttttaat ttttgtgggt acatagtaga tgtatatatt tatggggtac atgtgatgtt  50940
ttcatatagg catgcaatgt gaaataagca catcatagag aatggggtat ccatcccctc  51000
aaacacttat cttttgagtt accaacaatc caatgacact ctttaagtta tcaaatcaca  51060
gttttgccag ctactagcca tgtgattttg ggtaggttac ttaaattctc ttcatctcaa  51120
tttcattatt gtaaagtgga gataatgata gcacattttt tctttttctt ttttctttta  51180
ttttttatta ttatacttta agttgtgtga tacatgtgca gaatgtgcag gtttgttaca  51240
taggtatcaa caactctata aaacatgttc tatccaggaa aagaaactat catcagagtg  51300
aacaggcaac ttacggaatg ggagaaaatg tttgcaatct agatggcgat tgcaatggcg  51360
gttcgctgca tccatcagcc catcatctac attaggtatt tctcctaatg ctatccctcc  51420
ccttgctccc cacccccctca caggccccctg tgtgtgatgt tcccctccct gtgtccatgt  51480
gttctcattg ttcaactccc acttatgagt gagaacatgt ggtgtttggt tttctgttct  51540
tgtgttagtt tgctgagaat gatggtttcc agcttcatcc atgttcctgc aaggacatga  51600
actcatcctt ttttatggct gtatagtatt ccatggtata tatgtgccac attttcttta  51660
tccagtctat cattggtgga catttgggtt ggttccaagt ctttgctatt gtgaacgctg  51720
cagcaatgaa catacataag catatgtctt tctagtcaaa taagttataa tcctttgggt  51780
atgtacccag taatgggatt gctgggtcaa atggtatttc tggttctaga ttcttgagga  51840
atcgccacac tgtcttccac aatggttgaa ttaatttaca ctcccaccaa cagtgtagaa  51900
gcattcctat ttctccacat ccgctccagc atctgttgtt tcctgacttt ttaatgatca  51960
ccattctaac tggtgtgaga tggtatctca ttgtggtttt gatttgcatt tctctaatga  52020
ctagtgatga tgagcttctt ttcatgtttg ttggctgcat aaatgtcttc ttttgagaag  52080
tgtctgttca tatcctttcc ccactttttg atggggttgt ttttttcctg taaatttgtt  52140
taagttcctt gtagattttg gatattagcc ctttgtcagg tggatagatt gcaaacattt  52200
tctcccattc tgtaagttgc ctgttcactc tgatgatagt ttcttttgct ggatagaaca  52260
tgttttatag agttgttgtg agaattaaat gcattaagca catagaatag attctggtac  52320
atagcaagtg ctctctctat atatggaact ctatatgtag ttggtgcaaa agtaattgtg  52380
gttttcacca ttgaaagtaa tggcaaagac catcattacc ttttcaccaa tttaaatata  52440
```

```
tggaaggaat atatatataa aacctatata tatatgtcac atatatgtct ctaacccatt  52500
attataatat ataatacaat atatattata attataattg tatataacat atgttatata  52560
ataatatagt aatatttatt ctaaataaat atataatact ataaataata taataattta  52620
tatatatgat tataatatat aataggctat attatatatt attaacatat acatatgtgt  52680
atatatatgt ctttcataga cttaaatata tagagcaata ataggttaga aaatagcaaa  52740
catgtatata taaacatata tacatataga aaacatatat aaaaacatat atatatatat  52800
atatatgtgt gttttctgcc tttcattttt agagacaggg tctcatcatg ttgcccaggc  52860
tggtctcaaa ctcctgggct caagtgatcc tactgctttg gactcccgaa gtgctgggat  52920
ttcagacatg agacactgca cccagtccag tccctgtctt tttaaataga ctctctacct  52980
aagtgcacaa atactcatta tttacattta gttatttctg tatatatgct ataagcaaat  53040
cttgtagcac cagtttgatt tttataaggc acaagaatat attttactaa tgctttaaaa  53100
tggcagctag attctagtat tactttagaa attaaaatta atattttaac acatctttca  53160
ttattgtgtt atctgaacca aacctattat tgctgctatt tcagcaaatc caggggcttt  53220
ttcttataaa atatgaagaa tatagcttag atttctagtg aagatgttac cagtaataat  53280
taataaaatc agtaagcact aaaaggaaaa taccaaaact aaagcatttt gaattagtca  53340
ttgaatctaa aagaaaggta gatttttttc tgagattctg ttctaggtgt ggtatatgtg  53400
tatttttgca aaaactataa acaattgtgg caaaatgaag gaaatattta aaaacaaacc  53460
tcttaattct tcagtggatt aagcgtgaat atgtttttat tttctatgat gaatatggaa  53520
aaattcattt ccttagcaat ttgtatgagc ccaaaaacta ttgtcagact ctgctgtatc  53580
aaaatagaca aaaaattgac actcactttt accctgccaa aagcaaaatc ttaaactttt  53640
gctttagtat ataagccagc attcattgta tcctatgatg ggttctgagt gtaggtgtat  53700
ttgctttctt ccattttttg tatgcatgtt ttctttttat ttattattgt aagttgtatg  53760
aaatttttat ccaaattttt attttcttct gattaataat cagaataatc agataattac  53820
tggtaaattt gatgttaatc cttccagctt tttcccatgg gaatttatac ttaataaagg  53880
ggagaagtca tcattacata atgtgcatat taatctgctt ctccctttaa tgtgttgtga  53940
atgcctttcc atgtcattag atgtttttct acctagttac tttcatgaat catatggctg  54000
taccatgatt tatttaatca gttcctcatc attgagtatg taaattgcct ccattttttt  54060
attactataa aaggtccttc agtacacacc cctttaaaag ctgactctta gaaggtgttc  54120
ttgactctct acctaagtgt aaaaatacaa ataaattgct ttccagaaaa ggtgcactac  54180
tattttactt tcctgatact aaactatgaa aattcagtcc taacaataga tatttaaata  54240
aagttttaaa aatgccaagt gaaaaagagc atattattat tttcatttgc attacttttg  54300
gttcctggtg agtttaatct gtttttgtat attaattatg catttatatt tctttttgtg  54360
tgtgtgaatt gcctttcatg ttctttgtgt gtttttattt tgttgtattt gtctctttct  54420
tgatatatga gagaatattt tccctagcct gtcaattgcc ttgtaatttt gtttctagtg  54480
agtttttttt ttttttttta caattaaaag ctttaatttt tgaaaatttt gctggcaaat  54540
ctatatatct ttttctttgt tttctgcttt gacattattc ttttataaag gcccatgcca  54600
cccaaatatt atgtaagcat gcatctatgt ttttattact tcatctttta catttaaata  54660
tctactctat ttagaattca ttgtgatgca tgtatgaggt agaaatctaa tttcaaaaag  54720
atgagtatcc agtttgtcca tcatttattg catgatctct ttctccactg aattaaaatg  54780
```

-continued

```
ccgtatttta taatatatta aagtattaca tgtgcttgga catgttcctg gacttttgag  54840
ataaatcagt ctatttcttt gtcatgtcac atattattat ggctttatga tttaatatcc  54900
agtaatgtaa accctctgac acattattct tattcctcaa atgtttttga tgagttttct  54960
tccaaatgaa atttataatc attttattca ttgattcaac aaatatttgt tgaatggata  55020
ttctgtgctt ggtattgtgc atggtattag gattgttgca aaaattgaga ctgacagtcc  55080
ctactcttac ggtgctaaaa attcacttcc aaaaaaatct ttaaatgttg atgaagattg  55140
cactaatctt ataaaataac ttggaggga atgtaatctt tgcaacatta agttcttcat  55200
tttagaaagt tttaagactc tccatttatt tgagactttt aaaatatgtc ccaataatgt  55260
tttgtgagat gtatatttta agatatatat cttattgcta ttacattgta tcttttgtta  55320
tattgttact atgaatggga tactcattta attagatgtc atttttggta tatagaaatc  55380
tattttctta gcatagtcat tttttaaacc tcgatctatt aaattcttga ttcatttaca  55440
tttgttacac aatcatattc tatgctgata atacttcttg cttctttcca atatttgtac  55500
ctcgatcatt tttcttgttg agttgtatta gctagaagtt ctagaaaaat gttaaatggt  55560
agtaatagct agtattctgt tttttcctga ctctaaatgt aatgcatcta gacttttata  55620
attatggcat tgattgtaac attttgagga agaaatcctt tttcaggtta ataatgtatc  55680
tttatattca agtttattaa gaacatttat tggaaacata ttgaaatttt atcagattcc  55740
ttttcagttg ttactgagat aatcataggt tcttctgtat tcttttaatt aatttctcaa  55800
aattaaactg tcctattatt cttggaataa cgacatataa agtactgtat atttaaaaga  55860
agttaaaatg ataatggtga ttttattaag tgacctcaca caatagaaaa cagtgtagcc  55920
ttagaagttt tccaagtgac cattctactt agaaacaacc ctgctttggg atcagaactg  55980
taatttttaa agtaaagttt tctgggttta attcatttag tgtaattaca agcatgagtt  56040
caggtttcta tttttttcac ctgaactttc cttcatggtt tgaatatcta gaaaaagcag  56100
actttcctat ctctagacta aacatttgat cctatcttag gtatgcatta caatttttta  56160
accataaatg gttaaagaat ttagactcat ctacaataac tttgaagctc tggtcttgaa  56220
gaacatgtga gaaatgagat ataactccta gaagatatag gagacatttt tagtcttcca  56280
aattttccct gggaggctga tctaaattga gtcacaaaat tgttcccacc aggaatgcaa  56340
tcacttgagc tgttttctaa tctgagcccc tctacccaga tgatcttctg aactcatact  56400
gttcagactt tcatccttct gagtagaaaa cagccatagt catggcagga tgagggctag  56460
gacaattacc caaggaattc ttggcctctg ccatgggact ctgcagactc agatcatata  56520
atcagagatg ttagcactgg aggggacatc acaattagct ttctccacct cttagtttat  56580
cagtgaggaa aactgtccag agcgcggaag agactaaaat aacacagcca atgtaggtaa  56640
tgtgctggat aagaatttgg aattcacgat tttgaattca gtgtttattt caccatcacg  56700
ctggcttaca cgttggtatc aggcttcttc tattattgaa gtgagccatt aagtgaattc  56760
catcttgatt tgtgtctgat acagagtaat aaactatttt attaaatatc caaataatta  56820
tacattcctc cttcttacat gcaagcctaa gtttgcttgt actatttcat gtggtagcaa  56880
atcaggacgc ttcttgtgtc tctgaaaata ctctgagtaa tggagtacag tcagctttct  56940
tgtaccaaga atatagggac tatgtttctc ccagtcattc tggggataat ttttgtgaag  57000
gattgcactt cataggttaa gctaggtatc agttaccagt gtttttccca aataaaaaaa  57060
aaatcaggtg atatctgtaa atggttccat tgtaaatatt aaagaacatg atgcttaaaa  57120
cagattaggg aaaactatag aaggggtggg gtttcggagt gctaattttg tccttgaatg  57180
```

```
gtaacagctc catgtggtgg tgaggtttat gttggtttgc tgtttgcaga tgatcttatt  57240
attagaattt ttcataccga aaataaactg cattttagtt tgtaaacatg cccttccaga  57300
gtaatgctac cagttctttg tgaaatagct actgttgttc aaaggatgac tatgtcctct  57360
tcggttgagg aaagatgaca acaaactcag taatgacatg taaaataggt attacaaacc  57420
aggtatggtg gcatgagcct gtaatcccag ctacttgaga ggctaaagca ggaggatctg  57480
ttgatctatg gatttgaggc tgtagtgtgt tgtgatggca cctatgaata gcccttgcac  57540
tccagcccaa gcaacaaagc aagactgtct ctgaattttt gttttgtttt gtttttttgtt  57600
ttttttttt tgagacagag tcttgctctg tcacccaggc tgaagtgcag tggcgcgatc  57660
tccactcact gcaagctccg cctcctgggt tcacgccatt ctcctgcctc agcctcccga  57720
gtagctagga ctacaggcgc ccgcctccac gcccagctaa attttttgta tttttagtag  57780
agacgaggtt tcactgtgtt agccaggacg gtcttgatct cctgaccttg tgatcctcct  57840
gcctcggcct cccaaagtgc tgggattaca ggcgtgagcc accgcgcccg gcccctgtct  57900
ctgaattttt taaaaaggca ttccactcaa attaatacac attttaattg tgttttgttg  57960
taaattacaa ctgaataaaa attcagcaaa taagtctgtt gtggtaggga aaagtctatt  58020
gtgatctgga aaatataatg gagaaatcca gtggaagaga ttttatttca cattactcaa  58080
aataaaaaaa tcttatacaa gtctttacac ttgtaacttg aaaaattctg tgctaaaatt  58140
tagcttggtt gctaaaatat ttctcttttt ttctcagaag cttcttttta gcatcctata  58200
gacacaagtt actttttaaa atatttgcat acttgctttg caatgtattg tttatcagta  58260
gttctatatt ctttgagata gtctatccag tctttctgta tttatcgtat gtctgtatag  58320
atatatatta gcagataaat gagttctgaa aggggagaaa tgtgattatg ctaatcatga  58380
tataaagaat tgactttata agcagtgttc acaggtcata cctttcccgt tactgtctta  58440
cagtgaacaa gaaatgatgc tttgtctggt atgcatggta aataatgccc cttgctctct  58500
gcttcatgat cacatgtgat acttctaaca tagatagcac atgtaaatcc agtggccttg  58560
actgcaactc aagagagcat tttggccaag tacaaaccca ctagtcatga aaaaaaaaaa  58620
aaaaccaaat caaagtaaat tgatggtatt gacatttgtc tatgaaaaac aacataatat  58680
agaacaattc tggggtaaaa tattgatcta aaataatttt aaggattaaa tattgccatt  58740
gtaagcatac tatgagcaat tatgtttgta atgcagatat atttataatt ttaaatccaa  58800
gatttacctt aattgtacat tttcctaatt taaaaaagtt attttgaaaa aaaaatcctc  58860
gaatctagag aaaggttggc aaatacatat ggaactttgt aaaaaacatc cagggcagca  58920
ctttcactga ttgcagtagc ttaggagtga aaaacaacac aactgctcca atgtatggca  58980
atgggcaaat atcccgattt attcacaggg tggcatgtta ggcagtgctt agaataaatg  59040
agttggttat acaagtatca atagggataa atgtgaaaaa cacagtgtta agtttttaaa  59100
aagttgtaaa aagcacagta ggatgttatt tatataaaat ttaaaaacct caaaaaccat  59160
tcttctttga tatatattct aaagatgaac atatatgtaa tagaagtaca aaacatacat  59220
aaaataatat acactatgca gtcatttgtg tacttacttt tcaaaaatat ttcagtagat  59280
atagcaaaca gttaacatgt aatatttgga taggaggttg gcaattttct ttttagcacc  59340
tgcctgtctg ctatcattca aactcacatt taaaatgtgg ctatgtgaga tgagagaact  59400
ataatattcc aggtttgtga ttagtttgga aactttttaa aagtttgaat gtggtctgag  59460
agatagtttg ttataatttc tgttctttta catttgctga ggagagcttt acttccaact  59520
```

-continued atgtggtcaa ttttggaata ggtgtggtgt ggtgctgaaa aaaatgtata ttctgttgat 59580
ttggggtgga gagttctgta gatgtctatt aggtctgctt ggtgcagagc tgagttcaat 59640
tcctgggtat ccttgttgac tttctgtctc gttgatctgt ctaatgttga cagtggggtg 59700
ttaaagtctc ccattattaa tgtgtgggag tctaagtctc tttgtaggtc actcaggact 59760
tgctttatga atctgggtgc tcctgtattg ggtgcataaa tatttaggat agttagctcc 59820
tcttgttgaa ttgatccctt taccattatg taatggcctt ctttgtctct tttgatcttt 59880
gttggtttaa agtctgtttt atcagagact aggattgcaa cccctgcctt tttttgtttt 59940
ccattggctt ggtagatctt cctccatcct tttattttga gcctatgtgt gtctctgcac 60000
gtgagatggg tttcctgaat acagcacact gatgggtctt gactctttat ccaatttgcc 60060
agtctgtgtc ttttaattgg agcatttagt ccatttatat ttaaagttaa tattgttatg 60120
tgtgaatttg atcctgtcat tatgatgtta gctggtgatt ttgctcatta gttgatgcag 60180
tttcttccta gtctcgatgg tctttacatt ttggcatgat tttgcagtgg ctggtactgg 60240
ttgttccttt ccaggtttag cgcttccttc aggagctctt ttagggcagg cctggtggtg 60300
acaaaatctc tcagcatttg cttgtctata aagtatttta tttctccttc acttatgaag 60360
cttagtttgg ctggatatct ctcagaccac agtgcaatca aactagaact caggattaag 60420
aatctcactc aaagccgctc aactacatgg aaactgaaca acctgctcct gaatgactac 60480
tgggtacata acgaaatgaa gacagaaata aagatgttct ttgaaaccaa cgagaacaaa 60540
gacaccacat accagaatct ctgggatgca ttcaaagcag tgtgtagagg gaaatttata 60600
gcactaaatg cctacaagag aaagcaggaa agatccaaaa ttgacaccct aacatcacaa 60660
ttaaaagaac tagaaaagca agagcaaaca cattcaaaag ctagcagaag gcaagaaata 60720
actaaaatca gagcagaact gaaggaaata gagacacaaa aaacccttca aaaaatcaat 60780
gaatccagga gctggttttt tgaaaggatc aacaaaattg atagaccgct agcaagacta 60840
ataaagaaaa aaagagagaa gaatcaaata gacacaataa aaaatgataa aggggatatc 60900
accaccaatc ccacagaaat acaaactacc atcagagaat actacaaaca cctctacgca 60960
aataaactag aaaatctaga agaaatggat acattcctcg acacatacac tctcccaaga 61020
ctaaaccagg aagaagttga atctctgaat agaccaataa caggctctga aattgtggca 61080
ataatcaata gtttaccaac caaaaagagt ccaggaccag atggattcac agccgaattc 61140
taccagaggt acaaggagga actggtacca ttccttctga aactattcca atcaatagaa 61200
aaagagggaa tcctccctaa ctcattttat gaggccagca tcattctgat accaaagccg 61260
ggcagagaca caaccaaaaa agagaatttt agaccaatat ccttgatgaa cattgatgca 61320
aaaatcctca ataaaatact ggcaaaccga atccagcagc acatcaaaaa gcttatccac 61380
catgatcaag tgggcttcat ccctgggatg caaggctggt tcaatatacg caaatcaata 61440
aatgtaatcc agcatataaa cagagccaaa gacaaaaacc acatgattat ctcaatagat 61500
gcagaaaaag cctttgacaa aattcaacaa cccttcatgc taaaaactct caataaatta 61560
ggtattgatg ggacgtattt caaaataata agagctatct atgacaaacc cacagccaat 61620
atcatactga atgggcaaaa actggaagca ttccctttga aaactggcac aagacaggga 61680
tgccctctct caccgctcct attcaacata gtgttggaag ttctggccag ggcaatcagg 61740
caggagaagg aaataaaggg tattcaatta ggaaaagagg aagtcaaatt gtccctgttt 61800
gcagacgaca tgattgttta tctagaaaac cccatcgtct cagcccaaaa tctccttaag 61860
ctgataagca acttcagcaa agtctcagga tacaaaatca atgtacaaaa atcacaagca 61920

-continued

```
ttcttataca ccaacaacag acaaacagag agccaaatca tgagtgaact cccattcaca  61980
attgcttcaa agagaataaa atacctagga atccaactta caagggatgt gaaggacctc  62040
ttcaaggaga actacaaacc actgctcaag gaaataaaag aggacacaaa caaatggaag  62100
aacattccat gctcatgggt aggaagaatc aatatcgtga aaatggccat actgcccaag  62160
gtaatttaca gattcaatgc catccccatc aagctaccaa tgactttctt catagaattg  62220
gaaaaaacta ctttaaagtt catatggaac caaaaaagag cccgcatcgc caagtcaatc  62280
gtaagccaaa agaacaaagc tggaggcatc acgctacctg acttcaaact atactacaag  62340
gctacagtaa ccaaaacagc atggtactgg taccaaaaca gagatataga tcaatggaac  62400
agaacagagc cctcagaaat aacgccgcat atctacaact atctgatctt tgacaaacct  62460
gagaaaaaca agcaatgggg aaaggattcc ctatttaata aatggtgctg ggaaaactgg  62520
ctagccatat gtagaaagct gaaactggat cccttcctta caccttatac aaaaatcaat  62580
tcaagatgga ttaaagattt aaacgttaga cctaaaacca taaaaaccct agaagaaaac  62640
ctaggtatta ccattcagga cataggcgtg ggcaaggact tcatgtccaa aacaccaaaa  62700
gcaatggcaa caaaagccaa aattgacaaa tgggatctaa ttaaactaaa gagcttctgc  62760
aaagcaaaag aaactaccat cagagtgaac aggcaaccta caacatggga gaaaatttc  62820
gcaacctact catctgacaa agggctaata tccagaatct acaatgaact caaacaaatt  62880
tacaagaaaa aaacaaacaa ccccatcaaa aagtgggcga aggacatgaa cagacactac  62940
tcaaaagaag acatttatgc agccaaaaaa cacatgaaga aatgctcatc atcactggcc  63000
atcagagaaa tgcaaatcaa aaccactatg agatatcatc tcacaccagt tagaatggca  63060
atcattaaaa agtcaggaaa caacaggtgc tggagaggat gtggagaaat aggaacactt  63120
ttacactgtt ggtgggactg taaactagtt caaccattgt ggaagtcagt gtggcgattc  63180
ctcagggatc tagaactaga aataccattt gacccagcca tcccattact gggtatatac  63240
ccaaaggact ataaatcatg ctgctataaa gacacatgca cacgtatgtt tattgcggca  63300
ctattcacaa taggaaagac ttggaaccaa cccaaatgtc caacaatgat agactggatt  63360
aagaaaatgt ggcacatata caccatggaa tactatacag ccataaaaaa tgatgagttc  63420
atgtcctttg tagagacatg gatgaaattg gaaaccatca ttctcagtaa actatcgcaa  63480
gaacaaaaaa ccaaacaccg catattctca ctcataggtg ggaattgaac aatgagatca  63540
catggacaca ggaaggggaa tatcacactc tggggactgt ggtggggtcg ggggaggggg  63600
gagggatagc attgggagat atacctaatg ctagatgaca cgttagtggg tgcagcgcac  63660
cagcatggca catgtataca tatgtaacta acctgcacaa tgtgcacatg taccctaaaa  63720
cttagagtat aaaaaaaaaa aaaaaaaaag tttgaatgtt ttcttgcatt cagagccttg  63780
gttgacatag ttaattaaaa ataaaacatt gtatataaag cacagaatga gcagctacac  63840
aaagctgctc aatcaatgac agctctatat gggttagggt ttcttgtggg gatgacattg  63900
atgtagaaag catggtcatc tattgagaat gatggggctg gaggtattgg atacttgagg  63960
tttagaaaat acattgtaga aaatggacaa aaacccctca aattaaggga tgaggcagaa  64020
taatgcttgg caataccagg ggtaggctgc agtctttctt ggaaatatat attttaaatg  64080
gaaccaatta tcatagcatc atttcctctc agggttaccc tctgatccct attttactaa  64140
atcgttataa aacaaaatga ggaattatgt gtccttccct tttgaagcca atgtaacaag  64200
atgggtaaga attagacctc ctgagttcaa aatccctgga ttcagatcta ttcctgtata  64260
```

-continued

```
ttcaggagaa gtggtaataa attcgatgga caatttggtt tagtagtcga ttgaggaccc  64320
tgatgaggta tatttgggaa aacataactt ccgctctctc tcattgactc acgggccttt  64380
gaggagtcca ggagtcattg gaatctggcc tgaggttgag gctgctggca aaactccttc  64440
cccaaagtcc attcctattg ctgactgaga agggactagc attggaagtg gctgatttta  64500
aataccgcta gtgctggtgt gctcctccct cccattccca gctctgcttt gtgtagttgc  64560
cttgagaagc taagttcatt ctgaaaataa tgccattgca caaaacactt ttgaaagttc  64620
tagtttgaaa ttacatcagg tcacttggtc tgtgtggcct cagtttcttc atctgccatg  64680
tgaaaataat aatgcctact ctgtagcaaa gaaagtctct atagtaaaca aaaaaaaagc  64740
ctactctgat actgaaagtt gttatgaaaa ataaaaaagg gaaatgcttt agaaactgtt  64800
aagtgctatg tagatgttac taattaacaa accatttcag aaactatact ttttatttta  64860
tggccactat tcactgttta acttaaaata cctcatatgt aaacttgtct cccactgttg  64920
ctataacaaa tcccaagtct tatttcaaag taccaagata ttgaaaatag tgctaagagt  64980
ttcacatatg gtatgaccct ctatataaac tcattttaag tctcctctaa agatgaaaag  65040
tcttgtgttg aaattctcag ggtattttat gagaaataaa tgaaatttaa tttctctgtt  65100
tttccccttt tgtaggaagt caccaaagca gtacagcctc tcttactggg aagaatcata  65160
gcttcctatg acccggataa caaggaggaa cgctctatcg cgatttatct aggcataggc  65220
ttatgccttc tctttattgt gaggacactg ctcctacacc cagccatttt tggccttcat  65280
cacattggaa tgcagatgag aatagctatg tttagtttga tttataagaa ggtaatactt  65340
ccttgcacag gccccatggc acatatattc tgtatcgtac atgttttaat gtcataaatt  65400
aggtagtgag ctggtacaag taagggataa atgctgaaat taatttaata tgcctattaa  65460
ataaatggca ggaataatta atgctcttaa ttatccttga taatttaatt gacttaaact  65520
gataattatt gagtatcttc tgtaaactgc ctctgttgta gttttttttt tctcctaatc  65580
atgttatcat tttttggaa tccatggttt cctgttaaga tgactcacac agcctacata  65640
aaagtaattg acaaaatatc atcttatagt aaaatgccac atatctttat gttcagcaag  65700
aagagtataa tatatgattg ttaatgataa cccaaacaac aaaagatttc accttaactg  65760
gttgtcataa gtagtagtat ccaccgcctt attttgagtt ggatttttat catcctatga  65820
gccctacaaa tttaaagttt ttggaacagc acgtgcattg aacccataag aacctactct  65880
gcttttctgc atgtattgtc cagacaagag accaaattgc cgaggcatca tttaggtgaa  65940
ttctaattaa catttagcta ccttacaacc acaattcaag gttgtttcaa aggcatgtgc  66000
ttgcatcatc ctgattcact accatgtgtt actaacttgg atctgcaaag tcattataaa  66060
aagctgtttt gatggactta tttggatatt gctttaccct tcttctctct tttcttttat  66120
caatgtaaaa acattatatg ttaaatactt ggcttttaag agcatagatc tgaaatctgc  66180
ctctagcaaa taacccataa cacttctaag atatacctgc aaggtcaatt gtgttgtaaa  66240
accttgataa ccatacttta ttgttcaaaa aagcctttta tgaaggcaga agttaaaaaa  66300
aaaaaacaaa aaaaacagag tccacagtta tcacctcagc tacaatctca tcagttcaca  66360
agtaccagca aaacatgtga taagtcaaca aatgttttat ttcaatctga acattttacg  66420
taagtgaaga ctttgttaga tatcatttgg aatgtggaat ctacacagtt ggcatatcag  66480
agaaggttga attcagttta ataaatgttt atagaaagtg cttgttatca taatgataat  66540
agctcaggat gtgcatgaca agcttttaag cgattgggta cactatctca tttgatcttc  66600
tgcacaacta ttaatggtag gtactattat ccctatctta tggataagta aactaagatt  66660
```

taaaaagtac agaacatggt gtgaacactg cttcaaaatt tctaaaatag gtaaatcacg 66720
atctctaaac tggagggttg tccaaccact agggacaata gagtactgat atttagtggt 66780
cagactgtaa tgcgggaaga gacaggcatg ggctaaacgg gtgtagagat caaataaggg 66840
gcaggttagt ttgtaaacat gtccatatgt aacatttagc acaaatacag gatataggtg 66900
ctttcagacc cagctgcatt gataaaaagt taggtggtat tgtatctgtc ttcctttctc 66960
aatgttgcat atctgtgttc ttgcccagtt tgcttcatct ctctagccac acttattggc 67020
ctacaatggc atcatcacca aagaaggcaa tcccatctcc gtgtggcttt ggtttgctcc 67080
ctaaagtaaa ccttgtgttt acttttccca ggtctcatgc tttcccatat ctgacctgtt 67140
ttgtcctcat ggccaggata tgtgggacct ttcctacaat gttccaaagt ttgtaataga 67200
gctcttctct gctttgttcc aaattctgca acattttact ttaaataatg aatttaaata 67260
caaacaaact tgagctttgc ctatactttt caagaatgca gagataacta aattaataaa 67320
aatattcatt gagtccttac tgtgcacaca gctctatgtt aagccttgtg cagaactcaa 67380
agtcactcga gattaagcct gttactaagt tatgtgcaat ttagctcagt ggatttcccc 67440
cacttcatat tgctctgata atgttttgga attaactgcc ttgattcctt cttttctctg 67500
cttgtctata cactatttat tattctacac catctcaaat tctaactcct caagaaaatc 67560
cttccagatg atttttctaa ccaggagttt taacttcctt ttaactaccc tattactttc 67620
tacttcctta actcatctat catattatat ttagttattt atatactagg tcgccttgaa 67680
gaagggattg tgttttcata aatcttaata atccctgagg catcaagtac agtgatttgc 67740
atttactaaa tgctcaacaa atatgtgagg gattcacttg aaactaatat tagataattc 67800
ccagtcaaag tgatctaata gcaaatcaat tcttcagttt tataggcaaa gtatgactct 67860
ggttttccat aatcataatt aatttgtcaa ctttataatt ttaattaagt aaatttaatt 67920
ggtagataaa taagtagata aaaaataatt tacctgctta actacgtttc atatagcatt 67980
gcatttttct ttgtaaaatt taagaatttt gtattaataa actttttac aaaagtatta 68040
attattcagt tattcatcat atacttttat tgacttaaaa gtaattttat tcaaaagagt 68100
tagtatagga ctacatgaaa aattcaaggc caaggcttaa tttcaaattt cactgccttt 68160
ggctctatct tttaaaacaa aacaaaaaac tcccgcacaa tatcaatggg tatttaagta 68220
taatatcatt ctcattgtga ggagaaaaaa taattatttc tgcctagatg ctgggaaata 68280
aaacaactag aagcatgcca gtataatatt gactgttgaa agaaacattt atgaacctga 68340
gaagatagta agctagatga atagaatata attttcatta cctttactta ataatgaatg 68400
cataataact gaattagtca tattataatt ttacttataa tatatttgta ttttgtttgt 68460
tgaaattatc taactttcca tttttctttt agactttaaa gctgtcaagc cgtgttctag 68520
ataaaataag tattggacaa cttgttagtc tcctttccaa caacctgaac aaatttgatg 68580
aagtatgtac ctattgattt aatcttttag gcactattgt tataaattat acaactggaa 68640
aggcggagtt ttcctgggtc agataatagt aattagtggt taagtcttgc tcagctctag 68700
cttccctatt ctggaaacta agaaaggtca attgtatagc agagcaccat tctggggtct 68760
ggtagaacca cccaactcaa aggcacctta gcctgttgtt aataagattt ttcaaaactt 68820
aattcttatc agaccttgct tctttttaaa actttaaatc tgttatgtac tttggccaga 68880
tatgatacct gagcaattct tgttctgggt tgtcttatgt gaaaaataaa ttcaaggtcc 68940
ttgggacaga taatgtgttt tatttatctt tgcatatcca ttacttaaaa cagcattgga 69000
cccacagctg gtacaaaatt aattactgtt gaattgagca aatatttatt ctaaatgtct 69060
ctgtcaaatg acagagtgtg gttgtgtgga ttaagtccct ggagagagtt ctttgttctc 69120
tcatgttcta tgctgtggtt cttgctttat gcaaaaagaa gtaagttact taaaacctgg 69180
acatgatact taagatgtcc aatcttgatt ccactgaata aaaatatgct taaaaatgca 69240
ctgacttgaa atttgttttt tgggaaaacc gattctatgt gtagaatgtt taagcacatt 69300
gctatgtgct ccatgtaatg attacctaga ttttagtgtg ctcagaacca cgaagtgttt 69360
gatcatataa gctcctttta cttgctttct ttcatatatg attgttagtt tctaggggtg 69420
gaagatacaa tgacacctgt ttttgctgtg cttttatttt ccagggactt gcattggcac 69480
atttcgtgtg gatcgctcct ttgcaagtgg cactcctcat ggggctaatc tgggagttgt 69540
tacaggcgtc tgccttctgt ggacttggtt tcctgatagt ccttgccctt tttcaggctg 69600
ggctagggag aatgatgatg aagtacaggt agcaacctat tttcataact tgaaagtttt 69660
aaaaattatg ttttcaaaaa gcccacttta gtaaaaccag gactgctcta tgcatagaac 69720
agtgatcttc agtgtcatta aatttttttt tttttttttt ttttgagaca gagtctagat 69780
ctgtcaccca ggctggagtg cagtggcacg atcttggctc actgcactgc aacttctgcc 69840
tcccaggctc aagcaattct cctgcctcag cctccggagt agctgggatt agaggcgcat 69900
gccaccacac ccagctaatt tttgtatttt agtagagaca gggtttcacc aggttgccca 69960
ggctggtctc gaatgcctga cctcaggtga tccgcccacc tcggcctccc aaagtactga 70020
tattacaggc atgagctacc gcgcccggcc taaaaaatac tttttaagat ggtgtaaata 70080
ttactttctg tatcaatggt acatttttta cttgtcagtc tctagaattt ctttataaat 70140
atgttgattc agttcatttt tgtagattat aaaacaggta aaaaaggata aaacatttat 70200
gtgaattaaa gggaatacct aatttttgtg tagagtttat tagcttttac tactctggtt 70260
tatggatcat cacaccagag ccttagttac tttgtgttac agaataacta atatgagtga 70320
atgaatgact tacacaagtc actgcttagg ataaagggct tgagtttgtc agctagagta 70380
tgacagaaag tatctaagtt ttggagtcaa atagcacttt gtttgaatcc cagattgcat 70440
gcttactagt tatgtgacct tagtcaagcc acttcacctc actgagtctt tgctttttc 70500
atctctaaaa tagagatacc caccgctcat aggctgtcat aagggataga gatagcatat 70560
ggaatgagtc tgtacagcgt ctggcacata ggaggcattt accaaacagt agttattatt 70620
tttgttacca tctatttgat aataaaataa tgcccatctg ttgaataaaa gaaatatgac 70680
ttaaaacctt gagcagttct taatagataa tttgacttgt ttttactatt agattgattg 70740
attgattgat tgattgattt acagagatca gagagctggg aagatcagtg aaagacttgt 70800
gattacctca gaaatgattg aaaatatcca atctgttaag gcatactgct gggaagaagc 70860
aatggaaaaa atgattgaaa acttaagaca gtaagttgtt ccaataattt caatattgtt 70920
agtaattctg tccttaattt tttaaaaata tgtttatcat ggtagacttc cacctcatat 70980
ttgatgtttg tgacaatcaa atgattgcat ttaagttctg tcaatattca tgcattagtt 71040
gcacaaattc actttcatgg gctgtagttt tatgtagttg gtccagggtg ttattttatg 71100
ctgcaagtat attatactga tacgttatta aagaatttcc tacatatgtt cactgctgct 71160
caatacattt atttcgttaa aacaattatc aagatactga aggctgattg gtaactcaca 71220
tggaactggg agagtataca attctgaacc aaatagatga ttctctatta ttatatctta 71280
atttatgtgt tatggtatat taaacatgaa aaaaattgta tttggttaga atatgtttgc 71340
tcttccttaa ctcgggaatg acatagggta atattcacag attgggttcc tataaatcct 71400

```
ccacttgaag tgaagtcagt tcaagtaatg aaagctacct cctgagatag aatcagtact  71460
tggcacctat ctctagtgtt ctttcacctc atataacctt tcactgatta gtaaagatta  71520
tatccaacaa agaaagtaca gcacagactg agatatgatt actgagataa atttgggcaa  71580
aatataaact acagcatttc tgtagcaatg agaccatttt tcttcagttg agctccatgt  71640
tctacaaact tcaatcaaaa aaggttctag gagactcagt gaaagttgat acactgttca  71700
aggaacaaat aatttcagca catgggaatt tcacagggaa aaatatacta aaaagagagg  71760
taccattttg gatggtgtca atatgggtta tgaggaattc aggctgctga gtccagtgta  71820
caatggaaac tgagctgcag gtgtgtgatt gtaacaacaa aagaaatgct gaaatattaa  71880
gtcctttgcc atgtaaatag aaaaagagta tttatttccc aaacattatt gctcacctgt  71940
ttttgttatg cctttcaaga taaatccagg aaaggaattg cattttcttt ccagaaaaca  72000
agttcttggg ggaattgttc aattggtaga tgttgttttt ctcattaaca agtgagtgct  72060
ccatcacact tgctgagtgc tccatcacac ttgctctctg cattactcct ctgcctgcaa  72120
acacatatat agcaagggtg atgacaagga tatcagaggg tctggttttc tcaaactcat  72180
gataaactca tggctgggtc attcttggtg ctgattttac tttgtttttt gttgttattg  72240
ttccctcttc ctcaaaagat gaaatctatc cctcttactt ggaatttctc tttgatatat  72300
agcgaatgtt tggttgtaac ctgtataatc tggcatgaaa ttgtcactcg aaaaggctag  72360
aagtgttgac ataaatatgg gacagcaaga gttgctccta ctcaagagag caaatataat  72420
gttctggaag agattggcag aattcacatc aaaggagtga ttacttcagc ctgggccact  72480
gttgtactgg tcaaaaggct gtgcaaagct ctctgaaaat ccactctttt attgctcttt  72540
agtaataaag tcactttcaa ttttaaaaat aacaaactga tatattttta tgactcataa  72600
aatgttagca attatattat ggagaatcta ctttctgggt gattcttaca aatgttcttg  72660
gatctatttt tttttcttat agtacctatt cttcccattt ttctcagctc tagttaatat  72720
atttcaacaa cagttcaaca aatttaacat ttttataaaa agtgtttcct atcattttat  72780
aaataccagc ctagtccatg ttattccttt tcttgttgag gagaaaggac acacattgta  72840
aattcaaata tagacctcta ctgtgctatt taatcttggt aacaactcca caaaggagat  72900
gacatgtttt ccttctatag aggtagattc tgtaaagtta gagggaagag tgacttgctt  72960
aagatggcat aagctgtaac tggcagaacc aggattcaaa gccaggtggg atgccaaaat  73020
cataatctgt cttcagtgtc aagttactga aattggtaaa cattagacct aaatagacgg  73080
aattgcaatc cgggttgggc acattaaact ccattttctt catcaatgtg ctcagattac  73140
attttacttt tcaggctaaa aatggaaaaa aagagtccct cttagttctg cacttgagaa  73200
tgagaatagc ttttctgaat tatacaagga agaagaacta atgcccaaat gccaggtacc  73260
cacatgcact atgccatggc acagctgttg ccccctttca ccagagccct ctctctgtat  73320
cctggttgac ctttccttgg gcaagagctg ggtggggagg atcacaagtg actccaattt  73380
ggatggcttc gggaagactg ggaccgagct gaaggcagtg ttgtcctctg cactccctgt  73440
tttctgtctg ctggagcact gaagcctcac atatgtatta aaaaaataat ttccatttgc  73500
atttcagact agaagattga acgtatagtg taatgtgatt gcaaataatt atattgaaat  73560
gagacagaga ggatgtagta tctactgtca taatttttca aaacccacct gcaacttgaa  73620
ttaaaagaac cacttgggtt tttttttttg tttcaaacgc aaatcctgga aacctactga  73680
gactcattca gtcagtatct ctaagaggca agcttgagac tgtatattta aaaagcatct  73740
```

-continued

```
caggtgattt ttacacatgc taaggcttaa gaaccacttc tctgtagctt atatgttatt  73800
ttcaatgttc ctcaaagcca agttagaatt tccaaagtgt taagaatcca ttagacaatc  73860
acagaattgt ctttttcctt tataaatctt gcaatgttgt tctcatttcc atacttaatt  73920
acttaaaaca ccaaccaacc aacaagcaaa aaatgattag tctaactaat attacaagtt  73980
aataatgaag taaaggttta aaaataatgt cataataatg ttaataacaa attattaatt  74040
ataatttaaa aataatattt ataatttaaa aataatattt acaagtacta caagcaaaac  74100
actggtactt tcattgttat cttttcatat aaggtaactg aggcccagag agattaaata  74160
acatgcccaa ggtcacacag gtcatatgat gtggagccag gttaaaaata taggcagaaa  74220
gactctagag accatgctca gatcttccat tccaagatcc ctgatatttg aaaaataaaa  74280
taacatcctg aattttattg ttattgtttt ttatagaaca gaactgaaac tgactcggaa  74340
ggcagcctat gtgagatact tcaatagctc agccttcttc ttctcagggt tctttgtggt  74400
gtttttatct gtgcttccct atgcactaat caaaggaatc atcctccgga aaatattcac  74460
caccatctca ttctgcattg ttctgcgcat ggcggtcact cggcaatttc cctgggctgt  74520
acaaacatgg tatgactctc ttggagcaat aaacaaaata caggtaatgt accataatgc  74580
tgcattatat actatgattt aaataatcag tcaatagatc agttctaatg aactttgcaa  74640
aaatgtgcga aaagatagaa aaagaaattt ccttcactag gaagttataa aagttgccag  74700
ctaatactag gaatgttcac cttaaacttt tcctagcatt tctctggaca gtatgatgga  74760
tgagagtggc attttatgcc aaattacctt aaaatcccaa taatactgat gtagctagca  74820
gctttgagaa attctaaagt tttcaagtga taagactcaa tttatacaaa gctaattgga  74880
taaacttgta tatgattaag aagcaaataa atacttatta tgcttttttg ctgtttattt  74940
aaatatttaa cccagaaaat aagtcactgt gacagaaata aaaatgagag agaagggtga  75000
gccactctta ggtagttctg gcattattta atctaggcca gaggttgcaa atggtgtccc  75060
atagaactaa ttttggctcc tagacctgtc ttatttaacc tttcatttaa aaaatttgta  75120
ttggttgcca gcaattaaaa attgggagat gtctcacaca cacacacaca taaacacaca  75180
cactcatgtg tgcagcctct tttgaagaat tggaataact agtcaactgc gtcctccttt  75240
tccacaagct gtgacagctc cctgctcaca gagcacctgc cctctcctgt tcatcatgct  75300
ctcttctcag tcccattcct tcattatatc acctatttgg tcctgagact aagtgagttt  75360
gagatctgtg atttagacaa agtggtgaat ctagctctga atcatagtaa gtagctctgg  75420
gaatcatctt gtcttctgtt agcccattga gagagaaata gagagagaga gagagagaaa  75480
gaaagaagaa gaaacagatc tggggagagt cactgaatgg gagcatagag acagagaaac  75540
agatctagaa aaccaaactg ggagaaaatg agagaaacca aaagagaggt agagaggagc  75600
agagaagaaa atgaagaagc aaggcaagga ccaggctttt tcattatttc ttatggccaa  75660
gacttcagta tgcgtggact taattcttcc ttatgctcct accttcccta gggaaactga  75720
tttggagtct ctaatagagc ccttctttta gaatcacagt ttgatgcctt aaaactagtt  75780
atataccttc acatgcttcc ttaacccaca gaagtgatgc taatgaggcc cttaataagg  75840
agcgtgctat taagatgaag acattcattt tttttctccg tccaatgttg gattaaggca  75900
cattagtggg taattcaggg ttgctttgta aattcatcac taaggttagc atgtaatagt  75960
acaaggaaga atcagttgta tgttaaatct aatgtataaa aagttttata aaatatcata  76020
tgtttagaga gtatatttca aatatgatga atcctagtgc ttggcaaatt aactttagaa  76080
cactaataaa attattttat taagaaataa ttactatttc attattaaaa ttcatatata  76140
```

agatgtagca caatgagagt ataaagtaga tgtaataatg cattaatgct attctgattc 76200
tataatatgt ttttgctctc ttttataaat aggatttctt acaaaagcaa gaatataaga 76260
cattggaata taacttaacg actacagaag tagtgatgga gaatgtaaca gccttctggg 76320
aggaggtcag aatttttaaa aaattgtttg ctctaaacac ctaactgttt tcttctttgt 76380
gaatatggat ttcatcctaa tggcgaataa aattagaatg atgatataac tggtagaact 76440
ggaaggagga tcactcactt attttctaga ttaagaagta gaggaatggc caggtgctca 76500
tggttgtaat cccagcactt tgggagacca aggcgggtgg atcacctgag gtcaggagtt 76560
caagaccagc ctggccaaca tggtaaaacc cggtctctac taaaaataca aaaaattaac 76620
tgggcatggt ggcagatgct gtagtcccag ctgctcggga ggctgaggca ggagaatcac 76680
ttgaacctgg gaggcggagg ttgcagtgag ctaagatcac gccactgcac tccagcctgg 76740
gcaacaaggc gagactctgt ctgaaaaaga aaaaaaaata aaaataaaaa taaaaagaag 76800
tggaggaata ttaaatgcaa tataaaagct tttttattt ttaagtcata caatttgttt 76860
cacataacag atcaggaaat aatacagaga tcataagttt tggagctggg tttgaatcct 76920
ggctctgcca tttactttct gtgtaatcta agtcaagtta ctgaactttg tgggccctct 76980
ggctctccat gtgtaaaatg gagaatatta atatttacct tgcaagtttg ttgtgaagac 77040
tgaaggagag aatttaggta aaacattcat cagagtacca tgcacacagt tgttcctcaa 77100
taaacattag cttctctgat tgcaagttcc agtctaaagt gctttatata taccagccaa 77160
taaaaggatg cgagagagat ataccagtgt attgttttct accattttaa acctattttc 77220
atccactgtt acaaattcta tcatactgct ccacataaaa aatattatca atgattttta 77280
gtctctgaag tgcaatattt gattattgag cacacctgtt gaagttttag tttcttctca 77340
cttacatggg ttgtgtaaag gtaggaggta taaaaccagt gtcctaggtc taaatctttc 77400
ttaatgtcat actttggatt cattgatata agtaacttga gcaccagcgc ttcattttac 77460
ttcatttttt aaagatatag taagagtaat tcccatctgc ctagcaaaat tgttttgtag 77520
aaaagtttgt ggatcagatt tattttactt tgattttagg aatttcaagt gtcttcgtcg 77580
gcatgaagga aaaatatgca gtttgacatt ttctactact ttcaggtcat tattttccta 77640
ctctggtgca aaaaccctca attcctgtct cactccatct aatcaaatag gtagcatgct 77700
tgagccctta ctatgtgcca ggcactagga taagcacttt atatgttttg tcccaattaa 77760
ttctcacagc atttctatga cctaaataaa attaatattt tcatttcacc aataataaaa 77820
tggaggcttc aaaaagttta gggacttggc tcagctcaca caactggcaa ggactgaaaa 77880
tggattttag tcccaaatgt cataggctag agccctttca ctaaactgtt gtcttccatc 77940
tggtggcatc ctcttcctcc agtctttgtc acctaaactc tgggcacccc ttgatggcat 78000
ttacttatga tggtgatgct tgttaaactt cctgtttgcg acttcaacgt ccatataaat 78060
gagtcttcca atactgtact tagaacttat attttgtagt gacttcttta aaagctttct 78120
ctcttagtca tatcctgagt tttgttagca cctggactta ccttactttg gaaatgttgc 78180
actctgaaat ctctttctca gcttggaatt tcctaatctt ccaactgttt gagtctttta 78240
attctacatt tactgccttt ccatttcatc aggatttcta gtctctttaa ttcttccttt 78300
tgaactcctc ctgatttaac ctctgcttat tcgaagaaca ataattttat tctctcagct 78360
gcactctcaa ttccctttc cttttggtga tttttctttt tcctacagaa cacttacttt 78420
atcagttttg gagaaggaag tgctatctgg gtaacagtag tgctatctgt tgactctagt 78480

-continued

```
caactgtaag ttttatacat ttattgttta aaccttatat gggtctataa tccttcttgg  78540
gaaatccttt catttgtctt taatttcctt taccatttcc ctaaaggcta ttccagattt  78600
ttatcacatt cacaaaattc ccgtcttttc tcaggatctg ttcaccccca gtagatagcc  78660
ttgtctccca caatacatgg agaaaataga ggccaccgtc atatttgaat gtttccaact  78720
tctctcttca cctttggaat tatctttttc ttcttttgtg tctaagagaa agatgtatac  78780
ttcttcttac ccttgtctga actactctat tttgcttcat cttctcagaa caggggacca  78840
gcaattattc ttcctccaga agcttcaaca tcttttgtca actgactcct tctcatgttt  78900
aaatatttc aagttaaaca atttctttcc tgactttcgc tcacgcaacc tcatgcccaa  78960
aaccttatca ctcttcttcc ctttgctgtc aaggctgttc tcacttcttc actttttgtg  79020
gacttctccc cactacaaca tagattctgc tatcaccaat ctattaaaac tgttatactc  79080
ttgtggaatt tatcatttaa tttagcttca gtgaaccgtt ctttccagat tattttggcc  79140
tcagaccatg acttctaagt ctgccgtgct tgccacttaa gtgatgatgg gccagtgggt  79200
ccccacctag gcctctgtgt tagtctgttt tcatgttgct gataaagaca tacccaagaa  79260
tgggcaattt acagaagaaa ggggtttgag ggactcacag ttccatgtga ctggggaggc  79320
ctcacaatca tggtggatga tgaaaggcat gtctcacatg gaggcagata agagcataga  79380
acttgtgcag ggaaacttcc ctttattaaa ccaccaggtc ttgtgagact tcttcactat  79440
cacgagaata ggatgggcaa gaccctcccc catgattcaa ttatctccca ctgggtccct  79500
cccacaacac atgggaatta tgggagctat aattcaagat gagatttggg tgaggacata  79560
gccaaaccat atcagcctcc ttctggcttt ttatgttctc cgtgggtgac ctctctcagg  79620
ctcaagtgat aaccaatgtg ctgatgactc tcaaatgcgc atctctggct tcagtttctt  79680
ccttgaactt catacatatg tttccaaatt tcctgcgtgt acctcaaggt tcttgttcat  79740
cacttcccaa gcttcataaa cgcactcatt ttagtgtatt ctctgtctcc tttgatagca  79800
tccctgagag gcaagtccct ggtgagttat atacaactcc tcccttgctc caaacctgag  79860
agtaagtaac attcctatta acatattagg aagctgaggc ttagacagtt taagtaactc  79920
aagcatggtt acacaactag ctagggcaga gctaaaatgt caggctaggc ttctgtgact  79980
ccaaagccct ttctcactta gcatatcatc acttattttt ttttttaatc acatatatga  80040
tttttttttc tttaagagat agaatcttgc tctatcacgt gggctggagt gcagtggcac  80100
aatcatagct cactgtaacc ttgaacttgg gctcaagtga tcctcctgcc ttagcctact  80160
gagtagctag ggctacagac acacaccacc atgcctagct aattttattt tattttattt  80220
tatttttga gacagagtct cactctgtca cccaggctgg agtgcagtgg tgcgatcttg  80280
gctcactgga acctctgctg cccgggttca agcgattctc ctgcctcagc ctcctgagta  80340
gctgggatta caggtgcctg ccactgtgcc cagctaattt ttgtattttt agtagagacg  80400
gggtttcacc atcttggcca ggcttgtctt gaactcctga cctcgtgatc cactcgcctc  80460
ggcctcccaa agtgctggga ttacaggtgt gagccaccac gcctggccac ctacctaatt  80520
tttaattttt ttgtagagac agggtctcac tacgttgccc aggctggtct tgaactcctg  80580
ttctcaaaca atcctcctgc ctcggacacc ccaagtgcag ggattacagg catgagtcat  80640
tgcagctgac ctgtatatat gatttttagt atatgtaaat atacatattt attaaatgta  80700
aatataaata taaatgtgtg gagtgatatc cattgaaatg ttaaacatag ttctcagtgg  80760
tacaactaca ggtgatttct cttttcttat ttctggtttt ctgtgttttc caaatttctt  80820
gaaatgtgtc ttctgtaatc agaaataaaa gttattagta acaacagtct tccactggta  80880
```

```
caagtgctta ttggataaaa gtcccacttc taagcatgat actcacaact tttaggttaa  80940
tagcctttgt caccttgcca tatacatctg atccagccac tcacaccatt cctgagatat  81000
attttgttcc tttgtgccta aatcattgtg catgcagatc catcttcctg gaacacctat  81060
aaccatttct tagtcctgtg aaatcctact tacatccttc atagcctagc atgtatgtca  81120
tttatttggt caagggtgag ttggttgttc tcttgaatgt actgccatat gacgtggtgt  81180
gatttcaatt gtagcaccaa gctcattgca atattaattc gtttgtcatt ctcccatgta  81240
ggatgtttga agtagtttct aacacagaga ttatactcaa taaatattta ttagataaat  81300
aaatgaataa gggaataaca aatgcctttg tctcatttta aaatactttc attgttagct  81360
acccatataa taaaaaacta aaagcagtag ttttcaagca tgattgttta tgtatgcctt  81420
aaaagaattt tgaaaaccta tgtacccctg acacactttt aagttaactt ataaattttt  81480
caacatagtt ttaagtggtg gcaaatgatg tagtttcttg tgtattttaa actgcttaag  81540
tatgctatac atggatttct tcaaaaccct gaagctgcag tttcagtgca ttcaatttat  81600
ggaaaagaaa ttaatttata aaattggttc ttattgtcaa gtcaatcagc taaatataac  81660
ttgctttctg tcaggaaaag tctgacttta aaatacagat aagtaataac tattattaat  81720
taattaaatt attaaaatta aaataattaa ataatttgtt aattaaaatg ccttattccc  81780
ctacttattt ctgcaatttg actctaagaa tagataggac atgtagattg ccttaggttt  81840
gaaatctggg tgaaataaga tactgcctcc ttcagtattt ctgcctttgc ttttatggga  81900
gcctctttca agaaaaagtc attctctcat ggtccctttg tttgagtccc agaggttttc  81960
ctactccaga aagtgcaacg tagtgagact agtactatac tcccttgcat ggtaagtgag  82020
aaggctgtct gtataaaatg agggaaggac tcatgagagg gaagtaggtc aggagaaatg  82080
ataggttctc aggcaggtta attttaggaa agagtgaata gagtccctta aaacaaggtg  82140
catctgcttc ctcctgatca atctttagga ctgtttactt tgatttgaag accactatgc  82200
taaagcttcc cacgggggca atagtgaggc aaggaatttt taaaagggaa ttacttcttc  82260
gtagctactt ttgtgaaatg aattcatttg aattatctgg caatctcttc atatttatat  82320
tcaacaataa ttacttaaag aaatgctttg agcttctcag aggagggtgc taccagtgtg  82380
atggagtaga attcagattt gggtagtgac tttaaagctg tgtgacttta gtcatttaac  82440
tgctgagtca cagtctacag ctttgaaaga ggaggattat aaaatctatc tcatgttaat  82500
gctgaagatt aaataatagt gtttatgtac cccgcttata ggagaagagg gtgtgtgtgt  82560
gtgtgtgtgt gtgtgtgtgt gtatgtgtat gtatacatgt atgtattcag tctttactga  82620
aattaaaaaa tctttaactt gataatgggc aaatatctta gttttagatc atgtcctcta  82680
gaaaccgtat gctatataat tatgtactat aaagtaataa tgtatacagt gtaatggatc  82740
atgggccatg tgcttttcaa actaattgta cataaaacaa gcatctattg aaaatatctg  82800
acaaactcat cttttatttt tgatgtgtgt gtgtgtgtgt gtgtgttttt ttaacaggga  82860
tttggggaat tatttgagaa agcaaaacaa aacaataaca atagaaaaac ttctaatggt  82920
gatgacagcc tcttcttcag taatttctca cttcttggta ctcctgtcct gaaagatatt  82980
aatttcaaga tagaaagagg acagttgttg gcggttgctg gatccactgg agcaggcaag  83040
gtagttcttt tgttcttcac tattaagaac ttaatttggt gtccatgtct cttttttttt  83100
ctagtttgta gtgctggaag gtatttttgg agaaattctt acatgagcat taggagaatg  83160
tatgggtgta gtgtcttgta taatagaaat tgttccactg ataatttact ctagtttttt  83220
```

-continued

```
atttcctcat attattttca gtggcttttt cttccacatc tttatatttt gcaccacatt  83280
caacactgta tcttgcacat ggcgagcatt caataacttt attgaataaa caaatcatcc  83340
attttatcca ttcttaacca gaacagacat tttttcagag ctggtccagg aaaatcatga  83400
cttacatttt gccttagtaa ccacataaac aaaaggtctc catttttgtt aacattacaa  83460
ttttcagaat agatttagat ttgcttatga tatattataa ggaaaaatta tttagtggga  83520
tagtttttttg aggaaataca taggaatgtt aatttattca gtggtcatcc tcttctccat  83580
atcccaccct aagaacaact taacctggca tatttggaga tacatctgaa aaaatagtag  83640
attagaaaga aaaaacagca aaaggaccaa aactttattg tcaggagaag actttgtagt  83700
gatcttcaag aatataaccc attgtgtaga taatggtaaa aacttgctct cttttaacta  83760
ttgaggaaat aaatttaaag acatgaaaga atcaaattag agatgagaaa gagctttcta  83820
gtattagaat gggctaaagg gcaataggta tttgcttcag aagtctataa aatggttcct  83880
tgttcccatt tgattgtcat tttagctgtg gtactttgta gaaatgtgag aaaaagttta  83940
gtggtctctt gaagcttttc aaaatacttt ctagaattat accgaataat ctaagacaaa  84000
cagaaaaaga aagagaggaa ggaagaaaga aggaaatgag gaagaaagga agtaggagga  84060
aggaaggaag gaaagaagga aggaagtaag agggaagcag tgctgctgct gtaggtaaaa  84120
atgttaatga aaatagaaat taagaaagac tcctgaaagg caattattta tcaatatcta  84180
agatgaggag aaccatattt tgaagaattg aatatgagac ttgggaaaca aaatgccaca  84240
aaaaatttcc actcaataaa tttggtgtca ggctgggtgc agtggctcac acttgtaatc  84300
ctagcacttt tggaggcaga ggcaggtgaa ttgcttgagt ccaggagttt gagaccagcg  84360
tgggcaacat ggcaaacccc acctctacaa aaaacacaaa caaaagaaaa tagctgggtg  84420
tggtggtgtg tgcctgtagt cccagctact tgggaggctg aggtgggagg atcacctgag  84480
cctgagaagt ggaggctgca gtgagccatg attgcaccac tgtaccctag cctaggtgat  84540
aggctcaaaa aaaaaaaaaa ttggtgtttg caatgctaat aatacaattt ggttgtttct  84600
ctctccagtt gttttcctac atacgaaaca gcttttaaaa caaaatagct ggaattgtgc  84660
attttttctt acaaaaacat tttctttctt aaaatgttat tatttttctt ttatatcttg  84720
tatattatta ctagcagtgt tcactattaa aaaattatac tataggaggg gctgatacta  84780
aataagttag caatggtcta aacaaggatg tttatttatg aaaaggtagt aattgtgttt  84840
catagaattt ttaaaattaa ttctgcgtat gtcttcaaga tcaattctat gatagatgtg  84900
caaaaatagc tttggaatta caaattccaa gacttactgg caattaaatt tcaggcagtt  84960
ttattaaaat tgatgagcag ataattactg gctgacagtg cagttatagc ttatgaaaag  85020
cagctatgaa ggcagagtta gaggaaggca gtggtccctt gggaatattt aaacacttct  85080
gagaaacgga gtttactaac tcaatctagg aggctgcctt ttagtagtat taggaatgga  85140
acactttata gttttttttg gacaaaagat ctagctaaaa tataagattg aataattgaa  85200
aatattaaca ttttaagtta aatcttaccc actcaataca atttggtaat ttgtatcaga  85260
agcttaaaag ataacctaat agttcttcta cttctataac ttacccaaat atgtttgcag  85320
agatcttatg taaagctctt cattataaca ctgctttcag gagccaaaaa ttgggtgggg  85380
gagccccata aatgttgaat aataggggtt tgattagata aattttggtg tagttctata  85440
atggcgtgtt attcagccaa taaaaggttt gttaaagaat gactgtgacg gatgtatatg  85500
atatactctt aagtgaataa agagttacaa aatgttatgt acaagttaca aaatgtatgt  85560
acattatgat ccatttttca taaaatcata tgtatgtata tatgtgtgtc tggaaggata  85620
```

aatttatcaa gttgttatct ctgaaatttt gggtatattt tatatttcta gattttctgt 85680
tactttgtta ctttactgat aaagtaataa cgttgttgac ttttgtcact ctcccctatt 85740
aataatcatc taggctgcaa aaggatcatg tcttctttat ttttatattc caaggactgt 85800
caacaagtgc ctagcacttg acaggtatat tatagaaatt taactgaata tctttaggaa 85860
atagattttt gtttgtagtt gttctagtct acattaaatg tcttgcgctt atgaaacttc 85920
cttgaattat tttagtgaag caatattagt atagaatttt gcatcactgg atgcccttga 85980
ctgaaagctg gcttatggca tctcaccagt gtgtggggag tttcagtcct tctgttgtct 86040
gcatcacagc tgaagcagtg ctgttgctga caattcctga caccaccttg tctctattat 86100
tgatcattgc ctcactatgg tactgagttt tagcttattc ttgtaataac tgggactcat 86160
atgtatagaa taagctatta gctcacgttt ttgcttgctt tttatacaga atacatgtct 86220
gcaaatagtt ttatcaatat tttggaattt tgggagatat gaagttaaaa acatcattga 86280
atatatatat atacacacac acatatatat atgacactat acatgattta ttttatttaa 86340
tttttaaaat tttattcttt ttagagatta ggtcttactc tgtcacccag gctgaacttc 86400
agtggtgtga tcatagctca ctgtaacctt gaactcctgg gctcaattga cctttccgct 86460
tcagcctccc aaagtgctgg gtttataggc atgagccact gtgtctggtc caatatgcat 86520
atatatattt ttaacctgga ttatcagagc tatattgtgt ttaggtttat aaagctgtac 86580
tatgtgaaaa tatcacttct aggtttaatt ttgtacaaag gaattttata tagaaatgag 86640
gtaattcaga tttttcccca tgtaataaga attgtaaaat ttactgaaac aaacatcaaa 86700
aagatatctg ttacatgacc ttcctttctt ttgaatatat ttcaggtgat attatttatt 86760
aaaatttaaa aatgaaaatt aaaatatata aaaagttgaa aattattcct ttctttactg 86820
tctctcatct gtccattttc cattctcctg cattccctca tccaaccaag gtagccaatc 86880
caggtaactt tttttagtat cttcccagag atgtttctct ctatatatat aatcaatata 86940
catttttat tattccccac ctctcttttt atgtaacaat atgcagagtt ttgcttcttg 87000
cttttcccac tatcttggac aactttccat attcaaagca cagaggactt gcacatatgt 87060
tcagactgct gaatatttct gtctctcccc tgccattcat atgttgaaat cctaattccc 87120
aaggtgatgg tattgcaggg tggggccttt gggaggtgat tagtccatga gggtgaagtc 87180
tttagtaaat gagattagtg tctttataaa agaaacctta gagagaccct cacaccttag 87240
agagaccctc accccttttct gccatgtgag aacacagcag gaagacagct ggctatccag 87300
gattcaggag tctcttagca gacccaaatc tgctggcacc ttgatcttgg acttcccagc 87360
ctccagaact gtgagaaata aattcctgtt gtttataagc cacacagttc atggtatttt 87420
gttatagcag cctgaacaag gacacacaca cacacacaca cacatgcaca cacatttaaa 87480
tagatgcata gtattctatc atatggatgg atattctatg atataatgaa tcactattga 87540
ttgacatttg ggttgtttcc aatattttgt taacacaaag aacaacacta caaataactt 87600
tatatacata tcatttagca catctgcaat tgtatcagta ggcttcctat aagtggtcaa 87660
gcatttgtgt acttgtgatt ttggtagatg ttgtcaaatg tccttccctg aaatttgtac 87720
caattcgtac tcatgccata cactctaaat agagtgctga tttccccaca gcattactaa 87780
cagatgatat tatctaattt aaaaagtttc tcatcttata gggaaaatag tatgtcaatg 87840
tattcttaac ttgcatttct tttattataa gtagtgtaaa atatcatttc aacttataca 87900
caggaggaat ttctctctat ataaagtgat cctagaatca taatgaaaaa tatcaccaac 87960

-continued tcattaggaa aatgtacaaa ggattgaata gatatctcat caaaaataaa aatataagtg 88020
gcctttaaac attgaaaggt aacatttgaa caaagacttg caggaggtga gggattaggg 88080
aatgcagact ctgggaagag tcttccaagt agcaggtgaa gcaagtgcaa agctttcaga 88140
tgggactgac tatacctgtc tggtttgaag aacagtaagg aggtcactga ggctggcata 88200
gagtaagaca gggagggtag aatactgtca gagaagtaat cggcggtgga ggtagggggt 88260
aaaccataaa gtgctcgtaa agactaaggc ttatttctct gggtgagatt agaggccact 88320
ggagagtttt aaacagaagt aacagggcca ctttggctaa tgtttttagg ctattctgta 88380
gggagacaag ggaggaagca aggagatgag ttaggagtct attgtgccag ttcaggcaag 88440
tgatgatggt ggcttgatcc aggtagtagt ggaagtagta tagtaggaag tgatcagatt 88500
caggacatgc tttgaaggaa gatccaatag gattaatgga taagttgaac aatggcatat 88560
gagaaaagtc acagaggagt caaagatgat tccaagcttt ctggactgag taactggaag 88620
gataaatgtg ccgtttacta gaaagataat gggagaaaca ggttttggat ggagcttggt 88680
ttgggaatat taagtttgaa atgcctattt gacatccaaa tagagatgtt agttggatgt 88740
acaagtctag tttcaaggaa gagggggctg gtagtgtgaa gatggggctg gataagattc 88800
taaaggaaag agggttgata agaagagaaa ggggtgtagg ggttagccta agggcattct 88860
aagtattaga ggttaaggag gtgggtgaag aaaacccaat aaaataaaag tctgagaaga 88920
caaagctagt gaatgaatgt ggtatcccgg aacccaactg atgtcaagca gaagggtgtt 88980
atcaactagg tcaaatgctc attcatcaag taagatgaaa ctgttataat taaccggtgt 89040
cttctgaaat acggagataa ctcgtgactt aatgaaagca atagtagaga aggtcaaact 89100
tgaccagaat gaaattagaa agaataagag gaaagaaaag accaaataca gacaaccatt 89160
gatgccttat tcttttgata tactcctgga gtccacttgc taatacaatt gacccttaaa 89220
caatacaggc ttgaactgca tgggtccact tatttgtgaa ttttttttca gttaatacat 89280
tggaaaattt ttggggtttt ttgacaattt gaaaaaactc acaaactgtc tagcctagaa 89340
ataccgagaa aattaagaaa aagtaagata tgccatgaat gcataaaata tatgtagaca 89400
ctagcctatt ttatcatttg ctactataaa atatacacaa tctattataa aaagttaaaa 89460
tttatcaaaa cttaacacac actaacacct accctacctg gcaccattca cagtaaagag 89520
aaatgtaaat aaacataaaa atgtagtatt aaaccataat ggcataaaac taattgtagt 89580
acatatggta ctactgtaat aatttggaag ccacttcctg ttgctattac ggtaagctca 89640
agcattgtgg atagccattt aaaacaccac gtgatgctaa tcatctccgt gtgagcagtt 89700
ctctctccag taaattgcat attgcagtaa aaagtgatct ctagtggttc tcgcatattt 89760
ttcatcatgt ttagtgcaat gccataaacc ttgaataaca tcaagcaatc catacaaagt 89820
gccactagtg atgcacggaa aagttgtaac agtacaagaa aaaagttgag ttgcttggta 89880
tttaccatat attgaggtct gcagctacag ttgcctgcaa tttcgagata aatgaaccca 89940
gtataaagac tgttgtaaca aaagaaaaga aaatgtgaaa ccatcagtgc agctatgcca 90000
gcaggtgtga agtcttgcac tttttgcaaa atacaaaata tgaaatatgt gttaattgac 90060
tgtttatgtt atctgtaagg tttccactca acaataggct attagtagtt aagtttttgt 90120
ggagtcaaaa attatacgtg gatttttgac tatacagtgg gttggcaccc ctaaccttca 90180
tgttgataaa gggtcaatgg tatattattt aattttttttg tatttatatt cataaataag 90240
attaaatcta tatttccaag taatctctat aagattttgt tattaatatt actattattt 90300
ttgagacaga gtcttactgt caccaggctg gagcacagtg gtgcgatctc ggctcactgc 90360

-continued

```
aacctctgcc tcccgggctc aagcaattct cctgcctcac cctcccaagt agctgggact  90420
acaggcacgc acaaccacac tcagctaatt tttgtatttt tagtagagac ggggtttcac  90480
catgttggcc aggatggtat tgatctcttg acctcatgat ctgcctgcct cggcctccca  90540
aagtgttggg attacaggca tgagccactg tgcacagcca ttaatattat tgttacccaa  90600
taaaaaaaat ttggaaactt gtcttctttt cccctgattc tgtttaaata gcactggagt  90660
tacctgtttt gaattttttt tccaagcggt cccttatgag ttttctctat gttttatttg  90720
tttcatttct tttttttttt tttttttttt ttttgagacg gagtctcgct ctgtcgccca  90780
ggctggagtg cagtggcggg atctcggctc actgcaagct ccgcctcccg ggttcacgcc  90840
attctcctgc ctcagcctcc caagtagctg ggactacagg cgcccgccac tacgcccggc  90900
taattttttg tatttttagt agagacgggg tttcaccgtt ttagccggga tggtctcgat  90960
ctcctgacct cgtgatccgc ccgcctcggc ctcccaaagt gctgggatta caggcgtgag  91020
ccaccgcgcc cggcctgttt catttcttat atcgtatttt tgcaactcct ttattgatac  91080
ttttcttcct gattaggttt ctactaaaac caaacaagct ttccatgaat tagcttttag  91140
atttacttat tagtttaact gttctgttgt attgtaactc attaatttat aattttatct  91200
ttattaatta ttctattttt cttcgctttt ttgttgtttt tctagttttt gagttagatg  91260
tttgacgctt ttttaaaaag ctgtgcattt tcctctgggt aatactttag ctgtatatta  91320
tgtattctga tatatagtgt ttccattaca ttgttttcta gaaaatctgt agctttgatt  91380
tatatttgtt tcctctttga cctaagatat cctaagggaa aatttaacat tttccagaaa  91440
gaaaacaaat tttctttgtt ttccaagaat gttgttcaaa ttatttctac tgcttggaat  91500
ttttatcatt tttgtgtatc cagtaaatag tcaatatttg tacttgctct ctgaccacat  91560
aaaagaatat attcgtgtag tttctattaa tagattagag ttcaattcag atattaaatg  91620
tacatcatta ttcatgatat ttaggtcttc tacatcttca cttatctttt ttctacttgc  91680
tttgccatta acagataaag ttgaattaaa ggcttctact acatacattt ctccctgtta  91740
ttccttatag gttctgtaat ttttgcttca agaatattgc tttttaaatt taatatatag  91800
atacttataa ttacactcta gcattataaa gagccttttc tttttcattg aatgtatttg  91860
ggcctgcata tgtctaacat gaaaattata gtcctttttt tgtttctttg tttgtattta  91920
cagttttaag ttccattttc aacctttatg cactctttgc tttaggtgtg tctcttttag  91980
ttagcataaa gttaggtttg tctttaattt cacctgaagt cttttcctct taatagatgg  92040
gttaagccaa ctgaaaaata aaactgactt atatactttt atttcaagta tgtcctccac  92100
aaatattttt tgaatagatt agcttatata ctttggaatt tgttaaaaaa agatttttat  92160
aaaaaaataat tgtggtgaaa tgtacataac ataaaattta tcattttgac catttttaag  92220
ggcatagctc tgtggcataa agtatactca catagttgtg caactatcac ctccttttga  92280
ttttttttta ctaattttgt aaatttgttt catctgagct gtcttattat gttttgtttt  92340
atgtttttct ttcctttatt atgaagtcac tgtattgtct gtaggctata tgtatctgtg  92400
agtgtgtgtg tatatgtgtg tattatggtt tttaaaaaag tctatatttg ttttccagtg  92460
gctatactta atactaataa ctttatgtta aatttttcat tctatgtgac tctagttcac  92520
taatatgagc tctgataaaa tcagtgcttt ttcgaggtta ggagatcaag accatcctgg  92580
ctaacacagt gaaactccgt ctctactaaa aatacaaaaa attagccaga cgtgatggcg  92640
ggtgcccgta gtcccagcta ctcgggaggc tgaggcagga gaatggcgtg aacccaggag  92700
```

-continued

```
gcagaacttg cagtgagccg agatcgcgcc actgcactct agcctgggtg acagagtgag  92760
actctgtctc taaataaata aataaataaa taaataaata aataaaatca gtgctttttc  92820
ttcctctgct acctcctttc cttctactca gttttagtca gtagtattat ctttttttcag  92880
atttatcttt gtattgttaa atctgcttat gcttctatta ctttatttat tagctttaaa  92940
tgatacctttt tgactttcag cttttcttaa taaagcaatc agcaaatttc ctttacactc  93000
cacacttata ccccatttcc tttgtttgtt tatttggttt ttacttctaa cttttcttat  93060
tgtcaggaca tataacatat ttaaactttg tttttcaact cgaattctgc cattagtttt  93120
aatttttgtt cacagttata taaatctttg ttcactgata gtccttttgt actatcatct  93180
cttaaatgac tttatactcc aagaaaggct catgggaaca atattacctg aatatgtctc  93240
tattacttaa tctgtaccta ataatatgaa ggtaatctac tttgtaggat ttctgtgaag  93300
attaaataaa ttaatatagt taaagcacat agaacagcac tcgacacaga gtgagcactt  93360
ggcaactgtt agctgttact aacctttccc attcttcctc caaacctatt ccaactatct  93420
gaatcatgtg ccccttctct gtgaacctct atcataatac ttgtcacact gtattgtaat  93480
tgtctctttt actttccctt gtatcttttg tgcatagcag agtacctgaa acaggaagta  93540
ttttaaatat tttgaatcaa atgagttaat agaatcttta caaataagaa tatacacttc  93600
tgcttaggat gataattgga ggcaagtgaa tcctgagcgt gatttgataa tgacctaata  93660
atgatgggtt ttatttccag acttcacttc taatggtgat tatgggagaa ctggagcctt  93720
cagagggtaa aattaagcac agtggaagaa tttcattctg ttctcagttt tcctggatta  93780
tgcctggcac cattaaagaa aatatcatct ttggtgtttc ctatgatgaa tatagataca  93840
gaagcgtcat caaagcatgc caactagaag aggtaagaaa ctatgtgaaa actttttgat  93900
tatgcatatg aacccttcac actacccaaa ttatatattt ggctccatat tcaatcggtt  93960
agtctacata tatttatgtt tcctctatgg gtaagctact gtgaatggat caattaataa  94020
aacacatgac ctatgcttta agaagcttgc aaacacatga aataaatgca atttattttt  94080
taaataatgg gttcatttga tcacaataaa tgcattttat gaaatggtga gaattttgtt  94140
cactcattag tgagacaaac gtcctcaatg gttatttata tggcatgcat ataagtgata  94200
tgtggtatct ttttaaaaga taccacaaaa tatgcatctt taaaaatata ctccaaaaat  94260
tattaagatt attttaataa ttttaataat actatagcct aatggaatga gcattgatct  94320
gccagcagag aattagaggg gtaaaattgt gaagatattg tatccctggc tttgaacaaa  94380
taccatataa cttctagtga ctgcaattct ttgatgcaga ggcaaaatga agatgatgtc  94440
attactcatt tcacaacaat attggagaat gagctaatta tctgaaaatt acatgaagta  94500
ttccaagaga aaccagtata tggatcttgt gctgttcact atgtaaattg tgtgatggtg  94560
ggttcagtag ttattgctgt aaatgttagg gcagggaata tgttactatg aagtttattg  94620
acagtatact ccaaatagtg tttgtgattc aaaagcaata tctttgatag ttggcatttg  94680
caattccttt atataatctt ttatgaaaaa aattgcagag aaagtaaaat gtagcttaaa  94740
atacagtatc caaaaaaatg gaaaagggca aaccgtggat tagatagaaa tggcaattct  94800
tataaaaagg gttgcatgct tacatgaatg gctttccatg tatatactca gtcattcaac  94860
agtttttttt ttagagcccc attcttattt tttatacact ttgagagcat aatgaaaaga  94920
aaagctacct gcaaaagttt tggacttacc tcaaagagga tatacttcat tcctcaaaag  94980
gccttcttcc aggaatagta tttcataacc tggaggttgg aaaaatctgg atttgttaca  95040
aaaaaatctg agtgtttcta gcggacacag atatttgtct aggaggggac taggttgtag  95100
```

cagtggtagt gccttacaag ataaatcatg ggctttattt acttacgagt ggaaaagttg 95160
cggaaggtgc cttacagact tttttttgc gttaagtatg tgttttccca taggaattaa 95220
tttataaatg gtggtttgat ttcctcaagt caacctttaa aagtatattt agccaaaata 95280
tagcttaaat atattactag taataaattt agtactgtgg gtctctcatt ctcaaaatga 95340
gcatttacta atttctgaac actgtgctag gtcctgggaa taccaaattg aataagacat 95400
agtctatttt tctgaagggt ttatagcaga gtcccctgtg ttaataatga aggagtgtgt 95460
ggtatgtgaa tcatatatca atagggttgt taaaaataat gaaaaaagga gaagaggaag 95520
aacatctttt ttttttctga ttgcacgggc agccttaaaa ttatttttga agtgtacaat 95580
tcagtgtttt tttagcatat tcacagggtt gtattatcat caccatattt ttggcctctt 95640
gaaaagaaat cctgtgccta ttagcatcca attaccgttc ctttgtagct aagtctcccc 95700
cattccagct ttaaacaatc acccatctac tttctgtctc tataaatttg tctcttttgg 95760
acatttcaca taaatgaaat aatataatag ggttttttgt gcctaaataa gcttctaaag 95820
aagaataagg taaggaatca tcattcagca aatatttatt aagacttgct ttattttata 95880
cagtgtacta ggagctggag atgaaaatat gtgtagaaca tgaatcatat acttcgggaa 95940
tttgtggact agtgggaaag attgacatat caataacaaa tcgaattagt gatgtaatag 96000
aggcattttt acaggagtaa aatgaggtag catggactct atctgggtct gaataatgtg 96060
aggagtaacc tccttacaca aagaggcaca aggctaatgt cctctgatgg aatgattcac 96120
catgcaattc taagggtgac aagaatgaaa gttagggcct tgaagaaata ttttgattaa 96180
gagctgccaa taaagtagag taaagattag attgatgtga agaagtggga gattaatgag 96240
taaatggtca ctggcttgtt gagaagatta aatgagatgt acatgtaatg tacctaacac 96300
aacgtcttgt acaaagtagc cattcagtag agactagctt gtattatctc cctttgaggt 96360
aaagaaaact gttagaaata gtatttctac tactgatagt atttcttcta cttatgcctc 96420
cctttgaggt gaagaatact gttagaaaac atgacatagg agaaataccc ctgagagaca 96480
gttcttatta gtgactactg tgcagaaaag atggaggttg gtgtaattaa ggagaaggaa 96540
agccatgaag ccaaagtatt atgaaaaagc atcaatatga attttcatgt tgacaaagtg 96600
gtataaaaga taattataaa gatggtcact tataaatacg gtagttctgt gtgacacaat 96660
ttacagaagt tggtatatcg tgtggaagaa aacagcataa gatcctgaag gtttgaactg 96720
tgggcacatt ggctccatgc tcaggaaatg gcaatggggt tgggaagtga ttccacttta 96780
tgtccctttc agacacataa aaattacttg tgtgagtatc ttatgccaga cactattcac 96840
tgtgtagtga gcatggtggg tatgaaatga caactttatt gtctttcctg tcaaagaact 96900
tgtaggctgg ttgggggaaa gagaccattt caatatgaag tgctgagcta gaggtaccct 96960
tagggcacta cagaagccta gctgatggct tttagcctgg ctagacagtt caggatctct 97020
aaaagcaggt gccttgaagg ctgagtcaaa tacaaaaatg tattttggac agaggaaatt 97080
gtatgaacag aaacacagaa catgaaacta cttggttggt gcagggtatc atcagcatag 97140
aaccagacag aaccagagtg taaataagcc agaaggccat gtcatggagg ccttgtatac 97200
cagtctcagg aatttggttg tggagagctt tcatcagggg aatgatgtaa tcagcttgga 97260
aatgtagata tatcactgac tgtgatagtg aggagcagaa ttaaggtgga cgtgattaga 97320
agctttgtga atagcagaaa gaacatagat tttgaaagct ggcagacgta ggttactgaa 97380
gaaagttact taaccttgct atgtctttag ttttatcctc tgcaatatgg ggataatact 97440

-continued gcctattttg tagagtcttg tggattcttc tggcatatat aatagaaaat aaaacagcta 97500
ttattattat tgttgatggt actatttgct atatctgact acaaggagaa agactaatag 97560
gaaaccattt caggaatcca gatatggtca tgatggacag gaagagacaa gagttacata 97620
gaggaattct gggaagataa gaaatgtcat ttttatgtac tgtttgcatc catcagacaa 97680
ggcatcagga aaaatgatcc ttcaggaaag agtgattttt tttcttcaag aaattagaag 97740
aggggagaaa ttggtttaag attaaggact ccatgcataa gagaaactgg gagggaagac 97800
aggtagaaat gctatggggt taggaaggaa gaatgcagag gtggattact tagaattgag 97860
acatctgatc aagacagagg gatcacagct tttgctaaca aagtactagt ggaggatgcc 97920
actaggtgag gtttaataaa taattgttga caataagttc catttaaaaa ataaacaatt 97980
tatgcttctt ctttgcctaa gtgtcaaata aaacattcag atttttattt caaagtatcc 98040
ctgagtccct gttccctttt ttgtcctgct gacttttgga actgatttag gcttccttag 98100
tcatctcata atagaaaaaa tcagccaggt atttcctaca tttcttgtat tttaaaaaaa 98160
tgtaatggat gtaatgaatt ttaagcaaat gtaatgaata caataagtaa cttagtatat 98220
gctgttttct tctctatgct gaatgtttca tacatgttat tttctataca actacatggt 98280
caattccttg aaaatatcaa ctccaaaatc tttattttgg tatactccac gtagcacatt 98340
gagagagttt taaactcttg ttggatgact gtttcaaaag tgttttgaag taggcatgtc 98400
agttgcaaaa agtttgctca gcaaatgttg ttctgtctca cagtctcaga cattgagcag 98460
atgattacat gacagcacgt gattgctggg agtaacagac aaaagtaact gaaagtgctc 98520
ggttatcttg acagtcaaaa tcaaaagtgt cccctatttt cagtgaccta agagtttctt 98580
tttgtgtttt tggtattgtt gttaaataag tgttctcacc tttgaaaagg tcaataagaa 98640
ttcaatacag tataatgtct gtgtgccaaa tgaaggtgcc ccttattttt aagtgtggag 98700
gagttttgat cataagaact tgaaatacct acagaatcct tgatggttaa gcagctggtg 98760
ccagcacaag aatccctcaa tatgttctct atgaagcccc gatcaccaaa tgcaaacatt 98820
catgattcag tatattttca tcttgactgc caaagttgat ctgtttctta atatattaca 98880
tctagacttg gaactggaga tgagaacaga atattatctt cctcattttt gtgtttttgt 98940
tcaactctaa tgtctgcaaa gcacttgcgt atgtaatgat gctcagtgtc ataggagcag 99000
gcaggtaagt gtaaatttgt ctggatagga gaaagcatgc acaacatatt tcacatagtt 99060
ttctgatttc agtttgtttt tgcaaattat tcactcagtg agatagctta aagacgttat 99120
cacagggaaa ggcatggaga tagttctgtg ttgatagaaa acttgtaatg tacagccatg 99180
agtgagaagt caggttcaga ttcttcacct tcagtcctcc tctttcataa acagctccat 99240
gtcctatttt acatatccta ctttaaaacg agattataga agaatgaatt tctaggcaaa 99300
gtgacactta ttttaaaata ctattacgta tccctgtgcc cattaactta tcctaccatt 99360
tttcttcccc tgtgtccaaa ccacctttag aatctcctaa atatttgtag ctattgtaaa 99420
cagcactgga gactttgcta gtttaaaagg agaaatcaac gcaattaagc cctagttaat 99480
ttacttatcc cttatgagat tataattgta ttttgttatt aaaaggggga cagagtacac 99540
tgttctcttg cctttttaat ttccagacta ccacttctcc tgcacttgac aataccgcag 99600
tctaccacgt agtcccatgg ctgacaggag gagaattcta ggcaggccag tgtttgagta 99660
gtgagtaatt ggactgtctt tacccagcaa ctcactgttt tgtaaatgta cctgagtttg 99720
gagaagtaat tggcttttat aaggggtgcg gggtggaggg ttggggtggg gagagtgaga 99780
aggaggtcag agctttagga tatataattg gtctccacaa agttgttgtg atacttttgg 99840

```
aaccacgtaa tggtcttcat taactaagtg tctgtcatga cagccattac atatgcatta  99900
taataaaaat ttatttacag tgtaagttga agaaggtaaa atctggatgt agtttctaaa  99960
ctctgcttgg cagttttcat atttaagcca ctagaagaaa aaaattggga gggaagctga 100020
gaagaattta ctgaaagaaa aaaatacttg ggagggaaat tggcaagaag tatgaaaaag 100080
cttgggaggg aagtaagcaa ataaatgagt taatgactgt tctggaaaat aaactctatc 100140
atgcagatat cacatgactg attaaatttg aatttgacct cctgctttcc aggtctggta 100200
aaaactaacc tgtaagaact tgaaacttag cctttgaatg gtcaatccac cactgtagga 100260
gaatttatga atgttcagtt gagagaactg aaaataaaga agtaccatag gaattaacat 100320
ttgcattcag tagccaagat ataatggaca tctgaaacag gtatttgagg ccaggcgtgg 100380
tgtctcatgc ctgtaataat agcactttgg gaggccgagg tgggtggatc acaggaggcc 100440
aggagttcaa gaccagccta ctaaaacaca cacacacaca cacacacaca cacacacaca 100500
cactagccag gcgtggtggt gcacgtttgt agtccaagct acttgggagg ctgaggcatg 100560
agaatagctt gaacccagaa ggcggaggtt gctgtgagct gagattgcgc cactgcactc 100620
tagcctgggt gacagagtga gactctgtct caaaaataaa ataaaacata tatttgaaac 100680
acattgaatt atgtccctta aacaagaata aacatcacta aatgactgta ccttgaacta 100740
cctgtaattt tctcctgata ggtaattaag cttcaaagta ctgacactta tttactgtaa 100800
tatgaagcaa taacttaaaa aaaaaaaaaa actattgaac cagaaccaaa caggaatgcc 100860
atagcatttt gtaaactaaa ctgctatttc atttcatttg agccctggaa cttgaaaata 100920
aatgctagct aacatctgtg aacagaacat acccatcagt actgtgctaa gcacctttca 100980
tgaactggtc attaaatcct cactttccat ttatttagtg acaacttcac ccagagtttg 101040
cagtcaaagt gaaaatgtgc tgaattccaa aagtgtgagc taggttttag aagttaatca 101100
caattctgga acaaattact agcttaacaa atgagagttc ttatgtctct aaaaccaaaa 101160
tagccctaag tctgtccctc ccagtaagat ttgggccagt caatggaaca gtaatataca 101220
aatataatta cagctgtcta ggagcaaact atcctatgaa tagataataa aattaagaca 101280
cttaagccat gttttcatat taaaacacaa agtaaaaaat cattgttttc caaagataaa 101340
agccatactg tatcatgaca tatatatgcc cgatgtttcg accctcttga agaattgaga 101400
ttctcgactc tacactctta gcgttttcta tattgaacag atgtttaatt taaggaggtc 101460
aagagaaatc ttacacttat tttttaatgg taccttagac atagaaggaa cctcagaaat 101520
ctctggctga atatttccat ctgcagatga tcatgtcatt aggcttctga ctctatagcc 101580
atagaaaaat attcatgaag acctttcagg aagggaatgt tggtatttct aaaaattgag 101640
tacaagtatt ctctagacaa aacagctctt gaaatggcag attgtattcc cattattata 101700
tttcagaatc aagacattaa tacctacttt ttatttacca ggtttagtta tccttgaatt 101760
agattttata aattaaagaa atagatttca ataaatattt gttgagttcc tagtatggaa 101820
acatcgtgtt tggcaccagg gatgttgcct gcaagtataa caggagttcg tatttgtaat 101880
gagtttatga tttacagata tttggggggc aaagatatca ttcggtaaat acttatgagt 101940
gcaaactttg aactagggac tggccaaac tctaggaaca tatttgatga cagagacaca 102000
atccctgtcc tcaaggagct ttcattctag tagagaagat gaaaaccagt acagtttggt 102060
aagttagatg atattggtta atgtagggtt cttatgtaag tctagagaag tagcatttaa 102120
tctgttctta gaaggtcagg aaagatttcc ctggaggaag tgacatttaa gctgagagag 102180
```

gatggataaa caggagtcat ctgagtgaac aacagggaga acattccaga aagagaacaa 102240
aatgtacgag gcctgatgcc aagagagaac attcattgca ttggggaact atagtcactt 102300
ctgtgtggct gggatgtaga atgaaatgag cctggaccca agagagcact ttgccctttg 102360
gggaagctgt aggtattaca gtaaggttgg agtctggaaa gaaaggggta tattgtgaga 102420
tctgaattgg gagaggacag ttatatccag acctttatat gctccagtaa gaagactgaa 102480
ctttacactg gggccatgg gactcactga atggcattaa atttgagagt ggtcatatga 102540
ccagatttgc attttacaaa gattgtcatt gactgcaaca tgaagtatgg agtattggag 102600
gagcggtaag gctggtggca gggagataat ttaggaggct ttaggtgagg gatgataatg 102660
acttgccagg taggaaggag taaatttctt ctcagtggat aattagaaga ttgaatggat 102720
ggacttggtc actatttggt atagaagggg aaaaaagatg tcaaagatga tgccaatttt 102780
taaaaataat ttaacattta tttttaaata ttttttcagc cttattaagg tataatggac 102840
aacaattgta ggtatatgtc atttacaaca tgatgttttg atttatgtat acattgtgaa 102900
atgactgcca tagtcaagct cattaacata tccatcactc acataattaa cattttgtgt 102960
gtatgcagtg agaacatcag gctctactct cttagcaatt ttcaagtata gattacattt 103020
gttaccaact atagtggcca cactatacaa tagagctcca ggacttattc atcctgccta 103080
actaaaactt tgtactcttt gaccaacatc ttcccattcg tctctcctcc ccatgccaag 103140
tttccatctt ggtcagttgg gtggatagta gtactatctg ccgaggcagg ttggtagggt 103200
gaaaacaatg tgttcccttt tggaaatgct gaggtgacca gggaacttcc aagggaatct 103260
gtctggatct agagcttaga agagatgttt gggctggaaa cagacatcag gtattcttca 103320
gtatatgggt tgtaaatgaa gtcacaggag tgggtgatat caccaatggt gagtgtagta 103380
taagaagact ggactgagga cagatttcca aggaatttca atacttaaga ggtacgcaga 103440
gaaaagaggg gctgtgaagg acaccaagga ggagactaag agccaggagg gaaaactttc 103500
aagagagtat tgcattatgg aagggaagaa gagagaacat tttaaatgat acgcaatgct 103560
caataatggt atccgctttg gagaggccaa gtaagattcc taagtaccca ttggatcaag 103620
gtccttaatc ttacaaaaac ttatgcaaat caataataaa gagatgataa cccgataatc 103680
aaaaatagac aaggcatata agaagaaaat gaattaaaaa tattcaaagc attcaacata 103740
tacaaatgcg ctcaatctga tatataatga aagaaaagta aattaaaaca acaatgggca 103800
tgactaaata acagtatgag ggagcctgag gagaaggagc atttgaaatt tcagtacaga 103860
agagaaaagg ggtgacttat agaaaaagga gacagaaacc atagaacatg tttggaggat 103920
aagactcaaa caggtagtgg ggaccctttt ctagagtagg atgaaaacag gtaatgtgtg 103980
tggatgcaaa tatgaggtag gatgtaatgg gaagttgagc gaattcatat ttagtcattc 104040
attcaaaaat acttaattga gttactgctg tgtggcaagc atcattctac aaacagaggg 104100
cacagtgata agcaagccag tttgtactct cgtgtaactt acattctact ttgagaagac 104160
agattataaa taggttaaaa agtcaataat atgatgtttc agcatcaaca ataaaaaatt 104220
agggtgatat atagagtgcc agggaaagtg ctttcatgga cctcttcatt ctctcctctc 104280
ctggtgtcat aagctactcc ttcatccatg ctgccatttc tcttggttta cggttccagt 104340
atagtactca tcacattatt actatagagc catccacctt atgaaggtga aggtgtccat 104400
ctccttactt aaaaaaaaaa aaaacaaaca aaaaaacaaa aaacccgaaa aacaaaaaaa 104460
gaggcagaaa gacagaaggt cctccactaa ctttcacgtg ccatgtaacc agcgaaatcc 104520
aattatttta cagcattcta gctatagaag agtttgggaa gcgtagtgct tagtgttcta 104580

-continued

```
gcctttgtag cacaggaaag ggcctggaag gaaaggaatt gtgtcttccg cagttgcttt 104640
tctttatggg gaagtgctat agcccaaaca atattttagg aattttcatc tattgtcaat 104700
atgcaaactg gaaggggata atgaaaatgt tgtggttaga agtttatgaa atattgttat 104760
tcacatttta aagtaaaaag agggaatgtt taagagactt gtttaagatc acatgtctca 104820
taattggtgg gaccagcaat acaatccaaa tctaactact tatctttttg ctatgcccta 104880
ttagtgttca tattagaaaa gaaattctat ctcagacact aatgatttgt tctttggaca 104940
ccaatgactt taagttaaaa cttcatacta gttaatttaa ttatggtgta gcagtattat 105000
taaactatca agactataaa ttttctattt gtaaaggaga ttatgatacc aaagattagt 105060
gaactaatga tattgagaat tctatgacat aattttgaaa aatatttgca ggatatttat 105120
ttttgtgtaa atgatgcttt caagctacca taatcctaag taagtgtata tttgggaaaa 105180
ccacctattc taacacactt gaaatttaaa taagtcagga aattttttc cagatcttct 105240
cccaaattat cttcatcttt ttcctctccc cttgggaaag aatctcttca tgcctcataa 105300
tatcaaattt aaactatgga agtccaggtg gtggacagtc agcaaagggg aagatgagaa 105360
gcttgtgtta taaagccagc tcttgtcaga ataaggatct ggtaggaact tcagaagtga 105420
tgggtaggta agtatgaagg ccaggtccta agatctaaat tacaaagcag aagacttact 105480
taccagggag ctggaaaaca tgttaggaaa tccagagcag gaacagattt caagatagca 105540
caataatata gcagtgaagt actgagaaaa gagtttttt cacgggttgg atttattcta 105600
gcattttagg cagcatttgg gcatttctaa gtggtcagac ttagaggaga tagttaagga 105660
attagcagct gctaaatgcc aattcttaga ccagttgaat caaaatcatc taaaaagctt 105720
tcagaaacca gactttttaa gggccatttg agagactctc aaatctggaa tccagaaatc 105780
tatagctaga tgagtttaag gtagagccag aataagaaaa ataaaatagt ttgtttgttt 105840
caggtatctt ttccaatatt atttccgaac ctaccccaaa caccttaaat cactgcattc 105900
tatagccatt cttttaaaaa tgcttgagtt attagttttc aaaaacaaat acaaatctgc 105960
acacatacag aaataaacat taaagagaca taaagatatt aaacagagtt acatatactt 106020
acaacttcat acatatatat tatatataaa actgaatatt aagtgtttga tattagtgac 106080
aaaatctgta acatccatta tattagtgct ttttgtactt tttgttgggt gtagtaaaaa 106140
ttgcattcga atttgagttt tctgctatat atttggtcag ttcctatcag tgaaggaaaa 106200
accttttttt attattttat tgttttttta ttttttgaga cggagtcctg ctctgttgtc 106260
caggctggag tgcagtggca tgatcttggc tcactccaac ctctgcctcc cgggttcaag 106320
cgattctcct gcctcagcct cctgagtagc tgggactaca ggcacctgcc accaggtcca 106380
gctaattttt gtatttttag tagaaatggg gttttgccat gttggccaag ttggtctgga 106440
actcctgacc tcaggtgatc tgcctggctt ggcctcccaa agtgctggaa ttacaggtgt 106500
aagtcaccac gcctggcccc tttttatttt ttaagctgat tgaagattct tagttctcat 106560
gctttctagt ggtgattaat ctttagccaa tatttctata tacagttatt agtaatcatg 106620
tttgacttag gtcaacaaac aatctttcct aaaaaaacag aaccccaatt ttaatttctg 106680
aattatttag tatctatttt ctgctgtgga agttgaatta tgttgataga tatcatacag 106740
ggccatgtaa cactctcaga tacacgttca catgtatagt agctgtatac aaaaatgtta 106800
cttcattctc tctctcttta taatactctt ggctctctta cgttctctca cacactctac 106860
tcttcccttc ctctgttctt tctacttgtt ccctctgctc ctaccacact tattcccccc 106920
```

-continued ttgtccattt tccttgtgca taaagcacaa gtgcttagta attatcaaat attaataaca 106980
atgacactaa ccacccaatg atttagtgtt aatgacatgc tttattgaat ggcattacct 107040
ctaaagttca tgtttccttt acccaaccaa gcttcttacc ctcctccctt accacaagca 107100
tctatattgt caaggttgtt ataaagagta ataagccagc cattaaaaaa gggtttatgg 107160
tattttccta tctacaaagt cacaggaagc tcaaatgtac tcagtaaata ttgcaaaatt 107220
acacaggacc attaaatgta acactccacc ctttctctct ctctctctct ctcttgctct 107280
ctctctctct ttctgtcaat atagcaacac cctatatcat tgccctttgt atgtgcaaat 107340
cagagttaat aagctttata ttagcaatta ctccttaaca acttctggtt tgtttggtcc 107400
agttgaataa tgtaagcact taaaaaaatg aaattataaa catttatgtg aaaagtgcat 107460
atatcacatt ggatatgttg ttatgcactc cttaataata aagtaagtta atctttattg 107520
cacacttatt ataatattac tttgaccctc tctagtactc tttatctaag tattctcaag 107580
tgctttacaa tctcaaacag acccaatgtg ttgtatacac agaatccttt gaagctgaca 107640
tttgcctttc tgaccagctt gttgtaaagg aaatcagcca aaaaacaagt atctagatga 107700
gtagctcaaa cattagtaca catagtaatc acaggtcaaa atgcagatag attaccctgt 107760
ccaaattctc ctgagtaaga gtaggtgaaa catttttaaa taagctcccc aggtgattct 107820
gaaattggtc caaggaccac atattaagaa ctaatgatcc aaacaatttg actttttatt 107880
gtagattaaa ccatgctgag aaaattatta aaaattgaaa tggcagtgga ggatggtttg 107940
aaagaaaggt ttttcagggc cctttcaaca ataaaattaa ttgaacacaa tattaaaact 108000
ctatatttga tttaagacta aggttttcat tgtttttaaa tctcagtaat ttttatgtaa 108060
caggtcaatt catacccagc atcttaattc caatgaatga tttcccacaa caatttttgt 108120
ggataactcc aagggaactc gaaggaagtt gtagtatgaa caaagagaag tagaatttgt 108180
ccctgtgtgt aaggcttctc tgataagcag cacaggctct catactgctt tttaaaaaaa 108240
ttatgatagc atcaagtgga attaattttt tttagattat actttcatgg aagggaagat 108300
ctactgtgaa ggctggaaaa ccaacaccct taagataaat atattaccag atttgagcgc 108360
tcttagtaat cagcaaagat aaatgtttaa cagtgcatac aaaatgaagt gttttatgtt 108420
aaatcaaata gagaaagcca aacactaata atgtggttac aaatgaacaa taaattaggt 108480
aatcagaaca ggtacagaca ttaatagcag gatattggta ttattaatgt attttgtttt 108540
aaaataatga acttaattac aattctcctc atcctacccc actattttat tttattccag 108600
attcagcagc ttcatattat gtctctgaaa cacttattat taaagttatc caaatgtaca 108660
catttctctt tatataaatg tttcagtcca gaaaaggagg ccaaatacat tagctcagaa 108720
catcaaatct tctcagatgt gggaatcttt tattttcaca cttttaaagg taatctgtat 108780
ttctagcgtc tattatagac agaaaacttt catatgacaa cattcctatt ttcttaactg 108840
ccttgatagg ggcgaagaca aattctaagt aggacttttt accccattct tcttaccatc 108900
attctttcac aaaaccccca gctttagaca atcgctatta tgaatttgac atgtactatt 108960
ccaatccatt cccataaatt tacacccata tatacatata gttatctatg aacaatattt 109020
agtagctttt ttgtgtgtgg ctttaaaatt tacataaatt gtataatttg tgcacattct 109080
tctttaattt gccttcttgg ctacggttat ctttttgaga tctagctatg ctgctggtat 109140
gtagaattct atttcattct tttttcattg ttgttttgta cccataacgt gtcacatttt 109200
atttatacct tctgttcctg atggacattt agattcttcc aggattttac tcaatactgc 109260
aatgaaaatc tttgaatttt tctcttttgc acatattcaa gagacttttc tgacatatat 109320
atctataggt gaattgtgta gtcatatgat acatacacac attttaaatt tcactagata 109380
ctgccaattt gccctttgaa atagccatac aatttatagt accaccagcc acttatgaaa 109440
gttcccattt cctcaaatct ttgaaagttc ttattataaa cagacatatt aattcttgcc 109500
attctgattt gtaaatcaga atctctattg ttctacctct agttctaatt tggaattccc 109560
caattacttg taagatgcta tatattttca tgtttgttag tcattctgat ttcatatcct 109620
ttaccaatta tctttttggt aagttattgt ggtggccatg agatgtgcct tacagaggcc 109680
ttgctagagg gaatgtgatt gaatgagagc cccagatgct gtgtattaaa atcctgcact 109740
gagtttgtct caagatttct tgcacgtgaa tgaatgagta cagctgggat actaaagcag 109800
atgtgtattt gggagatatg agacttcttt agtggctgat ttttggctca taaatgactt 109860
tgccaaacct tccttagact gctcagtgtt ctaacatctt ccatccagcc ttctaccctt 109920
ctttccttta ctaggggatt gaatttacat tgaggtctca tagccttctc tgcctctctc 109980
cttatttcct tttatacaaa tatttcccct aataaatcca tgcacattta ataccatttt 110040
gctatttgca acctgcaggt cctggactaa cacagttcta tacattgcat taccattctc 110100
tagagtggga tcttttgttg tagagagttt taaaattttt atgtagtcac ttttatccat 110160
atttttcttt atggtttata tttttgtgtc ttctctttaa cacatctttt ctagcagaat 110220
tcataaatat attattctat attgccaaaa gtttgaaagt tgcaatcatt agaattaatt 110280
tttgtatatt gtgtaagtta agaatctaat tttattgttt ttcattggaa agccatttgt 110340
cccaagataa ttttttagta gtccctcctt cccctattgt cattctgaca tatttttttct 110400
aggttccgat ctatgcatgt gtttctttat ggaagagttg gccctttgta tctttgagtt 110460
tcaaatccat ggattcaatc aaccacagat agaaaatatt tagaaaagcg tcagaattga 110520
acatgtacat acattttgct tgtcattatt ccctaaacaa tatagtataa caactattta 110580
tgtaggattt acattgtatt aggtattgta agtaatctag agatgattta aagtatacag 110640
gaagatgtgc atatgttaca tgcaaatact accccattta tataagggtc ttgagcattc 110700
atggattttg gtatccacag agagtcctgg aaccaattcc ccacagatgc caaggcacaa 110760
ctgtatttat tctatcatct acttgtttaa tctcacatca gtatctactt ttgaaataac 110820
aataacttta ttatttaact ttttttatta cttaggatta gagaatttcc tctggtgagg 110880
catcatagtg tctcaagctg gccataaaga caagtgaggg ctaggatcgg taagactggg 110940
cagaggaaga tacaacagat ctcctatgca tgaagcaaaa gtgcagctca gaagccagct 111000
ctttcattaa gttgtcctct ataccctcac tagattgtaa gctcttgaaa tgagaggcta 111060
taccttaatt gtctctgtta tctaaaatac ttccactcac tgcttggaac atattgcctg 111120
caataattaa gcttgccctg gctcccaaag catagagcaa atcacactcc tccccttgcc 111180
tttgagaagc tcacagtctt cgaaggtaga gatatgtgaa cagataagaa aatggatgac 111240
aggagaacag aaacgcatga ctgtcagaga agtcattgga gactttacag aggaaattaa 111300
atttttattg atcttgaaag agtttgccag atgaagtaga ggacaggcat tttagacaaa 111360
gggaacagga aatgtgaaaa cacaaagtga tggaagtcat ggtgagtttg gagaactata 111420
aaacttcaat gtggctgaag ggtaaggtgg atatagagga gtgctgggag gtgaggctga 111480
agaaataagc taggaaatgt ctttttatgc cattttttaa agtttggact ttattctgaa 111540
gttcacatgg atccaatatt ttttgttttg tgttgtttta agcagaagcg tgacatgatc 111600
agcttgaatg atgaacaact tgaattgttt aaagtggatc acacagtcta ctgttttaca 111660

-continued

```
gttattcttt gaccaagata ttctttatta actgaggaaa aaaagggctt tcctgaattt 111720
tgcagtcatg ggatatatga taagcattct tgatttatca tcttcaatcc tgttacataa 111780
cataataacc attgttatta cctttagcaa tgctttcctc agtattatct aatggcctat 111840
aaaatgtgac tttcatttgc aaatacagta catctaacaa gaacttacca cagctgctat 111900
gcaaaatacc aatacaattg acccttggac aatgtggggg ttaggggtgc tgattcccca 111960
tgcagttgaa catgttacat aacataatac ataaccattg ttattatgta acaggattga 112020
aaatgataaa tctttggaaa gtggggcaaa tgaattctta tgaattccat atcttccaca 112080
tgtgttttac ttttttgata agaagtagta acctagttca gaaagaaaat aatcatcccc 112140
ttttacttat gcaggatacc aagtctatct tagcaccata atagtgaatg ataggaatca 112200
agctctatga atacattcac atgtacatat atatggctat ataggacaca tgcatgcaca 112260
tatacatata tacacttgca tatatgtgta tatacatgta catatatgca tgtatattca 112320
attgtatatg tgtatatagc caagttattg tacagttgac ctttgaacaa cacgggtttg 112380
aactatgcag gtccacttac acgtattttt tttttccgtt tctgacaccc ctaaggcaac 112440
aaggccaact cctccccttg ctcttcctcc tcagctgact caacatgaaa actatgagga 112500
cgaagacctt tatgaagatt cacctccact taatgaatag tacatacatt tctttttccc 112560
catggttttc ttaataacat tttcttttct ctagcttgct ttattgtaat aatatagtat 112620
ataatacata taacatacca agtatgtgtt aattgactgc ttatgttatc agtaaggctt 112680
ctggtcaaca gtagactatt gctagttaag tttctggtag ttacaagtta tatgtgggtg 112740
ttcgactgca tggggagtca gcaccccaac cctcatgttg tccaagggcg ttgtccaagg 112800
gtcagttgta attggtattt tggatagcag ctgtggtaaa ttctggttag atgtactata 112860
tttataaatg aaactcacat tttataggcc attaaatatt attgaggaga gcatttctaa 112920
gggtaaaatc ttgtctaatg cttgaaacat cttcattttc ctgtcagttt agatcttttt 112980
gaagtaattc tgaaaatctc tcttttaagc taaatttaac acaaccaaat agccaaatat 113040
ttaagttcca ctaatgaaga tatctaaatt tctgttaaaa atttaagata tatgttaaac 113100
ccttctaata taactcttct ctcagtcaaa cttttttttt taacagttgc tttgcttctt 113160
ctttcaaagt catacttcaa caaagttgct attgaatatg tctgactaaa catgttagct 113220
atatgataag atggctggat aagagataaa tatagaaaat gtagcttttt ttctacttgc 113280
aataaccctt taggaattaa aatggaaaac taataactat ttgattcata atagtagcaa 113340
accgtaaaat atttagacat aaatctacta agaaatttat aagacatata tggagaaaat 113400
tcaattgaat aaaccgttat tgaagtatat aaaataagat ctggatgaat agaaagatca 113460
taatttttaa taaaatttg catcttaaaa agtgaaccct ctccaaatat atgcacattt 113520
aataaaatta taaatacatc ccaatgaggt tggttttgaa attttgttaa ttggaactta 113580
aatttcacct aagaagaaaa aataaagaat agttaagagt gcatgctttg tagacaaatt 113640
gccttagtta gaatcctggc tctatcatct attagctatg ttatctttgg gataacattc 113700
atcttttctt atagatatgc ttaaaacagt gcctgacata tagtaagcac aaatatccat 113760
tagctattct tcttattatt tatgttatta gtattgttaa tatttgttat tatatggaag 113820
actaaatgac caaagagagt caagaaattt atgaataaga tttatgcgtt gttagatatt 113880
agagccatta aaaaaaaaaa aaccaaagtg ccaaaaaacc tagcacagtg ttaatacagg 113940
aataaaaaaa tggatcagag gaaccaaaca gaaaagccag aaatggatct taggaaacat 114000
gagaatatga tatatgatag atgctaaatg aattcagtat aaaaatatta atgtaataaa 114060
```

tcatgcttgc tattcaagta aaagaaaatg aggttagatt catgtctcat accaaatata 114120
accataaatt ataccttgat taaatttttt aattaaaaag caataatatt tgaaaagaaa 114180
tataggatac tcaatgtata acctgaaggt tgggtagtac ttttcaacaa atataggaat 114240
ttttcacttg aaatactaga agaaaaaaag atagcaaaca aatacaggaa ttccaatttc 114300
aagcagatat aatgatttca tgaaatgtta actgtgcaca tgatagatgg tctatggata 114360
gtgcaaaaga aaaagagaaa agaaaaaatg tttttttaaca tatgcagcaa aaaaggtttt 114420
taacatctat tacatacaaa taaaaatgaa tgtataacac agacttcaat aaaaataggc 114480
atttcacagg agaacaattc agatggccag tatttacaat ttcataggta ttaaggaaaa 114540
tacaaattaa aatggcaaat tagcaaaaat tgaggtgtga ttatattaat atctgttggt 114600
ggtggtgatt atggggaaaa gggtactttc aaaacttgct aatataaata taattctttt 114660
ggttgttttg taaaggaacc tgacaatatc ttttaaaaat aaagaaaacg catacttttg 114720
acctagccat cccattcatg agggtatgtc ttagaaaaat aagatcacaa aatcatagag 114780
atttatgtgc aatgatatta ttggtaggtc atttttatga ggaggggtgt ggatagtaaa 114840
tgccagggta aatcacatag catctaataa acgtatttat gaactacaaa agcttacact 114900
ttcagtctag tctagtccag actgcaaata aatgtgagca agtgaattca agcacagaag 114960
tgcttgaagg caggtttcat aaatctactt tcttacagta tcctgatatt gacttatcga 115020
gacagttact gtggggttga ttattaaaat atttatgtat ctaggtattt ttcattcagt 115080
agtatgttat tcaattagca acaagtgtgg ggatttaaag atattcttgt ttgtttttac 115140
tgctgaaaca tattctagtg gaaatttcga ataaacgatt agtcatccta aaagcaagat 115200
acattttctc agaaaagaca aggtaaagaa cttgtatatc ctccctcaat tcgtttataa 115260
ggtaataaga tgaataaaaa tatcatagta caatttagca ttgtaaaata aaattaattg 115320
gtcatctcta gtgtggtcgt gcttggaagg tgaaagaagc caagatcttg tctgggaata 115380
tcatgtctac cttgacctca cccttaagaa tcctagcctt tagtttaaaa tcacatggct 115440
acatacatac caacttcaac aatagtacat ctggcaaggt catgcaaacc tgggacttga 115500
gcttctgatt ctaagtccag tgctttttgt gtacatcatc tcttgtacat accttatgat 115560
gatatgctaa taaaagctac gtgatcaggc cttaaaaatc tgcttttttt ttgtaatggt 115620
agaatggggc atattatcac atcaggtaaa cactctattc aaggataaat ggaaatgaat 115680
gtcatatata gatcattgat aaatatctca ttacaaaatt atgagagtta ccaatgtttg 115740
agtgtatatt atgggccagc cctttatatt aaattacttc aaatttttac aactgttaaa 115800
ggaagatatt attataccca ttttatagat ggacaagtta gggccagaaa agacttcctc 115860
aaagctgtta gtccagtaat ggagacaggg ctagaaaaca ggtcattttg ctctttgact 115920
aatgttacta ctcatgtttt gtattttgtt taaagtttta ttttattttg ctttatttat 115980
tttttgagac aagatcttac tctgtcaccc aggctggagt gcaatggagt gatcacggtt 116040
cattgcagcc ttgacctcct gggctcaagc gatcctccca cctctcaatc tccagagtag 116100
ctaggactac tacaggtgtg tgccaccata cctggctaaa ttttgcattt tttgtgggga 116160
cagggtttca ctatgttgcc caggctggtc ttgaactcct gggctccagc gattcacctg 116220
ccttgacctc ccaaagtgcc agtatcacag gcttgagcca ccatgtccag ccaagtttta 116280
ttttagaatt aaaaaaaatt ccacttggat tgttacattt tatctcattg ctttatattt 116340
atagaattac tttataaatg ccactttctt aattttcata gttagcactc tttatgaaac 116400

-continued ataaactatt atttgaccca ggtttttgtt agaggaattg agtcagagag ctgttaagta 116460
actgagattt cacaataagc cagacagacc agggttcaaa ttctgggtct cacattatcc 116520
aattcaatat tccagctttg ttacttattg agcaaccact acaagcacag tttacatgac 116580
atctgatagc tctcaaaatg aattttacaa acataattca gatttcaact cagcagtgac 116640
tcaggagaaa ggacacttgg atgcatttct ttatggcatt tttcccaggg tacacgcaac 116700
ctggaagatc tcccaagtat gggggaaggt ttcaccctga ggaatcccat tccctctaat 116760
ctgggacaag ggggaggaga gtactgtctc ttatcagcca tctccccagg gaggcctggg 116820
ccctcctgga atgcatacca tggcttactg actcaaagtg ttgaaaagac caggcattgg 116880
gacacacaac actactctta aaataaaaaa agaatcagag tagcttgtgg ttataattga 116940
aatggacaga gtaacatggt accaagaaac tattagcaat tccttcccta aatccctcat 117000
tttcttaaag cattttctcc ttttcctcaa caagctttaa gttggatttg aagaatgata 117060
agactaaaag gagggctgtt tctggtcttt ggaggaattt gatattccat tcgatctgag 117120
tgtgcaaagc ctgagttcac atgaactctt ctgatctctt tctctaatat tttttcacct 117180
tattcatatg ggaaagaagg aggggaatac tttagttcca ttctccctcc tcctatttcc 117240
ttgacttgtt taaaatataa atgttataga cacctaagat agaaatttga ctgaaacagc 117300
ctcttaatta ttgtcttaaa aaattggtat aatgaaattg catttgtagt ctttggacat 117360
ttaaatccag aagggatatt ttctttttct tttttaaaaa tttaattcaa tagtttttgg 117420
gctacaggtg gtttttggtt acatggataa gtgctttagt ggtgatttct gagattttga 117480
tatacccatc acctgagcag tgtgcactgt acccaatatg tagtctttta tccccccccc 117540 gctccacccct tcctttatcg tccccaaagc acattatata attattatgc ctttgcagcc 117600
tcattggtta gctcccactt gtaagtgaga acatgcgata tttggttttc cattcctgag 117660
ttacttcatt tagaataaat tgtctctagc tccattcaag ttgctgcaaa ggccattatt 117720
tcattccgtt ttttggctga atagtattcc atagtgtata tatgccacat tttctttatc 117780
cacttgttga ttgataggca tttaggttgg acccatattt tcgcaattat gaattgtact 117840
gctgtaaaca tgagtgtgct tttttttttt ccatataatg acttcttttc ctttgggtag 117900
atacccagca gtgggactgc tggatcgaat ggtagttctc cttttagttc tttaaggaat 117960
ctccatactg ttttccacag tggttgtact agtttacaac ccccaccagca gtgtaaaact 118020 gttccatttt cagcacatcc atgccaacat ctattatttt ttgacttttt aattgtggct 118080
attcttgcag gagtaagatg gtatctcatt gtggttttaa tttgcatttc cctgataatc 118140
agtgatgttg agcatttttt cctgtgtttg ttatttgttt gtatatcttg agaattatct 118200
attctgtcct ttgcccactt tttgatggaa ttatttgttt ttttttcttg ctgatttgtt 118260
tgagttcctt gtagatcctg gatactagtc ctttatcgga tgcatagttt atgaatattc 118320
tttcccactc tgtaggttgt ctgtttacca tgctaattat ttattttgct gtgcaaaagc 118380
ttttcagttt aattatttcc catctattta tttttgtttc tgttttattt gcttttggga 118440
tcttagtcat gaacttttta cctaaaccaa tgactataag agtttttcca atgttatctt 118500
ctagaatgct tatgttttct ggtcttagat ttaagtcttt gattcatctt gagttaattt 118560
ttgtataagg tgagcattga ggatccagtt tcattcttct acgtgtggct tgccagtttt 118620
cccagcacca tttattagat agggtatcct gtccccactt tatgtttttg tatgctttgt 118680
caaagatcag ttgactttaa gtatttggct ttatttctgg gttctctatt ctgttccatt 118740
gtctacttgc ctatttgtgt accagtacca ggctgtttta gtaactatag ccttgtagta 118800
taatttgaag tcgggtaata tgatgcctcc agatttgttc tttttgctta gtattccttt 118860
agctatgtgg gctctttttt agttccctat gaattttagg attttttttct agttctgtga 118920
agaattatga tgatattttg atgggaattg tattgaattt gtagattgct tttggcagta 118980
tggtcatttt catagtattg attctaccca tccatgagca tgggatgtgt ttccatttgt 119040
ttgtgtcacc tgtgatttct ttgagcagca ttttgtagtt ttccttgtag agatctttaa 119100
cctccttggt taagtatatt ttcatgtatt ttagtttttt ttttttgttt gttttgtttt 119160
gttttgtttt gtttttgcag ctgttgtaaa agggattgag ttcttgattt gattctcagc 119220
ttggttgttg tcagcaggga cattttctaa agtatagact gtagttcctt atcttctatc 119280
tgtttcttac tgtccccttc agtattcttg tcctttttc ccgctattat ctttttgacc 119340
ttttaatata tagatatcta cttctacttc tgacaatttt tgcttctcca attttctttc 119400
tttttctcct ctgcacacat ttatttattt tcttctatgt acttctttat ttttaactta 119460
atatttgatt aacttccctt ccctgtctct tttccttctt tccataaatc ttcattaatt 119520
gcctgcactg agctaggatt ctatactctc taaatcaata atctattttc tatagtcaac 119580
tgtgttataa tcgtactgtc aagataacta cttattttta atacttaaaa atattttgaa 119640
attttaacca atttaattaa tacaatgttg agttcaaatt tgaaaaaaac aatggaaaac 119700
tgtaataatt ctagcaacct cctgcttttt aataatgtat tagaaaattt gcctcttttt 119760
caaaagccta cagtgaatct attcatacaa ggcaaaagca aaccattctc ttcattctct 119820
ttttttctcc aaaagattta agtgtttttt gtttgtttgt tttgttttgt tttttagata 119880
ttgagtcttg ctctgtcatc caggctgcag tgcagtggtg tgatcatagc tcgctatagc 119940
ctcgaattcc tgggttcaag caatcctcct ccctcaccct cctgagtagc tggggctaca 120000
ggtgcatgct accatgccca gctaatttaa aaggaaaaaa attgtgtaga gatgggtctt 120060
gctatgttgc ccaggctggt ctcaaacttc caatctcaag catttctccc acccagcatc 120120
ctgaagtgct gagattataa gtgagccact atgcccaacc agatttagtt tttaaaaaga 120180
gaatacgatt tgaaaaagga aaaatgtgag gcaggagaga agaaatacac acacgagctg 120240
ttttgtaatt gctgtaaaac tgaaatcttc agcctcacta aaggagcact tgcatgaaca 120300
cctctaaatt accttattac cttctaaatt aggtgtgaag tctaacttct aaattatgag 120360
tgaaatccac tgcaattctt gttatttgga tggaatccta ggtatgtggt ccagttcatg 120420
agttgaacaa aagcatgctc atttaggcca ggtagaaaga aataaagacc tatgttttac 120480
atgtctcata accactgaag gtccttctca taagcagtgc ttatgggtat taacgacctc 120540
tctatatttt acttctccag tgcctaagta gccgagtcca ctgagtcctg ctacatctcc 120600
tccaacatgt cagcattttt ttcacaggcc ttttgttact ctagatcaga aatgttgata 120660
gcaacagttc cttgagggca gcagctagca tgatgccagc caacaggaac caccaaatgg 120720
ttcttaatat aaattactac ttattaatct atttactttg tgcatttgga gttttgcatg 120780
taaagtccta tttatgtcca tatggtagat aaatggaaca aatgaataac agaagtaacc 120840
attttgatac tttagatata gataatattg gattatttct ggattgtgaa agaagaagga 120900
agaagcatat ggaagagaag ttttagtaga ggggaggaag gaggaggtgg aaacgaatgt 120960
acaaggatgg gaggagaaaa gggagagaga cttttttttt tttaaggcga gagtttacta 121020
cctatctaac tcttcgcatt cttgaagtct cagaccaaat cccatcggtt tgaaagcctc 121080
tagggtattc tatctattgt atacttctgt tatgtacaaa attaatttgc caattaattg 121140

-continued

```
tgaactgttt tataaactat cttaaaatgg ttagttaaat ctttgggata gtatttagct 121200
ttctccagga ttatgactta ccttctaaat tagacataca atgcctagga gtcaaggact 121260
attttgcata aattccagtc ttcttttaca atgcctagaa tgattgttac cacagaaata 121320
ttcattacct gggagaaagg atgacaggag gggcagaatg aatggagaga ggtcgtgaga 121380
atgaggtgct gaggatggac gaggaagaaa gctgttttag ttgggaggat aggtgacaga 121440
agcatggaaa ggaattgcct tggacccatg gaagcccagt gaagatactt agatcctgca 121500
ggggtgtgaa taatgttctt ttagtttctc ttcttaggag gtttgttcat tttgggagat 121560
ttcttttgaa aagagtgaac ttaaattgga gaaaagtaca ttttagtatg ttgataacat 121620
ttgaatttgt aaaatggacc tatggatgat ctacacatat ttatataccc ataaatatac 121680
acatatttta atttttggta ttttataatt attatttaat gatcattcat gacattttaa 121740
aaattacaga aaaatttaca tctaaaattt cagcaatgtt gtttttgacc aactaaataa 121800
attgcatttg aaataatgga gatgcaatgt tcaaaatttc aactgtggtt aaagcaatag 121860
tgtgatatat gattacatta gaaggaagat gtgcctttca aattcagatt gagcatacta 121920
aaagtgactc tctaattttc tatttttggt aataggacat ctccaagttt gcagagaaag 121980
acaatatagt tcttggagaa ggtggaatca cactgagtgg aggtcaacga gcaagaattt 122040
ctttagcaag gtgaataact aattattggt ctagcaagca tttgctgtaa atgtcattca 122100
tgtaaaaaaa ttacagacat ttctctattg ctttatattc tgtttctgga attgaaaaaa 122160
tcctggggtt ttatggctag tgggttaaga atcacattta agaactataa ataatggtat 122220
agtatccaga tttggtagag attatggtta ctcagaatct gtgcccgtat cttggtgtca 122280
gtgtatttgt ttgcctcata gtatagttta ctacaaatgg aaaactctag gattctgcat 122340
aatactggac agagaagatg taaatatctg ttagttccat catagaccct gccactccaa 122400
tgtacacacc agctttaggc ttcttggtat agataaacat acattttcaa aatttttcat 122460
cataattttc ataacaaaat aggaaggcaa atgatgtcac ttggcttaaa atctataata 122520
tttaaaataa acaggacaaa tgcattaaca ttgttggggg aggaggtccc ttagtagaaa 122580
cactcttggt ccaagcattt taaagctgtc aaagagatgt aaatatagat aatgtatgtc 122640
aaggagagag ctttgtggtt aaactgtaac tttcagttta aacaattatt ggtgactctg 122700
atgtcaaatg tttctcaagc tttatctgaa caaaattctt ctcactttgt tgccaaagtc 122760
gttaacaaga aatcacattg actcattgat gttttggctc ctttccctta ctttctgttg 122820
ctttccaaaa gctgagacag gaaactaacc ctaactgagc acctgcaatt gcctggtagt 122880
attctagtca tgtgtgtact tttgtgtgta tgtaatcccc ttacagctct gcaaagtaag 122940
aattgttctc cctgctttac agaagagatc ataagataat tgaggctgtt agatgttaac 123000
ttgccaaaag ccatacagga aaatggtaga gtcacagttt gaaccaggtc cttttgattc 123060
tttacattaa accatgcttt gatcttggaa atacactgta aggcaataaa tcaatagata 123120
cggataattc acaggcttct aaataaatgg aagttgattg tttttatctg tgagccaaag 123180
taagacttat tctaagaatt ccacaaattt agataagata gagtatatgg cttctagaca 123240
tccaacatag aactgagttt gtgttatcag tttaagattt ggttttgctg taaggtgcac 123300
acactttgag gaactaaaaa taattgtctg ttcttattct gatcagaatg tgtaatgtgt 123360
tgtccagttt tggatgatga atttcttatt tctaatctca taagaaactt gtcatagatg 123420
tgagggagag aattaagaac agagtgtggg gaagaaactg tgtacatttt gatgggatcc 123480
attatgtagc tcttgcatac tgtcttcaaa aataagttac actataaagg ttgttttaga 123540
```

cttttaaagt tttgccattg gtttttaaaa aaatttttaa attggcttta aaaatttctt 123600
aattgtgtgc tgaatacaat tttctttatt acagaagtac caacaattac atgtataaac 123660
agagaatcct atgtacttga gatataagta aggttactat caatcacacc tgaaaaattt 123720
aaatgttatg aagaaattat ctcatttcta ttaatatggg aactgtgtct tcatctttat 123780
tactgttcta aggtcaactc aatgtagatt ttacttgctt atggtttcat attttagcta 123840
aatagtaaaa taatatggat atacattttg ttgtgactta ctcatacttt ccttatttgg 123900
aacttttatg aatatgatat agagactgaa actacaagga acaaaatgca atatcaatta 123960
tacagttgtg gcagcactgc tatcaatttg ttgatagtgg ttaacactta gaaaaacatt 124020
ttaaaaataa tttcacataa gtaatgtaat ttattagctg tctctgacat tttacagttt 124080
ggaatagttt attttctttt tggtgtcctc accaaaaccc aacatcttca agggcaggaa 124140
ctgtataatt tttgccattg tattttgagc acatagcatg gtacttgcct ctaaatagat 124200
actattgtta aaatattttt taaggtaata ttttaaagtg tatgctatgg tacagttcag 124260
tttgtgactt ttgctagttt atgccactta cagttagcaa aatcacttca gcagttcttg 124320
gaatgttgtg aaaagtgata aaaatcttct gcaacttatt cctttattcc tcatttaaaa 124380
taatctacca tagtaaaaac atgtataaaa gtgctacttc tgcaccactt ttgagaatag 124440
tgttatttca gtgaatcgat gtggtgacca tattgtaatg catgtagtga actgtttaag 124500
gcaaatcatc tacactagat gaccaggaaa tagagaggaa atgtaattta atttccattt 124560
tctttttaga gcagtataca aagatgctga tttgtattta ttagactctc cttttggata 124620
cctagatgtt ttaacagaaa aagaaatatt tgaaaggtat gttctttgaa taccttactt 124680
ataatgctca tgctaaaata aaagaaagac agactgtccc atcatagatt gcattttacc 124740
tcttgagaaa tatgttcacc attgttggta tggcagaatg tagcatggta ttaactcaaa 124800
tctgatctgc cctactgggc caggattcaa gattacttcc attaaaacct tttctcaccg 124860
cctcatgcta aaccagtttc tctcattgct atactgttat agcaattgct atctatgtag 124920
tttttgcagt atcattgcct tgtgatatat attactttaa ttattattat acttaacatt 124980
tttatttact ttttgtgtta gtattttatt ctgtcttctc cttagatagt aaccttctta 125040
agaaaatata tatgctaagt gttttactgg tttaatatgc ttagactact catctacctc 125100
aatacttcct tggagatctc ctcctcagtc acacagagct caggacttat atttccttgg 125160
aactcctgtt agggtccaat gtacatgaaa ttccctagac agacagacag tcagttatat 125220
ggcttgattt caaagtttca aaatgattta atggactatc aagtagttta ttaggagaac 125280
agttattata ctcttctaaa aataaagact ttaagcaata aagatgtata tgtatataaa 125340
atggctgggt tattcctaga agtacctttc ttagaattta gttaaattta atatccaaga 125400
tactatcttt tcaaccctga gattgtgaaa agtaacttct atcaatataa actttactac 125460
atttgtattg tgttagtgtg ttacagtata atctagaaca atgtgtcttt ctatatgata 125520
tatgacattt taatgcctaa aaaaactgat atgtcttaga tgattctagt caggatttac 125580
ttctagaata gattaaaatt ctatttgagg agagtcaaat taattatcga attctcagtt 125640
gttattattg ctgttttatt tttagtgaaa cagattagtc ttaatgtaaa cacttgagaa 125700
ataaattgat ggtcaaccta aaatgtaaaa aagaaattaa tagaaaattt aaagagcaac 125760
aaagctctga catttaaaag aaatgaagta caaatctcta gggaccttaa agatcatcta 125820
ataatttcct cattttctag ataaataaac tgagagaccc cgaggataaa tgatttgctc 125880
aaagtcaaat atctacttaa tataggaaat ttaatttcat tctcagtctg ttaacatgca 125940
acttttcaat atagcatgtt atttcatgct atcagaattc acaaggtacc aatttaatta 126000
ctacagagta cttatagaat catttaaaat ataataaaat tgtatgatag agattatatg 126060
caataaaaca ttaacaaaat gctaaaatac gagacatatt gcaataaagt atttataaaa 126120
ttgatattta tatgttttta tatcttaaag ctgtgtctgt aaactgatgg ctaacaaaac 126180
taggattttg gtcacttcta aaatggaaca tttaaagaaa gctgacaaaa tattaatttt 126240
gcatgaaggt agcagctatt tttatgggac attttcagaa ctccaaaatc tacagccaga 126300
ctttagctca aaactcatgg gatgtgattc tttcgaccaa tttagtgcag aaagaagaaa 126360
ttcaatccta actgagacct tacaccgttt ctcattagaa ggagatgctc ctgtctcctg 126420
gacagaaaca aaaaaacaat cttttaaaca gactggagag tttggggaaa aaaggaagaa 126480
ttctattctc aatccaatca actctatacg aaaattttcc attgtgcaaa agactccctt 126540
acaaatgaat ggcatcgaag aggattctga tgagccttta gagagaaggc tgtccttagt 126600
accagattct gagcagggag aggcgatact gcctcgcatc agcgtgatca gcactggccc 126660
cacgcttcag gcacgaagga ggcagtctgt cctgaacctg atgacacact cagttaacca 126720
aggtcagaac attcaccgaa agacaacagc atccacacga aaagtgtcac tggcccctca 126780
ggcaaacttg actgaactgg atatatattc aagaaggtta tctcaagaaa ctggcttgga 126840
aataagtgaa gaaattaacg aagaagactt aaaggtaggt atacatcgct tgggggtatt 126900
tcaccccaca gaatgcaatt gagtagaatg caatatgtag catgtaacaa aatttactaa 126960
aatcatagga ttaggataag gtgtatctta aaactcagaa agtatgaagt tcattaatta 127020
tacaagcaac gttaaaatgt aaaataacaa atgatttctt tttgcaatgg acatatctct 127080
tcccataaaa tgggaaagga tttagttttt ggtcctctac taagccagtg ataactgtga 127140
ctataagtta gaaagcattt gctttattac catcttgaac cctctgtggg aagaggtgca 127200
gtataaataa ctgtataaat aaatagtagc tttcattatt tatagctcgc aaaataatct 127260
gtatggaagt agcatatata aggtatataa acatttagcc tcttgatagg actaactcac 127320
attctggttt gtatatcagt cttgcctgaa tttagctagt gtgggctttt ttttatcttg 127380
tgagtttgct ttatacattg ggtttctgaa aagatttctt ttagagaatg tatataagct 127440
taacatgtac tagtgccaat cttcagacag aaattttgtt ctattaggtt ttaagaataa 127500
aagcatttta tttttaaaac aggaaataat ataaaaagga gagtttttgt tgttttagta 127560
gaaaacttaa tgccttggat gaaatgagcc atgggcaggg ttgtaatgaa ttgatatgtt 127620
taatagtata gatcatttgt gaataaatatg acctttgaca agacacaagc cattaacatc 127680
tgtaggcaga agtttccttc tttgtaaaat gagggaataa aatagatccc taaagtgtgt 127740
aattttagta tttctaaact ttatgaaggt ttcctaaatg ataattcatc tatatagtgt 127800
ttttttgtgt gtttgtttgt ttgtttgttt gagatggagt ctcgctctgt cacctaggct 127860
ggagtgcaat ggtgcaacct cggctcactg caacctctgc ctcctgggtt caagctaatc 127920
tcctgcctca gcctcctgag tagctgagat tacaggcatg caccaccatg ccgagctaat 127980
ttttgtattt ttagtagaga aggggtttca tcatgttgac caggctggtc ttgaactcct 128040
gaccttgtga tccacccacc tcagcctccc aaagtgctgg tattacaggc gtgtgccacc 128100
acgtccagcc tgagccactg cgcccagccc atctatatag tttaatatca atctaaatga 128160
atttctcagt cctgagccta aaaatttagt tgtaaagaat gatatccttg actaataata 128220
gtttctatta atggattgca tctagtgcta ggtggcatat atttagtccc cacaactacc 128280
ctggaaggta tttaaaattt ttcacatttg cagataagga aactaaagtt cagagttcgg 128340
caacatgctt gaattcaagc agctcctagg atgttaatgg tggaggttgg gttcaaatcc 128400
agatctgtct gactcaaaaa atgcatactc ctaaccagtg cactatatcc caattccata 128460
ggagcccttc tttgtgattc atagcacttt cccatgagtt ttgttgattt tgtgagaaac 128520
aaaactcttt ttcctttgga ctgtctggaa tctctctttt tcaaattttt gaaatgtatt 128580
tctatgccaa aagacaaaga tttctagagg aatatgccta ggatgagaat tatgtaattt 128640
aaatcacagc tggaaagaga gaaagtccta agttactaag aaatgttcaa acacaaatga 128700
gctttcagtc tattggaaga cctttatagc tagaagtata ctgaactgta cttgtccatg 128760
gacccctgaa gaaacaggtt aaatcaaaga gagttctggg aaacttcatt tagatggtat 128820
cattcatttg ataaaaggta tgccactgtt aagcctttaa tggtaaaatt gtccaataat 128880
aatacagtta tataatcagt gatacatttt tagaattttg aaaaattacg atgtttctca 128940
tttttaataa agctgtgttg ctccagtaga cattattctg gctatagaat gacatcatac 129000
atggcattta taatgattta tatttgttaa aatacactta gattcaagta atactattct 129060
tttattttca tatattaaaa ataaaaccac aatggtggca tgaaactgta ctgtcttatt 129120
gtaatagcca taattctttt attcaggagt gctttttttga tgatatggag agcataccag 129180
cagtgactac atggaacaca taccttcgat atattactgt ccacaagagc ttaatttttg 129240
tgctaatttg gtgcttagta atttttctgg cagaggtaag aatgttctat tgtaaagtat 129300
tactggattt aaagttaaat taagatagtt tggggatgta tacatatata tgcacacaca 129360
taaatatgta tatatacaca tgtatacatg tataagtatg catatataca cacatatatc 129420
actatatgta tatatgtata tattacatat atttgtgatt ttacagtata taatggtata 129480
gattcatata gttcttagct tctgaaaaat caacaagtag aaccactact gatattttat 129540
tatttcatat tacatataaa atatatttaa atacaaatat aagaagagtt tttaatagat 129600
ttttaataat aaaggttaag agattcgaaa gctcaaagta gaaggctttt atttggattg 129660
aaattaaaca attagaatca ctgttgatat tttattattt catattacat ataaaatata 129720
tttaaatata aagataagag tttttaatag attttataat aaatgttaag agattaaaaa 129780
actgaaaata gaaggctttt atttggattg aaattaaagg ccaggcatgg tggttcatgc 129840
ctgtaatccc agaattttag gagactgagt ggggaggatt gcttgagccc aggggtcaag 129900
accagcctgg gcaacacagt gagacaccgt atctacaaaa taattaaaaa attagctggg 129960
catggtggtg tgtgcctgta tgctaccatt aactaaggag gctgaggtgg gagaatcgct 130020
tgagcctggg aggtcaaggc tgccctgaac tgtgattgtg ccattgcatt ccagcctggg 130080
tgccagagag agaccctatc tctaaataaa taaataagta aataaataaa cagcaacaac 130140
aaaaacactc aaagcaaatc tgtactaaat tttgaattca ttctgagagg tgacagcatg 130200
ctggcagtcc tggcagccct cgctcactct cagggcctcc ttgaccttga cgcccactct 130260
ggctgtgcgt gaggagccct tcagccctcc cctgcactgt gggagcccct ttctgggctg 130320
gccaaggcca gagccggctc cctcagcttg cggggaggtg tggagggaga ggcgctgggg 130380
gaactggggc tgcgggtgcc ttgtgggcca gcgcgagttc tgggtgggtg tgggctgggc 130440
aggccccgca ctcggagcag ccggccggcc ccgcgagccc caggcagtga ggggcttagc 130500
acctgggcca gcagctgctg tactcgattt ctcactgggc cttagctgcc tccctgcggg 130560
gcagggctcg ggacctgcag cctgccatgc ctgagcctcc ccccaacctg ccgctgcagt 130620

-continued gggctcctgc gtggcccaag cctcctgacg agcaccgccc cctgctccac ggcacccagt 130680
cccatagacc gcccaagggc tgaggagtgt gggtgcaggg cgcagggctg gcaggcagct 130740
ccacctgcag ccccagtgcg ggatccactg ggtgaagcca gctgggcttc tgagtctggt 130800
ggggacttgg aggatcttta tgtctagcta agggattgta aatacaccaa tcagcactct 130860
gtatctagct caaggtttgt aaacacacca atcagcaccc tgtgtctagc tcagggtttg 130920
tgaatgcacc aatcagcact ctgtatctag ttaatctggt ggagacttgg agaaccttta 130980
tgtctagcta agggattgta aatataccaa tgtgcactct gtatctagct caaggtttgt 131040
aaatacacca atcagcactc tctgtctagc tcagggtttg taaatacacc aatggacact 131100
ttgtatctag ctaatctagt gaggaggtgg agaacttttg tgtctagctc agggattgta 131160
aacgcaccaa tcagcaccct gtcaaaacgg accaatcagc tctctgtaaa accaatctgc 131220
tgtctgtaaa atggaccaat cagcaggatg tgggtggggc cagataagag aataaaagca 131280
ggctgcctga gccagaagtg gcaacctgct ggggtctgta gaagctttgt tcttttgttc 131340
tttgcaataa attttgctac tgctcacttt ttgggtccgc attgcgttta tgagctgtga 131400
cactcactgg gaaggtctgc agcttcactc ctgaagccag cgagatcacg aacccaccag 131460
aagaaagaaa ctcctaacac atccgaacat cagaaggaac aaactcagga cacgcggcct 131520
ttaagaacta taacactcac tgcaagggtc cttggcttca ttctcgaagt cagtgagacc 131580
aagaacccac caattccgga cacaatttga ctgcagaaaa tggatgtcca accctgtggt 131640
ttccctgggc cacattggaa gaagaaagga gttgtcttgg gccacacata aaatacactt 131700
actatagcag atgagctaaa gaaaagaaaa aagtccatgc gtaatctttg tgatatgtgc 131760
caccaccaat aagcaaaatt gttctcttat tcaaaaggtt ggacacagct gctctagata 131820
ttttattatt aaatatgcag gcaattactg tttaaatgaa gatttcctca cagaatgaga 131880
ttaaaagtat atattagtgg cttagcattc attttagaca accattttag agattcaaat 131940
cacacacttg cttacagaaa ttttgttgtc ttcaatgtcc ccattgtggt ttctttacca 132000
agcctctact gttcttcaca tcaccaagtt aaaaaaaaaa aaggggcggg ggggcagaat 132060
gaaaattgca tggtaggcca caagttcaga tcctcatcga cacaagaggt gcctgaagca 132120
gtggatgagg cttttctatg gatcatgagc agccacataa atgcttaaaa gggcctggca 132180
gggagcatca gtgggtgatg tggctgggag gctgaatgga gagcatttgt tcttcagtta 132240
tctatagaag gcagctgtca ctcagcacca gctaagggct tcccatgagg gaactgggga 132300
tcaggtttcc cagatctttt tatgtaacag gataagacag agatccagct ttttttgggt 132360
aattatttcc tattttaaaa tacgggtagt tgattaaata aaaacaaacg aatgaacacc 132420
atatgggcac aacaaaacac atctgtggct tggattcagc ttgtgaatga ttactgcaga 132480
tatttattct agaggacacc cctgggtatg tcctaatata aaacctaaat ctaaactcaa 132540
gtcccatgct accttcagag aataaatgac ccagaaaaag aaccacctct cctaaggaag 132600
tataaatttg taaataactg agacccaaac ttacaactat acatttttct tattgttggg 132660
ctgttgctaa cctcaattaa gaaggcttga tgatatttgt aaagtgtcat cactccacca 132720
tggtccagta acatctgatc actccaccat ggtccagtaa catctgaatg gtcaagaaat 132780
atctaaacgt atgtaccaaa aatttgtgta tactactgta ccaataaacc atttgtttcc 132840
atttgatctc tgagtgtggt aatacatgtt atttgccctg ctgttgtaaa taaacaaacc 132900
aaatggaggc ttgatgcaag atgcagtgta gcatagtgcc aactctggac tccgactact 132960
cagggtgtaa attctaactc tgttctatta acaccatgaa actgagcaag ttagttaaaa 133020

```
ctcgctgggc ccattttctc atttatacaa tggagatttt aatagtacag ctacataggc 133080
cattttgtgg tttaaaatac atcatgatta tgaaacactt aatgtagggc ttgctacata 133140
atgagcaagg tttgttgctg ttatcattaa tatccttaat tctcattatt ataaaacttg 133200
agatagtatg aggtgaacaa gttcataaca gcaatataat gaaaatttta ataattcctt 133260
ttatacttta acaaaaatac gagattgggt aatttattat ttttacatga gtaataaata 133320
ttgcattaaa atatatttaa aatttaccac attaatgtct gccagtcatg ccaaatgacc 133380
aacatgaatg tgaataaaac tcagtctgtg cccatttaat cttaaccaac cctttataat 133440
tgttaatgat ttgaacctct gccttgaaag atcacattac ttgattgtct tcaacttatc 133500
tgaatgtggt agtgatttct gtaaatttat aggacctttg tctcatgcag ctccatggag 133560
ttgaacttat gcacctttaa aatggtatat acttaattaa ttaagtgttg atctgcttca 133620
catgtgtata atattattag ctcactaaac caagaaaaca gtggtccttt agggaaagaa 133680
actaaattac aacagagaat ataaatacca tataaatatc tattatttat tgaactgtca 133740
caattattgc aaaaaattac cttttagtgg acaaaacaat tgatattgcc cttttctgga 133800
aaagaaataa tgtaatatat gatgaatagt tttggccagt atcctctaga ccttgccagt 133860
taactggctc tcaaaatttt gaataataaa aacttggtga tagtagaaaa atagtaattt 133920
tttaaaagta tgtgcacaat tatacaacta aacaattcat tcaccagtgt tcacaattct 133980
attgccttct ttgaatcaaa atttacatag tttttctttt agactaagct cctttatgat 134040
accagtgtgc ccatttctca ttaccattga aatgtctcat gagcatgtca cattctggta 134100
caactgctaa tccaggatga cagtttagtt cttttaaatc caattgagag ccttctactc 134160
atgaccagag aacctaaaga aaggttaaga tacatttatt ccttggtgta agtgatttgt 134220
ctatttttag ttttcctaag ggtcatattt caatttagat ttttttttat aggttaggta 134280
aaataggctt cccttttgca atatgaaata tgtagtcttt taaaaaattt cttcaaagct 134340
attaaactga aaaaaaatta atttggtcta ttcagtttgt tagcacttac cattttggaa 134400
agagagtgac tctacttttg tatttggtaa cattttccct actacagggc agtatctttt 134460
gtaagttctt agatattagc accaaataaa taggcaaaaa aaatctatta tgttaattct 134520
tagaacccct gcttggcagt gcatcattga ctagatggag aagaaatgaa aataatacat 134580
taggaagcag tttcctggtt cttttgaaaa caactagaga gtcttgttgt tgactggaat 134640
atctgaagat cctgtttaat gctttcattc tatgattgtt aagaatatgt catagaactg 134700
ctgtatcctg tttctttatg tcttcccttc tgtttgttga ttagaaatcc ctgagtggct 134760
ttacattatt agtacagtag atatgtagta tattcccata ataccactgc tgctattgac 134820
taatagtaat aattttaggg cagctttatg acagttggtt tatgttttag ggtgtcattt 134880
gacttgtgaa gcattgaaat ctgggtatta agcacactgt tttctatgtg gtatggaatg 134940
attcttaaag ccctgagaaa atggaaaata aaaatatttt tccttttttac cataatcacc 135000
tatgactgtc actctatcat aaactgcata aactttataa cctcaaaaca ttttggaaat 135060
gaaatgacag aacttgctta ctcaattgct tctatataca ccaaatattt ttttaaagta 135120
ttatgttaag tccttgaaaa tattttgttc tactcaatag aagcagttta ggttggtagt 135180
tctatgtgga aaccgtgagg aaataatttt atattatgat gactagacca gtctttgaac 135240
atcactttgg ttattgttcc attagtaaat attataatta tttctgagat ttactcacct 135300
tcaaagaatg ttggcaatgc cagcattatt aacactcctc tagttagaac aaagaggaaa 135360
```

-continued tgtaataaca aaacataata atagccaaat aaagagtgac ttagaatgta cacccttatc 135420
taggatcctg agtaattcga ttattcttag gaaatacact tttgtgctag aacaaagact 135480
tttgaaatag ctaatttctg ggtttctttt cattttgaat taacttgaat ttcaaggaaa 135540
caagggtagt ttttacagat acagtgcata gaagctctgt gtacaatgaa gaaaagtagg 135600
aaagtgagaa aaatgccatt agatttttca tcgttatact atctgatatg tgaatttaac 135660
taaaacttat atacctcatt atagtacttc ctaatgtaat ttcttaattt aagtgttccc 135720
cataaggttt ttttttatat aaacttaagt actgttaaat atttaaggca aattcaggta 135780
taaaataaga cttgttgata tcttattcca agcatatttg tttctctcct atttattttt 135840
attctgtgtt catttccaaa attgttttac tcacaactgt ttgtttttttc tgtttcattc 135900 tgtggtaaag gtatcatttg gctaattgta taatttcagt gtcatttcta atattccaat 135960
tgtgatagta tcaacacaag attaaatttc tctacatggt ttatgagaat ggaatgccaa 136020
attgaaatag aacagagcac agatgatcta aatataaaaa gaactacaaa aatcacagtt 136080
gtttaaaaag gtttttgtt tgtttatata tggtgcagaa catttgttcc ttagccaaat 136140
gtttccacct tgagaaagct atagagattc tatgtagtcc tagtaccaat aatatgtttt 136200
aacctgaatg taccttatct ttattcataa actgtgactt tttacactgc tgaaactttt 136260 tttttaaga caatctcact ctgtcgtcca gtctggagtg cagcagtggt gtgatcttgg 136320
ctcactgcaa cctctacctt ctgtgttcaa gcaattctgg tgcctcggcc acctgagtag 136380
ttgggatcac aggtgtacac caccaggcct ggctaatagt ttttgatatt tctagtagag 136440
atgagttttg ccacattggc caggctggcc tgaaactcct ggcctcaagt gatctgcctg 136500
ccttggcctc ccaaagtgtt ggtattacaa gtgtgagcca ctgtgcctgg cctgaaactc 136560
ataattcatt tccattaata ttaatctcac cttttccaat aattaattga tttcacaagt 136620
attagtcccc tataatcatt gaatggctaa taaaattatt tatagcaaac agattaatta 136680
tctgccagca gtctgagatt agtttcttta aaaaatgttt attatttaaa acattcagct 136740
gtgatcttgg ctttcttgtg aggttcaata gtttctattg agtaaaggag agaaatggca 136800
gagaatttac ttcagtgaaa tttgaattcc attaacttaa tgtggtctca tcacaaataa 136860
tagtacttag aacacctagt acagctgctg gacccaggaa cacaaagcaa aggaagatga 136920
aattgtgtgt accttgatat tggtacacac atcaaatggt gtgatgtgaa tttagatgtg 136980
ggcatgggag gaataggtga agatgttaga aaaaaaatca actgtgtctt gttccattcc 137040
aggtggctgc ttctttggtt gtgctgtggc tccttggaaa gtgagtattc catgtcctat 137100
tgtgtagatt gtgttttatt tctgttgatt aaatattgta atccactatg tttgtatgta 137160
ttgtaatcca ctttgtttca tttctcccaa gcattatggt agtggaaaga taaggttttt 137220
tgtttaaatg atgaccatta gttgggtgag gtgacacatt cctgtagtcc tagctcctcc 137280
acaggctgac gcaggaggat cacttgagcc caggagttca gggctgtagt gttgtatcat 137340
tgtgagtagc caccgcactc cagcctggac aatatagtga gatcctatat ctaaaataaa 137400
ataaaataaa atgaataaat tgtgagcatg tgcagctcct gcagtttcta aagaatatag 137460
ttctgttcag tttctgtgaa acacaataaa aatatttgaa ataacattac atatttaggg 137520
ttttcttcaa attttttaat ttaataaaga acaactcaat ctctatcaat agtgagaaaa 137580
catatctatt ttcttgcaat aatagtatga ttttgaggtt aagggtgcat gctcttctaa 137640
tgcaaaatat tgtatttatt tagactcaag tttagttcca tttacatgta ttggaaattc 137700
agtaagtaac tttggctgcc aaataacgat ttcctatttg ctttacagca ctcctcttca 137760

-continued agacaaaggg aatagtactc atagtagaaa taacagctat gcagtgatta tcaccagcac 137820
cagttcgtat tatgtgtttt acatttacgt gggagtagcc gacactttgc ttgctatggg 137880
attcttcaga ggtctaccac tggtgcatac tctaatcaca gtgtcgaaaa ttttacacca 137940
caaaatgtta cattctgttc ttcaagcacc tatgtcaacc ctcaacacgt tgaaagcagg 138000
tactttacta ggtctaagaa atgaaactgc tgatccacca tcaatagggc ctgtggtttt 138060
gttggttttc taatggcagt gctggctttt gcacagaggc atgtgccctt tgttgaacct 138120
ccatttgact ggcatgcaca tgtctcagat attataggtt atcatatatt gttgctccta 138180
atatttctgt gttagataat tagagtagct tggtttgtaa gaatgtgatg ttggtgggac 138240
tgtagcagaa caagaaggcc cttatgggtc agtcatacct ctcttttcaa atatttggtc 138300
tagctctctt ctgggcatct tgttgccaat atatagtatt gctcaaaagg gcaggagatt 138360
tgaagtgatc aaggaaaata tattttttct attgattaag tcttttgatg gggtagaata 138420
atctaatttc atgtaactgc tcaaagttat atggtagggg gatcccaaat gtattttaaa 138480
actattttta tatcatcata tttgaagtaa tagaaagtca gagtagcaga ataaaggtac 138540
taaaaatttt aaaaactaat aaggtacttt gaaagaaatc aattatgttg attcctcatt 138600
aaacaaattt gcacttaaag actgaggtta ataaggattt ccccaagttt tttcatagca 138660
acctgtgagc actttctctg ttgaggcatt tatggtatga aaagatgagt aaggcacagt 138720
tcttgccctg gagaaggtca caggtgagag gaggagttga cacagaaaca tttgatataa 138780
agcaaggaat aaattccaag actaaaattt tcagaaatct aaaaaactca agataagaaa 138840
aacccattat attttctggg taacaaaatt tcagtgttat taacatgtag gaagatcttg 138900
atatttattc tgaagcccat gtgtgttgct gaaatattgc cgcatttgca tatactcatc 138960
accatcctct gttttggagc taagaatttt agactcaaga tgtctaatta agttgatcca 139020
ttgattttat tttttatgga aatctgagac ccacagaagg caggggattt gcccacattt 139080
ctagaagagt cagacatgag cgatgaggca cagtggaaag aacatgagca ttgcctgagc 139140
tctgagttgg cgctataaga gcagtgatca tgggcaagtg actcttctga gccttggcct 139200
cctcacctgt taagtgaaga aaagaatatt tcagaagatc tttgtgagaa tgaaacaagg 139260
caatttactt gcctgctaca tagccaatgg gaaatcaata taagttcccc gtggttccct 139320
tctgtggggt tttgttccca cagagggtgc actggccatt ccacttcttc ttttccaagc 139380
tcctcattcc ctttaacgct gttcatagtt ggttccaaac catttgaaat ataataagca 139440
ccaggatggt tttttctttc caccaaagca aatttcattt tctaaacact gtttataaat 139500
atcaatggct attttttcaa tttttgatta tcatgaaaat atacaaatat gtttaattaa 139560
atatgctaaa gaatgtatta ataaatatgt attaaataat tcctacatat aaggcctttt 139620
tgcttggggt atgggtgata caaaataaat gtggcatgaa cccactgacc tctagcaatt 139680
tataacctag aaaaagagtt atgatatgtt tataagttcc tgtgatataa gacatgcata 139740
tagtcattat aacagaggtg caaacaagat gtatcaagta tgtccagagg aggaagagat 139800
taatcccagc tggaggaaac actgatgctt tcttgcagca ggggcatttg agttgagaaa 139860
gggaggaaac atagattttg acaatgagag ctgaggggaa aggggtttca ggtggaggga 139920
accgcatgtg gaaagcaggg aggtaggaaa gtgtagagtg tgtttaaaga atagaccagt 139980
ttggctgaaa caggatattt gagcagagga agcttgtact aggtaggtgg gttgaggcca 140040
aattatgcaa ggcattaaat attaaactag gaattttgga ctttatcctg cagtttatgg 140100

```
ggggtaaatg ataagattca atatcacttt atttgtacag tattatgtta cattttatct 140160
aattgtttgt ttaattcctg tctagacaat gaattcctca agggcaagga gcatggctta 140220
ttcacctcag taatttcagt gcctagcatt gtgcctggta caaagtggac acttgtatat 140280
aacctttttt aattgaagca acaagttgtc aaccttacaa atgtgaatcc gtgattcaga 140340
tgacaggttg aaatgtagat tgtctgcgaa gagggcagaa agagagtatg acaaaggagg 140400
acaagacagt ggggcaggca gggagagaga gcagccaggg tttcggtaga ggtatgtcaa 140460
aaaggtatgg aagtcagagg agaaggagac ccctatgtta tagaatacaa atggaaggga 140520
aatgatgaca acagtaagtt gtcattaaat gcaaggttgc aaaagtaaga ttgtaaagca 140580
ggatgagtac ccacctattc ctgacataat ttatagtaaa agctatttca gagaaattgg 140640
tcgttacttg aatcttacaa gaatctgaaa cttttaaaaa ggtttaaaag taaaagacaa 140700
taacttgaac acataattat ttagaatgtt tggaaagaaa caaaaatttc taagtctatc 140760
tgattctatt tgctaattct tatttgggtt ctgaatgcgt ctactgtgat ccaaacttag 140820
tattgaatat attgatatat ctttaaaaaa ttagtgtttt ttgaggaatt tgtcatcttg 140880
tatattatag gtgggattct taatagattc tccaaagata tagcaatttt ggatgacctt 140940
ctgcctctta ccatatttga cttcatccag gtatgtaaaa ataagtaccg ttaagtatgt 141000
ctgtattatt aaaaaaacaa taacaaaagc aaatgtgatt ttgttttcat tttttatttg 141060
attgagggtt gaagtcctgt ctattgcatt aattttgtaa ttatccaaag ccttcaaaat 141120
agacataagt ttagtaaatt caataataag tcagaactgc ttacctggcc caaacctgag 141180
gcaatcccac atttagatgt aatagctgtc tacttgggag tgatttgaga ggcacaaagg 141240
accatctttc ccaaaatcac tggccacaaa gtgtgacatt ttggcattgg catcactatt 141300
tgatggaagc caacctcccc ccaaaaggcc tgtattagaa tgaagatgga ttccctgggt 141360
gggttacact tgaaactagc ctcacccatg aacactttgg cacagattag ctagcccatt 141420
cccccacagt aaggaccata aggaagggac agaagcaaag ataagtttta gaacaaaaga 141480
gaggggaaag aaaaaatcta gggttttatg agggctgtcc ctgagtgata gatgtgaata 141540
ggcctccagg gcaggctggc tcagaggctg actctttggg ttggggtgac tgattggtgg 141600
tgaggatgga gaagaaaagg ggagtggagg aggtgaaagt gaccttggga cattaggtct 141660
ccataagtga caggatttaa ggagtgttgt aagctgtggt tgttggacca ggtttaagca 141720
cagcttcctg agcttcctga ctggtttagg tcaagctcca gagagcaaat gccacagtct 141780
cagtgatctc cttggagaaa cagttggaat aggatgttgc ccatgttggg atgagtcatt 141840
gtccgctctt gctctttccc taccccctgca aaataataat actgtatttg attgaacata 141900
taaaacaaaa gaaggattat cacataagta tgtatatata accaacattg gcaggtgcag 141960
aaaaaccaga ctgtcagttt gcctcatctg aaatgattga cacaaacaaa tatatttact 142020
gtcccaagtg aactttggca ttttggatat ccttcagttg ttctgtttaa agatataact 142080
tagaagcagc tgatggaata tttaaatcca tgcgttgaat tcatgcattc aaagaaacat 142140
gtcctgagtc actaaatgct gacatttgtt tttcatgtta agagtgtaaa taactggtcc 142200
caaatataat attattacat cagataaaaa ctggaatgtg aacctcttaa cttgattgtg 142260
aaagtatttg ccaatggtgc ctcttgataa ttatttgagg ctcacttcag aactcctctg 142320
gaagggttaa tttttaaata gtcattttat aaattaacat ttttgacata tgtgatggct 142380
ctcaaatttt ttcttttatg ccagtttgaa tcatttctgc tcaatttttt tttttaattg 142440
ggatggagtc tcactctgtt gcccaggctg gagtgcagtg atgcaatctt ggctgactgc 142500
```

aacctccacc tcctcggttc aagcgattct ctcgcatcag cctccagagt agctgggatt 142560
acaggcgcgc accaccatgc ctggataatt tttgtattat tactagagat ggggtttcac 142620
cacgttggcc aggctggtct tgaactcctg aactcctgac ctcaagtgat ccacctgcct 142680
cagcctctta aagagctgga attataggtg tgagccactg caccaggccc tgttcaactt 142740
ttaatgctaa gattcatttg ttgttgtttc acaagtgatt aggcagaggt cttttatatt 142800
aatttaccca ttttatttgt aagagagtct catattaagg aagcataata tatgacaatc 142860
caaatacagt acaaatttgg ttaattttga ttttgttaaa taattaatca caggggtcct 142920
tcaaattgtg agctcctctg gttatactta tgttttacct ctggttatac ttaatttcaa 142980
acaaatgaaa tttcattcta ttcatgatat ttcagaagca gatctgttgc acaaaataaa 143040
gcatacctat aaattttctt tttttaaaaa aaagtctctg ttcactctat tttctattat 143100
ttttctcttt ttaaaatttg aattttattg tggcaagtcc acttaacatg agatttaccc 143160
tcttaacaga tttttatgtg taaaatacaa tattgttcac catgggtaaa tgttgcacag 143220
cagatctctg gaacttattc attttgcact actgaaattt tatacctgtt gattagtatc 143280
tccccatttc cctctctccc ctgtcctgtt acccatggtt ctgttctttg cttctttgag 143340
tttgagtatt ttgatacctc atgtaatctt cattctattt tctaactttg acaatgttct 143400
gacaaatttg ctttccggat tggagcactg tatagtgaaa attgaaaatc ttggttattt 143460
tctacagatt cccactattt taccttgagc agacacttat cttgaagggt ctcagatttg 143520
tcacttgtag aatggggaat ataaacctga taatggtccc tttcagttct aaagttatat 143580
cagttgaaaa tacatgtgtc acttatggta acgggtagag aactggctca ctgaacagca 143640
tatggatatt ataaagtggt ttttttaat cctttctgca gacagttact ttatacttta 143700
ttcaaatgga ttattgtgaa gtacatgtta gcggactttg taccttttaa aaatgtatgt 143760
atttggtgta atgtagaaat atagaaattt attaagtatg atttatttca atgttaagca 143820
tgagaaaata tgctccgaaa ggttagatag cttgcctaaa tgacaagctt gtatttcaag 143880
cagaactttc tgaatcaaaa gactccaaga cgaatgccca gctttcaaaa actgtctaac 143940
caaaataaat cctaagattc accttcatac taaaattatt taaaaatagt ttattttaaa 144000
ttaatattca cttaaaatgt atttatcatg caatacttta aagtgtctgg gaaatgaaaa 144060
tatccaaaga tcaaagaaca ccatgttttc aaacttcaaa aatgttatca gtgacctaaa 144120
caatttttaa aattttcata gagcctatga aaaatgtact tgcaaatggc tactttctga 144180
ctaggaatag aatggggaga gtatttagtc caacaatgat agactggatt aagaaaatgt 144240
ggcacatata caccatggaa cactatgcag ccataaaaaa tgatgagttc atgtcctttg 144300
tagggacatg gatgaaattg gaaaacatca ttctcagtaa actatcgcaa gaacaaaaaa 144360
ccaaacaccg catattctca ctcataggtg ggaattgaac aatgagatca catggacaca 144420
ggaaggggaa tatcacactc tggggactgt tgtggggtgg ggggaggggg gagggatagc 144480
actgggagat atacctaatg ctagatgacg agttagtggg tgcagtgcac cagcatggca 144540
catgtataca tatgtaacta acctgcacaa tgtgcacatg taccctaaaa cttaaagtat 144600
aataaaaaaa ataaaaaaaa gtttgaggtg tttaaagtat gcaaaaaaaa aaaaagaaat 144660
aaatcactga cacactttgt ccactttgca atgtgaaaat gtttactcac caacatgttt 144720
tctttgatct tacagttgtt attaattgtg attggagcta tagcagttgt cgcagtttta 144780
caaccctaca tctttgttgc aacagtgcca gtgatagtgg cttttattat gttgagagca 144840

-continued tatttcctcc aaacctcaca gcaactcaaa caactggaat ctgaaggtat gacagtgaat 144900
gtgcgatact catcttgtaa aaaagctata agagctattt gagattcttt attgttaatc 144960
tacttaaaaa aaattctgct tttaaacttt tacatcatat aacaataatt tttttctaca 145020
tgcatgtgta tataaaagga aactatatta caaagtacac atggattttt tttcttaatt 145080
aatgaccatg tgacttcatt ttggttttaa aataggtata tagaatctta ccacagttgg 145140
tgtacaggac attcatttat aataaactta tatcagtcaa attaaacaag gatagtgctg 145200
ctattactaa aggtttctct gggttcccaa atgatacttg accaaatttg tccctttggc 145260
ttgttgtctt cagacaccct ttcttcatgt gttggagctg ccatttcgtg tgcccccaaa 145320
ctctacttga gctgttaggg aatcacattt tgcagtgaca gccttagtgt gggtgcattt 145380
tcaggcaata ctttttcagt atatttctgc tttgtagatt attagctaaa tcaagtcaca 145440
taaacttcct taatttagat acttgaaaaa attgtcttaa aagaaaattt ttttagtaag 145500
aattaattta gaattagcca gaaaactccc agtggtagcc aagaaagagg aataaatatt 145560
ggtggtaatt ttttaagttc ccatctctgg tagccaagta aaaaaagagg gtaactcatt 145620
aataaaataa caaatcatat ctattcaaag aatggcacca gtgtgaaaaa aagcttttta 145680
accaatgaca tttgtgatat gattattcta atttagtctt tttcaggtac aagatattat 145740
gaaattacat tttgtgttta tgttatttgc aatgttttct atggaaatat ttcacaggca 145800
ggagtccaat tttcactcat cttgttacaa gcttaaaagg actatggaca cttcgtgcct 145860
tcggacggca gccttacttt gaaactctgt tccacaaagc tctgaattta catactgcca 145920
actggttctt gtacctgtca acactgcgct ggttccaaat gagaatagaa atgatttttg 145980
tcatcttctt cattgctgtt accttcattt ccattttaac aacaggtact atgaactcat 146040
taactttagc taagcattta agtaaaaaat tttcaatgaa taaaatgctg cattctatag 146100
gttatcaatt tttgatatct ttagagttta gtaattaaca aatttgttgg tttattattg 146160
aacaagtgat ttctttgaat ttccattgtt ttattgttaa acaaataatt tccttgaaat 146220
cggatatata tatatatatg tatatatata tatatatata tatatatata catatatata 146280
tatagtatta tccctgtttt cacagtttta aaaaccgatg cacacagatt gtcagatagc 146340
aattctgtga ttgaagggga aatatgtcac ctcttcatac tcatattggt gaagggtcct 146400
agcttcaaaa ttaatagatt cctaaagagg ggaaatgaaa catccgcatt tacacacaca 146460
cacacacaca cacacacaga gttcctcttg tcggtaagtt ttgttttttt taaatctcta 146520
ctagataaaa tttgttatct aattgtgagt tttacacaaa gaaaaactgt cacagaaaag 146580
aaagacagtg tcacattttt caaaagaaaa agaagaaaag aaagtgccat gtttttcaaa 146640
tacaaatgtt ctggattgat tttaggatct ttagtgaaaa acaaagtatt tcataataag 146700
taaaataaaa atctatgtag gtaaatttgt ttctctaatt taagaatttg aatttctgag 146760
tatttatgat aagtgttgaa ataacttctt atatgtgaca gtgaatactg gcagagcaaa 146820
tgccaaatca atgccaaatc tgtaggatca tttgattgta ggaacagaat tctactcaaa 146880
ccgaaagcag gcatttgctg gagttacaga aaggcctcat ggaacaccga gaaggtggtg 146940
ccattcgact cttaaagaag ctgcaacagg cacaagagag tcagctgcag ctcttcttct 147000
tgagtctata tctgtcctgg gtccattcct ttttgtggtt gcttcattcc tttctctctc 147060
tgaagactgg tttttctggt ctaccagggc tatgccacat tgactttatg tagtgtctcc 147120
attctggcct cctgaattta caggagagtt cctctgtaca aactcaaagt cctggagaga 147180
acagaaaaca gcttcctttt ggctcagggg tccaactgca gtctactctg ctgctatgag 147240
gatagtgggt tcaccacctt tgttgttctc tcagctaggg cagtgggaaa tgactctatg 147300
aaaggaatat acatgggcag gcaaatgtac taatcctcat cagtactgta attttaagca 147360
actttaaaaa attcttttaa gttatttgaa aataagatca aagaaggctg aattacataa 147420
atgaagattt gttaacaatt aattcaaacc aatataacac atgctataac atggttgagt 147480
gtgattgagt cttgatttat taggggcaat aatcaaaaca tttaacaatc attatagtac 147540
agaacttacc aatcaaatca gatgctcagc cggagtggat gttggccacc cagctattat 147600
tatccctggc tcaattggtc ttcagctgtg ttaacttgca aacattaatt aactatctaa 147660
gcccctcatt ttcctcaagt gtaaatagac acaataatat tacctattcc ataggtgtgg 147720
ggtgaatagt aaatgtaata atttgtccaa aacacttagt atagtgcctg gtccatggta 147780
aatactaaat aaatgttatc tgacttatta ttaaaatttt atcttctcag cttaaccttc 147840
agaacagtaa tatattgggg tctagataaa tcttgcctat atgaaaataa tttaatacta 147900
catgcagata tatgctgtgt atattatgcc ttctgttaga ggaattgcag aaacaaaaat 147960
ttcaattaat aataagatga attatttctc ccaattgtag aatcttttga caattttatc 148020
atgcattaca gatgtaagaa ctcttgattg ggacttgata gtctaacttt ataataattt 148080
aagaacattc ctcttagaga atttctatgg ccataatact gaacacatga attttaatta 148140
gctgtcctct ttagccctaa aaaaaaaatt actgtaattt aacacttaag tgttgttctt 148200
cccaggtaca gtaatctttt tttttttttt tttttttttt tgcatagagg gtaatctttt 148260
ctctttccaa atggcagaac tgttagtttt ctgactgtcc ggtgaaattc taagtccact 148320
tacttcccaa tagcatgcaa ttagcaaagg tcctccttgc aaaggcacag aacacaccta 148380
aacatcttgc agatgctgtt tggacactct tcccctgctt ttggtctctt tgtaaagcag 148440
ctcatctgga tacaggatct cttttcccca ttgcccattc taatatatgt taccgttatt 148500
acttatagaa taatagtaga agagacaaat atggtaccta cccattacca acaacacctc 148560
caataccagt aacatttttt aaaaagggca acactttcct aatattcaat cgctctttga 148620
tttaaaatcc tggttgaata cttactatat gcagagcatt attctattag tagatgctgt 148680
gatgaactga gatttaaaaa ttgttaaaat tagcataaaa ttgaaatgta aatttaatgt 148740
gatatgtgcc ctaggagaag tgtgaataaa gtcgttcaca gaagagagaa ataacatgag 148800
gttcatttac gtcttttgtg catctatagg agaaggagaa ggaagagttg gtattatcct 148860
gactttagcc atgaatatca tgagtacatt gcagtgggct gtaaactcca gcatagatgt 148920
ggatagcttg gtaagtctta tcatcttttt aacttttatg aaaaaaattc agacaagtaa 148980
caaagtatga gtaatagcat gaggaagaac tatataccgt atattgagct taagaaataa 149040
aacattacag ataaattgag ggtcactgtg tatctgtcat taaatcctta tctcttcttt 149100
ccttctcata gatagccact atgaagatct aatactgcag tgagcattct ttcacctgtt 149160
tccttattca ggattttcta ggagaaatac ctaggggttg tattgctggg tcataggatt 149220
cacccatgct taactgagtg gtgccaaatt gtcctcaagt ctgttgtact gatatatatc 149280
cccatcaaga gagtacaaga attctcatag ctatgtatct tcaacaacac ttggtgtctg 149340
gtagatgtga agtgattact aaaaatatag ggaagctgca tacataatta ttggcttttg 149400
ctgttctctt acattaattt cttattcatg ttgattactc atttgtcacc tagttttttc 149460
ttccttaatt aaattgtagg aatttatgaa ttatggattg atcatcagct ctatacattt 149520
caaacataat ccctcagtca gtggcttggc ttatagagtc ttttgatgaa aagaagcttt 149580
taagtttaat aaagttcaat ttattgtctt ttcctttatg ttttgtgctt ttggtatctt 149640
gattaagaac tccttcctta tattgggttc tcaaatttag cagcataaca ttttcatact 149700
attatttaaa tttttttcac attatttagt gatagcacct ttcttattcc taaagtgttt 149760
atcattgcct tctgtctttc tgcttgataa atattgccac acatttgtat actttattag 149820
tgtgtacaaa gaccacattt tagttgtgtt atttctcttg ttttggtttt ctagaatgca 149880
gagccattaa tattatagta atgcttatgt gctaatacca tatcaggggc acaaatccca 149940
ttgcagcggg actgagaaat taaaggaaat gatgcacatt tactcatttt tgtttaaaaa 150000
atcaaatgca tatttttcaa tcagactata tggttggtct ggatagcttc atcattgaat 150060
ttttaaagta tttttgtact actgtattta aaattattca ttcaccactg cttttgtaga 150120
tggtttagaa acccaagtta ggaatgactg tgcaacacta ttattatact ctttttaaaa 150180
ttatactttt tgcttaagtt tctttccttg ttctctgaga cagtgttcat gttcccaaac 150240
cacacacatt tattcagcta taaaatttgt atgatcaact cctgtcagaa caaacatcat 150300
tataaaaaat atctccagga aaaagaaaac ccttttaatg ctctcttctg gttcatgtgt 150360
cttcttattt tctttaagca ttttcataac ccattgagct gtaatttaat tggaacatga 150420
tttatactaa agttggtttc tttaccttta actttttttt ttagtttgat cagctctctt 150480
tagcttctgt agttcggtct ttaattccat tccagtatgc ttttggagtt gggtctcata 150540
aatgtataga aatgtttctg ttgggaaaca gcaggagaat attaaataaa tattgtgctt 150600
acatctattt aattctttgc ccaactttct acaactttga ctttacattt aagctcctca 150660
tgcacttaca tgtttcttta cctaaaaata tcttttcacc atgggtgtgt acaattcctt 150720
tgtccttgct gtattaattt tcttggttta catagtagcc tctacacatt gatgtcaaaa 150780
cctctgtttg gtgcatttct actctgcgtg ttcaatctcc atgaaagttt ctgtaaggta 150840
ttttcattcc tctagttttt cacatgtgca tcctggcttt gtgacctgtg ctttgatatc 150900
gtgcctttca tcttgtggca ttgaaggatc tttgcaagga cctattgtgt tataatacag 150960
tctatgaaaa atatcaatat ttgcatttga tcacatttaa aaaaatcaca ttcttttgtt 151020
tgaatatcaa agctaatatg tgagtgattt ccctgccaaa tagcacaagt agcctttcct 151080
gggtgtttat gggcatttat ctggttaatg attcccatca tagtgctgtc acccatgcca 151140
ttgctaaact tatacagtaa ctttttttgtt ttcacctcag catatgttga gagtaggaaa 151200
tagataggac tatgccctca aattttacgt ttatatgatg ttaatcctaa aggtccttgt 151260
gacttctgaa gtaaaaactc agtgttgtca ttttacttac tgaattgtta gctgagttta 151320
gagttgagtt tacaatggag taaacaaggt gtttagtttg atgtatgctt ttagtctttc 151380
agaaaaaaat gtttatactt ggaaagaata gtttatttac ccatctggcc tagtttagac 151440
aaaaacacag agtcaaatgt caacagaatt ctgaagttat aaaaatgaca gtgtggcttt 151500
tttttttttt aaccttccac ctggtgctta tgcccaagtg cctagctttc tttagctctc 151560
aactaataaa ggtaatgttt agataacatt taacgttaag ttgcattgtg tttatgatca 151620
catatctcaa atattggtac acgaaactgt acaacaacct tttttattag attttcctac 151680
gaaattcctt attatattcc ctaagatagc tttttcccac cttcttcttc cttctccctt 151740
ctcaggtgct ccaataattc caacccctgc agccagtgac tttattatat cttttttttaa 151800 aaatctaaaa aaaaaaattg atgcaaccag gaagaatttt ctcatttctc tccaccagtt 151860
gtaccagcct actgcacctc tcctcatgca ccaccttctg cctgtgttct tgctcctata 151920
ttcaggagca agtaatatgc aatacctccc tctttgtggg atctttctca ttagcataaa 151980
aatactttcc cttgatctcc agctactacc ccatttcttt gacctacata tagcaaaata 152040
tttgagaaag gaccactttc catcttttcc tcaatctact tccatttttt tctcaatcca 152100
ctttcatttc attgttctcc tcaacccatt ctttccacaa cctacttcat tttatttcca 152160
tcagccccat aactcaggat caacatcttg ccagagccaa tttccttgtc tcccttaaca 152220
gctccagcag tatttatgcc atggacaaat tattcttctt gtgatacttt ctctcttgct 152280
tccatgacac tactcccact tcattttctt tctacctctc tggctcttcc ttggtccctt 152340
ttcctggccc cttctctctt tcagatctct aaacatcagc tatatctcag ccctgttcta 152400
ctgacactct ctagctgtta ttttctaaac ccatgtttca gaaaccatat cttgatgaat 152460
cttggaaggc cgaggcaggc gaattacttg aggtcgggag tttgagacca gcctggccaa 152520
cgtggtgaaa ccccatctct cctaaaaata caaaaattac ctggccgtgg tggcatgcac 152580
ccagctactt gagaggctga ggcacaagaa tcgcttgaac ctgggaggtg gaggtttcag 152640
tgagccgaga tcctgccact gcactccagc ctgagcaata gaggagactc cgtctcacac 152700
acacacacac acacacacac acaaagaaaa taaaccatct cttgatgaat cataaatttg 152760
tgtctctagt ttagacctct atcctgctct ctaaatgatg tatccaacta tcatcttgac 152820
accatcatat gttcataaaa cataattata gaatatcttt cagtaggctt gacattttaa 152880
ggcatgagtt tccgttcagt atctccttaa aatataccca gggtctcagg agactattca 152940
aacaggacaa agcttctatt ctacttacta atgtgtctgg ccctatttgg caggttggat 153000
aaaaagtcat ctgaacattg tcactttatg aataatatag tttaatagtt tgtgaatcac 153060
ccctgcaatt taaaaaatag taaaattatc agaatctaat ttaataattc ctattggaac 153120
accccatgtt aggggatttc cagttatttc aattgatatc tcaatgtttt aaagattgtt 153180
tatttctatt actaattcac tctttatttt aacataaatt gtggctatct atctctattc 153240
atttcaatta tatttctcat accattctat agatggggtg aaaagaaaag tgttaatttt 153300
ttaaaactcc atacctcaaa tactatatga atttatagtt gttattgcta aagcaattat 153360
cttacatctt ttcctccaaa acaaagttat gtgctggttt attttctttg tactcataag 153420
atgccttcca tttttagtaa cataagtctt gtctttctcc tattcttagc tacttaagca 153480
ttatgtagct taaataagca ctaaagattc ctatctgtat gaaaaaaataa agattaaata 153540
aataagatct agaaagggtg acaaggtgat gcttcaaaat gaaccatacc aagccatcta 153600
gcgattgata aattactcac actcataatc acattgttgg aaagaagcca ttgacaattc 153660
agtttgtttc acaactgtct atcacatagt gagcacaact aaaagactac tttttgtctt 153720
ttactgcttg ttttgttgat caagtgactg attgtacaat gaccaacaag aagtctgatg 153780
tgtagagaaa aggggaacct ggcttttctg ccttactcct gatgcctaat tctgagcatg 153840
tgaatattat tctgtttctt taattctcca agtgaagcag cagataaacc atccttgttt 153900
ccattagctg tctaccctgt tcaactgtgt gtttctaata acataagaat aagaaagcca 153960
ccagggtgag cagggaaggc aatgagtctg caaggcttgt ggatagattt ctgttagtga 154020
ggctctagaa agttcttcca agattgatgc aatctgagaa gagttttctg tcaatacaaa 154080
ctccctgggt ttctcctttg tccttttact gcctgtgttt gttttgggtt ccagtaaaga 154140
tcaagtgact gattgtacca tgaccaacaa gaagcctgat gtgtggagaa aaggggaacc 154200
tggcttttct gcattactcc taatgcctaa ttttcttgta ctgaaagtag tttttgctgt 154260
aagaatctga ggggaggagt catttcttca attttttttt ttggtctcct tttaatggtt 154320
tcttgatcat gtctatcctt atttttctgt tttcacaaat ttttgtggta tattttcctc 154380
tcatgacctc tgtctcaaga cttctttcca tccatctctt ctcatttcat cctgtagagt 154440
gtctgtggta agagccctgc attctactct ggccttgcca tgtgtggcct tgggcaagtc 154500
ctagcctcct tgagggtctt atttttctca tttgtaaaat gaaacagttt gatgagaagt 154560
tttctaaggt tccttcaagc tttgacaatc tctctcttct ggatcttttt cccatgaaaa 154620
atttcaactc ttgattagca tgtaggcagg gattattcca catccttata ggaatcacat 154680
ttctgctact gtccctgaat gctagagtcc attgattaag ttattcactg ctgcaattgt 154740
cagagctgat caaagaactc tgaaccagtg tgttactaga actaacaaag aaaatgccat 154800
tatgatgttc tagagtcttg aattagtaga agaggtttaa taagaaccct aagggattgc 154860
tagaatgtta aaaacaaaca aacaaaaaaa aaggttgaaa agtttagaaa attcactggt 154920
ctttgtgccc atcattttac ttccagggtt tagataatct catttttgca atgaaggaat 154980
ggattagatc acaagttctc atcctagtag cacatgcaga atctttataa aaacacagag 155040
tagccaggtg cggtggctca tgcctgtaat cccagcactt tgagagcctg gggcaggtgg 155100
atcacttgag aataggagtt gaagaccaag ctggtcaaca tggcaaaacc ctgtatctac 155160
taaaaattca aaaattagcc aggcatgatg gcacatgcct cccagctact ggggaggctg 155220
aggcaggaga atcgattgaa cccgggagat ggaggttgca gggagctgag atagctccac 155280
tgcactccag cctggtgaca gggtgagact ccatcacaaa caaaacaaaa caaaagaaag 155340
caaaaacaca gattactcag ggtccactaa gaccagtgaa gtcagttctc ttggtagggg 155400
gcagggtgac tgagcatgat gtttgtaatt ttaaaagtgc tccaggtgat tctagcgtgt 155460
atcaagcaag acttgtgaac cactgaacta catgctaaga ctcattttag ctctgatttt 155520
ctgtgagtca tagcagaggg ctcagcaaac tttttctata aatgctaaga tagtaaatat 155580
tttcagcttt gtgggctgta tcgtctttat gacaactcaa ctcagtcttt gtagagaaaa 155640
gcagctgtac ataatatgta aactaatggg agtagctaga tgtgtcctgt gggccatagt 155700
tttgctgact cctggtctat gtcatagaat ttccttttga attgatggac caccagcaaa 155760
tgatttttgt cctgtatcaa tcaatgatac atacataaat ctctacaaga catgtaaagg 155820
atgaggctta atgacagagt actttgggga agacataata ttgcaaaatt aagatgctta 155880
gagaaaaatc atattaaaat agtgaaaact gtgagaaggt attttgattt gttgttttgg 155940
attcctcttt ttgcaaattc ttttgaaata ttttcagtgg aagctacata gatccaattg 156000
tattcaccaa gctagattgt aattaagctc cagagtaagt aatagatttg atgagtgatg 156060
tccaaccttt tacatggaag agtaagtttg agtcttcctt tgcccattga cacacttagt 156120
accatgttta ccaaagttct tagttattga aatgggcacc agcatatttt gaaacgttgg 156180
tgttaacttg ggatatgcct tttgtcatgt tgcaaataga ttttgtttct gttttgtgaa 156240
gatcaccatc tctgtcactt ctgatagaaa aagtgacact gacttctcaa gtgatttgac 156300
acaggttaaa atatgtaaac catttctgta gagagcaagc tgtaataata tactaaaggg 156360
ctaggtttat agtataatat aaataactca tttatgctgt taataattta tagcaacatg 156420
gcatttgact gactttttat gtgctctagt catgtaagta atagatgtgg aaacatagac 156480
cagagtttca agaacatgtt ttgggcagag tctgttttct tgctattatc tcttaagttt 156540
atgttcatgg cctaaagatt atgctaatgg atctgccttg gtcttgggtg tcaggtctgt 156600
gttagcgagt attgaaaagc atagtttttg cctactggga aggatttatg atttaaaagc 156660
cctaaatctc cccttttatg tacttcatac ttagaaaatt tttcctgtaa actgtgtgac 156720

-continued tttttacat tgtgccagtt ttctagatga ctctcgtcat atttatttct tgcaatcctt 156780
ctataactat cagttatgaa gtctctttat agtgttgcca gccaggtctc aggtgtgtga 156840
aatgtatttt ctattatgga ttttggggta tgatggcaca tagtttgggt gttaatgcct 156900
aatcttgatg tactggcttc tgaacaacca aaaggatgaa aggaaataga acaaatattt 156960
ttgtgaggga gaggagtctg gcttcttgac ttactctaga aaaagcctgt aagcctcctc 157020
ttccctcctt gtcacacaaa gtgacaaaga aaatcaagaa ttgttttctt cttggcttaa 157080
atgcatccct tataaagtaa ggctgagatc aggctgtgaa gctatctttt tgtcaagact 157140
gtcataattc caaaacactt tgttcttcta atgcttaggt tagtaacttt aaacattttt 157200
ataaagatag tgaggtccag ttttaaggat tgaccccttc tcaaggggct cagaagaggt 157260
tttggagaat aataaaatta aataatgaaa ccaataattt aaaccagatc atgatcctta 157320
agaaaaaatc ccatcaaatt tgggctaaac tctaatatac agaggtctgc acaacttatg 157380
tcaagtattc ttccccacaa atgaagaatg gggttcattg tgtcattggt tgggtctcat 157440
tttggcttca tcttctattt ctcaaagtct aagaaaagtg ctcctacgga agtgggtgtt 157500
ggctatcatg agactttgct gctggcaggc cagcttgctg ctctagacag agatatccct 157560
cgatcctcct tggacaactg ttttctgtgc acaggaagca gcaggctggg gttaaggagt 157620
ttgccaatcc agtcattctg ataattgctg aatatgaatt tctatccagc acaatctagg 157680
tagctacaat ggcacagtag tttttatgta tcaggtgaaa atgtttaata ggcactctaa 157740
atgagagaaa aggttaagtg aggttaaaag ctcaatgaaa acaaatagat gagactaaaa 157800
atagttcaat aggttgtaac ttccatctca tccaaacagc aatgaatatt ttgaggctga 157860
ggcgctgagg ggtaaaattg cagcctggac tacttgctaa tgtagaccta cagcactgtc 157920
attcttactg cacagacact gctttctgca taggaggtag aataatgaat tcatttatta 157980
ttaacaaaga tttattaagt gactgcatgg tgctaaccac tagatgggga gggatgtttt 158040
gaactgtcca ttgtttgact ataacaagga acgctttgaa cgaggttact atcataggca 158100
gaatttgttt aacatgaagc ctatgagaca taagccacag gtcctctcac gtgcaggaac 158160
tcctttgaag gccctatact taattttata tgcatagttt ggatttggat tcttttttt 158220 ttaagagttc cccaaattac ttaagcttca ggctccacaa aacctggatc tacccctggt 158280
agcagctatg aatctttgac tatgaaatta agtgtacaag aaatatgact ttactttttc 158340
tgtgattgag tttattttct atttgagcac gcattccact gagtgaaaga aataatatca 158400
ttgaattcag agattttgct gggttctaag tggagtttac agaatgccat gatattagga 158460
attaaggagt gtgttgccct acatcatctt ttgtccgtgc tcactgtctc tgaggcactg 158520
atgttcctat gtgacctaga ggggcatggt ccaggtagat ggagtctgtc cttgttctca 158580
ctgtgagctc tcgcttgctg acccttcttc agtttcttcc atgcccctga ggggtaaaaa 158640
gattcaaatc tgaagctata tcaagccatc tgtgcataga cattccaagc aaccatgttc 158700
actctactgc tcccatgtca tgcaaggcac aggaagcttc actatggcat gagtatttcc 158760
tgggctttgc cttggaattg aggcacgggc ctcctttgtt ctaaaattcc ccaaatctac 158820
ttgaggatag aaccaggatt tggttgcaag gcagaacttt tcttagagga cctggtatct 158880
aaaccctctt gttacccccca tttatggacc ccatttatgg ggtgaggaga gtgactgctt 158940
ctaatccatc ataattttg tctatggcta ctgtttttgc atagacacta tgttttgagt 159000
ccttaggctt tggcttttgg cgcttaatgg ccaatattca catggctcaa aattttcaaa 159060

-continued tgatccatat ctgacttgag tttcaaaagt cagtttttga aacttaaatg atcagaattg 159120
atttgttctg ctctggttct gatgtggcct ctccttccag aggtactgga ggtagaatat 159180
ccaaggtgga aagcccacga ctacaaggaa ttggttagta attcataatg ttagctgtcc 159240
acatctattc agtaatggca tttcagtggc tgcacaactg accatggtga aagtgtctgc 159300
acaagccact ttttcttcct gtcagaaaat gttctcaccc actgaattga atgactgtct 159360
gctcatatgc tgtgaatgag tgcccagtct taagattaaa tcacacgttc ttggctatgc 159420
atatttgggc atgctgtggg gagttataat aggctgtctt agagtcacat taagcagcta 159480
gacagacaat gagttggaaa gttacatttt ctaaatttga ttggtacatt ccatttgtca 159540
catttgacat tagaagttct ggattcaccc tctatggtga gcttcactaa tggagaatgt 159600
aatttgcaat gctcaaacac aagtcctaaa cagaaaacat tgtatgttac attccagtgc 159660
taccaaaata gtggttttga aagtccttat tttctaatac tactatgtgt aattttgagt 159720
catttagata gcaacagtta aatgttttat agattgtttg gaagtattaa aatgtgaagg 159780
atttttgtta tatagtgtct ttcctatctt gcttaataaa atataagttt agaattgtgt 159840
atagaattaa catgcaaaaa tatcaagtct caactttata cagttaatct acatttgtgt 159900
atacccttca attatttcaa gagagggata ctattcttat gcaggataaa tacaataaga 159960
tattttaaat gaattttaac tacatctctg gcagtttcat ctcaatagta gttgtaattt 160020
tatctcccag accttattat agactagcag ctctctatga aaattagtga cagtgtgagt 160080
gtattttaat tcaaagttaa tcaagaatga ctgagtcaag agttagctac ccctgaaagt 160140
aactcataat tcagaattta aaatattaca tgtggaacaa tcatgactat atgcctttta 160200
ctttctctat cattatttag gttgtgggct ttgggtcctt ttcacatccg ttaacagtgg 160260
gcttgacttc aaaggattat tttcttgaat cttgaataat tgctgaagac aatttgaaga 160320
tattttcaag atgaaggaaa ctgaagcaca gaatcactag agtgaaaaaa gaacttcaca 160380
aacagtgcag gcttgatcaa tggcatggga aaacaggcaa tacagttaga attgctaaga 160440
tggaatttta acgttcaatt aaggatctat ctctaaactc ctctgcttta tccaccaatc 160500
attccatatt aaagatgaag aattgttccc atttcacctt ttgataagga aaaatagaaa 160560
taacagaagc aaatacactt ttgcccacat ttttttccaa aaagaataat ttttgaagtc 160620
taaacgtttg gtgtaaataa gatgatgtgt taatattgta aaggaaagct agttaagttt 160680
ttgactgaat aaagccagca tcaataatta ctagtaagac taaaaataag agcagtaaaa 160740
ttgtgtctaa tcagctacta atatctggga aggattgagc cacaggatca aagatggtat 160800
cttttaaaaa tagaagttga gtgaattcgg tcttcaaatt ctttcttttt attcatttat 160860
atttatttac tcattagtat attcattcct ttattcatgt attgttcaaa tatatattgg 160920
gtacttatta tatgccaagt tgtttttaaa atcacattcc aaattcccgt aagtcataat 160980
tattcagaga tgtatgtttt ttttaaaaaa aattgaacac ctttaaaaat tatcaagtcc 161040
ttttatttct gtatgcatta aagataaact ttactaaatg ttacatgaat agatttataa 161100
agcagataaa tatttaattt caaatataac ccttatatgc aattatattt tccttagcac 161160
taaaaatgaa tatttaagta atttatatta aaagtgtaat tatttaactg cagatgtatg 161220
ccaatgactt aaattgttta aagattatag caaagttgtt taaaattgtc taatcatgaa 161280
gagttcactt aaccacctgg ttgacacata aaattatagt tagttactaa ggtagttcga 161340
gagaaagaga agaatcttca gtagtggttt tgaggtgtgg tacattttat tataatatac 161400
cggttataca gcattgtgca gtgctgctca tagtagaaat aaattttctc tttgatgtca 161460

-continued tctattccct tgtgtggctt acataactga gaattaggtg atcacaaaaa taaacaggcc 161520
tatacagagc ccatttatat aagtcctggt tatttctctt cagttaaact tttaattata 161580
tccaattatt tcctgttagt tcattgaaaa gcccgacaaa taaccaagtg acaaatagca 161640
agtgttgcat tttacaagtt attttttagg aagcatcaaa ctaattgtga aattgtctgc 161700
cattcttaaa aacaaaaatg ttgttatttt tatttcagat gcgatctgtg agccgagtct 161760
ttaagttcat tgacatgcca acagaaggta aacctaccaa gtcaaccaaa ccatacaaga 161820
atggccaact ctcgaaagtt atgattattg agaattcaca cgtgaagaaa gatgacatct 161880
ggccctcagg gggccaaatg actgtcaaag atctcacagc aaaatacaca gaaggtggaa 161940
atgccatatt agagaacatt tccttctcaa taagtcctgg ccagagggtg agatttgaac 162000
actgcttgct ttgttagact gtgttcagta agtgaatccc agtagcctga agcaatgtgt 162060
tagcagaatc tatttgtaac attattattg tacagtagaa tcaatattaa acacacatgt 162120
tttattatat ggagtcatta tttttaatat gaaatttaat ttgcagagtc ctgaacctat 162180
ataatgggtt tattttaaat gtgattgtac ttgcagaata tctaattaat tgctaggtta 162240
ataactaaag aagccattaa ataaatcaaa attgtaacat gttttagatt tcccatcttg 162300
aaaatgtctt ccaaaaatat cttattgctg actccatcta ttgtcttaaa ttttatctaa 162360
gttccattct gccaaacaag tgatactttt tttctagctt ttttcagttt gtttgttttg 162420
tttttctttg aagttttaat tcagacatag attatttttt cccagttatt tactatattt 162480
attaagcatg agtaattgac attattttga aatccttctt atggatccca gcactgggct 162540
gaacacatag aaggaactta atatatactg atttctggaa ttgattcttg gagacaggga 162600
tggtcattat ccatatactt caggctccat aaacatattt cttaattgcc ttcaaatccc 162660
tattctggac tgctctataa atctagacaa gagtattata tattttgatt gatatttttt 162720
agataaaata aaagggagct gaaaactgaa ttgcaaactg aattttaaaa ctttatctct 162780
ctgtggttaa ttgcaaacac agatacaaaa atatagagag agatacagtt agtaaagatg 162840
ttaggtcacc gttactaaca ctgacataga aacagttttg ctcatgagtt tcagaatata 162900
tgagtttgat tttgcccatg gattttagaa tatttgataa acatttaatg cattgtacaa 162960
attctgtgaa aacatatata taggatgtgc gaaaagtccc tgtgtatcat gtgaaatggc 163020
ttaaaacaga acaccatagg tattcatatc agtgaatacc ataggtagct gaaagtgttt 163080
tttcctgggg tcgccaagat gaatgccaaa agtgatatca ttattataaa caatagccag 163140
aataggttgg tataaacctg gtagaaagcc ttgataaatt gactttctct cctcctgaca 163200
tcctgccacc cctttgcttt gctgatgctc atttgtccac taaattaaac tcaagcaagc 163260
cctagtaaag taatagaatt tgtggagtcc tcattagtat aggaagtttc cctgatgtga 163320
gattagtaat tagagatgta gcaaaatgag aaagaagtaa tatgcttaga tatttcattt 163380
tctctgaacc tgtatataca aaataggcca tgcgtgttca gtaactattc actgcaaggc 163440
actctctagg tactttgggg gaattggaaa ttactcacat aaggctatgg attgtgccat 163500
ttgtcaaaag acaaaatgac aacaaattta gtttaaagac ctcagtcagc tttattttct 163560
attctagatt tggacagtcc ttcatttcac aaattggagt aagtgttcca ataagttgag 163620
caaaggagct tggctttata gacccaaaaa aagggccaaa ggaagcagaa acaaagaaca 163680
ataagagaat tggtcatttc aaagttactt ttcttgaaag gtggggacaa ggagacagaa 163740
taatagaaaa gtcactgatt ggttaacatt ggattaagaa ttaaaacaga ggaaacttta 163800
agattgaagt ttgaaactga cttgtttggg aaatcaggct gtcttctttc ttgatttctt 163860
agaaggccgg ataacaactg agttttgctt tggtgaacat gggtgactcc atttttactt 163920
ttagtctggt ctgttgaggc ctcgtgagag agcttaatct aaaacaatga cttcctataa 163980
tttttgtttg acacatccaa agagggactc taatatttat tgagagctta tcatatctta 164040
agtactgttt aaacactttt atttgctatt acatttgatc ttattataac tctaaaggca 164100
gaaatgattg cttttatttt ccacaatgga ggaaactgag gttcaattaa gtgagtaagg 164160
aagcagggat cttaaaccca gataccattg ctcctcttta aaggtggaag aacagaaaac 164220
atggggcagg ggaagagaga aagtttctgt cccaggacat gataatctaa aagggaaaac 164280
gtaagatcca ctgaaacctg aggcagattt attgtggcaa taacaaagct taagtttcac 164340
agaccttcat ttgcctgagc caactttgaa ggccatgtat ctaattttgt ttttataatt 164400
ctataatctt tattcttgaa aagagccctc cctccaaatt tacaagcttt gggcccccaa 164460
aatccttgaa atgcccttga ataagagata tccaggtaaa tgctatggga attcagagga 164520
ggaagcagtt agtatcagtt ggcggagagt taggctatta agagaaggtt ttatatagga 164580
agtggcattt agaatgaagc tttgagaact gagctgtgta tttgaacaag taaaggtggt 164640
gttgcagaat tttgctcctt agttctatta aaaacccggg ttcttgtcac atgatccgga 164700
aaatttaggc acacagatac attgaagcat gagtagagca ggattttatt gggcaaaaag 164760
gaaaaaaaga aaactcagca aatcgagatg gagtcttgct cacagattga atcccaggcc 164820
accacaaagg aactgaagag atcgggcttc tcccctgcat aaggtgcaaa ttccccatgg 164880
ctccacccac ttccccttag tgtgcatgtg gggctccagt ccacggtggg catgcccaga 164940
caagccttgg gcaggttccc tcatctgtgc aaaagcatct gatgtaaaca cttgaggggt 165000
ggttcggaga ttctctggga cccttttatt ttcttatctg cctaggcatt tggctgtctc 165060
agtgggtggg aaagggtgct ccaggcaaag ggcataacat gaggcaaagg gcatgcacag 165120
aaaacagtga ctggttcagt caggttgggg gatgccaaag gaagtaatgg gagacaagat 165180
tggagcaaga tagataagag attgtggatt tttttttcttt tttatctata taaatacaga 165240
gacagggtct cactatgttg cccaggctgg tctcaaactc ctggcctcaa gtgatcctcc 165300
cacctcatcc tcccaaagtg ctaggattac aggcatgagg cactgtgccc aacctccaat 165360
tttggatttt gagagctaaa gcaatatagt cgaaaactca gataatccag gtagattttg 165420
ctattaggtg ctatttggtt cctggtacag agctaaaacc cttggaattt cctaagtgat 165480
aagagctaca ggagcatctt ttgttatatg tttccccccc tagttcctga aatagctcta 165540
gagaaataca ggtgaataac atcctttgtt attcatatca agcccctatc aaccataccc 165600
cagtttctat ttatgaagtg gcttttggga agtccctaaa gacaggagtg gggaaaggct 165660
ggttgtcagg gggatgggtt gaaactttca tcttcccccc ttgacctcca gggagggatg 165720
agtggctgaa aattgtgtaa aatcaacaat ggccagtgat ttaatcaacc atgcctatgt 165780
aatgaagcca cccgataagc cttaactgga actttttgga gagcctccag gctggtgaag 165840
acattgaggt gctcagaagg tggtattcca gagagagcac agaatctctg ttccccttcc 165900
cacattcatt ttgctatgca tctctcccat ctggctgttc ttgagaggta tccgtttata 165960
ataaactggt aacctagtaa gtaaactgtt accctgagtt ctgtgagcca ttctagcaaa 166020
ttatcaaacc taaagagttc atggatacgt gcaatttaca gatgcacagt cagaagcaca 166080
gatgacaatc tgggcttgcc attggcattt gaagtgtgtt gggaggcagt cttacaggaa 166140
tgagccctta tcctgtgggg tctatgctaa taacagacag ttgtcagcat tgcttggtgt 166200
cgaaaaccca cattgttggt gtcagaagta ttgtcagtag gatagggaaa acagtttgtt 166260
ttcttttttt agtggtcttt ggtcatcttt aagagcaggg cttctcaaag tgtggtcctt 166320
gaaccagcat cacctgtacc acgtaagaac ttatgagaaa tgttcattct tgggccccaa 166380
caaagaatta aaaattctga gggtgtgaac ggggtctgag tttcagcaca acttcccgac 166440
catgctgatg cattcttgcc caagcatgaa agccctccct tgtttaagaa ggccattagg 166500
gccgggtgtg gtggctcatg cttgtaatcg agcactttga gaggacatag tgggaggatc 166560
acttgagccc tggagttcta gacaagcctg ggcaacatgg caaaatgctg tctccacaaa 166620
aatcacaaaa attaggtggg cgtgtgttgt gtgcctatag gcccagctac ttaggagact 166680
gaggcaggag gatcgcttga gcccaggaga ttaaggctgc agcgagctgt gatggcacca 166740
ctacagcctg gatgacagag tgagacactg tctcaaaaaa aaaaaagaaa aagaaaaaga 166800
aaaaagaaag gaaaatgaaa aagaacgcca ttaggtataa aggagcaatg gtaaaagacc 166860
agttgcaaaa ggttagggaa tgggtggtta ctgaaataag aagctatgta gaacactagt 166920
gttggtggca ggaagtagaa agcaagagca ctgctctgtg ggggatggtc atagcaaatg 166980
caatatggag gcatttgcct ctgcactgag gagaaaacta tcttttccaa gataggagga 167040
aaggagataa gtggaattaa agagaacctt tgagcacaga gttgggaaac tgaaggtatt 167100
tgtgttgtgc tccctcaatc ttttaattca actataagct aaacccatga aacttgagta 167160
gtttcagtta tctgactttt ttcttctctt ttgatacagt gttggctatt ctgggtcttt 167220
tgcctctctt tatgtactta agaatcagtt tgccaatgta tgcaaaataa ctggctggga 167280
ttttgattgt gattggcttg aatctataga tggagttggg aaggactgac atcttgacaa 167340
tgttgaagct tcctattcat cattatgaaa tatttctcca tttgtttgat tctttgattt 167400
cttttatcag aatttagttt tcctcatata gtcttttaaa atattttgtt atattttgtt 167460
caagtatttt gtttttgagg aatgccaatg taaatggtat tgtgatttta atttcaaatt 167520
ccaatttttc attgctgtta tataggaaaa tgattttttt tgcatgttag ccttatatct 167580
ttcaactttg ctataatcaa ttattgatag tttcaaggat tttttggtca attattttga 167640
atcttctaca tagattatca tcatctgaac ttagttttat ttcttccttc ccaatctgta 167700
tacctttatc tccttttctt atttcattag ctaggacttc cagtatgatg ttgaaagtag 167760
tggtgagagg ggatatcttg gtcttgttct tgatcttagt gggaaaactt caagtttctt 167820
atcattaagt atgattttag ctggagggtt tttgtagaag tttttttttt ttaagttgaa 167880
gaagtctcct tctattttta gtttgctgat ttttaaaaag aatcaggaat gggtgttaaa 167940
ttttgtgaaa tgcttttctg caactattga tttgagcact ttatttttct tctttggctt 168000
gttgatgtga agtacattaa ttgatttttg aatgctgaat caaccttttg tacctgagat 168060
taatcccgtt tggttgtggt atataattat ttgtatacat gttgagttcg atttgctaat 168120
actttttgag aatttttgca ttggtgttca tgaaaaaata ttggtgtgta gttttttgtg 168180
acatctttat ctgcttatgg ttttaaggta atgctggcct catagcatga gttagggagt 168240
atttcctcta cttttacatt tgagaagaga ttgcagagaa ttagtaaaat tcctacttta 168300
aatattttgt ggaattcacc agtgaaccca tctggacctg gtgctttctg ttttggaagg 168360
tcattaatta ttttaaaata gatataggcc tattcagatt acctattttt tctcatgcga 168420
gttttagcag attgtctttc aaggaattgg tctatttcat ttaggttatc aaatatgtca 168480
acgtagagtt attcatagta ttcttttatt atccttttaa tgtgcaaggg atctgtagtg 168540

-continued atgtcccctt ttttgtttta ttgatattag caatttgtgt cacatctttt attttgcttt 168600
gttagccagg ctagagatat ctctattttt gatgtttttg atgaaccaac tttttgtttt 168660
attgattttc tctgttgatt tcgtgatttc aatttcatga tttttaaatt atgcttacat 168720
ttgatttaat ttgatcttct tttgctagtt atccaaggtg gaagcttata ttgttaagat 168780
ccttttgcat tcttatgcat tcaatgatgt aaatttccct ctaagcactg ctttttctgc 168840
atctcacaaa tattcatgag ttgtattttc atgttcattt agtttgaaat atttttaaat 168900
ttctcttgat atttctcttt tgacccatgt gttacttaga agtgtgttgt ttaatcacca 168960
tttttaaaaa ttttctagct atctttctgt tattgatttc tagtttaatt ccattgtggt 169020
ctgagagcat atattgtata attttaattt ttataaaatt tgttaaggtg tgatttatgg 169080
cccagaatgt ggtctatctt ggtgaatgtt ccatgtaagc tttggaagac tgtgtattct 169140
gctatatttg aatgaggtag tctatagaca tcaattatgt ccagttgatt gatggtgctg 169200
ttgaattcaa ctatgtcctt actgattttc cacctgctag atctgtccat tctttgcaga 169260
gggacactga agtctccaac tctagtagtg aatattctat ttcttgttac agttttatca 169320
acttctgctt catgtctttt gatgctttgt tgctagaaac atacacatga agaattggta 169380
tgtcttttgg agcatgaccc atttatcctc atataatgcc cctcattatt tcctcgccct 169440
gatgtctgtt ctctctgaaa gaaatatagc ctctccaggt ctcttttggt tggtgttaaa 169500
atgacttaac tttctttatc cccctTactt ttagtttata tgtggtttta aatttaaagt 169560
gggtttcttg tagacagcaa atagttcaga gttgttttc gatccacttt gacaatcttt 169620
gtcttttaat tggtatattt ggactattga tattttaagt gattattgat atagttagat 169680
aaacatctac tatatttatt actgttttct gtctgttaca ctacttgttc tttgtttata 169740
tttttattgt ctactctttt tctttccatt gtggttttaa tcgagcattt tatatgtttc 169800
cattttcttt tcttagcata gtaattcttc tttaaaaaaa catttttag tggttgcccc 169860 tagagtttgc aatatacatt tacaactaat ctaagtccat tttcaaataa tactaaataa 169920
tttcatgtgt agtgcaagta ccttttaata ataaaacact cccagttcca ccttccagtc 169980
tcttgtatta tagctataat ttagttcact tacatatatg ggtataccta agtatataca 170040
ttatcatatt tatgattgaa tatattgatg aaattatttt gaaaaaactg ttatcgttaa 170100
atcaattaag agtaagaaaa atagttctaa ttttattata aaatgaaata ccttcattta 170160
ttcattctct aatacacttt ctttctttat gtagatccaa gtttctgacc tgtataattt 170220
tccttttctc tcttcagctt ctttgaacat ttcttaccag ccagacctac tgacaacaat 170280
tttccccaat ttttgtttgt ctgatagaga ctttatttct tcttgacttt tgaagaataa 170340
ttccacaggg cacagaactc tagattggtg atttcttccc ctcaaaccct taaatatttc 170400
attccactgc cttcttgctt gcattgtttc tgagaagtta gatataattc ttatctttgc 170460
ctttctatag gtaagatgtt ttttcctctg gcttctatca agattttttc tttatgaaca 170520
tgatatgcct ttctttttga acatgatatg cctttctttt tgaacatgat atgcctttgt 170580
gtcggatttt ttttggcatt attctgcttg gttttctctg agtttcttgg atatgtggta 170640
tggtatctga cactaatttg gaaaaattct cagtcattat tgcttcaaat atttcttctg 170700
ttcttttttt tcctttattc tccttctggt attcccatta catgtatgtt acagtttttg 170760
tagtcatccc gctgttttgg atattctgtt tttttcagtt ttttttcct tcgcatttca 170820 gtgttggaag tttctattga catattctca acctcagaga ttctttcttc agctgtgttc 170880
agtctaccaa tgagtccatc aaaggcattt tacattttta ttacagaatt tttgacctat 170940
agaatttctt ttgattccat ctttgaatct ccatttctct tctgcttttc atctgttctt 171000
gcatgttgcc tactttttcc atgaaaacct ttagcttttt tttttttctt ttttgaggtg 171060
gagtctcact gttgcccagg ctggagtgca gtggtgtgat cttggctcac tgcaacctct 171120
gcctcctggg ttcaagtgat tctcctcctc agcctcccaa gtagctggga ttacaggtgc 171180
ctgccaccat gcctgagtaa tttttgtatt tttagtagag atggggtttt atcatgttgg 171240
ccaggcgggt cttgaactcc taacctcaag tgatctgccc accttagcct cccaaattgc 171300
tgggattata ggtgtgagcc accatgccct gcctttagca tgttaatcat agttgtttta 171360
aattcctgat ctgttaattc caacatccct gtcatatctg actgtggttc tgatgcttgc 171420
tctgtgtttt caaatggtgt tttttttttt ttgcctttta gtaagccttg taattttta 171480 ttgaaaggtg gacatgatgt gctgggtaaa aggaactgta gtaaataggc ctttagtaat 171540
gtactggtag gtgtagcaga gggtgaggga agtattctgt agtcctatga ttaggtttta 171600
gtcttttagt gagcctgtgc gcctgcagct tggaagcact tgtgaagtgt tttttcaccc 171660
cttttggtgg gacatagtga ctagtgtgag cgggagttga gtatttccct tcccctaggt 171720
cagttaggct ctgaaaaaac cctgataggt taggcatggt aaaatagtct cttttgaggg 171780
caggcattgt tataagaata gaatgctctg gggccaggtg cggtggctca cgcctgtaat 171840
ccccgcactt tgggaggcta aggcaggtgg atcacctgag gtcaggagtt cgagaccagc 171900
ctggccaaca tggtgaaacc ccgtctctac taaaaataca aaaatcagcc aggtgtggtg 171960
gcacacacct ataatcccag ctactcagga ggctgaggca ggagaactgc ttgaacccag 172020
taagtggagg ttacagtgac ccaagattgt gccactgcag tctagtctgg gtgacagagc 172080
aagactccgt ctcaaaaaaa aaagaatgct ctggcatatt tgaaaatggt tacttttccc 172140
tttttttctc tgatcttcac tgtgagaacc tggtaagcat cctataggca aaattcataa 172200
aagtatagaa gtcggccagt gacttggacc cacttggaat tttcttgctc tcacatcatg 172260
cacactgaat ctccagcaat ttttcactta cagtttaggt tttcctaccc tactactggt 172320
tctctcagag gtttctgctt attggtttct gttttgtaag ttgtgattct ctgtacctaa 172380
ctgcctgtct cccattttgg ggggcagtgg tttgccctgt gacctcactt ctctgacaga 172440
tctaagaaaa gttgtttatt tttcagtgtg ctctgctttt tacttgttac gatgaagcca 172500
accactttca gaatttctac aaaccagatc agaatctgga agtcctgttt ttttattttt 172560
tttatccctt tgtttagcat gttacctatc ttaacacatt ttaaataagt gaatgcatag 172620
cttatatcta cttctaggtt atatgcttcc ttagaatagg aattgattct taaaatgtcg 172680
ttctgctcac gcctgtaatt ccagcacttt gggaggccaa ggcaggcgga tcacttgggg 172740
tcaggagttc aagaccagcc tggtcaacat ggtaaaaccc tgtgcctgca aaaaatacaa 172800
aaattagctg ggcatggtgg tggccatctg taatcccagc tactagggaa gctaaggcat 172860
gagaatcact tgaacctggg aggtggaggt tgcagtgagc tgagatcgcg ccactgcact 172920
ccagcctggg tgacaagagc aaaactccat ctcataaata aataaataaa taaataaata 172980
aataataaaa ataaaaaaat aaaataaaac aaaaatttta ttctgagcag tctctgaaga 173040
atataaattc tactgccttg cctttagaac ttataacagc atctcgcaaa ctatcacaag 173100
atgctccaaa catacttctt atgtgctgaa ttaagaagtc aactcaaatt tagtatacta 173160
gtaatatttt tggatatccc aaaacactgc cagctcagct ttaggctgcc cttcttgggg 173220
gggaaaaaag cagttgaaat ttaggactta agtgggcatc tcgtttaatt tttaatggat 173280
ttctatgttg ttggttatgg tgaagaggtg aaaagaataa atattctgtg cagaaaaatt 173340
attcagtctt catgtgaaaa cactttgtcc atagcaatta ctttatgaaa aagatgtggt 173400
attactttct ttgctcttaa ctgagacctt taatttaaag aacctatact ttacaagttt 173460
ttattttcaa tgcatgaaaa atgtagcagc tatttcacaa cctttacttt taaaatccat 173520
ttttcttttt aatctcaaat agttttttct taaaaccttt tgacttttta tctaaattgt 173580
aatagccaga gcaccttccc acaactagaa tatctcatcc tttttgtctt ttctttttcc 173640
tctcaaaatg cctactggga acttaatttg gagtcagatt cttcatgata aatctggact 173700
taatcaaaat tcctcatatg gtatattgta tatatcacag tactggatag tcctctgatt 173760
aaatagatat ttgatagtac tttaaggtct atacttttgg atgaacttaa ctgctttctc 173820
catttgtagt ctcttgaaaa tacagaaatt tcagaaataa tttataagaa tatcaaggat 173880
tcaaatcata tcagcacaaa cacctaaata cttgtttgct ttgttaaaca catatcccat 173940
tttctatctt gataaacatt ggtgtaaagt agttgaatca ttcagtgggt ataagcagca 174000
tattctcaat actatgtttc attaataatt aatagagata tatgaacaca taaaagattc 174060
aattataatc accttgtgga tctaaatttc agttgacttg tcatcttgat ttctggagac 174120
cacaaggtaa tgaaaaataa ttacaagagt cttccatctg ttgcagtatt aaaatggcga 174180
gtaagacacc ctgaaaggaa atgttctatt catggtacaa tgcaattaca gctagcacca 174240
aattcaacac tgtttaactt tcaacatatt attttgattt atcttgatcc aacattctca 174300
gggaggaggt gcattgaagt tattagaaaa cactgactta gatttagggt atgtcttaaa 174360
agcttatttg cgggaagtac tctagcctta ttcaacagat cactgagaag cctggaaaaa 174420
caaatcccgg aaactaatta ttatgtgcca gttatataaa caagaagact ttgttgggta 174480
caaaccagtg attccttgcc tttgaaaaat gtgtcagata tcatgcatta ccagcagttc 174540
aatgatataa ggaaaccaga gtaatagcta aaacctttaa agctaaacca aagatttaca 174600
aattgcctct tcatccagtc tttcccaacc taaaaactga gttctctaaa aattttagta 174660
tttttttctg aagaaaaggg aacatggaca tttatctaat cctcattaga aatctgacta 174720
atgataacaa ggatttagac ctcaagcact tcttaccaaa attcttgata tgaccttata 174780
gcaaattact ttcacctgtt gaactttcct ttcttttatt cccctgtacc tcacctgcac 174840
tgggcatatt caagttgctt atacaacact ttactattgt gttagaaaaa tcatgacaca 174900
tgatgaatgt gtttgtgcaa catgagctga ttcataaatg aaaatgtgca ttgaaattcc 174960
acaatatttt aaaattagga gtttatctag caattgaaca aaattgatta aatccattat 175020
ttgttagatc agctaaatta cataagttca ttcatctgct cataaatcca tccattcttc 175080
catctggcta tcccttagtc aattcaaata aatatttatg gggcactttg ggtaagccag 175140
gtgctaagaa ttcaatgcaa aacaagatag actcccctgt ccttgttgaa cttatatttt 175200
tggtacaaac aaaagcaata atcaagaaaa aataaaaaaa gtactgattg tgattaataa 175260
tatgaagaaa ttcaacagag tattgtactt aacatttgat tgatctgatt ttctcagttg 175320
tctgagaaca aacatttgtg aaaatctcat tgtagagttc ttacgatgga tagggggtca 175380
actgtgtcat tattgcttat cagcttatcc caaagaccta gtttattacc agattgcaaa 175440
tagtgttcaa taaattattc ttattaaggg ttgttatgta ctctaaaaca tttattgtgg 175500
tcccttcact ggttctggtt tacaaactta cttttctatg atgacatagt atagaaattg 175560
agagtgaata tttagaagtt catttttatt atatattttt gaagtattga tatgtagtga 175620
attagaaatt taaaaagaaa acaaaactgt ccttcactac agattgaaaa gcattatact 175680
aaaagaccat ttgctcagtt atagtatata aaggccaaat gacttaaaaa caaattatgt 175740
aaggagaagg aaacaaccat ttattcagtg ccactaactg tcagccagtt ttttcagtgg 175800
tcagttaatg actgcagtag tgttctacct tgctcaaagc accctcctca agttctggca 175860
tctaagctga catcagaaca cagagttggg gctctctgtg ggtcacctct agcacttgat 175920
ctcctcatgc agtgcatggt gctctcacgt ctatgctatg ttcttatggt ctttaggtaa 175980
caagaataat tttctttctt ttccttacta tacattttgc tttctgaaat tcccttctcg 176040
ccaatccagg tgaatgtcag aatgtgattt gacaactgtc caaagtactc attcactgag 176100
gagtggtaag gccttcgccc aacctgcctt ctctgggaat atactgctgc ctgaacatat 176160
cattgtttat tgccaggctt gaacttcacc aaattaattt attagggtca acatctaaat 176220
attagaacta tttcagatta atttttaagt cgtatccact ttgggtacta gatcaaattg 176280
caggtctctg cttctggctt gagcctatgt ttagagatga tgtgcatgaa gacactcttt 176340
gcttttcctt tatgcaaaat gggcattttc aatcttttg tcattagtaa aggtcagtga 176400
taaaggaagt ctgcatcagg ggtccaattc cttatggcca gtttctctat tctgttccaa 176460
ggttgtttgt ctccatatat caacattggt caggattgaa agtgtgcaac aaggtttgaa 176520
tgaataagtg aaaatcttcc actggtgaca ggataaaata ttccaatggt ttttattgaa 176580
gtacaatact gaattatgtt tatggcatgg tacctatatg tcacagaagt gatcccatca 176640
cttttacctt ataggtgggc ctcttgggaa gaactggatc agggaagagt actttgttat 176700
cagcttttt gagactactg aacactgaag gagaaatcca gatcgatggt gtgtcttggg 176760
attcaataac tttgcaacag tggaggaaag cctttggagt gataccacag gtgagcaaaa 176820
ggacttagcc agaaaaaagg caactaaatt atattttta ctgctatttg atacttgtac 176880
tcaagaaatt catattactc tgcaaaatat atttgttatg cattgctgtc tttttctcc 176940
agtgcagttt tctcataggc agaaaagatg tctctaaaag tttggaattc tcaaattctg 177000
gttattgaaa tgttcatagc tttgatagtg tttttcagaa gaccaaattt acagtgggag 177060
ccttgggctt ttgtttttta acagctcttt tttgttcctg cttcagtggc ctgacctcca 177120
agttagcaat cgccaggttg agaaatgctt tgcgagacat aacagatgct cctgaaataa 177180
caaacacttg gaatcatgag gtagtggaat tgaaaataga aagtgtagtg attgttttt 177240
gttatttgga tgggatgaac aatgtcagat tagtctgtaa ctattttttt ttaatgtcac 177300
tctgatttgg tcacaaagga tctctagtct cattgcctta gtatcattct acgaattaga 177360
atgtgttact gtgtaagagc acttcttgta tatgagagaa atagcaacag ttccagttta 177420
aagtgatata aatggaaacc aagaaatgtc tttactggga ccaaatctgg acagcattta 177480
ctgtattttt gctggtattt tctctagtct ttccgggtat attcacattt aatgatcact 177540
tttctccctt tgtgctaatg gacactgaat ccattccact accatagttc ttgctaatac 177600
tactctactt tttacacaaa attaaaatgc caggagcacc tccaggtaga ctgactataa 177660
atctagactg aaaaaaaagc ttgtatttct taacagatta ccttgtggaa catttgctcc 177720
tttcaactaa tgaggcacta aatattgtaa ctgctcaact ggtgctttta atttatttgt 177780
ctagactttg tcatgttgcc agaagcttta tcctggttgg agttttgaaa acagtattgt 177840
ttcttcagaa agaaaaaagg gattgtcaga tgatctaaaa ataaagaaac actggaaata 177900
caagtatccc aaggtgatag cattaggcaa gataaaaatg ttgaaaagcg aaaaagaact 177960
ggttgataga gaagtgttgt tattcagtag aacctaagtc ttgtggtccc atttttaatg 178020
aaaaatggtg aattttttgg tttttattgt tcttgttcac acaaatctgc ccattagaat 178080
aagccaagcc ctaaaaatta atttcagttt cactgggaat cctttagttt atctactatg 178140
tagtagagag gttttgtttt attgcatgtt tgacgtagga acgtatatat gcaagacatg 178200
gaggaaaacc aagtgggcca gagttttgaa aattctttat cttttctttc tgccaaagtg 178260
agtctcccaa gtttgtcttt ttttttcat ttccactctt ctatggtttc tagcattata 178320
taaaccaaac aaaaaaaata cgttcagaga ttccttcaga aatgctggat gatcttgata 178380
tcgatgcttt tcatatatgt gtttatgatg ctggtttctg gggctggctc tcagtatcac 178440
aaagatgtct gtaaacagaa tatgctattt cttctttgtg acaaattttg aacattatgt 178500
gaatgtccaa gaaagagcaa aagagggcaa acttctcata catttttgat gtcgaaacca 178560
agagacgctt ttattttcct aacttttctt tgaaagttca aattaagtaa ttttatcctg 178620
tcctaaagtt taaaaagaaa aaaaaaagga agaaggaatt aaaaatccaa agaaaattat 178680
gtttgtttgc ttttctgttt ttttcttcct tccaactccg agactttgca agggcatagt 178740
tctgaagatc tctgacactg agacattaga gatctctgta tcaatggatc atttgttttc 178800
agacatatga aacaggaact ttgaacaaga aatttcccct ctttttctca tagtgatcct 178860
gagacatcag ctgtggaatc acaacacgtc attagttttg gcaggtcctt gcaggtgttt 178920
tgttttgttt tattaatgtt cttccctcct gtagctagac agcaatcttg gagaatctgc 178980
cagcttggaa gactattgtg taaatttcaa ggtggagcct cctttaattt gttctgtgtt 179040
acctgtgagc tgtgaggtca tgaagaggag acaatgaggc taatcatgag agccccattg 179100
gtttaggcaa ttagaacaac aagatctaaa atggtttatt agccttgaat tgtgttaagc 179160
acataattca taaaaaacag aaaaaatatt tttaaatgta tgtctaaatc ttcagttaca 179220
agtttgaaag gtgacaaact attctgagga aatgattagg cctattcttg caacgagtct 179280
ttatgatctg aaaagaatct atgtccacac ataactccca cctcaaagat ggggcatctt 179340
ttgctctggg agatatcaaa tgcgaccaaa acaagtgttt gtagatttga atgatgattc 179400
agcagtgtag cagttctcac tcattttata ataattaaca acttaataat taattattaa 179460
actcctacat gcttaacatt ataagtatga taacttctgt ggttacataa aagatataca 179520
tagcacttgt ccttgatctg tcacagtgag gtcccaatcc aacctatgag cttcaaatga 179580
aaagttcaaa attacactca ttgtcataag tcagagatca aaggaagaaa ggatttaacc 179640
aaaatgataa attaaatata ggtgattaaa tatagtcatg gttcaaggca tgggccagtt 179700
agggagtgtg atgtgggtaa ttatgaaagg ccagctccca agccctgttg ttgctactcc 179760
cccacatcag tcatccttcc ttttttcta cttctactgc agtgccttcc tcatcttttc 179820
ccttgcatcc ctccattata tgagtcatac aaattagact tttcaaagca acattaacat 179880
tgtgtgaatt tggggttttt gactaatccc aacattccac ccccacattc cagtcccaca 179940
tgggatttgg agccttgttt ataaacctgg cacttctaat atatcttatc ttagagtaat 180000
ccttgtattt gtttaatttc cacttagcat tgtaaatact tgcaggtatc ctagttaaga 180060
aagcaaggtt taaacacaaa atcatcacca attaaagcag gctagataaa gaatgtaata 180120
gaaatgctag ataaaacaga ttttttctta ctaagttttc tgtcccttat agagtgcata 180180
acacaataac ttgcttgata agaattcaat gtacattgtt ttgtgctgaa tcactaaatg 180240
cttgatttct gtaacaagag attgtggttc catcagtatc tggattttag tctgtgtaat 180300
cttaggcaag ttatttgatt tctctgtgcc tctgttttct tgtctgtaaa atgagtataa 180360
tggtagtaac taattcattg tgtttttgtg aggattaaat gagttaataa ctagtactcc 180420
tccctggcac atagtaagta caatatgctg tgctgtggtg gttgttatta tttttatag 180480 ttccttgagc aaaagaaata atgtccccat cttagtataa tattggaggt atataccata 180540
gaagtgaaca aaagaatata gtttcacaaa gaaagtgata attaaggcgg ttcataaagg 180600
gtcataaagc ttgtagattt tagaaatgtg ggggcatgag gatgtggaga gggtattcca 180660
ggatgccaga cagggagatt atggatgagt actaagatga gaactagaaa aagctgaggg 180720
gcaaaaggtc agaggaggcc acaagttagg gagtattagg aaaaagaagt taatacttga 180780
caagtgccaa catggcttca cgaggaatgg gttgggcctt tttgagtgag gaagaggctg 180840
gtgaaagggt ggtggaggac actgctgctg ctgatggcat ggggtgtagg tggcaggaga 180900
ggcagggaca tgagctagga aactctccag ctatgaagtg atgagtctgg agtaatataa 180960
ggacagtagg ggtggagtgc tgaacttaag ggaggagaga aaaataattg gtatggaagt 181020
aggtacaatg caattttatt atttctgagc ctaaaaatgt gaaatttttg attatttggt 181080
cagaccaggg aagtattttc ttttatgcta tctctgaaaa tgtatacact aaaaagttgt 181140
agtataaaaa ggttgtaaag cattaagtaa ttttagagga aacaataatt tggatatttt 181200
acatgcaatc atttatatgc aaatatatgt aaatattaca aaattattct ctatttgtta 181260
caaaccttaa atatttttga ctgaggaata ttttattcat ctaattatag ctactttgtt 181320
ctaactaata gatattcttg aaaacaaagc aacacttttt tggagacaga gtcttgcact 181380
gtcacctaga cttgagtgtg ttaccttgaa ctccagggct ccagtgatcc tcccacctca 181440
gtctcttggg taggtggatt acaggcccac actaccatgc ccagctgtat tagtccatcc 181500
tttcattgct ataaagaaat accggaaact gggtaattta taaagaaaat aaatgtaact 181560
ggctcacggt tcttcaggct gtacgggaag catagcagca tctgcttctg aggaggcctc 181620
aggaagtttt caatcatggt ggaaggcaaa taagaagcag gcatgttaca cgacgaatca 181680
ggagcaagac aaagtgaggg aggaggtgcc acacactttg aaatgagcag atctcatgag 181740
aacagcgcca agaggatggt gctataccgt tcatgagaaa tccaccccca tgatccagtt 181800
acctcccacc aggccccgcc tccaacactg ggaattacaa ttcaacatga gatttgggca 181860
gagacacaga tccaaaccat accaccagct aataccaaaa aaaaaaaaaa attttttttt 181920
taagacatgg tcttactatg ttctacaggc tggtcttaaa ctcctggcct caagtgatcc 181980
tcccaccttg gcctcccaaa gcactgggaa ttcagacatg agtaacagtg cctggccaat 182040
acttattttt aaacattctc taccataaac ttaggatctt gatttgttca cattgaacag 182100
atttttatta tacagattga atttataaga aaatgttgca gacattgtca aaaagggacg 182160
tccaaaccac tgtgatattt ataagcattt gggccacatt ttgatagaac tatacacgga 182220
gtgtgtgtgt gtgtgtgtgt gtatatatat atacacacac acattattta tatatatgta 182280
tatatgtata tatatatatg tatttatata tatatgtgta tatgtatgta cacattattt 182340
acctacctac tgtgtgagtg tgtgcatata tacacgcaca cacacacaca caaatatata 182400
tatttccctt ctgagacaaa gccaaacagc actgtatgct taaagaaaaa cagtcacact 182460
tcccacttat gtaatttata ttacatccag tcaccacacc agccaaactg ctttattgtt 182520
ttttgtttga catccaatgc taaagcataa tgcctgttgc agtgaaatat acatgagcaa 182580
ccctgagaac tcaatatagc ctcacgtgtt gccactgagt tgagttgagg agtcaagctg 182640
tagcaaaaag gtttgtcacc gggtgagtaa tggtgctctt atttttctct gggtctcaag 182700
aagtgctctt tatgacatat atggcattaa ataaatatca gatatttgca catcctaact 182760
ttcctattgg tgaagtttct taaaagagag ataaagggcc attgtgtgat tgatagtttc 182820
aggtatattt ttgctgcaca gtcagtccga gtgtaccacg tagggcaaac cacgtaactt 182880
ctcagggcct tgactgtttc atttgtaaac cagagaaaag gacttgggtg acctccaaag 182940
acctttcaaa tttggagatg agtttgtgga aagttcaaac agtttagaaa acagaactaa 183000
gacacccact ggcacccctg gaagcaagag agtgccaggt actatttgta atacaggaat 183060
gaaataccta attgtatgaa attgaattct aactgaacca gtttgttcag ttaaattttt 183120
tttttcaatt agagtgctta cttcagtatc taacactaga cagtaaactg tagacaaaag 183180
acctacagaa tttctgaatg gtatcaaatt caccacactt aaaactttgg gatgtctaat 183240
ttcaaccaac agctttcttt cttcataatg ttgaatatat gtgtatctat tttagctaaa 183300
tttaatatat atcaatatac tttgatagat attttatata aactattaga ctatagtatt 183360
atgagtaaaa gacccaccat ttcccaagca attataaaga acgatcaaaa ttttaatggg 183420
ttgttagtat tatttcttta aagattgtga tactgataaa tatttggcca cattttaata 183480
gaattataca tgggatgtgt gtgtgtgtgt gtgtgtgtgt atatgtgtgt gtgtatatat 183540
atatggcagt agagatatat atatctacac acatctagat atatatatac atgtatatct 183600
atatatacac acatatatct gtgtgtatat atacatatgt atatatacct acatacatat 183660
gtacatatac atacatgcat atatctgtac atatatatat agtgtgtgtg tgtgtatata 183720
tatatatata tatatatttt ttttttcctg agccaaaaca aaatactagg ttgtaatagc 183780
tgttctttca gaaggaagaa aaacaacatg tgctgaactc tgagtttgat gtttttgtat 183840
tttacttcct attttcatat cagtccattt atttattcag gaagaattta ttgagcatat 183900
attatgaaca cagcttttgc taaggacagg gtatgcagca gttatggcct agtaggagat 183960
atggatgtta aaaacaaaat gctcacaaat gcacatataa tcttaatact cattgtaagc 184020
tatgaaagca gagtgtgagt attatgagac catatgttgg gagattttat ttggtattga 184080
ggatcaggaa agatacccct gaggaagtga tatttaattt gaaacctaaa gaaagcagtt 184140
ggccatggga agaaggtagg gaatgagatt cccaagcaat aggaatccaa tgtgtgaaga 184200
agctgaggga gtgaaagaaa gctagtgtgg tggcaggaag aaagagaaga gaatggagaa 184260
gggcactaaa tgagtcagag aagtaggagg ggctaaacca tgtagggtcg tgtaggccat 184320
cttaaaggcc tgagtgtagt ggaaaacctt tgaaggtttg ttaaaaggtc aatgaaatgt 184380
tctaatttct gttgtagtga attgctttga ttgctgaatg cgaatggatg ggtagagatg 184440
caagagtgaa agggaagaaa tcaattagga ggctcttgcc ctgctccaga taggactgat 184500
aattaatttt atttgggaag atcagggaga aagataagtc atgaatgact cccaagtttc 184560
tggattgaag aaatgaaggt accatacact gagatgggaa agcctagggg tagagtagct 184620
ttgagaagaa aggtagcatt tccccatttc ataaaacatg gaagaacaaa gaggctggat 184680
tcctgtttgt agacatacct tccaggccag aactgcatta ctacaacatc tttgcaagcc 184740
acattgcctt tcataactct gtgtcagtgt tgatgccgta acatctttgg ccttcccccct 184800 accatcctcc cgcagtcctc catgataatg ccattattcc gtttcaaatt gtgtgcttcc 184860
attggatgtg tgagtctcct tgaaagttat aatgaggctg tagcccatat gaaatgcttc 184920
aactcaggtc ctgcatagga agaggaagct aatctctcca ggaactgagc ctgtggctag 184980
agggatggat aattgtttaa ataaagaata tgctgctgag tactgatggg ctctttatgt 185040
acccatttgg ctgctgctgc ccaaccttta atctttcctg agctttaaat aggaaggaaa 185100
aaatggtcca caaaggattt gagccatttt gctgtggtga tgaggagcac gggtttagag 185160
acaaacactc ctgtgtttga attccagctc ctactatctc ctagctaagt gaccttggac 185220
aagtcactta ccttctccaa cctgctgttt cttcatgtac gtaataggat ttacctcatg 185280
aggttgacat gaagattgaa agaggtaaca tatagaatga gcctgtccca ggacatggtt 185340
catgataagt ctgccataaa tgggagctat gtgtcccacc cttttggagg agataactgt 185400
tctgtagcag gtaatatatt gtttgatact tggttaaccc ttacaattat catttcctgt 185460
tcttctcaat aatgctagaa accttttatt taaagaacca caatataaaa tgaaaaatat 185520
ataaaaaaag caaatggaaa aattctattg gcaaggcttt ttaactttat atactaaata 185580
aatccaattg cttaaataat gaactgactc aagttctcag cactgcttct tgtttaattc 185640
tctttagttt ttcagaattc tccaataatg acctttgtct actctcttca gtttattcag 185700
aaattacttt tatttacata gaagtttgga agtggataca caaacatatc cctcacatat 185760
cttatgatcc tatgagtcat atactcatct cttatattcc ctctgtaaag caatgtaggt 185820
acctttcagg aaggtgattt ttatgtaggt tgagaaatat cagcatggag gtcctagctg 185880
acctctctag agagtttctg agacatttga caacaacttt ttctttaagt catcagttat 185940
gccccggggt atgaaatttc taacatgatc ctcagtaaac ttggctgcct tgctgaggat 186000
actctccatc tgcctgagag acacagacac cattaattgg gaattgactt gacttgtgtg 186060
gttccttgtg gaccagatgg ccactaaata ttctcatttc aaggcaattg gtaaaaacta 186120
cacttcaaga aatttcattc ttaattcccc ttagtggatg ttattaacca aaggcaaaag 186180
aaaaaaaggg taaaaaaaat attctaaatg ttaatatcaa aaatattatt ttcaattcac 186240
cccaggcaca gagaactaag tattattatt gctattgcac cggcattccc caatgagaca 186300
gtgattttct tttaagacat ttttaaataa tataggcaga attaagtaga cggtgatctg 186360
gtaagtagat gtttcagggt aacagctgtg caatgctcca tgcagggaat tagattgtca 186420
ttttattcct taccaggaac atacattcag ttaaacaatt atttgacttc tgctcttcca 186480
ctgatttcta agttgaggct ctctcttgtg cctgtctgat cagataagta gagttgtgcc 186540
ttggtttata gatgagataa atgtgtattt gaataagcat aagttaaaga aattttaaaa 186600
tcccttagga agctaggctt atcagagaaa tccaaggaaa tacattaaca aactaggaat 186660
ttgttctaac aggttaatta taactcataa acttattggg tttttttacc ttttaatttt 186720
atattacatt tgcttataat aaggaatatt gctaggaata aaattttttta atattctaca 186780
attaacaatt atctcaattt ctttattcta aagacattgg gattagaaaa atgttcacaa 186840
gggactccaa atattgctgt agtatttgtt tcttaaaaga atgatacaaa gcagacatga 186900
taaaatatta aaatttgaga gaacttgatg gtaagtacat gggtgtttct tattttaaaa 186960
taatttttct acttgaaata ttttacaata caataaggga aaaataaaaa gttatttaag 187020
ttattcatac tttcttcttc ttttcttttt tgctatagaa agtatttatt ttttctggaa 187080
catttagaaa aaacttggat ccctatgaac agtggagtga tcaagaaata tggaaagttg 187140
cagatgaggt aaggctgcta actgaaatga ttttgaaagg ggtaactcat accaacacaa 187200
atggctgata tagctgacat cattctacac actttgtgtg catgtatgtg tgtgcacaac 187260
tttaaaatgg agtaccctaa catacctgga gcaacaggta cttttgactg gacctacccc 187320
taactgaaat gattttgaaa gaggtaactc ataccaacac aaatggttga tatggctaag 187380
atcattctac acactttgtg tgcatgtatt tctgtgcaca acttcaaaat ggagtaccct 187440
aaaatacctg gcgcgacaag tacttttgac tgagcctact tctctcctca ctggtatggc 187500

```
tccaaccatc aggccctatc ttggtccatt taggctgcta aaataaaata ccaaagactg 187560
agctgcttat aagcaatctt tggaggctga gaagtcaaag atcaaggtgc cagcaggttt 187620
gctgtctcgt gagagcatac ttcctggttc attgatggtg ctttcttgct gtgtcctcac 187680
ataatggaaa gggcaagacc tctctggtgt ctcttttaca atggcactaa tcccatcatg 187740
agggctttgt tctcatgacc taatcacctc ccacatgtcc tacattctaa tactatcacc 187800
ttgggggtta ggattttaac atatgaattt gaggaggtgg cggggggggac acaaatattt 187860
agaccatagc atttcactcc tgacctccaa agttcatgtc ttcttcacat gcaaaataca 187920
ttcattccat cccaatagcc cccaaagtct taacttgttc cagcatcaac ttacaaggct 187980
aaagtccaag gtttcatcta aatatcagct aaatcagcac aaacagctaa atcaggtaga 188040
gtgggactta aggtgtgatt cctctttagg cagattgctc tccaactatg aaattgtgaa 188100
atcaaaccta ttatgtactt tcaaaataaa atggtgaaac aggcacaggc tagacagtcc 188160
catttcaaaa aagagaaata gaaaagaaaa aaggagtgac aggtctctat aagtctaaaa 188220
ctttaaggct tgagaataat ttgctttgct ttgcctccag gctcactggg gtggtgtctt 188280
acctctggac acactggggt ggaggctcta tcctcatgga tttgagtgtc tcattctttg 188340
tggcaggtct gtgctccaat cccacaccta tggctccctg agtgtgcaat tgcatgcctg 188400
gtggttctac tggtctggga ttgcataggt ggcccagcct tcatagctcc actgggcatt 188460
gccctaatgt gggctctatg tggtgacctc acccctgggc ctctacctgg gccctgtgac 188520
tccctgggtt cttgaaatct aggtggaggc agccatcccc ctacagttgt gctgagtgta 188580
gtgcatgagt gctggggtct gctagagcta tacctagggt ggtggagatg tatggcaatg 188640
gagtatgggg agctgatatg gtttgggtgt gtccccaccc aaatcttgtc ttgaattata 188700
atttccataa tctccatgtg ttgagggagg gacctggtga gaggtgactg gatcatgggc 188760
atggttttcc catgctgttc atgtgatagt gagtgagttc tcacgagatc caatggtttc 188820
ataaggcagt tttccctgct cttgcaccct ctttcttgcc tgtcaccatg taagacataa 188880
ctctttccct tccgccatga ttgtaagttt cctgaggcct tcccagccat gtggaactgt 188940
gagtcaatta aacctctttt ctttataaat tacccagtct ctttacagca atgtgaaaat 189000
gtgctaatac aggagcaaag actgcagtgt gaggtggcaa tgtgaagtct gcaatgtgag 189060
gtggcacggg gcagttgtag cccctccttt gaaatctttc ttccctaccc caggcctctg 189120
cactctgaac tatgatggga aaggcagctt ggaagatctc caaatggctt tggagtcatt 189180
cttccattgt cttggactat aaattctggc ttctgtttag gtggctgact aatatcccca 189240
ctgtctgaat gcatagcacc tagtttctgt tgagatggct agtccatagt aatttactta 189300
tcaaatttgg ccacaccctt tgtattctct cctgagcagg ctttctcatc tttcacaata 189360
tggataggct gagaatttc caaattttga agttctgctt cccttttgat caataattcc 189420
attttaaagt catttctcat cttgaatttt actatgagca gtcaagagta actaagctgc 189480
tccttcaact ttgcttggat atttcctcag tcaaacattc aatttcattg ctttcaagtt 189540
ctgccttcca caaaacacta ggacacaaac agctcagcca agttctttga cattttataa 189600
gaaggatagc ttttcctcca ttgtccaata acatgttcct catttccatc tgaaaaccca 189660
tcagattggc ctttaccgtc catatttctg ggaacattct gctcatgacc acttaggtat 189720
tcggtaagaa gatagtagct ttctctatag ctctcctcct ctctggagcc ctcaccagaa 189780
tggcctttaa ttgtccattc acagcaatgt aggctttttc tagcatgtac ctgaaaactc 189840
ttccagcctc tactcattac cttgttccaa agctgcttcc acattgagta tttgttacag 189900
```

cagtacccag atcccagtac caatattctg tcttagtcca ttggggctac tacacgatgt 189960
cttataaaca acagtaaaat ttatttttca cagttgtgga ggctgggaag ttcaaaatct 190020
ggtgccagca gattttgtgt ctggtgaagg ccttcttcct cacagatggc tgtgttctca 190080
ctgtgttgtt acatggcaga agagtgggca ggctagctct ctgggatgtc ttttataagg 190140
gcagtaatcc aaatcatggg tttagggtag agccctcatg acctaaatca cctcccaaag 190200
gccccacctc ctaataccag catctttgaa gttaggattt caacatatga ctttggcagg 190260
gggacagaag ctttcagttt atagcaaacc ctataggtag cactactttg tcctttccta 190320
atcaatttgc gtcaatgaaa catgaattag aagagaccta ggcgactcca ctatactggg 190380
attattccca gtataaatta tcatctctcc acaccttctc atctactccc tatctgagtt 190440
ctgaagctct ccactacaag aaggaggctt tggtttgact tgatatactt ctctgggaaa 190500
caggtttagc ataaaacagt gatgctcatt ctagaacacc tgcaaatgac aatagttttc 190560
tttcgaagtc gccaggaatc gtctgccttt gggtatgtgg ctgtgagcac tgccgggcaa 190620
aatgccatat gacctagatg aggcatatgc catcctttga agccattagg acattatata 190680
ggaaatatat taactaaaat ggaataaaat tttctaaata acaccttatg tttatccaac 190740
aggtggttca ttatacttga gagcattata cagaggaatt tgatggggag gagagctgga 190800
gaaattctcg aaattctggg tttctttaac agaatactct agctataaac ttataatttt 190860
aaaaaataag cattatatta aagaaaaggg aacataaatt attttgtttt attaaactta 190920
agtccaaagg tctggattgt ggcagaatag gatcagggga cctaaaatgt tgagcctcaa 190980
aggtcttctt agagaacaac tgtattccac tattagcgct tttggtcctt ttagcccaat 191040
ttctgtttat cccaaatgtt cttccctttt ctgccttcct tcacagtgga ccctgccagg 191100
agctttgaaa tgcctgtgag tgttaaacac ttacccattg agtgcccaac cttaacatgc 191160
ccctaataaa atgtacttag attaaccgtt ttcattatca aagtttcctt attacccaac 191220
aaacacaggc gctttaaaga aaacattaac taaattgcaa gtgacacatt ttaagatctt 191280
tgatatgact tcagagaatg cactatagga acacaatgca atgggaggga aacttgggag 191340
ggaagacatt agcctttata aaatctgcaa gtattgccaa atcaaaataa aatttacagg 191400
aaagcaggat cataaatata atctaaaatc ttagaacctg tggttatgat tttaaatact 191460
aatacaatgc aaaattttta cctgtttagg tttttatttc atcagttcat atttaggtat 191520
atacttttac tgttctcctt ttttataatt taccattcac aaagatgatg atgttagtct 191580
aactttaatg tcatgagtgc tttgagtagt agtgctaagt ttttgttgag tagtagtgtg 191640
ctttttttgat tagtagtgat aggtttttga tgagtaagcc tgctagcagc atacaaacaa 191700
acaagcaagt atcagcctag agaagcagaa aaggcatttg ggtttcaaag tcacaaggcc 191760
taggctttag tctaatacag ctgataatac aatttgtcca aacaggacat ttttgggtgt 191820
gtcaaacact aaactggaca ggacattatg acaaaagtgc aaagcaggac tttccggggc 191880
aaaccaggat gtatgtcatc tcactgagtc ctctctttgt ccttgccatg actagtatct 191940
ctagaggtaa atgaacagag taatgacaaa tagccagaca cctgaatctt atcccaacag 192000
cacctcctac ataattcccc attatcccaa atggaaatta aaaatatata cagtgataat 192060
tccaggccaa gaaatgcttt atttctagct tggacttggc ttccatgtcc agtgtagaat 192120
cttatccttg ctgatctgga ctgtatctca tgaagccatg acttgtacct agttactagc 192180
tggaaggctt agaacaaaag ctggtccaga gagcctcctt tttccttatt tcctgggtcc 192240

-continued acacctttac catggcagtc tgcctatcat ttgatggagg aatttaaagc aagtccaagg 192300
gaagggaaga gagtttctaa aatctagaac ttggatagtt taatttacct atcccaaaac 192360
agcttaggcc cagacagctt ctctccaaga ttggtgccaa actgaaatta ccagctgtgt 192420
agaccaaaga gaatttcaaa agaaactgaa tcccaagaga aaaaaaaaag acttctggca 192480
ttgtggccca ataaattggt aggattgttg tgacttttca agtttacatg taaaatgggc 192540
ccagcgcagt gcctggcaaa tatgggtact aagtaaaagt aactataatc atgttttttt 192600
aatctggact tcacttggtc atcctttaaa tggtgtctga cagaatccta gttcttgtct 192660
cactttactt agtttccctg ggaaatttca tgtgtccttt tggctttaat taatatctct 192720
attttgatga cctccattat ctgcctattc ccagagcttt ccacctgata tctcagcaca 192780
tgaaaagcac cttatgtcaa taagtgagtt ccttccctgc cccaccacat acctgtcctg 192840
tgttcctaat tccactgaat ggcatcccat cctccagttt cccaaggcca agacctggga 192900
ctcatctttc actctcaagt tcctccacgg gtacccacat gtcacatcct gtcaatgctg 192960
tccctgggga gtatctgaaa tatattcact tttcttcatt tccacctgac accactatta 193020
acacttgcac aaatttctga ggttcctggc tcatttccct cattgacccc caatagttca 193080
ttctgctctt tgcagctctg gtgatctttc caaaccccac atctgatcac ttgtttcttc 193140
ccttcatatg gctccttaat gccttctgga ctaagtccac actgcttaag gtggcttacc 193200
aggtccttca tgattttgtc tttgtttggc tttctacact cactgcccaa cttcccctta 193260
cttcccatga ttcagttata ctgaatttct ttggttctct aaagcacatg tgctttctgt 193320
tctgcagagg ctttttgtt cacttgctat tctctacctg ggaaactccc ccagcccttc 193380
actgcctcct tctaccatct ttcaggcctc tccttacaca tcacttcttt ccaaaaatct 193440
gccttgacac tccaggtctc ggtttcctag gtgtacccta taactccacc cctttcatag 193500
catttctcac tctggctgga gatttacctt ttaacttgtc catgtccccc actggagtgg 193560
aagttcctgg aggtcaggga ttatatccta ttaattgttg tatttccagt gcctagagta 193620
gtcttgcata catggatggt attcaataaa tattggttga atgaataagg agttctttca 193680
tttcatatgt aatagatcat ggaaatagcc ttgtgattga tacacagcag gtattaccat 193740
cctcacttta gaatgaggac tcagagcctt gagatgtctg agggccttga ctgggacagc 193800
tggcagatgc aggagcagag ctgcatcacc cctgtgggct atctcagggt tgtctgtaat 193860
ctaagtacaa tgtctgttga ttttggactg aaggcttttt gggtaattgt ttgctttttc 193920
aatacttata aaatagtttc catccttact cattgatagt aaggttagtt attttagaaa 193980
acaagctaaa tagcagaaat agtggccttt taagttgaaa atttaccctg aaaaatctac 194040
agagtagcaa acagagtatc aaaaggagtt gactgtatct atttttataa ctgccactta 194100
tggattattc agtaaaacca caattcactt ttatgatttt ttttcatgtt tctctgtcac 194160
aagagcaaac tcttgctcca taataacatt ccagaataca gcaatagcaa aagtcaacat 194220
tttgaatcct ttacaaactc ttagacattt tttttttttt agtttaacat gttacaaaac 194280
aaaatttctt cttttttcac agcagtttgg gaagtacata ctatttatta gctcatcagc 194340
atgaagctgg aaaattcttt ttcctaaagt tctttatatc tacaaactgt tgatgttttc 194400
atttatttat ttttaatgct acgttgtaat gaaaatcatt ggaaaacttt agattctagt 194460
aattttgaag tcttcttagt ttggacagga ctgagctaaa gtttgtactt tttttaattt 194520
attgaaaaat ggtttctaat gatagtatta acaagattat attgggggca ggacgcagtg 194580
gctcacactt gtaatcctag cactttggga ggccgaggcg gttggatcac ctgaggtcag 194640
gagttcaaga ccagcctggc caacatgtag aaatcccctc tccactaaaa tacaaaaatt 194700
agctgggcat ggtggcaggc actgtaatcc cagctacttg ggaggctgag gcaggagaat 194760
tgtttgaacc tgggagtcgg aggttgcagt gagcccagat cgcaccactg cactccagcc 194820
tgggcaatag agcaagattc tgtctcaaaa aggaagaaag aaagattata ttggggatat 194880
atatgtgtgt gtgtgtgtgt gtgtgtatat acacacacat atatatatac atatatacat 194940
atatatacat atttaaagga taaaggattc tgctgccaca gatcactaaa tcagatgatc 195000
tctagcaatt tcctgtttgt ttgttttttg cccatagtgc ttatctcttt gaacagtaat 195060
tttccactta ctatttttct ccccttttgg accataattt cctttaaggc agagcctcct 195120
gttactcatc tttgaatctg gggtctgtca gagtacctag aatttaataa actctcatta 195180
agagccagtt gaaagaatat atgactaagc agtcatttac atccaaaaga tccgtaggag 195240
aattcttatc agcacatgtg attggtaaca ataactttgt acttttcaaa aacaattact 195300
aatctatctt gctttccatt atctcaccaa aacctattag catgtctggc agaaaataga 195360
tacttaataa atttcttaaa tgtttactga cttcaatttt aagttttatt aactatgttg 195420
acttttctct aatgaagatg attctaaaaa gctttttact atacttcaca gtgaataaaa 195480
cagtgagata ggaatattgc aaaatgtccc ctgtgttggt cagtcttagt gtcattcatt 195540
ttaaaaattc tgttctctaa atattgacag ttatatataa atttatgtaa ttgtttactt 195600
ctaataaaga atttcatctg gggaaaaaca tactttgctc agctctttgc cacaagtgca 195660
aagtctaaga cagtcaaata gctttcctag tacggcctta ggaacttagt atatgactgg 195720
tgtgaatcta gagggagcat actgcattct gaccaaaatc tccaccctgt tactatggcc 195780
atcactaact tcgcagtatt gcagtacttc ctgctagctt agttcccaag gcaacttgtg 195840
aaggaaaatt tttacaaagc tgttgtcaca caaaggtagt gtttcagttc ctgagcccat 195900
gtccttggag ttgcccaggc tccaataata ctaataatta ctgtacatta ggtacttacc 195960
atgtgccata ttctgtggga gccgctttcc acaaattatc tctggtaatc cttgtaacaa 196020
ccctttgaca tcaatattat tattttctcc attttttac atatgagata aatgagactt 196080
aaaataatgt gcctgatatc atcagcaaat gagctgagga gggcagattc aaagctgatt 196140
gtgtttgact ctagagctgc agtcttaagc cagacctttt cttgctggtt aattttactg 196200
aaaaaaaaaa aaaaaaaaaa aaaccctcaa atactgctga ttgatctaaa gtactaacat 196260
ttctatcagt gttagggaaa ttttaatttt ataatttgat tttgtgagaa atttatagca 196320
tcttgaatac tcacatgcaa agtgatatgt cttagataac attttacaat ggcagagctt 196380
aagccagtgc tcagtcattc attcatcctc aagttttgat tcatttatca ttcatcaaaa 196440
ctctgttttg tttggccacc cacattctag gagctcagta catatttgat aaatgaatga 196500
attgttgagg ttgacagtta cccaggactg gcattaggaa cacagagctg aagagcacgt 196560
ttttaccctc aagaagctta cagtctaacg agggaacttg cacaaatact actatcacta 196620
ggtgcctggt tgaatggctt aagagatgat cagggatatt cagaaggata tgtcaggctc 196680
agcaatggca tcacttgaga gcatcaaggt gtttagggaa ctacaagatg tttggttctg 196740
ctgggaataa gagtgaaggg ggctccattt ggatgcctca tacaccaggt gagagatctt 196800
agattttatt ccaccaggag gagaactacc ataggattta aaacagaaat gatatggtca 196860
aacctacatc ttaggaagat ccctggggtg tttgtatggt ggacttgcaa tttgactaat 196920
tgagatttgt aggatgattc ttaagagatg atgatgaccc agactgggat cactataata 196980

-continued gagttggtaa ggaggagaat gatttaaaaa gtagttggaa gaattctagg gatggagata 197040
aacatttgaa aattattaac ttataggtgg tcatcaatac cctgaaaatg actgggatct 197100
cagaggagag tctggagagt tggaaatgac aaagactaat attcaagggg gcaggaagag 197160
ggagagttgt tcacacatga caataggaag aaatggccat agagtgtgtg gtttctctca 197220
agccaaggaa tagatgtttt aagaaaggaa aattcttgtg gtgggaagca gtagagatga 197280
cagatacaca ttaatttctt gagatttcta gatgactaaa tgggcagatg ttgaatgata 197340
gctaaaggag aacccagaaa caagggaggg attttgtttt tgttttttaa aaaagataga 197400
ccatagcagc ttcatagact gaaacaataa aaaagttgaa ggcacaaaga aagacacagg 197460
tcctctaact ccctgcccag tgccctttat tcatattctc agcacttgta tttctaagtt 197520
ttatgtttga gtcttcgggg atacatcaga gtagtccccc ttgtctaata aatgtgttta 197580
catttcctgc cataccagaa acccttctca aactttaatg aatttctaca aggtgagatt 197640
actttaatga gaaaccaacc aaggaaagga gtatcatctg caatatactt tcaaatgttt 197700
tttgcttgtt tgtttcttgt ccagctaaaa aaaaaaaaaa aaaacaagcc attggtccta 197760
acacaacttt catattctac cccaatatca aagaggctta aaatctcctg gtcgtgtgat 197820
gggcacacag ttaatttttt gtgaacaaac acagtgttat gggccatttc tgaatttatc 197880
tctgaaatca taagattctt tctgagccat tatctcattc tatattacag tcaggtggag 197940
cccatcttac ctcctcatac taaattctag acttctcaag ggcaggagac aatcatctgt 198000
atatctcttt ggccttcata cactcaggag tacttgccaa aaataaacat ttaatgcaca 198060
tttatttgaa taattgataa gatccaatac ttcaataact ttgtcatatt tttatagaat 198120
gggtttctat atctcatttg cattttcaaa ctttactttt actgtctagc tttaaaaaaa 198180
aagcctttga ctctaataca gccctcatat tctaccccaa tatctaagag gctttatatc 198240
tcctagtgtt gtaccactat tttaactcca gtatttttta cttcatagtt ttacctattt 198300
gttacagtta gtttttatga attcaagaga tgaatagcaa ttttccatat gtaatttaaa 198360
aaaccccaca gttgactatt ttatgctatc ttttgtcctc agtcatgaca gagtagaaga 198420
tgggaggtag caccaaggat gatgtcatac ctccatcctt tatgctacat tctatcttct 198480
gtctacataa gatgtcatac tagagggcat atctgcaatg tatacatatt atcttttcca 198540
gcatgcattc agttgtgttg gaataattta tgtacacctt tataaacgct gagcctcaca 198600
agagccatgt gccacgtatt gttttcttac tactttttgg gatacctggc acgtaataga 198660
cactcattga aagtttccta atgaatgaag tacaaagata aaacaagtta tagactgatt 198720
cttttgagct gtcaaggttg taaatagact tttgctcaat caattcaaat ggtggcaggt 198780
agtgggggta gagggattgg tatgaaaaac ataagctttc agaactcctg tgtttatttt 198840
tagaatgtca actgcttgag tgtttttaac tctgtggtat ctgaactatc ttctctaact 198900
gcaggttggg ctcagatctg tgatagaaca gtttcctggg aagcttgact ttgtccttgt 198960
ggatgggggc tgtgtcctaa gccatggcca caagcagttg atgtgcttgg ctagatctgt 199020
tctcagtaag gcgaagatct tgctgcttga tgaacccagt gctcatttgg atccagtgtg 199080
agtttcagat gttctgttac ttaatagcac agtgggaaca gaatcattat gcctgcttca 199140
tggtgacaca tatttctatt aggctgtcat gtctgcgtgt gggggtctcc cccaagatat 199200
gaaataattg cccagtggaa atgagcataa atgcatattt ccttgctaag agtcttgtgt 199260
tttcttccga agatagtttt tagtttcata caaactcttc ccccttgtca acacatgatg 199320
aagcttttaa atacatgggc ctaatctgat ccttatgatt tgcctttgta tcccatttat 199380
accataagca tgtttatagc cccaaataaa gaagtactgg tgattctaca taatgaaaaa 199440
tgtactcatt tattaaagtt tctttgaaat atttgtcctg tttatttatg gatacttaga 199500
gtctacccca tggttgaaaa gctgattgtg gctaacgcta tatcaacatt atgtgaaaag 199560
aacttaaaga aataagtaat ttaaagagat aatagaacaa tagacatatt atcaaggtaa 199620
atacagatca ttactgttct gtgatattat gtgtggtatt ttctttcttt tctagaacat 199680
accaaataat tagaagaact ctaaaacaag catttgctga ttgcacagta attctctgtg 199740
aacacaggat agaagcaatg ctggaatgcc aacaattttt ggtgagtctt tataacttta 199800
cttaagatct cattgccctt gtaattcttg ataacaatct cacatgtgat agttcctgca 199860
aattgcaaca atgtacaagt tcttttcaaa aatatgtatc atacagccat ccagctttac 199920
tcaaaatagc tgcacaagtt tttcactttg atctgagcca tgtggtgagg ttgaaatata 199980
gtaaatctaa aatggcagca tattactaag ttatgtttat aaataggata tatatacttt 200040
ttgagccctt tatttgggga ccaagtcata caaaatactc tactgtttaa gattttaaaa 200100
aaggtccctg tgattctttc aataactaaa tgtcccatgg atgtggtctg ggacaggcct 200160
agttgtctta cagtctgatt tatggtatta atgacaaagt tgagaggcac atttcatttt 200220
tctagccatg atttgggttc aggtagtacc tttctcaacc accttctcac tgttcttaaa 200280
aaaactgtca catggccagg cacagtggct tacatctgta atcccaatac tttgggaggc 200340
tgaggtgggg ggattacttg aggccaggaa ttcaagacca gcccaggcaa catagtgagg 200400
ccccatctgt ctttattaaa acaaaacaaa actgtcacag cttctttcaa gtgatgttta 200460
caaattccct atggtttagt cacaaggaag ttctgaggat gatgtatcac gtcatttctg 200520
ttcaggcttt tgagcctcct ggaggtaaat ggtttcctta ctgaaggctt gttattacca 200580
tgattatcac taagcttgaa gtaacaaatt agggggcag actcacaacc tcttgccctg 200640
ccatggacaa gttcaagaat ctaagtaaag tcctctattg tctgatcttg gatttgctca 200700
acctgaacaa gccaaggagg tgtattaaac tcaggcacat cctgaccaat ttggaattct 200760
taagcttcag atcactgtgg aagaggctca actctttatg gtgctgtaga cttacgctca 200820
ttttctaggt aatttataag ggacctaata ttttgttttc aaagcaactt cagttctact 200880
aaacctccct gaagaatctt ccagctgctg agtagaaaat cacaactaat ttcacagatg 200940
gtagaacctc cttagagcaa aaggacacag cagttaaatg tgacatacct gattgttcaa 201000
aatgcaaggc tctggacatt gcattctttg acttttattt tcctttgagc ctgtgccagt 201060
ttctgtccct gctctggtct gacctgcctt ctgtcccaga tctcactaac agccatttcc 201120
ctaggtcata gaagagaaca aagtgcggca gtacgattcc atccagaaac tgctgaacga 201180
gaggagcctc ttccggcaag ccatcagccc ctccgacagg gtgaagctct ttccccaccg 201240
gaactcaagc aagtgcaagt ctaagcccca gattgctgct ctgaaagagg agacagaaga 201300
agaggtgcaa gatacaaggc tttagagagc agcataaatg ttgacatggg acatttgctc 201360
atggaattgg agctcgtggg acagtcacct catggaattg gagctcgtgg aacagttacc 201420
tctgcctcag aaaacaagga tgaattaagt tttttttaa aaaagaaaca tttggtaagg 201480
ggaattgagg acactgatat gggtcttgat aaatggcttc ctggcaatag tcaaattgtg 201540
tgaaaggtac ttcaaatcct tgaagattta ccacttgtgt tttgcaagcc agattttcct 201600
gaaaaccctt gccatgtgct agtaattgga aaggcagctc taaatgtcaa tcagcctagt 201660
tgatcagctt attgtctagt gaaactcgtt aatttgtagt gttggagaag aactgaaatc 201720

-continued atacttctta gggttatgat taagtaatga taactggaaa cttcagcggt ttatataagc 201780
ttgtattcct ttttctctcc tctccccatg atgtttagaa acacaactat attgtttgct 201840
aagcattcca actatctcat ttccaagcaa gtattagaat accacaggaa ccacaagact 201900
gcacatcaaa atatgcccca ttcaacatct agtgagcagt caggaaagag aacttccaga 201960
tcctggaaat cagggttagt attgtccagg tctaccaaaa atctcaatat ttcagataat 202020
cacaatacat cccttacctg ggaaagggct gttataatct ttcacagggg acaggatggt 202080
tcccttgatg aagaagttga tatgcctttt cccaactcca gaaagtgaca agctcacaga 202140
cctttgaact agagtttagc tggaaaagta tgttagtgca aattgtcaca ggacagccct 202200
tctttccaca gaagctccag gtagagggtg tgtaagtaga taggccatgg gcactgtggg 202260
tagacacaca tgaagtccaa gcatttagat gtataggttg atggtggtat gttttcaggc 202320
tagatgtatg tacttcatgc tgtctacact aagagagaat gagagacaca ctgaagaagc 202380
accaatcatg aattagtttt atatgcttct gttttataat tttgtgaagc aaaatttttt 202440
ctctaggaaa tatttatttt aataatgttt caaacatata taacaatgct gtattttaaa 202500
agaatgatta tgaattacat ttgtataaaa taatttttat atttgaaata ttgacttttt 202560
atggcactag tatttctatg aaatattatg ttaaaactgg gacaggggag aacctagggt 202620
gatattaacc aggggccatg aatcaccttt tggtctggag ggaagccttg gggctgatgc 202680
agttgttgcc cacagctgta tgattcccag ccagcacagc ctcttagatg cagttctgaa 202740
gaagatggta ccaccagtct gactgtttcc atcaagggta cactgccttc tcaactccaa 202800
actgactctt aagaagactg cattatattt attactgtaa gaaaatatca cttgtcaata 202860
aaatccatac atttgtgtga aactttgttg ttttcagatg cgttcacttg tcatgtttca 202920
tcagtctctc actccaattt ctaagcttca tggaacatga aacacgaatc tgtcttttag 202980
atatagcctc ttttgagaat tcacatgaat tagaacacac atttttagtt atctgtttaa 203040
actatggtaa aatatacata acataaaatt ttccatttta accattttaa agttcagttc 203100
agtgtcatta ggtacattca catggttgtg caaatatcac catcatcctt ccacagaatt 203160
tttttcttgc aaaactgaaa ctctttttac ccgttagtca ataatcccgc atttatcttt 203220
cctctaatgc ctggcaacca ccattttact ttctgtctct gattttgact actcgaagga 203280
cctaggagtg ggatcataca gtatttgtat ttttgtgctt atttcatcta gcataatgtc 203340
ttcaagcctc atccatgttg caacatgggt caattttctt ccttcttaag gttgaataat 203400
attcattata gagtagtccc cccttatcct tggggaatat gttccaagac ccccaatgga 203460
tgcctgaaat cactgatagc actgaacctg attactgtgt ttattcctat acatacacac 203520
atacatatga taacatttaa tttataaatt aagcacagta atagattaac aacaataatc 203580
ataaaataga acaattataa caatatatta tgacacgagc gatacaaatg tggtctctct 203640
ctttctcaaa atatctcatt atactgtgcc acaggtaact gaaaccacag agagcaaaac 203700
cttggatagg gggaccactc tataaaatatg taccacattt ttcctcaccc attcatccat 203760
cactggctac ttggtttgct tccacttttt ggatatagtg aataatgctt ctataaatat 203820
gggtgtacaa atgtttcttc atgtccctgc tttcattact taggatatgt ttgaagttat 203880
ttttattttt aaatggaggc ttatagaaca caaaagattt atattctgca agtgtccatc 203940
tatttctttt aaagcttatt caaaaagtgg tagctatctc atagctcttg gtaagttaaa 204000
aatcttcatc aacgaaaata ctatttctgc gttggcacct gcatggattt tctttgtcca 204060
aatccctctt tttaattgat gaggcttctt tagttccttt ttttcttcct tgttgagctt 204120

-continued cttcatgaaa tgtgcagttg ctagcatgtg gtggacggac tgcagatccc tactgaatgc 204180
caggccctcc ggccctgtgt tctctttctt ggagaggttt gttttcacac gtaaccccaa 204240
gagggcagtc tcagagcgtg ttctagtcta gttctttttt taaaattact aaactttatt 204300
ttttttaggg cagttttagg ttcccatcaa aattgaacaa aaagtatgga gagttcacat 204360
ataacttctc catacatgat agcctccccc attcaacatc ccacactaaa gtagtacatt 204420
tgttacaact gtgaaagcaa atagaatttc aagaccccaa gctcactatg ccaaagggca 204480
agttaagctt cagagctgaa ttactcaata ttgccttcct tttgttccct aacagccgta 204540
acttcacaat cttgtgtgat agcctcatcc ataaaccagg ttcccacaat gatagaaggc 204600
cacatatctc cccaaatgac ctccctcaca attgtgccca aggaaaatcc ttgtgagacc 204660
ctatctttta ggatacatat ccctcctata aaatagccct aaaactgagt tatgttgaat 204720
ttcaccctga tgatgtcaat taccagcttg tcttcatagg cacaggacgc gggcaagacc 204780
agaaatcatc gtgctgtcta ccctgcaatg aacacataat tgacttttcc tttactccct 204840
ctttttacct ataaaatttg gatttactga acactaacca aagcctcccc tgaatagaac 204900
catttgcctc actgcctacc ctctatcctc ttttccttct ccgtgtttgc actttactct 204960
ttaaatatta aagttcccaa accctctttg gaaaagcaca ggtcacagat gctcctctgg 205020
cttgtgttct tcctgggtgc atctgcaaac tttggctaaa caaacctcta tcgattaaga 205080
cacctgcctc agtcactttt tccttaacac aaccaatgaa cctacattga cacattatta 205140
ttgcccaaac acaatagttt atattagggt tcattattgg tattttacat ttcatgggtt 205200
tggacaaatg tgtaatgaca agttaactac cattacagta tcttacaggg tagtttcact 205260
gcccaaaaaa tactttgtgc tctgcatatt cattcccctt tctcccctaa cttttggcaa 205320
ccactgacct ttttattgtc tccatagttt tgcctttacc agaatgtcat ctacttagaa 205380
ttacgcagta tgtggccttt tcagattggc ttctttcact tagtaatatg catttaagtt 205440
tcctccgtat cttttcatgg cttgatagct catttctttt tagtgctgaa ttatattcta 205500
ttgtcagatg taccacagtt tattcattga cctactaaag gacatcttgg ttgcttcaac 205560
gttttggcaa ttttcaataa agctgctgaa acatctgtgt gtgggttttt gtgtaaatat 205620
aagttttaat ttctttgggt aagtaccaag gagttcaatt gttggatcat atagtaaaag 205680
atgtttcgtt ttgtaagaaa ctgccaaact gtcttcaaag tggctgtacc attttgcagt 205740
cccaccagta acgaatggga gttgtggttg ctccttatca ttgccagcat ttggtgtcct 205800
cggcgtttta gaatttggcc attctaatag ttttgtggtg gtatctcatt gttatttcaa 205860
tttgcatttc cctgatgaca tgatgtggag tatgttttca tatgcttatt tgccagctgt 205920
gtatcttttt tggcaaggca tctgttaagg tctttggccc gtgttttgat caggttgtgt 205980
cttgttgttg agttccttta ctggatttct tttgttagca tggtataact ttatccatcc 206040
ctttattaat ctacctgggg ctttaaattt aactaggttt cttatagaca tcatgtaagt 206100
cttgcttttt gattcactct cacaatcttt gttttttagc tcttgacatt taaaatgatt 206160
attgatataa ttggattaat atctaccata tttattcctg ttttctgttt gtttcctttg 206220
ttctttattc ctatttttac tttccccatt tttttgcctt tttaaatttt attgagcatt 206280
ttacaggatt ctattttctc accttcttaa catagcaatt cttctttttt taaacttttt 206340
tagtggttgc cctacagttt gcaataaaca tttacaagtg acctatgtgc ctttaaataa 206400
caatattcca tttcatatca gtgcaagtac cttaaattac aaatttctag cttctgtccc 206460

-continued ttttaccatt tcaggtattc atttcattta tatattagct tatatatatc cctacacttg 206520
atttttcctc atatgagatt ttctttcctc tttcccattt aaaaaaataa aataaactat 206580
tatagccaca gactttctat ttttatttgt tttctgtatt gaagtcttga ttttggggct 206640
ttacttgtcc ctgtctatgc ccactcctat ctgacacaca ctttcttaat ttatttccta 206700
gttgtttcac tttgtttatc ttcattatga ggaaaaaaag ccaaaacctg aaatgaatat 206760
gcttccttcc agtaaccagg gaccttccat ggttgggaaa ttgttaccta ttcgagtgaa 206820
aggctaataa aacccccaag gtaaatattt tagtacttca ctaaagaaag aacctcaaat 206880
actatgtgga agacaattta aaatgaggtt taaagagctc aatataaaaa cctgtttgac 206940
ctgttaaaac aggtgtggac aatcacaatt ccctatttaa aaatacagtg aaaaaaccta 207000
caaatgcaag acaaatacat tggagcatga gaactccaaa ttgttaggtt aggaattaga 207060
agctgttccc agtgtgtaga gctaagagac ccaagtcatt gtcagttgac agggagccgg 207120
gactcaatac ctgtgtactt tctcagagaa aggagaggtc ttggcaaaat tttgggttta 207180
tccttaattc catacaatgg gaatattcaa ttgctcttta atcactcagt attgataggg 207240
acagggggca gagaaattct aggcagaaaa gggcgggacc ctggtgaaac cccaccctca 207300
atccgaaaaa cctgaaactg ccaccgaaag tgagaacttc tatccctgtt ttcccactcg 207360
aatgttgcct ttttctaaac tacccgtggc ctgctccacc cccatccttt gcctataaaa 207420
accccagact cagttggtag atgggactat aactggacat tggagagaag tggcttgact 207480
tcagagcgac agcttgacag catactttgg agaagaatct gagaggagaa ggcaagactt 207540
caggggaaga ttacctatct gccctgtccc ctgttcagct ctatttccca ctgaaagcca 207600
ctttcatcag caataaaatc cctcatttac catccttcaa ttcgttcatg tgacctcatt 207660
ttttctggac gccagacaag agcttggagg ccacgagtat ggatacaaaa ggctgtcaca 207720
ctggctgttt gcccttgctg gtggagggca gctgcctcac atgaaaaggc aaagagctca 207780
ctgagctgtt aacacttaag ccttccgcag acggcagagc tgaaagagca ctgcaacaca 207840
ccctctgggc ctcaggctct caggcactcc tacctggttg cgccgctggg cccgcacaga 207900
gtttgctact gccggcacct gaaagcggtt ggctggttcc tgcactcgct cgttctggtt 207960
cctgcactta ttcattcgca cgctccctcc cacaaggggt agacggggcg ggatgggtaa 208020
atgaggcacc cctgtctcaa gtcccgtgaa ggcgtcaggg aaataatctg cttcagtttc 208080
tctagttgta aaatggttaa gaacattatg aaaggtggtc aacaacttta taagtgaata 208140
tgctaatgct ggccttaatt ctaaaatgct acttggatca aaagttatga ttcagttcca 208200
atacatcttc tattcattga agtacagaat ctgtacacaa agtacaattg tatcttcaaa 208260
aactgccacc ttgtggagat ttggttttat tgttaagaca gccagtgcca acaacagaaa 208320
tgagtacaga gcctcacata ctaatgtaag tgaatctcaa agacatttta tctttaagcc 208380
attttgaaaa gtagaaatta agcctgaata gttttggggc acaaattgct ctttaactct 208440
cttctttccc attcaccttt gtcactgatg gaataataga aggagcaatc tttatcagca 208500
atggcagatg tgctgataaa tgaaaccaaa actgaattga caaatattga cacaaatact 208560
tatagaagca atttaaaaat ctaccttgca attaatcctt atgaaattta agtcataatt 208620
tactaaaaat tataatataa agaaataaac tttctctgtt ttattaaaag aaaggatcaa 208680
tacatttggc cacaattgat tggccataat ttttgtcaat gttctataag ctaattgaaa 208740
ataagactat tttaaatata attatctccc ttctcctttg ccttttcatt ggcagcaggt 208800
gccatgggct tattcatatt ctaaaagaga agttgtgtga gcaaatttgt catcataggc 208860
aatcctcttg taaggaaaaa attatgattt gatttttatt ttctcttatc tcctaattgg 208920
gtcagatact ccagtgtcct cggggagcca aaccaggagc cagtgtgtcc ttacacaaac 208980
acagcttcct tcctgcttgg agctcacacc aagcatttgc atttgaacca agcaatgttg 209040
acaggctatt gagccacaga agttaaacat tccaagtgag cctgagacga ccattacatt 209100
cttttacatt ttctggtcga ttaaaatttt aattgtttaa aatttcaaat agatacaaaa 209160
atagacatag agtataataa acttcacacc cctgtcactg aacttcaata gttatcagct 209220
cacagtcaat cttatttcat ctatgctccc tcatgcttcc ctcctatatt attttgtgca 209280
aatccaaaca gcatataact ttagctctat gtgtctctaa aagacacggc tttctctatc 209340
attctttttc ttttgaaact gatccatatt acctttacca gaactagaaa aacagtcatc 209400
tttaatatcc tcaaatattc actccatgta taaacgtcat tgtcagtttt ttcccaaata 209460
taggtagtcc tcatgttgca cattaatatg gcactatgaa aatcaccatg caagataatt 209520
taaataatta atgggggaaa aattgttcca tgacctttaa aaatattaaa aatttaaaac 209580
tttcttactg ttggttataa acaataggga cacaaaaata gtgaaacatt tagtaagtaa 209640
tttaaaacat tagaaacact gagaattaaa atgtttcttt taaactactt atcaagagta 209700
gtttgagcaa tacttggttt cttttggtta tgtaacttgc aatatgaaga aagcatcttt 209760
tctatgcctg ggcaagttgt catactcctt tctaatttag gaccagcttc caacattgta 209820
tccttcgtga cttcaatgtt gtaaaatatc tccaagagtt tgtttaaggt aatgattttt 209880
gctgatgtca cctcctctgg ggcatctgac aggcattcct gctaggtcaa cctatagcag 209940
agggtggaag ggcccagaga tggcaagaga gaaaaggggg gaacctttta gaggtgatta 210000
ggctatgagg gctctgcttt catgaatgga ttaatgccat tacggcagtg agttcattat 210060
aaaaggacaa gtttggcccc cttctctctc tttcttgctc tcttttggcc cttttgcctt 210120
ctgccatggg atgacacagc acaaaaaccc tcaccagatg ctgacccctt gatactggac 210180
ttcccagcct ccagaactgt aagccaacaa atgtgtgttc tttataaatt accccagctg 210240
tggcattctg ttatagcagt acaaaataga tcaagacaaa gggggattgc aggcaggaag 210300
ggagcccctg acctcttagt ttcactcatc tggaatttag ccactacaac acagagctgg 210360
ggcttgaggg gataagaaat gctattgacc tgcacttccc agggtgatag tacagttaca 210420
ggctgtaaac tcaagggaga gggaatgcca tcatcttggc cacatcagcc tggagtagag 210480
cttctatcac accaagttgg gggagggaag agggagcagc ttgtgactga agtgccataa 210540
acttttgttc ttactgagat tagtatattt tctggaataa acgctgctgc ttttgctgta 210600
tgtgcttagg gccattttca gagactttaa atgattgata attgttacca gtaatggtta 210660
ttttgatggg tagttggtcc acagagctcc tcaccttgct gttctagaaa ttgtctttta 210720
gcttagtatt aattcctgaa tttttcagtt tttctgatct tttacctcca ggatgactct 210780
ttgaaacaac tctaaattat tgactgaaac ttttatgtat aattctcatt ttgttcttca 210840
cacaatctct gtgaaggagg ttctaagaac taagaggctt agagagggta aggatcttcc 210900
cagaaattac acagcactcc cagatttgga acctttagaa agtttatata cttattggaa 210960
aacttagctc atttttaatc agagggaagt cattttacag tgccccatac agggagtcag 211020
ataactactt cctagttagg ttttcctctc tatagagagt caaccagccc tgctgtactt 211080
tcccgtggga tctgaaactg cagaaatcta ctgagaaaaa cagaatgctc acagcaggat 211140
aaagctcatg ttttctagag ctactaagat tcaggcttat gcctctgtgt ttgatttttt 211200

-continued

```
aatagtcttg ctaatgtcaa agtgattcta tcttacacac cccaaagtct gtaaaggtat 211260
aataacaagg ggtgagattg tcttaaatct gcagtttctt gatctgttta gtgggctact 211320
ataggttact gcaggacctc tcaaggtttc tagtatgcaa aggtgcattt tgactctgta 211380
agagtggaat atcatatgta atgtttctca attgatttgt ctacataacc gtattttctt 211440
gtgccattta tatcctgtgt tttggggaag gttggcctag aacatttatt ctaaaaggaa 211500
agggcatggg aaattcttac cattggcagt gtcggggagg aaaaaatgca tacttcttac 211560
ccatttagtt tattttgcta gtttacaaat taaattgaga taagacagat taataggaga 211620
aaatcaactt taattatgtg tgtatacatg ggagtcccac aaaaatgtaa gactcaagga 211680
agcagccaga tgattgagac ctatatatta tcctgagcta cagaaaggga taagggtttg 211740
gggcttttgc ggggttgtgg aggcaaattt tgggaaggcg aggagaggaa atgtatgatc 211800
aataaatgtt gccttgttgt gcagataaaa gtgtcttagg tgataaagat gtttccaaag 211860
agtagttctc ttcatggtac agatatttta ctcatgatca tttcctttat agatataaat 211920
ttcctttacg aaagggggaa ttttatttta tgtagttagt ggagaagtcg gtaaagagct 211980
tttcctgtat tggctgattc tcagtttttt ttagctcaaa atgatcaata tgccgaagtg 212040
gcatgttctg aaatgacata ttctgaatcc tttcagctgg aatatatttg tatatcaaca 212100
gtgtttccat ctgtcagccc ttagggtctg cttatggaag atataagcac ctggatgacc 212160
atgacgaaaa tctggagatt ttgagaaaac actggtgcaa ggctccatcc aaaatcaatt 212220
aaagaagaat cttggaagat ggggttaggt cactgatagc ttgaaaggca tcccaggtga 212280
ttctaatacg cagccagttg agaagcacgg atttttttat tgggtttttc aggctggctg 212340
aaagaactgc gatgctcagg aaaccagggg tgcctggcag gagtttgacc ggggagactg 212400
aagcctgtca acagggacaa gaacggtagg ctggtgcctg gcacctgagg gtacttcaga 212460
ggtgctcatt aaaaaagagg aggggacatc aagcgagaat tcttaatcag acattcaaca 212520
aattgagggt cgtctatgtg ttctaggtgc taagaactcg gcagcaaaca aggcaaagtt 212580
ctcagtgtca tggagtttac attctagtgg atgaggacaa aagtaagtaa atgttaaaaa 212640
tatatagcag atggtaacta aagagacaaa gcagagaatt aggttatttg ctgtaacatc 212700
atcaaaaagt cattagtatg gtggcaattg agcagaaaca tgaaggaagt gaggaagtca 212760
gctgtgtggg tgtcttgaac agtgtttgaa gcaaagggaa gagcaaatgt aaaggcagaa 212820
tcatggctgg gatgttggag gagcagcaag gaagtgctgt gaatcttggg gaaaaagagg 212880
tttagatgat atgggcctct gtaagagccc tggcttttac tttaagtcat aagggaaaac 212940
ttcggagttt tgagtgaaga gtgatgtgat tggaggcaca ttatagcagg gtgactctga 213000
tgctgtactg acaccagact gaaaagtgta gagcatggaa gcagggagac cagttaggag 213060
tctattgtaa tagtcctggt gagagaccac agcggcttgg actaagatgg caactaaggt 213120
atatctgaga ggtggtcaga ctctgcattt atcttgggaa cagaagcatc cagatttgct 213180
gatgaattgt atatactgta ggagaaggag aggactcaag gatgatgtga aagatttcag 213240
tctgaggagt tttaaggatg agactgggaa gaatgaagga gaagttggtg ggatgggaag 213300
gatttagggc attttagaca ttaagtttga gacatcttgg tggaatgaca agcaagcagt 213360
tgaatctgag tctgaagttc aggaaaaaga ttcagagtgg agacagaatt ataaaagtta 213420
tcaaaatgga gattgtattt aacacgagtg tgaactagat tcttgttact tgcaccatca 213480
acatcacctg ggagcttgtt agaactgaag actctcagac cctacctcgg aactgctgag 213540
tcagtatcag gatattgtca cgatcccagg tgatctgtag gtactttaga gtttgaggat 213600
```

tcctagatta gatcatctag ggtatgaatg aatgtagaag agaaagactg agaacctgag 213660
acaatctatc tctggaggcc ttggaaaaga gctggagact gagatgatat aggaaagggg 213720
aatttagaga gaatagtgtt caaatccaag ttaagaatgt gtttcaagaa agagggagtt 213780
aaatgcgtag gtcaattaaa atgaggaatg ctagtttacc actggatata gaaatatgaa 213840
tgtcatttgt tacttctata agagcatttt aataggattc aagatattgg gaagagaaat 213900
gttagagact gaggatagac cttcatgagt tttttctaaa ggaaaggaga gaaaggggag 213960
gtaagtggat gggaaactca aggcaggtaa aagttctggg cacggtggct catgtctata 214020
atcctagcac tttgggaggc ttgggagaat tgctagcacc caggaatttg agaccccatt 214080
tctacaaact gaaaaaaaaa ttagccaggc atgatggcat gtgcctgtgg tcccagctac 214140
tcaggaggct gtggtgggag gattgcttaa gccccggtgg ttgaggttgc agcaagctct 214200
gatcacgaca ctgcactcca gcctgggaaa tggagtgaga ccccatctca aaacacaaaa 214260
aaggtgagag aagtaacatc ctactggcat agtggatata tagataacaa attaaggggt 214320
ggggcatttg gtggagctgg gggtatgtgg aggccaaagc aactctgtct tggaggctaa 214380
ttcacaattt tgacttctga ttaacccctt ttctgggaat gcctctaaga tttctatttt 214440
atctactgtt ccttgtgtaa gagcatgtac ttaccataaa tcctgccctt aatcaattgt 214500
tctatacatc ccttctgaag cacatatata tcctttccct atggtgtata agcccggggt 214560
atggaaagta agagtgtgga gatccagcat cttgtctcac tgccactgag atacagacat 214620
ggcttctgtt tttaagtctc tattaaatgt ttctttccaa gaaactggat acatcagcct 214680
cttccttcag cttcagcttc taagtttggg tatatccgcc cacagcagaa caggggagaa 214740
ttgagagtca ttccaggata ccctgaatag ttgagaggga aggaacgctt ggaacaagag 214800
aagggatcac ctttagtaag gaggatggaa agtcactcct agaagtagga gaaaaggtag 214860
cttggtagat gtggggatag aaaattgtaa gttttctttc aattgactca gttgttatca 214920
atgtaaaggg aagaatgtca ttaattaaga atgaggatgg gaaagaagct actggagatt 214980
taaggggaat aacatatgaa ctgtcactta agacagttcc cccaacgttt taaagccatg 215040
gcacacataa aaaatgagaa tatttgagtg acaactagga ggggatttgg atccctggcc 215100
aagtttactg gggcaggagg caaatggctc aggggttctg gttgccattt gcccagatgg 215160
ctaaagaaag taatatcttc tggcatcctg gttctgtttg acacatgaat tggggagctc 215220
tgaaagaaga gatgggaatg aataaagcag acaggcagaa aggtagtcag atagcaggaa 215280
ataccttatg tgagtgaaat tcatgaattt gaagaggagc tggtgaggat ggtcatattt 215340
ttaaccactt cagctacaca ggtatagtaa tgcaataggg ggagaactgg atttaactaa 215400
gtttggggtt atgcctagca agtatgacag agaggggatg agggagttga ggagagatgc 215460
caagtgtaga ctaattatga tcatgtaata taaactaggt gagaagagat attaggacat 215520
ggaataggag gggaatattg gaaaggtagt ttggattctg aattttgtgg ggtttcactg 215580
tttttggaga taagagagag aaggagatga ctggagaata gaatgcttgc aattgatcac 215640
tgatgagatg caggtgatgg taatgacaaa gtcagggtgt tatatgggag tgggaagtgg 215700
aggcaccgtg gaggagaaga ggctgttgga ctgagaggtc atggtattgg aggagttatt 215760
tacattgata ttaaaatctc taagagtgat ggcaggaggg tgacagtgaa cctggaggta 215820
aaattcaaca attcatttgc ttcattgaac aaatgaagca aatttagtag caaattttgt 215880
tgtataaccc caacaaattg acatgactat gaaaagaagg gccagtgtag tctggtggta 215940

-continued

```
gagtctgagg tcagaacttc agaaaggggc atttgtcggg gagggagata caatgtgtgg 216000
aagtgacaat aaggagcaag gaggccatca tcctctacct ccatgtctgg ttatcaaaga 216060
tattggggga ggaaagcagc ctgcttgaga aggcctctgg aaaaactgtg ttccccaaag 216120
ggagccaggt tttcattagg accatgtggt gaaagaactg tttaaagatg caggaagttt 216180
tgctgagaag gttgtgactc tggagggcac aaggagatag tttggggaaa ttgagaaggt 216240
ttgagagatg agagcccatt gtgggatgtg tgaggtacta aggagatgag agctcaagtg 216300
ccaaggtctg gcttgaagag gcaggcttct tgttatgaaa actgctgctt tatggatact 216360
ggagagcaaa caactccaga tagcttcagt gttttctacc caagcaacta caggttatct 216420
aacatcactt ttcagagatc atgtttcttc tggagacaga aaataatttc cccataatcc 216480
agctgagaaa attgcttggc cttcccttaa cccttccttg aaactttccg taaaattatc 216540
gattccagaa atgagaaatg aaagagaatc ttgtttttgt ttgtttattc tgttttgttt 216600
tgttttgaga tggattctag ctctgttgcc caggctggag tgcagtggta tgatctcggc 216660
tcactgtaac ctccgcctcc tgggttcaag caattctcct gcctcagcct cccgagtagc 216720
tggtattaca ggtgtacacc actacgccca ggtaattttg tgtttttagt agagacaggg 216780
tttcgccatg ttggccaggc tggtcttgaa gtcctgacct catgatccac ctgcctcagc 216840
ctcccaaagt tctgggttta caagcgtgag ccacagtgcc tggccaagaa tcttatctta 216900
atcctctgtc ttaagacaat ttatcctgga aaaatgatta tccattttct tcaagtctct 216960
ctccataaaa cctctttatg gaatctcctt ttgatttgaa ctttgatcca aatcataaac 217020
aatcctcatt ccctcttaat gttatgtatc acggatgtga gactgggtgt ataccggtgt 217080
atatgtgggg gaacagtggt gtcctgaatg ccctttagac ctgatcttta tgaatcacca 217140
tgatatttct atttcctatg acctgtgtga tttttggttg ttacttatct tgacaaatat 217200
tcttttcaaa aacattgcgc actgaaggac atctggaaaa ttccaggagt ctgtctaggt 217260
tctaattgag atgcaatttc ctaccttcat agccttttat tgggcaatgt ttgttgacac 217320
ttgttttcca agttactgga ttactcattt cagagttcag ttacccagaa accacctact 217380
tctatgccta caataagaag caaacaagag gtttttgcaa taaagacaat cagtatctag 217440
gataagggct ggcatgtggg ctggtcccat ctttgctgtg aagctacggg gaggaggtag 217500
ggaggggaga gtctggcttt ctcagtttgt tgagtaaccc cagcgggaca tcctgcctca 217560
catcctggca gttgaattag ctgggctttt caaggtcaca agaaggaatc ctatacccat 217620
cacctgcaat gataggagtt tattgttcaa atagtaggta ggaggggaag gatgggaaac 217680
ttcctcatca ctgttcaatt ccccctggtc ccagggcttc agagctggaa taacacacaa 217740
cagacttctt acctccaatc aaagggcagg caggtaattt gtcttctttt tgtttccctc 217800
acacaatgga gagtgcacaa ttgggtcggc ttttgatctc tcactataat gctctacaac 217860
tggacatggt taccaagtcg cttctgtgat ggtcagcttt tccagcatta ggagttttaa 217920
ctgaggcttc agggattcat accctgcccc tcgccctggg attttgtgcc agaatgaggg 217980
tctgagcatg tgtgcatttt tttgcgaaag gatatgatcc tgtttataaa ggggcctcaa 218040
tctttgcttc aattcactgt ggctagcgta acagatttat gttttactca tagctcgtga 218100
caatgcaggc agggatgagc ccatttgaat caccatcctc aaaaagaatc catatgctgg 218160
cagcgagtga ctcctcctgc agctggtcat gtatcagagt gttgtgtgag gtaatcccct 218220
cacttcctca cactgatttc tgatacctct ggtccttcca caagtcacag aaatgccccc 218280
atcttctggc tgtgtacacg tgctcataca ccacccctgc ctccatgaca gaatgtagaa 218340
```

aagttttctt gtgtggttct atagccaaat aagtcccttt catgctattc aaatagggtt 218400
tcatagtgct gcactcagtt ctatttttct tttaaaatga tcaaggttga ctaaatgaaa 218460
ggcatttcag gatttttagt tcctagaaag cagatggttt atatatcaat ctcctactct 218520
ttagtagcaa agattctaca actgcacata caaacttcaa gaattccagg caatcctaaa 218580
ggttttcctg ggccaagcct ctgtgcagag gtatgttttt aaccatctcc aatgggattt 218640
tcagtatttt cagcattgac tcaactccag tcaacagcga tatcaaaaca agtgaacatc 218700
aagtctgaaa agaaagtctg aatactgtta tccaatcaca aaaaagacgg gtgatgtgaa 218760
tgtgtgttgc tctttaaagt tggttatttt aagtcaaatc cactcacctt tcaatataat 218820
cagtaacctt catagcttgg ggctgcctgg gcttcagaca gcagagttag agaaaacaga 218880
acagtgattt gtgtgtttgg ctttggagca atgcaatatg cagttcaaat tcaacctcat 218940
ttcattaact ctgtaactga agtacctgat agcaactacc aaaactaaca tgtagaaaat 219000
aaactttatt tcacccaaga gttcagttca ctgacatcga aaggcttcag agatttggat 219060
cacatgaata taacatgaga gctttacaat ttttaaaaac aagtatgttt agaataggga 219120
tgaacactat tctgtcagca tcaagaatca tttctaattc ttgtagactc ttttccatga 219180
taagatcaat gtaatttgta acaaattacc cttgggttga gtccttggag aaagctggac 219240
tcatttttaa aaagagaatg aaaattaatt tcaatcaaag gcacttaagg cttttattta 219300
tactttgcat ttgttttagg gaatttttgt acgtttatca atagtccttt attacaatat 219360
tttatccttt gaggttaaaa aaacaaaaca aaaaacaaaa caaaacaaaa aaacctggct 219420
gggcatggtg gctcacgtct gtaatcccag cactttggga ggccaaggca ggcagatctc 219480
ttgaggccag gagttcaaga cctgcctggc caacgtggtg aaaccccatc tctactaaaa 219540
atacaaaaca ttagctaggt gtggtggtgt tcgcctataa tcccagctac tcggaggctg 219600
aggcaggaga actgcttgaa cctaggaaac ggaggttgca gtgagctgag atcatgccac 219660
tgcactccag cctgggcaac agagccagac tctgtcttaa aaaaggcaaa aaagctaata 219720
ttcagtaata cgtgcttaat acaaacctta aagttcccat ataaacctgg aatcaattct 219780
aggaaagaca cataaaatat ggtgattata ttttatttca ctctgctgtg ggaagaggct 219840
gggataatgt ttaaattaaa acaaaagtga caatacccct atgaaggaga ccaggtcaac 219900
ataaccggct ggcatcatgt ttatcttctc agcatttaaa acacacacac acacacacac 219960
acacacacac acacacacac acacacacac aaactttttg gctctacttc tgaccttggc 220020
ttttatattg gtgttcattt gtttttcaga ggggcttggt tcttttattt gaagatacat 220080
cctatttgtt ggaagaactt ccattaaatt atcttgtcag ttctcactaa attttctttt 220140
cacagctctt gctgtctggg ttataaaaac ccatggcaaa catgggaggc cccaaaggaa 220200
tgtgtgctgg gatcctcttg aaatattatt gccctggatc ctttgagctc tttgagtcca 220260
gaaagcagca tggagaagga gggcaaacct gcatagtttc tcagaatgga tgagtttttc 220320
ttcagagtag ccatgtagag cagctcagga aatgactgct cttaagctga caggctggca 220380
gaatattaat aaatgcaaaa taagcaactg tcctgcaagt atttcttgga tgctgtttat 220440
acttgatttc tatccaatgc tctttagcac atcttctcag agtctagaaa gttgtctcct 220500
ttttccctca agccaaatgg gttactgctt tcaagctatt tttgctatga agacaacaat 220560 aacaaaaacag ctatgccaaa ctacttctta ttttcaaaac cagtttgatt tcctctgaca 220620
aaccatcagg ccagtgtgac tttgcatcac tggattaggt tagtgtaggt gctgtggttt 220680
gaatgtgttc cctaaagctt attggaaact taatccccac tgcaacagca ctgagaagtg 220740
ggagctttaa cagctgagct gattaggtct tgagggctcc attccttgtt actgggttaa 220800
tgtcattata atgggagtaa gttaatcagc cagggagtga gttcctgata aaaagatgag 220860
ttccccaatt cccctcttct cttctgcaac agacatgctc tcttgacctt ctgccttctc 220920
ccatgggatg actcagcaag aagacccttg ttaaatgtgt gcccctcagc cttggactta 220980
gcctgcagaa ctgtaagaaa taaatttctg ttctttacaa attacccact ctcaggtatt 221040
ttgcttattt atagcagcac aaaatggact aagacagagt gtaactagat gtatgaggaa 221100
atgacctctc tctacatagg ctgtctatct ttggagtaca gctccaggtg gacagtggca 221160
ttgtttaggc ttgctaggag gacagctagg agtgaattaa aaaaatccat tttgcttcta 221220
aaactaaaag ggtcatttta attaaaataa taccataaac ataatttata ttaaaaacaa 221280
agtcatatac aaattagaga aaaatacaaa gaaatgccat ttcctaggtt tgattcgggc 221340
atcttcattt ctaaaattaa ctattcctga gttctgctaa tgtgtcctgc cacaagtgta 221400
ggcataaaaa ggtgaaggaa ttaaactacc aggctctgaa tcaagggact tgtttaatag 221460
aattatgtat aatgaagaat cctactcgct ttgaattcaa cgtggaagtt attcctccca 221520
ccaaaagaag cagagaggga aggaacctcc cagaaaagtc caggcagaac ttacaagttt 221580
gagccatatg aaacaggtaa tatttgacca tttttgctga agaaacatat caattccata 221640
ttgattgaca caatagaatc atcaacttct ataatgggag ctgtggcctt ttccactttt 221700
tcctttctcc tatatttgag cagaaattcc cagaagggag taaaacttgc tctacctata 221760
gaataggcaa gaaattgttt tctcttcctc catccttctg caatatcaaa aaatatcttt 221820
aagtattcaa gagacgtgaa cattattcct attctctcct gggattcagc catccagcct 221880
tctttacccc agtgggcctc aaagttctct ctctctcttt tttttttttt tttttttttt 221940
gagacagggt ctccatcatc caggctggaa tgcagtggtg caatcactgc aggctcaact 222000
tcccgggctt aggttattct cccacctcag cctcctgagt agctaggacc acaggtatgt 222060
gctgccacac taggcttttt tttttttttt tttttttgc atttttagta gagatggggt 222120
tttgccatgt tgtccaggct ggtctcaaac tcctggactc aagggatcta cctgccttgg 222180
cctcgaaaag tgctgggatt acaggtgtga gccaccacgc tcagccctta aagttctctc 222240
ttaattaatc ctcctaagtt tgctggggca gagggagggt ggggcggata tgggagtact 222300
ttatatgtat aaaattttgc catagggtag gttttaattc tcagttctta tgttttcata 222360
atttcttgga gtaaagaact ccttcaggta ttgttcatga tatatatcta taacctcaac 222420
tgactatctc aattaagatt ttggtacaca atgagtgtag gccacataat cctcatccct 222480
tacggaatgc tgtttagtga gtgttatacc tgtctaggca tgtttcttgt tacacttatg 222540
taagttttaa ctttcttgaa ggctgtctca gaatatattc ctatggctca atgcctttta 222600
tgttcttggc ttcccgtcaa tagaggccat agcaatgtgt gcttgctcac ctcatctgct 222660
gttcaactga gcacacatta cctggcatgg ggaaataact tcaaatttct tcagacaaag 222720
gtccaacagg ccagacaagc tcatggctag ttccttgacc tgaacaatct tgttatttac 222780
agaatctcca acattcaaaa tggaggaact tccagctcat gattaaactc tttagcattc 222840
tttcaacatt ggcaccatta tatatttcga ttaacagcat tttaaaaaga gatagtgtat 222900
tagcttcctg ggctgttgtg acaagggacc acaatctaga tagattaaaa agcagttatt 222960
ctctcacagt tttgaaagtt ctggaagtct gaaatcaaga tattagcaag gccatgctct 223020
ctctgaaggc tctagtgggg gattatttcc tgcttcttag cttctggtgg ttgctggtaa 223080
tctttggtgt tccttggctt gtaaatgtat cctttgaatc tctgcctcca tcacatggca 223140
ctctccttct gtgtggctga atttctctct tattatcctt aaggatacct tcatccattg 223200
tggcctcatg ttgatacgat taaatttgca aagaccctat ttccaagtaa ggccatattc 223260
acaagtttgg atagacatga atttggggca tactattcac ctccgtgcaa gtagtcttga 223320
agatttgctt ctaaatataa taaatccatt taaataaaac taaatgtgat tcaaataaat 223380
acttatacat aaataatcac cactatgtcc caagctccat cagctccatg tttatattta 223440
ttcatttgtt aatttaacaa atacagatta aaagtctatc atgtgttctg agcagtactg 223500
gggccaaaat aatgaaccag agggacaagg tccctgttta cgggatgttt atgttctagc 223560
tgggagagtg ataaacaagt ataatttcat ttgtgctctc aaagcaatat tgagaactga 223620
ccaagtgaca gtcactgaga atgaaaaagt gaaaagagta aagtccatgt cttcatagaa 223680
cttacattct attggtaggg agataatgca taaatgagta gataagtaca caaacaaata 223740
acattagcta gtgataagtg ctatcaggaa ttaagaggca gggcaaatgg ttgcagggtc 223800
agagagcttt gtgtcttttc atctgagccc tgaaggaagc cagggaatga gtcttgtgaa 223860
tgtttgggtt tagtgttctg gtgggaggaa ctgcagatac aaagaccttg aagagagcaa 223920
gttcctggtg tatttgggaa gaacaggagg ccagtgaggc ctcttgatgt gaatcaggac 223980
agagaaaggg attgagtggt agcctggggc tcaaacatcc tggtaaacca tgacaagagc 224040
tgttactcca agtactatgg gaaagcaagc agagggtttt gagcaggaga gcaacatgaa 224100
tgtacttgaa ttttaaaggg agaccctctg gcgacggtgt gagtactgga ctgtagggga 224160
caatgggtgg agaaggggtc acgcttgggt gggattttga ctacagagcc tgtggtattc 224220
agagagtgga aagtgctatg aagtagacat ggcatgatgg agagggggt aggaaggaag 224280
gtcattcatt gggtagctag catgtagaga ggcttcaccg agaagacgat gttttcgctc 224340
atatgtgaat gactagaaat cgccagcctt gtgaagatct tggaagatat tttcaagtag 224400
aagcaaaaat tggaaaaaga aaattggaaa gctctagctg tggtgtgttg gagaaaagaa 224460
aggaggacag ttgaaaccta gtaagccaga agatgccctg taggagacaa aggaaaacag 224520
ggaggcaggg cagtgtcagg aaggcccctg tggtccttcc tggtactgtg aacttcctga 224580
gagtactaga agaaagagtc tctgtccata gcttgctggc gcctgctatt ttgtatggta 224640
taacattacc caatgtgaga ggaggaagtg atgaacgttc taaggtgcat agagttagag 224700
gatgtctctc tacaaatttt acaggtcaca atttaaaaat gtcgatggcc ttacacatag 224760
caaaataatt tctaggaatt tatcctacag aaacaaaatt acagatactt aaatttagag 224820
cataaatatt ttactgtggc cttgactaca atagcaaaag taaccaaaaa taaccagaaa 224880
cacctggaaa cagtccattg ttaagaaaac agatgaataa tttatggtgt atgtataagt 224940
ggacatgtat ttagctatta aaataatgtg tgggagctat atttgttgtt gacttagaaa 225000
aatgtccaca atttatattt caaatggtaa attgacctac ataaataata tgtaaataaa 225060
gtataataca caaaatataa aattattttt aaaaactcac catggtggct gggtgcagtg 225120
gctctcgcct ataatcccag cacattggga ggcaggcaga tcatttgagg tcaggagttc 225180
gagagcagtc tggccaacat ggtgaaaccc tgtctctact aaaaatgcaa aaattatccg 225240
ggcgtggtgg cgcaggcctg tagtcccacc tacttgggaa gctgaggcag gagaatcctt 225300
tgaacccggg agggcggagc ttgcagtaaa ctgagatctt gctactgcac tccagcctgg 225360
gagacagagc gagactccgt ctccaacaaa acaaaacaaa gcaaaacaaa aaaacaacaa 225420
aaacacccac cgtgaggtga tggaagtgtt ttaaatctta tttttgctgg tagtttcaca 225480
ggtgtacaca actgtcaaaa cacgtggaat tatactttaa ggaaaggcag ttccttgaac 225540
atagtttctc aaagttgaac aaatgttctg tatcttaaaa agtgtctgtc ttctatcatt 225600
ttggtgtgta cctacatttg agtaggtttc tatgagcaaa ggaagaaaat ataggaagat 225660
acagtggtta catagagatg ggtttggaga gaatggtacc taattttgta accctagagt 225720
gtccttagcc ccaaattcct gtccaaccaa aatatctcaa tgtgaagata cacctttgtt 225780
gtctactgag cagaggtagc taaacatttg gactggctaa gtaaggaaaa tacttcccat 225840
gtcacttctg aactttttgt acatgtgcga gttggggaga ggtggcaagg acattctcca 225900
gcatggtggt agtcagctaa aattaaactt aagccagtga ttggaggatc aacaaaagga 225960
taattatcgt tttgcagtct atcatggaac atagtggaag aacaagatct ttgaggtcag 226020
aaatacctga attttaactc cagccttgtc ccttcctggt agaacaagtt ttgtgtggct 226080
ttggaaaatt aatctacatg gtctttattt tcctcaaatg caaacaataa ctcccatagt 226140
gttgtagtaa agattaaatc agatgaaacg gtcacagggc cttctatatt gtagaatgtc 226200
agtacttgat atcattatcc actgtggaag aaaagattgt aaatttctta ttctgaggat 226260
tagtgagttt aaagtgctta tttgcatggt tggcctaggt gttgttcttc aaaaaggact 226320
aattctagac tctgctacaa gcccactata caatattgtt gtgatctgat aagcttttaa 226380
aaattgaatc tgtaggccag gtgcagtggc tcacgcttgt aatcccagca ctttgggagg 226440
ccgaggtggg cggatcacga ggtcaggaaa ttgagaccat cctggctaac acggtgaaac 226500
cccatctcta ctaaaaaaga atacaaaaaa tttagctggg catagtggcg ggcgcctgta 226560
atcccagcta cttgggaggc tgaggcagag aattgcttga acccgggagg cggagcttgc 226620
agtgagcgga gatcgcaccg ctgcactcca gcctgggcga cagagagaga ctctggaaaa 226680
aaaaaaaaaa aattgaatct gtaatgactt cagcatgctc tccaatatcc caatggaatc 226740
attatgttta gtcagattgc tcaaaatttt ctgagctctg ttgtgccaag tttaaggcag 226800
ccggaactct cttcccttgc agacagtgaa atttctctgg tgtgaaatga tgctcataga 226860
tgtttatatg atgctcatat tgggaggatg acttgcccca aatggcctgt caccccaaat 226920
ggttggtggt cttgtggtct attatccagg gagacaccat tgctccctgt cacattggtg 226980
acaagcagaa gagattaggt tgtcctttga tttgttgata cacatgccac gctgtcagat 227040
gatatttgag attatgccct gagctcagag atgcatagcg tgaggatgac atgtgacggg 227100
tatctctgtg ccccattact gtggagcagc ctctgctgca agacctgacc tctctggcat 227160
ttacagaaga tcctccttat ccatggtttc gctttccata atttcagtaa tgtgagatca 227220
actggggtct gaaaataggt gagtataata caatgagaga gagagagaga gagagaacat 227280
taacatactt gttactaaag tatattgcta tacattttct attttattat tagtgttgtt 227340
aactcttact gtgcctgact tacaaactaa attttatcat aggtatgtat gtatagaaaa 227400
aacgtatata gggttcagta ctatattcca tttgaggcat ccattggggg tcttggaaca 227460
tatcctccac agctaaacag tgacttctgt accctctgtc agtgcagaat gaggtgcact 227520
gcattagcat cgtaggcctc ggtttctctt tacaacagac ttggtaggta gctttacgtt 227580
aatcactttg ggtccaagct atgcatctgg aaactgggga taagaatact atttccatat 227640
ctgtcaaaag gcagaggagt gaccacatgg tccttccaac tttaagtgtt attacaccca 227700
atttttaatt tttctgcttt tctcttgcca aattctttct ggttgtcctg tcctttatag 227760
ataggacatc atcacctgaa attgagatat ggagaaccaa gctcagaatt ttatgttaga 227820
aactactatc cacgcacttc ctaattttta gagggacaga ataagggtga tttgcatgtt 227880
tgtctttact ctcctgacaa ctgagacagg aaaccaagga taggagctca tgcaggtaaa 227940
gaagaaacag gttcagatgt ggacatgaca actttgaagt cactgtctga catctacttc 228000
acagccaatt agatcaaatt tacaagccac cacacacata tatagtgcta gtaaatatca 228060
gcatataagt ggttaaacca tgggagtgga tgagatccct caggaaaatt gcattgagtt 228120
gaagaggagg tgtcaagcgt aaattgtgct tggatgtttg gggtgaacag aagaagacat 228180
tgcagtgaag aaggctgaga agcaccatca gagcagaaag accaacagca cttggtgtca 228240
tgggggccat ggaaggagaa agcctttatg gggcaggag gagcctgatc agtaatgtcg 228300
aatagaacag acactatata atcgaaggct ttaacaacaa acatgaaaaa aggctcaaca 228360
tcactgatca ttagagaaat gggaatcaaa accacaatga tataccatct catgccagtc 228420
agaatggcga ttattaaaaa gtcaagagac agcagatgct ggtgaggctg tggagaaata 228480
gaaatgcttt tacactgttg gtgggaatgt aaattggttc aaccattgtg gaagacaatg 228540
tgacaatttc tcagagatct agaaccagaa ataccatttg acccagcaat cacattactg 228600
gatgtgtacc caaaggaata gaaatcattc tattatagag atacatgcac gtgtatgttc 228660
attgcagcgc tattcacaat agcaaagaca tagaatcaac ccaaatgccc atcaacgata 228720
gactggataa aatgtggtac acatacacca tggaatacta tgcagccata aaaaggaatg 228780
cgataatgtc ctttgcaggg acatggatgg agctggaagc cattatcctc agcaaactaa 228840
tgcaggaaca gaaaaccaaa cgctgcatgt tctcacttat aagtgggagc tgaacaatgt 228900
gaactcatag actcagagag gggtaaaaca cacactgggg cctgttgtgg ggggtgggga 228960
taaagagagg gagagtatca ggaaaaacag ctaatgtgtg ctgggcttaa tacccaggtg 229020
gtgggttgat aggtgcagca aaccaccatg gcacactttt acctatgtaa caaacctgca 229080
catcctgcac atgtattcca gaaattaaat ttaaaaaaaa attgaaggca ttaaaaatta 229140
ccttttgctt ctgaagacca gacggtcatt ggtgatttta ggaagagcat tttcactaat 229200
agagtgggca tagagcacat tttagttgat taaagaataa aggagaggaa gacaagcctg 229260
gattagacaa tctggaaaga gatgtcagtt gttagaaggt gatccttttt gtctcttcac 229320
tggggctttt tgagtgacat gctggctcaa gggaaagatc cacagcaagg gaagatgaag 229380
gcaaccaagt agatcattga gggagcaaag tcctggagta attgtatagg tgaaagggaa 229440
aagtctcatc ttattatctt ttgtaataag aagtagttta gttcattttc tctaagaaga 229500
agctatgaag atgtgattag atgtgcaaga gattcgttga gataacactt gtaaaggata 229560
aagaagaaag tggggagact cttcagatct caggagaggt ctgacacctg tgaaggagag 229620
gggaagaaaa gaccaggtag gaaatgtgtc tagctgtaag acagttccaa gaaaggccta 229680
tggagtgaaa aaaaccttca tttaaagaag acacatgtcc cacagaaatg ggcgtggaaa 229740
tgtcccctcc attctcagtc aacaattggg agcagcatgc tggaagcctg gtcccaaagc 229800
agatgcagag ggggacccag agtgtagcag ctgaagtcag cagcaattac gcacgctctg 229860
gacatctgag cagtgcgctt tcatggtaaa accctgatat aactggctga tctggatgtg 229920
cagaaatgag aacaggaaga taagtgagtt cccaggtggt ggcctcattt atttttgaag 229980
tatgaagtat taggattatt ctagctagaa tgggaataga gaatggaatt ggagaaactt 230040
gagtgatggt ttagaagagc agaaactgaa agaaggtagg actttgatct gcacaaggtc 230100
tcattgagaa tgggtcctgt aagggactgt gatgtgttgt ggcattaaca tggcatgact 230160
atgattttcc tctagaagga tgtagtaaga atagagaagg tagattttgt gacttatctc 230220
tttactgtta atgctactcc tggttccaag gctgccccag ttttataatt cttaagttat 230280
tagtaacttg tcctttattt gattaaacac acaaaaaaat acattgattg agccttatgt 230340
atgaagcaca ggaggagata taagaatgga tttctgccat ccaggagtgt gtacttaaca 230400
gcaataccta tgatgcaagg cagactacga caggtaatat aagagaggta gaaataaagc 230460
ctatggaact tcagaagagg aatagagtat ctgagtaggt aaaagagagg acagactcaa 230520
agactttatg gaggtggctt ggtttgggat tcataaagtg ggtataattg tgacagattt 230580
gttatctatg tctactattg tatggtagaa acctttcttc tttttaatct gcctttcaag 230640
gccttcatct aggctggatg gtgaccacct catgcccaga ttactaatga attgctcagt 230700
ccctctttaa atctactgtc tcatatattt gattacaaat acaactgggt aaattatgtt 230760
gttcatataa cctagaagtt ttggggccct ctcccctgtt tctcaagcat aactgatgct 230820
acagtacttt gtccttttg cacatttcca tgatgtctta ttgtactaat aagtgctctc 230880
tagactgtga tgaactagtt gagttataac cttgggtagg aaattacata agcttggtac 230940
atggtagtgt tagagcaagg tcttagttat ttgcttagtt ttctcacctg ccagtgagtt 231000
tgtaaatcac agtcaaggtc ttggtttgga gaggaaggga ggtagctctg ctgtattatt 231060
taatctgatt taccagtaaa gaagctaatg ttgaatgttg attcttcact tggataagac 231120
tccagttgtt tataatatgg aattgtaata tggaataata ttttcacacc tcagtaatcc 231180
ataatgagtt cctcttccac ctttccagtt acttgggata aaaactacct gaaattacaa 231240
gatatgcaaa atgttgtata atcagggcct ctatcttaaa aactgattta ctactatttc 231300
tgggaaatgt gcctatttta cactttggac cttattcact gttgttaaat ttttcagata 231360
aagctcaaca cagtccagca actagctatg cttagcctcc ttatcttcat ttttaatgcg 231420
acaccgtgaa ctccagtcaa gaaaacacat ttaagaccct ttacacttga ctgatgcacc 231480
tgaggctttg cagtgttatg cagaggtatc agtaaatatt taatagttgt gaatgaaatt 231540
aaagtcctgg aacccttgtc caactaaata ggcccctcca agagactgct ctgatgtcat 231600
ttactcacat agccagtgct tagatgcttc atgattagta atttttgtat cctttctgga 231660
ggtttttgc tctccatttg gtggtaaact ctggtaatga atttttcact ccaatttttg 231720
cctaggttgc tactattggt ctattagggt gcctttttc agacgaaaag acatcatctt 231780
ttaggaaacc ttgtcaaggt caacaaaaca tgaacttatt ttaataatcc ttttgtatta 231840
acagtattta cttttagaat tatgaagatg tgtttatcct tccaagcagc agtctgggtt 231900
gttgccactt gaaaaaaaaa tacggtctat tggagttgga gaataggcag gaaccttgat 231960
gtcataaagg aaaggaggta aatggacagt accttagtgt ggttaaggaa agggctgagg 232020
gaggtttagt ctctctcaga tgtggtagaa acttccatgt gagaacattt gccacctcag 232080
atgagaacac tttttccatt ctccataagt ctaactctaa gcttttttt tcttttttt 232140
ttttttgtac tttattttat tctttgagag gtggggaggt gagctgccct ttctttgact 232200
taaggttctt actttttgg cttacaattc tcagagactc tggctgtctg catacagagg 232260
ccattcagag ctccatttca acaagcaatt gcatatttga tccaataatc ctccagcacg 232320
aggatttggc aatcctttca aaaacatttt ccaagtagtt cttaaaacca tccctttca 232380
ttaggcaagt gccaggtgaa taaacatggc cctaaacact gtccaccctg ccttggcaag 232440
ggaacatcta aggcttgggt aattgatttc cccgtggttg caagaagttc acataacatt 232500
attcaatcat ctctcaagtt tgcttgtgat tgctaaatca tttgtgacat tggcctgacc 232560

-continued tcttacattt agacttcctt attcttacct ataaaacaag ataaaaggat tacttgattg 232620
atgtctccaa atggccagtc tgtggaccac tgaagcacac tggctgcctc atgtccaagt 232680
tcaactgtga acttcctata acacaagcct taataactcc atcctcttcc tctccaactc 232740
ctctcttaga gacccttgta attaatttag gtaaatggcc agcgctcagg cctaaaatta 232800
ggatctgcca aaggaattta ccatgaagtt acacttgtaa tgaccctccc taaacctcca 232860
aatattctcc tcagaggtcg caagataatg aagtagtcac agccatgtgc tacagtcctg 232920
caccagctag acctgtaccc tcatacttcc actacttgac cctggtagat ctcatccaga 232980
atcaaagtct atcttttgct ccgagtagaa aaatatgaat gagtaagatt gtgctttctg 233040
gtccagatga tcatgactca aactacatgg ccatctggcc cctccatcta cagttagaag 233100
caccaccttg gcaataattg aaatgaactt tcaacaaatc tgctagagtc aagactgaat 233160
tatgcattgt tttataatat cattgccata tgaagaggga aacaattgtg tgtggcctat 233220
gaaaaaggtg ttaccatccc tggattgcaa tttttttgtt agtttttttt gagacagagt 233280
ctcactctgt aaccaggctg gagcgcagtg gcgtgatctc ggttcattgc aacctccgcc 233340
tcccaagatt aagcgattct cctacctcag cctcccaagc agctgggact acaggcgtgc 233400
accatcacac ctagctaatt tttgtatttt cagtagagac gggctttcgc catgttggcc 233460
aggatggttt cgatctcttg acctcgtgat ctgcccacct tggcctccca aagtgctggg 233520
attccaggca taagccactg tgcctggcct gttagggttt tgtttgtttt tttttttgg 233580 catgacaact ttattgagat ataattcaca tacacatagg atatcataca atttgcccat 233640
ttaaagtata cagttcagtg gcttttagta tattcagttg tgcaactatc accactatca 233700
attttagaat cacctcaaga agaaaaccca ttccctttaa ctatcagccc ctgtcctttc 233760
tatctccccc agtcctaagc aacacttaat ctactttcta tctctgtata tttgtaaaat 233820
tttaaaaaag attgttcaat tggaagaatt tttaaaatat atccacaata atatagttta 233880
tatgtgttat atatcatttt cttaacatgt gttctctagc ttggatttct cccttttcta 233940
gatcattgat gtggagaaat agacactggg tcctgttctc tgccctccat ttgatctagt 234000
gcccacaact aaacacaatt ttctacaaaa ataaaggcag gacaaatggg atagcataac 234060
tgacccttct gatatacttt ttttataaaa aaggggaaaa aaattatctt ctcaagttag 234120
gaactacaga attgacctgg aaaaagagtg ggcccaaaag aaagattcct aaagtatctc 234180
attagtgcca tgactagcag gcaacataag cagctcgatt agctcaccat atgattgaca 234240
ggagatggag aagatgttgg gggtggtggt ggtggtggta gaattggggg aagagttatt 234300
tatatttggg tgtggcatat gagtttcctc agagattctt gctttgggta ttaaaagtgt 234360
ttaattttta taaaaatttt caataaaaag gcaaatacct aagtgccctg aagaagtttg 234420
agacttagat accaattcaa aattcaagaa ttatgactgt tctagaagtc ttatgaaact 234480
tgtatacttc atctgtgtga tatttggcaa tgtgcatctt gactttggca tagataagtc 234540
actcacctga ggttttaaag caataacttt ttaatttagg gtagactctt ttttcagctt 234600
gttcatgagt gatagatact ctgggaaggt ggacactttt ctcagtcgaa gggaggtatt 234660
attcatatgg aattctatat aaatgtatat aaatggtgtc ccctaaagca taagtctgtt 234720
gatgagtctt taaagagact ataccggtta gattctacaa tatacaggtt gacaatatcc 234780
gatgggaaat gtggcttgat ttgaaattag aaggcagaca ttcaaatgac taatctcaag 234840
tctgccccca aggtactgta taattctatg attctgggct tcatttttga aaagtctaaa 234900

-continued

```
gagatgatga agtacatctg tcaagaaagg catgagaaga aacaaaatga tccatcttgg 234960
ctgtgcaaat gctgtaatga atggggaagt tggtagatgt ggtcttaaca gggtgtaggc 235020
ttgtgctgaa ataaataaat aaataaataa atacaaacca caagactgac gtgactgccc 235080
agttgtgaac attgtatgaa ggtttagttg gcagagtaat gcttttcaag tatgttggat 235140
aaatattagg tttaaaggcc aagatactta taagtattta caggattaag tgaggtataa 235200
aataatattt agtgtctcaa aggatgggaa ggaagatagt gttgtggtca ttccacagag 235260
gaagttagaa ctgcacatcc aaaatttggt tcagatatca atgctaatga tgacacaaat 235320
acacacatac atatacacat acacctcaag atggtattaa caattttatt attcatataa 235380
tgaggtcttc tgagaaaaac aggccaggct cccaagcaag tctaaaaatg gattgagaga 235440
acagggaggg agaattgact tggggtttta tgtggtggag tagtgtggct ggagagagag 235500
ttgtcttgtg taagctgggg cttatttggt ttgaatttct caataatgca aaagttgagg 235560
catccaagca tctcatcagc ttctctagat gtggcttgag ttgccaggag gcaaattcaa 235620
ctgttagtgt tttgtgtcct aagacatctt gtctaatctg aggtaaaagc tttttcctat 235680
tttttagaag gtgtataatt ttggctcttc tgcttagctc taccatccat tttgagttga 235740
tttttatata tgttataaat taaggattgg agttttcttt tattggtatt tattgataat 235800
acaactgttt cagcatcatt tgttgtaaag attgtttttc tccatggaac aactttggca 235860
ctttataaaa aaaaataagc atgtgtgagt gggtctattt ttgaactcta ttctgttcca 235920
ggatctgtac atttgtcctt atgccagtac caccttatct taattaccgt agttttatag 235980
taagtatttt ctgttaatgc caattctaca actttatttt tttcaaaatt gttttggcta 236040
ttttatatcc ttcatatttc catataaatt ttaggttcag cttattattt tttataaaaa 236100
atcggaagtt tttttgcaac ttctgcaaag gttatcaaaa accatcaaag gagattgctt 236160
tgaatctatg aattatttgg gggagaattg acatcttaaa aatattgatc cttctcatcc 236220
attgacatgg tacatctcca tgttttttag gttacagtgt acacatctta tatattttat 236280
taaagtaccc atagatattt cttaattttg atgctattat aaatatctta aattacagtt 236340
tgctagtatg tggaattaca atttattttt atatattgat cttgtatctt aggaccttac 236400
taacttattt attagtttta gttgcttact tttaggttcc ttaattttta taacatcaat 236460
cacatctgca aaaaaagttt tactactttt tcaccatgca aactttaatt ttctttatct 236520
tgtctattta tactagctag aatctcacgt acaatgatga ctagaggagg caaaagtggt 236580
catctttgtc atatttctga tctcaggggc aaacataatg ttagctgtgt tcattttgtt 236640
tgttttttac agatgtactt ttcaagttaa gtgccttctc ttcctggtca gctgagagtt 236700
atttttaat cacaaatgaa tgttaaattt tgtcttatgt ttttctgcct gtattgaaat 236760
gatcatgtgt tttcctctcc tgtgtttcac ctttgtttta gaaagatatt ttcactagat 236820
aaagttttta ggttgacagt gtttttcttc cagcacttaa gaaatacttg attttcttcc 236880
agcacttcag aaatatttga ttttcttctg cagaatacag tttatgataa atcagaagtc 236940
attctttcct gtaacatgcc tttttctctg gctacgttta agattttctc tttatcactt 237000
agtacttcct aattaaaaat ccatgcccca gcagtggtca gctagcattc taaagaggaa 237060
tgctgaggca gctaccacaa acacttctct aactttatta ttgattgaca ttacagcctt 237120
tgctaattag tgtaataaat gtcagaaatt agtaacttga cagtcagctt actggaagtt 237180
agaattacga tcttgttggt taaataagta ttcaaattct gtagcctggc taaagtattt 237240
tgaagacact cttgagagag actagaacat aagcatcaaa ggaacccaag caccttctgc 237300
```

aaggcagaag gggttcggtg ggtatgaaat gatggaggtg ggaaaggaag atcaaaaaag 237360
gggttgggta atgccaaaac ccaaatactg gggattatta gaagacatgg ttcaagagag 237420
aagctaatcc atgggtgcag gccagtgtcc agagagagag accactgcaa gaggccctgt 237480
ctggatgttc aggacctctg agaatatatt gtttgctggc tgattgccca ctttccacag 237540
ggccagttct atttctttgt tttttgccct cctattatcc acttactcca tgcaatgtga 237600
ccgcaagagt tctaaaagcc tacataatag acatgtaaat accggtggtg gtgacagagg 237660
tggtgagagt gagaaactca caaatttaat tgagaggaac ttgaactgaa atgggttctt 237720
ggttaggcta ggacaccacc attatatcat gatgatcata tttttatagt tcttgtcaaa 237780
catatatctc ctatagtact tgtatatgat agtactaggt attggaagcc aaaataaatg 237840
agtaaagtat gaatagactt cgccttcaag cagctgacag ggtttggttg gtagtaaata 237900
tttggaacat tttttttccc cttaaagttc ctggactcag ctaggactag ccaaatgaaa 237960
tgtctcttta ccaaaatgct catcttcagc ctgtgttgct tttttgcact cgtgtccact 238020
tttccggctt ttggcccatt tccttggctt tgttgctccc cacttcggtt ccagcaggtc 238080
cttggtcact accccccaca taacaacatg cacctggggg catcgcctga gcttaaaggc 238140
ccccattcct caattgtatc tgatcccttc cctctaacta aatgcaggat tctgattcca 238200
ttccctcagc atttgggcag gaaaagaaat ctcaactatt tgagatgtgc ctgatgaatt 238260
acagaagcaa agaattctgg agttagaagt tatcttagtt ccaagttaaa aatccaggcc 238320
caggaaagtg tcacatggtc aatgacacaa atcactcacc ggcagaacag ggaggagttt 238380
cactacttca attctctatt taccatatca caaaatatgt aagatatcac attctaataa 238440
tgtaattcag aaataagaga aggatagcgt agcaggaaca ccacaccttg cctctcaaat 238500
tacaccacac agaggctgca tattacacta gttccaattt cattactcac aaagccaatc 238560
ttgaaaatgc ccaggtaaag taaattgtca ggaagttctg aataataaac tcgtttgata 238620
aaaccaactc acaatgcttc ttccttaaaa atattttggt ggaaatatta ttatatttgg 238680
acataaatac cccctgaagg acttgttagg aagaaaatag atcattgttt aggtccctta 238740
gcacagaggt ctgaaagtca aataaacttg gtcaggctgt tttctcttcc taaagagaat 238800
aaaaggcccc caatcaatgg gtggtcacca tagaaaaaat tcggctctaa gtcagagtga 238860
cttgaatatc tgtgtgctat ttttatttca gaaaaccaag aagacacacc aaaaaatccc 238920
gattaaaagg gaagaaatgt gtttaaagag cttgttgact tcttaaaaac aaaaattcct 238980
gcatagattt tggttaggat tgctttaaat ctgtagattt ggagattttc aaaaatatag 239040
tacattatta ttattattgt ttgagacaga gtctcgctct gttgcccagg ctggagtgca 239100
gtagcacgat ctcagttcac tgcagtctct gccttctggg ttcaagcaat tctcctgcct 239160
cagcctccca agtagctggg attacaggtg cccgccacca cacccagcta atttttgtat 239220
ttttcgtaaa gacagggttt caccatatca accaggctgg tctagaactc ctgacctcag 239280
ataatccacc cccctcagcc ttccaaagtg ctgggattac aggcatgagc cactgtgcat 239340
ggccaatata ttattattaa ccatagtcat catgatgtgc aatagatctc ttgaacttat 239400
ttctcccttc tgattttttt tttttttttg agacagggtc tggctttgtt gcctaggcta 239460
gagtgcagtg gcatgatctt ggctcacagc aacctccacc tcctgggctc aagccatcct 239520
cccaactcag cctcccaagt aactagtact acaggtgtac accaccacac ctggctactt 239580
ttttttgtat tttttgtaga gatggggttt tgccatgttg cccaggctgg cctcaaactc 239640
ctgagctcag gagattcacc tgcctcagcc tcccaaagtg ctaagattac aggtgtgagc 239700
caccatgcct agcctttaac tgaaattgtg taccctttga gcaatacctt cccaatctcc 239760
tctccattct actctctact tctatgagtt catatttttt aaagattcta ccacgtaagt 239820
gagattatgt ggtatttgtc tttctgtgcc tgacttattt tgcttatcat aatgtcctcc 239880
aggttcatcc acgttgtcac aaatgacagg atttccttaa gactgaatag cattccattt 239940
tgtatgtatg ccatattttc tttatccact catctgttga tggacactga ggatgattcc 240000
atatcttgga agttgtaaat agtgctacag taaacatggg agtacagata atctctttga 240060
cacgctgacg tcatttcctt tggaaatagc cctaccagta gtatgattgc tggatcctat 240120
gttctatttt tctttttctt tttccttttt tttttaattt ttattttttg agacagagtc 240180
tcgctctgtt gccaggctgg agtgcagtga tgcaatcttg gctcactgca acctctgcct 240240
cccaggttca aacaattttc ctgcctcagc ctcctgagta gctgggatta caggtgcatg 240300
ccatcacacc cagctaatta ttgtattttt agtagatatg ggatttcacc atgttggcca 240360
ggatggtctt gatctcttga ccttgtggtc tgcctgcctc agcctcccaa agtgctgaga 240420
ttacaggcat gagccaccat gcccaaccta tttttaattt ttaaaggaac ctctatactg 240480
ttttttataa tggctgtact aatttacata cctaccaacg gtgtacaagg ggccactcta 240540
catcctctcc aacacttgtt acctttcatc tttttcgata atgattattc taacaggtgt 240600
gaggtgacat atccttgtgg ttttaatttg cattgccctg atgattcata tgttgagcat 240660
tttttcatat ccctgttgcc ttctcttgag aaatatctat tcaggtcttt tgcccactta 240720
attgggttgt tttcttgcca ttgagttgac tttttatata ttttggatat taatccttat 240780
cagctatgtg gtttgcaaaa atgttcttcc attctgtagg ttccttcttc actctgttga 240840
ttgtttcctt tgctgtgtga tgctttttaa tttaatgtaa tttaatctca cttgtctatt 240900
tttccataag aagagttgcc agtgctgttt accctggctg ctacataccc tgatccctga 240960
agaccgtttc ttgaaccatt ctgctctaaa gtaatcctcc ttccatgatc tttaccaagt 241020
gctttgtatt attaatacat cactatactg atttccttta tagaacatac acaatgaaaa 241080
attatcttgc tttgtttatt tactcactgt ctcagcccta ttaagatgga aaatgcctgg 241140
catgtcttaa tgctttattc ctagtcccta gcacgatatt actttaatga ataagtaagg 241200
tttgaagcca ctctgagtag atgtgaatat ttgaattagc ttaggagaaa tatattctcg 241260
atttccttaa attacaactg aaatgacttt tgtgatatgt atagctgatg cccttactat 241320
aaggtatcag gatatactgg aaaaacttgc aggatttttt atttttccat tgtgtttttc 241380
tttctaggag gcagaaaaac cttctgaatt tttaccatga tgacattaaa gccagagatg 241440
ttaagtgtca ttgtagttag ctctgtggcc agaacctgag ctggcaactc ctgatatgag 241500
tgcttcacta tgaaagacag actagatatg gcaagtaact gcacattcct tctcagtgtg 241560
tttcccagtc ttctctttca aattaacact caatgggcat cctgatacac aactaaacat 241620
acatattcat ggtcaaatcc aggctaatag aggatatcta ttcactcatt tcctcctttg 241680
acacctgtag aatgttatct gaataaaatg attttgcaaa gggatgggat agaatttaga 241740
aagcatcgca ttacttcaga gagtgacttt tctttaatgg gtcttagttg ttaagaacag 241800
atgcctaaat aaggtgatgc ctaaagtgat gcctggggct agtcaactga atttaatgtt 241860
cactaaggat taactgctca caaaaactgt atttgtgaaa aattgacctt gtctatccaa 241920
attggctact tctaataact agcttttata gtctacttgt tttctttttt acataaacaa 241980
ctacaaaatg tattagtcta ttttggagaa actcttaaaa tagaatgaaa ttgaaaattg 242040
ctaaagtgtt atagttattt tcagttagat atttctatga attattttat acactcatgg 242100
tttaaaatcc aattttcata atatagttgc cagcatctgt gaattattac aatttgaaaa 242160
gatttggaat gccataactt tttaaaaatg ttctgctctg atctttattt cctttcttct 242220
aactctgggc ttagtttgtc cttgttttct tttttttat tattattata ctttaagttc 242280
tgagatacat gtgcagaatg tgcaggtttg ttacatagtt atacacgtga catggtggtt 242340
tgctgcaccc atcaacccgt catctacatt aggtatttct cctaatgctc tctctaccct 242400
agccccccac ccaccgacag accctggtgt gtgatgttcc cttccctgtg tccatgtgtt 242460
ctcgtggttc aactcccact tatgagaaca tgcggtgttt ggttcctgtg ttagtttgct 242520
gagaatgatg gtttccaact ttatccatgt ccctgcaaag gacatgaact catccttttt 242580
tatggctgca tagtattcca cagtgtatat gtgccacatt tctttatcca gtttgtcact 242640
ggtgggcatt tggggtggtt ccaagccttt gctattgtga acagtactgc aataaacata 242700
cttgtgcatg cgtctttata gtagaatgat ttataatcct gtgggtatat acccagtaat 242760
gggattgctt ttctaatgtc ttgaggtatg acatttaggt tattttggat ctttgtcctt 242820
ttttaatgta tattactata aacttccctc ataaaactgg tttgccgcac cccgtaaggt 242880
ttggtatggt gtttccattt ttgtctcaag acattttaaa tttgcctttt aatttattca 242940
ttgatccatt ggtagttaag catgttaatt ttcatatatt attgaatttt ctgaaatttc 243000
ttattgattt ctaatttcat accataggtc agaaaagata tttgatatga tttcaatctt 243060
cttaaagcta agtcttgttt tgtggcttaa taatgaccta tcctggagaa tgttctgtgt 243120
gtgcttgaga agaatatatt ctgctgttgg aagaaatgtt ctgtatatac ctatgtccat 243180
ttggtctaaa gtgtagttta agttcaatat ttccatatcg attggatgat ctgtccattg 243240
ttgaaagcgg gatattgaag tctcctactg ttattgtatt gctccaactt ctgatcctta 243300
aaatttgctt catatagaat accataaaaa gttctgagat attgattact tattttatga 243360
atgtgtgagg caactaggaa ggctttactg cgttatctaa cactcatgga caacctgtag 243420
gtttttttaa ctacagagaa aacgtaatag aaaagatgtg ccaggcacag tggctcatgc 243480
ttgtaattaa tcccagcact ttgggaggcc gaagcaggtg gatcacttga ggtcaggagt 243540
ccaagaccag cctggccaac atggtgaaac cccgtctcta ctaaaaataa aaaattagct 243600
gagcgtggtg gtgcatgcct gcaatctcag ctacttggag gttgaggctg gagaatcgct 243660
tgaatctggg aggtggaggt tgcagtgagc tgatattgca ccactgcact ccagctgggt 243720
gacagagact ccatcttaaa aaaaaaaaaa aaaaaaaaaa aaagattaac ttgtctcatg 243780
ccacacagct aataaatggc agtgcttaat tcatccccaa ggctgtttac caccaaagac 243840
tatatgaccc ctcaatgcag cctccactta agtaatgcag ttaagaactg ccaacactag 243900
gtgccatgat agggtattga ctctcaaaga tatttgacca tgacccagtt atattttgtg 243960
tcacatatac atacattcct acatccacga tagaaacaaa agtctcacca acagttcttg 244020
tattgactgt gagacaataa aagatgactc tgacattttc taatttttaa tgctagttgt 244080
aactcactaa attgctataa tgacccactg gtattatacc tgtatttgaa agccgtgttc 244140
taaatgtcct ttttagacat cttgcagtct gccctcaatt acaaaaagtg catttgttga 244200
atgttactga cagtcacatg gatcaattac tacaagtcat cttaataatg tattccaaaa 244260
atggttttgt tttctcacct ctagtccttg agtacactaa tgggatcttt atcttcagaa 244320
aagctgctaa tataaaacac aatgccttat cactaacaaa tcaaattaga tataatctaa 244380
gcaggtgtat gtgagcagga aaaaaaccac attagagcca cctgaatcta gatatgatct 244440
atgattttga cagcattcag ttttgttctc aagatcagtg acataatctt tactacatat 244500
tgttattttt aaggtatgtg cagttttgta acagcaatac aatgcaggta tgtacacttc 244560
attgtaaata accattctgg cgaaaaaaag gctttcaatg actttggaca agtaaatgat 244620
tcttggtaca aaatcatact tctttggtat ttatgaaaaa aaaggaaggt gttttaactc 244680
tgagcaccca attcctggtg ctccatttaa gtatttaaga tgtttctaat tagggttgag 244740
tcttgttgtg aacagctagt gaaatactaa catgggaggg caagttttat gagcattgat 244800
aaattgaaca caaattatct gttacagaga ctacaaagag ctatagataa aaagtacagc 244860
aaaatgattt catgaaatca atattttatt cagtgtcaaa gcatcttaac tgaattgtgt 244920
aagtaatttt gtctgtaatt ttagaagtaa catttgtaga aaatatcaat attatcagtt 244980
gtgctactag aaatattgaa ggagttaatt ctgaatttat tcatttatgc agttatctat 245040
atccacttag gtacaaaact tttgtaagaa agataacact tttattgcat tataatttca 245100
tattttacag gagtcataat gcaaacttat aagcataaat atatacatga tgctaccaaa 245160
tggcaatgta accactaaga gatttaaaac ataaaactag aatttaacaa gcaaaatact 245220
taatatggct tttaatggaa aataactgtt tagaaatgat ttgttattgc cccattctag 245280
tcattcccca tcaagtgaac ataaaattat gatctccatt taaaacggta caagttatct 245340
aagccaactt tgtacttttt tgctactttt ttgtagcatg tatgcagtat gatttctgga 245400
cttccttaaa tatacataca tatatacata tatacagata tacagtacac agttctgttt 245460
taatacccct gaacatcttg attaaaacta ttacaatttt tctattataa aactacttga 245520
aaagttggca taacttcctg gtattgaagt tcaatcctac agaattaaaa aaaaaagcaa 245580
caaaatgttg gttataaata cattctttac aaaaaaaaat tgaatagtgg tcccgcactc 245640
ataatttata ttacagtgaa aacattttat caatttaaag gtatttgtat cttgttgtcc 245700
ttggtttctg tgtgaaatag aggaagttaa taatgagaat attgtaggca ggcctatttg 245760
ttaggttttt ctaggtgttc atttttgtgt aagttccaat tcacttcttt tgagttgttg 245820
ttgatttcta tttgccttgt attactgctg ctgctgcttc ttttggtgtt ctgggaacac 245880
tgggtgactt tacttctagg aacaggaaga aaagatttaa ctcttgaaac acccaactca 245940
gtctttgatt tactgttgct gcattcagta gtttgatggc tgctgagagg actgacctcc 246000
tgtaagagac aagaaaccac acaagtttat cacaaacttc tcctgttatg agccctaccc 246060
ctgcctcctc tttgagcaaa tgtacaggag tttctctcta aaactatagg ttctcgtgaa 246120
aaatcaaaag aaaatggaga ggagaagctg agtaattaat ttcctataga cttactgcat 246180
gattttcatt aatccatctg ctgttacaaa attcctaaat acaggagtca gtgaatcaag 246240
tgctaaggcg tcgatctcct taccaacaga aacttcacaa aattacaggc atgaggaaat 246300
caccaaattg gagtagtccc atttgtaggt agctctacaa actatgtcac cttgggtaaa 246360
tcacctaact tttctgcttt ctactttcaa gtcttaaaag tgaactatta ctcaataatc 246420
aaataatctg ggggcatata ggagaaaaca taagagaaac attccttccc tagcagaacc 246480
tacattcatc tatggttagg ccactcaaga tcttccatac ttggaagctg catgttctca 246540
tttctctaat gtttcagaaa tcctgtgatt acctggtcaa tgtctctcat tttgcccatg 246600
aagaatctga gagctggata ggtaagatga tttgcccaca gtgaacggag tggtgaagct 246660
gggacaagac ctcaggtctc ccaactttca ctcaaggtat tttccctata ttgcattaaa 246720
ttctgcaaac taacaaacat gacatgactc ctactaagtg acctactctg aatgcctctg 246780
aaggagttga ccttgataac ttctcctctt caaaagtaat aatgcaccca acagcaatat 246840
aaccattaca agaatttaaa acaaaactaa aatttaacag gaaaaatctg gcttcatctg 246900
gcagttgcgg cagttgcatt ctcctgggta tcgtcttata tgacattgga atcacctggg 246960
ggagctttaa tagtcattgg ctgggcccta ttaccagaga ttcatattta atagttctgg 247020
ggtgtggcat ggacatacga ttttaaaaaa tcttgcggcc aaagaacgcc tagcttaact 247080
cctcactatc ctttttctcc attgagcaat taaatcaagg gtccccaagc cacaggctgt 247140
ggaccagtcc atggcctatt aataactggg cagcacagca ggacgtgagc gggggcgagc 247200
cagtattacc acctgagctc cgcctcctgt cagatcagca gcattagatt ctcatagtag 247260
tacaaaccct cttgtgaatt gtgcaagtga ggggtctagg ttgcccagtc cttgcgagaa 247320
tctaatgcct aaagatctga gatggaacag tttcatccgg aaactaccca ggtccgtgga 247380
aaaattgtct tccacgaaac cagtctccag tgccaaaatg gctggggact gctgtcctaa 247440
atggtagcat ttttcttagc cctctataag tcacacattg ataatctttc ccttcagagt 247500
atttcaagct ctaagtattt cccaaagttc tttctttagc cctcatttat ctcctgcatt 247560
tccaccccac taattcacct atatgtctag ccacacttca aattctttct aaaactgtat 247620
ttattgcatt tcttcaatac taatttctaa agcctttccg cttggctcat tactggctaa 247680
tgctgctctc ccagtgaatt tagcaggaaa tcctcagtta tctttagcag ctgcctttct 247740
ctctctcctc accaacctaa tccaatgtta cccacaaaat gggcagagaa ttatggctgt 247800
gtttgtgtga ataggaaggt aaaggataag tcctcactaa ctggcatgtc actaaagttc 247860
ttttaaagtt tggctccaat cccctttaaa tcctattttt cctttacttc cctgttaaag 247920
tcctaattct ttaaagccca acacaacatg ttcattaaac taccccctaaa tcaccaaagt 247980
gaaatctctt ggggtcagat tttcagactc agctaatctt aagtggaaca gcaatgtaac 248040
tctaatatat acttggctag tggtttggga aaatataaaa acactgaaac aacaaatatg 248100
taatggagaa taaagagggg acaaatctgg ggtccaggcc acctgcattt acagggaaag 248160
gaaagagaag tctagactgc aagaagctag cttagaaagg caagagcttc ctgataaaac 248220
aaaaaacaga tgggctcggt tttaactacg tccgaggaag cctggaaaaa ggctgagcta 248280
catctggtga gggaacacat cctagtccat cctcgtcacc tccatgtgta cttgatggta 248340
tgttaagggc gaatctgctt agtatgttct gcttttgttt tgtaaagatg cttatgctgt 248400
caagttacca gaaagaaaat gagaagttac attgcttgtc atgagttgga tggtgatagt 248460
cacaactgta aaaacagtgc aggtaccagg atccaatctc atttttccta acaagaaatt 248520
actgttaagt ccgcaaaatg ggacttggtc atgggcctac taaggccaat tagaacttgt 248580
aatttggttt aaaacaccag caaatgcaac acatacgtag tattcagaaa acatgaaata 248640
tggcattata ataaggataa cagttagttg ctatacagaa tctggtggtg aggggagttg 248700
tttaattttg ccattattgt caaatctaca gagttaatta atgccatggc ccagaggaag 248760
gaaaggagac atacactgtt ctagtctgtt tctgtacctg caacatgatg gtgaggggag 248820
tgtaccttca tggtctgagg caggaaatat ccacatgaaa taaagtactg agaagtaccc 248880
agaacaacta aaaacatgta gtttggtcag tccctggaag tgtgaggcta gaatggaagg 248940
agttaggatg agaacatgga gaatcacttg ggcttagcgt gagccacagc aattcaaggc 249000
caggagtgca agaatagagc aggtgaccaa tgcacagcat cctgcctgaa aagtgctcct 249060
gacaccctgg aagtcaagcc tagggggcag cggagtttag gagcaggaga gttacaggtg 249120

```
tttaatgctt cctgggctaa aacccccgaa ttatctgtat taaatgtata acgtttacta 249180

tccatattgc tgtgcatgtt aaactcaaaa actaatttgt gtagaaaggc actgacctaa 249240

agtaagtttt atttagcctt aaagaattgg taaatcagag caattcattc aatacacagc 249300

atctactaga agctaagaag atattgtaat tcctctagat gggaaagtta ggggcaggag 249360

gaaaagaaca acatgtaggg aaggtggcat tgggggtgag tctttaaaga ggcacaggac 249420

tgtgacgaga gaaggttcta tggggaggag tacagaggga agtagtaaat tacatgtaaa 249480

aaaggaacat gtgaaaagct acatgaaggc atctcaatcc ctctaaagat atatttggaa 249540

agaaagaaat gggtggaaaa tgaagatgac agatcagggc tatgttttag aacagtgggt 249600

ctcaaccctg gatgcatgta agaatcacca gggaccttta aaaaacccat tgtccaggct 249660

tcccctcaga ctagagtcca ggccctgaag ttaaaaaaaa aaaaaaaaaa gaagcctcaa 249720

gtggatttca tcatgcaacc aaagatgtga acttgtcctt tcagaggatt agtttggatt 249780

tacataaaag gaaaacattt attaacattt gttcttcctg ttgatttaaa tatgtatatt 249840

tgtttttaat tcagaaggcc tgctaaatgc cacttgatta gtaaacccaa ttactctccc 249900

ttactgttag agcagtgagg agttatattg ttgcaaataa taaagataac ttactcattt 249960

ttgttttcca acagataatg atggttgcag ggcccctctt caatggaggc attgccagcc 250020

ttctggccat gaaggagaaa gtgatttcaa ctaacccagg aaactcttac ctctaaatgg 250080

agatacttcc tgataacaga agaaactggg catctaaccc agaaatacca gctgagtagg 250140

agaagagaaa aggcatcagc cagtcaaggt ttcagaaggc tgccaaca             250188


<210> SEQ ID NO 131
<211> LENGTH: 300
<212> TYPE: DNA
<213> ORGANISM: Homo sapiens

<400> SEQUENCE: 131

atatgccaga aaagttgaat agtatcagat tccaaatctg tatggagacc aaatcaagtg     60

aatatctgtt cctcctctct ttattttagc tggaccagac caattttgag gaaaggatac    120

agacagcgcc tggaattgtc agacatatac caaatccctt ctgttgattc tgctgacaat    180

ctatctgaaa aattggaaag gtatgttcat gtacattgtt tagttgaaga gagaaattca    240

tattattaat tatttagaga agagaaagca aacatattat aagtttaatt cttatattta    300


<210> SEQ ID NO 132
<211> LENGTH: 420
<212> TYPE: DNA
<213> ORGANISM: Homo sapiens

<400> SEQUENCE: 132

tctcctctaa agatgaaaag tcttgtgttg aaattctcag ggtattttat gagaaataaa     60

tgaaatttaa tttctctgtt tttccccttt tgtaggaagt caccaaagca gtacagcctc    120

tcttactggg aagaatcata gcttcctatg acccggataa caaggaggaa cgctctatcg    180

cgatttatct aggcataggc ttatgccttc tctttattgt gaggacactg ctcctacacc    240

cagccatttt tggccttcat cacattggaa tgcagatgag aatagctatg tttagtttga    300

tttataagaa ggtaatactt ccttgcacag gccccatggc acatatattc tgtatcgtac    360

atgttttaat gtcataaatt aggtagtgag ctggtacaag taagggataa atgctgaaat    420


<210> SEQ ID NO 133
<211> LENGTH: 300
```

<212> TYPE: DNA
<213> ORGANISM: Homo sapiens

<400> SEQUENCE: 133
cctttactta ataatgaatg cataataact gaattagtca tattataatt ttacttataa 60
tatatttgta ttttgtttgt tgaaattatc taactttcca tttttctttt agactttaaa 120
gctgtcaagc cgtgttctag ataaaataag tattggacaa cttgttagtc tcctttccaa 180
caacctgaac aaatttgatg aagtatgtac ctattgattt aatcttttag gcactattgt 240
tataaattat acaactggaa aggcggagtt ttcctgggtc agataatagt aattagtggt 300

<210> SEQ ID NO 134
<211> LENGTH: 300
<212> TYPE: DNA
<213> ORGANISM: Homo sapiens

<400> SEQUENCE: 134
ttgaataaaa gaaatatgac ttaaaacctt gagcagttct taatagataa tttgacttgt 60
ttttactatt agattgattg attgattgat tgattgattt acagagatca gagagctggg 120
aagatcagtg aaagacttgt gattacctca gaaatgattg aaaatatcca atctgttaag 180
gcatactgct gggaagaagc aatggaaaaa atgattgaaa acttaagaca gtaagttgtt 240
ccaataattt caatattgtt agtaattctg tccttaattt tttaaaaata tgtttatcat 300

<210> SEQ ID NO 135
<211> LENGTH: 300
<212> TYPE: DNA
<213> ORGANISM: Homo sapiens

<400> SEQUENCE: 135
attattaaaa ttcatatata agatgtagca caatgagagt ataaagtaga tgtaataatg 60
cattaatgct attctgattc tataatatgt ttttgctctc ttttataaat aggatttctt 120
acaaaagcaa gaatataaga cattggaata taacttaacg actacagaag tagtgatgga 180
gaatgtaaca gccttctggg aggaggtcag aatttttaaa aaattgtttg ctctaaacac 240
ctaactgttt tcttctttgt gaatatggat ttcatcctaa tggcgaataa aattagaatg 300

<210> SEQ ID NO 136
<211> LENGTH: 360
<212> TYPE: DNA
<213> ORGANISM: Homo sapiens

<400> SEQUENCE: 136
gcatctattg aaaatatctg acaaactcat cttttatttt tgatgtgtgt gtgtgtgtgt 60
gtgtgttttt ttaacaggga tttggggaat tatttgagaa agcaaaacaa aacaataaca 120
atagaaaaac ttctaatggt gatgacagcc tcttcttcag taatttctca cttcttggta 180
ctcctgtcct gaaagatatt aatttcaaga tagaaagagg acagttgttg gcggttgctg 240
gatccactgg agcaggcaag gtagttcttt tgttcttcac tattaagaac ttaatttggt 300
gtccatgtct cttttttttt ctagtttgta gtgctggaag gtatttttgg agaaattctt 360

<210> SEQ ID NO 137
<211> LENGTH: 420
<212> TYPE: DNA
<213> ORGANISM: Homo sapiens

<400> SEQUENCE: 137

-continued

```
caaataagaa tatacacttc tgcttaggat gataattgga ggcaagtgaa tcctgagcgt      60

gatttgataa tgacctaata atgatgggtt ttatttccag acttcacttc taatggtgat     120

tatgggagaa ctggagcctt cagagggtaa aattaagcac agtggaagaa tttcattctg     180

ttctcagttt tcctggatta tgcctggcac cattaaagaa aatatcatct ttggtgtttc     240

ctatgatgaa tatagataca gaagcgtcat caaagcatgc caactagaag aggtaagaaa     300

ctatgtgaaa actttttgat tatgcatatg aacccttcac actacccaaa ttatatattt     360

ggctccatat tcaatcggtt agtctacata tatttatgtt tcctctatgg gtaagctact     420
```

<210> SEQ ID NO 138
<211> LENGTH: 240
<212> TYPE: DNA
<213> ORGANISM: Homo sapiens

<400> SEQUENCE: 138

```
catgtagtga actgtttaag gcaaatcatc tacactagat gaccaggaaa tagagaggaa      60

atgtaattta atttccattt tctttttaga gcagtataca aagatgctga tttgtattta     120

ttagactctc cttttggata cctagatgtt ttaacagaaa aagaaatatt tgaaaggtat     180

gttctttgaa taccttactt ataatgctca tgctaaaata aaagaaagac agactgtccc     240
```

<210> SEQ ID NO 139
<211> LENGTH: 300
<212> TYPE: DNA
<213> ORGANISM: Homo sapiens

<400> SEQUENCE: 139

```
gattcaagta atactattct tttattttca tatattaaaa ataaaaccac aatggtggca      60

tgaaactgta ctgtcttatt gtaatagcca taattctttt attcaggagt gctttttga     120

tgatatggag agcataccag cagtgactac atggaacaca taccttcgat atattactgt     180

ccacaagagc ttaatttttg tgctaatttg gtgcttagta atttttctgg cagaggtaag     240

aatgttctat tgtaaagtat tactggattt aaagttaaat taagatagtt tggggatgta     300
```

<210> SEQ ID NO 140
<211> LENGTH: 180
<212> TYPE: DNA
<213> ORGANISM: Homo sapiens

<400> SEQUENCE: 140

```
gtgatgtgaa tttagatgtg ggcatgggag gaataggtga agatgttaga aaaaaaatca      60

actgtgtctt gttccattcc aggtggctgc ttctttggtt gtgctgtggc tccttggaaa     120

gtgagtattc catgtcctat tgtgtagatt gtgttttatt tctgttgatt aaatattgta     180
```

<210> SEQ ID NO 141
<211> LENGTH: 420
<212> TYPE: DNA
<213> ORGANISM: Homo sapiens

<400> SEQUENCE: 141

```
tttcaggtac aagatattat gaaattacat tttgtgttta tgttatttgc aatgttttct      60

atggaaatat ttcacaggca ggagtccaat tttcactcat cttgttacaa gcttaaaagg     120

actatggaca cttcgtgcct tcggacggca gccttacttt gaaactctgt tccacaaagc     180

tctgaattta catactgcca actggttctt gtacctgtca acactgcgct ggttccaaat     240

gagaatagaa atgatttttg tcatcttctt cattgctgtt accttcattt ccattttaac     300
```

```
aacaggtact atgaactcat taactttagc taagcattta agtaaaaaat tttcaatgaa    360

taaaatgctg cattctatag gttatcaatt tttgatatct ttagagttta gtaattaaca    420
```

<210> SEQ ID NO 142
<211> LENGTH: 600
<212> TYPE: DNA
<213> ORGANISM: Homo sapiens

<400> SEQUENCE: 142

```
taaccaagtg acaaatagca agtgttgcat tttacaagtt attttttagg aagcatcaaa     60

ctaattgtga aattgtctgc cattcttaaa aacaaaaatg ttgttatttt tatttcagat    120

gcgatctgtg agccgagtct ttaagttcat tgacatgcca acagaaggta aacctaccaa    180

gtcaaccaaa ccatacaaga atggccaact ctcgaaagtt atgattattg agaattcaca    240

cgtgaagaaa gatgacatct ggccctcagg gggccaaatg actgtcaaag atctcacagc    300

aaaatacaca gaaggtggaa atgccatatt agagaacatt tccttctcaa taagtcctgg    360

ccagagggtg agatttgaac actgcttgct ttgttagact gtgttcagta agtgaatccc    420

agtagcctga agcaatgtgt tagcagaatc tatttgtaac attattattg tacagtagaa    480

tcaatattaa acacacatgt tttattatat ggagtcatta tttttaatat gaaatttaat    540

ttgcagagtc ctgaacctat ataatgggtt tattttaaat gtgattgtac ttgcagaata    600
```

<210> SEQ ID NO 143
<211> LENGTH: 360
<212> TYPE: DNA
<213> ORGANISM: Homo sapiens

<400> SEQUENCE: 143

```
ttccaatggt ttttattgaa gtacaatact gaattatgtt tatggcatgg tacctatatg     60

tcacagaagt gatcccatca cttttacctt ataggtgggc ctcttgggaa gaactggatc    120

agggaagagt actttgttat cagctttttt gagactactg aacactgaag gagaaatcca    180

gatcgatggt gtgtcttggg attcaataac tttgcaacag tggaggaaag cctttggagt    240

gataccacag gtgagcaaaa ggacttagcc agaaaaaagg caactaaatt atattttta    300

ctgctatttg atacttgtac tcaagaaatt catattactc tgcaaaatat atttgttatg    360
```

<210> SEQ ID NO 144
<211> LENGTH: 360
<212> TYPE: DNA
<213> ORGANISM: Homo sapiens

<400> SEQUENCE: 144

```
gggtgtttct tattttaaaa taatttttct acttgaaata ttttacaata caataaggga     60

aaaataaaaa gttatttaag ttattcatac tttcttcttc ttttcttttt tgctatagaa    120

agtatttatt ttttctggaa catttagaaa aaacttggat ccctatgaac agtggagtga    180

tcaagaaata tggaaagttg cagatgaggt aaggctgcta actgaaatga ttttgaaagg    240

ggtaactcat accaacacaa atggctgata tagctgacat cattctacac actttgtgtg    300

catgtatgtg tgtgcacaac tttaaaatgg agtaccctaa catacctgga gcaacaggta    360
```

<210> SEQ ID NO 145
<211> LENGTH: 6132
<212> TYPE: DNA
<213> ORGANISM: Homo sapiens

<400> SEQUENCE: 145

```
aattggaagc aaatgacatc acagcaggtc agagaaaaag ggttgagcgg caggcaccca     60
gagtagtagg tctttggcat taggagcttg agcccagacg gccctagcag ggaccccagc    120
gcccgagaga ccatgcagag gtcgcctctg gaaaaggcca gcgttgtctc caaacttttt    180
ttcagctgga ccagaccaat tttgaggaaa ggatacagac agcgcctgga attgtcagac    240
atataccaaa tcccttctgt tgattctgct gacaatctat ctgaaaaatt ggaaagagaa    300
tgggatagag agctggcttc aaagaaaaat cctaaactca ttaatgccct tcggcgatgt    360
tttttctgga gatttatgtt ctatggaatc tttttatatt taggggaagt caccaaagca    420
gtacagcctc tcttactggg aagaatcata gcttcctatg acccggataa caaggaggaa    480
cgctctatcg cgatttatct aggcataggc ttatgccttc tctttattgt gaggacactg    540
ctcctacacc cagccatttt tggccttcat cacattggaa tgcagatgag aatagctatg    600
tttagtttga tttataagaa gactttaaag ctgtcaagcc gtgttctaga taaaataagt    660
attggacaac ttgttagtct cctttccaac aacctgaaca aatttgatga aggacttgca    720
ttggcacatt tcgtgtggat cgctcctttg caagtggcac tcctcatggg gctaatctgg    780
gagttgttac aggcgtctgc cttctgtgga cttggtttcc tgatagtcct tgcccttttt    840
caggctgggc tagggagaat gatgatgaag tacagagatc agagagctgg gaagatcagt    900
gaaagacttg tgattacctc agaaatgatt gaaaatatcc aatctgttaa ggcatactgc    960
tgggaagaag caatggaaaa aatgattgaa aacttaagac aaacagaact gaaactgact   1020
cggaaggcag cctatgtgag atacttcaat agctcagcct tcttcttctc agggttcttt   1080
gtggtgtttt tatctgtgct tccctatgca ctaatcaaag gaatcatcct ccggaaaata   1140
ttcaccacca tctcattctg cattgttctg cgcatggcgg tcactcggca atttccctgg   1200
gctgtacaaa catggtatga ctctcttgga gcaataaaca aaatacagga tttcttacaa   1260
aagcaagaat ataagacatt ggaatataac ttaacgacta cagaagtagt gatggagaat   1320
gtaacagcct tctgggagga gggatttggg gaattatttg agaaagcaaa acaaaacaat   1380
aacaatagaa aaacttctaa tggtgatgac agcctcttct tcagtaattt ctcacttctt   1440
ggtactcctg tcctgaaaga tattaatttc aagatagaaa gaggacagtt gttggcggtt   1500
gctggatcca ctggagcagg caagacttca cttctaatgg tgattatggg agaactggag   1560
ccttcagagg gtaaaattaa gcacagtgga agaatttcat tctgttctca gttttcctgg   1620
attatgcctg gcaccattaa agaaaatatc atctttggtg tttcctatga tgaatataga   1680
tacagaagcg tcatcaaagc atgccaacta gaagaggaca tctccaagtt tgcagagaaa   1740
gacaatatag ttcttggaga aggtggaatc acactgagtg gaggtcaacg agcaagaatt   1800
tctttagcaa gagcagtata caaagatgct gatttgtatt tattagactc tccttttgga   1860
tacctagatg ttttaacaga aaaagaaata tttgaaagct gtgtctgtaa actgatggct   1920
aacaaaacta ggattttggt cacttctaaa atggaacatt taaagaaagc tgacaaaata   1980
ttaattttgc atgaaggtag cagctatttt tatgggacat tttcagaact ccaaaatcta   2040
cagccagact ttagctcaaa actcatggga tgtgattctt tcgaccaatt tagtgcagaa   2100
agaagaaatt caatcctaac tgagacctta caccgtttct cattagaagg agatgctcct   2160
gtctcctgga cagaaacaaa aaaacaatct tttaaacaga ctggagagtt tggggaaaaa   2220
aggaagaatt ctattctcaa tccaatcaac tctatacgaa aattttccat tgtgcaaaag   2280
actcccttac aaatgaatgg catcgaagag gattctgatg agcctttaga gagaaggctg   2340
```

-continued

```
tccttagtac cagattctga gcagggagag gcgatactgc ctcgcatcag cgtgatcagc   2400
actggcccca cgcttcaggc acgaaggagg cagtctgtcc tgaacctgat gacacactca   2460
gttaaccaag gtcagaacat tcaccgaaag acaacagcat ccacacgaaa agtgtcactg   2520
gcccctcagg caaacttgac tgaactggat atatattcaa gaaggttatc tcaagaaact   2580
ggcttggaaa taagtgaaga aattaacgaa gaagacttaa aggagtgctt ttttgatgat   2640
atggagagca taccagcagt gactacatgg aacacatacc ttcgatatat tactgtccac   2700
aagagcttaa tttttgtgct aatttggtgc ttagtaattt ttctggcaga ggtggctgct   2760
tctttggttg tgctgtggct ccttggaaac actcctcttc aagacaaagg gaatagtact   2820
catagtagaa ataacagcta tgcagtgatt atcaccagca ccagttcgta ttatgtgttt   2880
tacatttacg tgggagtagc cgacactttg cttgctatgg gattcttcag aggtctacca   2940
ctggtgcata ctctaatcac agtgtcgaaa attttacacc acaaaatgtt acattctgtt   3000
cttcaagcac ctatgtcaac cctcaacacg ttgaaagcag gtgggattct taatagattc   3060
tccaaagata tagcaatttt ggatgacctt ctgcctctta ccatatttga cttcatccag   3120
ttgttattaa ttgtgattgg agctatagca gttgtcgcag ttttacaacc ctacatcttt   3180
gttgcaacag tgccagtgat agtggctttt attatgttga gagcatattt cctccaaacc   3240
tcacagcaac tcaaacaact ggaatctgaa ggcaggagtc caattttcac tcatcttgtt   3300
acaagcttaa aggactatgg gacacttcgt gccttcggac ggcagcctta ctttgaaact   3360
ctgttccaca aagctctgaa tttacatact gccaactggt tcttgtacct gtcaacactg   3420
cgctggttcc aaatgagaat agaaatgatt tttgtcatct tcttcattgc tgttaccttc   3480
atttccattt taacaacagg agaaggagaa ggaagagttg gtattatcct gactttagcc   3540
atgaatatca tgagtacatt gcagtgggct gtaaactcca gcatagatgt ggatagcttg   3600
atgcgatctg tgagccgagt ctttaagttc attgacatgc caacagaagg taaacctacc   3660
aagtcaacca aaccatacaa gaatggccaa ctctcgaaag ttatgattat tgagaattca   3720
cacgtgaaga aagatgacat ctggccctca gggggccaaa tgactgtcaa agatctcaca   3780
gcaaaataca cagaaggtgg aaatgccata ttagagaaca tttccttctc aataagtcct   3840
ggccagaggg tgggcctctt gggaagaact ggatcaggga agagtacttt gttatcagct   3900
tttttgagac tactgaacac tgaaggagaa atccagatcg atggtgtgtc ttgggattca   3960
ataactttgc aacagtggag gaaagccttt ggagtgatac cacagaaagt atttatttt    4020
tctggaacat ttagaaaaaa cttggatccc tatgaacagt ggagtgatca agaaatatgg   4080
aaagttgcag atgaggttgg gctcagatct gtgatagaac agtttcctgg gaagcttgac   4140
tttgtccttg tggatggggg ctgtgtccta agccatggcc acaagcagtt gatgtgcttg   4200
gctagatctg ttctcagtaa ggcgaagatc ttgctgcttg atgaacccag tgctcatttg   4260
gatccagtaa cataccaaat aattagaaga actctaaaac aagcatttgc tgattgcaca   4320
gtaattctct gtgaacacag gatagaagca atgctggaat gccaacaatt tttggtcata   4380
gaagagaaca aagtgcggca gtacgattcc atccagaaac tgctgaacga gaggagcctc   4440
ttccggcaag ccatcagccc ctccgacagg gtgaagctct ttccccaccg gaactcaagc   4500
aagtgcaagt ctaagcccca gattgctgct ctgaaagagg agacagaaga agaggtgcaa   4560
gatacaaggc tttagagagc agcataaatg ttgacatggg acatttgctc atggaattgg   4620
agctcgtggg acagtcacct catggaattg gagctcgtgg aacagttacc tctgcctcag   4680
```

```
aaaacaagga tgaattaagt ttttttttaa aaaagaaaca tttggtaagg ggaattgagg   4740
acactgatat gggtcttgat aaatggcttc ctggcaatag tcaaattgtg tgaaaggtac   4800
ttcaaatcct tgaagattta ccacttgtgt tttgcaagcc agattttcct gaaaaccctt   4860
gccatgtgct agtaattgga aaggcagctc taaatgtcaa tcagcctagt tgatcagctt   4920
attgtctagt gaaactcgtt aatttgtagt gttggagaag aactgaaatc atacttctta   4980
gggttatgat taagtaatga taactggaaa cttcagcggt ttatataagc ttgtattcct   5040
ttttctctcc tctccccatg atgtttagaa acacaactat attgtttgct aagcattcca   5100
actatctcat ttccaagcaa gtattagaat accacaggaa ccacaagact gcacatcaaa   5160
atatgcccca ttcaacatct agtgagcagt caggaaagag aacttccaga tcctggaaat   5220
cagggttagt attgtccagg tctaccaaaa atctcaatat ttcagataat cacaatacat   5280
cccttacctg ggaaagggct gttataatct ttcacagggg acaggatggt tcccttgatg   5340
aagaagttga tatgcctttt cccaactcca gaaagtgaca agctcacaga cctttgaact   5400
agagtttagc tggaaaagta tgttagtgca aattgtcaca ggacagccct tctttccaca   5460
gaagctccag gtagagggtg tgtaagtaga taggccatgg gcactgtggg tagacacaca   5520
tgaagtccaa gcatttagat gtataggttg atggtggtat gttttcaggc tagatgtatg   5580
tacttcatgc tgtctacact aagagagaat gagagacaca ctgaagaagc accaatcatg   5640
aattagtttt atatgcttct gttttataat tttgtgaagc aaaatttttt ctctaggaaa   5700
tatttatttt aataatgttt caaacatata taacaatgct gtattttaaa agaatgatta   5760
tgaattacat ttgtataaaa taatttttat atttgaaata ttgacttttt atggcactag   5820
tatttctatg aaatattatg ttaaaactgg gacaggggag aacctagggt gatattaacc   5880
aggggccatg aatcaccttt tggtctggag ggaagccttg gggctgatgc agttgttgcc   5940
cacagctgta tgattcccag ccagcacagc ctcttagatg cagttctgaa gaagatggta   6000
ccaccagtct gactgtttcc atcaagggta cactgccttc tcaactccaa actgactctt   6060
aagaagactg cattatattt attactgtaa gaaaatatca cttgtcaata aaatccatac   6120
atttgtgtga aa                                                       6132
```

<210> SEQ ID NO 146
<211> LENGTH: 1480
<212> TYPE: PRT
<213> ORGANISM: Homo sapiens

<400> SEQUENCE: 146

```
Met Gln Arg Ser Pro Leu Glu Lys Ala Ser Val Val Ser Lys Leu Phe
1               5                   10                  15

Phe Ser Trp Thr Arg Pro Ile Leu Arg Lys Gly Tyr Arg Gln Arg Leu
            20                  25                  30

Glu Leu Ser Asp Ile Tyr Gln Ile Pro Ser Val Asp Ser Ala Asp Asn
        35                  40                  45

Leu Ser Glu Lys Leu Glu Arg Glu Trp Asp Arg Glu Leu Ala Ser Lys
    50                  55                  60

Lys Asn Pro Lys Leu Ile Asn Ala Leu Arg Arg Cys Phe Phe Trp Arg
65                  70                  75                  80

Phe Met Phe Tyr Gly Ile Phe Leu Tyr Leu Gly Glu Val Thr Lys Ala
                85                  90                  95

Val Gln Pro Leu Leu Leu Gly Arg Ile Ile Ala Ser Tyr Asp Pro Asp
            100                 105                 110
```

-continued

```
Asn Lys Glu Glu Arg Ser Ile Ala Ile Tyr Leu Gly Ile Gly Leu Cys
        115                 120                 125

Leu Leu Phe Ile Val Arg Thr Leu Leu Leu His Pro Ala Ile Phe Gly
    130                 135                 140

Leu His His Ile Gly Met Gln Met Arg Ile Ala Met Phe Ser Leu Ile
145                 150                 155                 160

Tyr Lys Lys Thr Leu Lys Leu Ser Ser Arg Val Leu Asp Lys Ile Ser
                165                 170                 175

Ile Gly Gln Leu Val Ser Leu Leu Ser Asn Asn Leu Asn Lys Phe Asp
            180                 185                 190

Glu Gly Leu Ala Leu Ala His Phe Val Trp Ile Ala Pro Leu Gln Val
        195                 200                 205

Ala Leu Leu Met Gly Leu Ile Trp Glu Leu Leu Gln Ala Ser Ala Phe
    210                 215                 220

Cys Gly Leu Gly Phe Leu Ile Val Leu Ala Leu Phe Gln Ala Gly Leu
225                 230                 235                 240

Gly Arg Met Met Met Lys Tyr Arg Asp Gln Arg Ala Gly Lys Ile Ser
                245                 250                 255

Glu Arg Leu Val Ile Thr Ser Glu Met Ile Glu Asn Ile Gln Ser Val
            260                 265                 270

Lys Ala Tyr Cys Trp Glu Glu Ala Met Glu Lys Met Ile Glu Asn Leu
        275                 280                 285

Arg Gln Thr Glu Leu Lys Leu Thr Arg Lys Ala Ala Tyr Val Arg Tyr
    290                 295                 300

Phe Asn Ser Ser Ala Phe Phe Phe Ser Gly Phe Phe Val Val Phe Leu
305                 310                 315                 320

Ser Val Leu Pro Tyr Ala Leu Ile Lys Gly Ile Ile Leu Arg Lys Ile
                325                 330                 335

Phe Thr Thr Ile Ser Phe Cys Ile Val Leu Arg Met Ala Val Thr Arg
            340                 345                 350

Gln Phe Pro Trp Ala Val Gln Thr Trp Tyr Asp Ser Leu Gly Ala Ile
        355                 360                 365

Asn Lys Ile Gln Asp Phe Leu Gln Lys Gln Glu Tyr Lys Thr Leu Glu
    370                 375                 380

Tyr Asn Leu Thr Thr Thr Glu Val Val Met Glu Asn Val Thr Ala Phe
385                 390                 395                 400

Trp Glu Glu Gly Phe Gly Glu Leu Phe Glu Lys Ala Lys Gln Asn Asn
                405                 410                 415

Asn Asn Arg Lys Thr Ser Asn Gly Asp Asp Ser Leu Phe Phe Ser Asn
            420                 425                 430

Phe Ser Leu Leu Gly Thr Pro Val Leu Lys Asp Ile Asn Phe Lys Ile
        435                 440                 445

Glu Arg Gly Gln Leu Leu Ala Val Ala Gly Ser Thr Gly Ala Gly Lys
    450                 455                 460

Thr Ser Leu Leu Met Val Ile Met Gly Glu Leu Glu Pro Ser Glu Gly
465                 470                 475                 480

Lys Ile Lys His Ser Gly Arg Ile Ser Phe Cys Ser Gln Phe Ser Trp
                485                 490                 495

Ile Met Pro Gly Thr Ile Lys Glu Asn Ile Ile Phe Gly Val Ser Tyr
            500                 505                 510

Asp Glu Tyr Arg Tyr Arg Ser Val Ile Lys Ala Cys Gln Leu Glu Glu
        515                 520                 525

Asp Ile Ser Lys Phe Ala Glu Lys Asp Asn Ile Val Leu Gly Glu Gly
```

-continued

```
    530                 535                 540

Gly Ile Thr Leu Ser Gly Gly Gln Arg Ala Arg Ile Ser Leu Ala Arg
545                 550                 555                 560

Ala Val Tyr Lys Asp Ala Asp Leu Tyr Leu Leu Asp Ser Pro Phe Gly
                565                 570                 575

Tyr Leu Asp Val Leu Thr Glu Lys Glu Ile Phe Glu Ser Cys Val Cys
            580                 585                 590

Lys Leu Met Ala Asn Lys Thr Arg Ile Leu Val Thr Ser Lys Met Glu
        595                 600                 605

His Leu Lys Lys Ala Asp Lys Ile Leu Ile Leu His Glu Gly Ser Ser
    610                 615                 620

Tyr Phe Tyr Gly Thr Phe Ser Glu Leu Gln Asn Leu Gln Pro Asp Phe
625                 630                 635                 640

Ser Ser Lys Leu Met Gly Cys Asp Ser Phe Asp Gln Phe Ser Ala Glu
                645                 650                 655

Arg Arg Asn Ser Ile Leu Thr Glu Thr Leu His Arg Phe Ser Leu Glu
            660                 665                 670

Gly Asp Ala Pro Val Ser Trp Thr Glu Thr Lys Lys Gln Ser Phe Lys
        675                 680                 685

Gln Thr Gly Glu Phe Gly Glu Lys Arg Lys Asn Ser Ile Leu Asn Pro
    690                 695                 700

Ile Asn Ser Ile Arg Lys Phe Ser Ile Val Gln Lys Thr Pro Leu Gln
705                 710                 715                 720

Met Asn Gly Ile Glu Glu Asp Ser Asp Glu Pro Leu Glu Arg Arg Leu
                725                 730                 735

Ser Leu Val Pro Asp Ser Glu Gln Gly Glu Ala Ile Leu Pro Arg Ile
            740                 745                 750

Ser Val Ile Ser Thr Gly Pro Thr Leu Gln Ala Arg Arg Arg Gln Ser
        755                 760                 765

Val Leu Asn Leu Met Thr His Ser Val Asn Gln Gly Gln Asn Ile His
    770                 775                 780

Arg Lys Thr Thr Ala Ser Thr Arg Lys Val Ser Leu Ala Pro Gln Ala
785                 790                 795                 800

Asn Leu Thr Glu Leu Asp Ile Tyr Ser Arg Arg Leu Ser Gln Glu Thr
                805                 810                 815

Gly Leu Glu Ile Ser Glu Glu Ile Asn Glu Glu Asp Leu Lys Glu Cys
            820                 825                 830

Phe Phe Asp Asp Met Glu Ser Ile Pro Ala Val Thr Thr Trp Asn Thr
        835                 840                 845

Tyr Leu Arg Tyr Ile Thr Val His Lys Ser Leu Ile Phe Val Leu Ile
    850                 855                 860

Trp Cys Leu Val Ile Phe Leu Ala Glu Val Ala Ala Ser Leu Val Val
865                 870                 875                 880

Leu Trp Leu Leu Gly Asn Thr Pro Leu Gln Asp Lys Gly Asn Ser Thr
                885                 890                 895

His Ser Arg Asn Asn Ser Tyr Ala Val Ile Ile Thr Ser Thr Ser Ser
            900                 905                 910

Tyr Tyr Val Phe Tyr Ile Tyr Val Gly Val Ala Asp Thr Leu Leu Ala
        915                 920                 925

Met Gly Phe Phe Arg Gly Leu Pro Leu Val His Thr Leu Ile Thr Val
    930                 935                 940

Ser Lys Ile Leu His His Lys Met Leu His Ser Val Leu Gln Ala Pro
945                 950                 955                 960
```

```
Met Ser Thr Leu Asn Thr Leu Lys Ala Gly Gly Ile Leu Asn Arg Phe
                965                 970                 975

Ser Lys Asp Ile Ala Ile Leu Asp Asp Leu Leu Pro Leu Thr Ile Phe
            980                 985                 990

Asp Phe Ile Gln Leu Leu Leu Ile  Val Ile Gly Ala Ile  Ala Val Val
        995                 1000                 1005

Ala Val  Leu Gln Pro Tyr Ile  Phe Val Ala Thr Val  Pro Val Ile
    1010                 1015                 1020

Val Ala  Phe Ile Met Leu Arg  Ala Tyr Phe Leu Gln  Thr Ser Gln
    1025                 1030                 1035

Gln Leu  Lys Gln Leu Glu Ser  Glu Gly Arg Ser Pro  Ile Phe Thr
    1040                 1045                 1050

His Leu  Val Thr Ser Leu Lys  Gly Leu Trp Thr Leu  Arg Ala Phe
    1055                 1060                 1065

Gly Arg  Gln Pro Tyr Phe Glu  Thr Leu Phe His Lys  Ala Leu Asn
    1070                 1075                 1080

Leu His  Thr Ala Asn Trp Phe  Leu Tyr Leu Ser Thr  Leu Arg Trp
    1085                 1090                 1095

Phe Gln  Met Arg Ile Glu Met  Ile Phe Val Ile Phe  Phe Ile Ala
    1100                 1105                 1110

Val Thr  Phe Ile Ser Ile Leu  Thr Thr Gly Glu Gly  Glu Gly Arg
    1115                 1120                 1125

Val Gly  Ile Ile Leu Thr Leu  Ala Met Asn Ile Met  Ser Thr Leu
    1130                 1135                 1140

Gln Trp  Ala Val Asn Ser Ser  Ile Asp Val Asp Ser  Leu Met Arg
    1145                 1150                 1155

Ser Val  Ser Arg Val Phe Lys  Phe Ile Asp Met Pro  Thr Glu Gly
    1160                 1165                 1170

Lys Pro  Thr Lys Ser Thr Lys  Pro Tyr Lys Asn Gly  Gln Leu Ser
    1175                 1180                 1185

Lys Val  Met Ile Ile Glu Asn  Ser His Val Lys Lys  Asp Asp Ile
    1190                 1195                 1200

Trp Pro  Ser Gly Gly Gln Met  Thr Val Lys Asp Leu  Thr Ala Lys
    1205                 1210                 1215

Tyr Thr  Glu Gly Gly Asn Ala  Ile Leu Glu Asn Ile  Ser Phe Ser
    1220                 1225                 1230

Ile Ser  Pro Gly Gln Arg Val  Gly Leu Leu Gly Arg  Thr Gly Ser
    1235                 1240                 1245

Gly Lys  Ser Thr Leu Leu Ser  Ala Phe Leu Arg Leu  Leu Asn Thr
    1250                 1255                 1260

Glu Gly  Glu Ile Gln Ile Asp  Gly Val Ser Trp Asp  Ser Ile Thr
    1265                 1270                 1275

Leu Gln  Gln Trp Arg Lys Ala  Phe Gly Val Ile Pro  Gln Lys Val
    1280                 1285                 1290

Phe Ile  Phe Ser Gly Thr Phe  Arg Lys Asn Leu Asp  Pro Tyr Glu
    1295                 1300                 1305

Gln Trp  Ser Asp Gln Glu Ile  Trp Lys Val Ala Asp  Glu Val Gly
    1310                 1315                 1320

Leu Arg  Ser Val Ile Glu Gln  Phe Pro Gly Lys Leu  Asp Phe Val
    1325                 1330                 1335

Leu Val  Asp Gly Gly Cys Val  Leu Ser His Gly His  Lys Gln Leu
    1340                 1345                 1350
```

```
Met Cys  Leu Ala Arg Ser Val  Leu Ser Lys Ala Lys  Ile Leu Leu
    1355                 1360                 1365

Leu Asp  Glu Pro Ser Ala His  Leu Asp Pro Val Thr  Tyr Gln Ile
    1370                 1375                 1380

Ile Arg  Arg Thr Leu Lys Gln  Ala Phe Ala Asp Cys  Thr Val Ile
    1385                 1390                 1395

Leu Cys  Glu His Arg Ile Glu  Ala Met Leu Glu Cys  Gln Gln Phe
    1400                 1405                 1410

Leu Val  Ile Glu Glu Asn Lys  Val Arg Gln Tyr Asp  Ser Ile Gln
    1415                 1420                 1425

Lys Leu  Leu Asn Glu Arg Ser  Leu Phe Arg Gln Ala  Ile Ser Pro
    1430                 1435                 1440

Ser Asp  Arg Val Lys Leu Phe  Pro His Arg Asn Ser  Ser Lys Cys
    1445                 1450                 1455

Lys Ser  Lys Pro Gln Ile Ala  Ala Leu Lys Glu Glu  Thr Glu Glu
    1460                 1465                 1470

Glu Val  Gln Asp Thr Arg Leu
    1475                 1480


<210> SEQ ID NO 147
<211> LENGTH: 152082
<212> TYPE: DNA
<213> ORGANISM: Mus musculus

<400> SEQUENCE: 147

aattggaagc aaatgacatc acctcaggtc tgagtaaaag ggacgagcca aaagcattga     60

cctggtcctg gatatccaga tgtcgagtcc aacctgaatt tagccgaaca cagacctcat    120

tgcctcacgg agacatcatg cagaagtcgc ctttggagaa agccagcttt atctccaaac    180

tcttcttcag gtgagagggt actcagcgga tctttgcacg gacacatgtg cctatgcagg    240

agaagggaat gaatatgggc agactttggg aaaacaggaa gagatttttg ttgtgtttgt    300

tttgttttaa aaggtgtgtt gtcattcagt gctttaaagg aaataagcat ttttgtacaa    360

taaaatgaag ctgattgaat agagaacaaa atatacttgc aactgtgaat cagacttgca    420

acagccaaat atgctacgga gcaatagata tatatttttt taatttcctg aaaaaagtta    480

tacttcataa gtgtacttaa tagaacattc ctaagattgg tctgttattt tctccaagaa    540

aagctgaccg caagtgcagt gcctgtgtaa taggtgctct gaaaacattt gttgactgaa    600

ttttttttaaa agtccaggaa ttatattgta tttacttttt gccgttgtaa tattgagtaa    660

gtctaacatg ctcatcacag ttacattatt ctttttaaaa atgagcaagt cagttaaaat    720

atctaacttt aaaaagaaat aatataagca atgcattaaa aaagtgagtt accatgggga    780

tatgaaacta gagttttagc cactgaagct atattcaatt gacaattagg acattgttct    840

cttatcctac attgtcaaaa aaccaaaccc tcaatctaat aggattttta aattagaatt    900

taagttggaa gacctaggca agaattaagc gctttgtatt tgaagtgctc cgtggagctt    960

cgtctgctct gatcctgtag tgtgaatgaa tgaaaagagc agcgctcatg ggtcctcagc   1020

tgactcaccc cccccccccc acacacacac caatgagtca gcacactgaa gtatcataag   1080

tgtcgaatat gttctcaacc tgccctatgc tgtgggtagg gggcaaggct cagccttagt   1140

cttcctgatg ttcctttttc agccggtcta gagctcaagg ctgaggaaag acaagtgctt   1200

ctgcaggaga gctccccccg gtggttggga gagaaggaag ggctttcttc tttagaatga   1260

atatttgtgg tgccttttgt tacttcatct ataaatctag cttatcggtc tggatctatt   1320
```

-continued

```
ttcttattac ttacaaaatc agaatgtcac ttgacataca tgtgaggctt ttatgaaagc   1380
ctattgagga acctaaatgt caatgtgtct gtaaaggcaa gttttcagga gaatgaatat   1440
ctcttgtgtg gttttcccac taagtagtaa gaaacttcaa aatttttcac ttatcaaagt   1500
gtttcaaaaa tttcccgttt ttataaccca cctaataaat tgtagtgtgc tttacaaatg   1560
ttcttaggct gatttggaaa ggaaatgtat tataatggct gtgaaatttg ttaagaacat   1620
actcatttct gccctccaaa tgatttcata atcagttgct ttaagaatag gtgtgttttt   1680
aagagtttag ttcctactat ttataggaac tgacatttag ctaagtacta gtcagtgatt   1740
ataaacttcc ttctggactt taattttcaa agagtaaaac ccttttctcc actggactag   1800
gcagtgccgc ctagtgacca gggcagtggg ccctggattc ccatggcctg gactcaggct   1860
gcagatctac tgcttagtag gcaagccctt tggtgtctct gcatgacttc agtgctacaa   1920
cttggagtct gtcagtgtga cacataatgt aatgggttag tctgttgagg aatatatgct   1980
gtgctttgag gacatgttag ctgcccttac tgttgtttac atgtttacat tcctcgaagt   2040
gctgggatcc tcactgtaaa ggacagtgag tttatttctg ctgggtgcac ttttgtgact   2100
atagcctgta tctatgccat ttgcttgaga agttagcata ggggatagat agcctcacgt   2160
agcatgggct tgttagatac ttagatgaaa gccatgctct tacatcagat ctccttcagt   2220
gccttagaat ttaacctatc ccatcaagct tagggttata aaagactcct aaaagctgac   2280
ttctatgtgt ctactattat ggtcttggtt ttggattata ttaattaaca ttttaattat   2340
ttagattatg ttactgagaa accaaaacaa gtttaataat aatttaagta ctttttattt   2400
ttttaagttt tcagtaagta aaaaaatgga aagacattgg aattggtcta acacagaaga   2460
taattttacc atgaaaattt caagtaattt tttttacttt catggaaaat aaatgcatta   2520
acttgaaggt gtaatgataa catttatgaa ataagttgtt tcaaaacaag tggtgatata   2580
tttatacaga atttatgatt gacatattag tggaattaat tcctaaaaac ctttgatttg   2640
tagaaatgtt tgaactttac actttcatag agatttaaga aaaaagatta tgcctaacgt   2700
gtacctgtta gtgtgtgtgt gtgtgtgtat gtgcgcgtat gcatgtttgt atgaccatag   2760
agtgcagtat aagctatcat ctcttgagtc atgtctctca ttggcctgaa tctcaccagt   2820
tatgttagac agacttgcca gtgaacccaa gggctttccc tgactctacc ttctcagcac   2880
tgggattaca atcttgtgtc actctgcccg ccttttcacc taggagcttg ggattgagct   2940
cggttcttca ttcatgtgaa gttcttctct gactgggtta tgaacagtcc caagaaattg   3000
ggtagcaaca tttccattct gtttgtgatc catattacag agattatact tgacaaaact   3060
taaggttatc caaatctgaa ggccactttt gatatactga ggatatggta tttagaaaac   3120
caagaattgc tgtcccttca gttgatggat gtcatacagt ggccacagct ccagatttca   3180
tttggctttt ctttaataga aatgggaaga agccacatct aggatggaga gaccctctgt   3240
ttggacagtg tacaagcact gcccgatact ggctctgtgc cagcaactta ggactcccctt  3300
ctgtttattt tcttttcact gataatgttt ggttgttaca cagctcagaa atttcaactt   3360
gggatttatg ttaggttcat gtcagttttg tttagtttaa tcaacagttc taagagcacc   3420
tcttgtacag gacatgatga aatcatgatt ttgtgtatgt gcatatatat gtgtataata   3480
aatatctcta tacagtgaaa tttattttag ttgatatcac aattattaaa atttatttta   3540
aggttttata gcacattact acacaatata ttttgatagt caattcctca gagcagagga   3600
agctattatc ttaaaaataa cttcttcaac attttgtttg atatacgatg aaatactact   3660
cagtgcacac tgatatacaa gggaaatcaa ggctttttgt tttctttatg gaagtttgac   3720
```

-continued

```
ttaactgtga taattcctaa gtgttaaaac atgtttaaga ggtccacaaa taaatatcac   3780
cataaagtat gttattactg ttaatgccct ttcataggaa cctgtaattt cactgcggta   3840
gcactataga taagtatagg attgccaaac cataagggaa gggcggtaac catttagcat   3900
gcagtgagat attatttgtt gagactttaa aaacacatct gagtcagcag agtttgggcc   3960
gttttgattt gctcttcacc atgcatcttg tgcatttcct cagagccaag tctgcaaagc   4020
agtgagtata agaggcgaaa actatgaaag aggtccactt atttggagat actaacagag   4080
ggatttcata aatacatttt tcatcatcag taagggaaac attttaatgg cttcccttca   4140
gctcttaaga atggaatgga tgcaccatgt agggttttct ttgtaaaatc agcattacaa   4200
agtggcctct tcatggactt gattgtcaga gaacttaggc ttttagcaag aatactctag   4260
tagttcagat gaggcttgtc aaaatgtcaa tttcagtata agccattaat tatcttttga   4320
cattaatgac tatttgaaat tgtaaactac ttttgtgttt agtattcaca tcatttcatg   4380
actccaggat tacatgatta taatacctgt ttcttgttga aattgtctca caatgctaaa   4440
catcatctat atgcagtata catacatact ctaccctcaa aataatggga caatcatttt   4500
gatacaatgg gtgaggggaa acaactgttg acacattttt taatagagta agtattcctt   4560
cacattttcc ttgtgatgtt tatcatataa actcttcaga aggcagtcta ctttatgact   4620
ccttgttcta gggcagtagt tctcaacctg tgtgtttcaa gggttaaatg acccttacac   4680
atgtgttgca tataagctat cctacatatc agctcttcac catacaatga ataacaatag   4740
aagaattaga ctcatgaagt agcaacaaaa attatcttat aatttggatt caccataaca   4800
tgagaaactg tattaaagag ttccagcaat agaaaggttg aggaccactg cgctagggta   4860
agggaatggt ttggagattt ttgaagtctt tagcattgtt agacttctta gcttggaaga   4920
tattctcttg atatcataag attagctgtc ctccccaccc aagtcaaagg ggtatttccc   4980
cagtatttcc tgtaggtcat gatgactcag agcaatgttt ggagggcaat ttcattcact   5040
ccctttttcac caccaccgta ctccatgctt ggcattaagg tggtagaggc gctgccctct   5100
gaatgaatga ataccttaaa actgatgatc tcaagccaca gagatcccta tcccatactc   5160
atggctgtct agcaaggttt gatagagaag tgttgtatag gaactgcaag aacaagtgag   5220
agaacagcag tggttcagag aaggtctgga gtctgtcctg aaagcatgtg acagaacttg   5280
ggaggtagat ctggaaacta gcaagggcta gacccctggg taccttatat atttcttagg   5340
gctttattgc actgctcatg aaatgaaagg tgggaaattt taagcaggca gagatgtgat   5400
tatttcaaga ttgttggcgt tttttttttt gttttttttgt tttttttgttt tttttaaaga   5460
ctgacagaag ggatagagaa agatgcctga aagatgtttg ggaagcaaaa taatcatatt   5520
tttaaattag aggtggaagg tgagagtgag gaaaaaaataa gagggcttgg atgggtcagt   5580
ttgggtggta gaatggtagg tgatacatac tatgaagtgg ggtccttcta ttagaggcag   5640
aggcctggtg tgaggttaga tgcctatgca agactgcagt ctctaaaaga aagtgcaact   5700
ggcttgaggt gggttataca gtttgaatga attctttgtc ttgtcaatac tgtttttcaa   5760
caaataataa ttagtcagaa ctaatatttt atttggtagt gctaggcacc aaacccagac   5820
ccatgtctat attaaagcat tctcctacta aactgcaccc cagccccaag taattacttc   5880
ttagcagaga aattcctagc acttagttca gacagatttg ccaactaaca tttgcttttc   5940
tactccatta cacctgacat ttaatagtca ctgttttctt tacataaaaa tattggtctc   6000
tccctctctc tgtctctctg tctctctgtc tctgtctctg tctgtctgtc tgtctctctc   6060
```

```
tctctttctc tttctctctc tctctctctc tcacacacac acacacaatt aaaagccatc   6120
atggatcagt gtcagtgatc gagtaagaca ttaggtattc ccataattca gtgcatcaag   6180
tacataatta caatgagacc taaaaaatta ttcactcttt taagagttta tagacctgtt   6240
gaatttaaga gtccgagata gcaatcccaa tagcagggcc aaggattttt gcaacagaat   6300
ttgatgaacc agataggcac tataagatga gttcattatg gtgaggataa taaccttgaa   6360
atataaatgt gactttttag tgatgtgtta attatttatt tatgcaagcc tgtgtatgcg   6420
catttattta tcattactag tgagcctcta tacttaccag gtttctaaca gttaacagtc   6480
ttagactcta tataagaatt tattaaaaat tctgtttatt ctgcctaaag tttcattgta   6540
ttatttttaa taacgcaacc tttttttctt tgtaataaga tggctatcac attcatttat   6600
aggttctgta attatattac ttagtttaat tagactaggc attaattttg attcataaaa   6660
tcattgactg tttaaagtag ttgatatata ataaaatatt acagttaaaa atggactttc   6720
ttgaaaacaa aaattattga atatttaaaa aaattaatga aatctttcac ctgtgttgtt   6780
agcaaaatgt aacttcattt agaaatgtgt aatgtgttag tagtccttta ctcagccggc   6840
ccatggattc cctggagtat gaaactgctg acttgttggc acaggtgtca tcggagcctt   6900
gagagccagg tgctttgctg ccacagaagg ggagcagaag cagtctcttg tggttcactc   6960
tccttttgtc accattgtga ccactgcttc tgcagagtga catcagacac agtccagtgg   7020
atttacaact cattagtaaa gcagtatgtc agggctctgc acttaatgga aacttgttca   7080
gggttagtgg tgtggtaaga tggaacccag ctgtaagttg taatatttta ttatgtatca   7140
actactttac atagtcagtg attttataaa tcaaaattaa aacaggatga ggagattctt   7200
gaaattagaa ccttctactt cacaaacaac agccatttct atagcttttc tttactctga   7260
caaatactaa gtatctatat aggttctctg tggaatatag cacacacata aaatggaaaa   7320
tatattaaat atgccaagtc ctagatccca tgtgtacctg ttaattaaat ttatgggaaa   7380
gaacaacttc tatgatctcc tttaacaaat gctaaggtaa ttcttctttt tgctaacatc   7440
taaaatcatc aactcaacga taaaacaggt ttggataacc caacaggtct tcattgggct   7500
aacatcctcc tcctcctcct cctccccctc ttcctcctcc tcctcctctt cagtaaatta   7560
acaataaaga cacaaaaata ggtcaactcg gaattctgta gttttgcctc tatcttccag   7620
cccttattaa gtacactcaa gagattacat acattatctc agtgaagttt ttaatctgtc   7680
tttgataatt gcacatataa gaaatgtggt tttaggggac tgcagtttag cagccaccaa   7740
gctaagagat gtgatgtcag atgtatcttt agattggtgt aaatccagac ataaaatttt   7800
aatcaataca tcacacacct agaatagaat tgatcaatta tttcacatgg ctttatatat   7860
actttaatgt tttttcttgg gtctgaaata attttttact gcatttgttt atagacaaca   7920
ttaaacaggc catcagttag tcttcttgga agggcttgtt gctttaacaa caacaaagaa   7980
ttactttatt ttatgtgtac agtagttttt ccagcttgtt tgtttgtgca cattctgcca   8040
gtggaagcca gaagagggtg ctgaatagac tggagttgca ggtagtggag agacatctga   8100
agatgctgaa aactgaggtg agggcctctg gaagagcagc tcttaagccc atctcttctc   8160
tgagccatct cttcagccca tttattcagt ctgtttctta gcataggtct ttatgacatc   8220
cacaggaggc aggatggaac tttcctaaaa ataacaatat ccttatagtt tactttcagt   8280
attatttgaa aacaaaacaa aacaaaacaa taaaaacaga caatatagca ggccagaaaa   8340
cgtggcagta gctaaacatt gtcacagtaa cagctcagtt acagtgagtg tgattccagc   8400
tgtgcttcct gtcctgaata aggtagctaa gtactaggca gtgcctttta ctcagcccca   8460
```

```
ctttcctact ttccattttc tctctaggat accaagctgg gactttgagt tttcacctcc   8520
taaccctact tcccttcact ctctaagcac atcacagcca tctttggcat ctatgccagc   8580
attaccaccc agtacttgtt ctcatcattc atgtcatctg atttttctat tggtctttct   8640
tcttatccac ctgctaaggt tgcaggaagt ggtagagaca cctgatagat ggttcttcaa   8700
ttttatactt gtcactttat atatacaaat ttcagatttt cttcatatgg tagtatctat   8760
agttctttta gaaagtgctt ttatcagtaa gtcttcatgg aatttaaata cttcatgaaa   8820
tttctagtgt aaacatgtat gtatggcaat aaaagaattg cttttccaca aacaaaaaga   8880
tataaagtcc caaataaaag caaaacattt atataatatt ttaagcatta ttttcttgat   8940
tccctttct gtgttttaca caattatata cttctgaaat tgaattgtct tataattgat    9000
ttttttccca aacttctttc tggccatcag atccaggaat aaattattat caacacataa   9060
aagttgcata tttcctgtat cctgtgactt caagtgattt ttttttttta cttttggcat   9120
taatttcacc caacaatgtt gacttttaac tttgattgct tgatattcct tgagaaagag   9180
tactttatga tccagttttg gaagtatcag gtaatgtgta cttggatgct tgtctggcat   9240
gctaggcatt gtaattacag tagacattca ccaagtttag tactctacct taacttgaaa   9300
ttgtacacct gtcccagagg tgaaggggtt ctgaaggcag atttacacta taaacctatt   9360
catagattct aaagggcaag agtgattcag aaaactaatt tttacttgag tatgaaaatg   9420
gcttaggcta aaactttaat tatggttcca aaagtaataa gtacttatat aaatgattat   9480
ataattttaa tttctaaaaa cagtatgtca tgtacatttt gacagtggaa gtgttggttt   9540
aatagtgaat ctcataatca gtgtcacctt agaatgaaca taaccacttt attttaaaaa   9600
catgataatg tcacctatgg tttgtcactt atcacttcct aggggttttg ttgccctggg   9660
ttatgctgtg atcttgtgtc aacaggtgta ctgcaggcat gctaggctgt taactgagtt   9720
tggctcatat gtcctatagg gacatgctca cttatgcact gtagagataa cagtaaatat   9780
cacagtaagt ttcaatattc accaaaaaag aaatgtccgg tgaagttttc ctatttgtag   9840
gactattatg ggactaaaat tatcatatat ttaagaatat gtaatttttt attcctttta   9900
ttcctaaaaa aaaaaaatga aaccaactca gtcactttaa aagatataca tttcagatca   9960
aaattttgtg gggtgtgtct ggagagtggc agatattagg attcaagatt tcaaagacat  10020
tgaaggtaga ttatgcttat cttgattgtg cctggcaatt tttgagtccc atgcttcatc  10080
tccccatgct tttagaaaag tctcacattt agcttctctg tcagttctta ggaaccagcg  10140
tgtagcggaa gaaatgtgca ctttggaatc aggcttagct ggagtcctca ttctgtgact  10200
tattaacgtg tgttcttagg cacttaatct ttctgatact caattattct cactgggata  10260
atgagttact ttcatttcaa cctggcctaa gaatataata atattcaata ttctctgagt  10320
acttactctg tatattagag ttctcctgag aataagaatc aatagtaaat ctatttaata  10380
tataagatta tttataaaga attagcttcc gtgactaaga aaactgtcaa gttcaatact  10440
tgcagggttg ttttcaaagt ggagactggg aaagctaata ttcaggtttg agttcaaaag  10500
cagtcgccag gagttcggtg tcatttgggg aggctggtct ttttttttgt cagactcatg  10560
ttttcagtgg attagggaag acagcttaca ttagagagca tgtagtggtg cacagacatc  10620
tggcttccct tgtgatttcc ggaacagaat taacacaaat aatagaacaa tccataacag  10680
gagctcaacc tgctctaacc taaatgctct catttaatgt tagtctgacc tccaagtatc  10740
ttatcaattg ccatagccat cacccctgtg aggactttct gtgtcttcag tgataagtag  10800
```

-continued

```
tgcaagatac agaatgcctc tttaataagt aaatggtaac agtcttatga acactaaggc  10860
acttaacacc tttccagtgt gtaacagact agctcgctct ttcctacatc taacattcct  10920
ctcctagaaa gtaggcacaa catgtcactg aattataatt ctctttccca aaatcccttg  10980
cccagtctac aagttttgtt taccatagac tttcatcctc aattgtgtgt gtgtgtgttc  11040
attgctgggt ttgaactcct gggtaaatgc agcatactaa gcaaatgctc tgaggcactg  11100
agttacactt ccaaccctca tcttaaattt taagtttatt ttaagcattc aggctactct  11160
ttttgctccg acatatttcc tttctgtttg gggcccatgt gtttgcagag gctgctatca  11220
catagtatat aaactgaatg gattagacac tcaaaattta tcgttatagt tctaaatgct  11280
acaaggctga catcaaggtg ttagttaatt gtttttttccc aaggatgtga gtgagaatct  11340
attctgtgct ttctggccta gcgtttgtca gcatgctggt ggggatcctt agcattttga  11400
gatctgtaga ggtatcacct ccagaggcac ccttttcaca gatttctcct tgtatcttca  11460
gataaatgtc caaaatcaat tcctttgtaa ggaaaacagt catgttgtct ggaacctact  11520
aaatgtgttt actccacatg ttttgagggt cataggttag agggggtggg tgggtggatg  11580
agcaccttca tagaagcagg gggaggagga tgggataggg ggtttccagc agggaaacca  11640
ggaaaggggc taacatttaa aatgtaaata aataatatat ccaataaaaa agtaaataca  11700
tatatatcct taaaaatatg gagacactac agaggacact gtaagacggg ataagggaac  11760
tatctaggga gtagttcatg aatctttagt atatctttag tatatctgta ctaaaacatt  11820
aatgaagatc aaatattgag aaggtttaga taatgaaaaa tatttcataa aattttattc  11880
aacaaaatta aataaattct tggttgaata tttagtattg tgggccatta atgatatgta  11940
aaatgaacat gttatctctg accaagtaca aatcctcaat gtttatatta cattcttgta  12000
gagttggttt ttcttttctc ctttcggtgc cttgaccaga agtaatgaat aagcaaaacg  12060
tccttgcaat cagtgtcctt agggtgccat aaacatacta tgtttgtgga attaattact  12120
aacagatcaa ttcaccaagt ttctaatttg ctcagtgcaa tgaacaggac aatgaacata  12180
ggaagataaa ttatacacta tgttgtcctt atgaatttaa tcttgtgagg aaaaataagc  12240
agagtgaaat atcttaactt ttaaattcaa aaatttaaaa tattaagtga gaattatgtg  12300
ccatgttcag tggacagtgc agagtagaca gtgcagctta aacagagctc tttatgcaat  12360
gtggtataca gtttagtgta cttggggacc tgtggttgat aaagggagga atagagaaag  12420
gtggggtagg gtaggacagt gtacacagga gactgattaa ccagactgga gagagagagg  12480
ctcttcctga ccaatatcaa tgcactaaac cttcttagaa atagaagtca ggctttgttt  12540
caaggaagct gtcagttttt attcagtgta actcagcaaa atcagagatt agcttgctca  12600
gtgatggtga taggaaaatc tttttaaata ttaagagcca ccctattatc agtgttttca  12660
tccagttgaa ctcctgcaga gttcaaaagc tggagagtct ggctcaatgt ttcctttaaa  12720
gttcattttc ttaaaaccta aatggaaaca aaagatcatg acatcttgag gaaaaaagga  12780
aaacaaaacc tttaaatagt tataaaaata atttttatta atctaccatg gtttgtgtta  12840
ggagctatcc ttttaagtac ctgattgcta agatggctaa cttgatctct taaattgctt  12900
attagaaaca atgaattaat cactattatt tatatatgtt atagtcttga aaaaatcagc  12960
aattttaatt tttgacagat cttaaaaggt ttgtattaac atgcattgct atgcttaaat  13020
gaacataaaa atattaagta gagacttaaa gtaaggcctt ggagtagttt tctttcatgg  13080
caaatcctgg actaatctgg tcaacaactc cattccctgc tgaatctcaa ttttccaaag  13140
gaatacgtgg tgagaaaggg tgaggacgag cctctgtttt cctctcctgc agctctgggg  13200
```

agcttcagtg tttgttctta gtgatgccaa ggtttttgga caatgcaaat agaaatactt 13260
cgcctcccaa attcaggaac aggatatgaa ccttatagtc cgagtcatga actgtgccta 13320
cttacatcct cctcagcact aaaagggaaa aggcataaag atttgaaact tccatttcaa 13380
tttgttgcat aatagaaggt aaaaaggatt aaaatgacat taataaacaa atttcatatt 13440
taactgggag gtaggaaaat atccacagat gagaagccca aatcaaatgc cacaccactc 13500
ttctaatccc actggggatt cacagtgggt atcagtgcct taaaagtggc atcatactta 13560
aacaaacttg gggaagagga ggttaagaca atgaggaaaa tttcagactg acttatcaga 13620
ctagttgatt gcatggagaa ctatggaaac tatgtttacc acaaactgaa gtttaacctt 13680
gtcttcctgg taccaaatta cttcttctag aaaacattaa cattcttatt gtgtatacat 13740
ggaatgtgtt ttgattaaat cctcctccta tctctttccc tctcatatat cctcttcttc 13800
ctactacttt tgcctcccaa cttcatgtgc tcttatttat ttaaatttaa tacccactga 13860
agccattcag tactgcctta tatgactata tgtgcatgga gaccatctac taaacatacg 13920
tatccaccct ttcaggaatg ggcatccctg aatactgatt ctcccttccc cagcagctac 13980
ggattcccaa taacttctca gatagagcta agacttcatg agtcccttcc tagtccatgc 14040
tggggttttg actggcttaa tcctgttact attttcattt aaaaaatgat atagatgcct 14100
ctaatctctg ctgtatcatt ttatctgcca agcaaatcta tcaaatgaga aaatgatctc 14160
aaatgatgtg ggcagatgca ttttaaaatt acatttgtgt ctttgtgtgt gtgtgtgcac 14220
atatacacat gcacacacac actgctgtgt actaatgtat ggaggtcaga ggacaacttg 14280
taagtcagtc ctctctttct accatatagt ttctatgtgt tgagcttagg tcatcaaact 14340
tgacaccaac tacctcctaa gccatctgct ggtcctggaa tatatagaag tcattttgat 14400
gtaatgaatg acaaacatct atcaaaagac aaaaagaact tctttgtaca catagtgagg 14460
agctattaaa tgatttagat attgaagatc acgagaagtt gtactttgtg ttttatgtgc 14520
catggctcat gccagatgat atctgtagga atctaccacc tgtccagaac ctcatagaag 14580
ttctttgtct ctaagaaata attatgttct ttatacattt ggggaaaacc ttggagagtc 14640
aagtaggtat gcttccaaat atttagtcac tgtcagaatg acagtcatgg ctcagtaaag 14700
gacatgctta tttccgtgat aaatgaaaag tattgaattt gggtctttgt gatgccatct 14760
gataaagcaa aatgaacaaa gaaccacaat aaaggataca aagttctaga gaaggggaga 14820
aaacactgaa ataaatcgaa taattatttt taaaaaagca gcaaggaaat gcgtatctcc 14880
catataggag atgtcatgaa tgccacttgt gcacagtcaa gtctttcagt tgcctagtca 14940
gaagccggga ggagcttatg cccatcttcc actttcacac ttccgtgagg atgcggtgag 15000
agtgcttctg acctctgtgt tccaggagat gattcaacac tgcacagagg gtcagttccc 15060
tgatagcaca gaggtttcca tctgaaagct tgcacacatg cctgtccata actcaggagc 15120
attgctacgg taaaactgca acaccaggct gtttcctgtc ttccttgttc ttttggtttc 15180
aaatatattt cttattgatg atgaaaatat cgctcagtaa tttgaaagcc attgtttcct 15240
cagaagtctc ctaaaaggaa actcgcatgt aggaaatagg cagcttcatg gggcaattag 15300
tactattttc ttggatttgg tgtaggtaca gtgatatctg tagcttcaca gaaaggcact 15360
taggctgctt tttcagagga cattggtact tgacagtaaa tgacatcctt tgtgtcttat 15420
gttacctcct aagatgagca ggattcctcc cctcccttcc cttcctctcc cttcccctcc 15480
tctcccctct gacctccctt ccaacctcct ctcccctcct ctcccctccc ctcccctccc 15540

-continued

```
ctcccctccc ctccttttcc ctcccccctt ccctcctctt cccttccctt tcctatttcc  15600
ttttctattt ttttcttgta gcgttgcttg ttgtctttag attttagaaa tgctcgtgtc  15660
ctctcactgc caacaaacac ttcttcattt ctatacaata tgatatcaca atgccatttt  15720
ttcccctcag aattcatagt agttccaaaa tctaagtttc tggctttgag agaccggaaa  15780
taaacaatgt ataacattca tgttgcttgt catcaaccgt taactggtcc catgagtttt  15840
ttacacactg tgatatcatt gtcaggagcc atcagaacaa ctgcgtatgt gaaaaggatt  15900
agagtttgaa aatcaccact ggaaagtttc accagttcta caagcatatc tatctcactt  15960
agaaaaccct tccagcacca acgttgattt ctcaaccctt cacactgctt ttctaactta  16020
tagctttatt gaggtagaat ttacacatca aacactttac ccatttacaa tatacaaaat  16080
aatgaatttt aagcatattt ataattttgt taaatatcac aaaataaatg taggaacctt  16140
tattcataca aagaaagaaa gaaagaaaga aagaaagaaa gaaagaaaga aagaaagaaa  16200
gaaaactatt cagctttctc atgcctatct gcagatctgt ttcaagggcc ttgtgtactt  16260
gaagcagata gagccacctg ggaagagcct acactgagaa actggcttca tcagactagc  16320
ccagaagcaa ggtcattggt tttatttatt tatttattta tttatttatt tagtggtttt  16380
tgtttgtttg tttgtttgat taatgattca tgtggaagaa gcaagcccac tgtagacaat  16440
gccattcatt agtaggtgac cttacaatat ataagaaagg aaatcctata agccatagag  16500
aacaaaccca taaacatact cctccttagg tcctctgctt cgattcctgt ctttaggttg  16560
ctgtttaagt tagttactgc cctgacttcc attcatgata aattgtgatg cacaagtgta  16620
agcttttctt cctcaagttg cttttggtca gtgtcttaac acagtagcag agaaacaagc  16680
tctatatttt gcctcccact tcttgttcta ggcaactgtt agtctacttc tgcctttatc  16740
ttgttgcttc ataaaaatga aacaattcag tgttttgtga ctggtcttgt tcaatggttc  16800
aaaaagttga cactattatt acatggttca tcacttggtt tagggatata tatgttgtta  16860
agtttttact tgacagttaa tgttttttaa ccatttgcct gttgtaaatg atactcatat  16920
gaatatcatt tgggtattag tttttatgta gatgtatgtt tttatccttt ggggtatata  16980
cctaagagtg gaatgggtaa gtcatgctgt aaatttatgc ttaatatttt aaatatctta  17040
ctgattattt tccaaaatat atacacaaat ttatattcct ctagcagaac acagggttac  17100
aattttccat acatttgcaa cgatttgtat gtttagtttg ttgttattac agcgattcta  17160
atgggtataa aatggaatct agctgtagtt ttgaattgca ttttcctact ttgtaatgac  17220
catttcatgt gcttactggt catttatgta atttctattt tagataaatt tttatccagc  17280
tcatgtaatt ttaaattttg gtttatgtct attactgagt tagaagtctt ttatatatct  17340
gatattaaaa ccacttagca gatatttgac ttgcagaaat tatatagact atacactatt  17400
ttctttattg tatattttaa aggataagaa gttttattca ttttatccat tttggttatt  17460
gttgtttatg cttctggtat tatatttaat tatgtgctac tttttcaaat taattatgaa  17520
atatggcaaa ttagacaaat aagctttgat attacatgcc tatttttaaa ttctaacttc  17580
acattaacaa attgcttaag catcactaga tccagtttca tatctataac atggatatgt  17640
aaggtctgtg cccagagctg gtccagtgcc acagtgctct gtacccaaat actgtccgga  17700
gagagctggt ctcccaggag tgccaacaca catgtgaaca caggtaagac caccactttt  17760
gattaaattc ctggcccaaa agggtctcgc ccagagccat caggacacag gaaccaagga  17820
acagctgggg acaggatcct tcagtttctg tctgtattct ggagcttacc ttgtgccaca  17880
gctctccata accaaattac tccaggaggg aactcccagg agtacagaca cacaggtttg  17940
```

aaggagggac aagccacagt cagagacagg aaggccagct aacagcagag atatcaagat 18000
ggcaagaggc aagggcaaga acataagcaa cagaaaccaa ggctacttgg catcatcaga 18060
aaccagttct cccaccacag ctatccctgg atactccaac aaaccagaaa agtaagactc 18120
tgaattaaaa tcatatctca tgatgatgat aagcgatgtt aagaaggata taaataactc 18180
tgtaaagaag tacaggggaa aacaggttaa cagctagaag ccttaaagag gaaacacaaa 18240
aattccttaa agaattacag aaaaacacaa acaggtcaag gaattgaaca aaaccttcca 18300
ggatctaaaa atggaaatag aaataataaa gaaatcacaa agggagacca gcctggagat 18360
agaaaaccta ggaaaaagat caggagttag atgcaagcat caccaacaga acacaagaga 18420
cagaaaagag aatctcaggt gcagaagata ccagagaaaa cattgacaca acagtcaaag 18480
aaaatgcaaa atataaaaat ctaacccaaa acatccagga aatccaggac acaatgagaa 18540
gaacaaacct aagaataata ggtgtagaag aaagtgaaga atcccaactt aagggccagt 18600
aaatatcttc aacaaaatta tagaaggaaa cttccctaac ctaaaggaag agatacccat 18660
aagcatacaa gaagcctaca gaactccaaa tatattagat cagaaaagaa attcctccca 18720
tcacataata gtcaaaacac caaatgcaca aaacaaagaa agaatattaa aagcagtaag 18780
ggaaaaaggt caagtaacat atacaggctg atctatcaga attacaccag acttctcacc 18840
agagactatg aaatctagaa gattctgggc agatgttata cagagcctaa gagaacgcaa 18900
atgccagccc aggttactat acccaacaaa actctcattt accatagatg gagaaaccaa 18960
gatattccat gacaaaaata aacttacaca atctctctcc acaaatccag tactataaag 19020
ggtaatagat ggaaaactcc aacacaagga gggaaactac accgtagaaa aagcatgaaa 19080
gtaatcttct ttcaacagat ccaaaagagg atccacacaa tcataaaaat aatataaaga 19140
ataacaggaa gcaacaatca ctattcttta gtatctctta acatcaatgg actcagtttc 19200
ccaataaaaa gacatagaat aacagactgg atacatacac agaacccagc attttgctgc 19260
atacaggaaa cccacatcag agacaaagac agaaattacc tcagagtaaa gggctgaaac 19320
caattttcca agcaaatggt cccaagaaac aagctggagt agccattcta atattaaata 19380
agatcaactt tcagcaaata gttatcaaaa agaataagga aggacacccc atatgcatca 19440
aaggaaaaat caaccaagaa gatctctcca ttctgaacat ctatgctcca aatgcaaggg 19500
cacccacatt cataaaagaa actttgtact acagctcaaa gtactcattg caccccacac 19560
attaatagtg ggagacttca acaacctgct ctcagcaatg gacagatcat gggaacagaa 19620
actaaacaga gacacagtga aactaacaga agttatgaac caaatggatc taacagatat 19680
ctatagaaca tttcacccta aaacaaaaga atatactttc ttctcagcac ctcgtggtac 19740
tgtctccaaa actgaccata taattggtca caaaacaggc ctcaacatat acaagaagag 19800
tgaaataatc ctgtgcatcc tatcagattt tcaacagcaa caaaaataac agaaaaccca 19860
catccaaatg gaatctgaat gttctagtca atgataactt ggtcaaggaa gaagtaaaga 19920
aaaaaaaatt aaagactttt tagagtgtaa tgaaaatgaa ggcacaacat acccaaactt 19980
atgggacaca gtgaaagcag tgctaagaga aaaactcagc ccccagtccc ttttaaaaga 20040
aactggagag agcatacact agcggcttga cagcacacct gaaagctcta gaacaaaaag 20100
aagcaaacac acccaagagg agtagacggc aggaaataat caaactcagg gctgaaatca 20160
accaagtaga aacaaaaaga actatacaaa gaacaaaatc aggagctggt tctttgaaaa 20220
aaaatcaaca atatagatga actcttagcc agactaacca gatgtcgcag agacagcatc 20280
caaattaaca aaatcagaaa tgaaaagtga tataaaaaac tgaaactgag gaaattaaaa 20340
aaaatcagat cctactacaa aagcctatat tcaactatac tggaaaatat ggatgaaatg 20400
gataattttc tagagagatg ctaaatacct aaattaaatc aggatcagat aaaccatcta 20460
aatagtccca taacccctaa agaaatagaa gcagccatta aaagtttctc aacagaaaga 20520
agcctaggac cagatgggtt tagtgcagaa ttctatcaga ccttcaaaga agacctaata 20580
acaatactct tcaaactgtt ccacaaaata gaaacagaag gaacactacc caattcattc 20640
tatgaagcca cagttatact cccttggaga tggaatggtt tctgtctaat caggaaccgg 20700
tcacaatttc ataagactat aaggacttca taagagattt tttccatttt tatcatattt 20760
aatgttacaa atagattttt ttaagactgg ctgagtgcat attactttta gcttcagatg 20820
atatcgtgta tatttaagag gcattttgca attatagatt attttgatga cttaaaaatg 20880
tcaataccga gttgtaaata ttaaaataaa ttcctacccc cacagtgaca cacctacttc 20940
aacaaggcca tacccctagt cactgctcat ctccttaatt ggcttatttg gacaggtggc 21000
tgagccttgt atttagcaat tgtggagcag ggacttccac cctcaatctc tggcaacaca 21060
tcatttcatt attagaaatg agatgtcatc ctataaaaaa ttagagtttt cacaaagaaa 21120
tggaatgaac taagctaaac agtcgggtta atatgtgctt gtttaaaaac taaaatacta 21180
gcatttttca taataaaatc tgaagctttt catggttaag tgaacagaac agtatatcga 21240
agatactagg tttttttttt ttttcctgtg aatgttagtg aactcttaaa aatacacacg 21300
agtctgctaa cttatagttg attagctagt ttctgttaga agtagccaaa attttggaga 21360
ccactatatt tttgaggaat accattttat aagtccattg agtatataca tggctgggca 21420
tgaatcaaga tgcataaagt cacttggata tgaggtgaag agctatcagg gataatggaa 21480
agacagaaaa ggagatcctc aatgcattgc ctcccgttgt tccaagcgaa ccaccgagac 21540
tcatgaaatg cctgactgac tataaattcc ttgcctgaac attactgaat ttacacaagt 21600
tcactgaata taatcagaat cactgaaaag aagaatggct tgaatttcat atcattattg 21660
caaagtgtct aaaacttgaa tgcctgtctt ttaatttttt aatttttttt tacttttgtt 21720
ttatatttct tagactgacc tgcagttgac agagagaact cactggtagg agacatttgg 21780
tttgatttat tggtttaatc tcaagatata aaatctttct cgaagatgac tctctggtga 21840
ttgcatagag ctaatagatt ttagttttta aaaattcttt ttagacttat aaagtatatg 21900
atgagtgttt tgcctgtatg taaatatgtg tactgcacat gcgcttggag ccctcagagg 21960
tcaaaacaag acatctgatc ccctggccct ggagtcccag atgtgagtca ccatgtcggt 22020
gctgagaatc aaaccctggt tctctgtaag agcagcaaat gctctaaacc actgatcatc 22080
cctcctgtcc ctatatttta gtttttataa tttactttga accagtttca acttgggagc 22140
ataaatatag gttcatttta ttgtaacttc caaaaagaaa tgctaactaa taataaaata 22200
caggtggtga gctgtgtgat gtgtgggtat attatatcac cgaattttat tttgccttca 22260
gtcgttgatc taaggttctc ttgttaaaac tagatgtcac tgtataacat aatatcttaa 22320
aaattctgag atagcaaaga aggtttttat aaaagcatct cacacattgt gttactttga 22380
aatgagctgg aagctcattt atggggatgg ccactatatt ttatacatga gccaaaagaa 22440
tcatagttat attttttcaa ggggataaga tgatttcaaa tttgcctcta aatgcttttt 22500
gaggcatggg tttggaggac agtaaaattc tacttactta aaaggtgatg tgtccaagaa 22560
aatcaagaag aaggaagacc aacgcatgca tacttcattc ctccttaggg aacaaaatac 22620
ccatggaagg agttaacaga gacaatgttt ggaactgaaa caaaaggatg gaccatccag 22680
agactgcctc accctgggat ccatcccata atcagccacc aaacgcagac actattgcat 22740
atgccagcaa gatttttgtg gaaaagaccc tgatatagct gtctcttgtg aggctatacc 22800
agtttctggc aaatacagaa gtggatgctc attgccatct attggatgga acacagggcc 22860
cccaatggag gaactagaga aattacccaa gagctgaagg ggtctgcaac cctataggtg 22920
aacaacaata tgaactaacc agtacccccca gagcttgtgt ctctatctgc atatgtatca 22980
gaagatggcc tagtcggcca tcaatgggaa aagaggctcc ttggtcttgc aaactttata 23040
tgcctcagta tgggggaatg ccagggccaa gaagtgggag tgggtgggta gaggagcagg 23100
gcagggggag ggtatagggg actttcatga tagcatttga aatgtaaatg aagaatatat 23160
ctaataaaaa ttgaaaaata acataaaatg tgatgtgtca ttttaatatt ttcaaatcta 23220
ttgcgagcac aaggcttctg gtaggtggaa ttcatcttta aactgtgttc taaggaccac 23280
catccttcct gtcccatccc atcagccgtc tgagatttcc aatctcggcc agtcgtcaac 23340
acacgtgaat ctttctagct gaattgaact gtgaactagc tgctaagcac agccgttttt 23400
aaatttcaga ttgtagaacc taaattatga tatggtaaac aaaggttaaa gaggttgtca 23460
ctttgcattt attttgtacc ttgctgttat ggtattaagg gcatttgtgc ttgctgtctc 23520
tgaggaggta ggcatactac tattttatgc aggttagtcc tcttcccagt tctcatctgt 23580
agtagctaga agctgatcat ggaaagagtc cttataaagc agtgactgct gaaggtcatg 23640
agtcaggttt gcttttgttt tctggaaagg ggtttattat ttgtttacag atcacacccc 23700
caccctcagc ctagtagttt tcagttccct tactttaatc taagtttgtg tcttatttta 23760
atacaactca ctctacctac ttttgtaaag ctgaacatgg ttaaatgaat tcagaagaat 23820
gtgaagaaat ctttgatgtt agtaattcag aaaagttttg tgcctctgag taccatttcc 23880
taaccctggt aataaagcaa cagccctttt gtcctgtttg cctaacagga acttaagatg 23940
caaataaagt gctaatggtg tggaatttct ttggcaattg ctaaatagat actttaaaaa 24000
aattgtagta aactcttgct ttaagtttat ggagaataat agcccaaatc acaacatccc 24060
acaaggccat cttcctttta cctcctatac ttattgccag atacttttca gtgtcacttt 24120
ccttctgtga gatgctgggc aataagtacc tagctgtaga actaactttc tttctttctt 24180
tctttctttc tttctttctt tctttctttc tttctttctt tctttcttta tttcttcctt 24240
ccttccttcc ttccttcctt ccttccttcc ttcctttctc tctctctctc tctctctctc 24300
tctttctttc ttctttctaa atttattaga tattttcttt ttccttcctt ccttccttcc 24360
ttccttcctt ccttccttcc ttccttcctt cctttctttc tttctttctt tctttctttc 24420
tttctttctt tctttctttc ttaatttttt attagatatt ttcttcattt acatttaaaa 24480
tgctatcccc aaagtcccct ataccctccc cctgccctgc tctccaaccc acccactctt 24540
gcttcctggc cctggaaatc ccctgtactg gggcatatgc tcttcccaag accaagggcc 24600
tctcctccca ttgatggctg actaggccat cctctgctac atatgcaact agagacatag 24660
ctctaggggg tactggttag ttcatattgt tgttccacct atagggttgc aaaccccttt 24720
agctccttgg gtactttctc tagttccttc attaggggcc ctgtgttcca tccaatagct 24780
gactgtgagc atccacttct gtatttgcca ggcactggca tagcctcaca acggagagct 24840
atatcagggt cctgtcagca aaaattctta ggcaaatgga tcgatctggt ggatatcatc 24900
ctgagtgagg taacctaatc acaaaagaac atacatgata tgcactcact gataatctgg 24960
tattagccca gaaacctagg atattcaaga tacaatttgc aaaacacgtg tagtaccctt 25020

```
tcttagatga tgccactaga ggcactacac cattgtggca ccattttcct catgcatcca  25080
gaccactttc ataaatattc actacttttt ccctctcaca aaatgaccag tgaatcacag  25140
tgagctgtga agatatctag ttaacctttg tcaaagaagg cttttgttaa agtgtaagct  25200
ttcaagttaa agggagaaag tgacacacta aaccatagtc aatcactaat gtcttagcaa  25260
ggaatagata ataagtttac ttagtcttat ggattgacct aaatttagat tagccttaaa  25320
ggcaacttac agaacaatta aggacatagg gctggtgcta gtgatcaagc cagagatgga  25380
agtagtgtaa agaatatgga ccccttataag ggagggagga gggtaatcat gaaggccacc  25440
tggaacattg tgtcctagag aggtatcaaa atgttgacat ttggcaagac atttctttgc  25500
tctctcaaat gactttgata gtgtcttagt tagggtttta ctgctgtgaa cagacaccat  25560
gaccaaggca agtcttataa aaaacaacat ttaattgggg ctggcttaca ggttcagagg  25620
ttcagttcat tatcatcaag gtgggagcat ggcagtatcc aggcagactt ggcacagcag  25680
gagctgagag ttctatgtct tcatctaaag gcgactagtg gaagactgac ttccaggcaa  25740
ctagggtgag aatcttaaac ccacacccac agtgacacac ctactccaac caggtcacac  25800
ctattccaac taggtcacac ctccaaatgg tgccacttcc tggcccaaga atatacaaac  25860
catcatagat agagtatgtt tttctgttac atgtttatct tgcttctcag atactgactt  25920
ttggtggttt agtgtgcata tttcttcttc tttttttttt tttttacat cattaagaag  25980
tctcaataac gataaatctt agacatctct gagttacaaa aaggtgctga gggagaaacc  26040
agttttgtaa accactaaat ccagatgaat ttcttcctta agcaaataca caaaacgact  26100
tgcagtaatc acacatgtct ttaatctcag cactctagag gcagaaatag gtggatctct  26160
atgagttcaa ggtcagtatg gtttacagag tgagttccag gacagctagg gttacacaga  26220
aaatactgtc tcaaaataac aaaaaattta agctgagaaa tatctcattc ttttgaattt  26280
attttacaat tttctcttga tatatgattg atttttttta aatataattc tccttttctt  26340
ctcagcctgt cttcctctca tatttttcag gcttcctcta atacacacac acacatacat  26400
acatacatac atacatacat ttccaaaggc taatacttta atacttggtc accagttggt  26460
gaagctcttt ggggaggatt aagaggtgtg gccgtgtgtg tgtgtgtgtg tgtgtgtgtg  26520
tgttagaatt tctgattttt gtcattgtga aggttatcct gcctgttgcc ttaatagtta  26580
aagcagcatg tttgagcaaa tagggctaat ctgcttattt cttccatcat aaattatata  26640
ttaaattcct aataaatatc tacagtgtaa agagaacaga tggtgatgat tcatatttcc  26700
aagcaatgat atagtgataa ttatatcagc taactggtat aagctactca atgtttatac  26760
tcacttttta attttttaaa acttttaaaa aattttattc tttaatcctt tcttacagtc  26820
cagtctttct ctccctctca ctcttcccac tgaccactcc ctgtccccta ccttcccctt  26880
gtctccaaga gaatgtcacc atcttccacc ccaaacccaa cccccactcc accagacctc  26940
cctggggcct caagtctcta gatactgctg gtcttcccat ggggccaccc tactcctcag  27000
gttcctctag cttttcccca attcaaccac aggtttctcc agcttccata tattggttgg  27060
gtcctagtat ctgcatccaa ctctttcagg tgcttgttgg gcctttctga gggcagtcgt  27120
gctaggttcc tgtctgcaag cacaccacag catcagtaac agtgttatag ctaacacatt  27180
gctgaattgc catgggctac ttttaggaaa gactacactg taatagattt cttgtctgtt  27240
agaactaagc aatggcatca gtttagagat gttagtgttt atgtgggtat atcaactaag  27300
atatgaatta ctgcatttat gtaagttgtc ttatttaact ttcatctttt tgtatgcata  27360
cagttggtat aagaatcatg tctacattag agacccaacc aagtgaataa atctgtctgc  27420
```

-continued

```
cctcttctct tttagctgga ccacaccaat tttgaggaaa gggtacagac accacttgga  27480
gttgtcagac atataccaag ccccttctgc tgattcagct gaccacttgt ctgaaaaact  27540
agaaaggtat gatcttatca ttgactttac tggcaaaaga aagatgtttt tcatgtcttt  27600
taaagaacag aaagctggaa tattagaggt tccatttaaa agtgatgcat ttaaataaaa  27660
tcgtactctt gatgaatctt gatctactca agaattaaac aatgaaacaa tgaattaaag  27720
ataataactt tcttaagaaa tggcctcttc tacaaaaata gataatgcat agtctgagaa  27780
tttctatcta gtgttggaat tgatgctttt tttactcttt gtcaagcatt cttaacaatg  27840
aggtgcattc ttagccttgg ccttttgata caaaatatca ttagtccagg ataactctaa  27900
actcactata taaccaggat ggcctcaaaa cctcttcctt tttgcattaa cctcctaaga  27960
actaaaggca tataccacca agtctggctt ttttgaaaat atttttaagt tgaagatttt  28020
tataatgatg gtggtctgag tgagaatggc ccccataagc ttatatattg aatacttggt  28080
actgagttgg agaggctgtt tgggaaggaa tgggaagtct tgcctttaag gtttcaaaag  28140
cccatgctgt tcccaattag ctctctctct ctctctctct ctctctctct ctctctctct  28200
ctctctctct ctctcagctg ccccaggatc atgcctgcct actgctaaac tccccaccat  28260
catgaactct ccctctcaaa gtataagctc ccaataaact aattcttctg taagttgtct  28320
gagtcacagt gtcctggcac aatagtataa aagtaactaa aacaattata ttagtcaaaa  28380
tacataagcc agttgaatat tcttaaaata gtagtttctt ttatgattat tataagtagg  28440
agtagtttag ctttgtgata ttaaaacaaa atatatttgg aatttttgag atgagaactt  28500
atgtattttt tctttctaat tttggtttat tatattgata atttcatgca agcatatatg  28560
tttttgtcaa gtccatcttt gattccagtc tactcaatgc ctatctgatc ctcccccccc  28620
tcaccctccc agcttccatg tgctttttaa aaatcacagt tagagctacc atatgcggat  28680
aatataggac catctactgt gttgtgggtt gcctctccag ctgcatttct gaaaaccagc  28740
tctccattaa ttactagtag ctcctcaggt agtagtggga cttcataagc ccctctcatc  28800
catgctgaga ttctcttgac atgattgtat acaggtcttg tacatgcagt tgcagctgtt  28860
atgagttcat atgtgctgtc atgttcagca catactgtat ttctgcatgt atccaataac  28920
tttagctctt aaactcatcc tacatccact tctatgatga tccctgaaca tataggtatc  28980
ttatttatag ctgaggactc cacagtcatg tcttcatata ctgatcagtt gtagacctca  29040
aaattaattg ctatctactg caaaaagtag cttatctgat gaaggttgag gtatgcacaa  29100
atctgtaaat atagataact taggcagcag gttaatacta tgtctattta tcaggataat  29160
agtaataggt tctcccctgg gtaccaagca taactcctat cttgtgaagt gggccttcaa  29220
tccaatcaga aaaaggttaa ttacgtgagt tgacatcatt catgtctctg tgtcctactc  29280
atgggcatgt ctttctgaag ccagtcttca ttatagatgg cagtgtttat atgtaagcct  29340
gttacttttt cctccagtca catgcataga attttcagca ctatgaccac cggccactat  29400
gggtgaagct tactttttgc tacctgattg attttttttt tttttttttt tacatttttt  29460
ggctcaagta tccaattact tgagcagtag ggtgtttcca tcaaactctg gaagcttacc  29520
aaaaacattg gcaatatgta aagcctgtaa tatttggggg attatgggat cccagtaacc  29580
aaaaactcta gagagataat cactgcctgg cactgggaat ttttttatta atttacttta  29640
tatcctgatc atagcttccc cttcctcctc ttcttcctcc tccctctcaa cttacccccct  29700
ctgttttcta caggatcctg tctgattaga tttcccaata agattttta cttggattat  29760
```

-continued

```
tgatgttttt tcatttccag aatcatttta gtttgaaatt gtccaacaat tctcttaatt  29820
gaaggttatt atcctatctt ctaatgactt ctttacttca ttgatccctt tattcttttt  29880
aatacattca tgccttttc cagatgtttg aatatactca tactttatta ggtgctatta  29940
ttgtaggatt agtaatctgt tgaggaaaca tggtatcttg atttttcatg tttatttcct  30000
ttctatgctg agacttgtac atctcaaata gttgttgagt tccctccttc tccttttcat  30060
tcacatcact gcctttcact gaagtcatct acaatggcca tgagagtact aggtctcagt  30120
agggttgaga atgccatttc catctgtggt gcttttagag ggaatgtggg tctgagtaga  30180
tggcctaaga aagggtagcc agctttcctg ctacctgtac aaagatacat agttgaggca  30240
tctggagcaa aatttatgtg agctgaatgt gtgaatgcca ttatacttca tgggaaccat  30300
tatactttat gaatttgaat ctttcacatt tcaaccataa tttctcatct cggccactct  30360
ggaagaaaaa ccgtaattat cttcagctta cagataaaca catcatggct tagagataat  30420
gtaatttgcc aaccactgaa tgatgaataa ttcagtcctg gtgaatttat catagttccc  30480
ttttctgact attggttggg gccattgtga ttgtgagtga cagaagccta atcaactagg  30540
ttcatcaatt aagaagagga catttaatag ctcacaaagc ctaaagtatg tgagtgtcta  30600
gatagatgac tagcctgagg gctcagtggg tccaatatat ctgcactcaa atttctactt  30660
gtgatatttt ccctctgttg gcttattttc ttagattagt tttctcctca ggttgacctc  30720
tcagaactct atgcttatac ctgtctgctc cacagaagat aataagcctc ccttcccttc  30780
ctttcccctt ccccttcccc cttctctcct tccctccttc cctccttccc tccatccttc  30840
cttccttcct tcctctctgc tttttatttc atcaccaaat ttatagaatt atttagactt  30900
agttttatgt cccctattct gatagagttt ttaaaattta tctattgtgt tttaattcaa  30960
acactgtctc agactggata cataagttct agtaagaaat aaattctaac ctatattgtc  31020
tttgatacaa ttttgtatct ctttatctta tttcttatat atttatgaaa accactcctt  31080
tacccacttg gggagtgact gaagttctca gtctgtggct gagatccatt gattgactca  31140
tctgcttcaa ttttgtgacc atgagattga atctgcagtg tgaaaaccat gagcccactc  31200
tgtgttccta actaacttat gagctttgcc agtctggaac tcttttccct cattaagttt  31260
ctttactgtg ttgctggatt aataccatct acttttattg ataattgctc tagagctaca  31320
gatttttcaa gtcctatgat taaaaataac agcttctttt cccctcaagt ctatatgtct  31380
tccatttcat agctgacaat tctttgctgt tctcgtttcc acttgtttat cattcattta  31440
tatatcaatg cctgaaatat ggtttctcat cagactatgt tcctcaaact gcatagatga  31500
gggataacag tgacctgtta ctgtcaaatg tgacactttt tttttgtatt tactatccta  31560
ctgttattgg tatcttcatc ttgaaaccat ttctttgatt tatggacatt ctctcctctg  31620
catttcctag atcattaaat tataagtgaa gtattgatga aaatttttaa cgagacctat  31680
tgtgtggaga ttatactgct actatgtatt ttagtgcctt atttttttta ttaaatttat  31740
ttacttattc cctttacaac tcaatatcag cccttcctct cctcccagta ccccctgaca  31800
caagttctcc tccattactc ttctgaatgg gaagcccccc tttgggtgtc cacccctcca  31860
ctctagcata tcaagtcact gtgggactag gtgactaggt atatcctctc ccacttagac  31920
tctctaaata ttacagatgg agaaactggc tctctgtttg tgaataaaga gtagaagaga  31980
accataggtt gactaggctt tatagatcag ctgccgttag catgtttctt agggaagtca  32040
tggtccatgt agtgcgactt ccaagctttt cattaatatc agttgtatgc tcttcctatc  32100
aagtgagata ggaccatatt tagttatgct aacttaatga taatgagaat agccattaaa  32160
```

```
gaaatccaag gcctttatct gatcattcag ttctggtctg tggtttatgg aattttttt  32220
catctcagga taatttgaaa attgagatga aagtgagact gagacatatt ttattccatt  32280
acaaaaattg taaatagttt tttttttaaa taaaaagcag tggtagtact gaaataaaac  32340
tttttcaata ctatttagta cctatcctta ctataaaaca tatttttatt ttgctctatt  32400
ttcaaagagt tagatactat taaatgaatt cagtagttgg atatgaagtt taatgatggt  32460
tctctcattg tttttcttta aaactccaaa tgggtttttc ttgtgttaaa tcacaaaatg  32520
ttccccttc attagaatgt ctgttggtat tgtcattgtt caggtctctt ttaggcaacc  32580
aggttgtatt atggctgtca cttcactgtc atttctaaga gacatatctt aagtagactt  32640
tctggccttc tggctcttac agtgcttcag ccccttcttt caagagcccc acttctaaac  32700
aaagaactat agacaactga gagagaaatg ttttttcta gaggtgagct ccctaattag  32760
ttatcaaatg ccaaggagtc atccctgaat catatttata caagcagcac taaaaggact  32820
caccaggttg tttgtatgta tgtatttatg tatgtaaata ttttaaaata ataatagata  32880
ttataatcaa agacatgagg ctatgaattt gagaaggaat gtggaagagg gacaggggag  32940
gggctgaagg gaagagacat aggaggggct agaacgtgaa caatgaaaga gaaaatgatg  33000
caaattatag tagttaaaat taaaatatat atatttaaaa caaaaaattc acctgatatt  33060
ttgttgtttg aaagttgcat attgtgaagt atgtgacagt taaaaacaca taaatatcat  33120
gaggtaacag gaaaaaagct taaaatatgt atttttgcat cttgttctga gcacaaatgc  33180
attctcagtg ttatccatca tttgctcacc cttgtcattg cttttaagaa acctagtatg  33240
gttctttaac atacaaaact tagtattttt ataaatgaaa ctggacagag tgatttcatg  33300
gaagaccatc agattatgac agatatctat tgggcagttg gtactggagc aacttcacaa  33360
ggttttatca cttacatcac agttaatctc tttgacactc atgggacaga aagtatgaag  33420
ggagatagag cagctcatat atttgcacct gcagttcact ggtttcattt tcttattcct  33480
tgcagagaat gggacagaga acaagcttca aaaaagaatc cccagcttat ccacgcccctt  33540
cggcgatgct ttttctggag attcctcttc tatggaattt tgctatacct aggggtaaga  33600
atctcacgtg taaatatggt gtcatatatt attaagatat aatcatagtt ttgtgattac  33660
agaagggtga ggacaatctt gtaaccaaag ccttttgttt tctgtttagt atttgttttc  33720
atttttttat atagaatttt attacaagtc caaacacaaa tgactgaaaa ttctatcaaa  33780
gataagtgaa aattcttaaa atgtagatct caattgatag ttcaaaatta gaatgggtcc  33840
aaaaatcaaa ttacttgttt caaaattatg ctcatttatg aatccagatt ataatgactt  33900
aatagtatat gaggttactg gcacctttac ttttctgtgc taaaaaagag aatgttagaa  33960
ggcaatctca taccaagaat gagactccat tcagtcagtg ataccaagga atgtttatga  34020
tattttctgc tcagatagat agatagatag atagatagat agatagatag atagatagat  34080
agatagatag aggtaatgta atgtttatat tttgaaaaca tatatatgta tatatgtata  34140
aatagatata tagatagaat tatatagagt aatgtagatt aatgtttatg atattttgaa  34200
aacacacaca catatatgga gagagagaga gagagggaga gagagagaga ctgaattgtt  34260
tacaaaagat aataaaaatt taaaatgagg tggtgaggtg cacatagaat gtattttgtc  34320
agcaccctat gtcttcatca ttgtaaagag aatagcagcc tgggaacctg ggctttgtgc  34380
tgtttaagaa ctttggatat atcccagatg tgttcagaag tggttattgt tttctgggtc  34440
atgcgagcat cactttgaag cttgatcata gcctgtaaaa agggtgacaa gtggaaagtg  34500
```

```
tgttgagtct gatgtatcaa ctcagcacaa tactgccttg gggtgttatg tttcatctgg  34560
gttgacttgc attgtatttc ttcaggtctt tatcctcaga ttgcatgggc tttggtttct  34620
cctcaaatga tgtatgaaca atatgtagcc gtgctactta aataatttta ttttatcctg  34680
tcccagaaaa agtcattaaa aatttatctt gataaaattg actataatta ctctagaatc  34740
ttttctagtg ctattatttt ctagaagaaa ttcttctggt ctttcttaat ccatatatat  34800
gtatgaacat aaatgtatag atgtatagat ttgaatttct ttttaagcaa attcatgcat  34860
attatattat cacatatttc catgtagatt catatattat attcacatat aataaataat  34920
gtgttatata ttatagatct gttatttaat ggtagttcta tatatgaaag aaaagactat  34980
aaaaaagata atataatttc ttctagtaga atatgtgtta taaaatgcat atatagacac  35040
ataaagatat agacagaaga atgagatatc gtttaaagat atctttgtgg tcatttttat  35100
cagtgagcac acccaagcat ttgaagatat tttcagtcaa gatctccttg tgagtagaca  35160
ttaagaagag ggagatgcag taaatatgaa aaaatattta aaattttgaa gattaaaaat  35220
agcaaaaaaa aatcacaaag cattcacaat gtattaatta tctatggata gtgattagaa  35280
gtacttctga gacaaacgga gtgctggaat gtatctctgg acccatcaca gcctttggag  35340
ccgaagatca aatttctgca aatacccaat aaaatgggta aggaaaggtc ctgatgggag  35400
agagtagatg aatgtgcaga gtgagaaggc acgagaaaca aagtgagcag gacacagtgt  35460
aatgatgttg aagggtctct tttatccctc cccatccccc atacacagtt tcactgagat  35520
cacaaagttc agtgttgtaa aactgttgaa atctagatcc cacttattta ggtaagtata  35580
atttccaaga tctattattt atttcaattt aagttttatc ttaaaatatt tatttgacaa  35640
atataaattg tcattgtaga atatacagtg tatatttcaa tatatgtata caatttttca  35700
tgatcaaata agggtaatta acatacagat cactcagtca tttaccattt ctttatggtg  35760
agaagagtaa aatactctcc tggttgtttt gagatactgt tgctaactat aatcactcta  35820
gcagaacgta ttccctcaat acttgaattt gttgctgata acagagcttt cccagcatcc  35880
tcgtccctcc tacccttact agtctttgtt atcttaactc ctcttccaac tcacagtgga  35940
aatgggacaa agttgagcca ttttaataag cttctactgt gtcaagtaac cgctgccgtt  36000
gctttactgt tgtgtgttct ttctgagcat tttcttcttc ctgttaaata aacaaacatt  36060
actgagacag atataacaat tgtacagata aagataacgg gacatacatt caaaatgtgt  36120
ttatattctt ggtcgctgta ggccatgata attgtggcat aacaattatt tagttgtttt  36180
cagtattgat agaaaaaaac actattaaaa atgccttcaa ctatgaaagg ttaagacaaa  36240
ggaaatacca ttacaaagga ccttatttct acaacagtga tgcaatttta aaatcatatt  36300
agctatagta catccccatt aactgtggac ttgtttttc tttatctgat tcagcagcca  36360
gacatagcat gctctttaat atttcagact tccagcagag aagagcaaca ggctgctgaa  36420
aacctaagta ggagaatcaa ctaaggataa tcattttttt attttatttt atttttaaac  36480
tagatgtttt ctttatttac attgctaatt ttgtcccctt ttctcatttc ccctcaaaac  36540
ccccccctgtc ccattcccct ccccttgctc actaacccac ccactcccac ttccctgacc  36600
tggcattccc ctacactggg gcatcaagcc ttcacaagac caagggcctc tcctcccatt  36660
gatgtcccac aaggtcatca tctgctatgt atgcagctgg agccatgggt ccctccatgt  36720
gttttctttg gttggtggtt tagtccctgg gagctctggg ggtactggtt agttcatatt  36780
gttgttcctc ctatagggct acaaacccct tccgctcctt gggtcttttc tctggctcct  36840
ctactgggga tgctgtgctt agtctaatgg ttggctgaga gcatccacct ctatatttgt  36900
```

caggtactgg cagagcctct caggagacag ctaaatcaga ctcctatcag caagcacttg 36960
ttggcatcca taatagtgtc tgggtttgat aactgtatat gggatggatc cccaggtggg 37020
acagtcactg gatgacattt ccttcagttt ctggctcaaa ctttgcctct gtatttccta 37080
caatgggtat tttgttcccc ctaagaagga ctgaagtatc ctcactgtgg tcttccttct 37140
tcttgagctt catgtggtct gtgaattgta tcttgggtat tgtgaacttc tgggctaata 37200
tccacttatc aatgaatgtg tgttcttttg tgattgagtt acctcactca ggatgagttc 37260
catccatttg cctaagaact tcatgaattc atcattttta atagctatgt agtactccat 37320
tgtgtaaatg tgccacattt tctgtattca ttcctctgtt gaaggatatc tgggttcttt 37380
ccagcttctg gctatcataa ataaggctgc tatgaacaca gtgatataag tgtccttatt 37440
acgtgttgga gcatcttcta ggtatatgcc caggagaggt attgctggat cctctggtag 37500
tcctatgtcc aattttctga gcaactgcca aattgatttc cagagtacca gcgtgcaatc 37560
ccactagcaa tggatgagtg ttcctctttc tccacatcct tgccagcatc tgctgtcacc 37620
tgagtttttt atcttagcca ttctgattgg tgtgagatag actctcaggg ttgttttgat 37680
ttgcatttct ctgatgacta aggatattga atatttctct aggtgcttct cagccactcg 37740
atattcctta gttgagaatt ctttgtttag ctctgcaccc catttaaaaa tagcgttatt 37800
tgattctcta tagtcacttc ttgagttttt tgtatatatt ggatattagc ccactattgg 37860
atgtagggtt ggtaaagatc ttttcccaat ctgttggttg ccattttgtc ctattgacag 37920
tgtcctttgc cttacagaag ctttgaaatt ttatgaggtc ccatttgtca attcttgatc 37980
ttagagcata aactatttgt gttttgttca gaaaaaaatt tcctctgtgc ttatgtgttg 38040
gagacgctgg tattggtacg gtgacaggca ggtagataaa tggaatagaa ttgaagacac 38100
agatatgaac ccacacatct atggtcacct gatctttgac aaaggagcta aaaccatcca 38160
gtggaaaaaa agacagcatt ttcaccaaat ggtgctggtt caactggcag ttatcatgta 38220
gaagaatgcc aatcgatcca ttcttatctc cttgtacaaa gctcaagtcc aaatggacca 38280
aggatcacca cataaaagca gataaactga aactaataga aaagaaagtg aggaagagcc 38340
ttgagcacat gggcacagga gaaaattcag ggtaatctaa gggaagctaa ataaagggaa 38400
tctgtaagca tgttcctgac agactgtgat caccagagag agcttgttac tgtagaagtc 38460
acaggtgtat actcacacgt atcttcgatt ccatgtttcc atcactacat gtaagtatca 38520
ttagttcagc ttaaatcgag accttttttt ttaagtccca gaaagctaac ggacatgaag 38580
aaagcctggt tctcacaatg ccacagttct tatattcccc agactgttat aaaagaggat 38640
ctgtctctca tatttagaca aagacaggct tttgaatcca agcctcctgc tcctgaagca 38700
agagtatttg cggtaattct gcttatgagt aggctctgcc tagggtactt tttcttcata 38760
catcccctca gtacgaatgc tctcagcaaa gcttctagag gcctgctatc taggattcac 38820
ttctcatctc tgtcccatcc ctgcgaacac ccacagctgg ttgcttctct ggattcagct 38880
tcactcacac ctgaactctt cctaagccat ttctctagcc cctctatatg tgttattatg 38940
tcatgtttta cacttacata tctatgccac ttagaattta cttctccact gaattaagtt 39000
ccatgcatta taagttaaat tgttatatat atttgggtct tttactggaa tttctagata 39060
aatcagtata ctttctttga cctgtgaagt gtatacatgt atggtttaat atccagtagc 39120
ttaaatgttc atattatttt tattcttcaa atagtttcaa ttagaattta ttcctaaatt 39180
aaattcagaa taattttatt tgttgtttta acaaatattt attggttaag catgctcact 39240

-continued

```
aagaatgtat tatatatgtc ataacacttg tgacaatata aacatatagc caataacctg  39300
gtgcaaattt attcattttt aaaatatact taaaattttt atgtgattac actaatctta  39360
caaaatggat taggtgaaac atcatctttg taatatgtag attttttag ttcagttagt  39420
ttttttaaaa tgtgcttagt agtttctgga atcaatcaca tatcatacta atacaggtgc  39480
tttttacttt ttatataatt catagctatc atttttctca ttaaattatc ttagctagac  39540
atttcagaat aatgttaggt ggtcatagta gtcaaggttc ttttgctttc ctgcctccca  39600
cacttgtgtt tatcaactat tcctgattct ggaagaaagt ctttcttagg ttaacaagca  39660
atgttgcgat tcagctttgt agaaatttta accagatact gatacttttt atcaaattag  39720
ttatttcatt gttactgtga tattcacagc ttgttcagta gtatattagt attctgttag  39780
ttgatttctt ggtatcacta gcattaatat tctaaatgta acaatataca aaatgtgctt  39840
gcaacaagtg aaggtgatac tattacttag tagctgcaca agatatagca agaaactctt  39900
aaacctcaca tgctagcaaa gcaagcactc ctgaactaaa tccgcaggcc tgtaaaaatg  39960
cagtattttt ttttaagtat aaagataaag tccatataat ttagctgcaa gcctgagtct  40020
gcacttgttt ttgtatgaac ttttctctat ggtctgcata tgcactcaac acagacttac  40080
ctgtctgtct ctagaaacat ctgattattt gtcaggtaca atggaaatgg cttaagggta  40140
tgcatctaca gtgacttaga gctttgttct ggaagtgcat tcaggtgtcc cctggtcggc  40200
tgcagtgaga actgaattat tcctaccatg agtgcaagtc ttttagctag tttttacatg  40260
gtcacttacc cagatgacac atggtcttat agtgggaagg aagtatatat agactggcct  40320
ggaattcata ataatccttt tgcagccttc ctagataggg ttatactcat gtggcaggcc  40380
tctgcatagt actcctagac tcaggtcatg cttccagggg tgatgttata ggagcgaacc  40440
ttgtaggtaa ccagagtttg ccaataagga gaactgtcca aacaacagaa gtgcctgagg  40500
tgacacagaa taaatataca ggaataagaa tagtaaggaa gaaggcatga actcgtgagg  40560
gagtcagatg ggacatggat ggagttggaa gtgagaaagt ggtaaagtgt ttctgtgtgt  40620
gtgaagtatt catgtatgaa attctcaaaa aataaatgga aaaatgggta tttgagtttt  40680
atgattctga atttagtgtt cttattgtca taaacattag tattaagctt attttctaag  40740
gaaaacaatt aagaaacttg cgttttgatt tatgcctgat aaaattgtta aaatacgtca  40800
ttgaatatta tcttatttaa aatagttttg catttttttct attggataca attctatttg  40860
gagtagtatt tcaatgtggt gaaaattagg gaattttttt tcggaaaata gtctgagcag  40920
cagaggacat gcaactcgca tgcaccaatg ctgattttta aaaaggggct gtgctttata  40980
gattaactga ggtatcagtt acagtttttc ttcacactta aaaaatgtca tgtggatcta  41040
tgaatggttc cattgtaaat attagagaac atgatacata aaagagatta ggggaaatga  41100
tagaaggaga gagtctagaa gtgctggttt tgtccttgag aactgtgagg tagtaaggtt  41160
tatgctgtgc tctacaaacc atcttgttat tgaaattttc cagtaaagaa acaagctgta  41220
tcttactgtg tgaatatatg ctcctccaga gtaatactgt cagtgtcctt atgagatgac  41280
gtgtattgtt gaaaagatga gtatgtcttg ctagttgagg caagatgaga tctaactcat  41340
tagtagcaat atgtaaaata ggcatgccat ttaaagtatt gaaagctata attactgtat  41400
taaattgtaa tcaaataatt aagcaaataa gtctagtatg ataaagtagg ttattgaaaa  41460
ctgtaatgga gttctaacat tagtaaacag aagaaaaaca tttaagctta taacttacaa  41520
cttgaaaaaa aatctgtgta tttataagag ccagaagctg gaaagaaccc agatgtccct  41580
caatagagga atggatacag aaaatgtggt acatttacac aatggagtac tactcagcta  41640
```

```
ttaaaaacaa tgagttcatg aaattcttag gcaaatggat ggaactagaa aacacacaca  41700
catggaggga cccatggctc cagccacata tgtagcagag gatgaccttg ttggcatcag  41760
tgggagaaga ggaccttggt cttgtgaagg cttgatgccc cagtgtcggg aaatgtgaag  41820
gtgggaaaga gggagtgggt gggtgggtgg gtggataggg gcacaccctc atagaagcag  41880
gagaatgggt gatgggatag ggaatctcca gagagggagt tcgttaaagg ggatagaatt  41940
tgaaatgtaa ataaataaaa tacccaataa aataaattat agataggcca tatcaccctg  42000
aatgtgcctg cttagtctct aatataattc aacatctaaa tatgttaaag atgtttagct  42060
atgtaataaa aatatgatgc atatgtaaga tgatgtacaa taagaaatat tttatatact  42120
ttttaaaata agttttattt attagatgtc tcaaacaatt ggcatattat atctgggtaa  42180
gaggttagaa attctttttg atacctccct ttttatttgg cataattcaa atccatttca  42240
accctgcatg taaaaggaaa gaattatatc tcattttgtg attatcttgg aaacttttcc  42300
aaaggcttga atcttctttt ctatgcagag ctttgaatta tactaatatg aagtgctgta  42360
tataaagtag agaatgagca tctacaataa aggcaatgat taatgacagt taggttgtag  42420
ttaattccct gtgaagatga aggtgagata caaaacatgg tcatattctg ggactggtgg  42480
gacaggtagt gttggcactt gggatttgga aaagccatca tagagaacaa tgaaaagcaa  42540
attaacagta aaaatttgat gtcacatcta tattaatctt ctttcaagat ttagccctaa  42600
gttctatttt actaagttat cataaaataa aaattgggag atgatgtctt tttgtaattc  42660
aaaggccatt tgtggttcaa atccatccat gtacatttag aagggttgat gaatcagttg  42720
aacggcttgg ttggtaatca gttttggatt attgaagttt atgggtttat tggaaactgg  42780
ctcaagatag agtgctctag tgcacacctt actgatgcac atacccagct ctacactggc  42840
aaagggaagg aacaggaccc aagcggctgg ctttaaataa taccagtggt gctggcatgc  42900
tcttccctcc tgaatccagc tccgctcaat ggttgtactc ttgagaagct gttccttctg  42960
atcataatac catggctcaa aatccttaaa gaagttcatt ttgaaatttc ttagtgtctt  43020
gcttttcttg gcctccattt cttcacctgc ctgcatagtg aaaacagttc gtacatgact  43080
gagagttgtg aaatcctctg ggacatattt taggaatggt ttgtgacatg tacatgttac  43140
tagttaatgt accacttcat caagtacccc tttacaatat agttgctatt catgcaggtt  43200
ttagtgaaca cctcacacaa acttgtctct aaatgacttt tgctgtaaac taataaccaa  43260
gtcttatttc agagtatgca caaagacact atcagcagtt tcataaattg tccaaccttc  43320
tctgtaaaat tattttaaat tattgtaaag atgaaatttt cataattaaa atgtgaacaa  43380
gaaatgaaat ttaatcactg ccttctcctg caggaagtca ccaaggctgt ccagcctgtc  43440
ttgctaggaa gaatcatagc atcctatgat ccagaaaaca aggtggaacg ttccattgcc  43500
atttaccttg gcataggctt atgccttctc ttcattgtca ggacactgct tcttcaccca  43560
gctatttttg gccttcatcg cattggaatg cagatgagaa cagctatgtt tagcttgatt  43620
tataagaagg taatactttt tggaagatgt tatttggtct tgttttacta tttcagtgct  43680
ggatattaaa ttcagggttt cttgtatgcc aggcaagttc tttgctgagt ttgctgccct  43740
gcacagtctc aggtattcta cctgacatgt cttcagtgcc ctaaatgtga gcttgtacaa  43800
gaataggtgt gaatacttat tcctgtttta ggtgcctatg aaatatatgg caggtgcaag  43860
tattgttctg agttatctat ccttgataat gcaaagtgat tcagtcgaca gttattaaat  43920
atcttctgta aattacctat atttcagatg tcatatttta ggggaagtat ttgaatagtt  43980
```

tagtggtttt ttttaattgt cacacaaaat agacaagtga gcagtaagct aaatcaatgt 44040
cagatttttt aatccacttt ttttcagtta aaatggcaaa tagtacaaga ctcattgaca 44100
aaatatcatc ctatgataaa attctatttt tactagcaat aatatatcac tgttaatgat 44160
aacctaagaa atacattccc accttagcca gctgccacag atggtgacag tgtcacagtg 44220
gtgacactca tccatctcca ctgtcttact ttgagtttga tttttttgtc atccagtgaa 44280
ttctgaaact ttataacatt tttgaaatag catgtacgtt gagatcatgt gaacttaact 44340
ttgcttttct gcattcatta gctagataag aaggctttgt aggatctaaa tagattgaaa 44400
tgaacagtaa acctccctgc actccagcca cagccacctg ccaaaccaag caggcctctg 44460
accaagacaa agactctcct ctctgtggga cctagcctgg agccccgtcc tcctgccctt 44520
ttcccttctg cccggggtag agtctgcccg ccggttccca ctctgttctc agttcttctg 44580
tgacaggcat ctgaggtgtt caagactgag aacttgacgt tcctagcctc catgtggccc 44640
agggacccca gaactggctc ttctacaacc cccagtggaa ggcctgccca gtggtgccat 44700
gtgggtgtgt gcagttaaac gccctgcatc tgccttgcct agtggcccga gccctgatag 44760
gatgtgggat cccacttttt tttttattag atattttctt tatttacatt tcaaatgtta 44820
tcccctttcc taatttcccc cctgaaaatc ccctatccta tcctctcctc cctcccctgc 44880
tccccatccc acccattccg gcttcctggc caggcattcc cctattctga agcatagaac 44940
cttcacagga ccaagggcct ctcctctcat tgatgactga ctaggccatc cacagctaca 45000
tatgcagcta gagccatgag tctctccatg tgttttcttt gattggtggt ttagtcccag 45060
ggagctctgg ggttactggt tagttcatat tgttgttcct cctagggagc tgcagacccc 45120
tttagctcct agggtccttt ctctagctcc ttcattgggg accctgtgtt ccatctaata 45180
gctaactgag catccccttc tgtattagtc aggtactggc agagcctctc aggagacagc 45240
tatatcagtt tcctgtcagc aagctcttgt tggcatctgc aatagtgtct ggggatccca 45300
ctttttaact cacatctaaa tgttgtctta aattttgaca aaactcaagt tatttcagtg 45360
gcaccaatgt gacttcattg ctctaccaag tgatcaaaga aagatatatt ggtggtattt 45420
agatattacc tttatctttg ctattttctt tctttagtaa cacattatat atatatttgg 45480
cttataaggg ctatgggtct gaaattgacc tctaacaagt aatccattat accactacag 45540
tacatactca aggtcagttg tgttataaaa tcttgatagc catactttat tgcttaaaaa 45600
acacttttat gccaggcgtg gtggcacacg cctttaatcc tagcacttgg gaggcagaga 45660
caggcagatt tctgagttca aggccagcct ggtctacaaa gtgagttcca ggacagccag 45720
gactacacag agaaaccgtg tctcaaaaaa aaaaaaaaaa aaaaaaaaaa aaacaacaac 45780
aacaacaaaa aatcagtttt atgaaggcag agaagaacaa aaagaagtca gagtttaatt 45840
caatctctta tgctacaaaa tcatcaattc ataagttcca agaaaacatg aataaacaaa 45900
aattttagag attatttgga atgtagaatc tataaacttg ctatcaaaga aaattgaatt 45960
tactttaata aatatttgtt aaaagtactt ctaataaaga taataactaa gcatatgtat 46020
attgcaccaa tgaattattt aaatgtgatc taattttatc tacccacaag tttctactat 46080
agttgctatt atccttcttt taaggaaccc aaatcctata aagaaagaac attgaaaaaa 46140
aaggtatttc aaaactttaa aatagataag taacagcctt agaaaatggt ttccaagtaa 46200
ttaggtaaaa cagaagtatg gaaacataat attgaggcaa aggacatgtg aagtaaaatg 46260
aaggggatgg ttaattggta atcaagtcct tagagatatt ggtgaagaat ttgaagctgc 46320
tgcatattta tttccctcac aacatcacct actgtgattg ctgatcaatt agtttatctt 46380
atagaccaca tttaacttcc cgatactggc ttatcaccaa agagtatgag gacatcttca 46440
tggttctcta gctggtccct acttgcactt tgtcttggct tgtcccgtag cttatatcca 46500
ttcccctatc cgtactgttt caggttcaag gcaaggacac ataggatcct tccaacaaca 46560
tctgcaattt atagtagaga aatccactcc cattaaattc tgaaaccaaa catgttatac 46620
tcaaaataat gaatactaac acaagctgaa ctttgcccat cattttgaag attaccaaga 46680
taactgaata ttaactatgt gctatggatg aagctccatg ctttagcctg tgcattgctt 46740
tatctgacac tgaaattcct tctaaacata tgtaatctac cacagtgggt tctccctctc 46800
ttcttatttc tctaataata ttttgtaatt acctatactc attccttctt catctttgct 46860
tctctaaata tatctatttt ataattttat ctctataaaa tctttcatat ttttaatcca 46920
aattttgagc ccactctaca ttctgccttc cttaactaat ttatcatatt atctatatga 46980
taaacacaca ctcacacaca tatgtgtgag tgtgtgtttg tgtatatata tatgaatttt 47040
ttctaggtta ctcccaggaa agaattgtat cttaataaat gctaattcct gatacataca 47100
gaacaatggt ttacatctat taaatactca acaaatatgt gatgagttga aacatataaa 47160
atgggtgctt tgctgcaaag ccatctaaca gaaaataagt tactaaattt caccaggcaa 47220
aggattactc tatttcatga tcataattta tctaataagt taaaacatta atttatagat 47280
aaataaatgt ttttaatcag tgatcttcca tgtttttcct ttgtaatatt tgaagacttt 47340
gttttgttaa cataaaaata ctgattcagt tattagtaac atacttttgt tggatttaag 47400
tacttttatc ccaaagaatt agtgaaggac tttatgaaaa aattaagaca aggattcact 47460
gccttaggtt ccatctttta tttctaaact ttcaattttt ttattgtttg acgtctttaa 47520
atggttacat aattaatttt agttatctgt atcctcagtt tctctctcat tccttgcctt 47580
ccctctctgg aactcattgt agcagtactc gtctatttta atgccttttt gcgtgtggct 47640
cattaagttt aatgagagca tgggtgcaat gatatttagt ggagcaaggg acgcttacat 47700
gtgttgcaga catgagaaca gaataggaca actcctctct aacaaccatg agcctgcctc 47760
acccatccta aaatgtttta ccatgtacag ataaccccag ctctaatggg ttcatgactg 47820
taagtggtat gtcctgtagc aaaggtgtgt gtctactctt tctataggtc agctcttaaa 47880
ttcttcatgc tcccacttct gccatgttct ctgaatcatg gtggaatgat acaaccttcc 47940
catttatgcc aaatattctg ttaccactta tttgccactg gttaggtttc tgcagtcacc 48000
gggaaccatt gtagtaagaa acttttacag taacagctgg gtgcaagctc taatctatgg 48060
tataaacatg agtagtgaga aggtagcttg ataacatgac catttagcag aataacagtt 48120
acttgcatac cttggtggtc aaagacctcc ccagtcagag acttaactag ggttacagaa 48180
ccaaatataa gttcccattt gtggaacagg ccatacatat aatcagcaag caggtagtca 48240
tcaccataag aattacacta ctgctctact agaggacaca ttttacaaag gtatgtgatt 48300
actatagctt atagtcccag ctgggtaagg ctgatgatgc tttccccagt gacttgcata 48360
tgctgcctct ggcactacga accagtaagc aggaagctta cacttcatct ccatgacctg 48420
tgaccatagc atacaatact taacatcaag ttctggtagg tatccaagag cactgggaaa 48480
agcctgtgtt gtttggggca cctctgagat ccccccttgtc agtcactcat agggaggtat 48540
cccctaccca gcactgggac ttttgtttga ttattcatgg tatctgagag gaatagcatc 48600
taaaagaaga cctctattta agctttttaa agattacata tatttcttag aactgtagaa 48660
tagtttacta aaatggtaaa tttgaactca aatatgtata gtttttaaac aggttcaact 48720
attattaact aatttctcaa ggcatgatat atgttattgg caagacaaac actaataata 48780
atgtttacaa atctctatat taaatcatct tgataattgc aatttgggac acacttcatt 48840
actacatagg atagcatatg ttttcttgca ttattggtga cagagacaga tgatgagtaa 48900
atgagtctct gccagtgtat ttctgtatgc tgataagatt gtattattgt ggtgctggag 48960
agatggctca gcagttaata acactgacta ttcttccgaa ggtcctgagt tcaaatccca 49020
gcagccacat ggtggcttac aaccatccgt aatgagaact gacaccctct tctggtgcat 49080
gtgaagatat aataattaat aaatcttaaa aaatagattg tattattgca aatcctatcc 49140
ccaccacata gtcctctgtg gaactccatt ctgagaaagc tagttaagtt aaaactaggt 49200
agtgccattt tgaagccact caacagagaa tgcctcagcc acccaaagta gagggaagat 49260
gactgtctac cctactcctt attgaactct ccactgtgaa ctactacttg ctactcttct 49320
tgctgtctac tgtctcccca ccatgttcct ttcataagtc tttaccttaa gtagccctca 49380
accctggcct ccattttcat gtctaatgtg taatactatc ctcctctctt tctctactgt 49440
ctctctctat ttttcttact tttgtcaaca tattattaca cttgatattc taaaaatgaa 49500
aagctgagat cctcacatga ggaagatctg gtagatttgt cctttggggc ctggcttacc 49560
tgactcagtg taatatttat ttctgttaaa aaaaataaaa gaaaaacaaa tccccaaaac 49620
tcaaacaaaa ccactcaaaa caacaacaca aaagattcaa ccttatattt tgcaagtgga 49680
aataaaatat cattcttatt gtcaaagaca acaaagtttc tatatgacag aaaatatcta 49740
aatgtaagca tttcaatata tttgtttttc agttgtatat ttttaaagct gaaaaagtat 49800
aacagtaaca aatatgaaac aaggttgacc tctcaggtta agatacattc agtcacatct 49860
tactaatgtg ttattgatga atacatttta tatttgtttg ttgacatcac ctaacttgcc 49920
actttttctt ttagacttta aagttgtcaa gccgcgttct tgataaaata agtattggac 49980
aacttgttag tcttctttcc aacaacctga acaaatttga tgaagtatgt accattgact 50040
taatgtttta tgcattttat tagaaatcaa acaattctaa agaaagattt atcctgcatc 50100
agctaacagt gataagtagc aaagtcccac caatagctag tttggctatt tctggaaact 50160
gggaaagcta gtcctgtagc agagcaccat tctgaggtca ggtacgattg cccaactcaa 50220
acatacctca gcttgctctt aataatgttt ttcaaaactt gatccttatc agacttagct 50280
tgcttccttt tagtataata ctttaaattg ttatgtactt tgactaaata tgatactctg 50340
agcagttctt gttctgtgct gtcttatgtc acaagtaaat tcaaggacct tgaggacaga 50400
taccatgttt tatttatctt tgcattttca atatttaata gagcaagtgt tacggctgaa 50460
ttgagtagca gagagagaga gagagagaga gagagagaga ggaaaacctt tttggagagt 50520
cccttgttct catgtgttct gtgtgagaac actagcttta ttttaaaaag gtattaataa 50580
aacctaggcg caatttcaaa gatacacaat cttaattcca ctgaataaaa acataatgca 50640
taaattgtaa tatgctaaga accatgaatt tattgattgg ataactcttc agtgttcatt 50700
ttcttccaca tgtgtctctc tgcttggttt tgattgtgga atgtaatata ccacttgatt 50760
ttctctgtgc ttttattttt cagggacttg ccttggcaca ttttatatgg attgctcctt 50820
tacaagtgac tcttctgatg gggcttctct gggacttgtt acagttctca gccttctgtg 50880
gccttggttt actgataatc ctggttattt ttcaagctat cctagggaag atgatggtga 50940
agtacaggta gtggtctttt tcaaagcttg aagaaatttg aattgggctt ctctaagccc 51000
taacaataaa actatgccat gtcacttaga agggattatt ttaattctgt aaataatttt 51060
ttctataaga aaaaggcaat tattttccct attggtctat agaatttctt tattcatgtt 51120
ctaagtaagg ttcagtacat tttatattca taaagtttag gtaaaatgga tattgtattt 51180
ctttgaactg gaaggaatgc ctaaattttg tatggaacaa actggcctct tcctctccat 51240
atagtagggc cattctacca aagcatttat tacttttatt ggtaatatga gttatatgat 51300
gtgcttattg cagagaattt gtagtttgcc tgtttgaatg tgatagaaag ttgaaaatct 51360
ggggctatac agacaggttt ctgttttagt ttgtatatgc tttcatttgc ttcacaaaat 51420
ggaggtgatc tcctcttaga gactttgtaa aggattggat tagagatatt gtccaaagtt 51480
catctaatgg cgggtatctg acacttttta aaaatttttt ctcttcctgt ttttctgtga 51540
cagagcgtct ctctgtatcc ctggctgtcc tggatctcac tctgtagctg atctagaact 51600
cagaggtcta cctgcctctg cctcctgagt gctggattta aaagtgtgca ctggctatga 51660
ttttgtttgt tcccagctgt ttaataacaa aatgtttatc tatgtaataa aaatatggaa 51720
tttttcaaaa ttttgaatag ttattagtag ataatttgac ttgtttttgt tattgattgt 51780
ttgatcaatt gattggttta cagagatcag agagctgcaa agatcaatga aagactcgtg 51840
atcacatcag aaattattga taatatctat tctgttaagg catattgttg ggaatcagcg 51900
atggagaaaa tgattgaaaa cttgagagag taagttgaca taattacaat actggtccaa 51960
ttttatattt aacatttaaa actgaccact caggtggatt ttcaactcaa ctcatctaaa 52020
actcaaatat atgtatgtcc tgagttttac atggtttata tgtcagtgcc tataatcatt 52080
ttggtgagca aatgttttct tttgtttttt gagactggtt ctcaatatac ccttggctag 52140
catagacctc tgtatgtaga tctagacctt aaaggcatgt gccaccacac ctgtccctgg 52200
cttatggttt tacagttgat tcagtttttt tgtagtgcat agatagttat ctcttactaa 52260
tgattctgct atactagttc acagttgttt catacccttta atttaattaa aacaatgatg 52320
aagatgctgg ggggctaatt gaaaccataa atggaaatac tgaaatatat aattgtaaga 52380
ggaaagggtg atcttgtatg acactgtact tcaagtatta tgacacaaag agcgggtgac 52440
agccacattt ggacaacttc tgttattctg agcctgagga ataatgacaa aggaaatttt 52500
ccttagggct actcatataa attgcttaca agaggctaag tcagtccttg taacaaaagc 52560
catctcctga gatggaatct ttacttagca cctgtgtgta tcttatcttc tttcacctca 52620
gataaccttt tgcagatcag taaagattac ctctgaccaa aaaaaaaaaa aaaaaaaaaa 52680
gcacagcaag gctgatacat cattactaag ataattttgg gtaaaataac catgagcatt 52740
gctgtggcca tggaccgttt ttatttagtt gacttccgtg tcctaccaac tacagtcaag 52800
gaaatgtttt agacttctgg ggatgagcgg accacgaaag atactactaa tttaaagaca 52860
tgagatatat gagtatttca cagggaaaag gaaataaaga gtgctctttg caatggtgtg 52920
aatttgatta tttcatattc agggtgctgg agacctgtag acaatggtaa ctgagccaca 52980
gctgtgtgat tggaacaaca atggaaatgc ttaaatgtta agtcctttgc catgtaaata 53040
gaaatagcaa aaagagtgtt tattttccaa atactattgc tcacctgttt ttgttatgcc 53100
tttcaaggta aatctaggaa aggaattgca ttttctttct agaaacatcc ttaaagatct 53160
tggggaattg ttgagttgat aagagttgtt tctcacgtta acaggttgag tgctcccctg 53220
cactgcctgt aaacacagtc atggcagggc tggttatcac agaatccagt tttctcaggc 53280
ttcataatca gcttgcagta ggccgttcct gtggctgacg ggtttttgtt tcctttttgg 53340
ggttggtttt ctttttttga cattggtatt ttacccctct tttcctcaca taataaaatc 53400
catctttcct attctgaatt tcaggctggt taattctaat agctagcatt tgtctggttg 53460

```
taacctgttt gatacatcat gaaattgtta cctgaaaaag ctggagagtt ctgacgtaaa  53520
aaggaaagca ggaattgctt taccccgcag agtaaataca atgttctagg ggagactgac  53580
tggatgttct taggattacc tcagcctaga aagctgttga actcggccaa aggctatgtt  53640
aatgttcttg aaaaaaaaat ctgcctttta ttgcttttta gccattaagg tactttcaat  53700
tttttatacg aaactgatag aatttttta tgactcataa aatgttaggg attttatgtt  53760
agtgtataga tgattctgtt gcgtgtttgg gatcaattat tctttttcct atgtgacttc  53820
ttccttttct gagctgttct aaaatattgg aacagttttg acactttact accatttgta  53880
aacattcttt ccttttataa ataccaggct tatcaatgta tttttttatc tctagaagaa  53940
agggatacac attgctcttt tacatctgct atgctgtcat ctaagcttaa ttacatctct  54000
acaagggaag tattacggtt tttttagtga tagaatcaca tttaattaga tggaagagtg  54060
tcttccttta aacataagta agactagtcc atcttcagta caaatttatt gaaacactac  54120
aactcactag gctgatcaca atataggcta tacacatgac ctctatccgt gagctcaata  54180
gtatattgtt ttctttgagg acttattttt tttttttttt agttctacca cttgacaata  54240
acacttgctt ctatggatta gaggaacagt ggaagcatag tgcctgtata tcatgtgcct  54300
tcctgcacca ggctgtagat cagatactgt tcctttccga cagagccttc attttgtgtt  54360
caccattggc ctttgcccac acaagaactg gttgttttta caaatgatca caattgggtt  54420
gaggtttatg gctcctggaa cagtggcgag gttgactgca gtattgttct ccatcttcct  54480
tttgtcacta aagcatttaa cctcttcctg tatatgttaa aaaagtaaat acctcccagt  54540
tgaagtacag actagaacag actagaggac tgcaactcta gtgaggtgcg actgcagata  54600
attacatgac aatgagaggg actaggaggg aggagctact ccctgctctt tgaaggaccc  54660
cctgcaactg agtgacttgg cctctgactc cagagtggct cctgggaagc tcaggcagca  54720
gctcagcaga tgtcagcaga tgtgactgag agacaatgcc cagtcacgtg tttctcactg  54780
ctctttgata tacacacctc gccagtgcta tttaaagcca agctagaatc tcaaaactac  54840
taagaatatg atggataact acagaactgt ccctttttgtt cataaagctt gtaacattgt  54900
tttcccttcc acacatcact tcaagcgtta ataaagaagt tactaaagat ataaaaataa  54960
tataaaagta aatctattta gataatacaa tttaaataaa ttttaattat aattataaat  55020
ttaattatga tagcaattga agttcttaat tgttttatgt taacaagcat tctgtgtaaa  55080
taaatggtat attctttaag agtcatataa gctaattaag gtcaagagaa gttttgtaac  55140
ttgcccaaac tttggactgt atattcagat tttgtattct aagacacctg attattgaaa  55200
gaaaataacg tgtcacgtct tcttctgttt tgcacagggt ggagctgaaa atgacccgga  55260
aggcggccta tatgaggttc ttcactagct ctgccttctt cttttcaggg ttctttgtag  55320
tctttctatc tgtgcttccc tacacagtca tcaacggaat cgtcctacga aaaatattca  55380
caaccatttc attctgcatt gtcctacgta tgtcagtcac acggcagttc cccactgccg  55440
tacagatatg gtatgattct tttggaatga taagaaaaat acaggtaact tccatgatgg  55500
tatacttaca tgattttgga aacattttag aatttgtata gtggggaaaa tctctaaaat  55560
gaatttcttg attttggatt tattaatgga ttagatttcc actcttcatt ttcatacata  55620
atttcatgag cgcttacagt gaaaatctaa tgaaataaaa tcctaggaga ttttgtaggt  55680
caaatgaatt taaaataatt atttctataa tctagaaaat cccatccaag aaatctgtga  55740
atagatcatt tctaggcagc ttgtaaatat ccaaaaacat tgaaaataaa tttcagcagg  55800
aagttaaaaa aatgttctag ctagccctgg aatgctcacc ttgtaggcca ctgtactttc  55860
```

ccatgaagca ttgctatgtt ccaagaactt cagcttccag cagaccagaa agttacctga 55920
tccctggcca ggtgggactt acagggttat tttgagcatt aggtaagaag tagtttattc 55980
agagcaagtt gaataaactt ctgagaaaaa aaatgtctta ttatccctta aaatgtatat 56040
ttaaatattc agtgcagaaa gtaaatcatt gtgaagaata aatgtgggat cgagggtaga 56100
ctgcttttta agaggttctc caattgttta ccttggactg atgtcacaaa tgacagaaaa 56160
catgtaattt tggcttttaa atctgtttta tttggtcttt gaaacttttg aattaattaa 56220
tagaaattag aagtagagag attatcatgt gtacctctgt ccacaggcat ccatgtgtat 56280
tcacttacgt gtattgagtg tcttctggag atttgcgatt atgtagtaat ttgggttccc 56340
acagttacag caactgccct caaatgtgta tagcctgccc agctcatcaa atcttttaca 56400
gccttttcta ttcagcgttt cacccccaag gttaaatcaa cttgagttgt gtgactagag 56460
cagtcactca aacttagaat catagtggct ctatgacaaa tcttatttcc ctgctgacat 56520
caccctagtt gggtggaggg atgagagaag aaagacagag agaaggggag agatgtaaga 56580
ggagaaatgg gagtatctat gaacagtaac acagaaacat ctaaaaaaaa aaaagagaag 56640
gaaatgagac aaaccaatag aggaagagag gggggtacaa ggaagaaaga tcagagcaaa 56700
gattccaggt gcacagattt aagtcttatg ctctccacct ttcctaagaa ccatgtggct 56760
ggaattctct gatggaggcc tttctcagag aactgagaaa tagttctatg aagtccttct 56820
ccttcccttt atataaggag caatgattat gatgttgctc gtaaagagag tgttaaaaaa 56880
aattgttgtt cttttcactt gtactagcct tgaactggta catgaataat tgtcagggtt 56940
tcattagaaa ttcatattct atataacagt ataagaaaga aacaattgca ctgatatcta 57000
atgtataaaa ctaatttcat acattaatat atttaaagaa tatattttga ctatgatgag 57060
tcctactgct tggtacttta actttaagac aattgtaacg ttaatttatt aagaaacaat 57120
ttctaattta attgttaaaa tccatacaag acactgtaat gttagagtgg aagaagatat 57180
aacaatacat ttttgctatt gtgattctac aattgaaaga tttttgtctt cattgactag 57240
gatttcctgc agaaacaaga gtataaagta ctggagtata acttaatgac cacaggcata 57300
atcatggaaa atgtaacagc attttgggag gaggtgagat ttctaaatat ggtcgatttt 57360
taaaatatgt aaacaattgt gctttttcct tttcttgcac ctaaatttct actcaataac 57420
atataagatt caaaagatat tatatctcat agggatgtaa ggagggctat cctcttttat 57480
aaggtgaaaa gtgggtaacc aggaatatta aatgcagcat aaagtgcctt tatttcttta 57540
aagtcatata attgatttca tataatgggc caggaagatg attaccttcg atactagatc 57600
taaatcctgt ctctgcaata cactttccat gtaatctaaa tcatattatg ttcaagttat 57660
taagcctcaa gtgtcttcat gtgtaaaata gacattattt ccctactgac taagatgatt 57720
tacatggtct gttcattagt gcactttgca aataatggtc tttcagtgaa gattaacttc 57780
tctaatcatg actcctaagt cttccctgcc tatcactcag aattgatgag ccactgagtt 57840
cccatgagca gcttccagca gtttactcac tctgtatgtg gtgtaggtga cctcatccag 57900
cctcaacatc agtgagctga tgacatgcaa gtgcaaatct ctaggcctaa tttcaggctt 57960
gcatgctcct catcaacttc acagtcatca ctcctcaagc tttactgccc tcgtgctcca 58020
gcatgttctc catctccttt cctggccaca ctgagaggca agctaggata ggatgcatta 58080
catgccaaac tttcactaga taaatatttc tttttaccgt gttcaacttc cattcttcct 58140
ccttactcct aattgaatcc tcaatgttga acttagaact actgtttatg aaaggtgaag 58200

-continued

```
atagacccat acatttgaaa tctagatgaa atacaacgtt acttcctttt ttcccttact  58260
attttaacct ttgcttttgt ggttctctct tgtttcaaga catcatcatt ccttttaata  58320
ctattgtttg ggtctgagtt ttcatattct ggagccttag tgatattggc ataatattaa  58380
aaaagggagt tgattctgta gaaagcaagg caagaacaat tgtgaggtgc aagtggatca  58440
taagaagtag cagacaatga attctcaggc aggttacctt taggaaagag gatcgttgga  58500
tggtgtggac ctaaaaatag attcacttaa aactaggcac acaagtttcc caggcttctt  58560
catgaccact atttgatgat atatattttg ctttggagac agtacctccg agcttccatt  58620
gggcaataga gaggcaagca atttttaaaa gaggatttct ctccacccca tacatactct  58680
tgtacagaaa aattattttg aatccactag caactttgtc acttgtattt gtagccaatg  58740
ataaatgttt ggagcaagtc ttagaggatt ggaagtgagg attgccttgt aaatctacct  58800
tgtgagctac ttgtttttga ctttttgctg agccaaagtc tacagtttta aaagaggagg  58860
attgaaaaat tggtcttata tattatattg aagattaatt aatgtttatt tactaagtct  58920
gtaggaaaaa gggtatatgt gtatacttcc ttatagtctt ggtgtacaca cacacactca  58980
tacacacaca ctcacacata cacacacaca cacacacaca cacatacttt agccaataat  59040
atgagactga ggcaatgata agtaaaagtc tgataaagag aaattttgtt ctcattacac  59100
ataactattt ctcaaacaca ttcaaccata ctctccagaa accatgtgct ttatagttat  59160
atattataaa ttaattaata ctatgtatgt attttaatgg atcctgtacc atgtatttct  59220
taaactgatt gcatataaag ttttctatgg aaaatctgaa agcattatta tcttcaatgt  59280
gtatgaatag ggatttgggg aattactgga gaaagtacaa caaagcaatg gtgacagaaa  59340
acattccagt gatgagaaca atgtcagttt cagtcatctc tgccttgtgg gaaatcctgt  59400
gctgaaaaac atcaatttga atatagagaa aggagagatg ttggctatta ctggatctac  59460
tggatcagga aaggtactgt ctctttaaat tgttaatttt ctgagaaatt tgtacacaaa  59520
tactgtaatt atgtaatttc tatccccctt tccagtatct tactccttcc atgtacccct  59580
cctcacttcc attaaaattc aagacctttt tgtttatgat tattatatat aatgttcttg  59640
atctattttg tgttttatat atacacgtgt ttagaactga tcactcaaga ttggataacc  59700
tatcagcgag ctaattttta aagaaaactg attctccctc ataacaattt tgcctgtaaa  59760
ttttcatcta ggggatggag ccttgtgaga taacctcata tgcattgtca tgtcaactgg  59820
taatgtcatc ctgtaggact tgtttagtta acagtgtttt gaatatttca taggtgtagc  59880
atctcattgt ctaggagata ctatctagca gtagacatgc ctgttttctg gctatgtttt  59940
agccacatct tccacaatta gccctgagcc ttaaatacag agtttgcatt gtagatgtat  60000
caacatggtc agttcttctt tgactagctc tagatctctg caatgctttg catccagtgc  60060
aaaaaaaaaa gatgtgtcta caaaaagtgg tgagaactat gcttacctgt ggctatgaag  60120
agaagtattt agaacccagt tagaaattat attagtttac aaaatggcag tagtaagagc  60180
tatgacctct ccagctatgg gtagtagtta ggtctacatt acaagattac taggtatgaa  60240
ttgaatactc ttaatgattt ggtcttaggt ctaatcaggc agctgttagg tatccctagg  60300
ataccactgt tgtaccattg atgttgtatt ttgccaagac atcaggtttt tttttgtttt  60360
gcttgttttt taatctattt atttcatatc attaagaatt taatttacta ttcatttctc  60420
ctttttgtgt actttgaagt atatgtaata tttcagagaa aatcacatat gtatggaata  60480
tctggtgtaa tatatatata tatataaata aatatatata tatatatata tatatatgta  60540
atatgtagga atgtttgagt ataatgtata taagttgctt cagtaatgat ttccttcagg  60600
```

-continued

```
tttttcacat aattttatac ttttttgtat ataatttagc cttgtcatac atatagatgg  60660
ctttcaagaa aaccatcctt ttaaccgttc tttacttcag atctattttc aaaactggta  60720
caaaaaaaac cctgctttag atttcaccta tttctctata tatttgacat ctctctatat  60780
gtggattttt actgaataga cccaggcttg ctttttatat attattaaaa tatgtcaagt  60840
aagtgttaaa atgttaaaaa ttttaattta ttcagtggct atgttactcc ccacccagta  60900
ccaagaacaa tcaattatga tttggagaga tatctgacaa aatctaattg gctagaagtg  60960
aaaagcgctc agggattgtc acggtttcag atatgttctg tcatgtagat aatgatagat  61020
acttggtttt tggtagttac ctagataaat cattaaggac caaagaaatg aaatgtactt  61080
gagccaatgc tttgagcagc agagtacttg ctgtggggat ccataaaata gatccttgtt  61140
gcaatcagat tgttgtttta gagtaccttt cagtaataca aatatatatt tattaatctc  61200
taaaattcta tttcaaaata taaagcaatg ggagaggaag ggtgggaaga aaaaagaggt  61260
gggagaaaaa taaggacaag gcagtgttgt tataaaataa aaatgaaaat taaggatcac  61320
aggagcctag catagatgtc tcctgagaag cttcatctag cagtggatgg aaccagatgc  61380
aaagacccac agccaaacat caggctgagc tcaggaagcc ttgtggaagg gttgggggta  61440
ggattgaaca agccagaggg ctcaaacaca ccacaaaaga cctacagagt caactaagct  61500
gggccgatgg gtgctcccag agatcaaagc aaacaaagag caggcaggag ttgttcctag  61560
gctcgctaca cgtttataga agatgtgcag cttggtcttc atgtgagtcc cctagtaact  61620
ggaccagggc tctctgattc tgttgcctgc agttggatcc cctacccccct agcaggaatg  61680
ctttgttggg gcctcactgg gagaggatgc aaaaatttaa tcctactgag acttgatgta  61740
ccagaccagg ctggtaccca aggtgggctt ctctttctct gaggagaagg ggaggtggta  61800
atgggggtag ggatttgtga gaattcgact gggagagggg gctgaagcca ggatgtaaag  61860
tgaattaata aaccaattaa ttaatgaaaa caaaaagcat tctaaaaggt aatttgtttc  61920
tattttatac tagtatctta aacagggatt ttattttaaa gagttttata tgagattttg  61980
gaaatagcac aaattttcta atcactgtac attttgctta tttttctctc caattgtttt  62040
cttatctgtg acatagacat gttgttttgt tttattttat ttatttaaag actgaatgac  62100
ctttattgct catttttaat taattatttt atttatctac atctatgctc ccagaaatct  62160
tcaccctatt caccctcccc tttgcctctg agagggtatc taaggctggg catctctctt  62220
ctctgggaca tcaaatctct acaggattag gtgcatcttc tcacactggg gccagacaga  62280
tggcataggc atcttaaata aagtagctat aattttatat tctcttccta cagaaatgct  62340
tgctcctcag agtgttattt ctttcctcat tttctgatat ggaaatagag acagttttca  62400
cgattaaatg aaaatggtag cacaggaatc tgcataacta atgctataaa agacacagat  62460
gaccagaaac acactgtctg ctgaggaggg ggtattacta gcattacaca gaattttaaa  62520
aatgaattgt tcatgtactt aagatcaata catgaaagag gtataaaaat agctttggaa  62580
gcacagttgt tgaacttgtc agtagttaac catcaggcaa ttctatgaaa ccttaatgaa  62640
taagtaatta aaatctggga ctgttcttgc ctctcacaga aaattgctgt gaaggcagag  62700
aaagatctgg gttcccttct gacaacttac tcagagagac tgctgttttg taagaataag  62760
aaggaaaaac gattatttga ttgaaaaaat gtgaagctat aatataagat ttaaaatatt  62820
aatatttaaa gttaatttta tacctctcaa tttgatagtt tattatttaa gacttaaata  62880
taacctaata atcttatatg ttataccctt atatatttac agagattttt gtataggtat  62940
```

-continued

```
ctttggagta gtatggctat attttgaagt tctgtagtcc ttggttatag aaaaatttac  63000
aagatatgta gttaagtgag aaaagcaaaa caaaattttt gtatagtaat gctacaatgt  63060
actcaaggat actaaactat attattattt tccataaagt ctatattttg ttctactgga  63120
tacatttata atatctatat atgcttcata tttcacttat tcttaacagt ttcttcattc  63180
ataaggagct tggataaaaa aatcaatatt tttccttctc ctgctacctg tttttctttc  63240
taccaaatgg tacattagga gccctttctg tgtaagcacg gggacctaag cttgaattcc  63300
aagctcacat gttaggtgga tccataaccc cacaatgaga ggctcagaca gttggatcaa  63360
aggagctcac aggcagccag tgaagctgag actgtgagct tcagtttatt gagacacttg  63420
gtttgcctca agcaatggaa agagacatag aagatactag tatcctgctc tggcctctac  63480
atgtacacag aagggtacag gtgtccacat gttcacattg tagctctctc tctctctctc  63540
tctctctctc tctctctctc tctctctctc tctctctctc tcccccactc tgtgtgtata  63600
cacaaacttg acatccatca tttctttttt tattgtagtt tttttagaaa acatttatta  63660
ggttttttat tggatatttt ctttatttac atttcaactg ttatcctctt tccttgtttc  63720
ccctgtgaaa actcccctat cccatctccc ctctccctgc tcactcaccc acccactcct  63780
gcttctctgt cctggcattc ccatacatgg agcatcgatc ctttacagga ccaagggcct  63840
ctcctctcat tgatgtccca caaagccatc ctctgctata tatgtggcta gagccttgag  63900
taccgccttg tatactctgg ttggtggttt agaccctggg agatctgggg gtactggttg  63960
gttcattttg ttgtttccct tcagtttctt gggtcctttc tctagctcct ccattgagga  64020
ccctgtgctc agtcccatat gtttttataa tttcttaaag atgaaagcaa atttcatac  64080
tagtaaaatg aaagtacttt ctaagactga atctgtgtta gtttattata atgaacacac  64140
tcatgtagtt agagcatagg ggcagcccat agcccaagag ctttcagcaa gtgctcactg  64200
tcaccagtct cttactacaa actgatcaca gcaatttaag taggggctcg ctcttctttg  64260
tgaaccttag tcctatgttg cccagatctc tttcatcccc tttgtatttt ttatgcctag  64320
aaaagtccct gtatcatgaa gtactaaaac atctttaatc aaatgagtta cactctttaa  64380
acattgggag acttgtgatt ggaataattg gacgcaagaa agggataagt aatttgatca  64440
aacaatttag ctgttgtttt tatttgtaga catcactcct gatgttgatt ttgggagaac  64500
tggaagcttc agagggaatt attaagcaca gtggaagagt ttcattctgc tctcaatttt  64560
cttggattat gccgggtact atcaaagaaa atatcatctt tggtgtttcc tatgatgagt  64620
acagatataa gagtgttgtc aaagcttgcc aactacagca ggtaagcata tttatgaaaa  64680
atgctgattg tgttagctac ttgtgtcagt gttgtgataa aattgcttga ctactcacct  64740
tgaaaagggt tttattttaa attcttttca gggatgatac cgtccatctt ggcaaaggag  64800
gggcaggaat gggaagatgg cgagacatgt tatatccata gtcaggaagc agacagccag  64860
caggaagtgg ggcttcaagg cctaattcta gtagcttact ttctccagta aagctccaag  64920
ttgtaaacac tgtcctaccc cagtgtaccc ccaactggaa ataatgtttt caaacacatg  64980
agcccattgt aggtatttca cgttcacacc actacatgga ttatgctcat tcagtcttca  65040
gactaaccaa attacacagt tagttctcta ttgagttaat gtaaacatgt caaggacccc  65100
ctaggattaa gctggagtgg gtgggtcagt gaataaaacc atgctcctac tttaagttta  65160
caaaattata aatagatgca gtttattttt aaagtgtgtt tgggtgttgt aaaaataaaa  65220
attccttatg catggggtgt ggtacttcat gagtgcaatc ctaatactca agagactgaa  65280
gcaaaaaggt catgaagttg aagccagtct tagctgtcta atgagttcta ggccagtctg  65340
```

```
gatcacatgg taggatcatg ctaaaaacta acaaaccaaa agtctgtatg aattcaatag  65400
gagtattttg tgtacacttt gagaccacag tgaaaagaga agctatccta gaaacttgtg  65460
ctaaccttga agaagatagc catactttcc caaaagtcct tcttctacaa catgggggtt  65520
gatgtgttct gggcttgtta ccagatctgt ttttagaaga gtttttctgg gcaagaattg  65580
gagggagtaa taagtcttac ttggcttatt ttgggggtgg tgggggtgag atagggtggt  65640
actttcttgc tagatttaga ttttgctttg cttgagtatg tattttccca tataaatgat  65700
ttcacagatg atattttgag taatcaaagt cgatctacaa aatgtacata atccaaatat  65760
agcatttata cattactatt aataaattta gagctgtgga tcatccatgc aacaagtatt  65820
tacaacattc tggacacagg tagatcattg gaatgcttag atgaagaaaa ttgtatttat  65880
tgttaaagct tcatagtagg atggtatata ttaataatag aggattatat ggtttgtata  65940
gtatatatca ataaaatagt gagagaagga gaagcaaaat atattgttct ttcatttgga  66000
tgcaaggaca tattacaatt attttatagt gtatgattta ttgtgtttta gaatagttac  66060
agtggtacag tgatgaccac ccttttagaa cccctgaaaa gaaactccat attcattaat  66120
agtcaaatcc tattttttta aaatattttt tattattaca tattttcatc aattacattt  66180
agaatgctat cccaaaagtc ccccataccc tcccccccca cttccctacc cacccattcc  66240
cactttttgg ccctggcatt cccctgtact ggggcatata aagtttgtgt gtccaatggg  66300
cctctctttc cagtgatggc cgattaggcc atcttttgat acatatgcag ctagagtcaa  66360
gagctccgga gtactggtta gttcataatg ttgttgcacc tacagggttg cagatctctt  66420
tagctccttg gttactttct ctagctcctg cattgggggc cctgtgatcc atccaatagc  66480
tgactgtgag catccacttc tgtgtttgcc aggccccggc ctagtctcac aagagacagc  66540
tatatcaggg tcctttcagc aaaatcttgc tagtgtatgc aatgatgtca tcgtttggag  66600
gctaattatg ggatggatct ctgggtatgg cagtctctag atggtccatc cttttgtctc  66660
agctccaaac tttgactctg taactctatg caaccactga tctatctcca taaattctcc  66720
tggtcctttt ctttttcaca ttttacataa aggaaattta ttgagaattt catacatata  66780
tctagtgtat gttttatcta atccatctct ctctatcttt cctttaactt ctctcatact  66840
cccttcaacc acttcaccca cccacatctg tgctctgcct taaccttcag agttcagtct  66900
gtgatcctag tatatggcct tgtacccatg ctatgctggc agctctaagg aaattttaat  66960
gtaaagcaat taatgtaaag caattagttt tcatcgactt agacttgctg tgctttatac  67020
agtgtcctga agagtgatag aaacagacca ataatgaatt tagttaaaaa tgggggaaaa  67080
aagagaatat tttaggagta aaaagaagaa acagagagac tccatcaggg tctacccaaa  67140
aatagcagcc tccacatgca gaaaagggta ataatattcc tgatggtgtg attctttgta  67200
gaattctgag gttcacaggg aaagcgagcg gcccaagagt tctttattag gaacattgga  67260
actatgaaaa aagagagcca gactggactt aagaagtagg gaaatggggt ctggttgttt  67320
agagtaactg atagttgccc agtgaaacat tcggtataag atccttccag taaacactaa  67380
gttatttttg cttcttttga aatatagaat aatatcacta cagagaaaag caggaaaata  67440
ctttgagagc cagttgttct tagaaagtga attctgtaga gacaaagttg ttaaggacaa  67500
gaagagcctc caaaccaaag aataatgaaa agacattgat atgatatcaa tattgacaaa  67560
actggtcata gcgaagatga taacaatggc attttaaatt tttggctacg tgacatagtt  67620
aacaaaattt gggtatctat ggaagaaatg aaaatgacag cagagcctgg aggtttggaa  67680
```

-continued

```
tgtggatgca ctggctttct gcttagtgtc ggtgagagct ggaagtcact ccactttagt  67740
gtatcttcag acccccaaaa ctatatgtgt cattccttta tgtccgactg ttttggtttg  67800
atttccagtg ctataatttt gaccaaaaac atcttcaggg agaaaaggga taatgtggct  67860
tacacttcct ggtcacagtt gatcattggt gaactcagag taaggaacta aaggtgggaa  67920
cttgaagcag aaaccaaaaa gaatgctata ttctcatctg ttctttgtct tgctagcagg  67980
cttacactta cctagctttc tcttacaaag tagaatacct gccaggaagt ggcaccaccc  68040
aaaggttgtc tgggccctcc cacatcaatt agccatcaag acaacttccc acagatatga  68100
atagtccagt tgcactggaa aaatttctat ttccaggtga ctctgtccaa tttcaataaa  68160
aactgtctac tttaggagag tcaaggtgaa tagcaaatga aagcttaacc atctctcata  68220
taaaggattt atatgataaa tttgggggaa acaaacttaa ggttctaatt tctatatgct  68280
atgacagttg ttgggttaaa gtcagtggtg aaatttgagc ctacttggat aattcaggaa  68340
gcccctctct aagagaagac ttcttgaaga gcaggtcaaa aagaaaggta acattatgta  68400
taaaagaaaa tgaataggtg tgaaaccacc tattgcaggg attataagca tcttgataga  68460
gccacggtgc aattaaagag aatgaatgag caggaatgga tttagggaac cagacctggg  68520
aggtttatcc tagagaactg ttagcaagag tgctgtgaga gctttgaagt ctgtccctgt  68580
cattctggga tgatggagag cacaattaag gtgggtacca catgaagctt agcacagcat  68640
aaatagcata gactttgaaa tcgtacaaag ctgagtcata aggttattta acttgtgcca  68700
atactcggct tttctgctct gcaataggaa gctaatatcg cctattctat agcttttgta  68760
aagtgctcta gtacatagaa agttcaccat aagtaaagca ccagttatta ttattactgt  68820
catcatcatt ggcaatagtg ctctgttcac ggttgtgact agaagaaggg agactaatag  68880
gaaactattt cagttacaca gattatggtc atgatgtaca agagacaaca gttatataaa  68940
agaattgtgg gaatatagga agttatttat gtaattttta ttcaatggaa aggacatcag  69000
tgaaaaaaat ggttattcat ggagaataag gtatttctgc aaataatgtc tttaaaagtg  69060
tataaatggg ttcaagatta agaaatctga gatctttaaa acaacagtca gaaaaatgga  69120
catgtatagg tcatggcctc aagaaggaca cagagagtga acaaagtaga gggtcgcaga  69180
tgtggctgac aaggaacaat ggaggggact aggaagggct taataaatag ttatgaaata  69240
gttatacact ctagattttc gtttttaacg tattgcatac atagatcttc aattacttct  69300
agaccatttc ctgttgttat gctttcaaag attatttcac ttttactgct ctccaaagct  69360
tcccattaac tgtgtgacag tgtctgccta gcctcctcta gtggagaatg aactcagggt  69420
cttgccgaac ctctgtcatc atatgcctag ttagtctcca aaccctcagg gtttctgttt  69480
tcatgcattc cattgtgtgt tatctaggct ctgtctttta gttttagttt tgagactgtt  69540
ctgtcactct cactcacacc ctctatcttg ctctcgttga aattaaaggt ctccttttcc  69600
tcagctgttg ctacttggac taccctcagc tttccttagc tgcctgtggt tctttgccca  69660
gggctgagac tcctgaactt ttccccttct gcattaaaaa gcccattggt gtcattgttg  69720
ttgattgtcc ctttaatttg caataccctt ctttttctta gttaaataaa atgtgaagta  69780
aaactatttt tttaatttta aagaatccct aagtctttgt tccttttgtg ccactgcttt  69840
ttgccaccaa gttagaacct tttagttaac atttgaaagg cttttttctt aaatcccttt  69900
gctctttaaa atggcaaatg tagtattaca atgagctatg tatatgctgt ggtattatct  69960
tttgaactac agagtaaagt tctgaacaca acaactctaa aaatgttaat ttaatttagt  70020
ctatttagtg tactgataga atagtccatt tttactggat gactgttttg gaatggtttg  70080
```

aggtaacatg atggttggga gaattttgct cagcaaaggt tctgtgagtg ttgtggtctc 70140
agaatctgag cagattggtt cttgaatgag cacacttttt ggaagcttgg gatgattgtg 70200
cttgtctgac tacaaagaaa agcatcagga gtctcccctg tgtccagtga ctgaaacttc 70260
catgtttgtt tctgttatat aaacacacat ttggtcaggt acataaggaa cttcaacaca 70320
ctaaaatacc ttgttttctt agataaataa aatgttaagt aaaacgtctt tttttaaatt 70380
ttaaagaatc cctaagtctt tttccttttt tatgccactt tttaccatat atacatatac 70440
atacgcatac acacgtgcat atgcacatac atacatacat acatacacac gtatgtatgt 70500
ataatgacaa tttaagaatg caggaatttt gatcacagga acacagtata cctacagagc 70560
tcagtggctc aagagctggc accaacacaa gaacccctca gcatgatctg tggacggtcc 70620
catttgcgaa acccagacat tcatgactct gtttgcattc tgactgctga agttgatctg 70680
tttctcagtg tgctgcatca aggcttggaa tcagagatgg ggatgggata tcctcttcct 70740
catgcttgtg attttgttca actccgagat cttcaaagtc ccctgtgtgt cgtgatgctc 70800
agtgtcacag gagtatgtga gtgtggaagg gcaaagcatg cacaacatat ttcacatagt 70860
tttctgattt cagtctgttg ttggaaatta ttcactagat gaggcagctc aagggggaag 70920
ggcatggtgg ttctgttgat agaatgattt ttagcatgaa gtctcaaata aatatgttat 70980
gggttttttt ttgtttgttt ttttttttac ttttaagctc tcctttggga aaaatctcca 71040
tgctttgctt tttaaaaatg aattttagag tctagatttt aagacaacag gcttttaggt 71100
gaattgagag tcacttgcaa acactgttct gcgtccttgt gtccattggc tctcttcatt 71160
ttcctctgcg ggccattagg gtttccttga cacatttctt ttcagggccc agcactagag 71220
actgttctag ctttgagaga agaactagtg tgatgtagct ctagtagaat aacatgtctt 71280
atgaaattag agtcctattt cagtgttgag agagagcaag ggcttacact gttctctcat 71340
ctaccttctc tgcctcacac agccccagtg acaagagaat tctggacagg ccagtgtttg 71400
agcaataaat gatttgatgg tctttattct gtgactcatt ttcttataaa agtacctggg 71460
tttggagaag taattaaagt ttataatact ttatggtggg gcgtaaggat gggcaatgtg 71520
caaaggaggt caggggctta ggatatgtaa tcagtttcca caaaattatt gtgatgcttt 71580
tgaaaccaca aaatgatcct catcaagtaa gtatctgtca tgacagccat tacacacgca 71640
ctgcagcaaa aattactatg tgagctgaag aaggaggaat cgtgcatgtc tttctctttc 71700
atagctgctt agtggttttt gtatttaact tgctagagaa aatactgaga agaaaattgt 71760
caagaattca gtaaaagatt aaaaaaaaga agaagaacca tcttgggaga gaaattggca 71820
agaagttatt aaaaagttgg gagggaaata agctgagaaa tgagggtgtt ccaaaaaaata 71880
aattccacca tagagattcc acatgactaa ctgaatttga atttgacctc tggctctcca 71940
tgttctgcat gactaaccta tgagaaggtg agacttaacc tttgaatagt caacttacca 72000
agttggataa ttcacagctt tacagttaga agtaatgaga agataagtgc cataggactc 72060
agcattgtac tagctcagac ataatgtata tctaaagaag atatttgaaa cacattgaac 72120
tatgtccctt tcaaccagaa taaatcacat tgactatacc gtaccatgga ctacctataa 72180
tttactgatt atatgtgatt aggaaacact agatattatt tactataaca tgaagccaag 72240
aatacttata gaattactga accagaacta aatgggaatg ccatgatatt tttatagtctg 72300
aactggtatt tcactgcatt tgagccttgg aacttaaaaa atatgtacta gctaatattt 72360
agggaaagag tatctatggc agcattgtgc taagcacgcg catgaactgg cccatggagt 72420

-continued

```
tgtctcttct gatttattta gtgatagctt caccaagagt ttgcagtaga gtgaaaatat  72480
gctgacttca aaatgcaggc taggctttag gccctaagcg catgaagttc ccgtgctaat  72540
tatcaggtta acacatcaga gttcttaagt cacaaaaacc aaaatagcac caggatagcc  72600
actcctagtg agatttgaag tcaacagagc agtagcttat gaacataatt ataactgtct  72660
gaacagacta cctcatgagt agactgtgaa actatgacat gtaagcctga ccttcatatt  72720
taaaacaaaa acaataggga aacttacaaa gataaaaata attttataca aatccttatt  72780
atgtgtttcc agtttctacc ttttttaagg tataggaaac ccagattcag agttctccat  72840
atttagatgg tgaataatat tatttaaacc aagaaaaaat ataattttag atgcaggatg  72900
gtgctccgaa gaccctagct aaacttcaca ttcgtggaaa atttgacatt ttaccagact  72960
tgtaactcta tagatgttca caaaagctta cccagagaag gaatcctggt gtttgctaaa  73020
ttgaatgtga agtcttctct agataggtga aatgttctag cattgacagc tattagaagt  73080
aactccatga tgataggata agtgctttta tttatattgc ttattcttgg tttagattga  73140
tgaattaaaa agaaattgat atcagctggg tatgatggca catgccttaa tcccagcatg  73200
tgggagatag aggcagacgt gtctctgagt ttgaggtcag cctggtttac agagcgagtt  73260
ccaggacagc cagggctaca acacagatgg agcctgtaga aagaaagaaa gaaagaaaga  73320
aagaaagaaa agaaagaaag aaagaaagaa aggaaggaag gaaggaagga aagaaaggaa  73380
ggaaggaaag aaaggaagaa aggaaggaaa gaaaggaaga aaggaagaaa ggaaggaaga  73440
aaagaaaaga aaaggaagga aagaaaggaa ggaaagaaag gaaggaaaga aaggaaggaa  73500
agaaaggaag gaaagaaagg aaagaaagag agaaagagag aaagagagaa agagagagag  73560
aaaggaagga agaaaaaaag gaaggaagga aggaagaagg agggaaaagg aaaggaaggg  73620
aaaggaaaga gaaagtgtgc gtgtgtgtga gggagagaga gagggagaga gagagagaaa  73680
gaaagaaagg aaggaagaag gaaggaaaag gaaaggaaag gaagggaaag gaaagagaaa  73740
gtgtgcttgt gtgtgaggga gagagagaga gggagagaga gagagaaaga aaggaagaaa  73800
gaaagaaaga aagaaagaaa caaaggaagg aagaaggaag gaaaaggaag ggaaaggaaa  73860
gagaaagtgt gcgcgtgtgt gagggagaga gagagggaga gaaagaagag agagggagag  73920
agaagaaaaa ggagagaaga agaagaggag gaggaggagg aggaggagga gaaggagaag  73980
gagaagaaga agaagaagaa gaagaagaag aagaagaaga agaagaagaa gaagaagaag  74040
aagaagaaag ttgttaatct cagcaacttt tcactgagct cccactataa gcacaatggt  74100
gcaataagca cagtagatgt tgcctgcagg tataactagt aacttgtcta tagtgagatt  74160
tttgttacaa aaatttatag caggatggca tatattcatt cagtaaatat ttttgaatat  74220
atgcatcaag ctaatgatta taccaaactc tgggaattac actggtaaga aaggcacaat  74280
gcttgctcta aaagaggttt tttttttttt cctcatagaa aagaacaatt aaagattagc  74340
ataggttaat gtatcgtatg tttcttaggg ctcttttata cattaggaag ttaacaatgt  74400
tctcctaaaa gatgatggaa gtttccccgc aaggaagtga catctaagtg agagctgaat  74460
gaagaagcag aagaacattt taggaaggga acagaatgta caagggtgca gaaccaaaag  74520
aagatactgt acccggcaac gtggggagcc ttgtgcatat agtagagtaa gcatgggcat  74580
ctgtaaagga aaggctgtgt gaagaggggc gaactgggga acggaaaggt agtcacattc  74640
tcagaaccca ttctgctata ctcaggaact cagactttaa agcttaggag attcaccaaa  74700
ggctttaaag taggaggtaa tgccacacaa ttaccttttt caaagatgtt ttcagttata  74760
atgtatagtt atcatgctct caattaaatg actagcaaag ctgctggcag atagataatt  74820
```

```
tcggttatct atctgagaga cagagacaga aggattctcc aagtcagggc ccaccttgtc  74880
tgtgtagtga gttccaggca agctggagct acacagtgag actgttaaaa caaacaaaca  74940
aacaaacaaa caaacacaaa tttaaaaact attcactgag cataaaatat aagatgtaat  75000
agtgactata gtcaccatgc tacagggtag atctctagaa cctattcatc ttgtctgaga  75060
cattctgtct tatgaatact tctctatgat ggtgctattt gctgagcaag ttgacacaat  75120
aaaagcattg tgcttcatta tggaaatctg gaagggatgt agaattgtga tgtatacatt  75180
ctatcaaaat gtatagaaac taagaagggc aaaaagtagg taaggtatat aagtagaata  75240
tttgtttaaa atatctaaaa caactaaaca tgtaatactc gagctaattg ataattaaga  75300
gaataagcac aactgagtgg caataggagg ctccgcggag gggatctccc aaaggctcag  75360
tgcagaagag cagagatgac ttacagcaca acaaggccaa tccatagagc aggctgttag  75420
tctgagctca gtacatgaag ggcaccttca tttggagaat taagagaatg aaaataagat  75480
attacatatg aaaatataag gtcagtgtag tgggaaatta aagaattcca tattcgttgg  75540
aaagttttta ctacgtttcc ttgtggcatc attgctttag aacaaaggac acacttagac  75600
aaggatcttt gttctcagct tacattttac tcaaaggaga tagacttttc acaggaaggc  75660
agctcttgag agacaagaga ttagttggga acttcaaagg tagtggggtt tgaagctctt  75720
ctaagaatct gagttataag agacttcata ataggaacca gaaaataatt tggggaacat  75780
agtctagata acacaagatg ttctattgaa gtatggtatt ctttccccca ggcattagag  75840
ttgtcctagc attagggata ggtatagtta gaggagaaaa taaggaattg taccacttaa  75900
atatccatac tgccaatgcc ataggagtta tttagagagt ttccttgcat ctgagctcgt  75960
gctatccaga agtctatgac taaatgagtc tgaatgaggc ataataggat tacagacact  76020
gaatagcatt tgaaaggatt tttggctggc tggctggctg gttggttggt tggtttcatt  76080
tagtaaaagc cagagaaatc cagttcccat atcattctct agctgtaggg gagttcagga  76140
atcccagcac ttttctattt ctggacactc tttccctgca cacataaaat cactgcactc  76200
tacagttcct ctcttaagaa tgcttgagct atccattctg aatataaacc cagatctata  76260
acacaaggaa gtacacaata gcaatagcta tatttatatt catacataca cacatgaaaa  76320
ctgattataa aacagtttag tttgtgttat gattttatac acacacacac acacacacac  76380
acacacacac acacacacat atatatatat atatatatat atatatatat atatatatat  76440
gctctcttct gtatgaggat gtgtgcatat catggtaaat gtgtagaggt cagatggcaa  76500
cattgggtac tgagctttac tgtctaccat gtttgaggca gagttgttcc ttttgttgct  76560
atatacacta ggctagttgg cttgtgagct actggatctc aggcagttct cctgctctac  76620
ttttcatctt ccagtacagg cataatggga ttacagacac tcagggcgtc tagttttaat  76680
gtggatcctg gggatccaaa ctcaaattgt tgggcctgtg aggcaggtgc tttatcccac  76740
tgcaccatct ttccaggcca gagcctttag tgttgatggc aactactata acatcaatat  76800
ttatattttt ctttgttata ataaagatga tgttaagtgt tttttttttc tgctataaac  76860
ttggttacta ttcactggtg aaggtaaatc tttttatctt taaatcgatg aaaaatctta  76920
caccaccatc ctttttagca gagcttagtc ttttgaaaat gtttcttcat gcagctattt  76980
gtaataaagt ttgacttatg tcaacaacct atcttattta ttagacataa gccaatttaa  77040
atgagctcct tagtgtctgc attctgttat gaggcttaca tctgtggatc tctgtcagag  77100
tctactaggt atctgcttac cacactcaaa tgtacaataa gctatgtaga aatgatcact  77160
```

agatttttct ctttttccag tgctttcttg gctgcccatt ttcccatcct gacttcttcc 77220
tacctgtttt tcctaccttt ctcttccatt ggctatcttc tgtatgcaca aaacaaagca 77280
gtgttttgtg ctttttaagc cttattaaca atggcattaa ctatccagtg attcaccgtt 77340
agagatatgc tttattgagc agcattcccc tgaagttaat gttcccttaa ccctggcttc 77400
tcactgtgcc caccctcttc ttcccacaag cgtctgtatt gtcaaggttg ttctaaaaat 77460
gataagccag ccatataaaa gtttatggta ttttcctatc ttcaaagcta caggaagctc 77520
aaataaactc agcaaatatt gctcaattac acaagactat taaatgtaac accccaccct 77580
tctaaaaagc acctcctctt ctatatcttt ccctttttctt tcttagtata acagcctaga 77640
tcattatggc tctattgtgt gatcaggtca gagcaaatga ggttcatatt aacaagtttc 77700
cttaataact tctggcttgt ttgatatagt tgaaggatac caagatgata aattctaaat 77760
ttctaagaga agtcagtggt aaatgtgaat aaatggaaca taccacaata agtatgttct 77820
ctagtcctta atgataaagt aagttaatct ttattgcaca cttattatag tattactttg 77880
accctctcca gtgtgcttat ctcagcgttt tcaagtgttt tacaacctca aacacacaca 77940
ttgtgttgtg tgcacagtct gctttgaagt tgacatttgc ctttctgacg aggctgtaat 78000
aaaggaagtc aaccacctga gagaacaagt gtcagatgag gatttcaggc cctggcgagc 78060
accgctgttc agggttaagt gcagaaaccc aggttccttc cagatgcctt tgagtcacca 78120
caggtgcagc aattttaaac aaataaagtt tctgtgaatt agctcaagag cctcacctta 78180
gtttggcaga tatttgatgt tatttgtaga taaactacac cgaaaaaata aataaaatat 78240
caaaaaatta aaataaatta aaattgggaa tagagaataa tttgaaagaa aagttaataa 78300
tgttctcctt ctataagagt agtctttgat tacataagtt tatatttcag gataagacag 78360
ttttctttta ttaaacaaaa ttcttctgga cacttaataa gcatgtgcaa gggcctctat 78420
ttcatccata gcaccaattt aaaaaaaaaa aaaacctaaa cgaaaatcca acagctaatt 78480
ttatagaata ttttatagct aattttatcg tcaaatatta tctaataccc ttgtctagga 78540
cccttattcc aatagatgca tttcttcaag gagttttatg gataaatgcc cctcaccccc 78600
caaaaaaaat ttccagagaa ttttcagtat taacaaagaa aagtagcccc tgtagctgtg 78660
tgccaggctt cctctaaaag ccacgtgtgc tcgtgcagca ttctaaagag ctcacaacac 78720
accctaatgg atggtcatgt acccatgctc atactgggca acactagttg aactaagggg 78780
attattgata aaaataaaaa gacaaggttt gagtaagaat ggggtaaggt gtagaagggg 78840
gcgttagagg gaggaaactg tgggatttat atgatcaaag tgcattgtat aaatgtgtgg 78900
ggttttcaaa aagaatatat gtatatacat atatttcaaa aagaatatct atgcattatc 78960
tatgccatta acaaaaacca ggaaaaaatg gaagggatgg atgaggaggg tttgcaggga 79020
gggagggaat ggataaatgt aattatgtta tagtctcaga cataaaaata aagattaaaa 79080
acaaatcctc atgataggca cgagtgatat aacagttttt aaattgtgat ttttacaggt 79140
ggggaaaatc tatgaagtct gaaaccaaca cccttaagat aaatatatta ccagatttga 79200
gtatccttag tagtcagcaa aggtcaatgt ttaacgatgc atgcaaaaca gagtgctttg 79260
ttttaaatca aacagaatgt taagtactca taaatttgca gacggatgag gcataaactg 79320
agtaatcaaa ccaagtgctc agattaaagg aggatattgg cgtgctgatg tattaggctg 79380
taatgagtgc aatctcagta gatccccgct gcctgtccct catttcactc tcagcagcat 79440
gaaatcttca ctcacggagt gaaagttacc catatttctc ttcacgagtg gattcagtcc 79500
ataaacaaca gttcaaacct tggctcagta ggcagatcta ctttcatacc attgaaagtc 79560
aattcctaga aataatatgt tatagaagag aacatgtatg tctcagtgtt cttattttgt 79620
tcaatgttaa aagcctggat agcatcacca aaactgtgcc acaaaactct aagattcagc 79680
aaatagaata atgaaatatg tatttttcca atccatttaa tacaagttac acccatatat 79740
gcagttcagc tttaaaattc acatacagta taatttgcac acattattct ctaacttatt 79800
cagttcccgt tatcttttta agatataaca atacctatat acatgtttat acactaattt 79860
agggatgagt gagtgtgtac atgtggcaga cggctcagat ggaggtctgc agtgtcagtc 79920
cttcatcctt gacggccatt aatgagtgtt tgctgggagg agaggtcctt ggtcctgtga 79980
aggctccata gatgcctcag tgtaggggaa ttcaaggtgg ggggaggtgg gagtgggtgg 80040
gtggggggag ggatactatc atagaagggg gggtggtata gggggtgtac gtgggggggg 80100
aacgggaaag gggataacat ttggaatgta aataaagaaa aatatccaat aaaaaaacct 80160
tcctatcagt gactttaatc tttttggtca ttctgactcc taaatcaaaa tttctattat 80220
tttgtctcta ttctatttag atgaatatgt aagagattat aaatatactt tcatgtttat 80280
taactatctt gatttcctaa catttaaact tgaacacttt ttgtaagata taatgatgga 80340
taaaatatgt attatataga tcactgctat aggaaacaat tgaatgaaga gtccagtttt 80400
gttttgaagt ccttaactga gtttgtcttg agactacctc tacattcatg aatgtttccg 80460
gcaggattac taaaatagat ttctattttg aaaacataag aactattagc taatttttga 80520
cataaaaatc accaagctgc tttgccaaat tctcccttgg actaaattgg tataatattc 80580
tcccatacca accatcaatc ctactttagg atcagagttg cagtgggctc ttcagactgc 80640
ccatctatcc tatgtgtttc cttttccaca gtatctcccc caattaaact cttggacatt 80700
tgatatcatg ttggaatctg gttggagaat tttgactgat agctgcatat attacattat 80760
catcttctgt agtgatagtt tttcttataa ttttatatag tcaattttat ctaaatgcca 80820
ttttatgttt tgacatttct gacttctctt aaagatgttc gttagagcaa aaaataaaga 80880
cattctgtcc taatagtttt acattttcat ttatcaagaa tatgggttat tagaattata 80940
tggtgtgcag ttttatgttg acattttaca ctcttaatta aaatataatg gctgcttttc 81000
ccgctcccct tccttccctc cattccttct catgtccctt ctctccaaac ccttccattt 81060
cacctctctt tcaaattggt gtcctcttta ttgttgttac atgcatatgc ataaatatgt 81120
aaatactcat atcttagaat tagccaaggg tggtttaact agatggaggg catgctcaat 81180
agtgagattt ttctatttag gaaagtaatg tgatatatct taatcataga aacttttaat 81240
atcactcttc ttcatcctga tcaaagtggt cagaatacag atttctagat ttctttgaac 81300
aaatctactc tactttgaag aaatttagtc cactgctgtt tctgttgaaa aagaaattga 81360
ctttgcatgt tagctctatg atcaaattgt agacaaacat ttaagataac tagctcttcc 81420
ttacagaaaa gtcatctaaa gatataaatg ggaaacaact attcagttca caataatggc 81480
aaaccttaaa gtatttagtg attgttatag ctctcatggg acatttacag aatatgaaga 81540
aaatgataaa tcttattgaa gtattgaatt caacatctga atcaggatta aaaaacattt 81600
tgatttagtg ttgcaaacta gaattctatg taagtgcaag gtatttaaaa gttgcaaata 81660
aattctaata aggttatctt aaactaaact taatataaaa tcttagaagt aatttattga 81720
caaattattt tggtggaatt tttgcttcat catatgtaga cttgatatca tggtatttgt 81780
acttcttata tttgaaatgt tagtgaggaa gaattactgc attaaaattg ttcaagtcag 81840
cacttgagac tatgttagct catcttttaa tgatatatta tttcaatagt tgacatggct 81900
actatgtcaa aaactaagaa agccaactct ttcatgaggt aggattatat tttatcagat 81960
attaaatgat atataatttt atttaaaatc aaggacccaa aagtccagaa aatattaata 82020
tagaaataaa aaaatggatc agaaaaataa gagaacccag aactaggaac catgacagat 82080
gatagaggca tcagtaaacc attcatttga tgattattgt tgccttgtaa caaatgaaag 82140
atagggtaga caaatagaaa actgtgccat aagggttttg aacattttat tttgaaaata 82200
gtattcaaga taacacatat agctagctgg tggggagtag atacatttat ttcacaaaat 82260
ctttttgcac atgataagtg atatgcacag tgaaaaaaag agaaacgaat ggagtttttt 82320
atatgcagcc tataaagttg caaaaactac atacaaatat tagacacttc aaagaagaaa 82380
atgcaacaca gcaaatattt aaaatctttg tgattaagaa aaatgtaaat gaaaagagaa 82440
aattagcaaa aattatcata atcatactag tacaacttag taaattgtaa tttaactctt 82500
tagttgcttt gtaaagcaat ctggtggtaa cttttgaaag tagaacatat gcatttgata 82560
tagtcatcct actcatgaga atatatcttc cagctacaga tcacaaaagc atatatgtat 82620
tcagtgatat taatagtagg ctttgtaggg aggaagtggg gagcaattgc tagggaagaa 82680
ttgcatgcct caccatttta atgtagtctg gactacaaag agaaaccaat gacttcaaat 82740
gaaccacctg gaagcagctt gcatggatca gctctcttgt agtattctgt tctcacagtg 82800
ttgtaagtac tgaaacattt atttttctga gtgcctcacc ttatagtgtg tcactcagcc 82860
aagagtatgg ggattacaaa cactgtttgt tctagtggaa atctcacatc tgtcattacg 82920
tcatcatctt caaaacagga gggagtgttt tagagacgtg atggtagtga acctgaatcc 82980
ccttcctttt tcctttcttt ttaaaaaagc aataaggtaa cagaggaaat aaatataaaa 83040
ttgtatttac tcttgtgaaa taaaatcacc aacaatctgt gctagctagt ttttatgcca 83100
caggtagagt tttatgacat gagctagaat aatttgggaa cagagaagtt caattgagaa 83160
aatgcctcac cagattggcc tgtggacaag cctatgggaa attttcttgg ttgaggattg 83220
tgggaggtcc cagttcatga tggttggtgc cacctctagg ccagtggtcc tgggtgctat 83280
aagaaagcag gctaaggagc cacatggagc aaatcagtaa gtagcactcc tccatggcct 83340
gtgtttcact ccctgcttcc agattcctgc ctgagttcct gcactggctt ccctcagtga 83400
tggacataaa agttgcaaaa tgaaataaac cctttcttcc ccaagttgct tttggtcctc 83460
tgttatcaca gtaacaaaca aacaactaac aaagacccca tgtctgcaat ggtgtatgtg 83520
ggaagtcact gatttatccc aagtctttgg tcacgctgtc aggaatgctt gttagacggg 83580
gttccttgtt aaaagtgaat agcatggcaa tctaaggagg tgatagaaaa catgagaggg 83640
ggctgggagg agagaatatt aaaggaaatt ggtacctaac ttgatcacat tttaactact 83700
caagtgaagc tcttcatgga aggcctcgaa cattctctct gtggtgtgtg ctttattcct 83760
atcgtctaaa taattaacat gccatgtata ctgttgtata atacgttgta aaattgtttt 83820
ttaagaagtt agattgttac ttaattctcg ctccaggatt agagcttatc ttctaaatta 83880
ggtttacact gtctggagtc ctggactatt tcttacaaac ccaggtcgtc ttttactgtg 83940
ccttcatagt tgttactaca gaaaagatca ttattgggca aggaatggca tatgtgacag 84000
gagaggagta gtaagtggac aaggacagaa aaataatgga agtggtgagg atgtttgtgt 84060
tgttgtttgg gaagatgaat gaaagaatgc ggaaataaac tgacatgtcc cgttgttagc 84120
cactgaagaa tgcagaaata aactgacatg tcccgttgtt agccactgaa gaatgcggaa 84180
ataaactgac atgtcccatt gttagccact gaagaatgag gaaataaact gacatgtcct 84240
gttgttagcc actgaagaat gcagaaataa actgacatgt cctgttgtta gccactgaag 84300
aatgcagaaa taaactgaca tgtcctgttg ttagccactg aagaatgcag aaataaactg 84360
acatgtcctg ttgttagcca ctgaagaatg tggaaataaa ctgacatgtc ctgttgttag 84420
ccactgaagt tgcctgcatg tttctgtggg tgtggagagt tttgttttag cttttcttat 84480
taacaggctt attcagtctt ttgacatttt ttaaaagtga ttttaagttg aaagtatatt 84540
tgaatggcac ttgagtttat atgatgggct tatgggtagt ctttgaatat aaacattccc 84600
caaataaata gttgcatctg aagaaaaatg ttcttttcaa ttttggattg tgcatgctaa 84660
attttatttc tggtgttatg ctttggataa taggacatca ccaagtttgc agaacaagac 84720
aacacagttc ttggagaagg tggagtcaca ctgagtggag gtcagcgtgc aaggatttct 84780
ttagcaaggt aaatatttaa ctgttggtct tgtgagcact tgctgtaaat actatgggtt 84840
tttaattata catacacatt tctcttctgc ttcctgttct gtctctggaa ttgatgcttt 84900
ttctttaaga actatagaca ttataatatt caaatttggt aaagatggtg gttttttttt 84960
ttcaaaatgt atacttttca aaatgtatac tcttatttat atttgtccaa acttgttgtt 85020
atggtgcatg gattgttatg aagagaaaag tatagaattc taaagaaaaa aagaaaagga 85080
aattacaagt ttctattaat ccccccttt tccctgtccc cagatgcctc tgatttgaat 85140
ttctgtttat tcttctaagt ttagatatac acattttcaa tttttaattt ttagaacata 85200
atctatgata gtataacaaa aataggaagg taaatgatgt cactaaggtt tctcatttgt 85260
ttacagacaa aggacaaggt ctccctattt agaaattagg atctttctgt gtttgtttct 85320
gtatactagg atgaaagtgt gtgccaccac acccggtaag ctttatactg aatacatgct 85380
ttcatttgtg atgctgattg tcctcatggt catgtttaat tattgtcaga acgaaagtat 85440
tttatttaaa ttgtagcttc cgtttaaaga caattggtgg tatgggattt caaatgctct 85500
ctaattttat tgaaacaaaa ttcttactac attaccaaag ctgttaatga gaaattacat 85560
tggctcagtg gtatcttggt atcttggcca tttatcttcc atctcctgga aaagtaaaca 85620
ctaagtatca caactgatcc ttgataccat tccttctccc cctccctttg tctgtgtgcc 85680
tgcctgtctg tctgtctctg aatgtatgtt tatgatctca atccccatac aagactagaa 85740
gcagaaattg ttttctttat tttatggaag aaatcacaag ataattgagg tagtcagaca 85800
ttaacttgcc aaaggccaca aggaaatgat acagtcacta tttaatcaag gtcatcttga 85860
ctccttacat taaactatgc ttcggtctgg aaaatacact gcgaaatcag atcaatagat 85920
agaatttcca gacaatggct tcaaaatgat tggaagctaa ttcccttatc tgtgtggcaa 85980
aagtcatatc ttaagcattc catttgagtt ttaagtaaaa tatggtatgt gacttcagta 86040
tagtattaac atttactagt ttaagattta gtcatatttg ctatgtacaa tatatggcac 86100
tactcaaaac agttgtctac tatttttata gttgcacatg ttattctcat ttacatatgc 86160
aataaatatg tcatccactt ttatatgaag aatatacaca ttttaatctt gagaaactgg 86220
ccacacatgt gaatgagagt ttttaccttg gttttgcact aataatttac caatatattc 86280
agagtaaatt ttacagaaaa tcacttttta ttcccactta ctgtttaagg taaaggagtc 86340
atatccagtg atggcttctt gttggcagag tcttgagaca gcacacacaa aaaaatcata 86400
tgtcaagaaa aaaaaggaat gtgtgtgtgt tctctgttat tcctttcctc atgaagccac 86460
cattatccaa tcatgaaacc ccaccttgat aatcttactt aatcctcatc attttgcaaa 86520
atgaccacca acagctttgc tgttggacta agtttccatc ttcttcctgc ctctgatgga 86580
tatgaaatct atattagttt cagaatggac aaatatattt gattatatta cagagaaata 86640
aataaaatct aaatgttgat aaagacagga gagttcattt ttatggagtc cattagctct 86700
tctgtttcct tccagacaat ttatagcata aagggcttgt ttgtttgttt gtttattttt 86760
attctttaat cctttttac agttcagaat tcatcccct cccagtctgc ccccgactgc 86820
tccccatccc atacctcctc cctaccccta acctccatcg ccaagaggat gtccccaccc 86880
tgagcataaa agagcattat gacttaatct ggaattttt ttgctatttc tattttattc 86940
attgtttttc ttatttgtga tgattaagta cattttaaaa acaaaagtat caataaatag 87000
tttctacagc atgtcctctg taactgggat agaggtagca ttattagtaa tcacacttga 87060
aaaaagtaag atgtataaag aaattatttc ctttttgtta gtttggaaaa tataccttta 87120
tatttttcct attgtaagtc aactcaaatt gtttttagtt tcaatttcaa gtgaaataag 87180
agctggggag agatagctca ttggtgagga gcgctggctg gtcttccaaa ggctccaggc 87240
ttgagtcaca gtactaatct gcttcacaat catctgtaat tggtaaccca gcacacctga 87300
catttccttt tggtctccat aggcactgaa cacacatggt acacatacat gtaggtaaaa 87360
accgtcaaac acacagtaca gaagttacta acagtactcc ctgtgctctg tgctgtgaca 87420
cgtgtgcttt cagtacatgg ttttgatgac cattgtataa cacaagttct gtgtttaaaa 87480
tatctattct caatgacgta aaagatcttg agggatccta actttctttc cattttgttt 87540
atagagcagt atataaagat gctgatttgt acctattaga ttccccttt ggatatctag 87600
atgtttttac tgaagaacaa gtatttgaaa ggtatgttct atgactgagt tacttataat 87660
gctcatgtta aaagataata aatgtctgtt tcaccaaagg ctgcatatta gcatattagc 87720
tccagagtaa tatccactat ttctattgct caaaacatca ggatctagca cagtgcttat 87780
tcagtcctgg catcccctta atggtcaagg gtgaagttgc ttctgccaca ccctttctg 87840
atgatcacat ctgaagccaa tttcttgatt gctatcctgt tctaacagtt gatatttaag 87900
aatcgtttat attttgctat cttgaaaagt cttccagtat tttaagtagt ttactttaa 87960
aattccacct accattctgt attagtattt ttattttatg ttgttttaga aagaaaataa 88020
tgtttattgg taaatgccca tactgtacct ctgtcttagt cctctttaga tgcccctctt 88080
tggtcacaga gaacatagat atttccttaa agtttttatt agagcccaaa tgggtgtaaa 88140
atctctaaga ggtaacatta gttataccat ttgatttcaa atgttaaaat aattttatgg 88200
gcaacaaagt agcttattag aatagacatt atagcactct agaaacaaat gagtttttgt 88260
tttaaggata gaatgtagtg tgtgtgttaa gatggtttga ttatttattg atttatttca 88320
aactttact ttaggacatt gtgctaaagg gttgaaatat tctagagccc tgcttattgt 88380
gtcttaaaat atgtggaata acatgtttca ctaatggact ttactgtact tacacatgaa 88440
gccagcaggt ctcagtcctg aagctacttt tattcagagg tggaatacta tggcatgttt 88500
gttttgacat tttccgttta cgtttctgtt gcatggtgtt tattagcatg gtttatccgg 88560
ccacaatccc aagaacatcg tgatctctga atgaagggcc aagtcccaac aatgccatct 88620
ctagcccaca gatcccagtc ctcattgttg ctcataagct tccgatcaaa tctatagtga 88680
agaagtcctt atatgacaat gtattttcat agttcccttc atcttctctt gcttattcta 88740
atctaatgca aacggctgta gaaggtccta gtacatttct gcctcccgca aagctttttg 88800
catctccttc actacagctg tgcattaaca ttgtcttctg agtctctaaa gttgttttgt 88860
aattcccatt gcatcaagtt ctctgtgtcc attacagtct gaatgctgac cactttaagc 88920
atataacact ctgtaagaca aacattttct tcttttattc tttcttttt ctctttcttt 88980
ttttttctt ttttctttt tttagatgca agctggctct cttttccctg atgattctca 89040
atattattta ttcttcaact tgaggttaat aatcagagag agcctaaaca ttgtatttta 89100
tttactaaag ctacatcatt aaggctttga taattgttaa ttcatttatt tattcacttt 89160
acaaaactcc tctcctccca gtatcaccct cacaaatttg cccccccccc cccatgagtc 89220
ttctcagaga agaggatgtc cccttggccg ttggatacct gccagccatg ggacatcaag 89280
tcacagcaca agcctatcct ttcccaatga ggcctgacta agcagctcag ctggaggaag 89340
gtaattccag tggcaggcaa tagattcaga gacagccccg ctgcagttgt taggggaccc 89400
acatgaaggc caaacagcac aactgctaca tatggtttag tctctgcagg ctctctggtt 89460
ggtgcttcag tctttctgag ctcccatggg cccaggttag tatactctgt aggtctttgt 89520
ggtgtcctta acccctctac ctccctcagt cctatcccct actcttacaa aagactcccc 89580
caaatctgct taatgcttgg ctgtggatct ctgcatctgt ttccatcacc tgctggatga 89640
agcctctaaa gagacacatt tgctagggtt ctatgtgcaa acataatatc attaatagtg 89700
ttgggagttg gctctctccc atgggatagg tatcaaattg gaccagacac tggtgaactt 89760
ccttcaatct ctatattttt tagtattttt ttttatattt tattatctgt aatcattttt 89820
ttaaagtgca gtcgttatcc ccctcctgtt ctgccctctg acagttcttc atctcattcc 89880
tcctccccta tatccaagat gatgtctcta cacccccaca catgcccaca ccgcaccaga 89940
cctccccatt ccctggggcc tctcaagggt taggtgcatg catcttctct cattgatgcc 90000
agaataggcc atcctcagat gtaaatatgt ttcccaacta gtgtatgctg cctggtgggt 90060
ggctcagtgt ctgagagatt tggggaagtt caggtttgtt gagacagcta gtctttctat 90120
tggatcaccc tcttcgtcag attcttccag cctttcccta gttcaaccac aggggtcccc 90180
aacttctgat cattggatct gcttctgtct cagtcatctc tttgttgggc ctctcagagg 90240
gcagccatgc taggctcctg tttataagta catcatagca tcagtaatag catcagacct 90300
tggagactca cgctgagatg gctcccagtt tggaccagtc agtggacctc ctttccctca 90360
ttcttttctc catttttgtc cctgcagttc ttttagacag gaataattct aggtctgagt 90420
tttggattgt acaatggcaa ccccatccct ccatgccctg tctttctact ggaggtggac 90480
tctataagtg ctctctcaac actgttgggt attttaccta aggtcccttt gagtcctgaa 90540
agtctctcac ttctcaggtc tctggtatat tctagaaggt ccccccacat cccacctcct 90600
gagttgcctg ttttcattca ttctgcttgc cctcagtgct tcactcctgt ttcctaccct 90660
gctaatacct gaacatgtta tgaaattctt aggcaaatgg atgtcctcat tcttaatagc 90720
tgcctagtat tcattgtgta aatgtaccac attttctgta tctattcttc tgttgtggga 90780
catctgggtt gtttacagct tctggatatc aaaaataagg ctactataaa cacagtggac 90840
ttgtagcatg gtgggacatc tttttggtat atgcctagga acagtatagc tggctcttca 90900
tttacaatta tttctaattt tctgaggaac ctccagattt atttccaaag ttgttgtacc 90960
agctagcaat cccaccagca atagaggagt gttcctctta ttccacattt ttgccaaaat 91020
gtgctgtgac ctgaggtttt gatcttaacc attctgattg gtgtaaaggt ggaatctcga 91080
ggtcatttta tttgcatttc cctgatcaaa aaggactttg aacatttctt taattgccat 91140
tcaaaatttc tctgccgtga attctctgtt tagttctata ccccattttt tttattggaa 91200
gttttttttgt ggaagttagc ttctttagtt ctttatatat tttggatatt agtcaactat 91260
gagatgtggg attagtggag attttttccc caatctgtag gttgccaatt tgtcctattg 91320
acaatgtcca ttgccttaca gaagctttac agtttcatga agtcccattt atcaattctt 91380
gatcttagag cctgagtcat tggagttttg tataggaaat ccccacccac accccctaat 91440
ccccaaattt ctccccaacc tccatggcca tgagttcaag gctctttccc atttttcttt 91500
tctgttagat ttatcttatc tggctttttt tgttaaggtt cttgatccac ttggacttga 91560
gctttgtgca aggtgacaaa tataaatcta ttttaattca tttacaaact gactcccagt 91620
tagatcagca ccatttattg acggttcttt tttacctttg tatatttttt gcttctttgt 91680
caaagatcaa gtatccataa gtatgtgctt ttactgttgg gtcttcaatt caattccatt 91740
aatcaactga tctgtctctg taccaaaacc attcaggttt gtttttgtt ttttgttttg 91800
ttttgttttg tttttatcac tattgctgta tagtatagct tgaggtcagg gtgatgattt 91860
cctcagaagt tcttttattg ttatgaattg tttttgcttt cctgtttttt tggtttcttt 91920
ccagatgaaa ttgagaattg ttctttccat gtctttgaag aattgtgttg gaattttaat 91980
gggtattgca ttgaatctgt agactccttt tgtaggatgg ccatttttac tatgttaatc 92040
ctaccaatcc atgagcatgg aagatctttc cattttctga tgatttcttt cttgagagac 92100
ttgaagttct tgtcatgcag atctttcact tgtttggtta gtttccccaa gatattctct 92160
ctctctcttt cttccttcct tccttccttc cttccttcct tccttccttc ctttctttct 92220
tcctttcttt ccttctctat ttctttcttt gtttctttct ctcattctct cttttttct 92280
tttttctttt tttctttctt tttcttttt ttttcttttt tttttttttt tttggtgttt 92340
ccctatttc attctcagcc ctgtttatcc ttagtataaa ggaaggctac tgatttgttt 92400
gagtaaattt tacattcagt cactttgctg aagatgtttg tcagctgtag aagttctctg 92460
gtaggatttt ggggtcactt atgtatacta tcatatcatc tccaaatagt gataccttga 92520
ctttttcttt gccagtttgt atccccttca tctccttttg ttgtcttatt gctctggcta 92580
gaaccttgaa aactatattg aataggtatg gggagagtga gcatccttgt cttgttcctt 92640
attttagtgg gattgcttca agtgtctctc catttaattt gatattttct gttggtttgc 92700
tgtatattgc ttttattatg tttagatatg ggccctgaat tcatgatctc tccaatactt 92760
ttaacatgaa ggcatgttat attttgtcaa atactttttc agcatctaat gggatgatca 92820
tgtgattttt ttctttgagt ttgttgatat agttgattat attaatgtat tttcttatat 92880
tgaaccaacc ttgcagccct ggaatgaagc ctacttcatt gtggtgaatg accgttttaa 92940
tgtgtgctta gattcagttt gctttatgag tactttctga agttcttttg ttgttgttgt 93000
tgggtctgtg tatagtttag ataacagagt aattatgtca tcatagagtg aattaggtag 93060
cattccttct gtttctattt tatggaatag tttgaggagt gttggctctt ctttgaaagt 93120
ctgtgtgatg ccttcttagc agaaaggttg ccacaaaatt ttacatgagt ctttctatgt 93180
ggtccagagc acaaagtacc tttgtctgaa ttacttgttc aaatcttcca ggagccactg 93240
tactgttttt gtttgttcag ttgttgtttt cctttatata taataatttt agcttcactt 93300
gtttgggggg agctcctttg tatctgtaga acctgcatag tgccagaaat atgaactagc 93360
actgtagcca tatgcatttc agaagtctgt ttccagcagg actctagttt aagacaaaga 93420
gaaaattcca ttaaatgaaa ttcccccctt ccccaatgct atttttatga tgctctgact 93480
atagttgcca atgtttactg tcataaactt acctaaaatt atattattta tacttaagag 93540
aatttaatgg ttcttatttt tttatatttt aatggataaa aggaacagat tttccctgta 93600
gtatccactg caatacttaa cttttttttt ccttttccat tttttattag gtatttagct 93660
catttacatt tccaatgcta taccaaaagt cccccatacc cacccacccc cactccccta 93720
cccacccact cccccttttt ggccctggtg ttcccctgta ctggggcata taaagtttgc 93780

-continued

```
gtgtccaatg ggcctctctt tccagtgatg gccgactagg ccatcttttg atacatatgc  93840
agctagagtc aagagctccg gggtactggt tagttcataa tgttgttcca cctatagggt  93900
tgcagatccc tttagctcct tgggtacttt ctctagctcc tccattggga gccctgtgat  93960
ccatccatta gctgactgtg agcatccact tctgtgtttg ctaggccccg gcatagtctc  94020
acaagagaca gctacatctg ggtcctttcg ataaaatctt gctagtgtat gcaatggtgt  94080
cagcgtttgg atgctgatta tggggtggat ccctggatat ggcagtctct acatggtcca  94140
tcctttcatc tcagctccaa actttgtctc tgtaactcct tccaagggtg ttttgttccc  94200
acttctaagg aggagcatag tgtccacact tcagtcttca tttttcttga gtttcatgtg  94260
tttaggaaat tgtatcttat atcttgggta tcctaggttt tgggctaata tccacttatc  94320
ggtgagtaca tattgtgtga gttcctttgt gaatgtgtta cctcactcag gatgatgccc  94380
tccaggtcca tccatttgcc taggaatttc ataaattcat tttttttca attttttatt  94440
aggtatttag ctcatttaca tttccaatgc tataccaaaa gtcccccata tccacccacc  94500
cccactcccc tgcccaccca ctcccccttt ttggccctgg tgttcccctg tactggggca  94560
tataaagttt gcaagtccaa tggcctctc tttccactga tggccgccta ggccatcttt  94620
tgatatatat gcagctagag tcaagagctc cggggtactg gttagttcat aatgttgttc  94680
cacctatagg gttgcagatc cctttagctc cttggctact ttctctagct cctccattgg  94740
gagccctatg atccatccat tagctgacag tgagcatcca cttctgtgtt tgctaggccc  94800
cggcatagtc tcacaagaga cagctacatc tgggtccttt cgataaaatc ttgctagtgt  94860
atgcaatggt gtcagcgttt ggatgctgat tatggggtgg atccctggat atggcagtct  94920
ctacatggtc catcctttca tctcagctcc aaagtttgtc tctgtaactc cttccatgga  94980
tgttttgttc ccaaatctaa ggaggggcat agtgtccaca cttcagtctt cattcttcat  95040
gagtttcatg tgtttagcaa attatatctt atatcttggg tatcctaggt ttggggctaa  95100
tatccactta tcagtgagta catattgtgt gagttccttt gtgaatgtgt tacctcactc  95160
aggatgatgc cctccaggtc catccatttg gctaggaatt tcataaattc attcttttta  95220
atagctgagt agtactccat tgtgtagatg taccacattt tctgtatcca ttcctctgtt  95280
gaggggcatc taggttcttt ccagcttctg gctattataa ataaggctgc tatgaacata  95340
gtggagcatg tgtccttctt accagttggg gcatcttctg gatatatgcc caggagcgga  95400
attgctggat cctccggtag tactatgtcc aatttctga ggaaccgcca gactgatttc  95460
cagagtggtt gtacaagcct gcaatcccac caacaatgga ggagtgttcc tctttctcca  95520
catccacgcc agcatctgct gtcacctgaa tttttgatct tagccattct gactagtgtg  95580
aggtggaatc tcagggttgt tttgatttgc atttccctga tgattaagga tgttgaacat  95640
tttttcaggt gcttctctgc cattcggtat ttttcaggtg agaattcttt gttcagttct  95700
gagccccatt ttttaatggg gttatttgat tttctgaagt ccaccttctt gagttcttta  95760
tatatgttgg atattagtcc cctatctgat ttaggatagg taaagatcct ttcccaatct  95820
gttggtggtc tttttgtctt attgacggtg tcttttgcct tgcagaaact ttggagtttc  95880
attaggtccc atttgtcaat tctcgatctt acagcacaag ccattgctgt tctgttcagg  95940
aatttttccc ctgtgcccat atcttcaagg cttttcccca ctttctcctc tataagtttc  96000
agtgtctctg gttttatgtg aagttccttg atccacttag atttgacctt agtacaagga  96060
gataggaatg gatcaattcg cattcttcta catgataaca accagttgtg ccagcaccaa  96120
```

ttgttgaaaa tgctgtcttt cttccactgg atggttttag ctcccttgtc gaagatcaag 96180
tgaccatagg tgtgtgggtt catttctggg tcttcaattc tattccattg gtctacttgt 96240
ctgtctctat accagtacca tgcagttttt atcacaattg ctctgtagta aagctttagg 96300
tcaggcatgg tgattccacc agaggttctt ttatccttga caagactttt tgctatccta 96360
ggttttttgt tattccagat gaatttgcaa attgctcctt ctaattcgtt gaagaattga 96420
gttggaattt tgatggggat tgcattgaat ctgtagattg cttttggcaa gatagccatt 96480
tttgcaatgt tgatcctgcc aatccatgag catgggagat ctttccatct tctgagatct 96540
gtaggaaaat gttattggag gacagtcaac tttattaggt atttctcagt tgtaatgttt 96600
tatcttaaag aaaacagatt agtcaacata aaatataaga gaaaattcat taaaaactaa 96660
aaatagaaaa tctctaacat cttagaagtt atatggacat ataaacttta ggaacatata 96720
ataattcttt tattttctag aaaaataaat caagaccaaa gagaaaatga tttggttaaa 96780
atcagatact tgattattta aaattgtatt tgattttatg tctgctagta tttactttac 96840
agtaagatat gctatttcat actgcaattc atgaggcacc taagagttat gatggagtgg 96900
ttatttgtat aagtgtatta aataaagcaa taaaatgcta tgatagattt tatgcaatga 96960
aactttatgc tgaagttaaa tatacatcac tatttatgaa gtaatatctt atatcttttt 97020
tatatttcca aagctgtgtt tgtaaattga tggccaacaa aactaggatt ttggttacat 97080
ctaaaatgga acacttaagg aaagctgaca aaatactaat tttgcatcag ggcagtagct 97140
atttttatgg gacattttct gagctacaaa gtctacgtcc agacttcagt tcgaaactca 97200
tggggtatga tacttttgac cagtttactg aggaaagaag aagttcaatt ctaactgaga 97260
ccttacgcag gttctcagta gacgattcct ctgccccgtg gagcaaaccc aaacagtcgt 97320
ttagacagac tggagaggtg ggagaaaaaa ggaagaactc tattctaaat tcattcagct 97380
ctgtaaggaa aatttccatt gtgcaaaaga ctccattatg tatcgatgga gagtctgatg 97440
atctccaaga aaagagactg tccctagttc cggattctga acagggggag gctgctctgc 97500
cgcgcagcaa catgatcgcc accggcccca catttccagg cagaagaaga cagtctgttt 97560
tggatctgat gacgttcaca cccaactcag gctccagcaa tcttcagagg accagaactt 97620
ctattcgaaa aatctcctta gtccctcaga taagcttaaa tgaagtggat gtatattcaa 97680
ggagattatc gcaagatagc acactgaaca tcactgaaga aattaacgaa gaagatttaa 97740
aggtatatac ccgtcaagtc ttaagataca tctcatccta accccataat tggagtaaat 97800
tttgtcacat actatgtatt tcatggcatc ccattgtggt ctatgggcta aggatacaaa 97860
gtccattacc tgtgtaagca acttgaaaca taaaactatt tctggttatc attgaaatat 97920
catccccacc ccacaaatgt gtggtaagcc aaaacagggc ctcagtgttg agtttttcta 97980
ctagactcat gaaatgatat tcacttttat aacttaataa ttgtctcctt tagtgttttt 98040
ctaggaaaag gcggaataga gtattatata aacaaatact tgcatttatg tagacaccaa 98100
aaagtgtttt taaggcatgg ccttgataag gattacacac acctggcttc ttgacaagat 98160
aaattcacat tcctgcctgc atttagttag catatatttt ctaacctttc agatttgtgt 98220
tgtgtttttt aaagggtttc tctaaggaag atatgtgcag ctcggcatat attagtgaca 98280
gtagtcagat taaagttctt aactctatgt gttaaggagc aaaacgacct ctcttaaaat 98340
agaaagcagt ggaaaacaag agggcgattg tttaccagtg gatgtacctt agatgaagtt 98400
aaagcagagt cctagtggat gatatattta atggtgactg tctttaatat aaagttaact 98460
tttgggcagt tgcaattcat ttagtatctc tgggcctgag ttcactctgt tgtgaaataa 98520
aggaataagt aattctcaaa aatatatgct cgatatttct ataatctaaa actgatttgc 98580
taaaagataa ttcatctata tgatttaata tccatctaaa taaaattacc aaattgaagt 98640
atatacattt tggtttgtgt gcattttaaa gaatgctttc tttacctgat tttgttacta 98700
agttatcaat tatttcacct tccaggcaac acactttttg tctccttcac tgtgacatca 98760
ttgtccctat taacaaagaa ataaaataaa gttctgagaa attcagtatc ttcatacatt 98820
caaacatcct acgatgttac catttggtct tgattttaaa taaagggcag tttagttcaa 98880
caatctaatt tttaatcagt aaaccttatt ccaggttaat aggcttcctt ctttgtgagt 98940
ctaatggcac ttaatgaact tcatggattt tatgagggca tcgtttccct ttagaatata 99000
tagactctct ttttctcaca tttttataat gtagcttcca aaagacaaag gcttttagag 99060
gctgtatttg gaattggatt ttgtaactta agttgtagct agaaaagcaa ccatgtaatg 99120
cctaaggact atacaaatat aagccagctt ctaaaataga agactcaagt agctagcaaa 99180
ttctacattg cccttgtctc tggctcactg aatcaagctc aatcatgaag agtttgggag 99240
cttcactcat ttgacaaaag gtgtgggctg taaagcattt acatgctaag gtttgggaag 99300
tctcactgtg tttggtactt tataaactat attgcttgag cagacatcct attctctgtg 99360
gccatcatca cccgtggcat ttttagtggc ttttattttt taaagatcct tggctgtaaa 99420
tggtactgtt cccttatttc cctgaattca taataaaagc tcagtggcag catggagtag 99480
gattgtctca gaatcacact tcttttctca ggagtgtttt cttgatgatg tgatcaagat 99540
acccccggtg acaacatgga acacatacct acgatatttt actctccata aaggcttact 99600
gctagtgctg atttggtgcg tactggtttt tctggttgag gtaagtatgt ttgtttggaa 99660
attgtcactg tgagtttaaa tttaggataa aaaagctgta tgtattcata tgagcatgta 99720
cacatgtgta tgtgcatgtg tacaacggta gtttcctgta aagttcatcg cttctgaaaa 99780
ccaagaggag ctgacgaggc agctatgtgg ttaagggcac tggttgcttt cccagacaac 99840
ctagccaaat tcccagaccc cacatggtgg tttacagcat ctgtaactga agtctcagga 99900
acctggtact cttttctggc ctctgtgtgt acaacatgtg tgtagtacac agatgtgtgc 99960
aggcaaaaca ttcatacaca gaaaaataag ttaaaacttt ttaaaatcca cagttagaat 100020
tactattgat attttagtac ttcagacata aggaaatatg cataaataca aatgctatat 100080
atgatgaatt gtcataaaat aaaatttatt gggaatattt tttataatca gcatattttg 100140
attcataagt attgtaaaga gattactata acaaaatcaa taacataact atgtcatctc 100200
aagtaacatt ttttgttgtt tttgtgacaa ggggtcctaa aatccacaca tctaacaagt 100260
aaaataatag tttgttattt ataatcctca catcatttat tacacctcca tacatttagt 100320
ttttaacaga ttcagaagcc caacctacaa agagtgaata tgagttgaag ttaagtactg 100380
aaaagaattc tagatgtcca tctagatgat ctaatgaggc aggcagtgac tcatgtggta 100440
atgatcctta cttgcctgct gtacctttgt ctcaggcagt gttcatcgag ggaagctttc 100500
acaatgatgt aattacttca ttgtgtgctg acctgctgca caagaatgca gtattagtca 100560
ctctattatt tttcctgttg ccatgataaa gcacctaaaa gttaaggaaa ggagatatat 100620
atgtgctttc tgtttgaggg aacatattcc acagaggctg ggaaggcatg atagcagaag 100680
tagcaggttg gtaggtcata ttgcaagcac actttggaag caaatagtga aaaagtgggg 100740
ccaggctgta aacctgaagg cctgctcaag aaccgaagga ttccatagcc ttcctaaaca 100800
gcacagtagc ttgagaccaa gtattcaaac acaggagtct ttagcacatt ttacatccaa 100860
atcatcaaca gtcacctgag gggaaaaaaa agacattttg ggaaaggaag tcaggggaca 100920
ggggcagggt tcatagtgga caaaattcaa tgatgcactt gtcagaaaac aatctaatgg 100980
tgtgcttttc tttcttttcg tcttccttcc ttccttcctt ccttccctcc ttccttcctt 101040
ccttccttcc ttccttcttt tcatttttgt cagtatctta taggcattgt ccagttaaat 101100
agctctcaaa tgctagatta aaagaaagca atgatatgca caattttaca actaaacaac 101160
atatttgcta atgtttatgt tgttttcctt caatcaaaat ttacatagac tttgtttaag 101220
tctaaacttt ttttctttgt gtcagtgcca atgtgtagat ttcttttggc tactggaatg 101280
tttcttggta cattccatca tggaacaggt gccaatccac agtggcagtt tagtttttaa 101340
agcactgttt aagtcctaag tgacaagaaa ttcccaaatg catatcctcc tccattaaag 101400
tgatttagat aattttaagt cttaataagg actgtatttc catttagatt tatgacttta 101460
tagcatctct tctgtgtgtg atcccttttg taataggaaa taaactttgt ggcccacgct 101520
gtcttttctt attccttcac agctacttaa attagtggtg ggggaaataa tatttctcag 101580
tcatgtgtta ttttgaaaaa gtgtatattt tgtattttcc ctcaaaagca atgttgtctc 101640
taagttctta acactgaaca aatagactaa tatttctatt gtgctgctct ttctagtgcc 101700
ccttcttggc agtgtattat ggacaagaga gggaaaatgt aaacactgga ttaatggatg 101760
tttacaataa cctgatggtg tgtagagtgc agcatctcaa gatcctgttt gctccttggt 101820
cttgtggtct ttaagactgt gtcaaaggcc tgctgtgtct gtttgttaat aaggagttgt 101880
tttacatcag taataaaatg gagattatag tgaacttcta taaaactacc tttgctagtc 101940
agtgttagag tccctttagc acatcatctt tattgtgaat gtggatttta gggttatatt 102000
tgtcccacaa aatatgtgaa aatctgcaaa ttatggtgta ttacattcca tgtgatatgg 102060
caccgtgtgt tacctcccca ccttaggaat aaaaatgatt attacttatt ttgttgctgc 102120
ttcagcgtaa tcctccaaga gtacccttct ttgaaaaatt acatgaactt tatatagtct 102180
tgaatcattt tgaagtgaaa taatagtgtg tattccatta tctctttaat tcccaaatat 102240
ttttcctaaa ggcttcctac caagtatttg aaaaaatttt tatctactgt agtcagtaaa 102300
tatagcttgg attggtcaat ctatgtgata gacaagaaac tactttgtta ggatctaggc 102360
ctccattggt aactacgtat ttctcttatt gcttctattc agagtgtgtt ggcagtgctg 102420
gtgctgctga tttttctctt cttggatcaa aggagatgta atggagaagt ggctcagaac 102480
atgtgcccca tctagggtct agagtcattt gattagtctg aagattgagg aagacttttc 102540
tataagaata aagacatttt aaaagcttag attattacca ggtttctagt tttgcattaa 102600
cttgagtctt aagacatcag aagtttttct ttcttactga gacagtacac agagactatg 102660
tgtacattga gaaaacatga caattaaaat aataccatta gatcttcatc atagaagtta 102720
ataagataaa ctaaaataaa atatattatt taaacagaca acccttacct ttcctgtatg 102780
attcaataaa tagtgtttgt ggaaaaatga atgtgcaaaa tgagagagtg gaattccata 102840
agcttaatgt gctcttaacc aatagcaatt gctgaagtga cttcagaggt gtaaagccaa 102900
gacactaaga gtgtgtgcac ttcgatgttg gtcatattga atttagaaat gggtgtggaa 102960
ggcttagata aagacgctag aaaaaaatca actgtggatt gttccattgc aggtggctgc 103020
ttctttattt gtgttatggt tgcttaaaaa gtgagtatgc cacactttat gtggattgtg 103080
ttttgtttat atttagaggt tataaactat tttaatatat actatgttca ttacaccctt 103140
ccatattcct gctgattatg aggggagaaa ccatgtttca ataattcttc aatttctgag 103200
gagactgggt cccagaacaa agataccaaa ttctgcactc gtgctccatg tgtaaaactg 103260 tttttacac atacaataca atagtatttt gcatatagcc taggcatatc accacatata 103320
ctttaaaaca tttctagatt tatatgatgc ccagtataat gtaattttca tgtaagtagt 103380
tatatccttt agagaaatga tgataagaaa aataagtatg tgcgtgttca ctaaagatgc 103440
aattttaaga ataattttct cagtaaactg atggctgaat ccatagatac acaggagata 103500
cataaggttt gctatatttg ttcaagttga aagctgttca gtgcctttat ctcttcattt 103560
ctaaaatata tgttgttttc agttttcatg aaatgcaata aaatatatga agcaacagtt 103620
catatttaat agtttctact aattattttg ttcaaataag aatcaattac atctatttca 103680
attatgagaa accttaacac cttttggcaa tacaaaattt ataaaactaa gggtatagtc 103740
tcttttaaag tcagcatttc atgtttcctt atacttattt ttattagtga ttcacttggc 103800
aagtttggtt gtcaaataat ccttttcttt tgttttacag caaccctgtt aacagtggaa 103860
acaatggtac taaaatttcc aatagctcct atgttgtgat catcaccagt accagtttct 103920
attatatttt ttacatttac gtgggagtgg ctgacacttt gcttgccctg agcctcttca 103980
gaggtttgcc gctggtgcat acgttaatca cagcatcaaa aattttgcac aggaaaatgt 104040
tacactccat tcttcacgcc cctatgtcga ccatcagcaa gctgaaagca ggtacttgtg 104100
actaggtata aagtggagct gcccgcttgc catctgtgtg gctcatcggc ctgcctgcct 104160
tcagtagcag catgagcggg aacacaggca tctgcccctc atccaactac cttgtttggc 104220
atttctaaga tactgcaggc aagcataccc atgctcccca gcatttctgt atcagcctag 104280
tagagtaaat tatcttgtta caatgtgatt tgcgttcagt ggactcactt gaagcaacct 104340
cttttggata acttgacctt ctcacatact tatcttgatg ggaaaaaaaa taactgtttc 104400
ttgtgcctct tcaagagtgg tcatatgaat gcattagatg actttggggg gagggggata 104460
gtttttaatt attatgagac aattatagta catgatcctt gtataatgca tttgacaccg 104520
atttaattac agtcacagaa agtaagataa tttgaaaaat agaaccaaac atttcaaaac 104580
ctatggtaag aagggtcttt gaaaatgtgg tgcattgatt cgcctctgag ttagcttact 104640
ttaaagacca tgaagataat aagcctccta agttctcctt cactggagag cctgctgtgt 104700
gacactaagc cagggaagtc ctggcgcata caaataatta aagtatcatt catgtcaggc 104760
atagaaattc aactaaatgt agagaaagct acagtattga gaccttttta ctgtaatctg 104820
tctaaaaatc tcaaatgtgc atcagatttt tttaggtgac aaaattaagt gttgatgtat 104880
gaaaaagatt atatttatcc tggagccctt atgcctcggc aaagggttgc ctcatttgca 104940
tatgatcctg gtcatcctct tttagtctaa gaatcttaaa actaaggaaa tgggcaattc 105000
actctttaag agaggcgttc tctcacattt ctggcagaat tgaacatgga cacgtggaaa 105060
ggacacagac atttgaggct taggcttagt ttggccacac accattggta gtaatggctg 105120
tcagcagcct acgtgaaatg aatattagca tatttctgcc attcttttct gtgaggttgt 105180
tgctctcaaa ggaagtgaac catcctcttt ctcccaaaat ccactcacag cgccctctcc 105240
gccctctctg ttttccctct cagtgatcac catacattct tcttttctca tttgtcttcc 105300
caaaatgtca tctgtgtctc aggttagttc ctaaccactt tatgctgtgt tcctccttat 105360
tcaacctcct ggacctaagc agcaagatga cctcaagaga tttccaatca gcctgcactc 105420
attatttggt agctgtggta catatagttt gcttttaatt aaaaaaagtt attagattca 105480
tggtttatga ttctcatctg atactgaatt attctgctat actttgcaac aacttggaat 105540
ttcccttgga tgagctcttc agaattgtgc attgaccatg cttttccttg acagtaattt 105600
tctcaggctt ttttttcct gttactttct cccactttgt catactcaaa ttgcgatcat 105660
acagacacat aataaaggtc ctcagcaaaa tgcggttata atacacagat gctcctggtt 105720
gaaataaaat ttgaaatata aatatcacta tgagtatact attttgccca agcatacttt 105780
cagttttaaa tagttattac aaatgtcatg gaatatacat tatttctctg acttatttat 105840
ggaaggatat ccataatggg tatccatata atatattcat aaaatatcct aaattaatat 105900
gttttctaat gtatcacatg tctgcataag actttttact tttgtctgtg ggtcatataa 105960
aatagacatg gaattatcta tcctattgac ttcaaaaatc tcctatctgg gaaaagagat 106020
aagttatatg tacacacaca agcagctgtg atatacagca cgtatgtagt ctctgcaact 106080
caggcataca gacaaggaca ggaagagatt tttttccaga tgcagtaaat accctactct 106140
cttgcagaca ggctatttga attgaaccag gaaagaggta cagatttgac aagaggagac 106200
agggctttta gatagaaagg aacaacacat aggcaaagta ggaaaaggta gactaaagaa 106260
gacatactta ccagaagcag tgggtttgaa tagcaggatc taggttagtt aaggacaaat 106320
tatgggaaac tattaaatat taaagaattt tggactttaa tccagtaggt aatagtgaac 106380
gagtgataag gttcactatt acattgttgc catagtgttg tgttacactt tatctgttgg 106440
cttagctcct tttttagaag atgaattcct gcactacaag gagaatgact taatcacctc 106500
cctgtagcca gcattaccaa agcatgtagt agacatggaa tttttagttc attgacacaa 106560
caatcaagac tcaaatgggg tgaatctgga atttagaata caggttgaag cttatattcc 106620
cagtgaagaa gatagacaaa ataaaaaagg aagtctggtg tgtactgaga gagacagctg 106680
tgggttttgg atcagcatat ctaaatggca gaaaactcca cagggagggt gtatgtgccc 106740
tgtttggtgg agttgaacat aaaaaattga tgaaagcacc gccattaaga caccttgaaa 106800
ccgagagcag cagaagtgag gcccaagggg tacgatgacc agacattcct acccttaatt 106860
atagtaagaa cttgattaaa gacactgctt ggagctgagt cgtaggggac tatgtgtttt 106920
ataaaagttc aaaagtagga ggcaataact taaataaata catagaattc tcaacaaagc 106980
taatatttgt aagttcttga atttctgact agatgataat tcttatttta aatgattttg 107040
ctgtgctgtg aatttaggat aaaatatatt ggtgtccttc taaaagtgat taatatttga 107100
gaatatttat ttgtatcaca ggtgggattc ttaacagatt ctccaaagat atagcaattt 107160
tggatgactt tctgcctctt accatttttg acttcattca ggtttgtaaa gaataactat 107220
tatcaagttt ttctatttgc cataaagttt tgtgaataat ttcaaaagga agcaagtgaa 107280
tttgttgcta attttccaca tactagttga agtcctggct agtgaataag ttttatgaag 107340
aacagcaatg tttaatagtc ataaatttag tgaattcagt aactagctat gtctatctat 107400
ttcaggcatg ccctggatat gatactatcc tcttgaattg gtttgaaagg tacaaaagac 107460
agttttccgc ccaatcattg accataaaat ttgactcata gaacatttct taagtccaac 107520
actgaaatga aaatgaagtt cctggagagg ctacactcta atccagccat acccatgaac 107580
acttaaacac aaatttagct aagcagtttc cccacaaaag tataacttaa tggaaggatg 107640
aaaaatggat tgttgaaaaa atgtgaagga aaagaaatat ttagagcctc tgaggctctc 107700
ccttagtgac tgctgtgaca gacctccagg gtagccatgc tatggagatg actgaaagtc 107760
acttaataac aaaagaaggc cattgagtgg agaccaaagt gaccatgaaa gcatcacatt 107820
aggactccaa tgtcaaagga cttacaggag ttgtaagctg atactcttgc ctgttgaatc 107880
aggcagtttt ctgagctccc tgttggcttc ctgaagcttc agagagcaaa tgcacttgga 107940
gaagtagttg taacacaaca tggtccttgt tggaatgaca cagtctcata gcttgtccct 108000
tcccttctct ttaaaatagt actgcatctc tgaaaacttg gaaaaaatgt ggaactattg 108060
cccctgtatg tatacacaca agccacatca gcagatgcag agaaagcagc tgttggttca 108120
cctcctctga aatgattgac ataattaaat acacttactg tactaagtga actgtgtttt 108180
ggatttcctt cattgctgtg tttaaagata taactttacg gtagcagcac ctactggaat 108240
ttttttaacc caagttttga tttatgtact caaaagtgtt agtttatgtg tgtttcttta 108300
gcatgagaca tttgtttccc agtctcagaa aataaaccaa aggtccgtaa taaaagtata 108360
ctaaatacta tatactaata taatataatg caatataata tagtatggtc aaaaactgga 108420
atgtggatat ctatctgaat ctgcctacaa aagtcttaaa aatggtgctt gagtgatata 108480
tatatttatg gtctcctaag tatctcttgt tatttagttt atctcagaaa tctgggagag 108540
ctaattttca aatatttatc ttacaaatta aaggttattt gacatttgtg atggctttca 108600
agtcctttta tgtatcttaa acacttttat ttcaggttct agagctgcta aagcttcatg 108660
aggtagcaaa tctctcagag ctttcttttg agctgagatc taccctgccc atttcccttc 108720
aggacaccag ccagaaagcc catggaaact agtggagaat tagcgtatga aagttacact 108780
aagttggttt taaagttagc acatgtttga tgtcatgtgg accatttatt tggtaaactg 108840
tagtgaggtt gcaaacagta ttctaatttt ctggggtgta atacagtaag atgtctgcat 108900
tgcatggcag aattcatttt gatagtgtgg ctagaaaaat acttaatttc aaattaaatc 108960
catctactat aaacctttg agttactgga gtatctccag ttattacagt aggcataggt 109020
gaggtgagat ataaataaca cttattaaat aatactcctt tcaatattac atatgaaaaa 109080
ttagagtcag aaaagtgaac ttgtcaacat gactaaacct aggtttaaaa cagatatttg 109140
taatttaaaa tgttctgtta agaatgtttc attttaaacg actccaacaa aatcacaaaa 109200
gataatattt atactaaaat tattttgaaa ttttaatttt tcaatggaca ggatgaagaa 109260
aatcataatc atttcacatt tacttcttat aaaatttaga gtgtgtgata aataaaaata 109320
tcccaagaac agaaagcacc gtgtaaagct tcagcagctg aactatcaca tcagcaaact 109380
aaacaatttg aacattgttt ctctgcagcc ggcagactgc cttcgagctg gcaccttatt 109440
catggatgca tgtttcctca ctgagaatag tgcagtctaa gaacgtgtgt agacacagct 109500
cagcaatgcc cctgtccact taacaaagtg aaaatgtctc tcactaccat gttctctttg 109560
accccgcagt tggtgttcat tgtgattgga gctataatag tcgtctcggc attacaaccc 109620
tacatcttcc tagcaacggt gccagggcta gtagtcttta ttttactgag ggcctacttc 109680
cttcatacag cacagcagct caaacaactg gaatctgaag gtacagcatg gaatgcattg 109740
caggggttcc tggaagtggg tgagggggac cacatttact aaccactata ctgctttaaa 109800
tctctaatta tataacagtg gtgtgtgtgt gtctgtgtgt gtgtctgtgt gtgtgtctgt 109860
gtctgtgtct gagtagtagt agtagtagta tgtgtgtggg catacttgct cgtgcaggca 109920
tgtgtgggaa ccaaaggcta cctttgtcaa ttgcttctct tcttttttcc cttatcatct 109980
tctttctact tcctccttct ctgttccctc cctccctccc ttccctctcc ctctctcccc 110040
cctcccccca ccatccctct tttcttcctt cctccctttc ttccttccct tctctctctc 110100
tcatgagttt ctcacagaac ctggcatttg ctggttcagc tggactggct ggccagggag 110160
gccccgggac ccatgtgtct tcatctctag cattacagac attcagtaca ggcccaaagt 110220
ttttcatgtg tgcttggaat ctgacctcag gttcttatgt ttgtgtagca gacatattac 110280
cgactgaact ctcccggccc aacaatgaaa cttataaagt acgtgaggat tgactttgtt 110340

-continued aactactatg gctttgtttt ggctttcaaa caagtgtata cccttaccat tgtgtatgca 110400
tagacatgca tacgttctta tactgctcaa agtcaaaacc agcaatgcta tttttcctca 110460
gagtttctcc cagatttcaa gtgagactgg atggaattct tccatttggc ttatcgtctt 110520
caggcctttc cttattggcc tggcttggtt aatctttgct ccatctcctt aggaagcatc 110580
tctttcagaa ggaaccttgg tgtgaggcaa ttattttttt aatatttttt attaggtatt 110640
ttcctcattt acacttccaa tgctatccca aaacccccca taccccccca ctcccctacc 110700
cacccactcc cacttcttgg ccctggcgtt cccctgtact ggggcatata aagtttgcaa 110760
gtccaatggg cctctctttg cagtgatggc agactaggcc atcttttgat acatatgcat 110820
ctagagtcaa gagctccggg gtactggtta gttcataatg ttgtttcacc tatagggttg 110880
cagatccctt tagctccttg ggtactttct ctagctcctc cattgggggc cctgtggtcc 110940
atccaatagc tgactgtgag catccacttc tgtgtttgtt aggccccggc atagtctcac 111000
tagagacagc tatatcaggg tcctatcagc acaatcttgc tagtgtgtgc aatggtgtca 111060
gcatttggaa gctgattatg ggatggatac ctggatatgg cagtctctag atggtcgatc 111120
ctttcatcac agctccaaac tttgtctctg taactccttc catgggtgtt ttgttctcaa 111180
ttctaagaag gggcaaagtg tccacacttt ggtcttcgtt cttcttgagt ttcatgcgtt 111240
tagcaaattg tatcttatat cttggatatc ctaagtttct aagccaatat ccacttatca 111300
gtgagtacat attgtgtgag ttccttttta tttttaagag agtaaactta atgtgtgttt 111360
ctgctttgaa acttaggagc taaatcaatt cacagaaatt ctacactgag agacttagag 111420
attgagtctc aaaagacaaa acccattttc tcagcagtta ctaatttagg attagccaag 111480
aatattgact actcttagac aaggaaatgt gagttaacaa ggaaagtggt tctgtccact 111540
acctacctat ctaccatggt cagcaggtaa aagggcaggg ccatgcactt taaaagtaaa 111600
ttccggtttc agtgagaagc ccacaccata gatgcttatc gtgaagttac tctggagttc 111660
atctttgtca gaaacatggt agtatgaaat tctgttctgt attgcaagct gtacattatc 111720
tcctatggga tgatttacag gcaggagtcc aattttcacc caccttgtga caagcttaaa 111780
aggactctgg acacttcgag ccttccgacg ccagacttac tttgaaactc tgttccacaa 111840
agctctgaat ttgcacactg ccaactggtt tatgtatctg gcaaccttgc gctggttcca 111900
aatgagaata gacatgatat ttgtcctctt cttcattgtt gttaccttca tctccatttt 111960
aacaacaggt aatctgaact tattttttttg tcagtgatta aaatgccata tgtttatatt 112020
aaaatattta gatgatttta agtagacttg tagagcttac aagtaatttc tttgcatttc 112080
tgttgttttg tttctaaata atttatttaa aggtttatat ggtattgtta ctagtttcac 112140
tatttaagaa taatgagaca ctgagtcaga tagcaaatat gtgactaaca agaaaaatgt 112200
ctttttcatg ccaatgttgg aaatctatat ggggaaagaa aaacatattt gtatacacat 112260
gcacacatgt acacacactt atcatttcac acttcctgta aaatttcttc acttaacaac 112320
tacttattgg taaaattctt gtctaatatg aatttgaata aataaaaatt agcatagaag 112380
taaaataact gacataaaag tgcattattt ttcaaatata aatgttctga aatttaggat 112440
cttcaaggaa aaaataagtc acaataagaa aaattaaaat ctatacagat aaatgagtat 112500
tttaaggtgc tggatttctg agtcaaaatg ctatgttact tatatataca ccattttatt 112560
atatataaaa tattgtatat tatttatagc aaaatttcag agcgaatgac acatcaatgc 112620
cagatttgca acattatttg attataagaa cagaattgct caactccaat gaagcagcct 112680
ttgacaagtt atcaaattgt gtcatgcagc ctcagggtgg gtatcacact tgattacctg 112740
aaggaaccag cacaggcact ggagagtcag gcataagtat gactcatgta gatactggtt 112800
tctgttctct tcattctgtg gatgatgcat ttctttctca ctctgtctct ctgtatctct 112860
ctgtctttct ctgtctctct atgtcatatc tatatctata tacacacata tataatatta 112920
tataatatat ttgtatataa taaatgtata ttatgtatat atttcatgta taatacatat 112980
ataatatata cacatataac atatatatat atatatatat atatatatat atatatatat 113040
atatatatat gagagagaga gatctgtgta tgtgtctccc tctctcttcc tccctgccct 113100
ctctcagaat aatagttatc ttcatttaac aggaccataa cacatgagct tcatgtgcca 113160
tcttcattct tcttcttgaa ttaatggtat ggatcctgtg tccaattatt aaatcctaga 113220
gaaggcaaaa aacatattcc ttctggcttt gggcccactg cagattgaca actgctatga 113280
ggatggttaa cttacccata tattgctttc ttcatgcatg gctatgaaat gaatctatat 113340
gtaggtatat ttgtggatac acatatagtc attttgacac cttaaaataa tttttggaag 113400
gtataatatt gattatttgt atataaggta attcagaggg gatcaaagat gactaaatta 113460
catggattaa gacttcacaa ttaactcaag ccaatgtatc acatgctgta tcagactgta 113520
tattatgact aagtcctggg ttactaaggc cagtactcaa aatcttcact agtcaacaca 113580
gtagaacctc caactgtgat gagcagcaca gcccaggaac ccagccataa ccaaccaact 113640
ctattggtct taattttatt gatgatatta acttacatta atttacagcc attaattaac 113700
ttccctaatt ccctaatcgt gtgggcagat gcacactaat aacactttca taatattgtg 113760
tgatattttg tgtaatacag tgtagtcttg tttgtaataa atggccagtg attattaaat 113820
aatactactt ggtattaaaa tattacctta cttttttta accctcagaa taagaaatgt 113880
ataagggacc tatataaaat gaactattaa caattttcaa tatattattt gatattaaca 113940
cagcataaca tgtgttatct atggtgtacc taagaaggag aaaatgtcaa catgaaattt 114000
ttcagctatt aataggatga cttgttcatc ttgatgttta actttatagt aatttaatgg 114060
tagattaagc attatcattt gggatatgat atcctaactt taaaataatt tatgaacact 114120
tatcttaaaa atatttgtag tcataatcct catttttaa aattttaatt agttgccctt 114180
tctaatccta aatgaaattt actctaaaat aacatattaa cactgttctt ttcaagcaga 114240
ttgggcattt ttcttcttgc ttttaatgta atgtgcaaac ttctccctta aatggctggc 114300
attagtttc tgactgcctg gtgacaagtg aagactcctt tcttagaaac agcttttgat 114360
gagcagagac catgaccctt acagaggtgc tcagcacatg tgctagtgct actcggatgg 114420
atgtggccct cctttgagtt ctgtacagga tctcatttcc tatttatttt tatctatcta 114480
tctacctatc tatctatcta tctatctatc tatctatcta tctatctatc tattcactca 114540
tttatggtgt ggtattcaat cagtatttgt ttatattgtt acatacagag taagagtaga 114600
caattactca ctaccaacat taccttcaag acctaagcat catttaaaag tgcagcagtt 114660
cccaatattc agtcactatt tgattttaaa ttctggatga aagcttactc aatgaaggca 114720
ttattgttca aaggagtcac taaaactgca ttaaattgaa acataaattt attggcaagc 114780
gatgagagag agatgaatac aataattcac agaagagaga aataacatat actttgttca 114840
aaaccctttt ccatgtctag gtgaaggaga aggaacagct ggtattattc taactttagc 114900
tatgaatatc atgagtactt tgcagtgggc tgtgaactca agcattgata cagatagctt 114960
ggtaagttac tatttttaat tttatgaaaa gttgagagaa caaaacaaaa agagtaggca 115020
ctaacatatg aaatatatat atatatatta ctcagtttaa gaaataaaat attcaggtta 115080
ctttaaggac attctgtatt ccacattaag ctgtggcatg atttatcttt cgtcctcatg 115140
gattatcatt attatgtgtc tttgccctgg agttttccaa agcaaatctt agaagtggaa 115200
gacattgctg aggttagaat ctccccaaac ttggcttcac taacgccaaa ttactccagt 115260
ctgttgtgcc actatatact tccagcaaga gagcatgtga atgtttccag cagtatttct 115320
tattcaggct tttacaattt tgccagcttg atgaatgtga agtaactact aaaatttctg 115380
gataacttag taagtctcta ttgttgacca cttggatttt tattgttgtt tatttctgtt 115440
aaatgcttgt ttctgttatt tgcaacctga tgaggtttga tgtgcttgtt tgtttttcct 115500
tatgttatag gtgttcttaa gtcctggatc agtcatcagt tctatacatt tcaatggccc 115560
ttgagccagt ggctttactc acagtatacc ttaatgaatg gaaacattga atttgataga 115620
gagtagttta ttttccttta cctttatggc ttgtgcattt ggtgtcttgt ttatgaaatc 115680
cttctgtata ttaggtttcc acattcaaca gcctgacatt tttcataatc ctcttgtctt 115740
attttgaaaa tgtctggtca tagtgtttgt cattgctctg ttcctttgtg cttaacggat 115800
gctgtcttgc atttgaggac tttgtgtgtt caaagaccat atttggtgta ttcttccata 115860
gagtgagagc ctgaagtgat atttgtgtgc taaaatgata caaaggacta ctaattcaca 115920
agggccaggg caagaaatga aaagaggttc cataaacttc cctatttata ttttaataaa 115980
agccatatta tcagttagac tttagaattg gcctgagaat gtcataactg atttcttttt 116040
acatatttga ttacagttat ttgtgtcagt aaggaatgtc cataccacag catgagtgtg 116100
gagggttcaa agggaaactg gtggggctca cctccctctt ttcaccatgt gggtcctagg 116160
ggctgaactc aagtcatcgg gcttagcagc agttgccatc acatgctgat ctgtcattgc 116220
ggacctgtca ctgaagctta aggctttgga catacattca tccattcctt atgtcatttc 116280
taagaggtct agaatccata caactcccct tacttccatt ttcagacacc cattcatgtg 116340
attgcaaaat ttctatagtt ataatatata aatacataca gtatattttt ttcataaata 116400
tgtcacaagg gaaaaaccta aaatctttta aagcctcttc ttgtttgttc attttcatca 116460
ttccatgagg cagcttagta attccttgaa atacagtttt cttaggtttt atttagttag 116520
accagtccct agtctcttct ccacacttct tggttttgtg ttggaattag ctgaagaaga 116580
ttatataaat gctgtttcta tttacttaaa tttttaaaac tatgacttca taattcaaaa 116640
cccttgtgca cattatatat ttctttacat aaaaattctc ttcttgtaca tgtacaattc 116700
cctttgcaac cttaatttc tggcttaatc acatagccaa acttttgaca ttgcaacaca 116760
atgttgtcac ctacagagtt cacactcaag atatgtacag ttaagctcct aaacttagtc 116820
acacacattc aacctaagat tttcagtaag tagtaagttt ttgatttgtg ttgggcttct 116880
ttcatagctc tgtttgtgca gctggatgtg gcctgtgaac tgtggattgg acagtcctgt 116940
tagaatagcc tttgcacagg ctgacaaaac cgttgctaaa tacatttcta cttcatgtat 117000
ctagtgtcca tgaaagacac ttaaagtatt tctccaggtt ttcccatggc tatgctagac 117060
tttgttgtct gacattgtat ctttcatggt gtgtgaaagg accctttaca gacctattgt 117120
gtttgtgaca tggtctatga aatgtatcaa tatttgcagt tgattacgtt ttcaaaagta 117180
atgctctttt gtttaatatc aaagagcgta tgttagtttg catctctttg ccaagcaatg 117240
ctggcgggcc ttcctgggtg ttggtggtcc cttcctgcta ttacctccca tcgtgctggt 117300
ctcacctgca ctgctgcgaa aactacccgg tagtgctctt ctttccacct cttgcttggg 117360
aatctgaagg gagaatgtct gatcagtggc cagtagtgct cttctttcca cctcttcctt 117420
gggaatctga agggagaatg tctggtcagt gctttcagat ttcacaccca cctgatgtaa 117480
ccccaaggtt ttacaacact aagcaaaaac tcagtgtgat gtaattttat cttactgtgc 117540
tttaaactgc atcaagagtg atctgagttt aaaatggaac aaatacaatg ttttctttac 117600
tatattataa agctaagtac aaggctattc aggaaaaact tcagagttgg aataattact 117660
tcatttccca tctgtcccaa tttaaaaatt aatacagtca atttgactat gaagttatga 117720
atatagcagt ataactttgt ttttattttc tacctgttac atacccacat atctctagct 117780
ttctttatct ctcagctatt aaatccaata tcacaacaac acaagttatg ttgtgtttat 117840
tatcacatat ctggaatgct gatactcaga actatccagc aaccttttca ttatgttttc 117900
ataataaaat ttactcccaa gctctttcct ttatttctac atccttttag acattataat 117960
aattctattc tttaaactct tagccaaaga cctttctata tatctcacag aaatacatac 118020
atataaccag aaataattcc cttacatctc tctactatct ctttctcttt tgtcttttta 118080
aaattttttt aattaatttt ttacactcca tattccattc cccacccccc catccactct 118140
cccactgctc cacatcacac acttcctccc cactccccca tcccccactc ctccaccccc 118200
acctgatctc taaactccct ggggcctcca gtctcttaag ggttaggtgc atcatctctg 118260
aatgaacaca gatctggaag tcctctgctg tatgtgtgtt gggtgcctca tatcagctgg 118320
tgtatgctgc ctgtttggtg gtccagtgtt tgagagatct caaggttaat tgagactgct 118380
gctcctccta caggatcacc cttctcagct tctttcagcc ttccctaatt caacaacagg 118440
ggtcagctgc ttccattggt tgaatgcaaa tatctgcatc tctttcagct gcttgttggg 118500
tctttcagag ggcagtcatg atagatccct ttttgtgagc actccatggc ctcagtaata 118560
gtgtcaggaa tgccttttga gctggatccc actttgggcc tgttgctgga ccttcttttc 118620
ctcaggtttc ctctccattc caatccctgc aattctttca gacaggaaca attatgggtc 118680
agagatgtga ctgtgggatg acaaccccat ccctcacttg atgtcctgtc ttactgctgg 118740
agctgagggc cagcaggaag agtggaaaca gggcaacctc aggaaatagg aggttggggg 118800
gggggggacg acgaccctcc agaatgcacc agaggcctgg gaggtaagag actctcagga 118860
atcaaaggga gggaccttag atgaaatgcc caacagtagg gagagggaac ttatagagct 118920
ctttcttaat gtagcatact actagaaaat cttgcagtag acatgacatc ttagagtatg 118980
agtacaggtt tattgaatct ctagtcatat gtactctctt tacccatgtc cttgcttcta 119040
tctagaggca agtcctgtgt agttgcctgc cctttatgag acttttcacc agtgaatact 119100
ttcatttggt ctccagtttc tgccctaatt atttgacctg tttacagcaa aacttctaaa 119160
gagattgcct ttctctgtta tatcttctgt tctttacaca gtttcttcca tattcatcac 119220
ccatgtgagt cacaataaac atcatgtaca aagcaatgtc cttgtcttct gaagttgttg 119280
agcactattt cacatggatg aatccttata ctatttcatt tttctgctac ctcctgggcc 119340
ttcatctcat gtatccttta aatcatcatt tgtattactt cttctttcca catgcattct 119400
ctatagctat tggtatctaa ccccatggtt caaaagttgt ctcttgatga attatagatt 119460
catatattta gtgtacatct ctctattcct ctctatacat gtccagctac catcttgata 119520
cctccatgaa tctataaaat attctgctag attgttttct agtagatttg acatgcaagc 119580
atatgagttc ctgtacatca cctcagagtg cacatatgat cttaagtggc catcgaaatg 119640
atacaaagtt tatactccct gaaaggccaa ataaataaat gagagccaac aaaggtataa 119700
aaggtgatat tttaaacttg gcagtattaa accatctggt gtctaagagg ttgctcacac 119760
ataatttctt catttgataa ctcatatcct tccagaactt tctaccacag aaggaacaga 119820

-continued

```
aagtgagcag tcttaatatg tgaatgccat tgccttcgtt tttcaagaag accagcaaat 119880
aagcatccct gtttccacta gattattgaa ctgaactgta tgtccctagt aaaaagaagg 119940
aagttgcaaa gttaagaaca atgagcttat aagacttcca tttagatcac tattagtgaa 120000
gttccagaaa gttcttgcat ggttggtgca atctgagaag agttttctgt cagcacaaag 120060
tcactctgtg tctcctttgt gctctcatca cctgtgttta ttttgggttc cactgaggat 120120
caggtgacta attgtagaat gagcaacatg aaatgtggga ggacaaaaaa gaatttctcc 120180
ttccttcatg actgccgtca ccaaatgtcc ttgtattgaa agcagttcct gttgtaccaa 120240
tctgacggat gagttaattc atcctctttg tcttttgcct ccttttaatg gtagcttgat 120300
tgtggtttgt tgttgttctt acaagtcttt gtggtgtatt tttcaagaca ttatgcattc 120360
aaccgcaaag agccttgcat ttctttctgg ctcagacact aaaaagttga gtgcctttag 120420
acaagtcatt tttcctcatt tccaaggcct tattttcctc ctctgtaaaa ttaaatggtt 120480
tggttaggaa tttttcagat tgctggcatg tttgacattc tctctctgct gaacccttcc 120540
atataaaaat ataaactctt aacctacatg tagatattat ttcagttctt aggaaatcca 120600
cacaccaacc ctatcctgaa tgctgacatt cattgaatac tagcctgtag ttactacagc 120660
tgactcagta tgttactaca gccaacaaag aaaaagtaac taatagaatg atatttttga 120720
accttgaatt aagacaagaa atttaacagc cccctcagga attgctggag tgtacaaaat 120780
tgtgtgataa acttggaaaa ttgactaggg ctttggtcct gccactttat cttcctggtt 120840
taggttttgt cctatgtaca atgaaaggat ggattagatc atgggctctc tcagtctggc 120900
tacagatgaa taaagctgct tttcaggtt cacagaggcc agggaaatta gttcttctgc 120960
tggggcaagt atcagggcct gtttctgta ttttgaaatg tgcccaggtg attctaatgt 121020
gtatggaggc ctttaaatca ctggattaag tggtcctgca gattcctttt tgctttgaat 121080
gtctgtgagt cacgttacaa ggattagcaa attttttcta ttaaggttga aatgaaaata 121140
gtttcagctt tgtaagctta tgggctcatg acagcaactc aactcaacct ttgtatgaca 121200
aagcagccat agacgttcat gagtggtgtg tgtgtttcat ttcactttgg caattattat 121260
tttcagttta tttgaatttt gagtggtttg ggtttgagag atagggagaa aatatgaaat 121320
tgagaggata gagagatagt aagtagaatc tggaagaaac tgggggaaga ggaaagaata 121380
tagtcaaaat acgtaaaaaa aatataaatg aacctaaaat aacaaatcaa aatatcctat 121440
caagaattca gtattttcct ctaagcatct atattttgaa atattctaac ttctccaaag 121500
cattctgtca gtcagcttca ttttctgtat gtaacatgaa tacttaggta agcatcattg 121560
acagcacaaa acatggtttg ctagtggtcc ttccatttac tagtaactat accctgtagg 121620
ctaagcatga gtagaaatat ggccactatg tcatattcct ccactccatc tgcttatata 121680
ttgtattcac caactaatgc tatgcaagag gcctggtttg gtctgtggta catacaccag 121740
tgacactcca ttgaaaggat tgatttttct ctttcccagc aaatatcaat tgcaaatagt 121800
ttattagtta agggtgagac atgtccaatt ccccttttccc ttctcagccc tgagagtttt 121860
gtctgctttg aacatgtggc aaccttgtga atgctatcac tgtctctgtg agttcacttg 121920
tgtacaatcc tgttgtatct ggatgacact atttccttga aatcatctac caccacttgc 121980
tatctcccct tcctataaat ctctcagttt tgagaggagt ggttctctca ttctctgcac 122040
attgtccagt catggattgt tttgttcatt agtttctgct gtaaggaaag gcttctctga 122100
tggtggctga gtgaggcact aatctatggg tacaacatta ggtcattaag agacatgttc 122160
ctgttatatt ctttaggctg aataatagaa gtaggctttc ccctacagcc catgacctac 122220
```

ctaataaggt ttttgcccac tttagatgtg tcaagtatcc tatctcatgg aataggtctt 122280
aactccaatt atctaattgt tggttagtct ataatacttg tgcctctatt gcacttctat 122340
tatagtttct ggatttgtag ctagatgata ttaatgattt gtaattactt tatgtgtgtg 122400
gggggtttgc ctgcatctga tcaccatatg tatatctgat gtccatggag gacaggagac 122460
agtgttagat cctctggaac tggagttata gacagttgtt agctacttta tgaatgttga 122520
gaaccaaaac caagtcccct agaagaatag cctgtgctct taaccactga actatctctc 122580
aatcctcccc cataatgaca tttttgtctg ggattgatga acattttggg catgggaaac 122640
aatgtcacta ttgccatgac tttggagtgc ttggtcattc attgaagcat aattttgtta 122700
ttctgccttc taaagaacta agtaaaatta gcaaatattt ttatgagaca tttctggatt 122760
cctgaaaatg ctgtaatgac ttctgtgatt agctagaaaa gatgaacagg aaaatttaga 122820
gtcgttttca tgataaccga gttgcctcct ttataaatta acattgaaag gaagctattg 122880
aactacattt tgttcttgcc atcatcattg tcatcttggt gcttagatta gtacatttag 122940
gcattactgt aaggataata acagttttaa ggattacctc ttcctcaata tatttagggg 123000
aaggctttgg ctcttaatac aattaatgta ccagaaatta caagcacacg aatcgcaagc 123060
aaacatttca ctttatcttg gctacattcc aatttgaaag aataagaacc tatgctatgt 123120
taagttttct tgtccataaa taaaaaacag attcagtgtt ttagcacctg gctcacctgg 123180
ctctcctttt gtcctttgcc tttaaagtat gagaacatgg tgttaattcc ttacctgact 123240
tcattgtaat ttaactctag ccacacagag atttttccta tccatggggc tgactaacct 123300
tcctgggtag ggctgcccat actccttcct tcctaaatct tctaagcaca gcagacagca 123360
gcttgagact ggggagtatg tcagtctaca gctataatga taattaccaa tgctgagtga 123420
ctgtctagcg ctaagacacc aaggttttta cataccatgt ggaaatatat agtagacaat 123480
cctttaagaa aggattaagt gagttttgca agttttatga aaacagatag gggtaatctc 123540
tgcaggggta atctctgctg tagtatgtgg aagaataacc tgtcatatgt gctttcctga 123600
tggagagatg cttccaaggt gccgcccacc ctttgagggt ctccagggtt gtgatgggca 123660
gctcctatga tgaacacact atgctcaagg ctgacccggt ggtgtttctt aacactctca 123720
cctgctttaa ggatcaatta aagtggcaga gaaagttcat tgaggaaatt tgagaactct 123780
gtgccatttg cagcaagaaa aacaatttga agcaagaagt ttaaggtcca cagctcagag 123840
caacccaact ccaggtctct gagccccacc cccaccccca gcgctagcag gaagtggaat 123900
ttgatgtgca gccagcctat gatgtcctta tgaaatgaga aactacaaga actttgactc 123960
caatagctac aacaaaatct atacccaact catccatgag tgcatcacgc taaagaagaa 124020
ggatgaattc ttgatctgct tcacagacat ccatcaaaac ttcctgaggt atcgtgcacc 124080
caggctatgg actctcctct gtctggtcaa gcactggtat caactgtgta aggagaagct 124140
gagggagcca ctgtccccac agtatcccct ggagctgctc acagtctatg cctgggaatg 124200
caggctccaa gacagctctg gactacatac agcccagtgc ttctgaactg tcttagaact 124260
gatcactaac tatccatgtc tttgaatcta ctggacatgg tgttatgatt ttaaacatga 124320
gatctctgac tacttgcgca gagagatcca aaacgacagg cctctgatcc tggatccagc 124380
agactcaaca aggaatgtgg ctgggtcaga cttacaggcc tggcaccttc tggcaagaaa 124440
ggctctgatc tggatgcgtt cgagactttc tttatgaact gtgatgtgtc ctttgtgaat 124500
ggctgggaag tgccaccaga gagaaaagaa tgtgtcttcc agtgagtact gcagtacttg 124560
cccaggaggc tccagagtca gggcatgcac tcactcctct gctgcaagac cttgatctag 124620
agaggacagg aaggtgctca aggcttcagt gaggggcatc cagcctgtga tcagactcca 124680
ggcttctgat tcctgcctgc ccatggacag ccttcctcac agcctgattc atctgccttg 124740
tcctccaaca gtgttctctg ggagtaagac tctgaaggaa agagaagaac tcaagcttga 124800
cttccatcta tctacccatt gggaggttct acctccccca aaatttctga tcatcagcaa 124860
taaaccacag gaagccatga gtgggtgtgt gtactctgag ggatgtatcc tcatcccaca 124920
aagaaactgt tcagcattgc acgtagccct ggagccctgg agccctggag ccctggagcc 124980
ctggagccct ggagccctgg agccctggag ccctggagcc ctggagccct ggagccctgg 125040
agccctggag ccctggagcc ctggaaattt gacaagtgtt catcaagctg cactatttct 125100
tcaacatgca ggctggggtt acagcagtgc aggaaaataa aattgcaagc actttaaaat 125160
gtatgacttt aaaacttagg tgggtgtgtt aggatgagac ctgaagcact gatttaaagc 125220
aaaatgcatt gaaaaaaaag aataaatggg ataataagtt cagagttact tggggaacca 125280
gccctgccta tggcctaggc atttattaat aatattaagc ctctccgttt ttattcaggt 125340
actggcacat gggtgaaaaa gcccatggct atataaaact agtgttctat gttataacct 125400
ctgactaatc cagttagcaa tatacagttt tagactaaga aaatgagata taaattccca 125460
gtcttgaaga cataccttat catcctcaca gcattgccat tatcactgca tagtagagaa 125520
aacaatggct ttattagtta gtgaaaaagg tttacatgtc tttgtatggt taagcactag 125580
atgttctgaa gattccgttc ttcgagtaca agaaatactg tggacattta caatagtgag 125640
taggatcatc accaggggac ataatcttca ggtcttgact tggatcgacc tttccacagg 125700
cccttgagtc agtctggttt ctgtcactgc aacaaaatac ctggtgtaaa ccccatgaag 125760
aaatgaaatg tttctttggg cttacacagt ccccgaagtg tcagtccatg gttacctgcc 125820
ttgacttcag tcctttgctg aggcagaaca tcatggcaac aggaatatgt gttagagaag 125880
gcagcttacc tcatggcagc caggaagtgg ggttagggat ttaggattgg ggacaaactc 125940
tcaggggcca actttcagta gttatccata cctcccaatg tttctactat actctaaaag 126000
ccccatcatc ttggaaccaa gcctttatct tggagtgaca tttacaatcc aacttataac 126060
tactaggttt tagggacaag ggtaggttca agagagatat atgttggatc atcattcagg 126120
cactgagggg gtcattagca tgactagcat ggcaggggct gtctctatcc ttctccattt 126180
aggaatctgc tacctgcaag tcctgtttcc gggaaggatg ggctccttat tttctgactt 126240
gatattacct ctatagttaa tttggtatgt acaatttgaa ttctattttt gtaagaagga 126300
cctaccaaat tgcttgagct ttccacaaag ctgagatccg tttttataga ggatatgaaa 126360
ttttgacagg gaaatcaagc gtacaatgaa taggacttca actttcctgt agttagtttt 126420
ttattattgt tgcttttgct gtacggaggg aagaactctg gctaattgag accctcttag 126480
ttttgtagtg gagctgagct ctttcgcagg ctcctttgtg agttctcttt ccatgactca 126540
ccgaagttcc tgtcttgtct acaagaatca tctgggagac ttggtcttgt tctgtcttct 126600
ctttttgcag aaccttcttg gtttcttcca tgcttcttag gatacaggac aggacacctt 126660
cttgcacctt gcccatattc atgcttcata tcgtgagtcg aggagggtga ctgttctcgg 126720
acatcctaag ttaatcaatg acaaaatttt tttctaaaac tcctaagtct tcagtgttcc 126780
agacagtgga ttttcatttt tataagcaac agtcttgctt tcttgcccaa gctgacatct 126840
gagcctgaac tcaaatgacc acttcttaga agacatgaat acctacagtt gtatgtctct 126900
ttgggacttg gcctttgaag cataaaagtc attgttcata tgactacaaa atgctgaact 126960
gttactatgt cttgactttt aaaagactgt ttgtgagact tgaaagaatg ctgtggttcg 127020
ggggtgactc ctccttctag aggcaatcaa catgctgaca gccccctggt tcaagaaatt 127080
ggttagtgac tagtctattc cataatggca tttcagtagt tgctacttta tctgactgtc 127140
agaaaacgtc ctcagatatt gaattgaact acactttgct catattgtta taacgagtgt 127200
tggttaggga tattttcacc agggtgagaa tagttagact tgaggttcat tttaagcatt 127260
gatattgtaa gaaacaactt ataaactttt atttttaaca ctcaataagt atgtgctgtc 127320
tagcacatag aatgttaaat gttctggatt tgtctttaat ggtgactatc actgatcaag 127380
ttaggctaca gtgcttcagt caaagaaatg tgtattactt ttcaaatgac caaaatcccc 127440
catctctctc tctctctctc tacatataca tatatatgta tatatatata tatatatata 127500
tatactccat catatattca tttactaatt gttcaaatag ataatatctg ttgtcatcat 127560
attttaaaat tatcacaaca aagttaatca gattattaaa atcagagtat taaaataaaa 127620
ttaaagcagc attcttttgt tgttgaaaat ttgccaagtt cctgtatttc tgtgtgcact 127680
aaatatgtac tttattaaat gtcatattgg aatatttata aaccagattg ttgcattaac 127740
tttttccaag gaaaggtgaa caaatgtatt ttcactccca accagacact gaagaagggc 127800
aaaagtaaga atttcatcca agtctaactt ggtgaacaat gagtttattg agagtacaat 127860
aagcatggat gacggatcac ttacagactg tgagcgaaca taaaacactt tcacactaca 127920
atgttcaact ctagcatgga tgatgacctt gtggaagctg ctccaacgtg ccctacttcc 127980
tctcttaggg tctcccaaga tcacttcagc tgaaagggaa gagaaacaga aggggactga 128040
tggttggagt cccagaggag ggtcccgaac tctactctcc tcccttctag tatggagcat 128100
cactatagac ctagctgtca gtgaatatta tcctgtctat tttgccacat ggctaccagg 128160
cccaagcata tctccactct aagatgagga aagaacaagc cactcttcca caattccatg 128220
gaattgagaa tataaccttt atataaagtc accttttgct aatgatgcaa attgatttca 128280
aagtaatatt tattagaagt gtaaactttt tcactttcta tctgtgcaat aacttaaaca 128340
ttgtggattc actaaaaatt gatatatgcc ttcagttcca gtactcagaa ggtagagaca 128400
gacagatctc tatacattca agggcagcct ggtctacaga atgagttcca gaaaagctag 128460
agctacacac acacaaaaga aaaaccctgt tttgaaaaaa caccccccccc cccaacgaaa 128520
aagaaggaga aaaaaagaaa ttgactaagc atcaggtgtc tacaaataac ttagttgaca 128580
tacaggatta tagatgttaa agaaagtgga gaggcagtac tgtctgcagt gctacaatct 128640
tacaacataa tatgtagtac tgtcatagtg gggaaaagag ttctctttga catcatctat 128700
gcccttgaga atactttggt tatttgtgtg tggactgcgt aactgagatt taagcaatca 128760
caaaaataaa caggtctcta cagaacccaa ttatatgtgt cttagttgtt tcgctggcta 128820
aacatttaat tatatctaat tatttcctgt tacttcactg aaaaccctgt caaataacct 128880
agtgacagtt ttcttgcatc ataatttaaa ggttatcttt ttaggcaacg tcaaactaat 128940
tatggccact gtctagagtt ttcaaacaaa caaacatact gttattttca tttcagatgc 129000
gatctgtgag cagagtgttt aagtttattg atatacaaac agaagaaagt atgtacacac 129060
agataattaa agaactacct agagaaggat catctgacgt tttagtcatt aagaatgagc 129120
atgtgaagaa aagtgatatc tggccctctg gaggcgaaat ggttgtcaaa gaccttactg 129180
tgaaatacat ggatgatgga aatgccgtat tagagaacat ttctttttca ataagtcctg 129240
gacagagggt gagatttcag cattacttgc tttgttagtg ggtcccaact accagagcaa 129300

-continued tatgttcgta aaaaccattt gtaacataat tatataatca gtatccctta tacatagttg 129360
aaggtgtgac tgtgcaaagt ttttatgttt catatgaaat ttgaattaca gactctacac 129420
aacaggttat tgtaaatgtg attgtatttg aatgtgacta tacttgcaaa tatgtaagat 129480
tttccaactg cagatgcctt taaatacaca cagacaccaa aaatacaacc atcactatga 129540
acagtagcac caaattggtt gattggcaca gtataaatta atccatccct taattaactt 129600
agatgaaact ttaaacttga gtgattttct tgcaggcaat gggtagttat atcttagttc 129660
tttgggccac tctgtcagtc catgtttctc aagtggtgca tttagaccat gagcatctag 129720
agtggtaggc acacattcag gcattataac ttgttctgct ttttgttcct tgcttttgct 129780
ctttatccct atttttacct tgaatccttt tctttctgtt gctgttcctt agtatttatg 129840
attccaagac tttctcattt cctaacatag cgattctact tttgtggttt ttatgagttt 129900
ctctagaggt cacaatatat attcacaatg aatccaggtc cattttaaaa gaataatgtt 129960
atcacataag aggcatcagc accctgtagt cccaattgct ctctcatgtg tgtcatattc 130020
ttcctatggg tcattttgtg tattcacaga taatatgtgc aaatagatgt tattaaaatg 130080
actttaagta agcttccctg ttagatccag taagagtaag aaaagcattt tagtttctaa 130140
aatgcttcct ttattcattt agcttcaagt ttgcaactcc ttgtagatct gagttgtgtc 130200
ttttctctga gtaagttctc ttaacatatc tttcaagata agcccattga cagcacatag 130260
cttctgtgtt ggtttgataa tttcttactt tgccataagt tttaaaagat aactgcacaa 130320
ggttcacgat cctagtttgg cagagttttg cttttcctct tcttttctac tcgtttcctg 130380
actttgtggt gtccataaag ttataagtca ttcttatctc aaattgtttt gttttgtttt 130440
tttgagacag ggtttctctg tgtagccctg gctatcctgg aactcactct gtagatcggg 130500
ctggcctcaa actcagaaat ccgcctgcct gtgcctccca aatgctggga ttaaaggtgt 130560
gtgccacttt aggggaaatt ttcctgaaca taatgccata acttatgctc tgagatcagg 130620
aatcaacaaa ttggacctta taaaattgca aagattctgt aaagcaaggg acactgtcaa 130680
taggacaaaa tggcaaccaa catatttgga aaagatcttt atcaatccta catgatagaa 130740
ggctaatagt caatatatat aaagaactca ggaaattaga ctttagataa tcaaatagct 130800
gatttaaaat ggtgtaaaga gcttaaaaaa aaaagaaaga aagaaaggtg tgtgccacga 130860
ctgcctggcc ctcaatattt aataaataat atatttttta ctgggctttc ttcaagagga 130920
tttctttaaa aaattttttg tacttttaag atgatatgct gtggtatggg tttttagctt 130980
taagcaacat tctggttatt tttctctgtg tatggattga gtatatgaca ctaatttttg 131040
agggaaccct cttagtaact attatttgaa atatccccct ctatctttct cagcatcctt 131100
ttcttctctt tttctttctt cttcatttct gtcttctttc tctttctggt atctacatta 131160
tatacaagtt acacctttcc taattgtgcc atgattcttg gatatgctgg gggagggggt 131220
tgtttgttgt gcagaggcat gttggtgttg gctgctttta gtaacatatc ctcaagctca 131280
gggttctttc ctcacacatg tctaaactat tgttgaactc ctcaaggcat cctccatctt 131340
tgttgtacat ggtttttgtt tgtttgctta cctgcttgat tttttttttt ttgctatact 131400
tgtagaagtc ttttgatttt gctttagaat gacgcctttc tgtttactaa ggatccatct 131460
gttactatat gccaattttt tcatgatgaa atccttatca cattagtcat agttgttttg 131520
cattcccaac gtatgaatta gagtgtcatt gtcacatctg gctttgttct atcctagtat 131580
tgcttattat ttcctctttt ccctttcaac atgtctcatt gttttttctt gagagggaac 131640
atagatgacg tgcttgggaa agggaccgtg ataataggct gttagtaata gactggctat 131700
gctgtgttgg actgtagagt tctgtagctg catagttatg ttagagaaat tacattttcg 131760
gctgtgagct tttaaatggc accagcttag ttactttagg tagtacagac tggttagagt 131820
gagttagcac taaatattac tgtttcctaa agtcagttag tctgggcttt tggaaaaaaa 131880
atctctaagt tacaaatgat aaaatagtct cactcaagat gggccttaaa tgggagaccg 131940
tgctctggcc taacagaatg atcactgtct tgtggggtcc ttgaaagcta gggaaacttc 132000
ctctagtctt cctgtgaggt cactggaggc tgacaggaat tgtttccctc tccatggtcc 132060
acaatgagcc caggtcatct tctcagtgta gtgcttgtac ttgctccctc cagctgtctg 132120
cttgctggtt tctgctggtc tctgtgactg tatctgcttg cctttctctc tggctctagg 132180
ggcagagtca ttcgttctat ggttttacct ttctgacaga aaatgtgttg cttacctttt 132240
tacttaagat ggagtgactt ttcagttagt ggtagcacat acctttaatc ccagcacttg 132300
agattcctgt gaattcaagg ccagcctggt tcacagagta agttccagaa caaccaaggc 132360
tacacaaaag accctgtctt taaaaaacaa aaacaaacaa caacacaacc caaaaagaat 132420
agcaatgttc tctacaaatg aagacatcta aataggtgct ggatttgtta aaagtgcacc 132480
ccattctgcc tttatagaat ctggcgtgag gctgctgact catttaacaa tctgagtggc 132540
ccatgtgtct tattaacaat aaacagatgt gtcgacatat gagaggctca gttataatca 132600
cccatgaatc tgatgtttca tttgattgtc tgtcttggtt tctggggacc acaaggaaac 132660
aagataatta tagtgcactt ccctctgcca ttaaagtgca gagaaggtgc tttaaaggga 132720
ctgtgcccca actgcgctac tcttgacaca atggaattcc tgctcctacc tagtttggca 132780
ctgaatagct ctccagattg tagtctgatt tatgttgatc taaattttgc agagctgagg 132840
tgcattgagg ttaataaaaa cgttgactca tacttaggac acatctttaa agcttgtttg 132900
caggaagtac tcttagaaat aagaagataa ttagtatgtg acaattactc aaccagacaa 132960
ccttgttagg gtacaaatca attaagttcc ttgctgttga aaaactggtc agacttaata 133020
catgccagca ctttgatgtg aggaaactag agcaatagac aaagggtttc aagctaaaga 133080
aagtatttat tcattgcctc tcaggccagt attatgccag cataagaact gagttttctg 133140
aaaatgtatt tccttctgga ggaaatgcag tgaactcatt taccccctact aggtccattc 133200 aaggtccttt ctgccaacta tcctgtaatg aacttagcac tcttccatcg gtccactgtc 133260
actttctttt ttcctcctgt acatcacctg cactgaccga ttctgatttc ttatttaact 133320
tatttaacat tgcagtattg gaaaaatcct aacatggtga atgtgtattt gtatggcatg 133380
gtctagcaca gagatgggag catgcagtgt gaaattcctc cagattttaa aattaatgct 133440
ttatctagtc attgaacaaa attattgtat tatttattta taaggtacaa taatatgtat 133500
gctcattcat ttgctctcct atctgactgt ctttcagtcc acctcaatat ttcttgagta 133560
cctttttaaa gccaagtaca catgggtcct tttattcctc cattcttcca gccatctcac 133620
tttcccatcc tttcaccctc caatctgact atcagctaat ccaagtattt attatttaag 133680
tacaccatta ttccagatgg agaaactgaa aaaacaatca aaacggataa actatgcaac 133740
ctttgttgaa tttatattct ttatgtaaat acaaagctac aagaaggaga aaataaatca 133800
ttacaaaatt cttcttcata acatttgttt attttcccaa caacaatgat ttatataaat 133860
taccttgtag agctcttttg agggttagga aggcaattat tcttgtcact gtcctttacc 133920
agcttatcac aaaggcctac attattgcca agtaatttac tcagtaaatt attattattt 133980
ccattggttg tggcccatgc caccattgga gtttataagt tattactagt ctacaatgaa 134040
ataagtatag agtctgtaaa tatttagaaa ttcatttttt aatttattta aagtactgat 134100
ttgcagttca ttaaaaacag atggtttttc accaaccaca tatatgtaaa gaacactttt 134160
caaaaagacc attttctcct taaagaggtc aaacaatagg aaataaaggg gcagtgtgaa 134220
cagcatgaaa caaatttaag tgttgcatat atactgcagc ttattctgtg atcagttagt 134280
cattgcaagg aactgagctt atatcataac aaagaatgtg agctttgagg gctacctgga 134340
caactgatct ctgtaatggg aagtagcctt aatctgatgc tgtgctcttg cagctgtggt 134400
ctttgcataa tgagaacagt ttaatatcct ttttgcttct tagagtttcc ttcttgccag 134460
aagagtcata tgttagttag catttgattc aaacattgct gagaagctga gtgatcttgg 134520
ctctcgactc aacctgaatt ctgtgagaat gtatacttta ctgaacatgc ctgtatctta 134580
tcatcaggcc tgaacttgac actgctcatt ccttaagggc agaatccatc tgcctcttca 134640
atgccggggc ccaatccctg gaccttgtac atgctagaca actgtacatg ctccaccaat 134700
gaggaaataa gtttagtcca gggacagtaa gtagtgttag gcctattttg agtaaacttc 134760
aagtttgtat ccatattcaa aagtacatcg ggcagcaggt ccctgcttct ggtttgagct 134820
gacgtgcatc aagatagact gtttttactc ttccttgact ttaaatggac actttctccc 134880
tttttctcat tagtaaaagt cagtggtcaa tgaagcccac atcaggaata cagttctgta 134940
tggccagttt ctgatttcag ttgcagatta tgatgagttc cagatcagtt ccagatagtg 135000
atgagaattc ggagtgtgta aacaggctta cgtggctcca tgagaagaga acccattcca 135060
ctgctttctg tccaaggagc agtgctgatt ggataatagg tgctatcctt ggtgcaagag 135120
taatgccatc actttctcct tctaggtggg gctcttagga agaactggat caggaaaaag 135180
tactttgctt tcagcatttt tacgaatgtt gaacattaaa ggtgatatag agattgatgg 135240
tgtctcatgg aattcagtga ccttacaaga atggaggaaa gctttcggag tgataacaca 135300
ggtgagcaca aaaatgtaaa aagcaatacg aattaacatt tttatcatta tttgacatac 135360
ttaagaaatt catatcactc tgcaaaatat atttggtggg tcctaccatc tcgtctactg 135420
tgcaagagaa ctgtagcata tggaatgaga gtacctccca atgtctggaa ttctgcgtgg 135480
tgtatatttc ttaaagtgtt ttgatagtgt tctcccaaag cacaatctgt aacagcagcc 135540
tgggtagttc cttgtgcagg cttcctagtc ttgcttaagt acttgatctc cgagggagtg 135600
atagcagcct gtagataaat gctttgcaag atgtggaaga tgcttctgag atcataagct 135660
ctcggaagca ggacatagtg gaattgaaag ttgaagtgca gtgatgtttt ccctttggag 135720
tctgagtagg aagaagtatg tcaggtcaat ctagattctt ataaagggca gtgtttgatt 135780
caggcagtac agcatctcga acatcgccat ttagtgctat tctgtctgtg ttactgcaca 135840
tgctgatttc ttgtgtagag gagaaacggc aatggttgcg ggcaacatga cccaaatgtg 135900
aaccaagaga tgctgaagcc agaagaattg cagtatttct gctgctgttg gcccttttct 135960
ctgagacttt tcctcctttt gtgctactag acactaaatc caacccacta agatggctct 136020
ttgaagcact tctgtatttt taacacaaaa ttaacattcc gggactatca ccaggtagac 136080
caactacaaa gctagaccaa gaaaatgctt gtacttcttg ataaatgatc ttcacagaac 136140
atttgctcct ttcaagtggt gagacaatag atactgtaac caccaaactg atgctttcaa 136200
tttgtttcta tggtgtgcca ttttttttcaa atgcttcatc ttggctgaag ttgtggaaac 136260
actgtgtgtt caaaaacaca aaagggattg tcagatggcc taaagaaaaa gaaacgctag 136320
gagtacaagg ttcctgaggt gagagcacta gtcgagtaaa aatgctaagg ccagtggaag 136380
ggtgtggttg tctgagaagc actgctgttg gacttgccca ggtcctgtgc tgccagttga 136440
actaaagcag ggtaggcttt gccttggttg ctcttgttcg aacacattgg cctacaagaa 136500
gcgtcaacct ctaaaacttc tatcctcttg ctcatcatcg tagctgctac acaatagaag 136560
ggctccgtct tcctcactag ctctgcttag gagcttactt atgccaggca cagagtacac 136620
tgcagtgggc cagagctgga aaatctcccc tgcctttctg cctaaatgac tcttcagact 136680
tgactcaatt catgtctgct cttttatgga ttcaaggctt acatttaaaa aaaaaaaaaa 136740
gaaaaaagga aaaaaaaaag tgtgttcagg gcatccttca gaaatactga agggtctctg 136800
gaacatcagc cagcatggtt aacatgtctc agtgacaatt tttgaatgtc atgtgaaacc 136860
taaggaagga aggagagaga gagagagaga gagagagaga gagagagaga gagagagaga 136920
gagagagaga gcaaaccaag tccttatatg cttgatgtct aaactacggg ttactttgct 136980
tttcctatct tttcttggaa cgtgaggatt gcagcatgct tctcctttcc ttagaaagat 137040
aaaagaagga gaaaagtgaa tatccacaga aaactaacta gtttggtctg ctttttcatc 137100
ttttcttttc tcctctgtct cctttaacaa ggatgtactt cagaaggtcc cacactgagc 137160
tagtgtaatg ttaaaggttc actggccact ggttctcaga tacatgaaac aggtattttg 137220
aaaagtaccc tcttatacag agatccaaaa gcatttgctg ggcagtcaca aaaggtcctg 137280
ttggtttgga cggttcttaa caattttttc cctcctttta tagtttagta actacatagc 137340
aatctcagaa tacgtgcagc ccagaattca gactatcatg tgcattccaa aacagagcct 137400
ctttcatttg ttctgagtca agcagagcag gcagtgaagc cgatagatgg catctgattt 137460
actttggcaa ttagagcacc aagaagaaag cacccactaa tgctgcgcct ggctaggcag 137520
ataattaata aaaagcaact attttaaagc ttcagttaca attttggaag gctgtaagtt 137580
cttctgagta aaggactaga agtttttcct tttgttgatt actattgtat gtggtatgtg 137640
tctgagagga ggggagaatg ggtggggtat tcatcacgtc atggctcact tggagaggtc 137700
agcacacaac tttcaggaac aagttctccc cttccagcat ggcatttaga cactggattc 137760
aggtcatcag ggctgtgtgg caagcgtgag ttatccactg agccatctca ctggctcctt 137820
ttcttaatga attgaaaata ctcaccatcc acccatcatt ctcaccacag acagaggtga 137880
ggcatctttt gttttgaaag agatcagaca gcatgtatag atataaacag tgaaattggt 137940
ggtgacagct taaaattcac tatataaaat aattacatct tgtgcttaca attataaatat 138000
cacagtcatt ttatttatat caaatgtaga gatactactt gccattaata tgccagagaa 138060
gttccagtcc aacctgtaaa cttctaatga gaaactcaaa acgatgttca tagtcgtgtg 138120
acagaaatta aaaacagaaa cagtaaagcc aaagtgagtg gctgagagtt agtaatgaaa 138180
ccatagctgc ctgtaagctg tgggctaaca agggagtata taggcagaga gaactgtcca 138240
gattaagcta gctgtcactc ctgccagtac atctgtgtct ttcctgtcct gctgttttgt 138300
ctcccttctt ttcttgtttt ctctctgatt gcagaaaaca tgtaactgtt tactggttag 138360
acattatgaa ttgaggggtt ttctttcttt gtttgttttg ggggtatttt tttaacacaa 138420
atactttgct tgactgccca aacccagatg ggatctcaaa ccttgcttat gtatttctgc 138480
gtgtagttct aatatgtctc attttcaaat tatccacata tctcccttaa ttatgcaaga 138540
tttaaacaga gtgaccagaa aatggaagca gagttataaa aagaaggata gaaatacata 138600
gtaaaatact tttcttctga gttttctccg ttgtaagaca tctaacataa caccttggat 138660
gagaagaatt caaaagacag tgttctatgc tgaatcatta aatgttgctg tctctcacat 138720
gtgtggttct ttcagcattt ggaccctaat ctgtataatc ttaggacagc tatataattt 138780
ctctgtcata gtttccttgt ttgtaaaatg agtatagtaa taataacaat tatttgtact 138840
ttgggggaaa ttgaacgaga aatacttaaa cttttacttc ccacatggct tgataattat 138900
cctctgttat ggtagttatt atttttaatt cagtgggggt ggggagtcat gtctcctctg 138960
tctttctact ggactggggg tatgttctat gaataagtat gaataagtat gaataaatga 139020
gcttgcacaa tttcacaaag aaagttgtaa tgaatacatg ccatagagtg tcataaagtt 139080
tataggttta gaatgattgg gtacatggag ttctaggcag gaagactgtg aacaatcaaa 139140
aggataggtc agtgtgaagg gaaagggaga agggtcagag ggaaccacag cttagagggt 139200
attagacgtc atggcatggt ccagtaggaa ggggctaatt ctcctgggct gaggaaggga 139260
atggagaacg tttggtggca cattgctata tacatgatga actagcaaat gattatactg 139320
tgatgtggtt aattagaact tactgaggta gacagttgga cagagtgtag aattcaaggg 139380
agggcagaaa aataactgtc atgtccaatt ttcaaattag tataacacaa tttagctatt 139440
tcagagacta aactttgaaa cctttgatta tatgctttgg ttagaaaaca tttttatgta 139500
tctttggaaa tgtttatact aaaactttgt agtataaaaa ctgttaggaa gctgggcagt 139560
ggcagcgcat gcctcggcag aggcagtcag atctctgaat tcgaggccag cctggtttac 139620
agagtgagtt ctaggacagc cagggctgca catagaaacc ttgtctcaaa aaaaaaaaaa 139680
aacaacaaag aaaaaacaac ctgtaatgaa gcactctgga tttctagaaa actaaacttt 139740
aactatcctg tatgcagtct tttatattta aatcaatagc atatacactg gtagtatagc 139800
aatctatatt tgttacaaac tgttaatagt tcttagtaga aatatgtcat tcataatttt 139860
atagttgggc cacatttcaa gggaactatt catgatgtac acatacatac ataagcaggg 139920
gtagtcattt ctcctattaa tctattttat attaagtgca atcaccacat aagctggatt 139980
actttttttt catttgacat ctagtactat aaagcatatt agctgttgca acgatatatg 140040
gtcagctgtg ggaagtccat gtaggcttag ccacttccac agagttgagg agtggaggca 140100
gcagctgcag ggaggagatg ggacatgtgg ggaacaatga tgatctcttt gttctgctta 140160
gagtctcaag aactgctcat tatagcatac atgacattaa ataaatatca aatatttgct 140220
tgccctaact gacttattag tgagtagttt cttttaaggg cgacagggga tccctgggat 140280
gtgacagctt caggtgcatt ttttaattgg tgcacagcag atctgagagt gccatgctgg 140340
ccaaatcatt ccacttctca gggccttcat tttgaatatg taaaccagag agagagggtt 140400
taggttgacc tccaaagacc tttaggttag acagaggagt ttgaggatga ttaaacagct 140460
taggaaacaa gtaagacctc tgctggcacc gtgaaggcaa gggactgcca gattctcttt 140520
gaattaaagg aatggaatgt ctgattgatg gtatacaatt gaattctagc tgaaccggtt 140580
tctttagttg atttttcttt aaaattggat atgttgtcca ttacctttta ccagacatga 140640
aattatgaag gaaagcctgc aagatttctg agttgtgata aatctaccac acctacagct 140700
tctagattcc tgacagcttc tttccttcat aattttgaat gtgtatctgc ttaaaataaa 140760
ttagttaaaa catcataaat ttagtaaact agtatacatt atagatttta tgactaaaag 140820
ttaaataatt tctgaagcac ccgtaggaat cttcacaggt gtattgggtt gttagtgtta 140880
cacttaaaga actgtgatag ctgtgagcat ttgggtcaca tttagagatc tctctctgtc 140940
tctgtctctc tctgtctctc tgtctctcac acacacacac acacacacac acggagaggg 141000
ggagggagga gagaaaaaga ggaggagggg agggaaggat gagagagaga actttattag 141060
ccagaaaaat agccttatag aagttaactt tcaaatctga ggaaaaacag catttactct 141120
gattgttatt attttctact tttacttctt cacgtctgct cactcatttg ggacttttgc 141180
tgagcttatt caaaatttgc atctaaaaaa gaaagtaaag acatggcctt cgacactcat 141240
agatatccac ggacttagta attttctttg atacacacta ccgagattgg gctccatctt 141300
catatgtaac aaagaataac tctgaaactc taatcctctt ttttctattt cctgtgtgtt 141360
ggaattaagg gcacatacta cagtgccaag tttatatgct tctgggataa gacccaaggc 141420
ctcttgcaaa ttaagtaagc attttttgcc aactgagcca catccccacc aactaaactt 141480
ggtgttattt aaggaatgaa agtataagaa ataattgggg agcttgtttg gtctgaggat 141540
aaggaacagt gcccctagga aatgaagctt gatttgaaac ctgaaggata tagattgttg 141600
tgtgaagatc agggaggata agatttccag ctgagaagaa aacttaggtg actaagctaa 141660
gaaagtgtgt gcttagaata gaatggagtg gaaaggagcc ctgagatctt gggaccatcg 141720
taaggatatt gtacccttag tgaaggggaa agtcattgac atttttcatg aattacttgg 141780
gtatattgta agagaagcaa aagtataaag aagaagatca atttaggaag ctcctgcagt 141840
gacacaaaaa ggactagtga tagtttggca tgttcagtgg gaacagaaat tgagaaagaa 141900
attgatttga catatagttt gaggataata taaatgacca atgactcatt tttaagataa 141960
gctgaggaat aagatgaatt atgagtgact ctcagttcct gatgtgcact gagatggaga 142020
tgcagaaagg acaaaagtag ggtggcattt ctctgcttta caaagcatgg ggatgaaaga 142080
gactgggttc ctatgagcaa ctgtctgttt taaagataaa acatcttgtc cattcctttc 142140
attcttccgg gataatgaaa ttattctgtt tgtcccaagt aaatatttct attgtatatt 142200
tcaactaaat atataactct ttcaaagtta cagagatgca accaaaacaa taagaggaaa 142260
gaaaattatt ttagacattg acatcaaaaa ttttttgcca gtcttgtata tataaagagt 142320
actaaatatt atttttaaaa tattattacc tgagatctct taagacagtg gttttctctt 142380
aagcacatgg tccacctaag tggaagtgtt actgcaagtg gagcatcttg acaatggtca 142440
tacagtgcta tttgcacacc agagcatctg cctcttccct agcacacatg cccctgaaca 142500
aacggttgat ctatgatcac atgggtttct gagttgtcct ttcagcttct ctttgttcat 142560
agaagtaaga agatgtgtaa agggatgtta gtagaagaag agtctcaatt cttcccagag 142620
cacagtggcc tcaatttcct tatctcaagg gcattgaaat aaaaaaaatc caaaaagagt 142680
tttaaatgtt gccctatttt tctttaaaat gatgtaaagc aaatgtagaa aagtatgact 142740
agctaatggg taccatagat gataggcagt tttacacatc taccagtgtg tgtatgtgtg 142800
aatacagaaa tgcatgtata ctcaccttgt agcacagtgc tctagtggat gctcatttgt 142860
tccttttctt acttgaaatt ggtttgaata aagagaaaaa cattaaaaga tgtataggtt 142920
atttatactt tctaattatc tttaccattg cagaaagtat ttatcttttc tggaacattc 142980
agacaaaacc tggatcccaa tggaaaatgg aaagatgaag aaatatggaa agttgcagat 143040
gaggtaagga tgacaaataa agtagtttta aagaagtaga tcatacacac aagtgtggtt 143100
gccatagatg ataggcagtt ttacacatct actggtgtgt gcatgtgtga acacagaaat 143160
gcatgtatac tcaccttgta gcacagtgct ctcatttact ggcacatcct tgtcagaacc 143220
tttgactcat ccccctttca ggagtgtcgc tcctttccat atactctatt cgtggtgctt 143280
tactaaagtt ctatagaccc ttgctcctag acgacgtatg tttctctcac tattttgaag 143340
actgagaagt ccaaggttaa ggagccagca gacagtattt actatctgct aaggccctac 143400
ttgctgtcac tcccgaggtg tttttctgca cctcactcag tataagtggt cagtgagcgc 143460
tgtggagcct cttttcatta tagtgttaat tccatctatg ggtactcag agcccatgac 143520 ctaatcactt cctaaacatt ttattttatg tctcagtagc actgccttgg acagtcaggt 143580
gttaacatga gtttctgaag acatgcggac ctagaactcc ctcctttcct cccctccaag 143640
ttatgtcttg ttcttatgaa aatagattac tccacttaaa caaatgccaa agtcttaaca 143700
cattttggtg tcagtgtaca actggaaatc acaaagtctc aattcagcca ccatgagact 143760
tgggacttta ggtttttcat gttggcattc caccattccc tgcactttgc ccattgttgt 143820
tcccttgatg ttcgctcttc ggcctccccc agaacagatc ttgccaggag ctttgaagcc 143880
tctgagtgct aaatgctaac cccttgagta accaacctta accttctcct aataaaatga 143940
actgagatta accgtttttc attatcaggg tttccttatt acccagcaaa cacaaggttt 144000
ttaaagaaaa cattaactaa attgctagtg atatactgta agatccttga tgtactttta 144060
cagagtgacc tgtcagaata cagtgtgctg ggagagagct tgggaaagaa ggaattagcc 144120
tttgtaaagc ttaccaggta ttgccaagtc tccataaaat ttgcaggaaa ctgagatcat 144180
aaaatcatct aaaatgttag gagataggtt tagaagactt tagattccag aataatacag 144240
gtagttatgt gattagattt tgtctaccag tccatcttta gatgtacgtt ttcattggat 144300
tctcttttta aatttatgtt cataaagatg ctgctcctga gctaaccgta atgtcccatg 144360
gtttgagtaa gagtgacaaa ttttttgctg aagagtccac aaagaaacat aaacaccaac 144420
ccctagctta cagcagcagg caggagattt aggttaaagg caggaatcct aggctttaat 144480
cctgtatggt tgatgatcca atatagtcaa ataggaacac gttgaggtgt gtcagcctac 144540
taaggcacta ggacaaaagt ctaaccttcc tgccctggtt catggcagct tgctgcccta 144600
ttcagctctg gggatctttc ttttttttt taattttttt atttaaaaca attttttaaa 144660 tatttttat tacatatttt cctcaattac atttccaaag ctatcccaaa agtcccccat 144720
accctccccc cccacttccc tacccaccca ttcccatttt tttggccctg gcgttcccct 144780
gtactggggc atatacagtt tgcgtgtcca atgggcctct ctttccagtg atggccaact 144840
aggccatctt ttgataccta tgcagctaga gtcaagagct tcggggtact ggttagttca 144900
taatgttgtt ccacctatag ggttgcagat ccctttagct ccttgggtac tttctctagc 144960
tcctccattg ggagccctgt ggtccatcca atagctgact gtgagcatcc acttctgtgt 145020
ttgctaggcc ccggcatagt ctcacaagag acagctacat ctgggtcctt tcgataaaat 145080
cttgctagtg tatgcaatgg ctttctaaag gctgcatctt tagcctactt ctcacccctc 145140
cctgtgctgc tgctggacag ggttcctgtt gtacactgac tgcttaaagg acctttatga 145200
tttggtcttt gctgctctac tttcagcccc agcccccatg tgtcctgtga gtccactact 145260
gtgaatttta attttcttta gagcacagtg tgctgctctc tgttctatgg tacgggttgg 145320
ggcagttgtt tctgcttttt accttctggt ttctggacct gggaaaccct tgcagagcac 145380
tactcctgct ccttctcacc attcaagcct tccttcacac atcactttgt tctgaactcc 145440
atcctgaccc tcctgctttg ggaaaagaga ctttcctagg tatagctatg cctcggctcc 145500
tcaaaatttc ctacactgaa tcaaaattca cctcttggct actccatatc tcctatgatt 145560
atggaatcat gccctgctct ctgttgttcc tgcagtagtt ggatccctgg gtggtttttg 145620
ataagtactg actgaatgat ctgagcaagt aaagaattct tttaactcat gtaaaatatg 145680
ttgtgaaaat atcctcatgc ttaatgccca atagacatta ctaccttcat ctcagtaaag 145740
gtcttgcaag atggctggcg gattctgaaa agaactgcag ccctgacttg gggccctctg 145800
ctgttttagc cctactaagc tatgtgatct tggccccttg actctggctc ttagatgtgg 145860
ggactttgtt tgtttgtttg tgtttcctta ttagaataat ttttaaattt atcatcttta 145920
catcctaata gtcaagggaa ctgttgtaga gacaatttaa atagcagaaa cagggaccct 145980
gtaagtggga catttccctg agaagtttgc agaatggaaa cacaaggagc tgagggtatc 146040
catttttaca ttgcccacta gtgcttacag gcaaagcata atccaccttt tttactgaaa 146100
aaaaaaaact gtcatagaaa acaaaaatcc tacaaatact tctgagtagt ttggtataga 146160
gtactgattt atctaaacat atttgaatac ttttaacttt gttatttgat ggatggtcat 146220
agagttaaag atttacagag tacagtatat aatttctgag ctaaaactag cactaattca 146280
ttcattctta agttctaatg cttaaagact catagtacat attaaatgaa tgactgaaag 146340
gaagatgaat gaatgaatga atggattaat aaatatatga atgaatgaat gaatgaatga 146400
atgatgaatt gttgaggctg agagtgttcc taactgaaaa acacatattt gctttcaaga 146460
aatgtatggt ctaacaggga aaaaatacac aattctaata caggatgcct ggctgtcctg 146520
tgggtaggca aggatattta agagagtaat cagactgagc agaaggacaa accctgagaa 146580
tgttaagctg tataaagaat taaaagttga tgctgctgga cacagtagta ggtgtgtgtg 146640
tgggggcgga ggaggtcagg atgtcctgtg ggccacatga gaacaattat attttatttt 146700
tccagtaaaa gaacttctgt aggatttaaa acagagaaat gatccaagtt caaacctgca 146760
ttttagggag agctcttaaa tatttctgtg acatgttgac aatttgactc attgatactt 146820
gcagtatgat gtttaagaaa tgacagaagg ccagacgagg atcagtgtgc cagaactgac 146880
aaaaagaacg gtttcagaaa ccctggggga acttctaggc tggagagagg cattgaaagc 146940
cattagctta aacatacaca ttgatgccat gtacataacc aaaatctgga cacaggaggg 147000
gaggggacat tggtgttgaa acctgatatg gatgggacaa agctgtatag tatagtatcc 147060
cctgtgatac accaggcagt cttccttgtc ttctgtgcct acattcccta ctatctcagg 147120
aaccttttaa acattaacga gtttacacaa agggtagttt taacaagcca catgtttgaa 147180
cttccataat gagcacataa gagtctggca ttaacaatga tatgagccac ttctgaactc 147240
atctccaaaa tcatgaatct ttcttaaggc cttatctaac tctgcacatg ttagagtgat 147300
atgggtatat atcttacctg tacatacaaa attccagatt catgaagcac aagaaacaat 147360
cctgtctgta tttatttaac tcttatacac ctagtggttc ttagcaaaga agacacaatg 147420
tacatgtatt gaataaggaa aaaccaccaa gacatctata attatgcctt aattttgaca 147480
gactactttt tgatcttttt attaaacccc ctttaaaatt gcagtttaaa aatataagcc 147540
attaattcta aaataatctt catattctac cctaacaata agagccttta aattttagtc 147600
gtgttccatt tttaactaag taacttctta ctttatgaga aagttatcag tttctcagat 147660
tttataagtg aaggagataa gtattatgat ggcatgattt ttttaaagcc tcctcagcta 147720
attttcatga tatttctcat cctgtattac agatagaaga tgaacatgtc atgctatgtt 147780
ttctaccctt tctgctcttg aatcctttgc catcagttat aatggagtga ataactgtgt 147840
tctctatctg ttatctttaa agcccatatt gaattgtatt gcaattgcat ctatccatct 147900
atctatatct gtatctgtac ctatccatct atataatgtg acaggaatag gtataattgt 147960
ttatcactgc tagggaacat gacacttaca aggtgaacac tgaatgattt tgtaatcaag 148020
tgtggggctg aaagaaatcc tccagtctgt ttagagctac cgatattatt gccagatttt 148080
ggttactcaa actaagtagg agttgggagt tgagggtgat gtgaaattta ttctgtgcaa 148140
actcatgtct gcttttagaa tgcaagcctc ttaagtgatt ttagttatgc cccttctaag 148200
cacagtgttt ttctttattt tctacaggtt ggactcaagt ctgtaataga gcagtttcct 148260
ggacagctca actttaccct tgtggatggg ggttatgtgc taagccatgg ccataagcaa 148320
ttaatgtgct tggcccgatc agttctcagt aaggccaaga tcatactgct tgatgagccc 148380
agtgcccatc tagaccccat gtaagttcca aaaatcttta gataatcatg caatagaagt 148440
agagtccttg aagttacctc atattggtac aaattcccat tcagctacca cacctacaag 148500
tagggggtac aaaataattt tccaggggaa aaatcactat ttaacatgag cacaagtact 148560
ttttttttt tcaacaagag ctttgttttt cctcctgact ggagtctgga atttataaac 148620
ccttcaacct cattaacaca taataaatac ttagttaggt atgcacacac ttatggcttc 148680
cctctgtatc ctatttatat cataaataca ttaacagcac aaaataaata actgatgctg 148740
aatctacata aaatgtagtc tcatttttat gaaattttct tctaagcatt tgctttatta 148800
gtgtatgaaa ttatattaaa tacttagaat ggcttaaaag ctgattgtag ctcattctgt 148860
atcatcatta tcctaaaagt atttttaagt aaagaattaa gtccatagaa tactatacgt 148920
attgtcaaag ataaaggcag aaaattcaca ctctataatg tcttatgtgg tattttcttg 148980
ctttgctaga acataccaag tcattcgacg agttctaaaa caagccttcg ctggttgcac 149040
agtcatcctc tgtgaacaca ggatagaagc gatgttggat tgccagcgat ttttggtaag 149100
tcatttacac ttgattgata tctcattctc catttattta aataatcctg cacagctgga 149160
tttgcacacc ctttcttcac acttatgtca cacatttacc acctaccctc agtctctttc 149220
cctggacttg agctatgaag tggtgaggaa atttagcaca cttctctggt atcatatcac 149280
taaacgacac tgtagataag gtaactatgc tttcagatct tttgtggcga acaagtcaca 149340
aaatgtacaa ttgaaaaaaa aaatgtctgt ttcttacagt aactcagctt cccatgggga 149400
agataagggt gggccttacc attagtggtt caatgtagta ggagagaagc ctgttccatc 149460
atccccatta ctactggaac tcagggtagt gtccctgtca gacaccttct cattctcccc 149520
ccgcccccaa aaaaaagtca ctgttcctgt ttagacatgg gaagttccaa ggatcatgta 149580
aaatttttac tttcccaagg cttttgaata ttctggaggt aaatgctttt ttactgaagc 149640
acttttgatc ctattgttat tgcccagtta caagtgccta gagagtagat gcatctcttg 149700
ttctgtggtg gtcaagtaca gggactaggt aaggggctct actctctgac ctcaagcttg 149760
caaacagttt aacatgcact gaaggcgtta ttctctgtca ttcctggcca atttgaaacc 149820
tttcggcctc aaccccaggt atgaggaagc tcaaagttaa tggttatata tagctcggtt 149880
taagagtgcg tgggtcattg attattttgc tttgcaaagc tccttcagtt cctcaactgt 149940
tctctgaagg atggcaacag ctagtattac attaattttt caaatcccta tcgctacttt 150000
cccggatgtg aaagctaaga gaaaagtaca agctctgaat cctgtgcttt ctttggactt 150060
ttgttcttct ttgggcctgg ctcagtttat gtgtcagcac tggcctgctc ttcactcaga 150120
ggtctcacta atgccctctc ccttaggtca tagaagagag caatgtctgg cagtacgact 150180
cccttcaggc acttctgagt gagaagagta tcttccagca ggccattagc tcctcggaaa 150240
agatgaggtt cttccagggc cgccactcca gcaagcacaa gcctcggacg caaattactg 150300
ctctgaaaga ggagacagaa gaagaagttc aagaaacccg tctctagtgc tgggatgctg 150360
aggaagcaac tcagtgcact gagtccattc ccagaaccca tgcagaatga aaaaagccag 150420
gcatttccca tgcttctaac cccagtgctg gggacacaga gacaggtgga tccctggggc 150480
tctgtggcaa gtgatcctag cccacaaaga gagttccagg ctgggcacct gagggacaat 150540
acctgtggat atactcttgc ttccacatgc aagtacatat acacatgcat gcacattagt 150600
ggacatacac acagaaaagc aaagaagaag gaaagaggga agaaaatagt gcaaataatt 150660

```
gcaaaacgat catgtatgga gtctgctcat ggacttagag gaggtgaact ctactacctg 150720

tgcctttgaa agaagggtga agcctgcgac ttgctcttta agagactgtt ttggaagaga 150780

gttcaaaaac gttcatatgg gtatgggtaa ctgactttcc agcagtagtc aaattgtttg 150840

aacttcagat agttgataat gaccacttgt gtattgcaag gcagattttt ctgaaaacat 150900

ttgcccccta atagtagctg aaaaagcagc tataaatgcc aaccaggtta gtcattcggc 150960

ttattgttca gtacagctgg ttaatttgca ttattgaaga actgaaatta tagtgcttag 151020

atataggaca aagtaaagag aactaaaaac agtgtcttat ataactcaaa gcccaactta 151080

ctttcctcta agatatgtat tgccttctat acattgtctg ccccattcca agcaaatgtt 151140

agaatattat acaaaatact gggtggtatt gattgaaaga tgcccgacat ctggtgatct 151200

agtaacccat caggattaag gatatccagg tcttggaaat taaggttaag accatctagc 151260

cttactaccg tacagctaaa cattcttatt accagaataa gacctaggaa aagaactgtt 151320

tcagtcccat aaagtggcct ggataatttc cttgatatgg aaatcgacac acttatgttc 151380

ccagaaagca acagatcttt aagacttctg aagtgaagga aggttgtgtt agtgcaaact 151440

agtgcagccc agtgccaggt ccaggagtta acatgtagac aggccatgga ctgtgtgggt 151500

agatgctcat ggaaatgtgc agtagtatgt tcatgtgctc tcagctagct gtgtgtactt 151560

caaactgtct ccacagagtt gttggggaga cactctgaaa aagaattaat tgtgaattag 151620

ttttatatac tttgttttat aatttgtgat gcaaatgaaa atttctctgg gaaatattta 151680

ttttagtaat aatgtttcaa actcatatat aacaatgctg tattttaaga atgattacat 151740

aatgacttat atttgtataa aataattttt atatttgaaa tgttaacttt ttatagcact 151800

agctatttta aaacagggga gtgaggagga cagggatgat aaggatcatt caacttcatg 151860

ttgtgaagac gagctgatgt aaatcttgta cccatctgtg tggttctcag acaacacatg 151920

ctctctttta atgcagcttt gaagaagatg gtaccaaagg ttaagacggc cccctgatgg 151980

gcacatcaac ttctgaactg caaactaagc tttagaggaa tgtattatat ttattactgt 152040

aatagaatat catgtgtcaa taaaatcctt ttatttgtgt ga                   152082
```

<210> SEQ ID NO 148
<211> LENGTH: 6305
<212> TYPE: DNA
<213> ORGANISM: Mus musculus

<400> SEQUENCE: 148

```
aattggaagc aaatgacatc acctcaggtc tgagtaaaag ggacgagcca aaagcattga     60

cctggtcctg gatatccaga tgtcgagtcc aacctgaatt tagccgaaca cagacctcat    120

tgcctcacgg agacatcatg cagaagtcgc ctttggagaa agccagcttt atctccaaac    180

tcttcttcag ctggaccaca ccaattttga ggaaagggta cagacaccac ttggagttgt    240

cagacatata ccaagcccct tctgctgatt cagctgacca cttgtctgaa aaactagaaa    300

gagaatggga cagagaacaa gcttcaaaaa agaatcccca gcttatccac gcccttcggc    360

gatgcttttt ctggagattc ctcttctatg gaattttgct atacctaggg gaagtcacca    420

aggctgtcca gcctgtcttg ctaggaagaa tcatagcatc ctatgatcca gaaaacaagg    480

tggaacgttc cattgccatt taccttggca taggcttatg ccttctcttc attgtcagga    540

cactgcttct tcacccagct atttttggcc ttcatcgcat tggaatgcag atgagaacag    600

ctatgtttag cttgatttat aagaagactt taaagttgtc aagccgcgtt cttgataaaa    660
```

-continued

```
taagtattgg acaacttgtt agtcttcttt ccaacaacct gaacaaattt gatgaaggac    720
ttgccttggc acattttata tggattgctc ctttacaagt gactcttctg atggggcttc    780
tctgggactt gttacagttc tcagccttct gtggccttgg tttactgata atcctggtta    840
tttttcaagc tatcctaggg aagatgatgg tgaagtacag agatcagaga gctgcaaaga    900
tcaatgaaag actcgtgatc acatcagaaa ttattgataa tatctattct gttaaggcat    960
attgttggga atcagcgatg gagaaaatga ttgaaaactt gagagaggtg gagctgaaaa   1020
tgacccggaa ggcggcctat atgaggttct tcactagctc tgccttcttc ttttcagggt   1080
tctttgtagt ctttctatct gtgcttccct acacagtcat caacggaatc gtcctacgaa   1140
aaatattcac aaccatttca ttctgcattg tcctacgtat gtcagtcaca cggcagttcc   1200
ccactgccgt acagatatgg tatgattctt ttggaatgat aagaaaaata caggatttcc   1260
tgcagaaaca agagtataaa gtactggagt ataacttaat gaccacaggc ataatcatgg   1320
aaaatgtaac agcattttgg gaggagggat ttggggaatt actggagaaa gtacaacaaa   1380
gcaatggtga cagaaaacat tccagtgatg agaacaatgt cagtttcagt catctctgcc   1440
ttgtgggaaa tcctgtgctg aaaaacatca atttgaatat agagaaagga gagatgttgg   1500
ctattactgg atctactgga tcaggaaaga catcactcct gatgttgatt ttgggagaac   1560
tggaagcttc agagggaatt attaagcaca gtggaagagt ttcattctgc tctcaatttt   1620
cttggattat gccgggtact atcaaagaaa atatcatctt tggtgtttcc tatgatgagt   1680
acagatataa gagtgttgtc aaagcttgcc aactacagca ggacatcacc aagtttgcag   1740
aacaagacaa cacagttctt ggagaaggtg gagtcacact gagtggaggt cagcgtgcaa   1800
ggatttcttt agcaagagca gtatataaag atgctgattt gtacctatta gattcccctt   1860
ttggatatct agatgttttt actgaagaac aagtatttga aagctgtgtt tgtaaattga   1920
tggccaacaa aactaggatt ttggttacat ctaaaatgga acacttaagg aaagctgaca   1980
aaatactaat tttgcatcag ggcagtagct atttttatgg gacattttct gagctacaaa   2040
gtctacgtcc agacttcagt tcgaaactca tggggtatga tacttttgac cagtttactg   2100
aggaaagaag aagttcaatt ctaactgaga ccttacgcag gttctcagta gacgattcct   2160
ctgccccgtg gagcaaaccc aaacagtcgt ttagacagac tggagaggtg ggagaaaaaa   2220
ggaagaactc tattctaaat tcattcagct ctgtaaggaa aatttccatt gtgcaaaaga   2280
ctccattatg tatcgatgga gagtctgatg atctccaaga aaagagactg tccctagttc   2340
cggattctga acagggggag gctgctctgc cgcgcagcaa catgatcgcc accggcccca   2400
catttccagg cagaagaaga cagtctgttt tggatctgat gacgttcaca cccaactcag   2460
gctccagcaa tcttcagagg accagaactt ctattcgaaa aatctcctta gtccctcaga   2520
taagcttaaa tgaagtggat gtatattcaa ggagattatc gcaagatagc acactgaaca   2580
tcactgaaga aattaacgaa gaagatttaa aggagtgttt tcttgatgat gtgatcaaga   2640
tacccccggt gacaacatgg aacacatacc tacgatattt tactctccat aaaggcttac   2700
tgctagtgct gatttggtgc gtactggttt ttctggttga ggtggctgct tctttatttg   2760
tgttatggtt gcttaaaaac aaccctgtta acagtggaaa caatggtact aaaatttcca   2820
atagctccta tgttgtgatc atcaccagta ccagtttcta ttatattttt tacatttacg   2880
tgggagtggc tgacactttg cttgccctga gcctcttcag aggtttgccg ctggtgcata   2940
cgttaatcac agcatcaaaa attttgcaca ggaaaatgtt acactccatt cttcacgccc   3000
ctatgtcgac catcagcaag ctgaaagcag gtgggattct taacagattc tccaaagata   3060
```

-continued

```
tagcaatttt ggatgacttt ctgcctctta ccatttttga cttcattcag ttggtgttca   3120
ttgtgattgg agctataata gtcgtctcgg cattacaacc ctacatcttc ctagcaacgg   3180
tgccagggct agtagtcttt attttactga gggcctactt ccttcataca gcacagcagc   3240
tcaaacaact ggaatctgaa ggcaggagtc caattttcac ccaccttgtg acaagcttaa   3300
aaggactctg gacacttcga gccttccgac gccagactta ctttgaaact ctgttccaca   3360
aagctctgaa tttgcacact gccaactggt ttatgtatct ggcaaccttg cgctggttcc   3420
aaatgagaat agacatgata tttgtcctct tcttcattgt tgttaccttc atctccattt   3480
taacaacagg tgaaggagaa ggaacagctg gtattattct aactttagct atgaatatca   3540
tgagtacttt gcagtgggct gtgaactcaa gcattgatac agatagcttg atgcgatctg   3600
tgagcagagt gtttaagttt attgatatac aaacagaaga aagtatgtac acacagataa   3660
ttaaagaact acctagagaa ggatcatctg acgttttagt cattaagaat gagcatgtga   3720
agaaaagtga tatctggccc tctggaggcg aaatggttgt caaagacctt actgtgaaat   3780
acatggatga tggaaatgcc gtattagaga acatttcttt ttcaataagt cctggacaga   3840
gggtggggct cttaggaaga actggatcag gaaaaagtac tttgctttca gcatttttac   3900
gaatgttgaa cattaaaggt gatatagaga ttgatggtgt ctcatggaat tcagtgacct   3960
tacaagaatg gaggaaagct ttcggagtga taacacagaa agtatttatc ttttctggaa   4020
cattcagaca aaacctggat cccaatggaa aatggaaaga tgaagaaata tggaaagttg   4080
cagatgaggt tggactcaag tctgtaatag agcagtttcc tggacagctc aactttaccc   4140
ttgtggatgg gggttatgtg ctaagccatg gccataagca attaatgtgc ttggcccgat   4200
cagttctcag taaggccaag atcatactgc ttgatgagcc cagtgcccat ctagacccca   4260
taacatacca agtcattcga cgagttctaa aacaagcctt cgctggttgc acagtcatcc   4320
tctgtgaaca caggatagaa gcgatgttgg attgccagcg atttttggtc atagaagaga   4380
gcaatgtctg gcagtacgac tcccttcagg cacttctgag tgagaagagt atcttccagc   4440
aggccattag ctcctcggaa aagatgaggt tcttccaggg ccgccactcc agcaagcaca   4500
agcctcggac gcaaattact gctctgaaag aggagacaga agaagaagtt caagaaaccc   4560
gtctctagtg ctgggatgct gaggaagcaa ctcagtgcac tgagtccatt cccagaaccc   4620
atgcagaatg aaaaaagcca ggcatttccc atgcttctaa ccccagtgct ggggacacag   4680
agacaggtgg atccctgggg ctctgtggca agtgatccta gcccacaaag agagttccag   4740
gctgggcacc tgagggacaa tacctgtgga tatactcttg cttccacatg caagtacata   4800
tacacatgca tgcacattag tggacataca cacagaaaag caaagaagaa ggaaagaggg   4860
aagaaaatag tgcaaataat tgcaaaacga tcatgtatgg agtctgctca tggacttaga   4920
ggaggtgaac tctactacct gtgcctttga aagaagggtg aagcctgcga cttgctcttt   4980
aagagactgt tttggaagag agttcaaaaa cgttcatatg ggtatgggta actgactttc   5040
cagcagtagt caaattgttt gaacttcaga tagttgataa tgaccacttg tgtattgcaa   5100
ggcagatttt tctgaaaaca tttgccccct aatagtagct gaaaaagcag ctataaatgc   5160
caaccaggtt agtcattcgg cttattgttc agtacagctg gttaatttgc attattgaag   5220
aactgaaatt atagtgctta gatataggac aaagtaaaga gaactaaaaa cagtgtctta   5280
tataactcaa agcccaactt actttcctct aagatatgta ttgccttcta tacattgtct   5340
gccccattcc aagcaaatgt tagaatatta tacaaaatac tgggtggtat tgattgaaag   5400
```

atgcccgaca tctggtgatc tagtaaccca tcaggattaa ggatatccag gtcttggaaa 5460
ttaaggttaa gaccatctag ccttactacc gtacagctaa acattcttat taccagaata 5520
agacctagga aaagaactgt ttcagtccca taaagtggcc tggataattt ccttgatatg 5580
gaaatcgaca cacttatgtt cccagaaagc aacagatctt taagacttct gaagtgaagg 5640
aaggttgtgt tagtgcaaac tagtgcagcc cagtgccagg tccaggagtt aacatgtaga 5700
caggccatgg actgtgtggg tagatgctca tggaaatgtg cagtagtatg ttcatgtgct 5760
ctcagctagc tgtgtgtact tcaaactgtc tccacagagt tgttggggag acactctgaa 5820
aaagaattaa ttgtgaatta gttttatata ctttgtttta taatttgtga tgcaaatgaa 5880
aatttctctg ggaaatattt attttagtaa taatgtttca aactcatata taacaatgct 5940
gtattttaag aatgattaca taatgactta tatttgtata aaataatttt tatatttgaa 6000
atgttaactt tttatagcac tagctatttt aaaacagggg agtgaggagg acagggatga 6060
taaggatcat tcaacttcat gttgtgaaga cgagctgatg taaatcttgt acccatctgt 6120
gtggttctca gacaacacat gctctctttt aatgcagctt tgaagaagat ggtaccaaag 6180
gttaagacgg ccccctgatg ggcacatcaa cttctgaact gcaaactaag ctttagagga 6240
atgtattata tttattactg taatagaata tcatgtgtca ataaaatcct tttatttgtg 6300
tgaaa 6305

<210> SEQ ID NO 149
<211> LENGTH: 1476
<212> TYPE: PRT
<213> ORGANISM: Mus musculus

<400> SEQUENCE: 149

Met Gln Lys Ser Pro Leu Glu Lys Ala Ser Phe Ile Ser Lys Leu Phe
1 5 10 15

Phe Ser Trp Thr Thr Pro Ile Leu Arg Lys Gly Tyr Arg His His Leu
20 25 30

Glu Leu Ser Asp Ile Tyr Gln Ala Pro Ser Ala Asp Ser Ala Asp His
35 40 45

Leu Ser Glu Lys Leu Glu Arg Glu Trp Asp Arg Glu Gln Ala Ser Lys
50 55 60

Lys Asn Pro Gln Leu Ile His Ala Leu Arg Arg Cys Phe Phe Trp Arg
65 70 75 80

Phe Leu Phe Tyr Gly Ile Leu Leu Tyr Leu Gly Glu Val Thr Lys Ala
85 90 95

Val Gln Pro Val Leu Leu Gly Arg Ile Ile Ala Ser Tyr Asp Pro Glu
100 105 110

Asn Lys Val Glu Arg Ser Ile Ala Ile Tyr Leu Gly Ile Gly Leu Cys
115 120 125

Leu Leu Phe Ile Val Arg Thr Leu Leu Leu His Pro Ala Ile Phe Gly
130 135 140

Leu His Arg Ile Gly Met Gln Met Arg Thr Ala Met Phe Ser Leu Ile
145 150 155 160

Tyr Lys Lys Thr Leu Lys Leu Ser Ser Arg Val Leu Asp Lys Ile Ser
165 170 175

Ile Gly Gln Leu Val Ser Leu Leu Ser Asn Asn Leu Asn Lys Phe Asp
180 185 190

Glu Gly Leu Ala Leu Ala His Phe Ile Trp Ile Ala Pro Leu Gln Val
195 200 205

```
Thr Leu Leu Met Gly Leu Leu Trp Asp Leu Leu Gln Phe Ser Ala Phe
    210                 215                 220

Cys Gly Leu Gly Leu Leu Ile Ile Leu Val Ile Phe Gln Ala Ile Leu
225                 230                 235                 240

Gly Lys Met Met Val Lys Tyr Arg Asp Gln Arg Ala Ala Lys Ile Asn
                245                 250                 255

Glu Arg Leu Val Ile Thr Ser Glu Ile Ile Asp Asn Ile Tyr Ser Val
            260                 265                 270

Lys Ala Tyr Cys Trp Glu Ser Ala Met Glu Lys Met Ile Glu Asn Leu
        275                 280                 285

Arg Glu Val Glu Leu Lys Met Thr Arg Lys Ala Ala Tyr Met Arg Phe
    290                 295                 300

Phe Thr Ser Ser Ala Phe Phe Phe Ser Gly Phe Phe Val Val Phe Leu
305                 310                 315                 320

Ser Val Leu Pro Tyr Thr Val Ile Asn Gly Ile Val Leu Arg Lys Ile
                325                 330                 335

Phe Thr Thr Ile Ser Phe Cys Ile Val Leu Arg Met Ser Val Thr Arg
            340                 345                 350

Gln Phe Pro Thr Ala Val Gln Ile Trp Tyr Asp Ser Phe Gly Met Ile
        355                 360                 365

Arg Lys Ile Gln Asp Phe Leu Gln Lys Gln Glu Tyr Lys Val Leu Glu
    370                 375                 380

Tyr Asn Leu Met Thr Thr Gly Ile Ile Met Glu Asn Val Thr Ala Phe
385                 390                 395                 400

Trp Glu Glu Gly Phe Gly Glu Leu Leu Glu Lys Val Gln Gln Ser Asn
                405                 410                 415

Gly Asp Arg Lys His Ser Ser Asp Glu Asn Asn Val Ser Phe Ser His
            420                 425                 430

Leu Cys Leu Val Gly Asn Pro Val Leu Lys Asn Ile Asn Leu Asn Ile
        435                 440                 445

Glu Lys Gly Glu Met Leu Ala Ile Thr Gly Ser Thr Gly Ser Gly Lys
    450                 455                 460

Thr Ser Leu Leu Met Leu Ile Leu Gly Glu Leu Glu Ala Ser Glu Gly
465                 470                 475                 480

Ile Ile Lys His Ser Gly Arg Val Ser Phe Cys Ser Gln Phe Ser Trp
                485                 490                 495

Ile Met Pro Gly Thr Ile Lys Glu Asn Ile Ile Phe Gly Val Ser Tyr
            500                 505                 510

Asp Glu Tyr Arg Tyr Lys Ser Val Val Lys Ala Cys Gln Leu Gln Gln
        515                 520                 525

Asp Ile Thr Lys Phe Ala Glu Gln Asp Asn Thr Val Leu Gly Glu Gly
    530                 535                 540

Gly Val Thr Leu Ser Gly Gly Gln Arg Ala Arg Ile Ser Leu Ala Arg
545                 550                 555                 560

Ala Val Tyr Lys Asp Ala Asp Leu Tyr Leu Leu Asp Ser Pro Phe Gly
                565                 570                 575

Tyr Leu Asp Val Phe Thr Glu Glu Gln Val Phe Glu Ser Cys Val Cys
            580                 585                 590

Lys Leu Met Ala Asn Lys Thr Arg Ile Leu Val Thr Ser Lys Met Glu
        595                 600                 605

His Leu Arg Lys Ala Asp Lys Ile Leu Ile Leu His Gln Gly Ser Ser
    610                 615                 620

Tyr Phe Tyr Gly Thr Phe Ser Glu Leu Gln Ser Leu Arg Pro Asp Phe
```

-continued

```
625                 630                 635                 640

Ser Ser Lys Leu Met Gly Tyr Asp Thr Phe Asp Gln Phe Thr Glu Glu
                645                 650                 655

Arg Arg Ser Ser Ile Leu Thr Glu Thr Leu Arg Arg Phe Ser Val Asp
            660                 665                 670

Asp Ser Ser Ala Pro Trp Ser Lys Pro Lys Gln Ser Phe Arg Gln Thr
        675                 680                 685

Gly Glu Val Gly Glu Lys Arg Lys Asn Ser Ile Leu Asn Ser Phe Ser
    690                 695                 700

Ser Val Arg Lys Ile Ser Ile Val Gln Lys Thr Pro Leu Cys Ile Asp
705                 710                 715                 720

Gly Glu Ser Asp Asp Leu Gln Glu Lys Arg Leu Ser Leu Val Pro Asp
                725                 730                 735

Ser Glu Gln Gly Glu Ala Ala Leu Pro Arg Ser Asn Met Ile Ala Thr
            740                 745                 750

Gly Pro Thr Phe Pro Gly Arg Arg Arg Gln Ser Val Leu Asp Leu Met
        755                 760                 765

Thr Phe Thr Pro Asn Ser Gly Ser Ser Asn Leu Gln Arg Thr Arg Thr
    770                 775                 780

Ser Ile Arg Lys Ile Ser Leu Val Pro Gln Ile Ser Leu Asn Glu Val
785                 790                 795                 800

Asp Val Tyr Ser Arg Arg Leu Ser Gln Asp Ser Thr Leu Asn Ile Thr
                805                 810                 815

Glu Glu Ile Asn Glu Glu Asp Leu Lys Glu Cys Phe Leu Asp Asp Val
            820                 825                 830

Ile Lys Ile Pro Pro Val Thr Thr Trp Asn Thr Tyr Leu Arg Tyr Phe
        835                 840                 845

Thr Leu His Lys Gly Leu Leu Leu Val Leu Ile Trp Cys Val Leu Val
    850                 855                 860

Phe Leu Val Glu Val Ala Ala Ser Leu Phe Val Leu Trp Leu Leu Lys
865                 870                 875                 880

Asn Asn Pro Val Asn Ser Gly Asn Asn Gly Thr Lys Ile Ser Asn Ser
                885                 890                 895

Ser Tyr Val Val Ile Ile Thr Ser Thr Ser Phe Tyr Tyr Ile Phe Tyr
            900                 905                 910

Ile Tyr Val Gly Val Ala Asp Thr Leu Leu Ala Leu Ser Leu Phe Arg
        915                 920                 925

Gly Leu Pro Leu Val His Thr Leu Ile Thr Ala Ser Lys Ile Leu His
    930                 935                 940

Arg Lys Met Leu His Ser Ile Leu His Ala Pro Met Ser Thr Ile Ser
945                 950                 955                 960

Lys Leu Lys Ala Gly Gly Ile Leu Asn Arg Phe Ser Lys Asp Ile Ala
                965                 970                 975

Ile Leu Asp Asp Phe Leu Pro Leu Thr Ile Phe Asp Phe Ile Gln Leu
            980                 985                 990

Val Phe Ile Val Ile Gly Ala Ile  Ile Val Val Ser Ala  Leu Gln Pro
        995                 1000                 1005

Tyr Ile  Phe Leu Ala Thr Val  Pro Gly Leu Val Val  Phe Ile Leu
    1010                 1015                 1020

Leu Arg  Ala Tyr Phe Leu His  Thr Ala Gln Gln Leu  Lys Gln Leu
    1025                 1030                 1035

Glu Ser  Glu Gly Arg Ser Pro  Ile Phe Thr His Leu  Val Thr Ser
    1040                 1045                 1050
```

```
Leu Lys  Gly Leu Trp Thr Leu  Arg Ala Phe Arg Arg  Gln Thr Tyr
    1055                 1060                 1065

Phe Glu  Thr Leu Phe His Lys  Ala Leu Asn Leu His  Thr Ala Asn
    1070                 1075                 1080

Trp Phe  Met Tyr Leu Ala Thr  Leu Arg Trp Phe Gln  Met Arg Ile
    1085                 1090                 1095

Asp Met  Ile Phe Val Leu Phe  Phe Ile Val Val Thr  Phe Ile Ser
    1100                 1105                 1110

Ile Leu  Thr Thr Gly Glu Gly  Glu Gly Thr Ala Gly  Ile Ile Leu
    1115                 1120                 1125

Thr Leu  Ala Met Asn Ile Met  Ser Thr Leu Gln Trp  Ala Val Asn
    1130                 1135                 1140

Ser Ser  Ile Asp Thr Asp Ser  Leu Met Arg Ser Val  Ser Arg Val
    1145                 1150                 1155

Phe Lys  Phe Ile Asp Ile Gln  Thr Glu Glu Ser Met  Tyr Thr Gln
    1160                 1165                 1170

Ile Ile  Lys Glu Leu Pro Arg  Glu Gly Ser Ser Asp  Val Leu Val
    1175                 1180                 1185

Ile Lys  Asn Glu His Val Lys  Lys Ser Asp Ile Trp  Pro Ser Gly
    1190                 1195                 1200

Gly Glu  Met Val Val Lys Asp  Leu Thr Val Lys Tyr  Met Asp Asp
    1205                 1210                 1215

Gly Asn  Ala Val Leu Glu Asn  Ile Ser Phe Ser Ile  Ser Pro Gly
    1220                 1225                 1230

Gln Arg  Val Gly Leu Leu Gly  Arg Thr Gly Ser Gly  Lys Ser Thr
    1235                 1240                 1245

Leu Leu  Ser Ala Phe Leu Arg  Met Leu Asn Ile Lys  Gly Asp Ile
    1250                 1255                 1260

Glu Ile  Asp Gly Val Ser Trp  Asn Ser Val Thr Leu  Gln Glu Trp
    1265                 1270                 1275

Arg Lys  Ala Phe Gly Val Ile  Thr Gln Lys Val Phe  Ile Phe Ser
    1280                 1285                 1290

Gly Thr  Phe Arg Gln Asn Leu  Asp Pro Asn Gly Lys  Trp Lys Asp
    1295                 1300                 1305

Glu Glu  Ile Trp Lys Val Ala  Asp Glu Val Gly Leu  Lys Ser Val
    1310                 1315                 1320

Ile Glu  Gln Phe Pro Gly Gln  Leu Asn Phe Thr Leu  Val Asp Gly
    1325                 1330                 1335

Gly Tyr  Val Leu Ser His Gly  His Lys Gln Leu Met  Cys Leu Ala
    1340                 1345                 1350

Arg Ser  Val Leu Ser Lys Ala  Lys Ile Ile Leu Leu  Asp Glu Pro
    1355                 1360                 1365

Ser Ala  His Leu Asp Pro Ile  Thr Tyr Gln Val Ile  Arg Arg Val
    1370                 1375                 1380

Leu Lys  Gln Ala Phe Ala Gly  Cys Thr Val Ile Leu  Cys Glu His
    1385                 1390                 1395

Arg Ile  Glu Ala Met Leu Asp  Cys Gln Arg Phe Leu  Val Ile Glu
    1400                 1405                 1410

Glu Ser  Asn Val Trp Gln Tyr  Asp Ser Leu Gln Ala  Leu Leu Ser
    1415                 1420                 1425

Glu Lys  Ser Ile Phe Gln Gln  Ala Ile Ser Ser Ser  Glu Lys Met
    1430                 1435                 1440
```

-continued

```
Arg Phe  Phe Gln Gly Arg His  Ser Ser Lys His Lys  Pro Arg Thr
    1445                 1450                 1455

Gln Ile  Thr Ala Leu Lys Glu  Glu Thr Glu Glu Glu  Val Gln Glu
    1460                 1465                 1470

Thr Arg  Leu
    1475


<210> SEQ ID NO 150
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 150

cctttcaggg tgtcttactc accat                                        25


<210> SEQ ID NO 151
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 151

cctcttacct cagttacaat ttata                                        25
```

ANTISENSE COMPOUNDS TARGETING GENES ASSOCIATED WITH CYSTIC FIBROSIS

CROSS REFERENCE TO RELATED APPLICATIONS

This application is a continuation of U.S. Application Ser. No. 16/730,517, filed Dec. 30, 2019 (now U.S. Pat. No. 11,116,785; issued Sep. 14, 2021), which is a continuation of U.S. Application Ser. No. 15/835,698, filed Dec. 8, 2017 (now U.S. Pat. No. 10,525,076; issued Jan. 7, 2020), which is a continuation-in-part of U.S. application Ser. No. 15/045,999, filed Feb. 17, 2016 (now U.S. Pat. No. 9,840,709; issued Dec. 12, 2017), which is a non-provisional application of U.S. Provisional Application No. 62/118,794, filed Feb. 20, 2015, the disclosures of which each of which are incorporated by reference in their entirety.

SEQUENCE LISTING

The sequence listing submitted herewith is incorporated by reference in its entirety,

FIELD OF THE DISCLOSURE

The present disclosure relates generally to compounds comprising oligonucleotides complementary to a cystic fibrosis transmembrane conductance regulator (CFTR) RNA transcript. Certain such compounds are useful for hybridizing to a CFTR transcript, including but not limited to a CFTR. RNA transcript in a cell. In certain embodiments, such hybridization results in modulation of splicing of the CFTR transcript. In certain embodiments, such compounds are used to treat one or more symptoms associated with Cystic Fibrosis.

BACKGROUND OF THE DISCLOSURE

Cystic fibrosis (CF), also known as mucoviscidosis, is a genetic disorder that affects mostly the lungs, but also the pancreas, liver, kidneys, and intestine. Long-term issues include difficulty breathing and coughing up mucus as a result of frequent lung infections. Other signs and symptoms include sinus infections, poor growth, fatty stool, clubbing of the fingers and toes, and infertility in males among others. Different people may have different degrees of symptoms.

CF is inherited in an autosomal recessive manner. It is caused by the presence of mutations in both copies of the gene for the cystic fibrosis transmembrane conductance regulator (CFTR) protein. Those with a single working copy are carriers and otherwise mostly normal. CFTR is involved in production of sweat, digestive fluids, and mucus. When CFTR is not functional, secretions, which are usually thin, instead become thick. The condition is diagnosed by a sweat test and genetic testing. Screening of infants at birth takes place in some areas of the world.

There is no cure for cystic fibrosis. Lung infections are treated with antibiotics which may be given intravenously, inhaled, or by mouth. Sometimes the antibiotic azithromycin is used long term. Inhaled hypertonic saline and salbutamol may also be useful. Lung transplantation may be an option if lung function continues to worsen. Pancreatic enzyme replacement and fat-soluble vitamin supplementation are important, especially in the young. The average life expectancy is between 42 and 50 years in the developed world. While CF is a multi-organ disease, lung problems are the dominant cause of morbidity and mortality. Other CF symptoms include pancreatic insufficiency, intestinal obstruction, elevated electrolyte levels in sweat (the basis of the most common diagnostic test), and male infertility. CF is most common among people of Northern European ancestry and affects about one out of every 2,500 to 4,000 newborns. About one in 25 people are carriers. While treatments for Cystic Fibrosis are available, more effective therapies are needed.

SUMMARY OF THE DISCLOSURE

The present disclosure relates to general compounds and methods to treat cystic fibrosis in subjects using antisense oligonucleotides (ASOs) that induce specific pre-mRNA splicing events in CFTR gene transcripts that result in mRNAs that code for proteins that fully or partially restore the function of CFTR (i.e., resulting in increased levels of correctly localized CFTR protein at the plasma membrane and with increased function).

In one aspect, the disclosure provides a compound comprising a modified oligonucleotide having 8 to 30 linked nucleosides having a nucleobase sequence comprising a complementary region, wherein the complementary region comprises at least 8 contiguous nucleobases complementary to an equal-length portion of a target region of a cystic fibrosis transmembrane conductance regulator (CFTR) transcript. In certain embodiments, the target region of the CFTR transcript comprises at least a portion of intron 1, exon 2, intron 2, intron 3, exon 4, intron 4, exon 5, intron 6, exon 7, intron 7, exon 9, intron 9, exon 10, intron 10, exon 11, intron 11, intron 12, exon 13, intron 13, intron 14, exon 15, intron 15, exon 16, intron 16, intron 19, exon 20, intron 20, intron 21, exon 22, intron 22, exon 23, intron 23, exon 24 or intron 24 of the CFTR transcript. In other embodiments, the nucleobase sequence of the antisense oligonucleotide comprises any one of SEQ ID NOs: 1 to 144, or SEQ ID NO:150.

In another aspect, the disclosure provides a pharmaceutical composition comprising at least one compound as described herein and a pharmaceutically acceptable carrier or diluent.

In yet another aspect, the disclosure provides a method of modulating splicing or expression of a CFTR transcript in a cell comprising contacting the cell with at least one compound as described herein.

The yet another aspect, the disclosure provides a method of treating cystic fibrosis, comprising administering at least one compound as described herein to an animal in need thereof.

The present disclosure provides the following non-limiting numbered embodiments:

Embodiment 1. A compound comprising a modified oligonucleotide consisting of 8 to 30 linked nucleosides and having a nucleobase sequence comprising a complementary region, wherein the complementary region comprises at least 8 contiguous nucleobases complementary to an equal-length portion of a target region of a cystic fibrosis transmembrane conductance regulator (CFTR) transcript.

Embodiment 2. The compound of embodiment 1, wherein the target region of the CFTR transcript comprises at least a portion of intron 1, exon 2, intron 2, intron 3, exon 4, intron 4, exon 5, intron 6, exon 7, intron 7, exon 9, intron 9, exon 10, intron 10, exon 11, intron 11, intron 12, exon 13, intron 13, intron 14, exon 15, intron 15, exon 16, intron 16, intron 19, exon 20, intron 20, intron 21, exon 22, intron 22, exon 23, intron 23, exon 24 or intron 24 of the CFTR transcript.

Embodiment 3. The compound of embodiment 1, wherein the target region of the CFTR transcript comprises at least a portion of exon 2 of the CFTR transcript.

Embodiment 4. The compound of embodiment 1, wherein the target region of the CFTR transcript comprises at least a portion of exon 4 of the CFTR transcript.

Embodiment 5. The compound of embodiment 1, wherein the target region of the CFTR transcript comprises at least a portion of exon 5 of the CFTR transcript.

Embodiment 6. The compound of embodiment 1, wherein the target region of the CFTR transcript comprises at least a portion of exon 7 of the CFTR transcript.

Embodiment 7. The compound of embodiment 1, wherein the target region of the CFTR transcript comprises at least a portion of exon 9 of the CFTR transcript.

Embodiment 8. The compound of embodiment 1, wherein the target region of the CFTR transcript comprises at least a portion of exon 10 of the CFTR transcript.

Embodiment 9. The compound of embodiment 1, wherein the target region of the CFTR transcript comprises at least a portion of exon 11 of the CFTR transcript.

Embodiment 10. The compound of embodiment 1, wherein the target region of the CFTR transcript comprises at least a portion of exon 13 of the CFTR transcript.

Embodiment 11. The compound of embodiment 1, wherein the target region of the CFTR transcript comprises at least a portion of exon 15 of the CFTR transcript.

Embodiment 12. The compound of embodiment 1, wherein the target region of the CFTR transcript comprises at least a portion of exon 16 of the CFTR transcript.

Embodiment 13. The compound of embodiment 1, wherein the target region of the CFTR transcript comprises at least a portion of exon 20 of the CFTR transcript.

Embodiment 14. The compound of embodiment 1, wherein the target region of the CFTR transcript comprises at least a portion of exon 22 of the CFTR transcript.

Embodiment 15. The compound of embodiment 1, wherein the target region of the CFTR transcript comprises at least a portion of exon 23 of the CFTR transcript.

Embodiment 16. The compound of embodiment 1, wherein the target region of the CFTR transcript comprises at least a portion of exon 24 of the CFTR transcript.

Embodiment 17. The compound of any of embodiments 1 to 16, wherein the complementary region of the modified oligonucleotide is at least 80%, at least 85%, at least 90%, at least 95% or at least 100% complementary to the target region.

Embodiment 18. The compound of any of embodiments 1 to 17, wherein the complementary region of the modified oligonucleotide comprises at least 10 contiguous nucleobases.

Embodiment 19. The compound of any of embodiments 1 to 17, wherein the complementary region of the modified oligonucleotide comprises at least 12 contiguous nucleobases.

Embodiment 20. The compound of any of embodiments 1 to 17, wherein the complementary region of the modified oligonucleotide comprises at least 14 contiguous nucleobases.

Embodiment 21. The compound of any of embodiments 1 to 17, wherein the complementary region of the modified oligonucleotide comprises at least 15 contiguous nucleobases.

Embodiment 22. The compound of any of embodiments 1 to 17, wherein the complementary region of the modified oligonucleotide comprises at least 16 contiguous nucleobases.

Embodiment 23. The compound of any of embodiments 1 to 17, wherein the complementary region of the modified oligonucleotide comprises at least 17 contiguous nucleobases.

Embodiment 24. The compound of any of embodiments 1 to 17, wherein the complementary region of the modified oligonucleotide comprises at least 18 contiguous nucleobases.

Embodiment 25. The compound of any of embodiments 1 to 17, wherein the complementary region of the modified oligonucleotide comprises at least 19 contiguous nucleobases.

Embodiment 26. The compound of any of embodiments 1 to 17, wherein the complementary region of the modified oligonucleotide comprises at least 20 contiguous nucleobases.

Embodiment 27. The compound of any of embodiments 1 to 26, wherein the nucleobase sequence of the oligonucleotide is at least 80% complementary to an equal-length region of the CFTR transcript, as measured over the entire length of the oligonucleotide.

Embodiment 28. The compound of any of embodiments 1 to 26, wherein the nucleobase sequence of the oligonucleotide is at least 90% complementary to an equal-length region of the CFTR transcript, as measured over the entire length of the oligonucleotide.

Embodiment 29. The compound of any of embodiments 1 to 26, wherein the nucleobase sequence of the oligonucleotide is 100/a complementary to an equal-length region of the CFTR transcript, as measured over the entire length of the oligonucleotide.

Embodiment 30. The compound of any of embodiments 1-29, wherein the nucleobase sequence of the antisense oligonucleotide comprises any one of SEQ ID NOs: 1 to 144, and SEQ ID NO:150.

Embodiment 31. The compound of any of embodiments 1-30, wherein the modified oligonucleotide comprises at least one modified nucleoside.

Embodiment 32. The compound of embodiment 31, wherein at least one modified nucleoside comprises a modified sugar moiety.

Embodiment 33. The compound of embodiment 32, wherein at least one modified sugar moiety is a 2'-substituted sugar moiety.

Embodiment 34. The compound of embodiment 33, wherein the 2'-substitutent of at least one 2'-substituted sugar moiety is selected from among: 2'-OMe, 2-F, and 2'-MOE.

Embodiment 35. The compound of any of embodiments 31-34, wherein the 2'-substituent of at least one 2'-substituted sugar moiety is a 2'-MOE.

Embodiment 36. The compound of any of embodiments 1-47, wherein at least one modified sugar moiety is a bicyclic sugar moiety.

Embodiment 37. The compound of embodiment 36, wherein at least one bicyclic sugar moiety is LNA or cEt.

Embodiment 38. The compound of any of embodiments 1-37, wherein at least one sugar moiety is a sugar surrogate.

Embodiment 39. The compound of embodiment 38, wherein at least one sugar surrogate is a morpholino.

Embodiment 40. The compound of embodiment 38, wherein at least one sugar surrogate is a modified morpholino.

Embodiment 41. The compound of any of embodiments 1-40, wherein the modified oligonucleotide comprises at least 5 modified nucleosides, each independently comprising a modified sugar moiety.

Embodiment 42. The compound of embodiment 41, wherein the modified oligonucleotide comprises at least 10 modified nucleosides, each independently comprising a modified sugar moiety.

Embodiment 43. The compound of embodiment 41, wherein the modified oligonucleotide comprises at least 15 modified nucleosides, each independently comprising a modified sugar moiety.

Embodiment 44. The compound of embodiment 41, wherein each nucleoside of the modified oligonucleotide is a modified nucleoside, each independently comprising a modified sugar moiety Embodiment 45. The compound of any of embodiments 1-44, wherein the modified oligonucleotide comprises at least two modified nucleosides comprising modified sugar moieties that are the same as one another.

Embodiment 46. The compound of any of embodiments 1-44, wherein the modified oligonucleotide comprises at least two modified nucleosides comprising modified sugar moieties that are different from one another.

Embodiment 47. The compound of any of embodiments 1-46, wherein the modified oligonucleotide comprises a modified region of at least 5 contiguous modified nucleosides.

Embodiment 48. The compound of any of embodiments 1 to 47, wherein the modified oligonucleotide comprises a modified region of at least 10 contiguous modified nucleosides.

Embodiment 49. The compound of any of embodiments 1 to 48, wherein the modified oligonucleotide comprises a modified region of at least 15 contiguous modified nucleosides.

Embodiment 50. The compound of any of embodiments 1 to 48, wherein the modified oligonucleotide comprises a modified region of at least 20 contiguous modified nucleosides.

Embodiment 51. The compound of any of embodiments 45 to 50, wherein each modified nucleoside of the modified region has a modified sugar moiety independently selected from among: 2-F, 2'-OMe, 2'-MOE, cEt, LNA, morpholino, and modified morpholino.

Embodiment 52. The compound of any of embodiments 45 to 51 wherein the modified nucleosides of the modified region each comprise the same modification as one another.

Embodiment 53. The compound of embodiment 52, wherein the modified nucleosides of the modified region each comprise the same 2'-substituted sugar moiety.

Embodiment 54. The compound of embodiment 52, wherein the 2'-substituted sugar moiety of the modified nucleosides of the region of modified nucleosides is selected from 2'-F, 2'-OMe, and 2'-MOE.

Embodiment 55. The compound of embodiment 54, wherein the 2'-substituted sugar moiety of the modified nucleosides of the region of modified nucleosides is 2'-MOE.

Embodiment 56. The compound of embodiment 52, wherein the modified nucleosides of the region of modified nucleosides each comprise the same bicyclic sugar moiety.

Embodiment 57. The compound of embodiment 56, wherein the bicyclic sugar moiety of the modified nucleosides of the region of modified nucleosides is selected from LNA and cEt.

Embodiment 58. The compound of embodiment 50, wherein the modified nucleosides of the region of modified nucleosides each comprises a sugar surrogate, Embodiment 59. The compound of embodiment 58, wherein the sugar surrogate of the modified nucleosides of the region of modified nucleosides is a morpholino.

Embodiment 60. The compound of embodiment 59, wherein the sugar surrogate of the modified nucleosides of the region of modified nucleosides is a modified morpholino.

Embodiment 61. The compound of any of embodiments 1 to 60, wherein the modified nucleotide comprises no more than 4 contiguous naturally occurring nucleosides.

Embodiment 62. The compound of any of embodiments 1 to 61, wherein each nucleoside of the modified oligonucleotide is a modified nucleoside.

Embodiment 63. The compound of embodiment 62, wherein each modified nucleoside comprises a modified sugar moiety.

Embodiment 64. The compound of embodiment 63, wherein the modified nucleosides of the modified oligonucleotide comprise the same modification as one another.

Embodiment 65. The compound of embodiment 64, wherein the modified nucleosides of the modified oligonucleotide each comprise the same 2'-substituted sugar moiety.

Embodiment 66. The compound of embodiment 65, wherein the 2'-substituted sugar moiety of the modified oligonucleotide is selected from 2'-F, 2'-OMe, and 2'-MOE.

Embodiment 67. The compound of embodiment 65, wherein the 2'-substituted sugar moiety of the modified oligonucleotide is 2'-MOE.

Embodiment 68. The compound of embodiment 64, wherein the modified nucleosides of the modified oligonucleotide each comprise the same bicyclic sugar moiety.

Embodiment 69. The compound of embodiment 68, wherein the bicyclic sugar moiety of the modified oligonucleotide is selected from LNA and cEt.

Embodiment 70. The compound of embodiment 64, wherein the modified nucleosides of the modified oligonucleotide each comprises a sugar surrogate.

Embodiment 71. The compound of embodiment 70, wherein the sugar surrogate of the modified oligonucleotide is a morpholino.

Embodiment 72. The compound of embodiment 70, wherein the sugar surrogate of the modified oligonucleotide is a modified morpholino.

Embodiment 73. The compound of any of embodiments 1 to 72, wherein the modified oligonucleotide comprises at least one modified internucleoside linkage.

Embodiment 74. The compound of embodiment 73, wherein each internucleoside linkage is a modified internucleoside linkage.

Embodiment 75. The compound of embodiment 73 or 74, comprising at least one phosphorothioate internucleoside linkage.

Embodiment 76. The compound of embodiment 73, wherein each internucleoside linkage is a modified internucleoside linkage and wherein each internucleoside linkage comprises the same modification.

Embodiment 77. The compound of embodiment 76, wherein each internucleoside linkage is a phosphorothioate internucleoside linkage.

Embodiment 78. The compound of any of embodiments 1 to 77, comprising at least one conjugate.

Embodiment 79. The compound of any of embodiments 1 to 78, consisting of the modified oligonucleotide.

Embodiment 80. The compound of any of embodiments 1 to 79, wherein the compound modulates splicing of the CFTR transcript.

Embodiment 81. The compound of any of embodiments 1 to 80, having a nucleobase sequence comprising any of the sequences as set forth in SEQ ID Nos: 1 to 144, and SEQ ID NO:150.

Embodiment 82. The compound of any of embodiments 1 to 81, having a nucleobase sequence comprising any of the sequences as set forth in SEQ ID Nos: 64, 65, 66, 71, 76, 78, 79, 81, 82, 84, 91, 92, 93, 94, 102, 111, 116, 117, 120, 122, 127, 128 or 129.

Embodiment 83. The compound of any of embodiments 1 to 81, having a nucleobase sequence comprising any of the sequences as set forth in SEQ ID Nos: 1, 4, 8, 9, 10, 12, 13, 17, 18, 19, 20, 22, 23, 24, 26, 27, 36, 37, 38, 42, 43, 44, 47, 48, 49, 50, 53, 55, 57, 59 or 60.

Embodiment 84. The compound of any of embodiment 82, having a nucleobase sequence comprising SEQ ID NO, 91, 97, 99, 100, 103, 104, 110, 114, 126, 127, 128, 129, or 150.

Embodiment 85. A pharmaceutical composition comprising a compound according to any of embodiments 1-84 and a pharmaceutically acceptable carrier or diluent.

Embodiment 86. The pharmaceutical composition of embodiment 85, wherein the pharmaceutically acceptable carrier or diluent is sterile saline.

Embodiment 87. A method of modulating splicing of a CFTR transcript in a cell comprising contacting the cell with a compound according to any of embodiments 1-86.

Embodiment 88. The method of embodiment 87, wherein the cell is in vitro.

Embodiment 89. The method of embodiment 87, wherein the cell is in an animal.

Embodiment 90. The method of any of embodiments 87 to 89, wherein the amount of CFTR mRNA without exon 11 is increased.

Embodiment 91. The method of any of embodiments 87 to 89, wherein the amount of CFTR mRNA without exon 16 is increased.

Embodiment 92. The method of any of embodiments 87 to 89, wherein the amount of CFTR mRNA with exon 23 or exon 24 is increased.

Embodiment 93. The method of any of embodiments 87 to 92, wherein the CFTR transcript is transcribed from a CFTR gene.

Embodiment 94. A method of modulating the expression of CFTR in a cell, comprising contacting the cell with a compound according to any of embodiments 1-86.

Embodiment 95. The method of embodiment 94, wherein the cell is in vitro.

Embodiment 96. The method of embodiment 94, wherein the cell is in an animal.

Embodiment 97. A method comprising administering the compound according to any of embodiments 1-84 or the pharmaceutical composition of embodiments 85 or 86 to an animal.

Embodiment 98. The method of embodiment 97, wherein the administering step comprises delivering to the animal by inhalation, parenteral injection or infusion, oral, subcutaneous or intramuscular injection, buccal, transdermal, transmucosal and topical.

Embodiment 99. The method of embodiment 98, wherein the administration is by inhalation.

Embodiment 100. The method of any of embodiments 97-99, wherein the animal has one or more symptoms associated with cystic fibrosis.

Embodiment 101. The method of any of embodiments 97-99, wherein the administration results in amelioration of at least one symptom of cystic fibrosis.

Embodiment 102. The method of any of embodiments 97-101, wherein the animal is a mouse.

Embodiment 103. The method of any of embodiments 97-101, wherein the animal is a human.

Embodiment 104. A method of treating cystic fibrosis, comprising administering the compound according to any of embodiments 1-84 or the pharmaceutical composition of embodiments 85 or 86 to an animal in need thereof.

Embodiment 105. Use of the compound according to any of embodiments 1-84 or the pharmaceutical composition of embodiments 85 or 86 for the preparation of a medicament for use in the treatment of cystic fibrosis.

Embodiment 106. Use of the compound according to any of embodiments 1-84 or the pharmaceutical composition of embodiments 85 or 86 for the preparation of a medicament for use in the amelioration of one or more symptoms associated with cystic fibrosis.

Embodiment 107. A compound comprising a modified oligonucleotide consisting of 8 to 30 linked nucleosides and having a nucleobase sequence comprising a complementary region, wherein the complementary region comprises at least 8 contiguous nucleobases complementary to an equal-length portion of a target region of a CFTR transcript.

Embodiment 108. The compound of embodiment 107, wherein the CFTR transcript comprises the nucleobase sequence of SEQ ID No. 130.

Embodiment 109. The compound of embodiment 107 or 108, wherein the complementary region of the modified oligonucleotide is 100% complementary to the target region.

Embodiment 110. The compound of any of embodiments 107-109, wherein the complementary region of the modified oligonucleotide comprises at least 10 contiguous nucleobases.

Embodiment 111. The compound of any of embodiments 107-109, wherein the complementary region of the modified oligonucleotide comprises at least 12 contiguous nucleobases.

Embodiment 112. The compound of any of embodiments 107-109, wherein the complementary region of the modified oligonucleotide comprises at least 14 contiguous nucleobases.

Embodiment 113. The compound of any of embodiments 107-109, wherein the complementary region of the modified oligonucleotide comprises at least 15 contiguous nucleobases.

Embodiment 114. The compound of any of embodiments 107-109, wherein the complementary region of the modified oligonucleotide comprises at least 16 contiguous nucleobases.

Embodiment 115. The compound of any of embodiments 107-109, wherein the complementary region of the modified oligonucleotide comprises at least 17 contiguous nucleobases.

Embodiment 116. The compound of any of embodiments 107-109, wherein the complementary region of the modified oligonucleotide comprises at least 18 contiguous nucleobases.

Embodiment 117. The compound of any of embodiments 107-116, wherein the nucleobase sequence of the modified oligonucleotide is at least 80% complementary to an equal-length region of the CFTR transcript, as measured over the entire length of the oligonucleotide.

Embodiment 118. The compound of any of embodiments 107-116, wherein the nucleobase sequence of the modified oligonucleotide is at least 90% complementary to an equal-length region of the CFTR transcript, as measured over the entire length of the oligonucleotide.

Embodiment 119. The compound of any of embodiments 107-116, wherein the nucleobase sequence of the modified oligonucleotide is 100% complementary to an equal-length region of the CFTR transcript, as measured over the entire length of the oligonucleotide.

Embodiment 120. The compound of any of embodiments 107-119, wherein the target region is within intron 1, exon 2, intron 2, intron 3, exon 4, intron 4, exon 5, intron 6, exon 7, intron 7, exon 9, intron 9, exon 10, intron 10, exon 11, intron 11, intron 12, exon 13, intron 13, intron 14, exon 15, intron 15, exon 16, intron 16, intron 19, exon 20, intron 20, intron 21, exon 22, intron 22, exon 23, intron 23, exon 24 or intron 24 of human CFTR.

Embodiment 121. The compound of embodiment 120, wherein the target region is within exon 11 of human CFTR.

Embodiment 122. The compound of embodiment 120, wherein the target region is within exon 23 or exon 24 of human CFTR.

Embodiment 123. The compound of any of embodiments 107-119, wherein the target region is within intron 1, exon 2, intron 2, intron 3, exon 4, intron 4, exon 5, intron 6, exon 7, intron 7, exon 9, intron 9, exon 10, intron 10, exon 11, intron 11, intron 12, exon 13, intron 13, intron 14, exon 15, intron 15, exon 16, intron 16, intron 19, exon 20, intron 20, intron 21, exon 22, intron 22, exon 23, intron 23, exon 24 or intron 24 of mouse CFTR.

Embodiment 124. The compound of any of embodiments 107-119, wherein the modified oligonucleotide has a nucleobase sequence comprising any of the sequences as set forth in SEQ ID NOs: 1-144, and SEQ ID NO:150.

Embodiment 125. The compound of any of embodiments 107-119, wherein the modified oligonucleotide has a nucleobase sequence consisting of the nucleobase sequence of any one of SEQ ID NOs: 1-144, and SEQ ID NO:150.

Embodiment 126. The compound of any of embodiments 107-119, wherein the modified oligonucleotide has a nucleobase sequence comprising the nucleobase sequence of SEQ ID NO. 64, 65, 66, 71, 76, 78, 79, 81, 82, 84, 91, 92, 93, 94, 97, 99, 100, 102, 103, 104, 111, 114, 116, 117, 120, 122, 127, 128, 129, or 150.

Embodiment 127. The compound of embodiment 125, wherein the modified oligonucleotide has a nucleobase sequence consisting of the nucleobase sequence of SEQ ID NO. 64, 65, 66, 71, 76, 78, 79, 81, 82, 84, 91, 92, 93, 94, 97, 99, 100, 102, 103, 104, 111, 114, 116, 117, 120, 122, 127, 128, 129, or 150.

Embodiment 128. The compound of any of embodiments 107-119, wherein the modified oligonucleotide has a nucleobase sequence comprising the nucleobase sequence of SEQ ID NO. 91, 97, 99, 100, 103, 104, 110, 114, 126, 127, 128, 129, or 150.

Embodiment 129. The compound of embodiment 125, wherein the modified oligonucleotide has a nucleobase sequence consisting of the nucleobase sequence of SEQ ID NO. 91, 97, 99, 100, 103, 104, 110, 114, 126, 127, 128, 129, or 150.

Embodiment 130. The compound of any of embodiments 107-129, wherein the modified oligonucleotide comprises at least one modified nucleoside.

Embodiment 131. The compound of any of embodiments 107-130, wherein each nucleoside of the modified oligonucleotide is a modified nucleoside selected from among: 2'-OMe, 2'-F, and 2'-MOE or a sugar surrogate.

Embodiment 132. The compound of embodiment 132, wherein the modified nucleoside is 2'-MOE.

Embodiment 133. The compound of embodiment 132, wherein the modified nucleoside is a morpholino.

Embodiment 134. The compound of embodiment 131, wherein at least one modified nucleoside comprises a modified sugar moiety.

Embodiment 135. The compound of embodiment 134, wherein at least one modified sugar moiety is a 2'-substituted sugar moiety.

Embodiment 136. The compound of embodiment 135, wherein the 2-substitutent of at least one 2'-substituted sugar moiety is selected from among: 2'-OMe, 2'-F, and 2'-MOE.

Embodiment 137. The compound of any of embodiments 135-136, wherein the 2'-substituent of at least one 2'-substituted sugar moiety is a 2'-MOE.

Embodiment 138. The compound of any of embodiments 107-137, wherein at least one modified sugar moiety is a bicyclic sugar moiety.

Embodiment 139. The compound of embodiment 138, wherein at least one bicyclic sugar moiety is LNA or cEt.

Embodiment 140. The compound of any of embodiments 107-139, wherein at least one sugar moiety is a sugar surrogate.

Embodiment 141. The compound of embodiment 140, wherein at least one sugar surrogate is a morpholino.

Embodiment 142. The compound of embodiment 141, wherein at least one sugar surrogate is a modified morpholino.

Embodiment 143. The compound of any of embodiments 107-142, wherein the modified oligonucleotide comprises at least 5 modified nucleosides, each independently comprising a modified sugar moiety.

Embodiment 144. The compound of any of embodiments 107-143, wherein the modified oligonucleotide comprises at least 10 modified nucleosides, each independently comprising a modified sugar moiety.

Embodiment 145. The compound of any of embodiments 107-143, wherein the modified oligonucleotide comprises at least 15 modified nucleosides, each independently comprising a modified sugar moiety.

Embodiment 146. The compound of any of embodiments 107-143, wherein each nucleoside of the modified oligonucleotide is a modified nucleoside, each independently comprising a modified sugar moiety.

Embodiment 147. The compound of any of embodiments 107-146, wherein the modified oligonucleotide comprises at least two modified nucleosides comprising modified sugar moieties that are the same as one another.

Embodiment 148. The compound of any of embodiments 107-146, wherein the modified oligonucleotide comprises at least two modified nucleosides comprising modified sugar moieties that are different from one another.

Embodiment 149. The compound of any of embodiments 107-148, wherein the modified oligonucleotide comprises a modified region of at least 5 contiguous modified nucleosides.

Embodiment 150. The compound of any of embodiments 107-148, wherein the modified oligonucleotide comprises a modified region of at least 10 contiguous modified nucleosides.

Embodiment 151. The compound of any of embodiments 107-148, wherein the modified oligonucleotide comprises a modified region of at least 15 contiguous modified nucleosides.

Embodiment 152. The compound of any of embodiments 107-148, wherein the modified oligonucleotide comprises a modified region of at least 16 contiguous modified nucleosides.

Embodiment 153. The compound of any of embodiments 107-148, wherein the modified oligonucleotide comprises a modified region of at least 17 contiguous modified nucleosides.

Embodiment 154. The compound of any of embodiments 107-148, wherein the modified oligonucleotide comprises a modified region of at least 18 contiguous modified nucleosides.

Embodiment 155. The compound of any of embodiments 107-148, wherein the modified oligonucleotide comprises a modified region of at least 20 contiguous modified nucleosides.

Embodiment 156. The compound of any of embodiments 149-155, wherein each modified nucleoside of the modified region has a modified sugar moiety independently selected from among: 2-F, 2-OMe, 2'-MOE, cEt, LNA, morpholino, and modified morpholino.

Embodiment 157. The compound of any of embodiments 149-156, wherein the modified nucleosides of the modified region each comprise the same modification as one another.

Embodiment 158. The compound of embodiment 157, wherein the modified nucleosides of the modified region each comprise the same 2'-substituted sugar moiety.

Embodiment 159. The compound of embodiment 157, wherein the 2'-substituted sugar moiety of the modified nucleosides of the region of modified nucleosides is selected from 2'-F, 2'-OMe, and 2'-MOE.

Embodiment 160. The compound of embodiment 157, wherein the 2'-substituted sugar moiety of the modified nucleosides of the region of modified nucleosides is 2'-MOE.

Embodiment 161. The compound of embodiment 157, wherein the modified nucleosides of the region of modified nucleosides each comprise the same bicyclic sugar moiety.

Embodiment 162. The compound of embodiment 161, wherein the bicyclic sugar moiety of the modified nucleosides of the region of modified nucleosides is selected from LNA and cEt.

Embodiment 163. The compound of embodiment 157, wherein the modified nucleosides of the region of modified nucleosides each comprises a sugar surrogate.

Embodiment 164. The compound of embodiment 163, wherein the sugar surrogate of the modified nucleosides of the region of modified nucleosides is a morpholino.

Embodiment 165. The compound of embodiment 163, wherein the sugar surrogate of the modified nucleosides of the region of modified nucleosides is a modified morpholino.

Embodiment 166. The compound of any of embodiments 107-165, wherein the modified nucleotide comprises no more than 4 contiguous naturally occurring nucleosides.

Embodiment 167. The compound of any of embodiments 107-165, wherein each nucleoside of the modified oligonucleotide is a modified nucleoside.

Embodiment 168. The compound of embodiment 167, wherein each modified nucleoside comprises a modified sugar moiety.

Embodiment 169. The compound of embodiment 168, wherein the modified nucleosides of the modified oligonucleotide comprise the same modification as one another.

Embodiment 170. The compound of embodiment 169, wherein the modified nucleosides of the modified oligonucleotide each comprise the same 2'-substituted sugar moiety.

Embodiment 171. The compound of embodiment 170, wherein the 2'-substituted sugar moiety of the modified oligonucleotide is selected from 2'-F, 2'-OMe, and 2'-MOE.

Embodiment 172. The compound of embodiment 170, wherein the 2'-substituted sugar moiety of the modified oligonucleotide is 2'-MOE.

Embodiment 173. The compound of embodiment 171, wherein the modified nucleosides of the modified oligonucleotide each comprise the same bicyclic sugar moiety.

Embodiment 174. The compound of embodiment 173, wherein the bicyclic sugar moiety of the modified oligonucleotide is selected from LNA and cEt.

Embodiment 175. The compound of embodiment 169, wherein the modified nucleosides of the modified oligonucleotide each comprises a sugar surrogate.

Embodiment 176. The compound of embodiment 175, wherein the sugar surrogate of the modified oligonucleotide is a morpholino.

Embodiment 177. The compound of embodiment 175, wherein the sugar surrogate of the modified oligonucleotide is a modified morpholino.

Embodiment 178. The compound of any of embodiments 107-177, wherein the modified oligonucleotide comprises at least one modified internucleoside linkage.

Embodiment 179. The compound of embodiment 178, wherein each internucleoside linkage is a modified internucleoside linkage.

Embodiment 180. The compound of embodiment 178 or 179, comprising at least one phosphorothioate internucleoside linkage.

Embodiment 181. The compound of embodiment 179, wherein each internucleoside linkage is a modified internucleoside linkage and wherein each internucleoside linkage comprises the same modification.

Embodiment 182. The compound of embodiment 181, wherein each internucleoside linkage is a phosphorothioate internucleoside linkage.

Embodiment 183. The compound of any of embodiments 107-182, comprising at least one conjugate.

Embodiment 184. The compound of any of embodiments 107-183, consisting of the modified oligonucleotide.

Embodiment 185. The compound of any of embodiments 107-184, wherein the compound modulates splicing of the CFTR transcript.

Embodiment 186. A pharmaceutical composition comprising a compound according to any of embodiments 107-186 and a pharmaceutically acceptable carrier or diluent.

Embodiment 187. The pharmaceutical composition of embodiment 186, wherein the pharmaceutically acceptable carrier or diluent is sterile saline.

Embodiment 188. A method of modulating splicing of a CFTR transcript in a cell comprising contacting the cell with a compound according to any of embodiments 107-187.

Embodiment 189. The method of embodiment 188, wherein the cell is in vitro.

Embodiment 190. The method of embodiment 188, wherein the cell is in an animal.

Embodiment 191. The method of any of embodiments 188-190, wherein the amount of CFTR mRNA without exon 4 is increased.

Embodiment 192. The method of any of embodiments 188-190, wherein the amount of CFTR mRNA without exon 16 is increased.

Embodiment 193. The method of any of embodiments 188-190, wherein the amount of CFTR mRNA with exon 23 or exon 24 is increased.

Embodiment 194. The method of any of embodiments 188-193, wherein the CFTR transcript is transcribed from a CFTR gene.

Embodiment 195. A method of modulating the expression of CFTR in a cell, comprising contacting the cell with a compound according to any of embodiments 107-185.

Embodiment 196. The method of embodiment 195, wherein the cell is in vitro.

Embodiment 197. The method of embodiment 195, wherein the cell is in an animal.

Embodiment 198. A method comprising administering the compound of any of embodiments 107-185 to an animal.

Embodiment 199. The method of embodiment 198, wherein the administering step comprises delivering to the animal by inhalation, parenteral injection or infusion, oral, subcutaneous or intramuscular injection, buccal, transdermal, transmucosal and topical.

Embodiment 200. The method of embodiment 198, wherein the administration is inhalation.

Embodiment 201. The method of any of embodiments 198-200, wherein the animal has one or more symptoms associated with cystic fibrosis.

Embodiment 202. The method of any of embodiments 198-200, wherein the administration results in amelioration of at least one symptom of cystic fibrosis.

Embodiment 203. The method of any of embodiments 198-202, wherein the animal is a mouse.

Embodiment 204. The method of any of embodiments 198-202, wherein the animal is a human.

Embodiment 205. A method of preventing or slowing one or more symptoms associated with cystic fibrosis, comprising administering the compound according to any of embodiments 107-185 to an animal in need thereof.

Embodiment 206. The method of embodiment 205, wherein the animal is a human.

Embodiment 207. Use of the compound according to any of embodiments 107-185 for the preparation of a medicament for use in the treatment of cystic fibrosis.

Embodiment 208. Use of the compound according to any of embodiments 107-185 for the preparation of a medicament for use in the amelioration of one or more symptoms associated with cystic fibrosis.

These and other features and advantages of the present disclosure will be more fully understood from the following detailed description of the invention taken together with the accompanying claims. It is noted that the scope of the claims is defined by the recitations therein and not by the specific discussion of features and advantages set forth in the present description.

BRIEF DESCRIPTION OF THE DRAWINGS

A better understanding of the disclosure may be obtained in light of the following drawings which are set forth for illustrative purposes, and should not be construed as limiting the scope of the disclosure in any way.

FIG. 4 shows the genomic DNA of exon 2 in human CFTR and surrounding introns (the sequence of FIG. 4 is given the sequence identifier SEQ ID NO: 131).

FIG. 5 shows the genomic DNA of exon 4 in human CFTR and surrounding introns (the sequence of FIG. 5 is given the sequence identifier SEQ ID NO: 132).

FIG. 6 shows the genomic DNA of exon 5 in human CFTR and surrounding introns (the sequence of FIG. 6 is given the sequence identifier SEQ ID NO: 133).

FIG. 7 shows the genomic DNA of exon 7 in human CFTR and surrounding introns (the sequence of FIG. 7 is given the sequence identifier SEQ ID NO: 134).

FIG. 8 shows the genomic DNA of exon 9 in human CFTR and surrounding introns (the sequence of FIG. 8 is given the sequence identifier SEQ ID NO: 135).

FIG. 9 shows the genomic DNA of exon 10 in human CFTR and surrounding introns (the sequence of FIG. 9 is given the sequence identifier SEQ ID NO: 136).

FIG. 10 shows the genomic DNA of exon 11 in human CFTR and surrounding introns (the sequence of FIG. 10 is given the sequence identifier SEQ ID NO: 137).

FIG. 11 shows the genomic DNA of exon 13 in human CFTR and surrounding introns (the sequence of FIG. 11 is given the sequence identifier SEQ ID NO: 138).

FIG. 12 shows the genomic DNA of exon 15 in human CFTR and surrounding introns (the sequence of FIG. 12 is given the sequence identifier SEQ ID NO: 139).

FIG. 13 shows the genomic DNA of exon 16 in human CFTR and surrounding introns (the sequence of FIG. 13 is given the sequence identifier SEQ ID NO: 140).

FIG. 14 shows the genomic DNA of exon 20 in human CFTR and surrounding introns (the sequence of FIG. 14 is given the sequence identifier SEQ ID NO: 141).

FIG. 15 shows the genomic DNA of exon 22 in human CFTR and surrounding introns (the sequence of FIG. 15 is given the sequence identifier SEQ ID NO: 142).

FIG. 16 shows the genomic DNA of exon 23 in human CFTR and surrounding introns (the sequence of FIG. 16 is given the sequence identifier SEQ ID NO: 143).

FIG. 17 shows the genomic DNA of exon 24 in human CFTR and surrounding introns (the sequence of FIG. 17 is given the sequence identifier SEQ ID NO: 144).

Figure 1A:
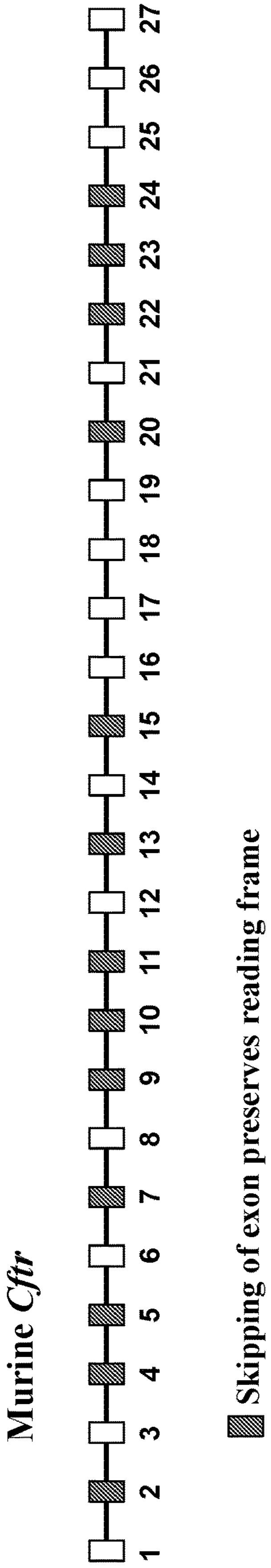
FIG. 1A shows a map of the murine/mouse CFTR gene. Boxes represent exons and lines represent introns. The exons that can be skipped or spliced out of the mature mRNA and still maintain the open reading frame of the mRNA are shaded. The CFTR mRNAs lacking any one of these exons will code for a full-length CFTR protein with an internal deletion of the specific targeted exon sequence.

Skilled artisans will appreciate that elements in the figures are illustrated for simplicity and clarity and have not necessarily been drawn to scale. For example, the dimensions of some of the elements in the figures can be exaggerated relative to other elements to help improve understanding of the embodiment(s) of the present disclosure.

DETAILED DESCRIPTION OF THE DISCLOSURE

The present disclosure relates to general compounds and methods to treat cystic fibrosis in subjects using antisense oligonucleotides (ASOs) that induce specific pre-mRNA splicing events in CFTR gene transcripts that result in mRNAs that code for proteins that fully or partially restore the function of CFTR (i.e., resulting in increased levels of correctly localized CFTR protein at the plasma membrane and with increased function). For example, some ASOs can base-pair with the target RNA and correct aberrant splicing caused by mutations, and other ASOs can induce skipping of exons with mutations that cause open reading frame-shifts. In such instances, skipping of the mutated exon using ASOs can restore the reading frame and generate an mRNA that codes for a CFTR isoform with partial function.

The CFTR gene encodes a member of the ATP-binding cassette (ABC) transporter superfamily. ABC proteins transport various molecules across extra- and intra-cellular membranes. ABC genes are divided into seven distinct subfamilies (ABC1, MDR/TAP, MRP, ALD, OABP, GCN20, White). The CFTR protein is a member of the MRP subfamily that is involved in multi-drug resistance. The encoded protein functions as a chloride channel and controls the regulation of other transport pathways. Mutations in the CFTR gene are associated with the autosomal recessive disorders cystic fibrosis and congenital bilateral aplasia of the vas deferens. Alternatively spliced transcript variants have been described, many of which result from mutations in this gene.

Human (*Homo sapiens*) cystic fibrosis transmembrane conductance regulator is located on chromosome 7: 117,465,784-117,715,971 (forward strand: SEQ ID NO: 130). The gene is 6132 bp mRNA (Gene ID: 1080; Official Symbol: CFTR; Official Full Name: cystic fibrosis transmembrane conductance regulator) and is assigned NCBI Reference Sequence: NM_000492.3 (SEQ ID NO: 145); ACCESSION: NM_000492; Ensembl: ENSG00000001626; HPRD: 03883; MIM: 602421; and Vega: OTTHUMG00000023076. CFTR is also known as: CF; MRP7; ABC35; ABCC7; CFTR/MRP; TNR-CFTR; dJ760C5.1. Human CFTR protein is assigned NCBI Reference Sequence: NP 000483.3 (1480 aa; SEQ ID NO: 146).

The mouse (*Mus musculus*) cystic fibrosis transmembrane conductance regulator is located on chromosome 6: 18170687-18322768 (SEQ ID NO: 147). The mouse CFTR gene is 6305 bp (Gene ID: 12638; Official Symbol: Cftr; Official Full Name: cystic fibrosis transmembrane conductance regulator), and is also known as: Abcc7; AW495489; ATP-binding cassette sub-family C member 7; ATP-binding cassette transporter sub-family C member 7; ATP-binding cassette, subfamily c, member 7; cAMP-dependent chloride channel; channel conductance-controlling ATPase; cystic fibrosis transmembrane conductance regulator homolog cystic fibrosis transmembrane conductance regulator homolog; ATP-binding cassette, subfamily c, member 7. The mouse CFTR gene has been assigned NCBI Reference Sequence: NM_021050.2 (SEQ ID NO: 148), and Ensembl: ENSMUSG00000041301. The mouse CFTR protein is assigned NCBI Reference Sequence: NP_066388.1 (1476 aa; SEQ ID NO: 149).

Antisense compounds, (e.g. antisense oligonucleotides (ASOs)) have been used to modulate target nucleic acids. Antisense compounds comprising a variety of chemical modifications and motifs have been reported. In certain instances, such compounds are useful as research tools, diagnostic reagents, and as therapeutic agents. In certain instances, antisense compounds have been shown to modulate protein expression by binding to a target messenger RNA (mRNA) encoding the protein. In certain instances, such binding of an antisense compound to its target mRNA results in cleavage of the mRNA. Antisense compounds that modulate processing of a pre-mRNA have also been reported. Such antisense compounds alter splicing, interfere with polyadenlyation or prevent formation of the 5'-cap of a pre-mRNA.

Pre-mRNA splicing involves the precise and accurate removal of introns from the pre-messenger RNA and the ligation of exons together after intron removal to generate the mature mRNA which serves as the template for protein translation. Pre-mRNA splicing is a two-step reaction carried out by a spliceosome complex comprising protein and small RNA components which recognize conserved sequence elements within the introns and exons of the RNA. Recognition of these sequence elements, including the 5' splice site, 3' splice site and branch point sequence, is the primary mechanism directing the correct removal of introns.

Splicing requires direct base-pairing between small nuclear RNA (snRNA) components of the spliceosome and the splice site nucleotides of the mRNA. This interaction can be easily disrupted by gene mutations or by artificial blocking using short oligonucleotides complementary to the RNA. Such so called antisense oligonucleotides (ASOs), when designed to be complementary to a splice sites, will compete for base-pairing with the snRNAs, thereby blocking an essential step in splicing at the site. In this way, antisense oligonucleotides can potently block unwanted splicing or redirect splicing to alternative splice sites, and can result in mRNAs that code for proteins that fully or partially restore the function to target transcripts.

For example, ASOs can target the 2789+5G>A mutation in intron 16 of the CFTR gene that causes cystic fibrosis. This mutation has been observed in 521 patients with cystic fibrosis. Because aberrant splicing of exon 16 due to the mutation is the cause of cystic fibrosis in patients with this mutation, improving splicing using antisense oligonucleotides to interfere with the deleterious effects of the mutation, can have a therapeutic benefit to the patients. In a non-limiting example, an antisense oligonucleotide that targets the 2789+5G>A mutation of the CFTR gene that causes cystic fibrosis can be SEQ ID NO: 97.

In another non-limiting example, antisense oligonucleotides can target the 3849+10 kbC→T mutation in intron 19 of the CFTR gene. This mutation has been observed in 496 patients, and in 1,100 patients in CFTR2 database. The 3849+10 kbC>T mutation creates a cryptic splice site that results in an aberrant mRNA that does not produce CFTR protein and antisense oligonucleotides targeted to the region of intron 19 surrounding and encompassing this mutation can potentially block splicing to this cryptic splice site. In a non-limiting example, an antisense oligonucleotide that targets the 3849+10 kbC>T mutation of the CFTR gene that causes cystic fibrosis can be SEQ ID NO:150.

In yet another non-limiting example, antisense oligonucleotides can target the 3272-26A→G mutation of the CFTR gene that causes cystic fibrosis. This mutation is found in 186 patients. The 3272-26A>G mutation creates a cryptic splice site that results in an aberrant mRNA that does not produce CFTR protein. Antisense oligonucleotides targeted to the region of surrounding and encompassing this mutation can potentially block splicing to this cryptic splice site. In a non-limiting example, an antisense oligonucleotide that targets the 3272-26A→G mutation of the CFTR gene that causes cystic fibrosis can be SEQ ID NO: 114.

In another non-limiting example, antisense oligonucleotides can target exon skipping in exons that have nonsense mutations. For example, skipping of exon 4, exon 23 or exon 24 all can result in an mRNA transcript that is in-frame so that translation will continue to the natural stop-codon (i.e., mutations such as CFTR 621+IG>T and CFTR 406G>T). Exons 4, 23, and 24 have a number of different patient nonsense mutations that cause cystic fibrosis and any of these can be treated by ASOs that induce exon skipping of the exons that house nonsense mutations to correct the reading frame and allow translation through to the natural termination codon.

In yet other non-limiting examples, 70-90% of all Cystic fibrosis (CF) patients have a mutation in exon 11 (deltaF508) which can be targeted by ASO 11-6 (SEQ ID NO.: 91). Five percent of CF patients have a splice site mutation in intron 16 which can be targeted and corrected by ASO 16-8 (SEQ ID NO.: 102); 2.5% of CF patients have a nonsense mutation in exon 23 which can be targeted for skipping and frame-shift correction using ASO 23-4 (SEQ ID NO.: 126); 2.5% of CF patients have a nonsense mutation in exon 24 which can be targeted for skipping and frame-shift correction using ASO 24-1, 24-2, 24-3 (SEQ ID NO.: 127, 128, 129; respectively); CF mutation databases indicate that nonsense and splicing mutations in and around exon 4 are common and can be targeted for gene expression correction either by splicing redirection or frame-shift correction using ASO 4-1 (SEQ ID NO.: 65); and CF causing nonsense mutations in exons 2, 5, 7, 9, 10, 13, 20 and 22 are also commonly annotated in the Human Gene Mutation Database and can be targeted by ASOs 2-4, 5-1, 7-4, 9-1, 11-6, 13-1, 15-1, 20-2, 22-1 (SEQ ID NO.: 64, 71, 76, 78, 91, 92, 94, 111, 116; respectively).

As used herein, "nucleoside" means a compound comprising a nucleobase moiety and a sugar moiety. Nucleosides include, but are not limited to, naturally occurring nucleosides (as found in DNA and RNA) and modified nucleosides. Nucleosides may be linked to a phosphate moiety.

As used herein, "antisense compound" or "antisense oligonucleotide (ASO)" means a compound comprising or consisting of an oligonucleotide at least a portion of which is complementary to a target nucleic acid to which it is capable of hybridizing, resulting in at least one antisense activity.

As used herein, "antisense activity" means any detectable and/or measurable change attributable to the hybridization of an antisense compound to its target nucleic acid. As used herein, "detecting" or "measuring" means that a test or assay for detecting or measuring is performed. Such detection and/or measuring may result in a value of zero. Thus, if a test for detection or measuring results in a finding of no activity (activity of zero), the step of detecting or measuring the activity has nevertheless been performed.

As used herein, "chemical modification" means a chemical difference in a compound when compared to a naturally occurring counterpart. In reference to an oligonucleotide, chemical modification does not include differences only in nucleobase sequence. Chemical modifications of oligonucleotides include nucleoside modifications (including sugar moiety modifications and nucleobase modifications) and internucleoside linkage modifications.

As used herein, "sugar moiety" means a naturally occurring sugar moiety or a modified sugar moiety of a nucleoside.

As used herein, "modified sugar moiety" means a substituted sugar moiety, a bicyclic or tricyclic sugar moiety, or a sugar surrogate.

As used herein, "substituted sugar moiety" means a furanosyl comprising at least one substituent group that differs from that of a naturally occurring sugar moiety. Substituted sugar moieties include, but are not limited to, furanosyls comprising substituents at the 2'-position, the 3'-position, the 5'-position and/or the 4'-position.

As used herein, "2'-substituted sugar moiety" means a furanosyl comprising a substituent at the 2'-position other than —H or —OH. Unless otherwise indicated, a 2'-substituted sugar moiety is not a bicyclic sugar moiety (i.e., the 2'-substituent of a 2'-substituted sugar moiety does not form a bridge to another atom of the furanosyl ring).

As used herein, "MOE" means $-OCH_2CH_2OCH_3$.

As used herein, "bicyclic sugar moiety" means a modified sugar moiety comprising a 4 to 7 membered ring (including but not limited to a furanosyl) comprising a bridge connecting two atoms of the 4 to 7 membered ring to form a second ring, resulting in a bicyclic structure. In certain embodiments, the 4 to 7 membered ring is a sugar ring. In certain embodiments, the 4 to 7 membered ring is a furanosyl. In certain such embodiments, the bridge connects the 2-carbon and the 4'-carbon of the furanosyl.

As used herein, the term "sugar surrogate" means a structure that does not comprise a furanosyl and that is capable of replacing the naturally occurring sugar moiety of a nucleoside, such that the resulting nucleoside is capable of: (1) incorporation into an oligonucleotide and (2) hybridization to a complementary nucleoside. Such structures include rings comprising a different number of atoms than furanosyl (e.g., 4, 6, or 7-membered rings); replacement of the oxygen of a furanosyl with a non-oxygen atom (e.g., carbon, sulfur, or nitrogen); or both a change in the number of atoms and a replacement of the oxygen. Such structures may also comprise substitutions corresponding to those described for substituted sugar moieties (e.g., 6-membered carbocyclic bicyclic sugar surrogates optionally comprising additional substituents). Sugar surrogates also include more complex sugar replacements (e.g., the non-ring systems of peptide nucleic acid). Sugar surrogates include without limitation morpholino, modified morpholinos, cyclohexenyls and cyclohexitols.

As used herein, "nucleotide" means a nucleoside further comprising a phosphate linking group.

As used herein, "linked nucleosides" may or may not be linked by phosphate linkages and thus includes, but is not limited to "linked nucleotides." As used herein, "linked nucleosides" are nucleosides that are connected in a continuous sequence (i.e. no additional nucleosides are present between those that are linked).

As used herein, "nucleobase" means a group of atoms that can be linked to a sugar moiety to create a nucleoside that is capable of incorporation into an oligonucleotide, and wherein the group of atoms is capable of bonding with a complementary naturally occurring nucleobase of another oligonucleotide or nucleic acid. Nucleobases may be naturally occurring or may be modified.

As used herein, "heterocyclic base" or "heterocyclic nucleobase" means a nucleobase comprising a heterocyclic structure.

As used herein, the terms, "unmodified nucleobase" or "naturally occurring nucleobase" means the naturally occurring heterocyclic nucleobases of RNA or DNA: the purine bases adenine (A) and guanine (G), and the pyrimidine bases thymine (T), cytosine (C) (including 5-methyl C), and uracil (U).

As used herein, "modified nucleobase" means any nucleobase that is not a naturally occurring nucleobase.

As used herein, "modified nucleoside" means a nucleoside comprising at least one chemical modification compared to naturally occurring RNA or DNA nucleosides. Modified nucleosides comprise a modified sugar moiety and/or a modified nucleobase.

As used herein, "bicyclic nucleoside" or "BNA" means a nucleoside comprising a bicyclic sugar moiety.

As used herein, "constrained ethyl nucleoside" or "cEt" means a nucleoside comprising a bicyclic sugar moiety comprising a 4'-$CH(CH_3)$-0-2'bridge.

As used herein, "locked nucleic acid nucleoside" or "LNA" means a nucleoside comprising a bicyclic sugar moiety comprising a 4'-$CH_2$-0-2'bridge.

As used herein, "2'-substituted nucleoside" means a nucleoside comprising a substituent at the 2'-position other than H or OH. Unless otherwise indicated, a 2'-substituted nucleoside is not a bicyclic nucleoside.

As used herein, "2'-deoxynucleoside" means a nucleoside comprising 2'-H furanosyl sugar moiety, as found in naturally occurring deoxyribonucleosides (DNA). In certain embodiments, a 2'-deoxynucleoside may comprise a modified nucleobase or may comprise an RNA nucleobase (e.g., uracil).

As used herein, "oligonucleotide" means a compound comprising a plurality of linked nucleosides. In certain embodiments, an oligonucleotide comprises one or more unmodified ribonucleosides (RNA) and/or unmodified deoxyribonucleosides (DNA) and/or one or more modified nucleosides.

As used herein "oligonucleoside" means an oligonucleotide in which none of the internucleoside linkages contains a phosphorus atom. As used herein, oligonucleotides include oligonucleosides.

As used herein, "modified oligonucleotide" means an oligonucleotide comprising at least one modified nucleoside and/or at least one modified internucleoside linkage.

As used herein "internucleoside linkage" means a covalent linkage between adjacent nucleosides in an oligonucleotide.

As used herein "naturally occurring internucleoside linkage" means a 3' to 5' phosphodiester linkage.

As used herein, "modified internucleoside linkage" means any internucleoside linkage other than a naturally occurring internucleoside linkage.

As used herein, "oligomeric compound" means a polymeric structure comprising two or more substructures. In certain embodiments, an oligomeric compound comprises an oligonucleotide. In certain embodiments, an oligomeric compound comprises one or more conjugate groups and/or terminal groups. In certain embodiments, an oligomeric compound consists of an oligonucleotide.

As used herein, "terminal group" means one or more atom attached to either, or both, the 3' end or the 5' end of an oligonucleotide. In certain embodiments a terminal group is a conjugate group. In certain embodiments, a terminal group comprises one or more terminal group nucleosides.

As used herein, "conjugate" means an atom or group of atoms bound to an oligonucleotide or oligomeric compound. In general, conjugate groups modify one or more properties of the compound to which they are attached, including, but not limited to, pharmacodynamic, pharmacokinetic, binding, absorption, cellular distribution, cellular uptake, charge and/or clearance properties.

As used herein, "conjugate linking group" means any atom or group of atoms used to attach a conjugate to an oligonucleotide or oligomeric compound.

As used herein, "detectable and/or measureable activity" means a statistically significant activity that is not zero.

As used herein, "essentially unchanged" means little or no change in a particular parameter, particularly relative to another parameter which changes much more. In certain embodiments, a parameter is essentially unchanged when it changes less than 5%. In certain embodiments, a parameter is essentially unchanged if it changes less than two-fold while another parameter changes at least ten-fold. For example, in certain embodiments, an antisense activity is a change in the amount of a target nucleic acid. In certain such embodiments, the amount of a non-target nucleic acid is essentially unchanged if it changes much less than the target nucleic acid does, but the change need not be zero.

As used herein, "expression" means the process by which a gene ultimately results in a protein. Expression includes, but is not limited to, transcription, post-transcriptional modification (e.g., splicing, polyadenlyation, addition of 5'-cap), and translation.

As used herein, "target nucleic acid" means a nucleic acid molecule to which an antisense compound hybridizes.

As used herein, "mRNA" means an RNA molecule that encodes a protein.

As used herein, "pre-mRNA" means an RNA transcript that has not been fully processed into mRNA. Pre-RNA includes one or more intron.

As used herein, "transcript" means an RNA molecule transcribed from DNA. Transcripts include, but are not limited to mRNA, pre-mRNA, and partially processed RNA.

As used herein, "targeting" or "targeted to" means the association of an antisense compound to a particular target nucleic acid molecule or a particular region of a target nucleic acid molecule. An antisense compound targets a target nucleic acid if it is sufficiently complementary to the target nucleic acid to allow hybridization under physiological conditions.

As used herein, “nucleobase complementarity” or “complementarity” when in reference to nucleobases means a nucleobase that is capable of base pairing with another nucleobase. For example, in DNA, adenine (A) is complementary to thymine (T). For example, in RNA, adenine (A) is complementary to uracil (U). In certain embodiments, complementary nucleobase means a nucleobase of an antisense compound that is capable of base pairing with a nucleobase of its target nucleic acid. For example, if a nucleobase at a certain position of an antisense compound is capable of hydrogen bonding with a nucleobase at a certain position of a target nucleic acid, then the position of hydrogen bonding between the oligonucleotide and the target nucleic acid is considered to be complementary at that nucleobase pair. Nucleobases comprising certain modifications may maintain the ability to pair with a counterpart nucleobase and thus, are still capable of nucleobase complementarity.

As used herein, “non-complementary” in reference to nucleobases means a pair of nucleobases that do not form hydrogen bonds with one another.

As used herein, “complementary” in reference to oligomeric compounds (e.g., linked nucleosides, oligonucleotides, or nucleic acids) means the capacity of such oligomeric compounds or regions thereof to hybridize to another oligomeric compound or region thereof through nucleobase complementarity under stringent conditions. Complementary oligomeric compounds need not have nucleobase complementarity at each nucleoside. Rather, some mismatches are tolerated. In certain embodiments, complementary oligomeric compounds or regions are complementary at 70% of the nucleobases (70% complementary). In certain embodiments, complementary oligomeric compounds or regions are 80% complementary. In certain embodiments, complementary oligomeric compounds or regions are 90% complementary. In certain embodiments, complementary oligomeric compounds or regions are 95% complementary. In certain embodiments, complementary oligomeric compounds or regions are 100% complementary.

As used herein, “hybridization” means the pairing of complementary oligomeric compounds (e.g., an antisense compound and its target nucleic acid). While not limited to a particular mechanism, the most common mechanism of pairing involves hydrogen bonding, which may be Watson-Crick, Hoogsteen or reversed Hoogsteen hydrogen bonding, between complementary nucleobases.

As used herein, “specifically hybridizes” means the ability of an oligomeric compound to hybridize to one nucleic acid site with greater affinity than it hybridizes to another nucleic acid site. In certain embodiments, an antisense oligonucleotide specifically hybridizes to more than one target site.

As used herein, “percent complementarity” means the percentage of nucleobases of an oligomeric compound that are complementary to an equal-length portion of a target nucleic acid. Percent complementarity is calculated by dividing the number of nucleobases of the oligomeric compound that are complementary to nucleobases at corresponding positions in the target nucleic acid by the total length of the oligomeric compound.

As used herein, “percent identity” means the number of nucleobases in a first nucleic acid that are the same type (independent of chemical modification) as nucleobases at corresponding positions in a second nucleic acid, divided by the total number of nucleobases in the first nucleic acid.

As used herein, “modulation” means a change of amount or quality of a molecule, function, or activity when compared to the amount or quality of a molecule, function, or activity prior to modulation. For example, modulation includes the change, either an increase (stimulation or induction) or a decrease (inhibition or reduction) in gene expression. As a further example, modulation of expression can include a change in splice site selection of pre-mRNA processing, resulting in a change in the absolute or relative amount of a particular splice-variant compared to the amount in the absence of modulation.

As used herein, “motif” means a pattern of chemical modifications in an oligomeric compound or a region thereof. Motifs may be defined by modifications at certain nucleosides and/or at certain linking groups of an oligomeric compound.

As used herein, “nucleoside motif” means a pattern of nucleoside modifications in an oligomeric compound or a region thereof. The linkages of such an oligomeric compound may be modified or unmodified. Unless otherwise indicated, motifs herein describing only nucleosides are intended to be nucleoside motifs. Thus, in such instances, the linkages are not limited.

As used herein, “sugar motif” means a pattern of sugar modifications in an oligomeric compound or a region thereof.

As used herein, “linkage motif” means a pattern of linkage modifications in an oligomeric compound or region thereof. The nucleosides of such an oligomeric compound may be modified or unmodified. Unless otherwise indicated, motifs herein describing only linkages are intended to be linkage motifs. Thus, in such instances, the nucleosides are not limited.

As used herein, “nucleobase modification motif” means a pattern of modifications to nucleobases along an oligonucleotide. Unless otherwise indicated, a nucleobase modification motif is independent of the nucleobase sequence.

As used herein, “sequence motif” means a pattern of nucleobases arranged along an oligonucleotide or portion thereof. Unless otherwise indicated, a sequence motif is independent of chemical modifications and thus may have any combination of chemical modifications, including no chemical modifications.

As used herein, “type of modification” in reference to a nucleoside or a nucleoside of a “type” means the chemical modification of a nucleoside and includes modified and unmodified nucleosides. Accordingly, unless otherwise indicated, a “nucleoside having a modification of a first type” may be an unmodified nucleoside.

As used herein, “differently modified” mean chemical modifications or chemical substituents that are different from one another, including absence of modifications. Thus, for example, a MOE nucleoside and an unmodified DNA nucleoside are “differently modified,” even though the DNA nucleoside is unmodified. Likewise, DNA and RNA are “differently modified,” even though both are naturally-occurring unmodified nucleosides. Nucleosides that are the same but for comprising different nucleobases are not differently modified. For example, a nucleoside comprising a 2'-OMe modified sugar and an unmodified adenine nucleobase and a nucleoside comprising a 2'-OMe modified sugar and an unmodified thymine nucleobase are not differently modified.

As used herein, “the same type of modifications” refers to modifications that are the same as one another, including absence of modifications. Thus, for example, two unmodified DNA nucleoside have “the same type of modification,”

even though the DNA nucleoside is unmodified. Such nucleosides having the same type modification may comprise different nucleobases.

As used herein, "pharmaceutically acceptable carrier or diluent" means any substance suitable for use in administering to an animal. In certain embodiments, a pharmaceutically acceptable carrier or diluent is sterile saline. In certain embodiments, such sterile saline is pharmaceutical grade saline.

Certain Motifs

In certain embodiments, the present invention provides oligomeric compounds comprising oligonucleotides. In certain embodiments, such oligonucleotides comprise one or more chemical modification. In certain embodiments, chemically modified oligonucleotides comprise one or more modified nucleosides. In certain embodiments, chemically modified oligonucleotides comprise one or more modified nucleosides comprising modified sugars. In certain embodiments, chemically modified oligonucleotides comprise one or more modified nucleosides comprising one or more modified nucleobases. In certain embodiments, chemically modified oligonucleotides comprise one or more modified internucleoside linkages. In certain embodiments, the chemically modifications (sugar modifications, nucleobase modifications, and/or linkage modifications) define a pattern or motif. In certain embodiments, the patterns of chemical modifications of sugar moieties, internucleoside linkages, and nucleobases are each independent of one another. Thus, an oligonucleotide may be described by its sugar modification motif, internucleoside linkage motif and/or nucleobase modification motif (as used herein, nucleobase modification motif describes the chemical modifications to the nucleobases independent of the sequence of nucleobases).

Certain Sugar Motifs

In certain embodiments, oligonucleotides comprise one or more type of modified sugar moieties and/or naturally occurring sugar moieties arranged along an oligonucleotide or region thereof in a defined pattern or sugar modification motif. Such motifs may include any of the sugar modifications discussed herein and/or other known sugar modifications.

In certain embodiments, the oligonucleotides comprise or consist of a region having a gapmer sugar modification motif, which comprises two external regions or "wings" and an internal region or "gap." The three regions of a gapmer motif (the 5'-wing, the gap, and the 3'-wing) form a contiguous sequence of nucleosides wherein at least some of the sugar moieties of the nucleosides of each of the wings differ from at least some of the sugar moieties of the nucleosides of the gap. Specifically, at least the sugar moieties of the nucleosides of each wing that are closest to the gap (the 3'-most nucleoside of the 5'-wing and the 5'-most nucleoside of the 3'-wing) differ from the sugar moiety of the neighboring gap nucleosides, thus defining the boundary between the wings and the gap. In certain embodiments, the sugar moieties within the gap are the same as one another. In certain embodiments, the gap includes one or more nucleoside having a sugar moiety that differs from the sugar moiety of one or more other nucleosides of the gap. In certain embodiments, the sugar modification motifs of the two wings are the same as one another (symmetric gapmer). In certain embodiments, the sugar modification motifs of the 5'-wing differs from the sugar modification motif of the 3'-wing (asymmetric gapmer). In certain embodiments, oligonucleotides comprise 2'-MOE modified nucleosides in the wings and 2'-F modified nucleosides in the gap.

In certain embodiments, oligonucleotides are fully modified. In certain such embodiments, oligonucleotides are uniformly modified. In certain embodiments, oligonucleotides are uniform 2'-MOE. In certain embodiments, oligonucleotides are uniform 2'-F. In certain embodiments, oligonucleotides are uniform morpholino. In certain embodiments, oligonucleotides are uniform BNA. In certain embodiments, oligonucleotides are uniform LNA. In certain embodiments, oligonucleotides are uniform cEt.

In certain embodiments, oligonucleotides comprise a uniformly modified region and additional nucleosides that are unmodified or differently modified. In certain embodiments, the uniformly modified region is at least 5, 10, 15, 20 or 25 nucleosides in length. In certain embodiments, the uniform region is a 2'-MOE region. In certain embodiments, the uniform region is a 2'-F region. In certain embodiments, the uniform region is a morpholino region. In certain embodiments, the uniform region is a BNA region. In certain embodiments, the uniform region is a LNA region. In certain embodiments, the uniform region is a cEt region.

In certain embodiments, the oligonucleotide does not comprise more than 4 contiguous unmodified 2'-deoxynucleosides. In certain circumstances, antisense oligonucleotides comprising more than 4 contiguous 2'-deoxynucleosides activate RNase H, resulting in cleavage of the target RNA. In certain embodiments, such cleavage is avoided by not having more than 4 contiguous 2'-deoxynucleosides, for example, where alteration of splicing and not cleavage of a target RNA is desired.

Certain Internucleoside Linkage Motifs

In certain embodiments, oligonucleotides comprise modified internucleoside linkages arranged along the oligonucleotide or region thereof in a defined pattern or modified internucleoside linkage motif. In certain embodiments, internucleoside linkages are arranged in a gapped motif, as described above for sugar modification motif. In such embodiments, the internucleoside linkages in each of two wing regions are different from the internucleoside linkages in the gap region. In certain embodiments the internucleoside linkages in the wings are phosphodiester and the internucleoside linkages in the gap are phosphorothioate. The sugar modification motif is independently selected, so such oligonucleotides having a gapped internucleoside linkage motif may or may not have a gapped sugar modification motif and if it does have a gapped sugar motif, the wing and gap lengths may or may not be the same.

In certain embodiments, oligonucleotides comprise a region having an alternating internucleoside linkage motif. In certain embodiments, oligonucleotides of the present invention comprise a region of uniformly modified internucleoside linkages. In certain such embodiments, the oligonucleotide comprises a region that is uniformly linked by phosphorothioate internucleoside linkages. In certain embodiments, the oligonucleotide is uniformly linked by phosphorothioate. In certain embodiments, each internucleoside linkage of the oligonucleotide is selected from phosphodiester and phosphorothioate. In certain embodiments, each internucleoside linkage of the oligonucleotide is selected from phosphodiester and phosphorothioate and at least one internucleoside linkage is phosphorothioate.

In certain embodiments, the oligonucleotide comprises at least 6 phosphorothioate internucleoside linkages. In certain embodiments, the oligonucleotide comprises at least 8 phosphorothioate internucleoside linkages. In certain embodiments, the oligonucleotide comprises at least 10 phosphorothioate internucleoside linkages. In certain embodiments, the oligonucleotide comprises at least one block of at least 6 consecutive phosphorothioate internucleoside linkages. In certain embodiments, the oligonucleotide comprises at least one block of at least 8 consecutive phosphorothioate internucleoside linkages. In certain embodiments, the oligonucleotide comprises at least one block of at least 10 consecutive phosphorothioate internucleoside linkages. In certain embodiments, the oligonucleotide comprises at least block of at least one 12 consecutive phosphorothioate internucleoside linkages. In certain such embodiments, at least one such block is located at the 3' end of the oligonucleotide. In certain such embodiments, at least one such block is located within 3 nucleosides of the 3' end of the oligonucleotide.

Certain Nucleobase Modification Motifs

In certain embodiments, oligonucleotides comprise chemical modifications to nucleobases arranged along the oligonucleotide or region thereof in a defined pattern or nucleobases modification motif. In certain such embodiments, nucleobase modifications are arranged in a gapped motif. In certain embodiments, nucleobase modifications are arranged in an alternating motif. In certain embodiments, each nucleobase is modified. In certain embodiments, none of the nucleobases is chemically modified.

In certain embodiments, oligonucleotides comprise a block of modified nucleobases. In certain such embodiments, the block is at the 3'-end of the oligonucleotide. In certain embodiments the block is within 3 nucleotides of the 3'-end of the oligonucleotide. In certain such embodiments, the block is at the 5'-end of the oligonucleotide. In certain embodiments the block is within 3 nucleotides of the 5'-end of the oligonucleotide.

In certain embodiments, nucleobase modifications are a function of the natural base at a particular position of an oligonucleotide. For example, in certain embodiments each purine or each pyrimidine in an oligonucleotide is modified. In certain embodiments, each adenine is modified. In certain embodiments, each guanine is modified. In certain embodiments, each thymine is modified. In certain embodiments, each cytosine is modified. In certain embodiments, each uracil is modified.

In certain embodiments, some, all, or none of the cytosine moieties in an oligonucleotide are 5-methyl cytosine moieties. Herein, 5-methyl cytosine is not a “modified nucleobase.” Accordingly, unless otherwise indicated, unmodified nucleobases include both cytosine residues having a 5-methyl and those lacking a 5 methyl. In certain embodiments, the methylation state of all or some cytosine nucleobases is specified.

Certain Overall Lengths

In certain embodiments, the present invention provides oligomeric compounds including oligonucleotides of any of a variety of ranges of lengths. In certain embodiments, the invention provides oligomeric compounds or oligonucleotides consisting of X to Y linked nucleosides, where X represents the fewest number of nucleosides in the range and Y represents the largest number of nucleosides in the range. In certain such embodiments, X and Y are each independently selected from 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50; provided that X<Y. For example, in certain embodiments, the invention provides oligomeric compounds which comprise oligonucleotides consisting of 8 to 9, 8 to 10, 8 to 11, 8 to 12, 8 to 13, 8 to 14, 8 to 15, 8 to 16, 8 to 17, 8 to 18, 8 to 19, 8 to 20, 8 to 21, 8 to 22, 8 to 23, 8 to 24, 8 to 25, 8 to 26, 8 to 27, 8 to 28, 8 to 29, 8 to 30, 9 to 10, 9 to 11, 9 to 12, 9 to 13, 9 to 14, 9 to 15, 9 to 16, 9 to 17, 9 to 18, 9 to 19, 9 to 20, 9 to 21, 9 to 22, 9 to 23, 9 to 24, 9 to 25, 9 to 26, 9 to 27, 9 to 28, 9 to 29, 9 to 30, 10 to 11, 10 to 12, 10 to 13, 10 to 14, 10 to 15, 10 to 16, 10 to 17, 10 to 18, 10 to 19, 10 to 20, 10 to 21, 10 to 22, 10 to 23, 10 to 24, 10 to 25, 10 to 26, 10 to 27, 10 to 28, 10 to 29, 10 to 30, 11 to 12, 11 to 13, 11 to 14, 11 to 15, 11 to 16, 11 to 17, 11 to 18, 11 to 19, 11 to 20, 11 to 21, 11 to 22, 11 to 23, 11 to 24, 11 to 25, 11 to 26, 11 to 27, 11 to 28, 11 to 29, 11 to 30, 12 to 13, 12 to 14, 12 to 15, 12 to 16, 12 to 17, 12 to 18, 12 to 19, 12 to 20, 12 to 21, 12 to 22, 12 to 23, 12 to 24, 12 to 25, 12 to 26, 12 to 27, 12 to 28, 12 to 29, 12 to 30, 13 to 14, 13 to 15, 13 to 16, 13 to 17, 13 to 18, 13 to 19, 13 to 20, 13 to 21, 13 to 22, 13 to 23, 13 to 24, 13 to 25, 13 to 26, 13 to 27, 13 to 28, 13 to 29, 13 to 30, 14 to 15, 14 to 16, 14 to 17, 14 to 18, 14 to 19, 14 to 20, 14 to 21, 14 to 22, 14 to 23, 14 to 24, 14 to 25, 14 to 26, 14 to 27, 14 to 28, 14 to 29, 14 to 30, 15 to 16, 15 to 17, 15 to 18, 15 to 19, 15 to 20, 15 to 21, 15 to 22, 15 to 23, 15 to 24, 15 to 25, 15 to 26, 15 to 27, 15 to 28, 15 to 29, 15 to 30, 16 to 17, 16 to 18, 16 to 19, 16 to 20, 16 to 21, 16 to 22, 16 to 23, 16 to 24, 16 to 25, 16 to 26, 16 to 27, 16 to 28, 16 to 29, 16 to 30, 17 to 18, 17 to 19, 17 to 20, 17 to 21, 17 to 22, 17 to 23, 17 to 24, 17 to 25, 17 to 26, 17 to 27, 17 to 28, 17 to 29, 17 to 30, 18 to 19, 18 to 20, 18 to 21, 18 to 22, 18 to 23, 18 to 24, 18 to 25, 18 to 26, 18 to 27, 18 to 28, 18 to 29, 18 to 30, 19 to 20, 19 to 21, 19 to 22, 19 to 23, 19 to 24, 19 to 25, 19 to 26, 19 to 29, 19 to 28, 19 to 29, 19 to 30, 20 to 21, 20 to 22, 20 to 23, 20 to 24, 20 to 25, 20 to 26, 20 to 27, 20 to 28, 20 to 29, 20 to 30, 21 to 22, 21 to 23, 21 to 24, 21 to 25, 21 to 26, 21 to 27, 21 to 28, 21 to 29, 21 to 30, 22 to 23, 22 to 24, 22 to 25, 22 to 26, 22 to 27, 22 to 28, 22 to 29, 22 to 30, 23 to 24, 23 to 25, 23 to 26, 23 to 27, 23 to 28, 23 to 29, 23 to 30, 24 to 25, 24 to 26, 24 to 27, 24 to 28, 24 to 29, 24 to 30, 25 to 26, 25 to 27, 25 to 28, 25 to 29, 25 to 30, 26 to 27, 26 to 28, 26 to 29, 26 to 30, 27 to 28, 27 to 29, 27 to 30, 28 to 29, 28 to 30, or 29 to 30 linked nucleosides. In embodiments where the number of nucleosides of an oligomeric compound or oligonucleotide is limited, whether to a range or to a specific number, the oligomeric compound or oligonucleotide may, nonetheless further comprise additional other substituents. For example, an oligonucleotide comprising 8-30 nucleosides excludes oligonucleotides having 31 nucleosides, but, unless otherwise indicated, such an oligonucleotide may further comprise, for example one or more conjugates, terminal groups, or other substituents. In certain embodiments, a gapmer oligonucleotide has any of the above lengths.

One of skill in the art will appreciate that certain lengths may not be possible for certain motifs. For example: a gapmer having a 5'-wing region consisting of four nucleotides, a gap consisting of at least six nucleotides, and a 3'-wing region consisting of three nucleotides cannot have an overall length less than 13 nucleotides. Thus, one would understand that the lower length limit is 13 and that the limit of 10 in “10-20” has no effect in that embodiment. Further, where an oligonucleotide is described by an overall length range and by regions having specified lengths, and where the sum of specified lengths of the regions is less than the upper limit of the overall length range, the oligonucleotide may have additional nucleosides, beyond those of the specified regions, provided that the total number of nucleosides does not exceed the upper limit of the overall length range. For example, an oligonucleotide consisting of 20-25 linked nucleosides comprising a 5'-wing consisting of 5 linked nucleosides; a 3'-wing consisting of 5 linked nucleosides and a central gap consisting of 10 linked nucleosides (5+5+10=20) may have up to 5 nucleosides that are not part of the 5'-wing, the 3'-wing, or the gap (before reaching the overall length limitation of 25). Such additional nucleosides may be 5' of the 5'-wing and/or 3' of the 3' wing.

Certain Oligonucleotides

In certain embodiments, oligonucleotides of the present invention are characterized by their sugar motif, internucleoside linkage motif, nucleobase modification motif and overall length. In certain embodiments, such parameters are each independent of one another. Thus, each internucleoside linkage of an oligonucleotide having a gapmer sugar motif may be modified or unmodified and may or may not follow the gapmer modification pattern of the sugar modifications. Thus, the internucleoside linkages within the wing regions of a sugar-gapmer may be the same or different from one another and may be the same or different from the internucleoside linkages of the gap region. Likewise, such sugar-gapmer oligonucleotides may comprise one or more modified nucleobase independent of the gapmer pattern of the sugar modifications. Herein if a description of an oligonucleotide or oligomeric compound is silent with respect to one or more parameter, such parameter is not limited. Thus, an oligomeric compound described only as having a gapmer sugar motif without further description may have any length, internucleoside linkage motif, and nucleobase modification motif. Unless otherwise indicated, all chemical modifications are independent of nucleobase sequence.

Certain Conjugate Groups

In certain embodiments, oligomeric compounds are modified by attachment of one or more conjugate groups. In general, conjugate groups modify one or more properties of the attached oligomeric compound including but not limited to pharmacodynamics, pharmacokinetics, stability, binding, absorption, cellular distribution, cellular uptake, charge and clearance. Conjugate groups are routinely used in the chemical arts and are linked directly or via an optional conjugate linking moiety or conjugate linking group to a parent compound such as an oligomeric compound, such as an oligonucleotide. Conjugate groups includes without limitation, intercalators, reporter molecules, polyamines, polyamides, polyethylene glycols, thioethers, polyethers, cholesterols, thiocholesterols, cholic acid moieties, folate, lipids, phospholipids, biotin, phenazine, phenanthridine, anthraquinone, adamantane, acridine, fluoresceins, rhodamines, coumarins and dyes. Certain conjugate groups have been described previously, for example: cholesterol moiety (Letsinger et al., *Proc. Natl. Acad. Sci. USA,* 1989, 86, 6553-6556), cholic acid (Manoharan et al., *Bioorg. Med. Chem. Let.,* 1994, 4, 1053-1060), a thioether, e.g., hexyl-S-tritylthiol (Manoharan et al., *Ann. N.Y. Acad. Sci.,* 1992, 660, 306-309; Manoharan et al., *Bioorg. Med. Chem. Let.,* 1993, 3, 2765-2770), a thiocholesterol (Oberhauser et al., *Nucl. Acids Res.,* 1992, 20, 533-538), an aliphatic chain, e.g., do-decan-diol or undecyl residues (Saison-Behmoaras et al., *EMBO J.,* 1991, 10, 1111-1118; Kabanov et al., *FEBS Lett,* 1990, 259, 327-330; Svinarchuk et al., *Biochimie,* 1993, 75, 49-54), a phospholipid, e.g., di-hexadecyl-rac-glycerol or triethyl-ammonium 1,2-di-0-hexadecyl-rac-glycero-3-H-phosphonate (Manoharan et al., *Tetrahedron Lett.,* 1995, 36:3651-3654; Shea et al., *Nucl. Acids Res.,* 1990, 18, 3777-3783), a polyamine or a polyethylene glycol chain (Manoharan et al., *Nucleosides & Nucleotides.* 1995, 14, 969-973), or adamantane acetic acid (Manoharan et al., *Tetrahedron Lett.,* 1995, 36:3651-3654), a palmityl moiety (Mishra el al., *Biochim. Biophys. Acta,* 1995, 1264, 229-237), or an octadecylamine or hexylamino-carbonyl-oxy-cholesterol moiety (Crooke et al., *J. Pharmacol. Exp. Ther.,* 1996, 277, 923-937).

In certain embodiments, a conjugate group comprises an active drug substance, for example, aspirin, warfarin, phenylbutazone, ibuprofen, suprofen, fen-bufen, ketoprofen, (S)-(+)-pranoprofen, carprofen, dansylsarcosine, 2,3,5-triiodobenzoic acid, flufenamic acid, folinic acid, a benzothiadiazide, chlorothiazide, a diazepine, indo-methicin, a barbiturate, a cephalosporin, a sulfa drug, an antidiabetic, an antibacterial or an antibiotic.

In certain embodiments, conjugate groups are directly attached to oligonucleotides in oligomeric compounds. In certain embodiments, conjugate groups are attached to oligonucleotides by a conjugate linking group. In certain such embodiments, conjugate linking groups, including, but not limited to, bifunctional linking moieties such as those known in the art are amenable to the compounds provided herein. Conjugate linking groups are useful for attachment of conjugate groups, such as chemical stabilizing groups, functional groups, reporter groups and other groups to selective sites in a parent compound such as for example an oligomeric compound. In general a bifunctional linking moiety comprises a hydrocarbyl moiety having two functional groups. One of the functional groups is selected to bind to a parent molecule or compound of interest and the other is selected to bind essentially any selected group such as chemical functional group or a conjugate group. In some embodiments, the conjugate linker comprises a chain structure or an oligomer of repeating units such as ethylene glycol or amino acid units. Examples of functional groups that are routinely used in a bifunctional linking moiety include, but are not limited to, electrophiles for reacting with nucleophilic groups and nucleophiles for reacting with electrophilic groups. In some embodiments, bifunctional linking moieties include amino, hydroxyl, carboxylic acid, thiol, unsaturations (e.g., double or triple bonds), and the like.

Some nonlimiting examples of conjugate linking moieties include pyrrolidine, 8-amino-3,6-dioxaoctanoic acid (ADO), succinimidyl 4-(N-maleimidomethyl) cyclohexane-1-carboxylate (SMCC) and 6-aminohexanoic acid (AHEX or AHA). Other linking groups include, but are not limited to, substituted $C_2$-$C_{10}$ alkyl, substituted or unsubstituted $C_2$-$C_{10}$ alkenyl or substituted or unsubstituted $C_2$-$C_{10}$ alkynyl, wherein a nonlimiting list of preferred substituent groups includes hydroxyl, amino, alkoxy, carboxy, benzyl, phenyl, nitro, thiol, thioalkoxy, halogen, alkyl, aryl, alkenyl and alkynyl.

Conjugate groups may be attached to either or both ends of an oligonucleotide (terminal conjugate groups) and/or at any internal position.

In certain embodiments, conjugate groups are at the 3'-end of an oligonucleotide of an oligomeric compound. In certain embodiments, conjugate groups are near the 3'-end. In certain embodiments, conjugates are attached at the 3'end of an oligomeric compound, but before one or more terminal group nucleosides. In certain embodiments, conjugate groups are placed within a terminal group.

In certain embodiments, the present invention provides oligomeric compounds. In certain embodiments, oligomeric compounds comprise an oligonucleotide. In certain embodiments, an oligomeric compound comprises an oligonucleotide and one or more conjugate and/or terminal groups. Such conjugate and/or terminal groups may be added to oligonucleotides having any of the chemical motifs discussed above. Thus, for example, an oligomeric compound comprising an oligonucleotide having region of alternating nucleosides may comprise a terminal group.

Antisense Compounds

In certain embodiments, oligomeric compounds of the present invention are antisense compounds. Such antisense compounds are capable of hybridizing to a target nucleic acid, resulting in at least one antisense activity. In certain embodiments, antisense compounds specifically hybridize to one or more target nucleic acid. In certain embodiments, a specifically hybridizing antisense compound has a nucleobase sequence comprising a region having sufficient complementarity to a target nucleic acid to allow hybridization and result in antisense activity and insufficient complementarity to any non-target so as to avoid non-specific hybridization to any non-target nucleic acid sequences under conditions in which specific hybridization is desired (e.g., under physiological conditions for in vivo or therapeutic uses, and under conditions in which assays are performed in the case of in vitro assays).

In certain embodiments, the present invention provides antisense compounds comprising oligonucleotides that are fully complementary to the target nucleic acid over the entire length of the oligonucleotide. In certain embodiments, oligonucleotides are 99% complementary to the target nucleic acid. In certain embodiments, oligonucleotides are 95% complementary to the target nucleic acid. In certain embodiments, such oligonucleotides are 90% complementary to the target nucleic acid. In certain embodiments, such oligonucleotides are 85% complementary to the target nucleic acid. In certain embodiments, such oligonucleotides are 80% complementary to the target nucleic acid. In certain embodiments, an antisense compound comprises a region that is fully complementary to a target nucleic acid and is at least 80% complementary to the target nucleic acid over the entire length of the oligonucleotide. In certain such embodiments, the region of full complementarity is from 6 to 14 nucleobases in length.

In certain embodiments antisense compounds and antisense oligonucleotides comprise single-strand compounds. In certain embodiments antisense compounds and antisense oligonucleotides comprise double-strand compounds.

Pharmaceutical Compositions

In certain embodiments, the present invention provides pharmaceutical compositions comprising one or more antisense compound. The pharmaceutical composition may comprise a cocktail of antisense compounds, wherein the cocktail comprises 2, 3, 4, 5, 6, 7, 8, 9, 10 or more antisense compounds. In certain embodiments, such pharmaceutical composition comprises a suitable pharmaceutically acceptable diluent or carrier. In certain embodiments, a pharmaceutical composition comprises a sterile saline solution and one or more antisense compound. In certain embodiments, such pharmaceutical composition consists of a sterile saline solution and one or more antisense compound. In certain embodiments, the sterile saline is pharmaceutical grade saline. In certain embodiments, a pharmaceutical composition comprises one or more antisense compound and sterile water. In certain embodiments, a pharmaceutical composition consists of one or more antisense compound and sterile water. In certain embodiments, the sterile saline is pharmaceutical grade water. In certain embodiments, a pharmaceutical composition comprises one or more antisense compound and phosphate-buffered saline (PBS). In certain embodiments, a pharmaceutical composition consists of one or more antisense compound and sterile phosphate-buffered saline (PBS). In certain embodiments, the sterile saline is pharmaceutical grade PBS.

In certain embodiments, antisense compounds may be admixed with pharmaceutically acceptable active and/or inert substances for the preparation of pharmaceutical compositions or formulations.

Compositions and methods for the formulation of pharmaceutical compositions depend on a number of criteria, including, but not limited to, route of administration, extent of disease, or dose to be administered.

Pharmaceutical compositions comprising antisense compounds encompass any pharmaceutically acceptable salts, esters, or salts of such esters. In certain embodiments, pharmaceutical compositions comprising antisense compounds comprise one or more oligonucleotide which, upon administration to an animal, including a human, is capable of providing (directly or indirectly) the biologically active metabolite or residue thereof. Accordingly, for example, the disclosure is also drawn to pharmaceutically acceptable salts of antisense compounds, prodrugs, pharmaceutically acceptable salts of such prodrugs, and other bioequivalents. Suitable pharmaceutically acceptable salts include, but are not limited to, sodium and potassium salts.

A prodrug can include the incorporation of additional nucleosides at one or both ends of an oligomeric compound which are cleaved by endogenous nucleases within the body, to form the active antisense oligomeric compound.

Lipid moieties have been used in nucleic acid therapies in a variety of methods. In certain such methods, the nucleic acid is introduced into preformed liposomes or lipoplexes made of mixtures of cationic lipids and neutral lipids. In certain methods, DNA complexes with mono- or poly-cationic lipids are formed without the presence of a neutral lipid. In certain embodiments, a lipid moiety is selected to increase distribution of a pharmaceutical agent to a particular cell or tissue. In certain embodiments, a lipid moiety is selected to increase distribution of a pharmaceutical agent to fat tissue. In certain embodiments, a lipid moiety is selected to increase distribution of a pharmaceutical agent to muscle tissue.

In certain embodiments, pharmaceutical compositions provided herein comprise one or more modified oligonucleotides and one or more excipients. In certain such embodiments, excipients are selected from water, salt solutions, alcohol, polyethylene glycols, gelatin, lactose, amylase, magnesium stearate, talc, silicic acid, viscous paraffin, hydroxymethylcellulose and polyvinylpyrrolidone.

In certain embodiments, a pharmaceutical composition provided herein comprises a delivery system. Examples of delivery systems include, but are not limited to, liposomes and emulsions. Certain delivery systems are useful for preparing certain pharmaceutical compositions including those comprising hydrophobic compounds. In certain embodiments, certain organic solvents such as dimethylsulfoxide (DMSO) are used.

In certain embodiments, a pharmaceutical composition provided herein comprises one or more tissue-specific delivery molecules designed to deliver the one or more pharmaceutical agents of the present invention to specific tissues or cell types. For example, in certain embodiments, pharmaceutical compositions include liposomes coated with a tissue-specific antibody.

In certain embodiments, a pharmaceutical composition provided herein comprises a co-solvent system. Certain of such co-solvent systems comprise, for example, benzyl alcohol, a nonpolar surfactant, a water-miscible organic polymer, and an aqueous phase. In certain embodiments, such co-solvent systems are used for hydrophobic compounds. A non-limiting example of such a co-solvent system is the VPD co-solvent system, which is a solution of absolute ethanol comprising 3% w/v benzyl alcohol, 8% w/v of the nonpolar surfactant Polysorbate 80™ and 65% w/v polyethylene glycol 300. The proportions of such co-solvent systems may be varied considerably without significantly altering their solubility and toxicity characteristics. Furthermore, the identity of co-solvent components may be varied: for example, other surfactants may be used instead of Polysorbate 80™; the fraction size of polyethylene glycol may be varied; other biocompatible polymers may replace polyethylene glycol, e.g., polyvinyl pyrrolidone; and other sugars or polysaccharides may substitute for dextrose.

In certain embodiments, a pharmaceutical composition provided herein is prepared for oral administration. In certain embodiments, pharmaceutical compositions are prepared for buccal administration.

In certain embodiments, a pharmaceutical composition is prepared for administration by injection (e.g., intravenous, subcutaneous, intramuscular, etc.). In certain of such embodiments, a pharmaceutical composition comprises a carrier and is formulated in aqueous solution, such as water or physiologically compatible buffers such as Hanks's solution, Ringer's solution, or physiological saline buffer. In certain embodiments, other ingredients are included (e.g., ingredients that aid in solubility or serve as preservatives). In certain embodiments, injectable suspensions are prepared using appropriate liquid carriers, suspending agents and the like. Certain pharmaceutical compositions for injection are presented in unit dosage form, e.g., in ampoules or in multi-dose containers. Certain pharmaceutical compositions for injection are suspensions, solutions or emulsions in oily or aqueous vehicles, and may contain formulatory agents such as suspending, stabilizing and/or dispersing agents. Certain solvents suitable for use in pharmaceutical compositions for injection include, but are not limited to, lipophilic solvents and fatty oils, such as sesame oil, synthetic fatty acid esters, such as ethyl oleate or triglycerides, and liposomes. Aqueous injection suspensions may contain substances that increase the viscosity of the suspension, such as sodium carboxymethyl cellulose, sorbitol, or dextran. Optionally, such suspensions may also contain suitable stabilizers or agents that increase the solubility of the pharmaceutical agents to allow for the preparation of highly concentrated solutions.

In certain embodiments, a pharmaceutical composition provided herein comprises an oligonucleotide in a therapeutically effective amount. In certain embodiments, the therapeutically effective amount is sufficient to prevent, alleviate or ameliorate symptoms of a disease or to prolong the survival of the subject being treated. Determination of a therapeutically effective amount is well within the capability of those skilled in the art.

In certain embodiments, one or more modified oligonucleotide provided herein is formulated as a prodrug. In certain embodiments, upon in vivo administration, a prodrug is chemically converted to the biologically, pharmaceutically or therapeutically more active form of an oligonucleotide. In certain embodiments, prodrugs are useful because they are easier to administer than the corresponding active form. For example, in certain instances, a prodrug may be more bioavailable (e.g., through oral administration) than is the corresponding active form. In certain instances, a prodrug may have improved solubility compared to the corresponding active form. In certain embodiments, prodrugs are less water soluble than the corresponding active form. In certain instances, such prodrugs possess superior transmittal across cell membranes, where water solubility is detrimental to mobility. In certain embodiments, a prodrug is an ester. In certain such embodiments, the ester is metabolically hydrolyzed to carboxylic acid upon administration. In certain instances the carboxylic acid containing compound is the corresponding active form. In certain embodiments, a prodrug comprises a short peptide (polyaminoacid) bound to an acid group. In certain of such embodiments, the peptide is cleaved upon administration to form the corresponding active form.

In certain embodiments, the present invention provides compositions and methods for reducing the amount or activity of a target nucleic acid in a cell. In certain embodiments, the cell is in an animal. In certain embodiments, the animal is a mammal. In certain embodiments, the animal is a rodent. In certain embodiments, the animal is a primate. In certain embodiments, the animal is a non-human primate. In certain embodiments, the animal is a human. In certain embodiments, the animal is a mouse.

In certain embodiments, the present invention provides methods of administering a pharmaceutical composition comprising an oligomeric compound of the present invention to an animal. Suitable administration routes include, but are not limited to, oral, rectal, transmucosal, transdermal, intestinal, enteral, topical, suppository, through inhalation, intrathecal, intracerebroventricular, intraperitoneal, intranasal, intratumoral, and parenteral (e.g., intravenous, intramuscular, intramedullary, and subcutaneous). In certain embodiments, a pharmaceutical composition is prepared for transmucosal administration. In certain of such embodiments penetrants appropriate to the barrier to be permeated are used in the formulation. Such penetrants are generally known in the art. In certain embodiments, pharmaceutical compositions are administered to achieve local rather than systemic exposures. For example, pharmaceutical compositions may be aerosolized and inhaled directly in the area of desired effect (e.g., into the lungs).

In certain embodiments, a pharmaceutical composition is administered to an animal having at least one symptom associated with Cystic Fibrosis. In certain embodiments, such administration results in amelioration of at least one symptom. In certain embodiments, administration of a pharmaceutical composition to an animal results in an increase in functional CFTR protein in a cell. In certain embodiments, the administration of certain antisense oligonucleotides (ASOs) delays the onset of Cystic Fibrosis. In certain embodiments, the administration of certain antisense oligonucleotides prevents the onset of Cystic Fibrosis. In certain embodiments, the administration of certain antisense oligonucleotides rescues cellular phenotype.

While certain compounds, compositions and methods described herein have been described with specificity in accordance with certain embodiments, the following examples serve only to illustrate the compounds described herein and are not intended to limit the same. Each of the references, GenBank accession numbers, and the like recited in the present application is incorporated herein by reference in its entirety. Although the sequence listing accompanying this filing identifies each sequence as either "RNA" or "DNA" as required, in reality, those sequences may be modified with any combination of chemical modifications. One of skill in the art will readily appreciate that such designation as "RNA" or "DNA" to describe modified oligonucleotides is, in certain instances, arbitrary. For example, an oligonucleotide comprising a nucleoside comprising a 2'-OH sugar moiety and a thymine base could be described as a DNA having a modified sugar (2'-OH for the natural 2'-H of DNA) or as an RNA having a modified base (thymine (methylated uracil) for natural uracil of RNA).

Accordingly, nucleic acid sequences provided herein, including, but not limited to those in the sequence listing, are intended to encompass nucleic acids containing any combination of natural or modified RNA and/or DNA, including, but not limited to such nucleic acids having modified nucleobases. By way of further example and without limitation, an oligomeric compound having the nucleobase sequence

EXAMPLES

The Examples that follow are illustrative of specific embodiments of the invention, and various uses thereof. They are set forth for explanatory purposes only, and are not to be taken as limiting the invention.

Methods

Antisense Oligonucleotides (ASOs). ASOs with phosphorodiamidate morpholino (PMO) chemistries were generated by GeneTools LLC and were dissolved in 0.9% saline.

Cell culture and transfection. T84 cells are a human colonic adenocarcinoma cell line and the mouse primary cell line, 208EE, was established from an adult C57BL/6 mouse kidney. ASOs (15 μM final concentration) were transfected into cells using Endo-Porter (GeneTools). RNA was collected 48 hours post-transfection.

RNA isolation and analysis. RNA was isolated from tissue and cells in culture using TRIZOL™ reagent (Life Technologies, Carlsbad, CA) according to the manufacturer's protocol. For human tissue, RNA was isolated and treated with 4 μg of DNase-4 (RNase-free) (Life Technologies) followed by reverse transcription with GoScript™ reverse transcription system (Promega, Madison, WI). Radiolabeled and cold PCR was carried out using primers specific for human or mouse CFTR region encompassing the ASO target exon. PCR products were separated by polyacrylamide or agarose gel electrophoresis and bands on gels were quantitated by densitometry analysis using Image J software.

Figure 1B:
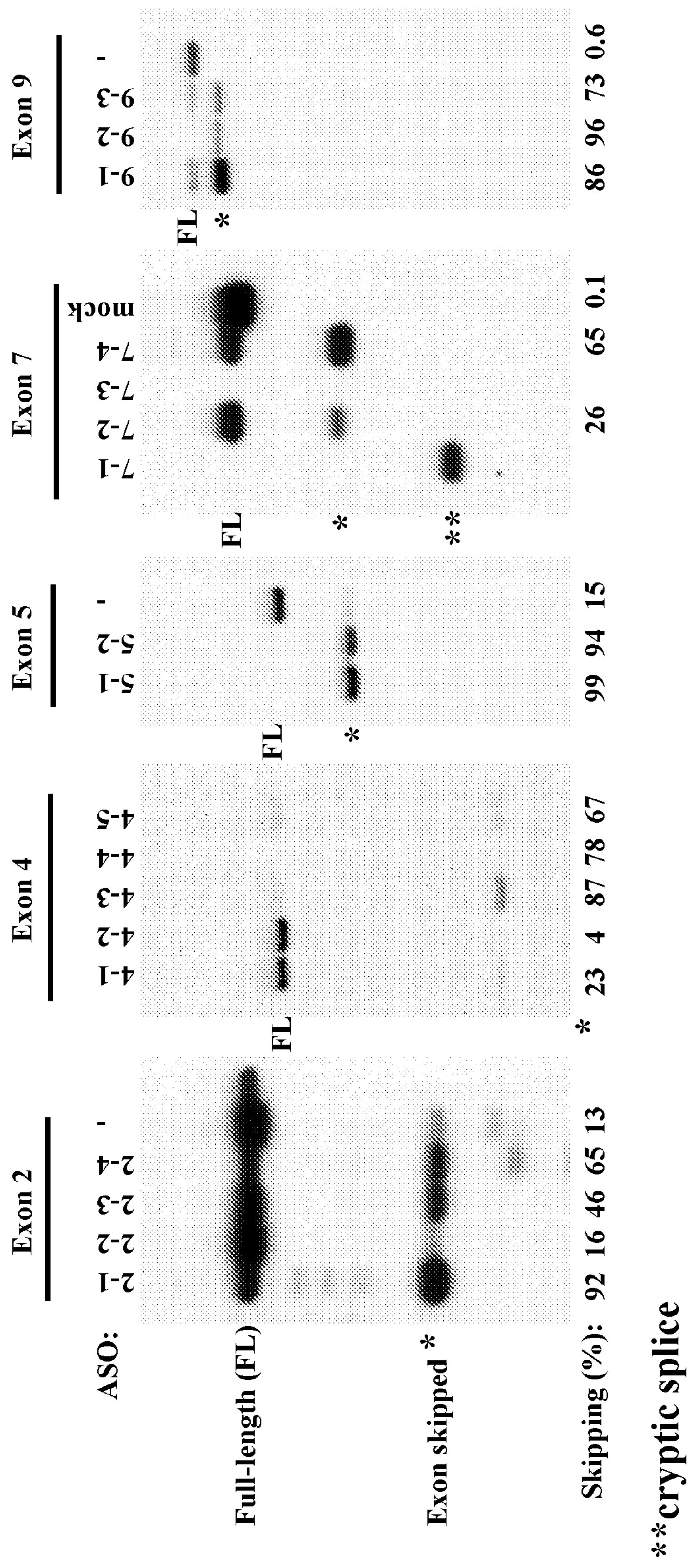
FIG. 1B shows antisense oligonucleotides induce skipping of targeted exons 2, 4, 5, 7 and 9 of the murine CFTR gene-derived pre-mRNA. Polyacrylamide gel images of radio-labeled reverse-transcription/polymerase chain reaction (RT-PCR) products separated by electrophoresis are shown. RT-PCR was performed on RNA isolated from a mouse primary cell line treated with the indicated ASO or treated with vehicle (saline) only (–). The products were amplified with primers specific to exons flanking the specific ASO-targeted exon in order to resolve the full-length (FL) and exon-skipped (*) products. The targeted exon is indicated at the top of the gel image. PCR products were quantitated and the percent of the products that are skipped [Exon skipped/(Full-length+skipped)]×100 is shown below the gel image.
Figure 1C:
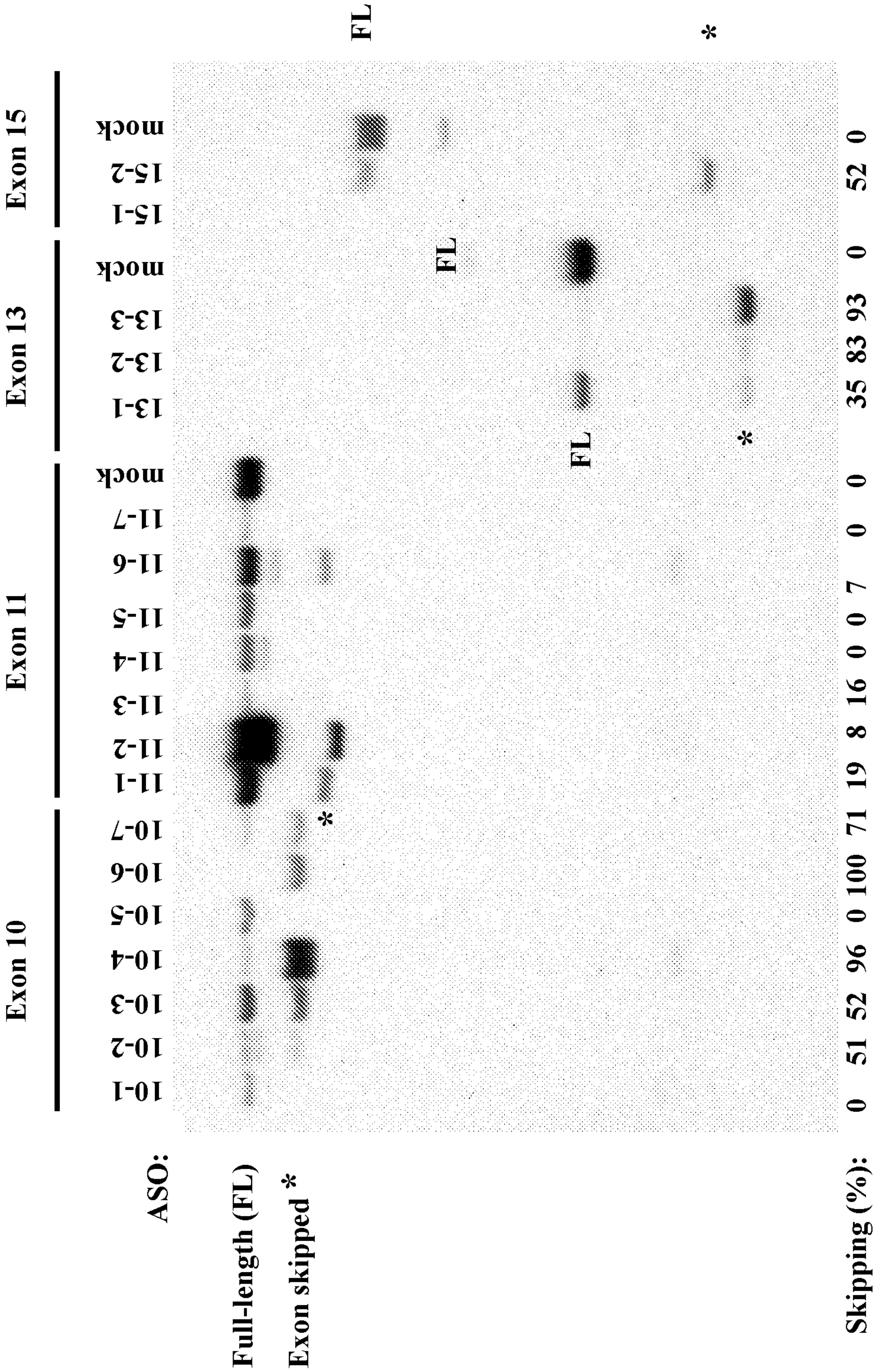
FIG. 1C shows antisense oligonucleotides induce skipping of targeted exons 10, 11, 13 and 15 of the murine CFTR gene-derived pre-mRNA. Polyacrylamide gel images of radio-labeled reverse-transcription/polymerase chain reaction (RT-PCR) products separated by electrophoresis are shown. RT-PCR was performed on RNA isolated from a mouse primary cell line treated with the indicated ASO or treated with vehicle (saline) only (–). The products were amplified with primers specific to exons flanking the specific ASO-targeted exon in order to resolve the full-length (FL) and exon-skipped (*) products. The targeted exon is indicated at the top of the gel image. PCR products were quantitated and the percent of the products that are skipped [Exon skipped/(Full-length+skipped)]×100 is shown below the gel image.
Figure 1D:
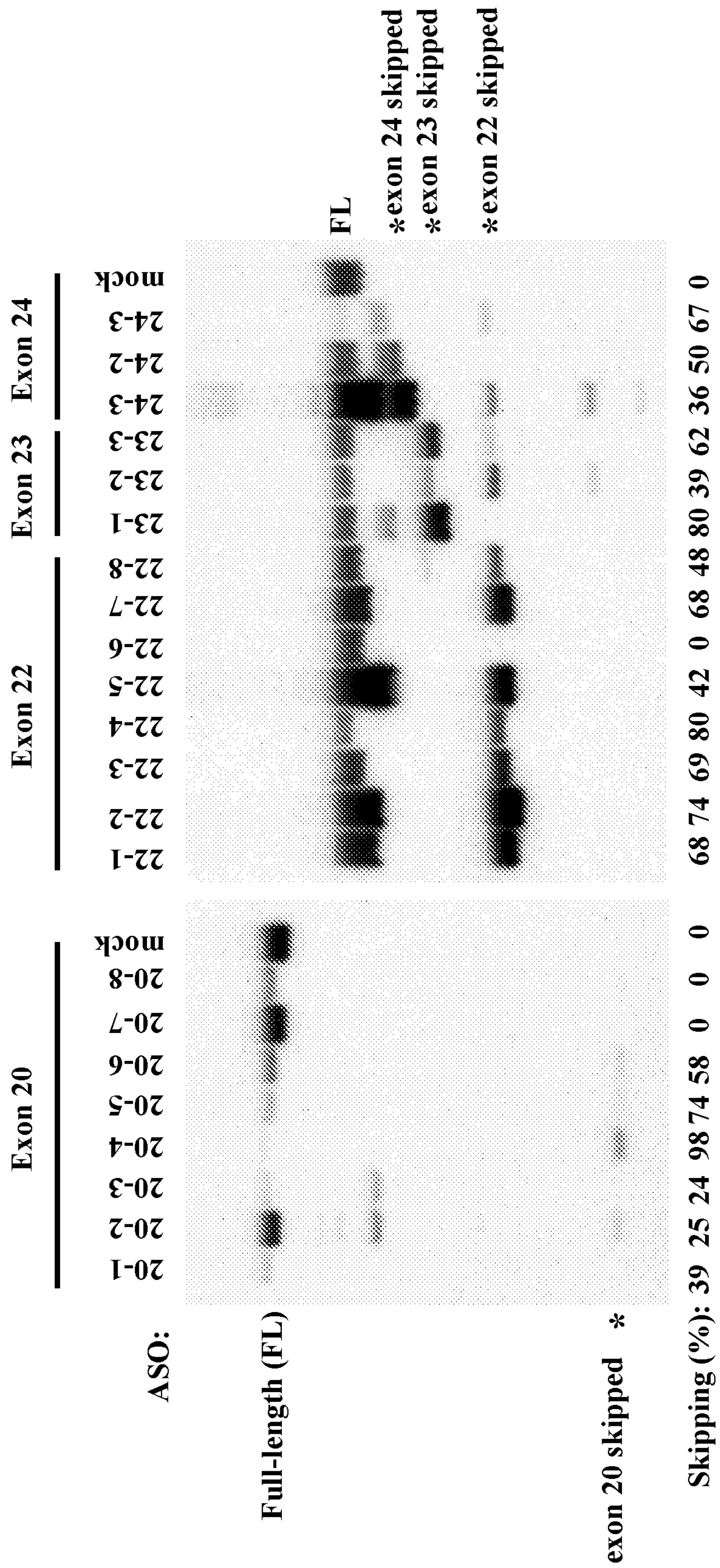
FIG. 1D shows antisense oligonucleotides induce skipping of targeted exons 20, 22, 23 and 24 of the murine CFTR gene-derived pre-mRNA. Polyacrylamide gel images of radio-labeled reverse-transcription/polymerase chain reaction (RT-PCR) products separated by electrophoresis are shown. RT-PCR was performed on RNA isolated from a mouse primary cell line treated with the indicated ASO or treated with vehicle (saline) only (–). The products were amplified with primers specific to exons flanking the specific ASO-targeted exon in order to resolve the full-length (FL) and exon-skipped (*) products. The targeted exon is indicated at the top of the gel image. PCR products were quantitated and the percent of the products that are skipped [Exon skipped/(Full-length+skipped)]×100 is shown below the gel image.
Figure 2A:
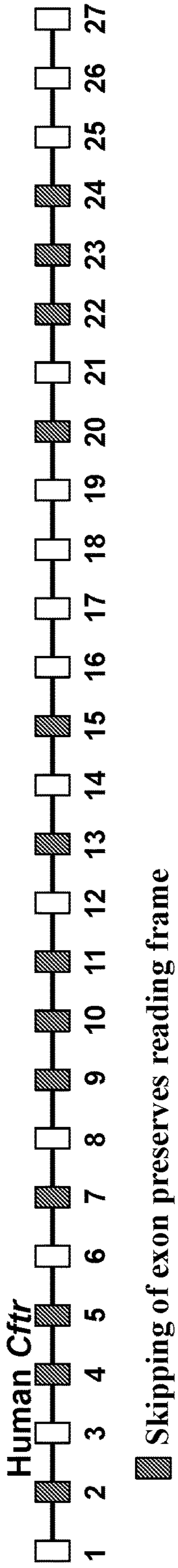
FIG. 2A shows a map of the human CFTR gene. Boxes represent exons and lines represent introns. The exons that can be skipped or spliced out of the mature mRNA and still maintain the open reading frame of the mRNA are shaded. The CFTR mRNAs lacking any one of these exons will code for a full-length CFTR protein with an internal deletion of the specific targeted exon sequence.
Figure 2B:
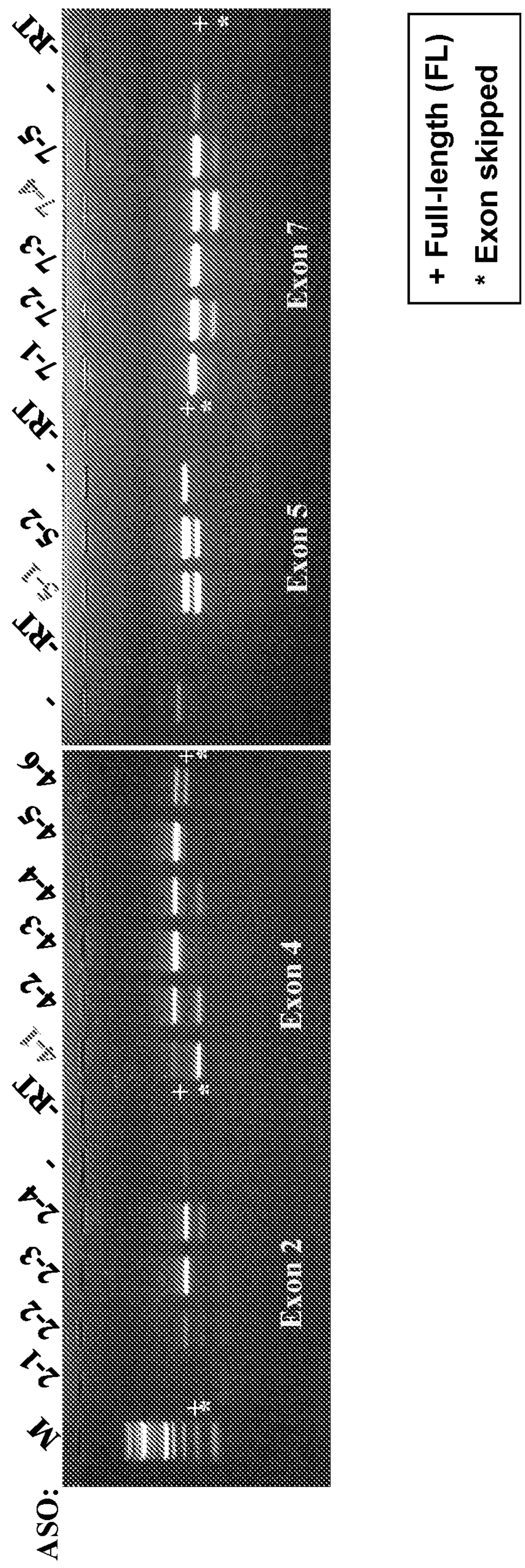
FIG. 2B show antisense oligonucleotides induce skipping of targeted exons 2, 4, 5 and 7 of the human CFTR gene-derived pre-mRNA. Agarose gel images of reverse-transcription/polymerase chain reaction (RT-PCR) products separated by electrophoresis are shown. RT-PCR was performed on RNA isolated from human T84 epithelial cells treated with the indicated ASO or treated with vehicle (saline) only (–) or a reaction lacking cDNA (–RT). The products were amplified with primers specific to exons flanking the specific ASO-targeted exon in order to resolve the full-length (FL; +) and exon-skipped (*) products. The targeted exon is indicated at the bottom of the gel and by the first numbers in the name of the ASOs.
Figure 2C:
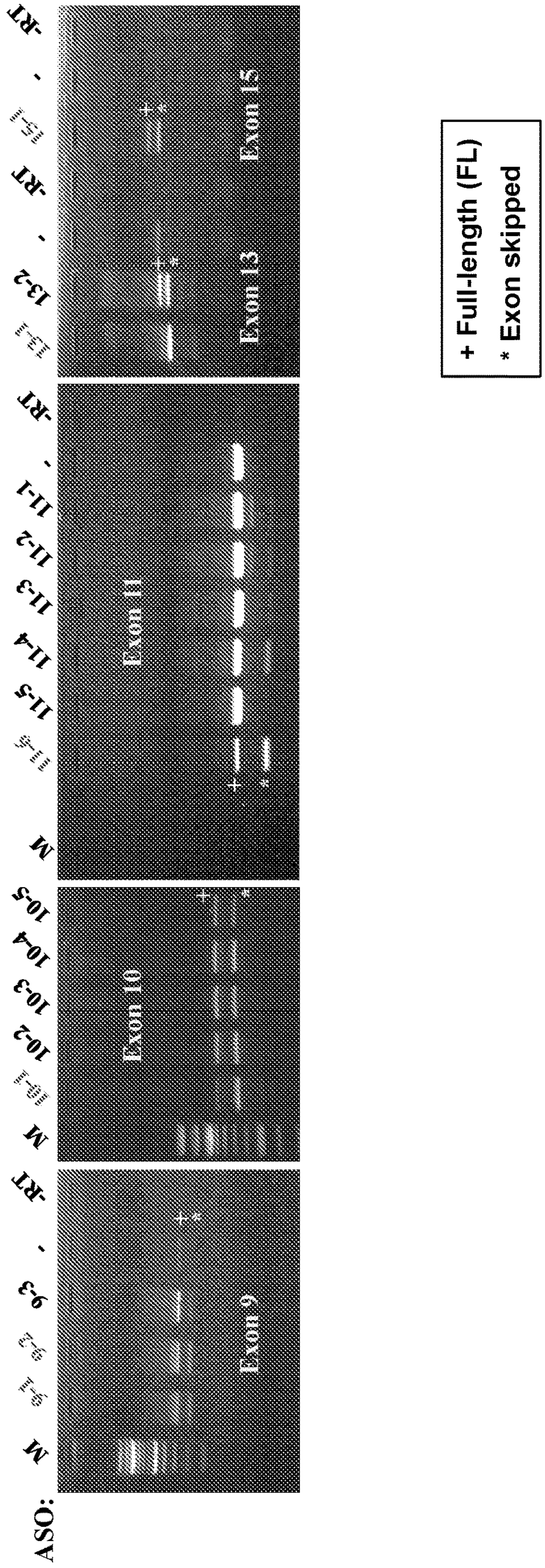
FIG. 2C show antisense oligonucleotides induce skipping of targeted exons 9, 10, 11, 13 and 15 of the human CFTR gene-derived pre-mRNA. Agarose gel images of reverse-transcription/polymerase chain reaction (RT-PCR) products separated by electrophoresis are shown. RT-PCR was performed on RNA isolated from human T84 epithelial cells treated with the indicated ASO or treated with vehicle (saline) only (–) or a reaction lacking cDNA (-RT). The products were amplified with primers specific to exons flanking the specific ASO-targeted exon in order to resolve the full-length (FL; +) and exon-skipped (*) products. The targeted exon is indicated at the bottom of the gel and by the first numbers in the name of the ASOs.
Figure 2D:
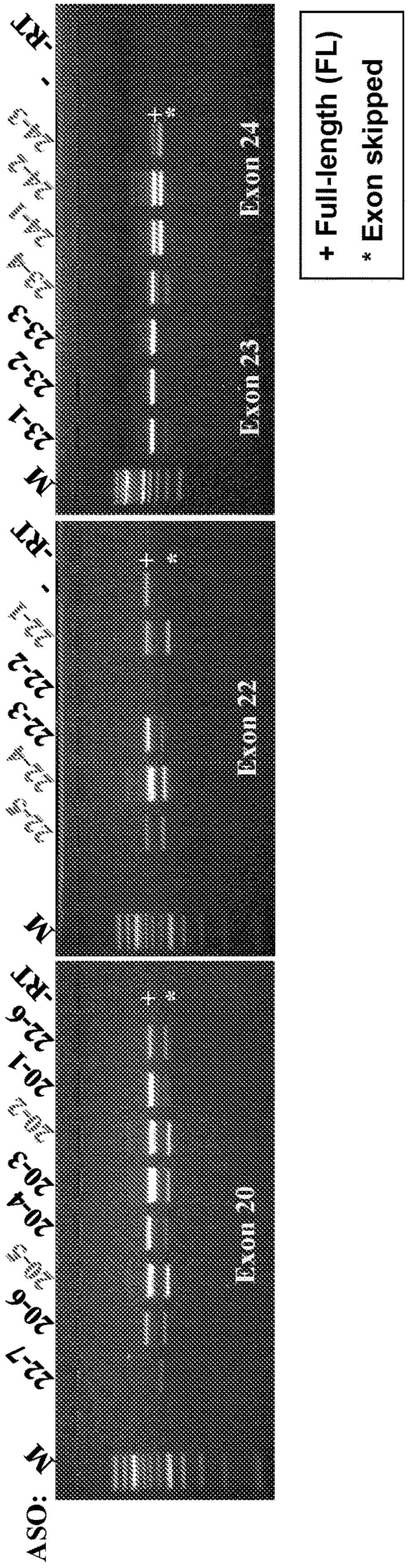
FIG. 2D show antisense oligonucleotides induce skipping of targeted exons 20, 22, 23 and 24 of the human CFTR gene-derived pre-mRNA. Agarose gel images of reverse-transcription/polymerase chain reaction (RT-PCR) products separated by electrophoresis are shown. RT-PCR was performed on RNA isolated from human T84 epithelial cells treated with the indicated ASO or treated with vehicle (saline) only (–) or a reaction lacking cDNA (-RT). The products were amplified with primers specific to exons flanking the specific ASO-targeted exon in order to resolve the full-length (FL; +) and exon-skipped (*) products. The targeted exon is indicated at the bottom of the gel and by the first numbers in the name of the ASOs.
Figure 3A:
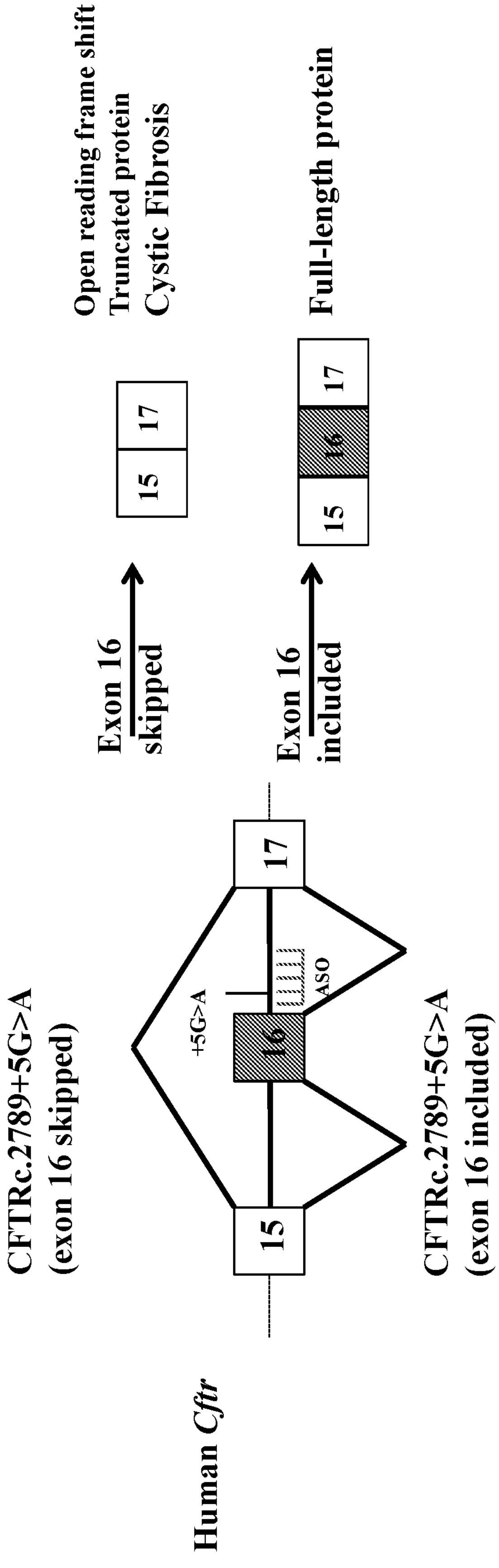
FIG. 3A shows a schematic of the splicing pattern of human CFTR c.2789-+5G>A without and with ASO targeting. Boxes are exons and lines are introns. Diagonal lines indicate splicing pathway FIG. 3B demonstrates that antisense oligonucleotides correct splicing of human CFTR exon 16 with c.2789+5G>A mutation. Polyacrylamide gel images of reverse-transcription/polymerase chain reaction (RT-PCR) products were separated by electrophoresis. RT-PCR was performed on RNA isolated from human lymphoblast cell line GM 11859, whose donor is homozygous for G-to-A substitution at nucleotide 2789+5 in intron 16 which results in an mRNA splicing defect (2789+5G>A). Cells were treated with the indicated ASO. The products were amplified with primers specific to exons flanking the specific ASO-targeted exon in order to resolve the full-length (FL) and exon-skipped products. ASO 16-8 was effective at correcting exon 16 splicing of CFTRc.2789+5G>A.
Figure 3B:
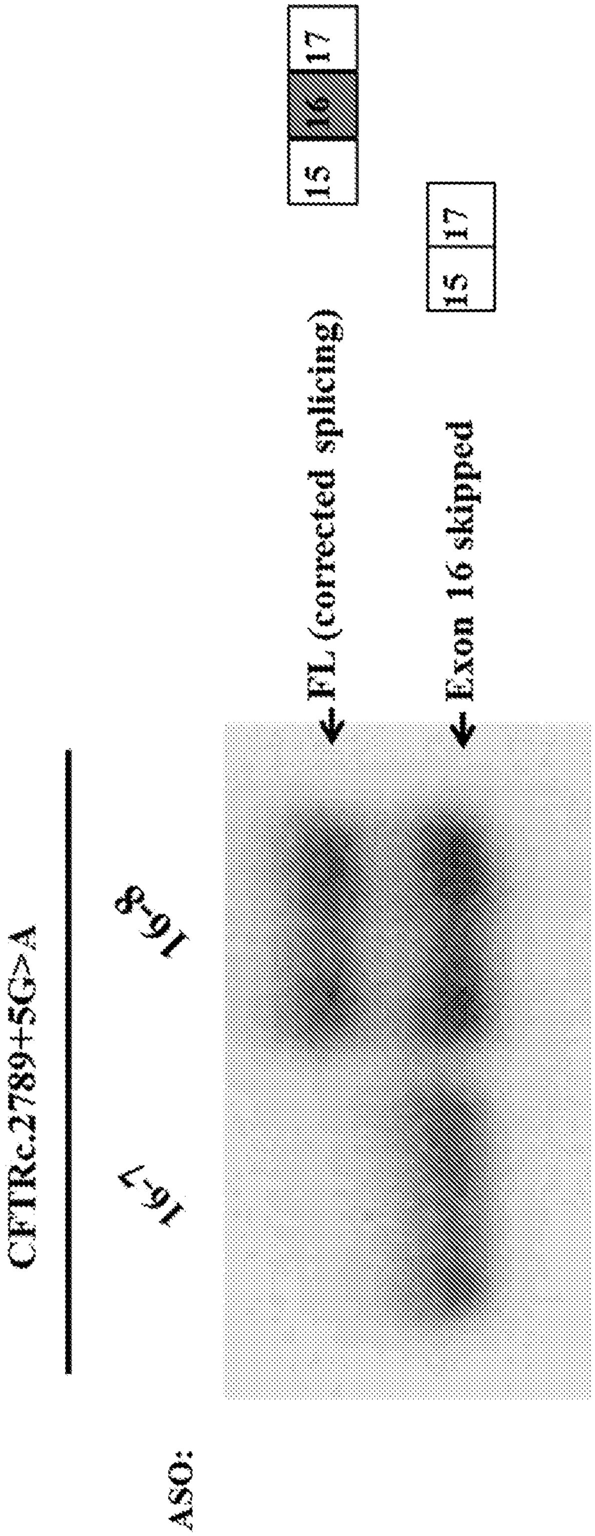

Example 1: Antisense Oligonucleotides Induce Skipping of Targeted Exons in Murine CFTR Gene-Derived Pre-mRNA Various ASOs (see Table 1; SEQ ID NOs: 1-60) were tested in the mouse primary cell line, 208EE (which was established from an adult C57BL/6 mouse kidney). ASOs (15 μM final concentration) were transfected into cells using Endo-Porter (GeneTools). FIGS. 1B, 1C and 1D demonstrate that ASOs induce skipping of targeted exons in murine CFTR.

TABLE 1

Antisense oligonucleotides targeting mouse CFTR induce exon skipping.

| Name | Target Exon | Sequence | % skipped * | SEQ ID NO. |
|---|---|---|---|---|
| 2-1 | 2 | GGTCCAGCTAAAAGAGAAGAGGGCA | 92 | SEQ ID NO. 1 |
| 2-2 | 2 | CTTTCCTCAAAATTGGTGTGGTCCA | 16 | SEQ ID NO. 2 |
| 2-3 | 2 | TATGTCTGACAACTCCAAGTGGTGT | 46 | SEQ ID NO. 3 |
| 2-4 | 2 | CTAGTTTTTCAGACAAGTGGTCAGC | 65 | SEQ ID NO. 4 |
| 4-1 | 4 | TTCCTAGCAAGACAGGCTGGACAGC | nd | SEQ ID NO. 5 |
| 4-2 | 4 | ATAGGATGCTATGATTCTTCCTAGC | 23 | SEQ ID NO. 6 |
| 4-3 | 4 | ATAAGCCTATGCCAAGGTAAATGGC | 4 | SEQ ID NO. 7 |
| 4-4 | 4 | TGTCCTGACAATGAAGAGAAGGCAT | 87 | SEQ ID NO. 8 |
| 4-5 | 4 | AATGCGATGAAGGCCAAAAATAGCT | 78 | SEQ ID NO. 9 |
| 4-6 | 4 | TAGCTGTTCTCATCTGCATTCCAAT | 67 | SEQ ID NO. 10 |
| 4-7 | 4 | CATCTTCCAAAAAGTATTACCTTCT | nd | SEQ ID NO. 11 |
| 5-1 | 5 | TTGTTCAGGTTGTTGGAAAGAAGAC | 99 | SEQ ID NO. 12 |
| 5-2 | 5 | ATCAAGAACGCGGCTTGACAACTTT | 94 | SEQ ID NO. 13 |
| 7-1 | 7 | CACGAGTCTTTCATTGATCTTTGCA | 20 | SEQ ID NO. 14 |
| 7-2 | 7 | CTGATTCCCAACAATATGCCTTAAC | 26 | SEQ ID NO. 15 |
| 7-3 | 7 | CAATCATTTTCTCCATCGCTGATTC | 42 | SEQ ID NO. 16 |
| 7-4 | 7 | ATTATGTCAACTTACTCTCTCAAGT | 65 | SEQ ID NO. 17 |
| 9-1 | 9 | GCCTGTGGTCATTAAGTTATACTCC | 86 | SEQ ID NO. 18 |
| 9-2 | 9 | CTCCTCCCAAAATGCTGTTACATTT | 96 | SEQ ID NO. 19 |
| 9-3 | 9 | TATTTAGAAATCTCACCTCCTCCCA | 73 | SEQ ID NO. 20 |
| 10-1 | 10 | CTTTCTCCAGTAATTCCCCAAATCC | 0 | SEQ ID NO. 21 |

TABLE 1-continued

Antisense oligonucleotides targeting mouse CFTR induce exon skipping.

| Name | Target Exon | Sequence | % skipped * | SEQ ID NO. |
|---|---|---|---|---|
| 10-2 | 10 | GTCACCATTGCTTTGTTGTACTTTC | 51 | SEQ ID NO. 22 |
| 10-3 | 10 | CTGAAACTGACATTGTTCTCATCAC | 52 | SEQ ID NO. 23 |
| 10-4 | 10 | AGGATTTCCCACAAGGCAGAGATGA | 96 | SEQ ID NO. 24 |
| 10-5 | 10 | ATAGCCAACATCTCTCCTTTCTCTA | 0 | SEQ ID NO. 25 |
| 10-6 | 10 | CTTTCCTGATCCAGTAGATCCAGTA | 100 | SEQ ID NO. 26 |
| 10-7 | 10 | TTAAAGAGACAGTACCTTTCCTGAT | 71 | SEQ ID NO. 27 |
| 11-1 | 11 | TCCAGTTCTCCCAAAATCAACATCA | 19 | SEQ ID NO. 28 |
| 11-2 | 11 | TGTGCTTAATAATTCCCTCTGAAGC | 8 | SEQ ID NO. 29 |
| 11-3 | 11 | ATTGAGAGCAGAATGAAACTCTTCC | 16 | SEQ ID NO. 30 |
| 11-4 | 11 | GATATTTTCTTTGATAGTACCCGGC | 0 | SEQ ID NO. 31 |
| 11-5 | 11 | ACACTCTTATATCTGTACTCATCAT | 0 | SEQ ID NO. 32 |
| 11-6 | 11 | CTGCTGTAGTTGGCAAGCTTTGACA | 7 | SEQ ID NO. 33 |
| 11-7 | 11 | CATAAATATGCTTACCTGCTGTAGT | 0 | SEQ ID NO. 34 |
| 13-1 | 13 | GGGAATCTAATAGGTACAAATCAGC | 35 | SEQ ID NO. 35 |
| 13-2 | 13 | CAAATCAGCATCTTTATATACTGCT | 83 | SEQ ID NO. 36 |
| 13-3 | 13 | ACTCAGTCATAGAACATACCTTTCA | 93 | SEQ ID NO. 37 |
| 15-1 | 15 | AACAAACATACTTACCTCAACCAGA | 52 | SEQ ID NO. 38 |
| 20-1 | 20 | CCTGCCTGTAAATCATCCCATAGGA | 39 | SEQ ID NO. 39 |
| 20-2 | 20 | CAAGGTGGGTGAAAATTGGACTCCT | 25 | SEQ ID NO. 40 |
| 20-3 | 20 | CGAAGTGTCCAGAGTCCTTTTAAGC | 24 | SEQ ID NO. 41 |
| 20-4 | 20 | CAGAGTTTCAAAGTAAGTCTGGCGT | 98 | SEQ ID NO. 42 |
| 20-5 | 20 | TTGGCAGTGTGCAAATTCAGAGCTT | 74 | SEQ ID NO. 43 |
| 20-6 | 20 | CTATTCTCATTTGGAACCAGCGCAA | 58 | SEQ ID NO. 44 |
| 20-7 | 20 | AGAGGACAAATATCATGTCTATTCT | 0 | SEQ ID NO. 45 |
| 20-8 | 20 | ATGGAGATGAAGGTAACAACAATGA | 0 | SEQ ID NO. 46 |
| 22-1 | 22 | AACTTAAACACTCTGCTCACAGATC | 68 | SEQ ID NO. 47 |
| 22-2 | 22 | CTAAAACGTCAGATGATCCTTCTCT | 74 | SEQ ID NO. 48 |
| 22-3 | 22 | TATCACTTTTCTTCACATGCTCATT | 69 | SEQ ID NO. 49 |
| 22-4 | 22 | ACCATTTCGCCTCCAGAGGGCCAGA | 80 | SEQ ID NO. 50 |
| 22-5 | 22 | CATCCATGTATTTCACAGTAAGGTC | 42 | SEQ ID NO. 51 |
| 22-6 | 22 | ATGTTCTCTAATACGGCATTTCCAT | 0 | SEQ ID NO. 52 |
| 22-7 | 22 | CCTCTGTCCAGGACTTATTGAAAAA | 68 | SEQ ID NO. 53 |
| 22-8 | 22 | GTAATGCTGAAATCTCACCCTCTGT | 48 | SEQ ID NO. 54 |
| 23-1 | 23 | AATTCCATGAGACACCATCAATCTC | 80 | SEQ ID NO. 55 |
| 23-2 | 23 | GTACTTTTTCCTGATCCAGTTCTTC | 39 | SEQ ID NO. 56 |
| 23-3 | 23 | CATTTTTGTGCTCACCTGTGTTATC | 62 | SEQ ID NO. 57 |
| 24-1 | 24 | CATCTTTCCATTTTCCATTGGGATC | 36 | SEQ ID NO. 58 |

TABLE 1-continued

Antisense oligonucleotides targeting mouse CFTR induce exon skipping.

| Name | Target Exon | Sequence | % skipped * | SEQ ID NO. |
|---|---|---|---|---|
| 24-2 | 24 | CTCATCTGCAACTTTCCATATTTCT | 50 | SEQ ID NO. 59 |
| 24-3 | 24 | TATTTGTCATCCTTACCTCATCTGC | 67 | SEQ ID NO. 60 |

* percent of the mRNA transcripts that skip out the targeted exon

Example 2: Antisense Oligonucleotides Induce Skipping of Targeted Exons in Human CFTR Gene-Derived Pre-mRNA Various ASOs (see Table 2; SEQ ID NOs: 61-129) were tested in the human colonic adenocarcinoma cell line primary cell line. T84. ASOs (15 μM final concentration) were transfected into cells using Endo-Porter (GeneTools). FIGS. 2B, 2C, 2D and FIG. 3 demonstrate that ASOs induce skipping of targeted exons in human CFTR.

TABLE 2

Antisense oligonucleotides targeting human CFTR induce exon skipping

| Name | Target Exon | Sequence | % skipped * | SEQ ID NO. |
|---|---|---|---|---|
| 2-1 | 2 | ATCCTTTCCTCAAAATTGGTCTGGT | 0 | SEQ ID NO. 61 |
| 2-2 | 2 | GTATATGTCTGACAATTCCAGGCGC | 35 | SEQ ID NO. 62 |
| 2-3 | 2 | CAGATAGATTGTCAGCAGAATCAAC | 18 | SEQ ID NO. 63 |
| 2-4 | 2 | GTACATGAACATACCTTTCCAATTT | 37 | SEQ ID NO. 64 |
| 4-1 | 4 | GAGGCTGTACTGCTTTGGTGACTTC | 77 | SEQ ID NO. 65 |
| 4-2 | 4 | GAAGCTATGATTCTTCCCAGTAAGA | 54 | SEQ ID NO. 66 |
| 4-3 | 4 | GTGTAGGAGCAGTGTCCTCACAATA | 0 | SEQ ID NO. 67 |
| 4-4 | 4 | AATGTGATGAAGGCCAAAAATGGCT | 39 | SEQ ID NO. 68 |
| 4-5 | 4 | GCTATTCTCATCTGCATTCCAATGT | 0 | SEQ ID NO. 69 |
| 4-6 | 4 | CCTGTGCAAGGAAGTATTACCTTCT | 0 | SEQ ID NO. 70 |
| 5-1 | 5 | CTAGAACACGGCTTGACAGCTTTAA | 58 | SEQ ID NO. 71 |
| 5-2 | 5 | TGGAAAGGAGACTAACAAGTTGTCC | 42 | SEQ ID NO. 72 |
| 7-1 | 7 | ACTGATCTTCCCAGCTCTCTGATCT | 15 | SEQ ID NO. 73 |
| 7-2 | 7 | ATTTCTGAGGTAATCACAAGTCTTT | 37 | SEQ ID NO. 74 |
| 7-3 | 7 | AGTATGCCTTAACAGATTGGATATT | 28 | SEQ ID NO. 75 |
| 7-4 | 7 | ATTTTTTCCATTGCTTCTTCCCAGC | 44 | SEQ ID NO. 76 |
| 7-5 | 7 | ATTGGAACAACTTACTGTCTTAAGT | 38 | SEQ ID NO. 77 |
| 9-1 | 9 | TCCATCACTACTTCTGTAGTCGTTA | 56 | SEQ ID NO. 78 |
| 9-2 | 9 | CTCCTCCCAGAAGGCTGTTACATTC | 53 | SEQ ID NO. 79 |
| 9-3 | 9 | TTAAAAATTCTGACCTCCTCCCAGA | 33 | SEQ ID NO. 80 |
| 10-1 | 10 | GGCTGTCATCACCATTAGAAGTTTT | 64 | SEQ ID NO. 81 |
| 10-2 | 10 | AATTACTGAAGAAGAGGCTGTCATC | 56 | SEQ ID NO. 82 |
| 10-3 | 10 | TAATATCTTTCAGGACAGGAGTACC | 49 | SEQ ID NO. 83 |
| 10-4 | 10 | GATCCAGCAACCGCCAACAACTGTC | 52 | SEQ ID NO. 84 |

TABLE 2-continued

Antisense oligonucleotides targeting human CFTR induce exon skipping

| Name | Target Exon | Sequence | % skipped * | SEQ ID NO. |
|---|---|---|---|---|
| 10-5 | 10 | AGAACAAAAGAACTACCTTGCCTGC | 47 | SEQ ID NO. 85 |
| 11-1 | 11 | CTCCCATAATCACCATTAGAAGTGA | 2 | SEQ ID NO. 86 |
| 11-2 | 11 | ATTTTACCCTCTGAAGGCTCCAGTT | 2 | SEQ ID NO. 87 |
| 11-3 | 11 | ACAGAATGAAATTCTTCCACTGTGC | 2 | SEQ ID NO. 88 |
| 11-4 | 11 | GTGCCAGGCATAATCCAGGAAAACT | 14 | SEQ ID NO. 89 |
| 11-5 | 11 | ATGCTTTGATGACGCTTCTGTATCT | 2 | SEQ ID NO. 90 |
| 11-6 | 11 | TTTTCACATAGTTTCTTACCTCTTC | 72 | SEQ ID NO. 91 |
| 13-1 | 13 | TCTAGGTATCCAAAAGGAGAGTCTA | 90 | SEQ ID NO. 92 |
| 13-2 | 13 | GGTATTCAAAGAACATACCTTTCAA | 66 | SEQ ID NO. 93 |
| 15-1 | 15 | ACAATAGAACATTCTTACCTCTGCC | 93 | SEQ ID NO. 94 |
| 16-1 | 16 | TCGTTATTTGGCAGCCAAAGTTACT | n/a | SEQ ID NO. 95 |
| 16-2 | 16 | GAGCCACAGCACAACCAAAGAAGCA | n/a | SEQ ID NO. 96 |
| 16-3 | 16 | TCCAAGGAGCCACAGCAC | n/a | SEQ ID NO. 97 |
| 16-4 | 16 | TTCCAAGGAGCCACAGCA | n/a | SEQ ID NO. 98 |
| 16-5 | 16 | TTCCAAGGAGCCACAGCACAACCAA | n/a | SEQ ID NO. 99 |
| 16-6 | 16 | AACAGAAATAAAACACAATCTACAC | n/a | SEQ ID NO. 100 |
| 16-7 | 16 | TTTCCAAGGAGCCACAGCACAACCA | 0 | SEQ ID NO. 101 |
| 16-8 | 16 | ACAATCTACACAATAGGACATGGAA | 56 | SEQ ID NO. 102 |
| 16-9 | 16 | CACAATCTACACAATAGGACATGGA | n/a | SEQ ID NO. 103 |
| 16-10 | 16 | ACACAATCTACACAATAGGACATGG | n/a | SEQ ID NO. 104 |
| 16-11 | 16 | GACTTTTTTTCTAACATCTTCACCT | n/a | SEQ ID NO. 105 |
| 16-12 | 16 | ATGGAACAACACACAGTTGATTTTT | n/a | SEQ ID NO. 106 |
| 16-13 | 16 | ATCGAACAAGACACAGTTGATTTTT | n/a | SEQ ID NO. 107 |
| 16-14 | 16 | GAGTGGAACAAGACACAGTTGATTT | n/a | SEQ ID NO. 108 |
| 16-15 | 16 | CACAATCTACACAATAAGACATGGA | n/a | SEQ ID NO. 109 |
| 20-1 | 20 | CAAGATGAGTGAAAATTGGACTCCT | 2 | SEQ ID NO. 110 |
| 20-2 | 20 | CGAAGGCACGAAGTGTCCATAGTCC | 29 | SEQ ID NO. 111 |
| 20-3 | 20 | AACAGAGTTTCAAAGTAAGGCTGCC | 8 | SEQ ID NO. 112 |
| 20-4 | 20 | AGTTGGCAGTATGTAAATTCAGAGC | 6 | SEQ ID NO. 113 |
| 20-5 | 20 | TTCTATTCTCATTTGGAACCAGCGC | 45 | SEQ ID NO. 114 |
| 20-6 | 20 | GGTAACAGCAATGAAGAAGATGACA | 35 | SEQ ID NO. 115 |
| 22-1 | 22 | ATGTCAATGAACTTAAAGACTCGGC | 59 | SEQ ID NO. 116 |
| 22-2 | 22 | GGCCAGATGTCATCTTTCTTCACGT | 65 | SEQ ID NO. 117 |
| 22-3 | 22 | ATCTTTGACAGTCATTTGGCCCCCT | 7 | SEQ ID NO. 118 |
| 22-4 | 22 | CCACCTTCTGTGTATTTTGCTGTGA | 45 | SEQ ID NO. 119 |
| 22-5 | 22 | TCTCTAATATGGCATTTCCACCTTC | 67 | SEQ ID NO. 120 |
| 22-6 | 22 | CCAGGACTTATTGAGAAGGAAATGT | 37 | SEQ ID NO. 121 |
| 22-7 | 22 | AAGCAGTGTTCAAATCTCACCCTCT | 63 | SEQ ID NO. 122 |

TABLE 2-continued

Antisense oligonucleotides targeting human CFTR induce exon skipping

| Name | Target Exon | Sequence | % skipped * | SEQ ID NO. |
|---|---|---|---|---|
| 23-1 | 23 | ATCCAGTTCTTCCCAAGAGGCCCAC | 0 | SEQ ID NO. 123 |
| 23-2 | 23 | AGCTGATAACAAAGTACTCTTCCCT | 0 | SEQ ID NO. 124 |
| 23-3 | 23 | AAGTTATTGAATCCCAAGACACACC | 0 | SEQ ID NO. 125 |
| 23-4 | 23 | CTAAGTCCTTTTGCTCACCTGTGGT | 24 | SEQ ID NO. 126 |
| 24-1 | 24 | GATCACTCCACTGTTCATAGGGATC | 59 | SEQ ID NO. 127 |
| 24-2 | 24 | CTCATCTGCAACTTTCCATATTTCT | 53 | SEQ ID NO. 128 |
| 24-3 | 24 | ATTTCAGTTAGCAGCCTTACCTCAT | 66 | SEQ ID NO. 129 |

* percent of the mRNA transcripts that skip out the targeted exon

Example 3: HCAI-CFTR Deletions in Fischer Rat Thyroid Cells

Figure 18A:
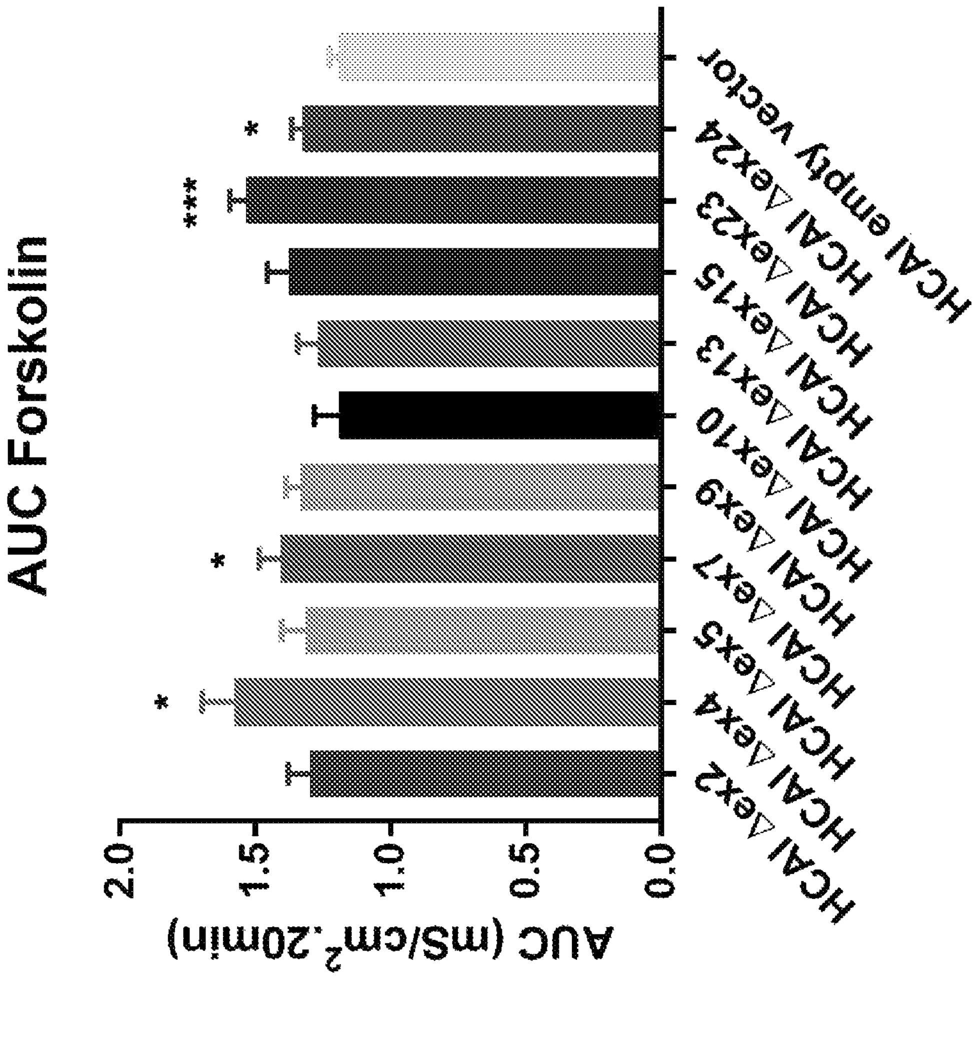
FIG. 18A shows a comparison of the AUC forskolin-stimulated HCAI-CFTR exon deletion channel activity in Fischer Rat Thyroid (FRT) cells to HCAI empty vector. Error bars represent SEM (*$p<0.05$, ***$p<0.001$, n=4, two-tailed t-test compared to HCAI empty vector).
Figure 18B:
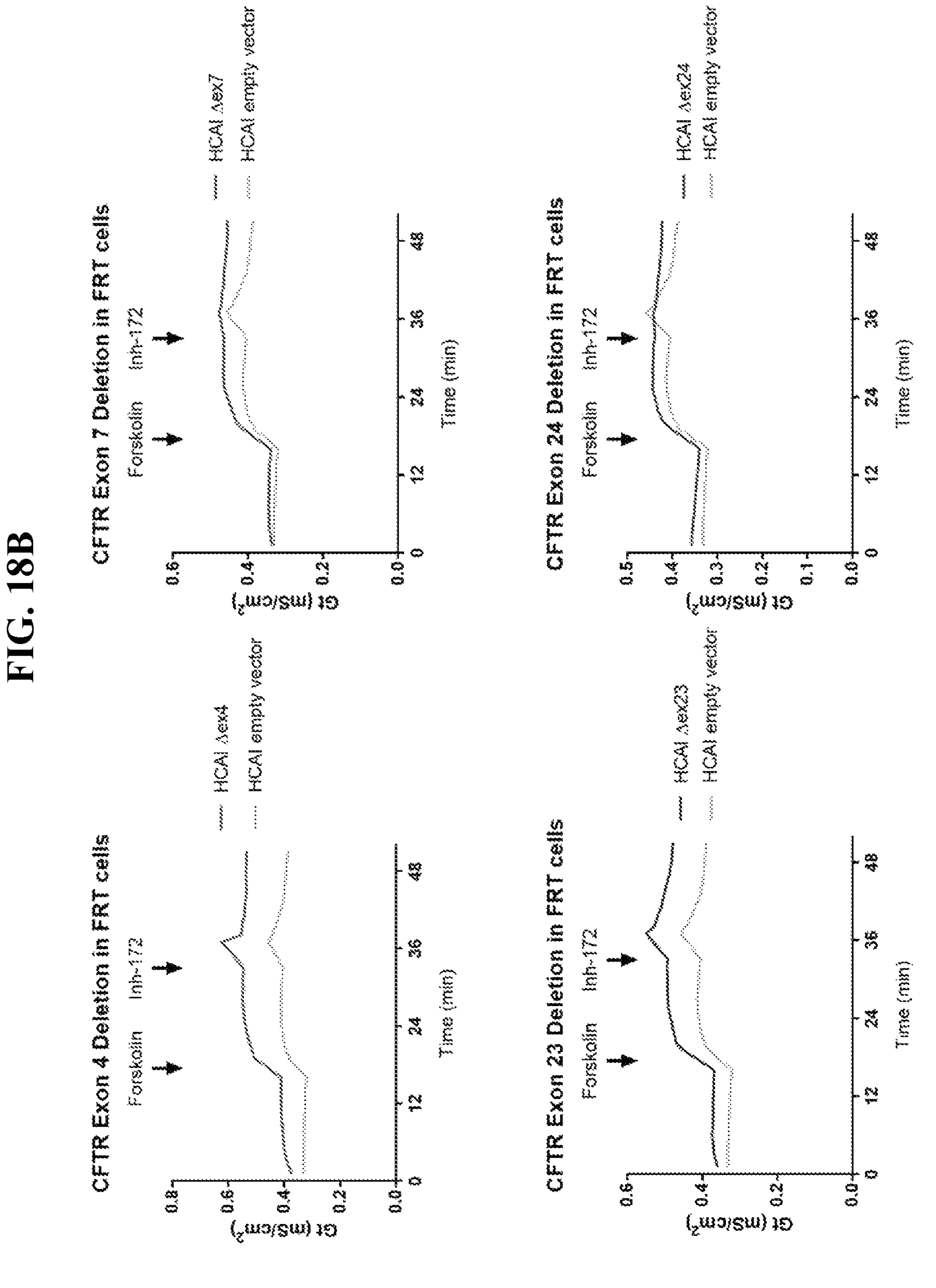
FIG. 18B shows representative Gt traces of CFTR exon 4, exon 7, exon 23, and exon 24 deletion constructs in Fischer Rat Thyroid (FRT) cells in comparison to HCAI empty vector.

Fischer Rat Thyroid (FRT) cells, which lack functional CFTR, were stably transfected with nucleic acids encoding human CFTR with deletions of exon 2, 4, 5, 7, 9, 10, 13, 15, 23, or 24 (HCAIΔex2, HCAIΔex4, HCAIΔex5, HCAIΔex7, HCAIΔex9, HCAIΔex10, HCAIΔex13, HCAIΔex15 HCAIΔex23, or HCAIΔex24). FRT cells stably the HCAI-CFTR exon deletions were seeded onto HTS Transwell®-24 well permeable filter plates (0.4 μM pore size, Polyester, Corning) and differentiated for 2 weeks. Transepithelial conductance was assessed in Gt assays that were performed 14 days after cell seeding. The data were recorded with 24-channel transepithelial current clamp (TECC)_Robot system (Design, Belgium). HCAI-CFTR activity was measured by the change in Gt upon stimulation with forskolin (10 μM). CFTRInh-172 (10 μM) was used to confirm CFTR dependence. A comparison of the AUC forskolin-stimulated HCAI-CFTR exon deletion channel activity to HCAI empty vector is shown in FIG. 18A (error bars represent SEM; $*p<0.05$, $*p<0.001$, n=4, two-tailed t-test compared to HCAI empty vector). Representative Gt traces of CFTR exon 4, exon 7, exon 23, and exon 24 deletion constructs in comparison to HCAI empty vector are shown in FIG. 18**B.

Figure 19A:
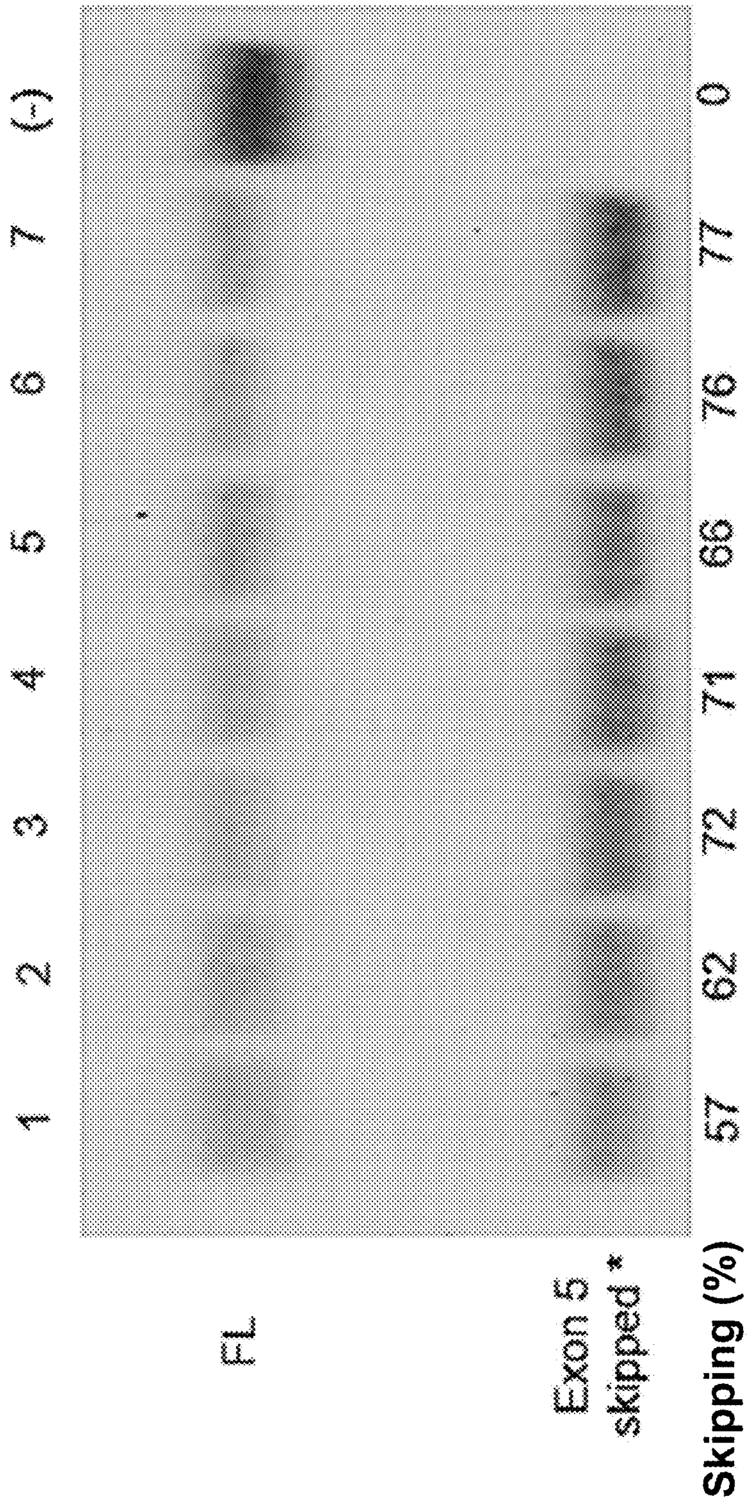
FIG. 19A shows a radioactive RT-PCR of CFTR RNA isolated from hippocampus that demonstrates that ASO 5-1 induces CFTR exon 5 skipping in vivo. Splice isoforms are labeled and exon 5 skipping quantification is shown at the bottom.
Figure 19B:
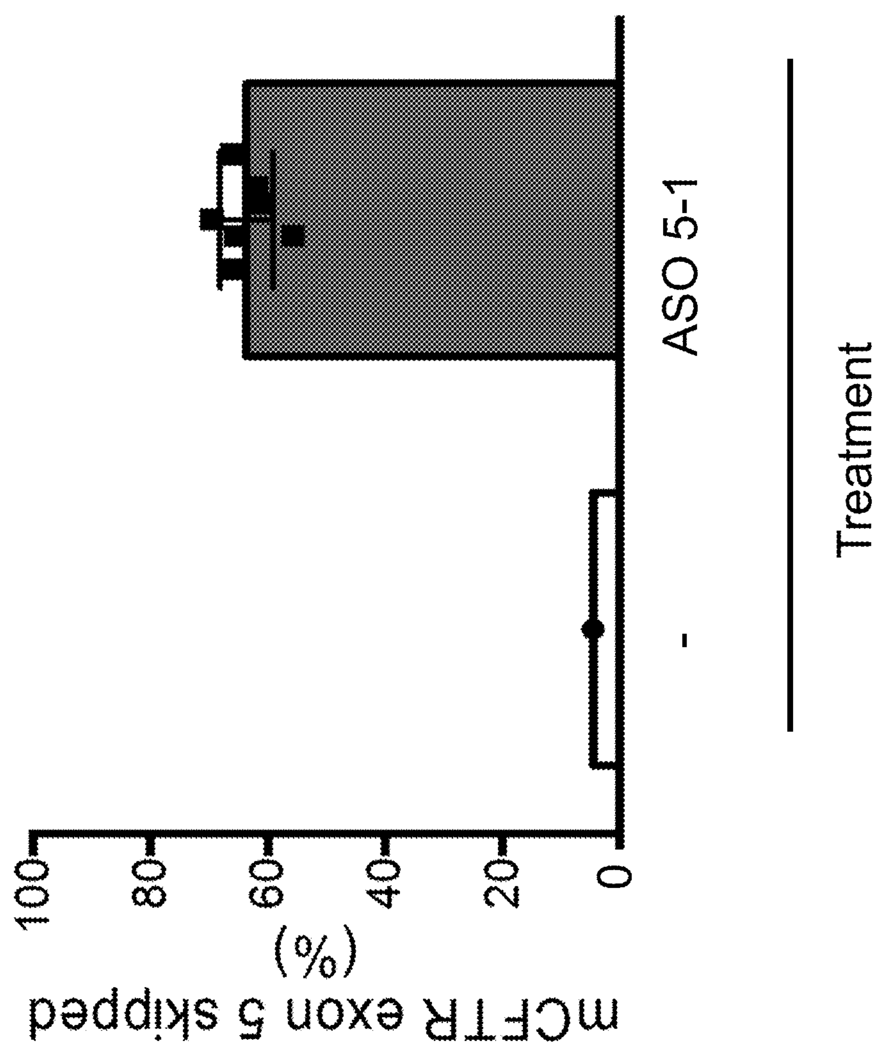
FIG. 19B shows a quantitation of the RT-PCR analysis of the RNA exon 5 skipping induced by ASO treatment. Approximately 60% of mouse CFTR gene exon 5 is skipped when mice are treated with ASO 5-1 by ICV injection.

Example 4: Antisense Oligonucleotides Induce Exon Skipping of Exons with Nonsense Mutations in CFTR In Vivo and Restore the CFTR Reading Frame ASO 5-1 (SEQ ID NO:12) was tested in mice and shown to induces CFTR exon 5 skipping. Intracerebroventricular (ICV) injection of mCFex5-1 was performed in wild-type mice (C57Bl/6) on post-natal day 2, and mice were euthanized on post-natal day 12. RNA was collected from the hippocampus. Radioactive RT-PCR of CFTR RNA isolated from hippocampus is shown in FIG. 19A (splice isoforms are labeled and exon 5 skipping quantification is shown at the bottom). A quantitation of the RT-PCR analysis of the RNA exon 5 skipping induced by ASO 5-1 treatment is shown in FIG. 19B.

Figure 20A:
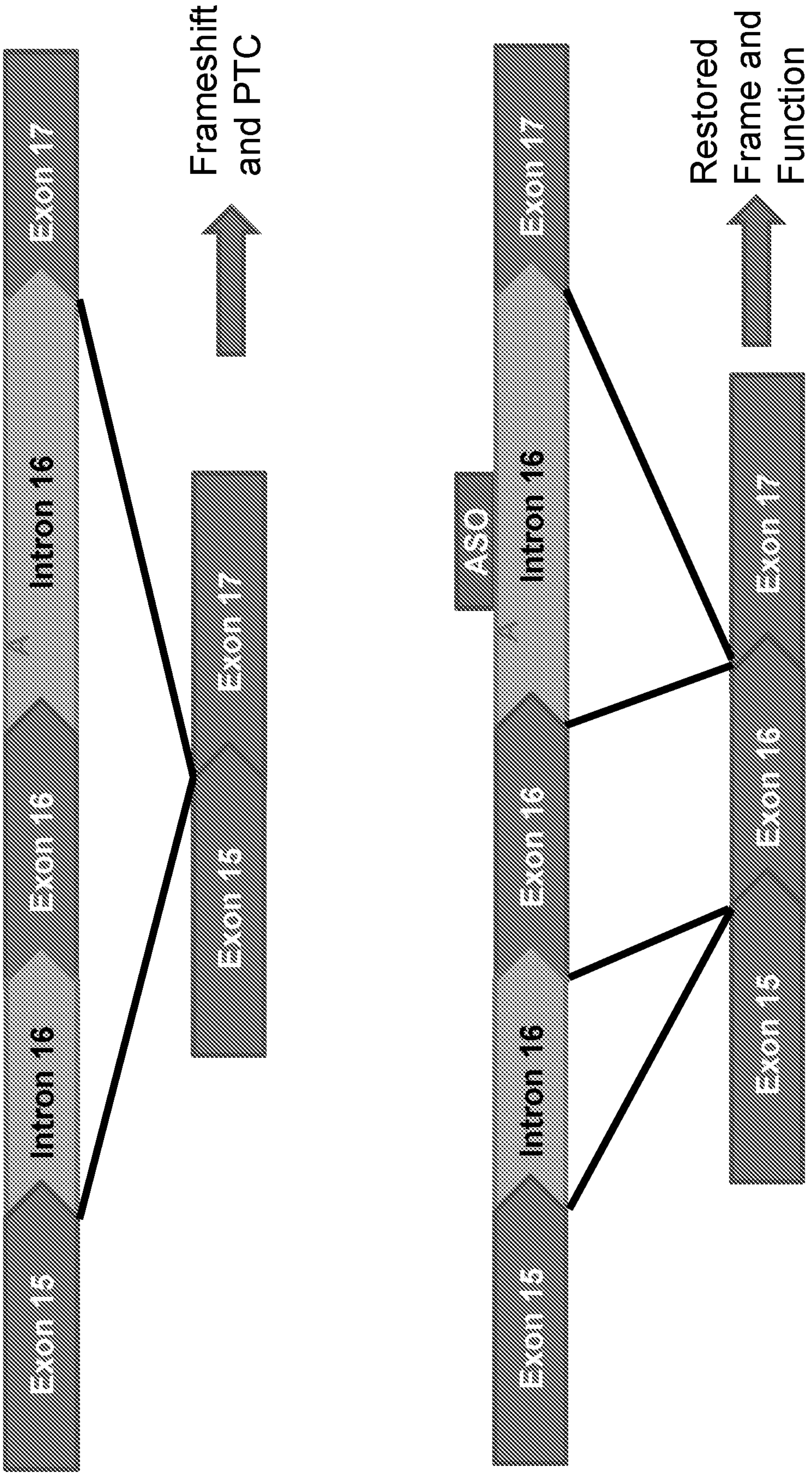
FIG. 20A shows a schematic for antisense oligonucleotides to correct CFTR 2789+5 G>A splicing mutation.
Figure 20B:
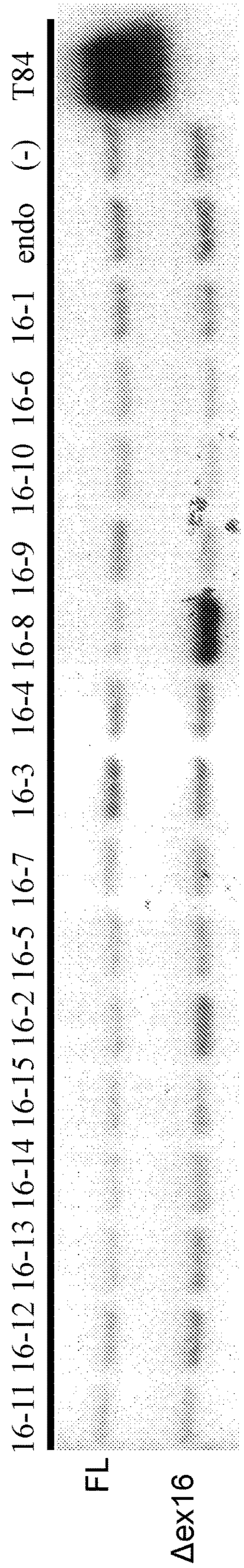
FIG. 20B shows a radioactive RT-PCR of CFTR RNA isolated from 2789+5 patient lymphoblast cells transfected with ASOs (15 μM) for 48 hours. The results demonstrate correction of CFTR splicing in 2789+5 patient lymphoblast cells using ASOs. The CFTR spliced isoforms are labelled. T84 cells were analyzed as a positive control for wild-type CFTR splicing.
Figure 20C:
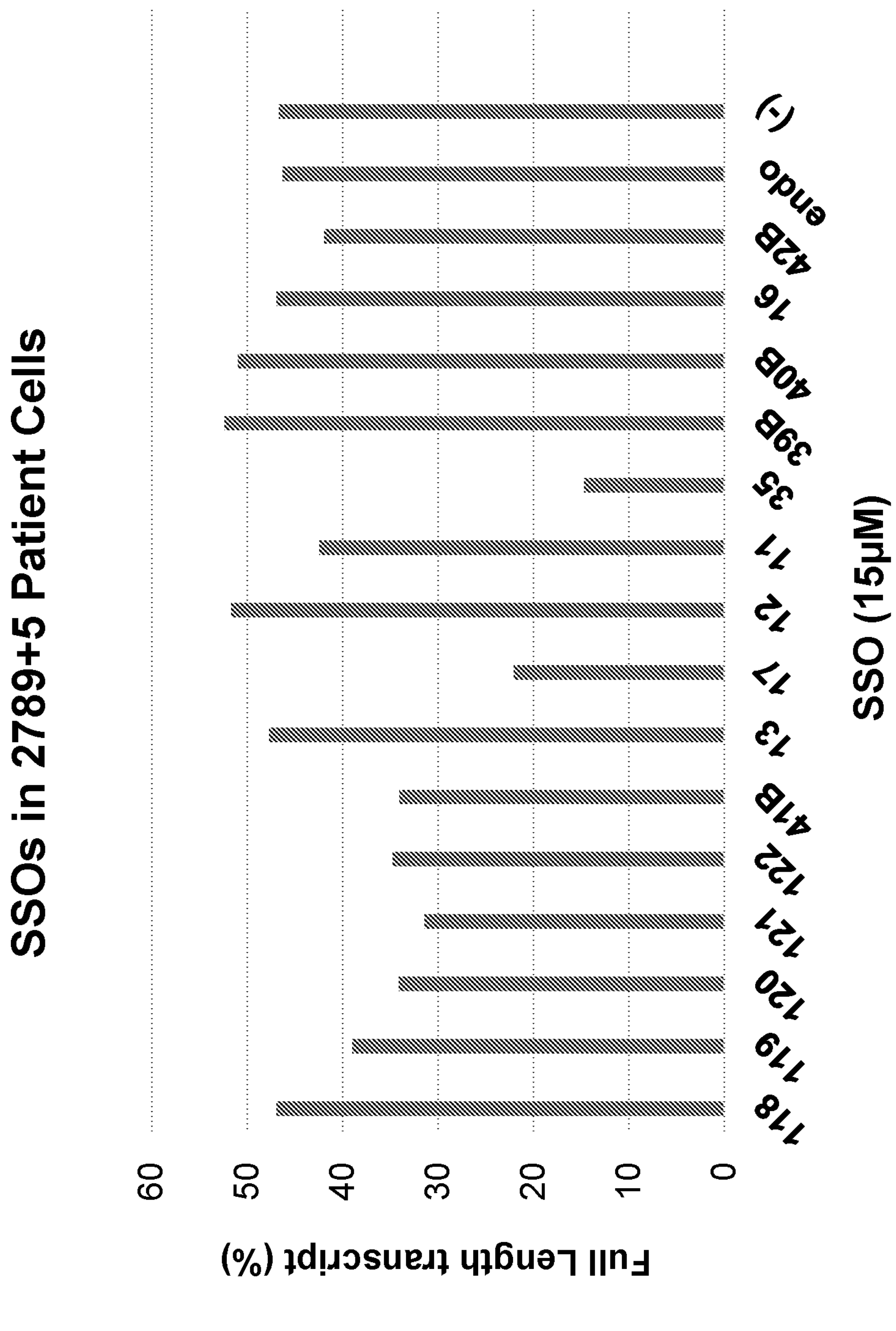
FIG. 20C shows a quantitation of the RT-PCR analysis of the RNA splice correction induced by ASO treatment in patient lymphoblast cells.

Example 5: Antisense Oligonuleotides to Correct CFTR 2789+5 G>A Splicing Mutation Antisense oligonucleotides were designed that increase correct splicing in 2789+5 G>A in patient lymphoblast cells lines. The lymphoblast cell line 11859, which is homozygous for the 2789+5 G>A mutation, was transfected with ASOs that were designed to correct the splicing in CFTR 2789+5 G>A (ASO concentration of 15 μM; and cells were treated for 48 hours). Correction of CFTR splicing in 2789+5 the lymphoblasts using ASOs is shown in FIG. 20B (CFTR spliced isoforms are labeled; T84 cells were analyzed as a positive control for wild-type CFTR splicing). A quantitation of the RT-PCR analysis of the RNA splice correction induced by ASO treatment in patient lymphoblast cells is shown in FIG. 20C. A summary of the 2789+5 ASOs targets, sequences, and correction activity in patient lymphoblast cells is shown in Table 3.

TABLE 3

ASO sequences tested in the 2789 +5 lymphoblast cell line.

| Name | Target Region | Sequence (SEQ ID NO.) | % Full Length |
|---|---|---|---|
| 16-11 | Intron 15 | GACTTTTTTTCTAACATCTTCACCT (SEQ ID NO.: 105) | 47 |
| 16-12 | Intron 15 | ATGGAACAACACACAGTTGATTTTT (SEQ ID NO.: 106) | 39 |
| 16-13 | Intron 15 | ATCGAACAAGACACAGTTGATTTTT (SEQ ID NO.: 107) | 34 |
| 16-14 | Intron 15 | GAGTGGAACAAGACACAGTTGATTT (SEQ ID NO.: 108) | 31 |
| 16-9 | Exon 16 | CACAATCTACACAATAAGACATGGA (SEQ ID NO.: 109) | 35 |
| 16-2 | Exon 16 | GAGCCACAGCACAACCAAAGAAGCA (SEQ ID NO.: 96) | 34 |
| 16-5 | Exon 16 | TTCCAAGGAGCCACAGCACAACCAA (SEQ ID NO.: 99) | 48 |
| 16-7 | Exon 16 | TTTCCAAGGAGCCACAGCACAACCA (SEQ ID NO.: 101) | 22 |
| 16-3 | Exon 16 | TCCAAGGAGCCACAGCAC (SEQ ID NO.: 97) | 52 |
| 16-4 | Exon 16 | TTCCAAGGAGCCACAGCA (SEQ ID NO.: 98) | 42 |
| 16-8 | Intron 16 | ACAATCTACACAATAGGACATGGAA (SEQ ID NO.: 102) | 15 |

TABLE 3-continued

ASO sequences tested in the 2789 +5 lymphoblast cell line.

| Name | Target Region | Sequence (SEQ ID NO.) | % Full Length |
|---|---|---|---|
| 16-9 | Intron 16 | CACAATCTACACAATAGGACATGGA (SEQ ID NO.: 103) | 52 |
| 16-10 | Intron 16 | ACACAATCTACACAATAGGACATGG (SEQ ID NO.: 104) | 51 |
| 16-6 | Intron 16 | AACAGAAATAAAACACAATCTACAC (SEQ ID NO.: 100) | 47 |
| 16-1 | Intron16 | TCGTTATTTGGCAGCCAAAGTTACT (SEQ ID NO.: 95) | 42 |

Figure 21A:
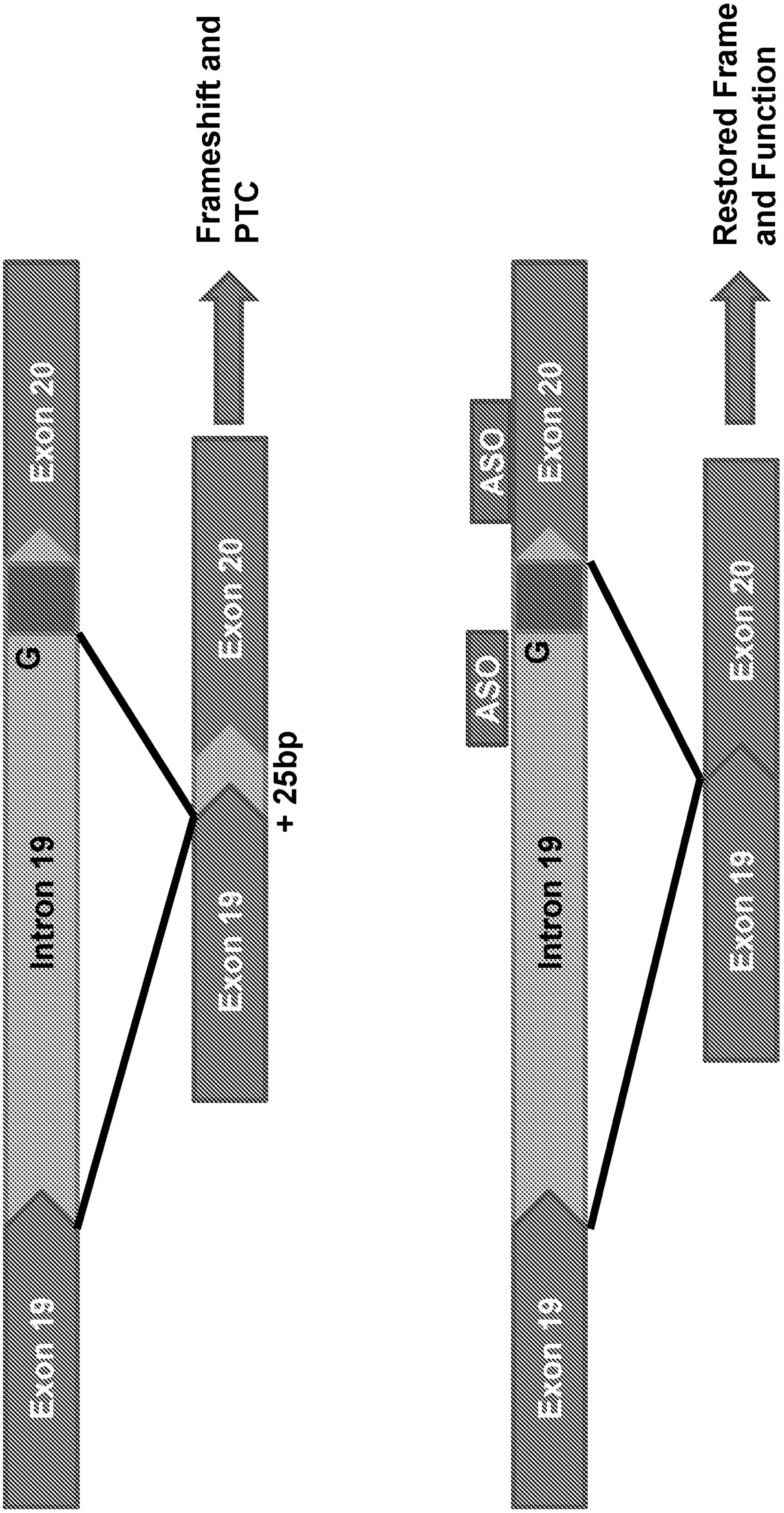
FIG. 21A shows a schematic for antisense oligonucleotides to correct CFTR 3272–26A>G splicing mutation.
Figure 21B:
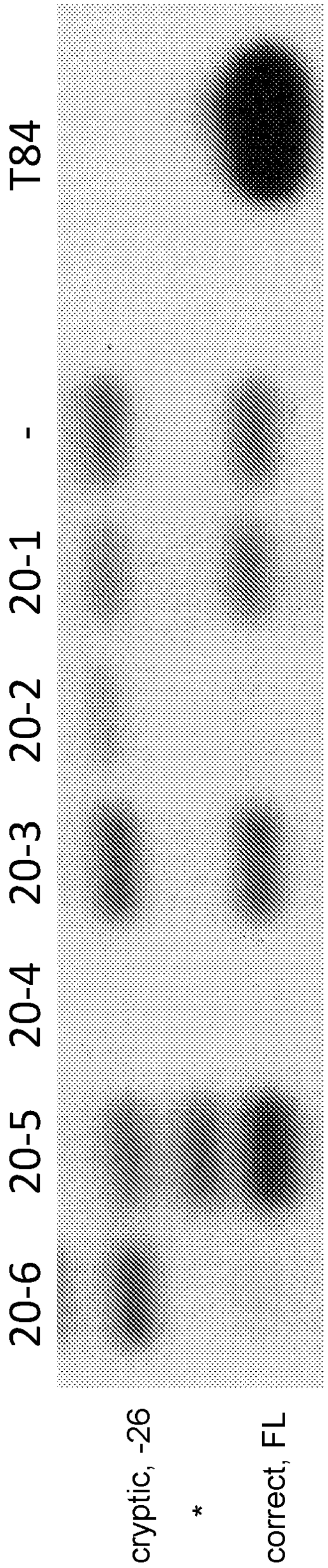
FIG. 21B shows a radioactive RT-PCR of CFTR RNA isolated from 3272–26A>G patient lymphoblast cells transfected with ASOs (15 μM) for 48 hours. The results demonstrate correction of CFTR splicing in 3272–26A>G patient lymphoblast cells using ASOs. The CFTR spliced isoforms are labelled. T84 cells were analyzed as a positive control for wild-type CFTR splicing.

Example 6: Antisense Oligonucleotides to Correct CFTR 3272-26 A>G Splicing Mutation Antisense oligonucleotides were designed that increase correct splicing in 3272-26 A>G mutation in patient lymphoblast cell lines. The lymnphoblast cell line 18801 (18801 is from a male donor with one allele carrying the 3272-26 A>G mutation, and no mutation was identified in the second allele) was transfected with ASOs that were designed to correct splicing in CFTR 3272-26 A>G (ASOs were transfected with Endo-Porter, the ASO concentration was 15 μM, and cells were treated for 48 hours). Correction of CFTR splicing in CFTR 3272-26 A>G in the lymphoblast cells using ASOs is shown in FIG. 21B (CFTR spliced isoforms are labeled; T84 cells were analyzed as a positive control for wild-type CFTR splicing). A summary of the CFTR 3272-26 A>G ASOs targets, sequences, and correction activity in patient lymphoblast cells is shown in Table 4.

| Name | Target Exon | Sequence (SEQ ID NO.) | % Full-Length |
|---|---|---|---|
| 20-1 | 20 | CAAGATGAGTGAAAATTGGACTCCT (SEQ ID NO.: 110) | 60 |
| 20-2 | 20 | CGAAGGCACGAAGTGTCCATAGTCC (SEQ ID NO.: 111) | 3 |
| 20-3 | 20 | AACAGAGTTTCAAAGTAAGGCTGCC (SEQ ID NO.: 112) | 50 |
| 20-4 | 20 | AGTTGGCAGTATGTAAATTCAGAGC (SEQ ID NO.: 113) | nd |
| 20-5 | 20 | TTCTATTCTCATTTGGAACCAGCGC (SEQ ID NO.: 114) | 56 |
| 20-6 | 20 | GGTAACAGCAATGAAGAAGATGACA (SEQ ID NO.: 115) | 12 |

Figure 22A:
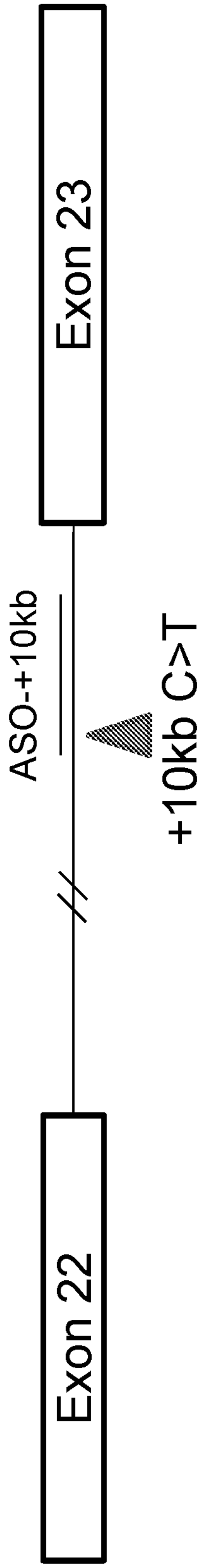
FIG. 22A shows a diagram of ASOs used for the correction of CFTR splicing in 3849+10 kb patient lymphoblast cells using ASOs. The +10C>T mutation is labeled.
Figure 22B:
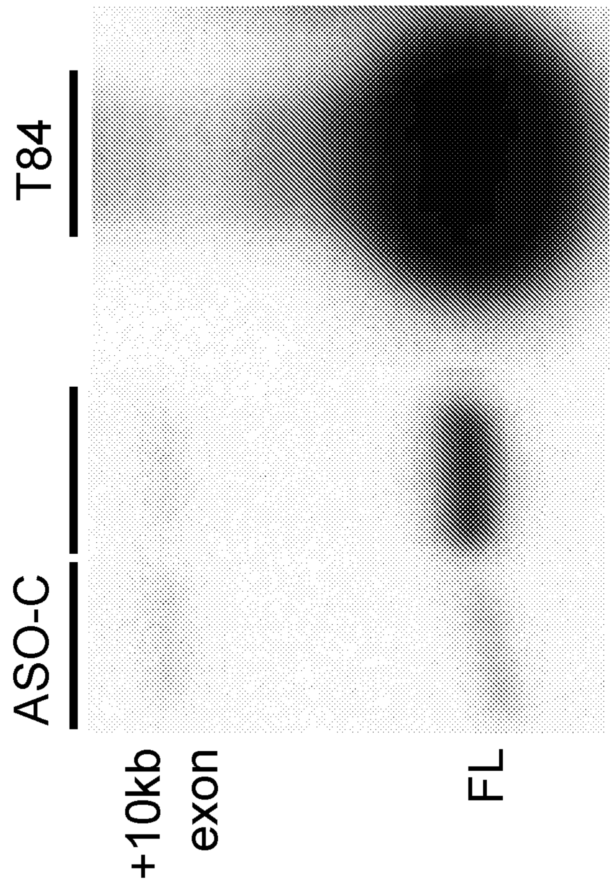
FIG. 22B shows the results of a RT-PCR assay of CFTR RNA isolated from 3849+10 kb patient lymphoblast cells transfected with ASOs (15 μM) for 48 hours. Results indicate a correction of CFTR splicing in 3849+10 kb patient lymphoblast cells using the ASOs. CFTR spliced isoforms are labeled. T84 cells were analyzed as a positive control for wild-type CFTR splicing (FL=Full-Length).
Figure 22C:
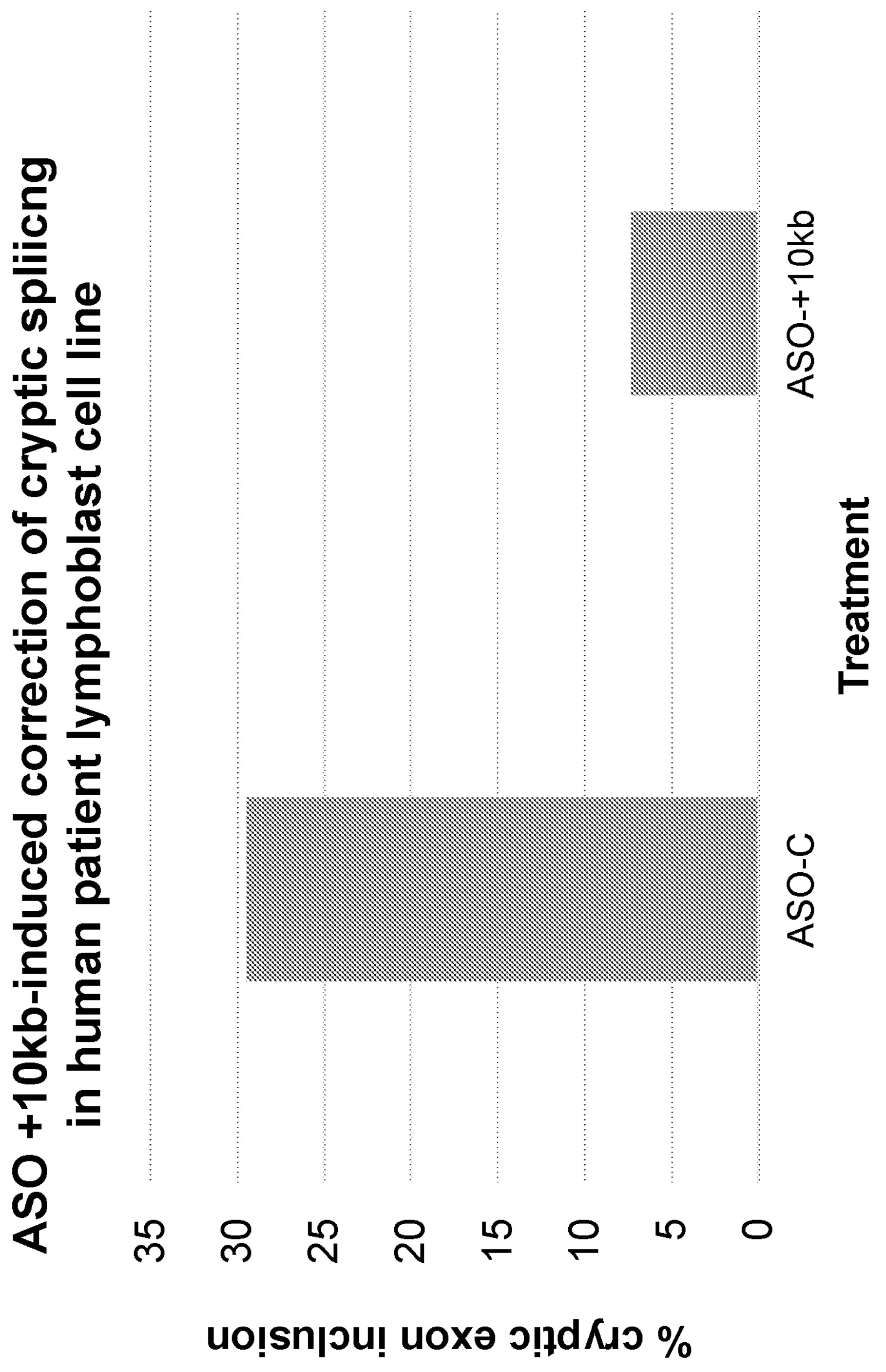
FIG. 22C shows a quantitation of the RT-PCR analysis of the RNA splice correction induced by ASO treatment in patient lymphoblast cells. The results indicate about a four-fold reduction of inclusion of the cryptic exon, resulting in approximately 93% of the CFTR transcripts being full-length.

Example 7: Antisense Oligonucleotides to Correct CFTR 3849+10 kb C>T Splicing Mutation Antisense oligonucleotides were designed to repair the 3849+10 kb C>T splice mutation and restore CFTR function. The C>T mutation creates a cryptic 5' splice site that results in the inclusion of an 84 bp insert from intron 22, and the mutated allele produces both wild-type and aberrantly spliced transcripts. The lymphoblast cell line 18860 (18860 is homozygous for 3849+10 kb CFTR mutation) was transfected with ASOs that were designed to correct splicing in 3849+10 kb C>T (ASOs were transfected with Endo-Porter, the ASO concentration was 15 μM, and cells were treated for 48 hours). Correction of CFTR splicing in 3849+10 kb C>T in the lymphoblast cells using ASOs is shown in FIGS. 22B and 22C (CFTR spliced isoforms are labeled; T84 cells were analyzed as a positive control for wild-type CFTR splicing). A summary of the CFTR 3849+10 kb C>T ASO target, sequence, and correction activity in patient lymphoblast cells is shown in Table 5.

| Name | Target Exon | Sequence (SEQ ID NO.) | % Full-Length |
|---|---|---|---|
| ASO-+10 kb | Intron 22 | CCTTTCAGGGTGTCTTACTCACCAT (SEQ ID NO.: 150) | 93 |

Example 8. Analyzing CFTR Function in Patient Epithelial Cells Treated with ASOs Primary patient human bronchial epithelial (HBE) cells (cells are compound heterozygotes with the 3849+10 kbC>T and ΔF508 mutation) were seeded on HTS Transwell®-24 well permeable filter plates (0.4 uM pore size, Polyester, Corning) and switched to air/liquid interphase after 3 days. Ieq measurements were carried out 99 days after seeding. Cells were treated basolaterally with C18 (Corr951/VX-661, 6 μM) or DMSO (0.1%), and apically transfected with ASO-+10 kb (SEQ ID NO:150 at 20 μM or 80 μM) or ASO-C (20 μM or 80 μM; 5' CCTCTTACCTCAGTTACAATTTATA 3'—SEQ ID NO:151) 4 days before Ieq measurements were taken. C18 is a corrector compound that improves F508del-CFTR folding and function. Cells were transfected using EGTA (4 mM) and Endo-Porter (Gene-Tools) for 10 hours, then EGTA was taken off and the cells were transfected again using Endo-Porter in the absence of EGTA. The data were recorded with 24-channel transepithelial current clamp (TECC) Robot system (Design, Belgium). Sodium current was inhibited by benzamil (6 μM) and CFTR activity was measured by the change in Ieq upon stimulation with forskolin (10 μM) and VX-770/KALYDECO™/Ivacaftor (1 μM), which is a CFTR potentiator that improves the transport of chloride through the CFTR channel. Inhibition with bumetanide/BUMEX™/BURINEX™ (20 μM) was used to confirm CFTR dependence.

Figure 23A:
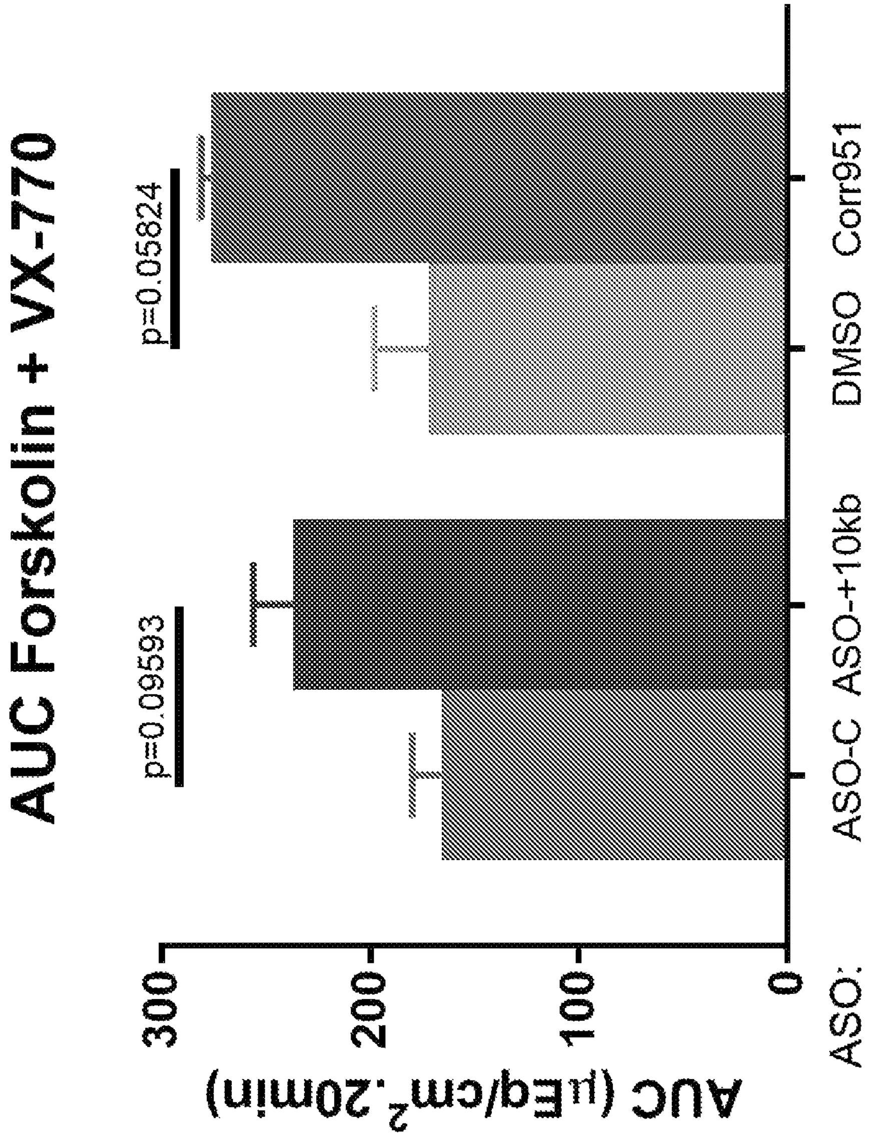
FIG. 23A shows that ASO-+10 kb rescues CFTR function similar to Corr951(VX-770) in patient HBE cells. The graph depicts the area under the curve (AUC) of time from forskolin+VX-770-stimulation of CFTR channels following indicated treatment. Error bars represent SEM (two-tailed t-test, n=2).
Figure 23B:
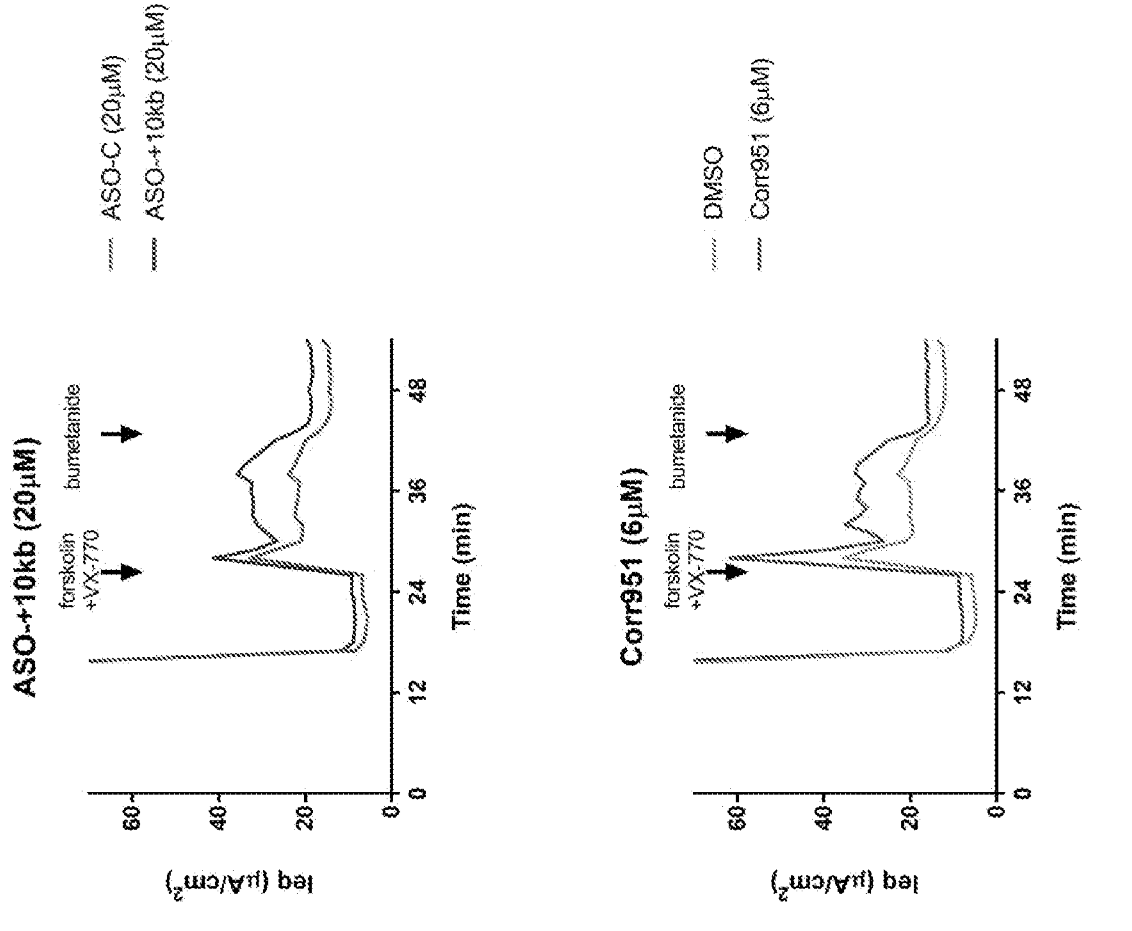
FIG. 23B shows ASO-+10 kb rescues CFTR function similar to Corr951 inpatient HBE cells. Representative Ieq traces of treatment (Corr951 or ASO-+10 kb) compared to control (ASO-C, top, or DMSO, bottom).

The results demonstrate that ASO-+10 kb (SEQ ID NO:150) rescues CFTR function similar to Corr951/VX-661 (CFTR corrector 106951 (1-(benzo[d][1,3]dioxol-5-yl)-N-(5-((S)-(2-chlorophenyl)((R)-3-hydroxypyrrolidin-1-yl) methyl)thiazol-2-yl)cyclopropanecarboxamide)) in patient HBE cells. As shown in FIG. 23, ASO-410 kb rescues CFTR function similar to Corr951 in patient HBE cells. FIG. 23A is a graph showing the area under the curve (AUC) of time from forskolin+VX-770-stimulation of CFTR channels following indicated treatment (error bars represent SEM; two-tailed t-test, n=2). FIG. 23B depicts representative Ieq traces of treatment (Corr951 or ASO-+10 kb) compared to control (ASO-C, top, or DMSO, bottom).

Figure 24A:
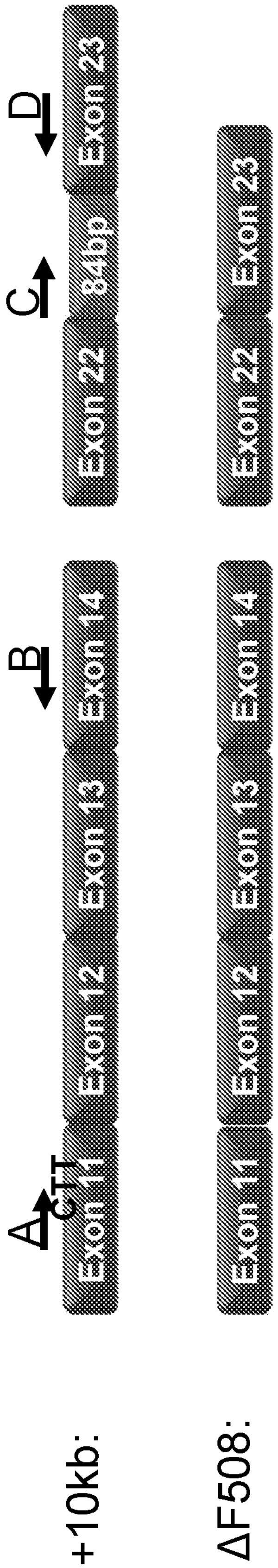
FIG. 24A shows a diagram of primer sets used to analyze splice correction by ASO-10+ kb. Primer set A-B is designed to amplify ASO corrected WT isoform splicing specific to the splice mutant allele. Primer set C-D is designed to analyze the amount of uncorrected mutant splicing FIG. 24B show a quantification of total mRNA transcribed from the CFTR 3849+10 kB allele indicates an increase with ASO-+10 kb treatment (A-B primer set shown in FIG. 24A).
Figure 24B:
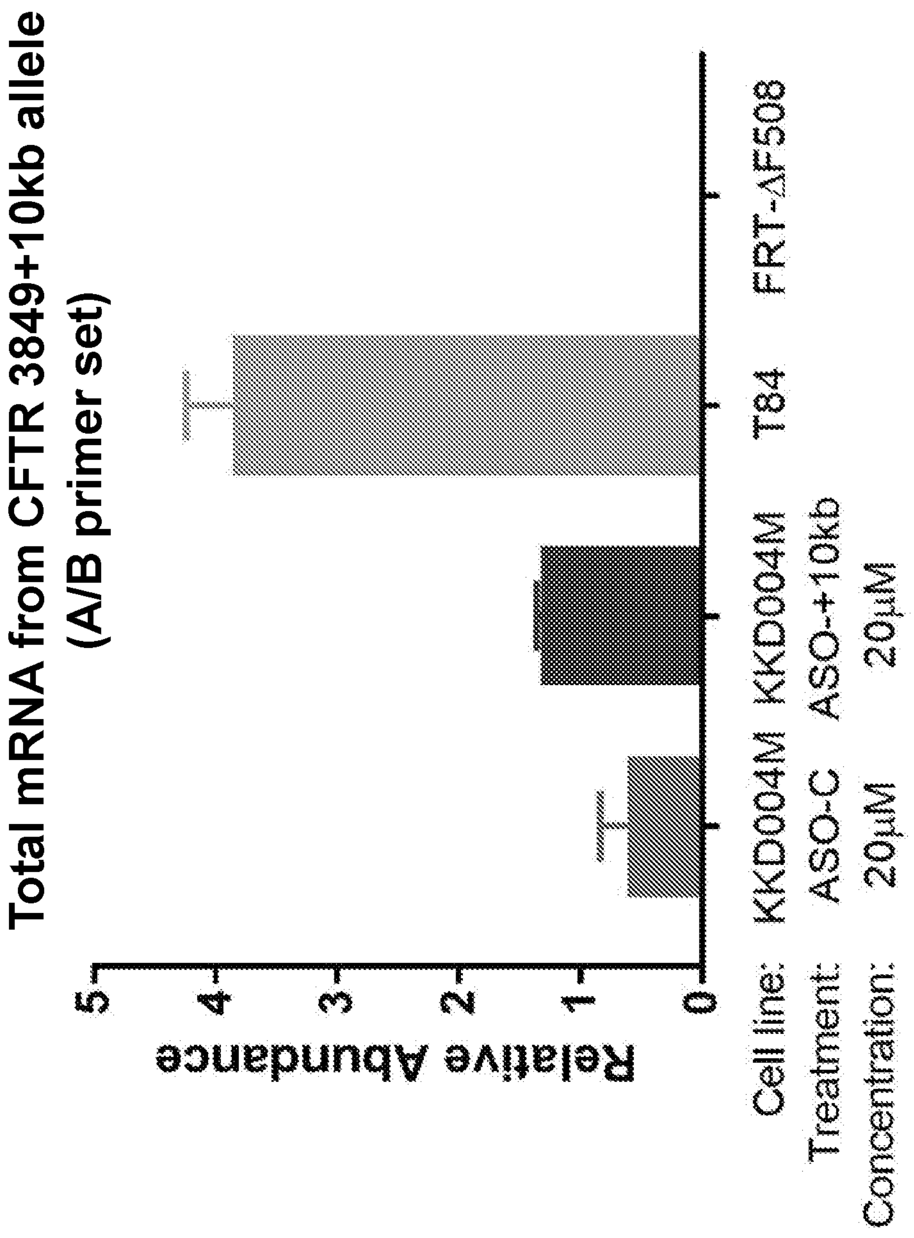
FIG. 24C shows a quantification of mutant, cryptically spliced mRNA isoform shows decrease of aberrant mRNA with ASO-+10 kb treatment (C-D primer set shown in FIG. 24A).
Figure 24C:
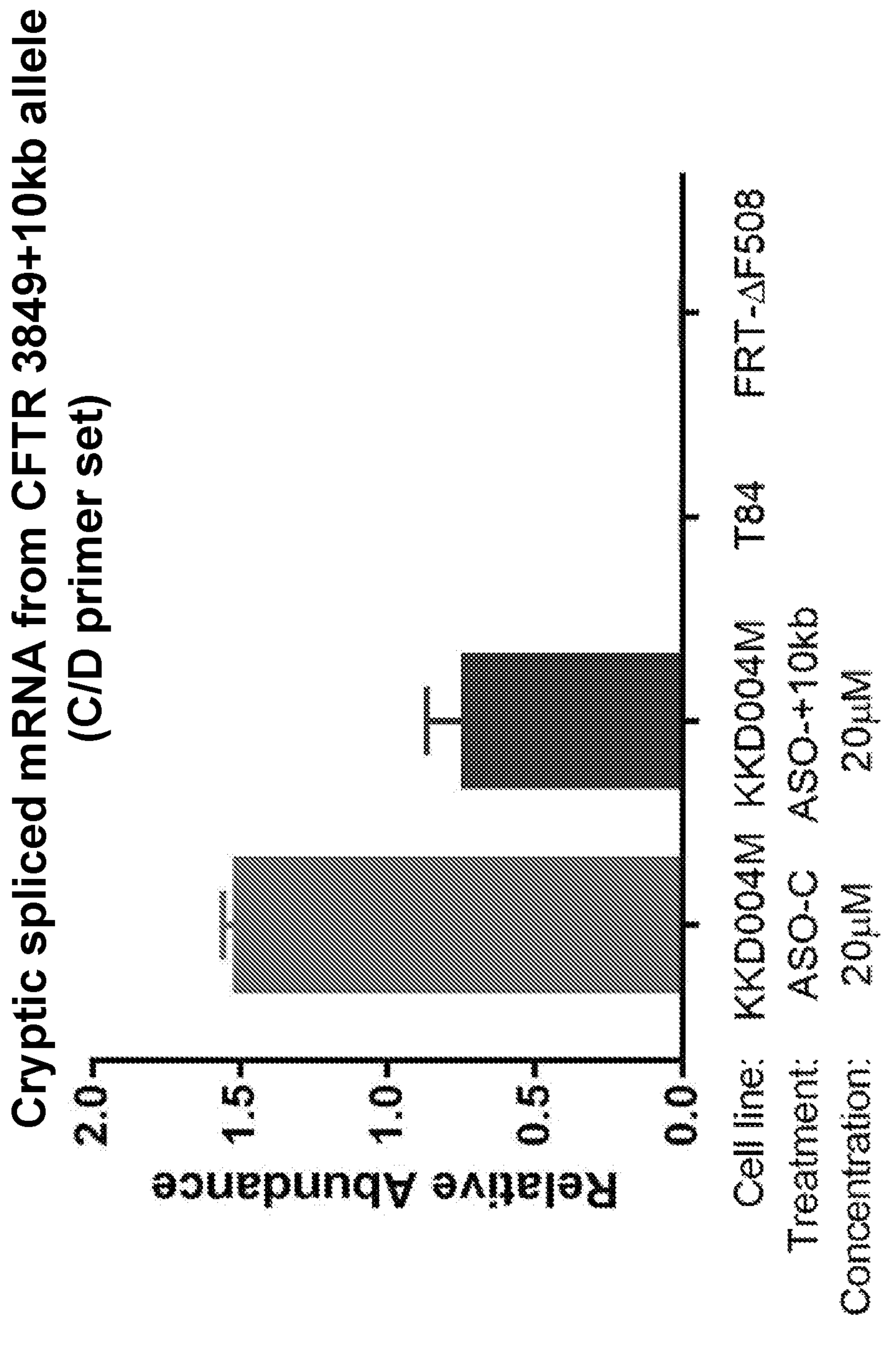

Additionally, the results show that ASO-+10 kb (SEQ ID NO:150) increases WT splicing in 3849+10 kb patient HBE cells. Primary patient HBE cells are heterozygous for the 3849+10 kbC>T mutation were transfected with ASO-+10 kb (20 uM). Total mRNA was isolated, reverse transcribed, and analyzed for splice correction using SYBER™ Green quantitative PCR. FIG. 24A depicts the primer sets used to analyze splice correction by ASO-104-kb (primer set A-B is designed to amplify ASO corrected WT isoform splicing specific to the splice mutant allele, and primer set C-D is designed to analyze the amount of uncorrected mutant splicing). FIG. 24B shows a quantification of total mRNA transcribed from the CFTR 3849+10 kB allele, and indicates an increase with ASO-+10 kb treatment (A-B primer set). FIG. 24C shows a quantification of mutant, cryptically spliced mRNA isoform, and shows decrease of aberrant mRNA with ASO-+10 kb treatment (C-D primer set).

Having described the invention in detail and by reference to specific embodiments thereof, it will be apparent that modifications and variations are possible without departing from the scope of the invention defined in the appended claims. More specifically, although some aspects of the present invention are identified herein as particularly advantageous, it is contemplated that the present invention is not necessarily limited to these particular aspects of the invention.

What is claimed is:

1. A compound comprising a modified antisense oligonucleotide consisting of the sequence of SEQ ID NO:127.

2. The compound of claim 1, wherein the modified antisense oligonucleotide comprises at least one modified nucleoside selected from a modified sugar moiety, a 2'-substituted sugar moiety, a 2'OME, a 2'F, a 2'-MOE, a bicyclic sugar moiety, a LNA, a cEt, a sugar surrogate, a morpholino, or a modified morpholino.

3. The compound of claim 1, wherein the modified antisense oligonucleotide comprises at least 5 to at least 25 modified nucleosides, each independently comprising a modified sugar moiety.

4. The compound of claim 3, wherein each nucleoside of the modified antisense oligonucleotide is a modified nucleoside, each independently comprising a modified sugar moiety.

5. The compound of claim 1, wherein the modified antisense oligonucleotide comprises at least two modified nucleosides comprising modified sugar moieties that are the same as one another or that are different from one another.

6. The compound of claim 1, wherein the modified antisense oligonucleotide comprises a modified region of at least 5 to at least 20 contiguous modified nucleosides.

7. The compound of claim 6, wherein each modified nucleoside of the modified region has a modified sugar moiety independently selected from: 2'-F, 2'-OMe, 2'-MOE, cEt, LNA, morpholino, and modified morpholino.

8. The compound of claim 6, wherein the modified nucleosides of the modified region each comprise the same modification as one another.

9. The compound of claim 8, wherein the modified nucleosides of the modified region each comprise the same 2'-substituted sugar moiety selected from: 2'-F, 2'-OMe, and 2'-MOE.

10. The compound of claim 8, wherein the modified nucleosides of the region of modified nucleosides each comprise the same bicyclic sugar moiety selected from: LNA and cEt.

11. The compound of claim 10, wherein the modified nucleosides of the region of modified nucleosides each comprises a sugar surrogate, and wherein the sugar surrogate of the modified nucleosides of the region of modified nucleosides is a morpholino.

12. The compound of claim 1, wherein the modified antisense oligonucleotide comprises no more than 4 contiguous naturally occurring nucleosides.

13. The compound of claim 1, wherein the modified antisense oligonucleotide comprises at least one modified internucleoside linkage.

14. The compound of claim 13, comprising at least one phosphorothioate internucleoside linkage.

15. The compound of claim 13, wherein each internucleoside linkage is a modified internucleoside linkage and wherein each internucleoside linkage comprises the same modification.

16. The compound of claim 15, wherein each internucleoside linkage is a phosphorothioate internucleoside linkage.

17. The compound of claim 1, comprising at least one conjugate.

18. The compound of claim 1, wherein the compound modulates splicing or expression of the CFTR transcript.

19. A pharmaceutical composition comprising the compound according to claim 1 and a pharmaceutically acceptable carrier or diluent.

20. The pharmaceutical composition of claim 19, further comprising one or more antisense compounds.

21. A method of modulating splicing or expression of a CFTR transcript in a cell comprising contacting the cell with the compound according to claim 1.

22. The method of claim 21, wherein the cell is in vitro or in vivo.

23. A method of treating cystic fibrosis comprising administering the compound according to claim 1 or the pharmaceutical composition of claim 19 to an animal.

24. The method of claim 23, wherein the administering step comprises delivering to the animal by inhalation, parenteral injection or infusion, oral, subcutaneous or intramuscular injection, buccal, transdermal, transmucosal and topical.

25. The method of claim 23, wherein the animal is a human or a mouse.

26. A method of treating cystic fibrosis, comprising administering a modified antisense oligonucleotide having 14 to 30 linked nucleosides and having a nucleobase sequence comprising at least 14 nucleosides of the sequence of SEQ ID NO:127, wherein the modified antisense oligonucleotide comprises at least 14 contiguous nucleobases and is at least 80% complementary to an equal-length portion of a target region of a cystic fibrosis transmembrane conductance regulator (CFTR) transcript to an animal in need thereof.

27. A method of treating cystic fibrosis, comprising administering a pharmaceutical composition comprising a modified antisense oligonucleotide having 14 to 30 linked nucleosides and having a nucleobase sequence comprising at least 14 nucleosides of the sequence of SEQ ID NO:127, wherein the modified antisense oligonucleotide comprises at least 14 contiguous nucleobases and is at least 80% complementary to an equal-length portion of a target region of CFTR, and a pharmaceutically acceptable carrier or diluent to an animal in need thereof.

* * * * *